US011447566B2

(12) United States Patent
Theunissen et al.

(10) Patent No.: US 11,447,566 B2
(45) Date of Patent: Sep. 20, 2022

(54) ANTI-TISSUE FACTOR ANTIBODIES, ANTIBODY-DRUG CONJUGATES, AND RELATED METHODS

(71) Applicant: Iconic Therapeutics, Inc., South San Francisco, CA (US)

(72) Inventors: Jan-Willem Theunissen, South San Francisco, CA (US); Andrew D. Avery, II, South San Francisco, CA (US); Allen G. Cai, South San Francisco, CA (US); Anthony Byron Cooper, South San Francisco, CA (US); Thi-Sau Migone, South San Francisco, CA (US)

(73) Assignee: Iconic Therapeutics, Inc., South San Francisco, CA (US)

(*) Notice: Subject to any disclaimer, the term of this patent is extended or adjusted under 35 U.S.C. 154(b) by 0 days.

(21) Appl. No.: 17/458,507

(22) Filed: Aug. 26, 2021

(65) Prior Publication Data
US 2022/0056151 A1    Feb. 24, 2022

Related U.S. Application Data

(63) Continuation of application No. 16/959,652, filed as application No. PCT/US2019/012427 on Jan. 4, 2019.

(60) Provisional application No. 62/713,797, filed on Aug. 2, 2018, provisional application No. 62/713,804, filed on Aug. 2, 2018, provisional application No. 62/646,788, filed on Mar. 22, 2018, provisional application No. 62/613,545, filed on Jan. 4, 2018, provisional application No. 62/613,564, filed on Jan. 4, 2018.

(51) Int. Cl.
| | |
|---|---|
| *C07K 16/36* | (2006.01) |
| *A61P 27/02* | (2006.01) |
| *A61K 47/68* | (2017.01) |
| *A61K 31/713* | (2006.01) |
| *C12N 5/10* | (2006.01) |
| *C12N 15/63* | (2006.01) |

(52) U.S. Cl.
CPC ............ *C07K 16/36* (2013.01); *A61K 31/713* (2013.01); *A61K 47/6843* (2017.08); *A61K 47/6849* (2017.08); *A61P 27/02* (2018.01); *C12N 5/10* (2013.01); *C12N 15/63* (2013.01); *C07K 2317/21* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,656,127 A | 4/1987 | Mundy |
| 4,676,980 A | 6/1987 | Segal et al. |
| 4,722,848 A | 2/1988 | Paoletti et al. |
| 4,816,567 A | 3/1989 | Cabilly et al. |
| 4,837,028 A | 6/1989 | Allen |
| 4,946,778 A | 8/1990 | Ladner et al. |
| 5,019,369 A | 5/1991 | Presant et al. |
| 5,132,405 A | 7/1992 | Huston et al. |
| 5,204,253 A | 4/1993 | Sanford et al. |
| 5,208,020 A | 5/1993 | Chari et al. |
| 5,217,879 A | 6/1993 | Huang et al. |
| 5,229,275 A | 7/1993 | Goroff |
| 5,279,833 A | 1/1994 | Rose |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,580,859 A | 12/1996 | Felgner et al. |
| 5,589,369 A | 12/1996 | Seidman et al. |
| 5,589,466 A | 12/1996 | Felgner et al. |
| 5,591,669 A | 1/1997 | Krimpenfort et al. |
| 5,622,931 A | 4/1997 | Edgington et al. |
| 5,662,907 A | 9/1997 | Kubo et al. |
| 5,814,482 A | 9/1998 | Dubensky, Jr. et al. |
| 5,843,723 A | 12/1998 | Dubensky, Jr. et al. |
| 5,849,561 A | 12/1998 | Falck-Pedersen |
| 5,849,589 A | 12/1998 | Tedder et al. |
| 6,015,686 A | 1/2000 | Dubensky, Jr. et al. |

(Continued)

FOREIGN PATENT DOCUMENTS

| | | |
|---|---|---|
| CA | 2705787 A1 | 6/2009 |
| EP | 0453082 A1 | 10/1991 |

(Continued)

OTHER PUBLICATIONS

Kipriyanov SM, Le Gall F., Mol Biotechnol. Jan. 2004;26(1):39-60. doi: 10.1385/MB:26:1:39. PMID: 14734823.*
Janeway et al., Immunobiology, 3rd edition, 1997, Garland Publishing Inc., pp. 3:1-3:11.*
Theunissen et al., Mol Cancer Ther. Nov. 2018;17(11):2412-2426. doi: 10.1158/1535-7163.MCT-18-0471. Epub Aug. 20, 2018. PMID: 30126944.*
Aalberse et al., IgG4 breaking the rules, Immunology, 2002, 105:9-19.
Aarnoudse, et al., TCR Reconstitution in Jurkat Reporter cells facilitates the identification of novel tumor antigens by CDNA expression cloning, Int. J. Cancer, 99, pp. 7-13, (2002).

(Continued)

*Primary Examiner* — Michael Szperka
(74) *Attorney, Agent, or Firm* — Goodwin Procter LLP

(57) ABSTRACT

Provided herein are antibodies that specifically bind to human tissue factor (TF), anti-TF antibody-drug conjugates (ADCs), and compositions comprising the antibodies or ADCs. Also provided herein are methods of making and using the antibodies or ADCs, such as therapeutic and diagnostic methods.

40 Claims, 47 Drawing Sheets

Specification includes a Sequence Listing.

(56) References Cited

U.S. PATENT DOCUMENTS

| | | | |
|---|---|---|---|
| 6,037,135 A | 3/2000 | Kubo et al. | |
| 6,083,716 A | 7/2000 | Wilson et al. | |
| 6,090,406 A | 7/2000 | Popescu et al. | |
| 6,194,551 B1 | 2/2001 | Idusogie et al. | |
| 6,296,854 B1 | 10/2001 | Pushko et al. | |
| 6,312,946 B1 | 11/2001 | Yeh et al. | |
| 6,365,394 B1 | 4/2002 | Gao et al. | |
| 6,413,935 B1 | 7/2002 | Sette et al. | |
| 6,610,321 B2 | 8/2003 | Huang et al. | |
| 6,737,056 B1 | 5/2004 | Presta | |
| 6,783,939 B2 | 8/2004 | Olmsted et al. | |
| 7,202,351 B1 | 4/2007 | Sette et al. | |
| 7,285,265 B2 | 10/2007 | Vogels et al. | |
| 7,291,498 B2 | 11/2007 | Roy et al. | |
| 7,332,581 B2 | 2/2008 | Presta | |
| 7,344,872 B2 | 3/2008 | Gao et al. | |
| 7,425,328 B2 * | 9/2008 | Wang | A61P 35/00 424/183.1 |
| 7,435,413 B2 * | 10/2008 | Kirchhofer | C07K 16/36 424/139.1 |
| 7,468,181 B2 | 12/2008 | Vogels et al. | |
| 7,494,647 B2 * | 2/2009 | Sato | A61P 9/00 435/7.1 |
| 7,531,180 B2 | 5/2009 | Polo et al. | |
| 7,541,038 B2 | 6/2009 | Kovacs et al. | |
| 7,557,200 B2 | 7/2009 | Wu et al. | |
| 7,572,453 B2 | 8/2009 | Polo et al. | |
| 7,572,628 B2 | 8/2009 | Dubensky, Jr. et al. | |
| 7,605,235 B2 | 10/2009 | Anderson et al. | |
| 7,732,129 B1 | 6/2010 | Zhang et al. | |
| 7,744,900 B2 | 6/2010 | Dubensky, Jr. et al. | |
| 7,771,979 B2 | 8/2010 | Polo et al. | |
| 7,820,440 B2 | 10/2010 | Vogels et al. | |
| 7,838,277 B2 | 11/2010 | Gao et al. | |
| 8,052,967 B2 | 11/2011 | Vogels et al. | |
| 8,093,021 B2 | 1/2012 | Hurtado et al. | |
| 8,119,336 B2 | 2/2012 | Sampath et al. | |
| 8,158,418 B2 | 4/2012 | Polo et al. | |
| 8,216,834 B2 | 7/2012 | Colloca et al. | |
| 8,252,574 B2 | 8/2012 | Mason et al. | |
| 8,258,082 B2 | 9/2012 | Ladner | |
| 8,647,864 B2 | 2/2014 | Polo et al. | |
| 8,673,319 B2 | 3/2014 | Colloca et al. | |
| 8,691,563 B2 | 4/2014 | Pushko et al. | |
| 8,691,730 B2 | 4/2014 | Vasquez et al. | |
| 8,722,044 B2 | 5/2014 | Almagro et al. | |
| 8,951,525 B2 | 2/2015 | Almagro et al. | |
| 8,999,333 B2 | 4/2015 | Almagro et al. | |
| 9,017,696 B2 | 4/2015 | Draper et al. | |
| 9,024,001 B2 | 5/2015 | Tang et al. | |
| 9,101,572 B2 | 8/2015 | Pushko et al. | |
| 9,150,641 B2 | 10/2015 | Kettenberger et al. | |
| 9,150,658 B2 | 10/2015 | Verploegen et al. | |
| 9,168,314 B2 * | 10/2015 | Satijn | A61K 45/06 |
| 9,192,661 B2 | 11/2015 | Jain et al. | |
| 9,217,159 B2 | 12/2015 | Roy et al. | |
| 9,234,181 B2 | 1/2016 | Tang et al. | |
| 9,249,191 B2 | 2/2016 | Ueno et al. | |
| 9,254,265 B2 | 2/2016 | Geall et al. | |
| 9,255,126 B2 | 2/2016 | Polo et al. | |
| 9,273,288 B2 | 3/2016 | Mason et al. | |
| 9,295,646 B2 | 3/2016 | Brito et al. | |
| 9,353,353 B2 | 5/2016 | Nabel et al. | |
| 9,453,240 B2 | 9/2016 | Chamberlain et al. | |
| 9,486,519 B2 | 11/2016 | Sahin et al. | |
| 9,487,563 B2 | 11/2016 | Nabel et al. | |
| 9,492,565 B2 | 11/2016 | Satijn et al. | |
| 9,512,190 B2 | 12/2016 | Ueno et al. | |
| 9,636,410 B2 | 5/2017 | Brito et al. | |
| 9,714,297 B2 | 7/2017 | Verploegen et al. | |
| 9,714,435 B2 | 7/2017 | Dicks et al. | |
| 9,790,308 B2 | 10/2017 | Han et al. | |
| 9,801,897 B2 | 10/2017 | Geall et al. | |
| 10,092,636 B2 | 10/2018 | Binder | |
| 10,240,128 B2 | 3/2019 | Thirion et al. | |
| 10,426,824 B1 | 10/2019 | Hacohen et al. | |
| 10,532,067 B2 | 1/2020 | Geall et al. | |
| 10,646,587 B2 | 5/2020 | Dicks et al. | |
| 2002/0137081 A1 | 9/2002 | Bandman | |
| 2003/0072767 A1 | 4/2003 | Gaiger et al. | |
| 2003/0157108 A1 | 8/2003 | Presta | |
| 2004/0115625 A1 | 6/2004 | Ebner | |
| 2005/0123555 A1 | 6/2005 | Olmsted et al. | |
| 2005/0196754 A1 | 9/2005 | Drmanac et al. | |
| 2006/0198854 A1 | 9/2006 | Pushko | |
| 2007/0031442 A1 | 2/2007 | Sewell | |
| 2007/0055049 A1 | 3/2007 | Grey et al. | |
| 2007/0224201 A1 | 9/2007 | Wu et al. | |
| 2008/0050393 A1 | 2/2008 | Tang et al. | |
| 2009/0081200 A1 | 3/2009 | Wang | |
| 2009/0093050 A1 | 4/2009 | Wu et al. | |
| 2009/0118181 A1 | 5/2009 | Walker et al. | |
| 2009/0253184 A1 | 10/2009 | Clarke et al. | |
| 2010/0041737 A1 | 2/2010 | Naldini et al. | |
| 2010/0120897 A1 | 5/2010 | Hurtado et al. | |
| 2010/0286070 A1 | 11/2010 | Verheyden et al. | |
| 2012/0237528 A1 | 9/2012 | Mmagro et al. | |
| 2013/0011426 A1 | 1/2013 | Tureci et al. | |
| 2013/0052672 A1 | 2/2013 | Varadi et al. | |
| 2013/0123199 A1 | 5/2013 | Lee | |
| 2013/0149375 A1 | 6/2013 | Geall | |
| 2013/0171241 A1 | 7/2013 | Geall | |
| 2013/0177639 A1 | 7/2013 | Geall et al. | |
| 2013/0177640 A1 | 7/2013 | Geall et al. | |
| 2013/0189351 A1 | 7/2013 | Geall | |
| 2013/0195968 A1 | 8/2013 | Geall et al. | |
| 2013/0195969 A1 | 8/2013 | Geall et al. | |
| 2013/0202684 A1 | 8/2013 | Geall et al. | |
| 2014/0141070 A1 | 5/2014 | Geall et al. | |
| 2014/0178438 A1 | 6/2014 | Sahin et al. | |
| 2014/0227346 A1 | 8/2014 | Geall et al. | |
| 2014/0234304 A1 | 8/2014 | Almagro et al. | |
| 2014/0242152 A1 | 8/2014 | Geall et al. | |
| 2014/0248314 A1 | 9/2014 | Swanson et al. | |
| 2014/0255472 A1 | 9/2014 | Geall et al. | |
| 2014/0271829 A1 | 9/2014 | Lilja et al. | |
| 2015/0110831 A1 | 4/2015 | Gilbert et al. | |
| 2015/0125465 A1 | 5/2015 | Binder et al. | |
| 2015/0125477 A1 | 5/2015 | Kuttruff-Coqui et al. | |
| 2015/0140068 A1 | 5/2015 | Barnett et al. | |
| 2015/0307897 A1 | 10/2015 | Soden et al. | |
| 2016/0074506 A1 | 3/2016 | Jain et al. | |
| 2016/0199513 A1 | 7/2016 | Bancel et al. | |
| 2016/0279258 A1 | 9/2016 | Valbjorn et al. | |
| 2016/0289674 A1 | 10/2016 | Bancel et al. | |
| 2016/0333113 A1 * | 11/2016 | Matsumura | A61P 35/00 |
| 2017/0136130 A1 | 5/2017 | Satijn et al. | |
| 2017/0210808 A1 | 7/2017 | Rosenthal et al. | |
| 2018/0044431 A1 | 2/2018 | Verploegen et al. | |
| 2019/0085080 A1 | 3/2019 | Kaplan et al. | |

FOREIGN PATENT DOCUMENTS

| | | | |
|---|---|---|---|
| EP | 1069185 A1 | 1/2001 | |
| EP | 2044947 A1 | 4/2009 | |
| EP | 2590670 A2 | 5/2013 | |
| EP | 2590676 A2 | 5/2013 | |
| EP | 3115061 A1 | 1/2017 | |
| FR | 2650840 A1 | 2/1991 | |
| JP | 2007-534295 A | 11/2007 | |
| JP | 2011-504724 A | 2/2011 | |
| JP | 2014-209917 A | 11/2014 | |
| WO | 1991/02087 A1 | 2/1991 | |
| WO | 1991/06309 A1 | 5/1991 | |
| WO | 1992/15712 A1 | 9/1992 | |
| WO | 1993/24640 A2 | 12/1993 | |
| WO | WO-9405328 A1 * | 3/1994 | C07K 14/745 |
| WO | 1995/13392 A1 | 5/1995 | |
| WO | 1996/13597 A2 | 5/1996 | |
| WO | 1996/18372 A2 | 6/1996 | |
| WO | 1999/51642 A1 | 10/1999 | |
| WO | 2001/073027 A2 | 10/2001 | |
| WO | 2003/085107 A1 | 10/2003 | |
| WO | 2004/023973 A2 | 3/2004 | |

(56) References Cited

FOREIGN PATENT DOCUMENTS

| WO | 2004/056312 A2 | 7/2004 |
|---|---|---|
| WO | 2005/016961 A1 | 2/2005 |
| WO | 2007/024708 A2 | 3/2007 |
| WO | 2007/047749 A1 | 4/2007 |
| WO | 2008/122811 A2 | 10/2008 |
| WO | 2008/145685 A1 | 12/2008 |
| WO | 2009/036379 A2 | 3/2009 |
| WO | 2009/079185 A2 | 6/2009 |
| WO | 2009/089004 A1 | 7/2009 |
| WO | 2010/105256 A1 | 9/2010 |
| WO | 2011/128704 A1 | 10/2011 |
| WO | 2012/006359 A1 | 1/2012 |
| WO | 2012/006377 A2 | 1/2012 |
| WO | 2012/009568 A2 | 1/2012 |
| WO | 2012/172058 A1 | 12/2012 |
| WO | 2012/172277 A1 | 12/2012 |
| WO | 2013/006837 A1 | 1/2013 |
| WO | 2014/179363 A1 | 11/2014 |
| WO | 2016/041082 A1 | 3/2016 |
| WO | 2016/124670 A1 | 8/2016 |
| WO | 2017/042352 A1 | 3/2017 |
| WO | 2017/106638 A1 | 6/2017 |
| WO | 2018/195357 A1 | 10/2018 |
| WO | 2019/102435 A1 | 5/2019 |
| WO | 2019/136309 A1 | 7/2019 |

OTHER PUBLICATIONS

Abdulkadir et al. "Tissue factor expression and angiogenesis in human prostate carcinoma," Human Pathology, 2000, 31(4):443-447.

Abelin et al., Complementary IMAC enrichment methods for HLA-associated phosphopeptide identification by mass spectrometry. Nat Protoc. Sep. 2015;10(9):1308-18. doi: 10.1038/nprot.2015.086. Epub Aug. 6, 2015.

Alexander et al., Development of high potency universal DR-restricted helper epitopes by modification of high affinity DR-blocking peptides, Immunity, vol. 1, Issue 9, pp. 751-761, Dec. 1994.

Anders et al., HTSeq—a Python framework to work with high-throughput sequencing data. Bioinforma. Oxf. Engl. 31, 166-169 (2015), https://doi.org/10.1093/bioinformatics/btu638.

Andreatta et al., Accurate pan-specific prediction of peptide-MHC class II binding affinity with improved binding core identification. Immunogenetics 67(11-12) 641-650, Nov. 2015.

Andreatta et al., Gapped sequence alignment using artificial neural networks: application to the MHC class I system. Bioinforma. Oxf. Engl. (2015). doi:10.1093/bioinformatics/btv639.

Arbabi Ghahroudi, Selection and identification of single domain antibody fragments from camel heavy-chain antibodies, FEBS Letters 414 (1997) 521-526.

Armour et al., Differential binding to human FcgRIIa and FcgRIIb receptors by human IgG wildtype and mutant antibodies, Molecular Immunology, vol. 40, Issue 9, Dec. 2003, pp. 585-593, <https://doi.org/10.1016/j.molimm.2003.08.004>.

Banu et al., "Building and Optimizing a Virus-specific T Cell Receptor Library for Targeted Immunotherapy in Viral Infections." Scientific Reports 4:4166, 2014.

Barbas et al., In vitro evolution of a neutralizing human antibody to human immunodeficiency virus type 1 to enhance affinity and broaden strain cross-reactivity, Proc. Nat. Acad. Sci. U.S.A., 1994, 91:3809-3813.

Barnstable et al., Production of monoclonal antibodies to group A erythrocytes, HLA and other human cell surface antigens-new tools for genetic analysis. Cell. May 1978; 14(1):9-20.

Bassani-Sternberg et al., Mass spectrometry of human leukocyte antigen class I peptidomes reveals strong effects of protein abundance and turnover on antigen presentation. Mol Cell Proteomics. Mar. 2015;14(3):658-73. doi: 10.1074/mcp.M114.042812.

Behrens et al., Antibody-Drug Conjugates (ADCs) Derived from Interchain Cysteine Cross-Linking Demonstrates Improved Homogeneity and Other Pharmacological Properties over Conventional Heterogeneous ADCs, Mol Pharmaceutics, 2015, 12, 11, 3986-98 <https://doi.org/10.1021/acs.molpharmaceut.5b00432>.

Binz et al., Engineering novel binding proteins from nonimmunoglobulin domains, Nat. Biotechnol., 2005 23:1257-1268.

Bodini et al. The hidden genomic landscape of acute myeloid leukemia: subclonal structure revealed by undetected mutations. Blood 125, 600-605 (2015).

Boegel et al. HLA typing from RNA-Seq sequence reads, Genome Med. 4, 102 (2012).

Boisvert et al. A Quantitative Spatial Proteomics Analysis of Proteome Turnover in Human Cells. Mol. Cell. Proteomics 11, M111.011429-1 (2012).

Boshart, et al., A very strong enhancer is located upstream of an immediate early gene of human cytomegalovirus, Cell, 41:521-530 (1985), https://doi.org/10.1016/S0092-8674(85)80025-8.

Breij et al. "An antibody-drug conjugate that targets tissue factor exhibits potent therapeutic activity against a broad range of solid tumors," Cancer Research, 2014, 74(4):1214-1226.

Brennan et al., Preparation of bispecific antibodies by chemical recombination of monoclonal immunoglobulin G1 fragments, Science, 1985, vol. 229, Issue 4708, pp. 81-83, DOI: 10.1126/science.3925553.

Bromberg et al., Tissue factor promotes melanoma metastasis by a pathway independent of blood coagulation, Proc. Natl. Acad. Sci. U S A., vol. 92, pp. 8205-8209, Aug. 1995.

Bruggemann et al., Designer mice: the production of human antibody repertoires in transgenic animals, Year in Immuno., 1993, 7:33.

Calis et al. Properties of MHC Class I Presented Peptides That Enhance Immunogenicity. PLoS Comput. Biol. 9, e1003266 (2013).

Cancer Genome Atlas Research Network. Comprehensive molecular profiling of lung adenocarcinoma. Nature 511, 543-550 (2014).

Carithers et al. A Novel Approach to High-Quality Postmortem Tissue Procurement: The GTEx Project. Biopreservation Biobanking 13, 311-319 (2015).

Carlring et al., A Novel Redox Method for rapid Production of Functional Bi-Specific Antibodies For Use in Early Pilot Studies, PLoS ONE 6(7): e22533, doi:10.1371/journal.pone.0022533.

Carneiro-Lobo et al. "Ixolaris, a tissue factor inhibitor, blocks primary tumor growth and angiogenesis in a glioblastoma model," J Thromb Haemost, 2009, 7(11):1855-1864.

Carneiro-Lobo et al., Ixolaris, a tissue factor inhibitor, blocks primary tumor growth and angiogenesis in a glioblastoma model, Journal of Thrombosis and Haemostasis, 2009, 7:1855-1864.

Carreno et al. Cancer immunotherapy. A dendritic cell vaccine increases the breadth and diversity of melanoma neoantigen-specific T cells. Science 348, 803-808 (2015).

Carter et al., Absolute quantification of somatic DNA alterations in human cancer. Nat. Biotechnol. 30, pp. 413-421 (2012).

Chahal, et al., Dendrimer-RNA nanoparticles generate protective immunity against lethal Ebola, H1N1 influenza, and Toxoplasma gondii challenges with a single dose, PNAS, 2016 E4133-4142, www.pnas.org/cgi/doi/10.1073/pnas.1600299113.

Chari et al., Immunoconjugates Containing Novel Maytansinoids: Promising Anticancer Drugs, Cancer Research 52, 127-131, Jan. 1, 1992.

Chen et al. "Immunolocalisation of tissue factor in esophageal cancer is correlated with intratumoral angiogenesis and prognosis of the patient," Acta Histochemica, 2010, 112(3):233-239.

Chen et al., Tissue factor expression in rheumatoid synovium a potential role in pannus invasion of rheumatoid arthritis, Acta Histochem., 2010, 3:233-239, <https://doi.org/10.1016/j.acthis.2013.02.005>.

Chowdhury, Methods Mol. Biol., 2008, 207:179-196.

Christensen et al., Urokinase-type plasminogen activator receptor (mPAR), tissue factor (TF) and epidermal growth factor receptor (EGFR) tumor expression patterns and prognostic value in oral cancer, BMC Cancer, 2017, 17:572, DOI 10.1186/s12885-017-3563-3.

(56) References Cited

OTHER PUBLICATIONS

Cibulskis et al. Sensitive detection of somatic point mutations in impure and heterogeneous cancer samples. Nat. Biotechnol. 31, 213-219 (2013).
Cieslik et al. The use of exome capture RNA-seq for highly degraded RNA with application to clinical cancer sequencing. Genome Res. 25, 1372-1381 (2015).
Cocco et al., Expression of Tissue factor in Adenocarcinoma and Squamous Cell Carcinoma of the Uterine Cervix: Implications for immunotherapy with hI-con1, a factor VII-IgGFc chimeric protein targeting tissue factor, BMC Cancer, 2011, 11:263, http://www.biomedcentral.com/1471-2407/11/263.
Coloma et al., Design and production of novel tentravalent bispecific antibodies, Nature Biotechnol., 1997, 15:159-163.
Cooper et al., Rescue of splicing-mediated intron loss maximizes expression in lentiviral vectors containing the human ubiquitin C promoter, Nucl. Acids Res. (2015) 43 (1): 682-690.
Cornet et al., (2006) Optimal organization of a polypeptide-based candidate cancer vaccine composed of cryptic tumor peptides with enhanced immunogenicity. Vaccine 24, 2102-2109.
Cox et al., "Immunoassay Methods," in Assay Guidance Manual [Internet], Updated Dec. 24, 2014 (Cox et al., "Immunoassay Methods," in Assay Guidance Manual [Internet], Updated Dec. 24, 2014 (www.ncbi.nlm.nih.gov/books/NBK92434/; accessed Sep. 29, 2015)/; accessed Sep. 29, 2015).
Del Val, Efficient processing of an antigenic sequence for presentation by MHC class I molecules depends on its neighboring residues in the protein, vol. 66, Issue 6, P1145-1153, Sep. 20, 1991, DOI:https://doi.org/10.1016/0092-8674(91)90037-Y.
Demoulins et al., Polyethylenimine-based polyplex delivery of self-replicating RNA vaccines, Nanomedicine: Nanotechnology, Biology and Medicine, vol. 12, Issue 3, Apr. 2016, pp. 711-722.
Depla et al., Rational design of a multiepitope vaccine encoding T-lymphocyte epitopes for treatment of chronic hepatitis B virus infections. Journal of Virology 82, 435-450 (2008).
Desrichard, et al., Cancer Neoantigens and Applications for Immunotherapy. Clin. Cancer Res. Off. J. Am. Assoc. Cancer Res. (2015). doi:10.1158/1078-0432.CCR-14-3175.
Duan, F. et al. Genomic and bioinformatic profiling of mutational neoepitopes reveals new rules to predict anticancer immunogenicity. J. Exp. Med. 211, 2231-2248 (2014).
Nussbaum, et al.. Cleavage motifs of the yeast 20S proteasome β subunits deduced from digests of enolase 1, Proc. Natl. Acad. Sci. USA, vol. 95, pp. 12504-12509, Oct. 1998, Immunology.
Nyren, et al., Solid Phase DNA Minisequencing by an Enzymatic Luminometric Inorganic Pyrophosphate Detection Assay, Analytical Biochemistry, vol. 208, Issue 1, Jan. 1993, pp. 171-175, https://doi.org/10.1006/abio.1993.1024.
Ouahabi Double long-chain amidine liposome-mediated self replicating RNA transfection, FEBS Letters 380 (1996) 108-112.
Panina-Bordignon et al., Universally immunogenic T cell epitopes: promiscuous binding to human MHC class II and promiscuous recognition by Tcells, Eur J Immunol 19, 2237-2242 (1989).
Patry et al. "Tissue factor expression correlates with disease-specific survival in patients with node-negative muscle-invasive bladder cancer," International journal of cancer, 2008, 122(7):1592-1597.
Paul, Fundamental Immunology 7th ed., Ch. 5 (2013) Lippincott Williams & Wilkins, Philadelphia, PA.
Pearson et al., MHC class I-associated peptides derive from selective regions of the human genome. The Journal of Clinical Investigation, 2016.
Pertea et al. StringTie enables improved reconstruction of a transcriptome from RNA-seq reads. Nat. Biotechnol. 33, 290-295 (2015).
Polo et al., Stable alphavirus packaging cell lines for Sindbis virus- and Semliki Forest virus-derived vectors, Proc. Natl. Acad. Sci. vol. 96, pp. 4598-4603, Apr. 1999.
Presta, Antibody engineering, Curr. Op. Struct. Biol., 1992, vol. 2, Issue 4, pp. 593-596.
Prezant, et al., Trapped-oligonucleotide nucleotide incorporation (TONI) assay, a simple method for screening point mutations, Human Mutation, vol. 1, Issue 2, 1992, https://doi.org/10.1002/humu.1380010212.
Pushko et al., Replicon-helper systems from attenuated Venezuelan equine encephalitis virus: expression of heterologous genes in vitro and immunization against heterologous pathogens in vivo. Virology. Dec. 22, 1997;239(2):389-401.
Qiu et al Reviving virus based cancer vaccines by using cytomegalovirus vectors expressing modified tumor antigens, Oncoimmunology, E pub Jun. 5, 2015, vol. 5 No. 1 pp. 1-3 doi: 10.1080/2162402X.2015.1056974.
Rajasagi et al. Systematic identification of personal tumor-specific neoantigens in chronic lymphocytic leukemia. Blood 124, 453-462 (2014).
Regina et al. "Increased tissue factor expression is associated with reduced survival in non-small cell lung cancer and with mutations of TP53 and PTEN," Clinical Chemistry, 2009, 55(10):1834-1842.
Rhême et al., Alphaviral cytotoxicity and its implication in vector development. Exp Physiol. Jan. 2005; 90(1):45-52. Epub Nov. 12, 2004.
Riechmann et al., Reshaping human antibodies for therapy, Nature, 1988, 332:323-327, DOI:10.1038/332323a0.
Riley et al., Recent Advances in Nanomaterials for Gene Delivery—A Review. Nanomaterials 2017, 7(5), 94, doi:10.3390/nano7050094.
Ripka et al., Two Chinese hamster ovary glycosylation mutants affected in the conversion of GDP-mannose to GDP-fucose, Arch. Biochem. Biophys., 1986, 249:533-545.
Rivas et al. Human genomics. Effect of predicted protein-truncating genetic variants on the human transcriptome. Science 348, 666-669 (2015).
Rizvi et al. Cancer immunology. Mutational landscape determines sensitivity to PD-1 blockade in non-small cell lung cancer. Science 348, 124-128 (2015).
Roberts et al., Identification of novel transcripts in annotated genomes using RNA-Seq. Bioinforma. Oxf. Engl. (2011). doi:10.1093/bioinformatics/btr355.
Rodriguez, et al., DNA Immunization Ubiquitination of a Viral Protein Enhances Cytotoxic T-Lymphocyte Induction and Antiviral Protection but Abrogates Antibody Induction, Journal of Virology, Nov. 1997, p. 8497-8503, vol. 71, No. 11.
Roy et al., Assessing long-distance RNA sequence connectivity via RNA-templated DNA-DNA ligation. eLife 4, (2015).
Ruf et al. "Antibody mapping of tissue factor implicates two different exon-encoded regions in function," The Biochemical journal, 1991, 278:729-733.
Sakuma et al., Lentiviral vectors: basic to translational, Biochem J. (2012) 443(3), pp. 603-618.
Sakurai et al. "Expression of Tissue Factor in Epithelial Ovarian Carcinoma Is Involved in the Development of Venous Thromboembolism," International Journal of Gynecological Cancer, 2017, 27(1):37-43.
Saunders et al. Strelka: accurate somatic small-variant calling from sequenced tumor-normal sample pairs. Bioinforma. Oxf. Engl. 28, 1811-1817 (2012).
Schier et al., Identification of functional and structural amino-acid residues by parsimonious mutagenesis, Gene, 1996, 169:147-155, DOI: 10.1016/0378-1119(95)00821-7 <https://www.researchgate.net/deref/http%3A%2F%2Fdx.doi.org%2F10.1016%2F0378-1119(95)00821-7>.
Schroeder et al., Structure and function of immunoglobulins, J. Allergy Clin. Immunol., 2010, 125:S41-52.
Schumacher et al., Neoantigens in cancer immunotherapy. Science 348, 69-74 (2015).
Shields et al., Lack of Fucose on Human IgG1 N-Linked Oligosaccharide Improves Binding to Human Fc RIII and Antibody-dependent Cellular Toxicity, J. Biol. Chem., 2002, 277:26733-26740.
Shukla et al., Comprehensive analysis of cancer-associated somatic mutations in class I HLA genes, Nat. Biotechnol. 33, pp. 1152-1158, (2015).

(56) References Cited

OTHER PUBLICATIONS

Siiman et al., Competitive Antibody Binding to Soluble CD16b Antigen and CD16b Antigen on Neutrophils in Whole Blood by Flow Cytometry, Cytometry, 2001, 44:30-37.
Silacci et al., Linker Length Matters, Fynomer-Fc Fusion with an Optimized Linker Displaying Picomolar IL-17A Inhibition Potency, J. Biol. Chem., 2014, 289:14392-14398.
Silva et al. "Increased tissue factor expression is an independent predictor of mortality in clear cell carcinoma of the kidney," International braz j urol : official journal of the Brazilian Society of Urology, 2014, 40(4):499-506.
Skelly et al., A powerful and flexible statistical framework for testing hypotheses of allele-specific gene expression from RNA-seq data. Genome Res. 21, 1728-1737 (2011).
Slansky et al., Enhanced Antigen-Specific Antitumor Immunity with Altered Peptide Ligands that Stabilize the MHC-Peptide-TCR Complex. Immunity, vol. 13, Issue 4, Oct. 1, 2000, pp. 529-538.
Snyder et al. Genetic basis for clinical response to CTLA-4 blockade in melanoma. N. Engl. J. Med. 371, 2189-2199 (2014).
Sokolov, Primer extension technique for the detection of single nucleotide in genomic DNA, Nucleic Acids Research, vol. 18, Issue 12, Jun. 25, 1990, p. 3671.
Song, L. & Florea, L. Class: constrained transcript assembly of RNA-seq reads. BMC Bioinformatics 14 Suppl 5, S14 (2013).
Staerz and Bevan, Hybrid hybridoma producing a bispecific monoclonal antibody that can focus effector T-cell activity, Proc. Natl. Acad. Sci. USA, 1986, 83:1453-1457.
Staerz, et al. Hybrid antibodies can target sites for attack by T cells, Nature, 1985, 314:628-631.
Stover, et al. New use of BCG for recombinant vaccines. Nature 351, 456-460 (1991) doi:10.1038/351456a0.
Strauss, JH and E G Strauss. The alphaviruses: gene expression, replication, and evolution. Microbiol Rev. Sep. 1994; 58(3): 491-562.
Strejan et al., Suppression of chronic-relapsing experimental allergic encephalomyelitis in strain-13 giunea pigs by administration of lopisone-associated myelin basic protein, Journal of Neuroimmulogy, vol. 7, pp. 27-41, Jan. 1, 1984.
Stronen et al., Targeting of cancer neoantigens with donor-derived T cell receptor repertoires, Science. (2016) 352 (6291):1337-41.
Syvänen, et al., A primer-guided nucleotide incorporation assay in the genotyping of apolipoprotein W, Genomics, vol. 8, Issue 4, Dec. 1990, pp. 684-692, https://doi.org/10.1016/0888-7543(90)90255-S.
Syvänen, et al., Identification of individuals by analysis of biallelic DNA markers, using PCR and sold-phase minisequencing, American Journal of Human Genetics, Jan. 1993, 52(1): 46-59.
Szoka, Jr., Comparative properties and methods of preparation of lipid vesicles (liposomes), Ann. Rev. Biophys. Bioeng. 1980, 9:467-508.
Target Capture for NextGen Sequencing—IDT. at <http://www.idtdna.com/pages/products/nextgen/target-capture> (Author, Title should be Integrated Data Technologies Hybridization capture).
Tatsis et al., Adenoviruses as vaccine vectors, Molecular Therapy, vol. 10, Issue 4, Oct. 2004, pp. 616-629 https://doi.org/10.1016/j.ymthe.2004.07.013.
Teplyakov et al., "Crystal structure of tissue factor in complex with antibody 10H10 reveals the signaling epitope." Cellular Signalling 36 (2017): 139-144.
Theunissen et al., Methods for Studying the Cellular Response to DNA Damage: Influence of the Mre11 Complex on Chromosome Metabolism, Methods Enzymol, 2006, 409:251-284.
Todorovska et al., Design and application of diabodies, triabodies and tetrabodies for cancer targeting, J. Immunol. Methods, 2001, 248:47-66.
Tran, E. et al., Cancer immunotherapy based on mutation-specific CD4+ T cells in a patient with epithelial cancer, Science, 344:641-645 (2014).
Traunecker et al., Bispecific single chain molecules (Janusins) target cytotoxic lymphocytes on HIV infected cells, EMBO J., 1991, 10:3655-3659.

Tripisciano et al., "Different Potential of Extracellular Vesicles to Support Thrombin Generation: Contributions of Phosphatidylserine, Tissue Factor, and Cellular Origin," Scientific Reports, 7:6522, Jul. 26, 2017, 11 pages.
Tutt et al., Trispecific F(ab')3 derivatives that use cooperative signaling via the TCR/CD3 complex and CD2 to activate and redirect resting cytotoxic T cells, J. Immunol., 1991, 147:60-69.
Ugozzoli, et al., Detection of specific alleles by using allele-specific primer extension followed by capture on solid support, Genetic Analysis: Biomolecular Enginnering, vol. 9, Issue 4, Aug. 1992, pp. 107-112, https://doi.org/10.1016/1050-3862(92)90049-B.
Vajdy, et al., Mucosal adjuvants and delivery systems for protein-, DNA- and RNA-based vaccines, Immunology & Cell Biology, vol. 82, Issue 6, 2004, https://doi.org/10.1111/j.1440-1711.2004.01288.x.
Van Allen, E. M. et al., "Genomic correlates of response to CTLA-4 blockade in metastatic melanoma.," Science 350, 207-211 (2015).
Van den Berg et al. "The relationship between tissue factor and cancer progression: insights from bench and bedside," Blood, 2012, 119(4):924-932.
Van Loo, et al., Allele-specific copy number analysis of tumors. Proc. Natl. Acad. Sci. U. S. A. 107, pp. 16910-16915, (2010).
Velders et al., Defined Flanking Spacers and Enhanced Proteolysis Is Essential for Eradication of Established Tumors by an Epitope String DNA Vaccine, The Journal of Immunology, 2001; 166:5366-5373; doi: 10.4049/iimmunol.166.9.5366.
Versteeg et al. "Inhibition of tissue factor signaling suppresses tumor growth," Blood, 2008, 111(1):190-199.
Vitiello et al., (1991). Analysis of the HLA-restricted influenza-specific cytotoxic T lymphocyte response in transgenic mice carrying a chimeric human-mouse class I major histocompatibility complex. J Exp Med 173, 1007-1015.
Vitting-Seerup, K., Porse, B. T., Sandelin, A. & Waage, J. spliceR: an R package for classification of alternative splicing and prediction of coding potential from RNA-seq data. BMC Bioinformatics 15, 81 (2014).
Walter, M. J. et al. Clonal architecture of secondary acute myeloid leukemia. N. Engl. J. Med. 366, 1090-1098 (2012).
Wilkerson, M. D. et al. Integrated RNA and DNA sequencing improves mutation detection in low purity tumors. Nucleic Acids Res. 42, e107 (2014).
Wolff et al., Direct gene transfer into mouse muscle in vivo, Science Mar. 23, 1990: vol. 247, Issue 4949, pp. 1465-1468, DOI: 10.1126/science.1690918.
Wright et al., Effect of glycosylation on antibody function: implications for genetic engineering, TIBTECH, 1997, 15:26-32.
Wu Targeting Genes: Delivery and Persistent Expression of a Foreign Gene Driven by Mammalian Regulatory Elements in Vivo, The Journal of Biological Chemistry, vol. 264, No. 29, Oct. 15, 1989, pp. 16985-16987.
Xu et al., Addressing polyspecificity of antibodies selected from an in vitro yeast presentation system: a FACS-based, high-throughput selection and analytical tool, Protein Eng Des Sel., 2013, 26(10):663-70).
Xu, G. et al. RNA CoMPASS: a dual approach for pathogen and host transcriptome analysis of RNA-seq datasets. PloS One 9, e89445 (2014).
Yachi et al., Altered peptide ligands induce delayed CD8-T cell receptor interaction-a role for CD8 in distinguishing antigen quality. Immunity 25, 203-211, 2006.
Yadav, M. et al. Predicting immunogenic tumour mutations by combining mass spectrometry and exome sequencing. Nature 515, 572-576 (2014), doi:10.1038/nature14001.
Yamane-Ohnuki et al., Establishment of FUT8 knockout Chinese hamster ovary cells: An ideal host cell line for producing completely defucosylated antibodies with enhanced antibody-dependent cellular cytotoxicity , Biotech. Bioeng., 2004, 87: 614-622.
Yao et al. "Tissue Factor and VEGF Expression in Prostate Carcinoma: A Tissue Microarray Study," Cancer Investigation, 2009, 27(4):430-434.
Ye, K., et al., Pindel: a pattern growth approach to detect break points of large deletions and medium sized insertions from paired-end short reads. Bioinforma. Oxf. Engl. 25, 2865-2871 (2009).

(56) References Cited

OTHER PUBLICATIONS

Yeh et al. "Upregulation of tissue factor by activated Stat3 contributes to malignant pleural effusion generation via enhancing tumor metastasis and vascular permeability in lung adenocarcinoma," PLoS One, 2013, 8(9):1-14.
Yeh et al., Deterministic Diffusion Fiber Tracking Improved by Quantitative Anisotropy, PLoS One, 2013, 8:e75287.
Yoshida, et al., Splicing factor mutations and cancer. Wiley Interdiscip. Rev. RNA 5, 445-459 (2014).
Zarling et al., Identification of class I MHC-associated phosphopeptides as targets for cancer immunotherapy. Proc Natl Acad Sci U S A. Oct. 3, 2006;103(40):14889-94.
Zhang et al. "Pathological expression of tissue factor confers promising antitumor response to a novel therapeutic antibody SC1 in triple negative breast cancer and pancreatic adenocarcinoma," Oncotarget, 2017, 8(35):59086-59102.
Zhang, J. et al. Intratumor heterogeneity in localized lung adenocarcinomas delineated by multiregion sequencing. Science 346, 256-259 (2014).
Zhang, J., et al. "PEAKS DB: de novo sequencing assisted database search for sensitive and accurate peptide identification. Molecular & Cellular Proteomics," 11(4):1-8. Jan. 2, 2012.
Zhou, Q. et al. A chemical genetics approach for the functional assessment of novel cancer genes. Cancer Res. (2015). doi:10.1158/0008-5472.CAN-14-2930.
Zufferey et al., Self-Inactivating Lentivirus Vector for Safe and Efficient In Vivo Gene Delivery, J. Virol. (1998) 72 (12): 9873-9880.
Kim et al. "A novel antibody-drug conjugate targeting SAIL for the treatment of hematologic malignancies," Blood cancer journal, 2015, 5(5):1-8.
Kinney et al.. Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. Jul. 30, 1986.
Koizume et al. "Tissue Factor-Factor VII Complex As a Key Regulator of Ovarian Cancer Phenotypes," Biomark Cancer, 2015, 7(S2):1-13.
Koizume et al., Tissue Factor-Factor VII Complex As a Key Regulator of Ovarian Cancer Phenotypes, Biomark Cancer, 2015, 7:1-13.
Kornher, et al., Mutation detection using nucleotide analogs that alter electrophoretic mobility, Nucleic Acids Research, vol. 17, Issue 19, Oct. 11, 1989, pp. 7779-7784, https://doi.org/10.1093/nar/17.19.7779.
Kost, et al., The nucleotide sequence of the chich cytoplasmic β-actin gene, Nucleic Acids Research, vol. 11, Issue 23, Dec. 10, 1983, pp. 8287-8301, https://doi.org/10.1093/nar/11.23.8287.
Kostelny et al., Formation of a bispecific antibody by the use of leucine zippers, J. Immunol., 1992, 148:1547-1553.
Kovtun et al., Antibody-Maytansinoid Conjugates Designed to Bypass Multidrug Resistance, Cancer Res., 2010, 70:2528-2537.
Kozbor, A human hybrid myeloma for production of human monoclonal antibodies., J. Immunol., 1984, 133 (6) pp. 3001-3005.
Kreiter et al., "Mutant MHC class II epitopes drive therapeutic immune responses to cancer," Nature 520, 692-696, Apr. 2015.
Kreiter Increased antigen presentation efficiency by coupling antigens to MHC class I trafficking signals, J Immunol 2008, 180:309-318, doi: 10.4049/jimmunol.180.1.309, http://www.jimmunol.org/content/180/1/309.
Krieg et al., Functional messenger RNAs are produced by SP6 in vitro transcription of cloned cDNAs, Nucleic Acids Res. Sep. 25, 1984;12(18):7057-70.
Kuppuswamy et al., Single nucleotide primer extension to detect genetic diseases Experimental application to hemophilia B (factor IX) and cystic fibrosis genes, Proc. Natl. Acad. Sci. USA, vol. 88, pp. 1143-1174, Feb. 1991, Biochemistry.
Kåll et al., Assigning [confidence measures] significance to peptides identified by tandem mass spectrometry. Journal of Proteome Research, 7(1):29-34, Jan. 2008.

Kåll et al., Nonparametric estimation of posterior error probabilities associated with peptides identified by tandem mass spectrometry. Bioinformatics, 24(16):i42-i48, Aug. 2008.
Kåll et al., Semi-supervised learning for peptide identification from shotgun proteomics datasets. Nature Methods 4:923-925, Nov. 2007.
Lam et al. Nucleotide-resolution analysis of structural variants using BreakSeq and a breakpoint library. Nat. Biotechnol. 28, 47-55 (2010).
Larsen et al. "Engineering of substrate selectivity for tissue factor. factor VIIa complex signaling through protease-activated receptor 2," The Journal of biological chemistry, 2010, 285(26):19959-19966.
Larsen et al. An integrative approach to CTL epitope prediction: a combined algorithm integrating MHC class I binding, TAP transport efficiency, and proteasomal cleavage predictions. Eur. J. Immunol. 35, 2295-2303 (2005).
Lefranc et al., IMGT unique numbering for immunoglobulin and T cell receptor variable domains and Ig superfamily V-like domains, Dev Comp Immunol, 2003, 27:55-77.
Li et al., RSEM: accurate transcript quantification from RNA-Seq data with or without a reference genome. BMC Bioinformatics, 12:323, Aug. 2011.
Liao-Chan et al. "Quantitative assessment of antibody internalization with novel monoclonal antibodies against Alexa fluorophores," PLoS One, 2015, 10(4):1-15.
Liepe et al., A large fraction of HLA class I ligands are proteasome-generated spliced peptides. Science, 21, Oct. 2016.
Liu et al. ATHLATES: accurate typing of human leukocyte antigen through exome sequencing. Nucleic Acids Res. 41, e142 (2013).
Liu et al., N-terminal Glutamate to Pyroglutamate Conversion in Vivo for Human IgG2 Antibodies , J. Biol. Chem., 2011, 286:11211-11217.
Ljungberg et al., Self-replicating alphavirus RNA vaccines, Expert Rev. Vaccines 14(2), 177-194 (2015).
Lo et al. "Tissue factor expression in the metaplasia-adenoma-carcinoma sequence of gastric cancer in a European population," British Journal of Cancer, 2012, 107(7):1125-1130.
Lu et al., Efficient identification of mutated cancer antigens recognized by T cells associated with durable tumor regressions, Clin Cancer Res. (2014) 20(13):3401-10.
Lundegaard et al., State of the art and challenges in sequence based T-cell epitope prediction. Immunome Res. 6 Suppl 2, S3 (2010).
Lundstrom, Alphavirus-Based Vaccines, Viruses 2014, 6, 2392-2415, doi:10.3390/v6062392.
Lyons et al., Influence of human CD8 on antigen recognition by T-cell receptor-transduced cells. Cancer Res 66, 11455-11461 (2006).
Maguire et al. SF3B1 mutations constitute a novel therapeutic target in breast cancer. J. Pathol. 235, 571-580 (2015).
Mannino & Gould-Fogerite, BioTechniques 6(7): 682-691 (1988).
Maretty et al., Bayesian transcriptome assembly. Genome Biol. 15, 501 (2014).
Marks et al., By-passing immunization: Human antibodies from V-gene libraries displayed on phage, J. Mol. Biol., 1991, 222:581-597.
Martinon et al., Induction of virus-specific cytotoxic T lymphocytes in vivo by liposome-entrapped Mrna, European Journal of Immunology vol. 23, Issue 7, Jul. 1993, https://doi.org/10.1002/eji.1830230749.
Mayor et al. HLA Typing for the Next Generation. PloS One 10, e0127153 (2015).
McGranahan et al., Allele-Specific HLA Loss and Immune Escape in Lung Cancer Evolution, Cell 171, 1259-1271. e11, (2017).
Merchant et al., An efficient route to human bispecific IgG, Nature Biotechnol., 1998, 16:677-681.
Miller et al., Design, Construction, and In Vitro Analyses of Multivalent Antibodies, J. Immunol., 2003, 170:4854-4861.
Milstein et al., (Milstein and Cuello), Hybrid hybridomas and their use in immunohistochemistry, Nature, 1983, 305:537-540.
Mommen et al., Sampling From the Proteome to the Human Leukocyte Antigen-DR (HLA-DR) Ligandome Proceeds Mia High Specificity. Mol Cell Proteomics 15(4): 1412-1423, Apr. 2016.

(56) References Cited

OTHER PUBLICATIONS

Morea et al., Antibody modeling: implications for engineering and design., Methods, 2000, 20:267-279.
Mose et al., ABRA: improved coding indel detection via assembly-based realignment. Bioinforma. Oxf. Engl. 30, 2813-2815 (2014).
Muyldermans et al., Recognition of antigens by single-domain antibody fragments: the superfluous luxury of paired domains, Trends in Biochem. Sci., 2001, 26:230-245.
Nagai, et al. (2012). Aurora kinase A-specific T-cell receptor gene transfer redirects T lymphocytes to display effective antileukemia reactivity. Blood 119, 368-376.
Ngo et al. "CNTO 859, a humanized anti-tissue factor monoclonal antibody, is a potent inhibitor of breast cancer metastasis and tumor growth in xenograft models," International journal of cancer, 2007, 120(6):1261-1267.
Nielsen et al., The role of the proteasome in generating cytotoxic T-cell epitopes: insights obtained from improved predictions of proteasomal cleavage. Immunogenetics 57, 33-41 (2005).
Nielsen, et al., NN-align—An aililicial neural network-based alignment algorithm for MHC class II peptide binding prediction. BMC Bioinformatics 10:296, Sep. 2009.
Nielsen, et al., "Prediction of MHC class II binding affinity using SMM-align, a novel stabilization matrix alignment method.," BMC Bioinformatics 8:238, Jul. 2007.
Dupuis, et al., Dendritic Cells Internalize Vaccine Adjuvant after Intramuscular Injection, Cellular Immunology, vol. 186, Issue 1, May 25, 1998, pp. 18-27, https://doi.org/10.1006/cimm.1998.1283.
Eggers, et al., The Cleavage Preference of the Proteasome Governs the Yield of Antigenic Peptides, Journal of Experimental Medicine, vol. 182 Dec. 1995 1865-1870.
Eng et al., A deeper look into Comet—implementation and features. J Am Soc Mass Spectrom. Nov. 2015;26(11):1865-74. doi: 10.1007/s13361-015-1179-x. Epub Jun. 27, 2015.
Eng et al., Comet: an open-source MS/MS sequence database search tool. Proteomics. Jan. 2013;13(1):22-4. doi: 10.1002/pmic.201200439. Epub Dec. 4, 2012.
Fang, et al. Stable antibody expression at therapeutic levels using the 2A peptide. Nat Biotechnol 23, 584-590 (2005) doi:10.1038/nbt1087.
Farina et al., Replication-Defective Vector Based on a Chimpanzee Adenovirus, Journal of Virology, Dec. 2001, p. 11603-11613 DOI: 101128/JV1.75.23.11603-11613.2001.
Felgner, Lipofaction A highly efficient, lipid-mediated DNA-transfaction procedure, Proc. Natl. Acad. Sci., vol. 84, pp. 7413-7417, Nov. 1987.
Finco et al., Comparison of competitive ligand-binding assay and bioassay formats for the measurement of neutralizing antibodies to protein therapeutics, J. Pharm. Biomed. Anal., 2011, vol. 54, Issue 2, Jan. 2011, pp. 351-358.
Fisher et al., Biochem. J., 299:49 (Apr. 1, 1994).
Fleeton et al., Self-Replicative RNA Vaccines Elicit Protection against Influenze A Virus, Respiratory Syncytial Virus, and a Tickborne Encephalitis Virus, Journal of Infectious Diseases 183:1395-1398 2001.
Frampton et al. Development and validation of a clinical cancer genomic profiling test based on massively parallel DNA sequencing. Nat. Biotechnol. 31, 1023-1031 (2013).
Frolov et al., Cis-acting RNA elements at the 5' end of Sindbis virus genome RNA regulate minus- and plus-strand RNA synthesis. RNA. Nov. 2001; 7(11):1638-51.
Furney et al. SF3B1 mutations are associated with alternative splicing in uveal melanoma. Cancer Discov. (2013). doi:10.1158/2159-8290.CD-13-0330.
Gabrilovich et al., IL-12 and mutant P53 peptide-pulsed dendritic cells for the specific immunotherapy of cancer., J Immunother Emphasis Tumor Immunol. 1996 (6):414-418.
Geall, et al., Nonviral delivery of self-amplifying RNA vaccines, PNAS, 14604-14609, Sep. 4, 2012, vol. 109, No. 36, www.pnas.org/cgi/doi/10.1073/pnas.1209367109.

Goding, Monoclonal Antibodies: Principles and Practice 3rd ed. (1986) Academic Press, San Diego, CA.
Goldman et al., HLA-DR monoclonal antibodies inhibit the proliferation of normal and chronic granulocytic leukaemia myeloid progenitor cells. Br J Haematol. Nov. 1982;52(3):411-20.
Graaf et al., Curr Pharm Des, 2002, 8:1391-1403.
Gros et al., Prospective identification of neoantigen-specific lymphocytes in the peripheral blood of melanoma patients, Nat Med. (2016) 22 (4):433-8.
Gruber et al., Efficient tumor cell lysis mediated by a bispecific single chain antibody expressed in *Escherichia coli*., J. Immunol., 1994, 152:5368-5374.
Guan et al. "Tissue factor expression and angiogenesis in human glioma," Clinical Biochemistry, 2002, 35(4):321-325.
Gubin, et al. "Tumor neoantigens: building a framework for personalized cancer immunotherapy," J. Clin. Invest. 125, 3413-3421 (2015).
Hawkins et al., Selection of phage antibodies by binding affinity: Mimicking affinity maturation, Journal of Molecular Biology, vol. 226, Issue 3, 1992, pp. 889-896. https://doi.org/10.1016/0022-2836(92)90639-2.
Hofer et al., An engineered selenocysteine defines a unique class of antibody derivatives, Proc. Natl. Acad. Sci. USA, 2008, 105:12451-12456.
Hofer et al., Molecularly defined antibody conjugation through a selenocysteine interface, Biochemistry, 2009, 48 (50):12047-12057.
Holliger et al., "Diabodies" Small bivalent and bispecific antibody fragments, Proc. Natl. Acad. Sci. USA, 1993, 90:6444-6448.
Holy et al., Tissue Factor in Cardiovascular Disease: Pathophysiology and Pharmacological Intervention, Adv Pharmacol, 2010, 59:259-592, <https://doi.org/10.1016/S1054-3589(10)59009-4>.
Hong et al, 2012, Immuno-PET of Tissue Factor in Pancreatic Cancer, J Nucl Med, 53(11):1748-1754.
Hoogenboom et al., By-passing immunisation: Human antibodies from synthetic repertoires of germline VH gene segments rearranged in vitro, J. Mol. Biol., 1991, 227:381-388. <https://doi.org/10.1016/0022-2836(92)90894-P>.
Hu et al., Immunization Delivered by Lentiviral Vectors for Cancer and Infectious Diseases, Immunol Rev. (2011) 239(1): 45-61, https://doi.org/10.1111/j.1600-065X.2010.00967.x.
Huang et al. "The mechanism of an inhibitory antibody on TF-initiated blood coagulation revealed by the crystal structures of human tissue factor, Fab 5G9 and TF.G9 complex," Journal of molecular biology, 1998, 275(5):873-894.
Huang, et al., The immunodominant major histocompatibility complex class I-restricted antigen of a murine colon tumor derives from an endogenous retroviral gene product, Proc. Natl. Acad. Sci., vol. 93, pp. 9730-9735, Sep. 1996, Immunology.
Hunt et al., Characterization of peptides bound to the class I MHC molecule HLA-A2.1 by mass spectrometry. Science 1992. 255: 1261-1263.
Idusogie et al., Mapping of the C1q Binding Site on Rituxan, a Chimeric Antibody with a Human IgG1 Fc, J. Immunol., 2000, 164:4178-4184.
International Search Report and Written Opinion of the International Searching Authority, International Application No. PCT/US2019/012427, dated May 17, 2019, 14 pages.
Ishioka et al., Utilization of MHC class I transgenic mice for development of minigene DNA vaccines encoding multiple HLA-restricted CTL epitopes. J Immunol 162, 3915-3925 (1999).
Jackson et al., In vitro antibody maturation. Improvement of a high affinity, neutralizing antibody against IL-1 beta., J. Immunol., 1995, 154:3310-33199.
Jakobovits et al., Analysis of homozygous mutant chimeric mice deletion of the immunoglobulin heavy-chain joining region blocks B-cell development and antibody production, Proc. Natl. Acad. Sci. U.S.A., 1993, 90:2551.
Jakobovits et al., Germ-line transmission and expression of a human-derived yeast artificial chromosome, Nature, 1993, 362:255-258.
James et al., Tetramer-guided epitope mapping reveals broad, individualized repertoires of tetanus toxin-speci?c CD41 T cells and

(56) References Cited

OTHER PUBLICATIONS suggests HLA-based differences in epitope recognition, International Immunology, vol. 19, No. 11. pp. 1291-1301, doi:10.1093/intimm/dxm099.

Janetzki et al., Guidelines for the automated evaluation of Elispot assays. Nat Protoc 10, 1098-1115 (2015).

Jayaraman Maximizing the Potency of siRNA Lipid Nanoparticles for Hepatic Gene Silencing In Vivo, Angew. Chem. Int. 2012, 51, 8529-8533.

Jensen et al. "Improved Methods for Prediting Peptide Binding Affinity to MHC Class II Molecules." Immunology, 2018, doi:10.1111/imm.12889.

Johanning et al., A sindbis virus mRNA polynucleotide vector achieves prolonged and high level heterologous gene in vivo, Nucleic Acids Research, 1995, vol. 23, No. 9, 1495-1501.

Johnson et al., Molecular Determinants of Alphavirus Neurovirulence: Nucleotide and Deduced Protein Sequence Changes during Attenuation of Venezuelan Equine Encephalitis Virus. J Gen Virol 67:1951-1960, 1986.

Jones et al., Replacing the complementarity-determining regions in a human antibody with those from a mouse, Nature, 1986, 321:522-525.

Jose et al., A structural and functional perspective of alphavirus replication and assembly. Future Microbiol. Sep. 2009;4(7):837-56.

Jørgensen et al., NetMHCstab—predicting stability of peptide-MHC-I complexes; impacts for cytotoxic T lymphocyte epitope discovery. Immunology 141, 18-26 (2014).

Kabat et al., Unusual Distributions of Amino Acids in Complementarity-determining (Hypervariable) Segments of Heavy and Light Chains of Immunoglobulins and Their Possible Roles in Specificity of Antibody-combining Sites, J Biol Chem, 1977, 252:6609-6616.

Kanda et al., Comparison of cell lines for stable production of fucose-negative antibodies with enhanced ADCC, Biotechnol. Bioeng., 2006, 94:680-688.

Notification of Transmittal of the International Search Report and the Written Opinion of the International Searching Authority, or the Declaration, International Application No. PCT/US2021/41191, dated Dec. 2, 2021, 17 pages.

Gaudrealut et al., "Preclinical Pharmacology and Safety of ESBA1008, a Single-Chain Antibody Fragment, investigated as Potential Treatment for Age Related Macular Degeneration," ARVO Annual Meeting Abstract, Mar. 2012, Investigative Opthalmology & Visual Science, vol. 53, 17 pages.

Notification of Transmittal of the International Search Report and the Written Opinion of the International Searching Authority, or the Declaration, Int'l Application No. PCT/US2020/40711, 17 pages.

Rudikoff et al., "Single Amino Acid Substitution Altering Antigen-Binding Specificity," Proceedings of the National Academy of Sciences, Naitonal Academy of Sciences, US., vol. 79, Mar. 1, 1982, pp. 1979-1983.

Feck e tal., "Protection of hDAF-Transgenic Porcine Endothelial Cells against Activation by Human Complement: Role of Membrane Attack Complex Introduction X," Xenotransplantation, vol. 9, Mar. 2002, pp. 97-105.

\* cited by examiner

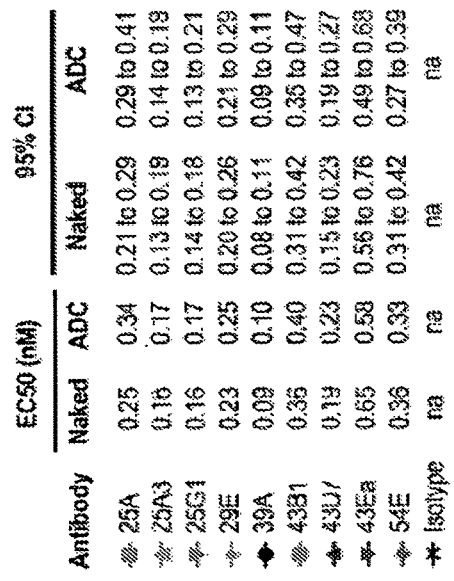
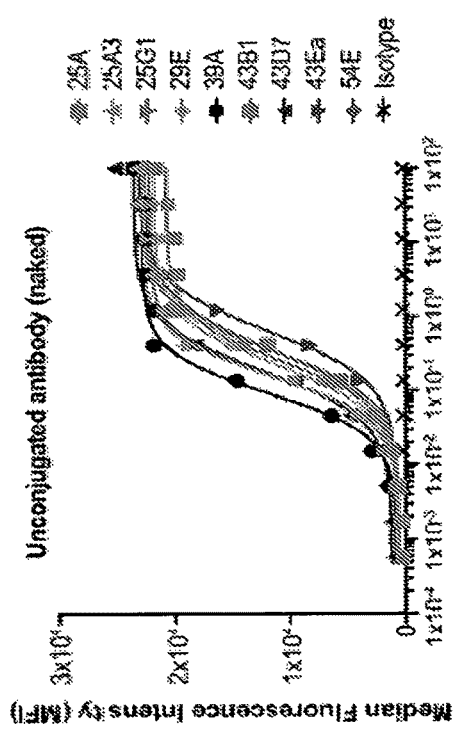
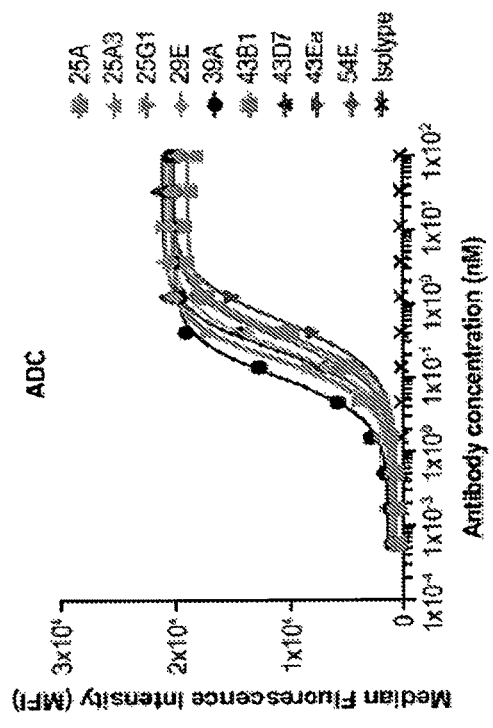

Figure 20A
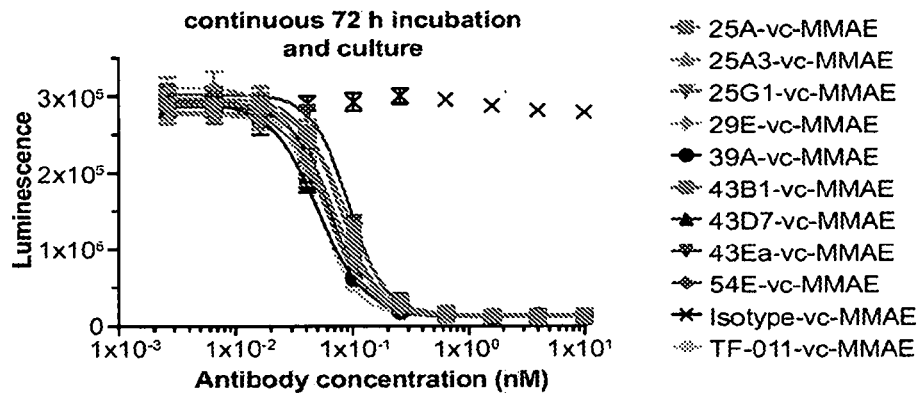
Figure 20B
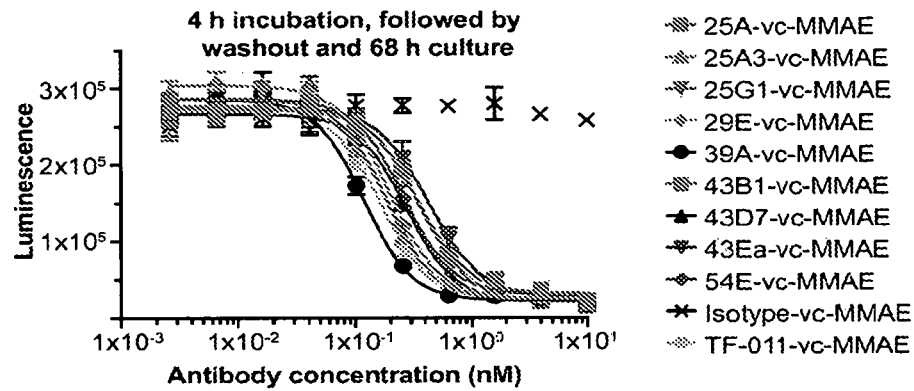
Figure 20C
|  | IC50 (nM) | |
| --- | --- | --- |
|  | Cont. | Washout |
| 25A-vc-MMAE | 0.09 | 0.35 |
| 25A3-vc-MMAE | 0.07 | 0.19 |
| 25G1-vc-MMAE | 0.06 | 0.19 |
| 29E-vc-MMAE | 0.06 | 0.20 |
| 39A-vc-MMAE | 0.05 | 0.12 |
| 43B1-vc-MMAE | 0.08 | 0.36 |
| 43D7-vc-MMAE | 0.06 | 0.28 |
| 43Ea-vc-MMAE | 0.09 | 0.43 |
| 54E-vc-MMAE | 0.07 | 0.26 |
| Isotype-vc-MMAE | na | na |
| TF-011-vc-MMAE | 0.05 | 0.17 |

Figure 21A
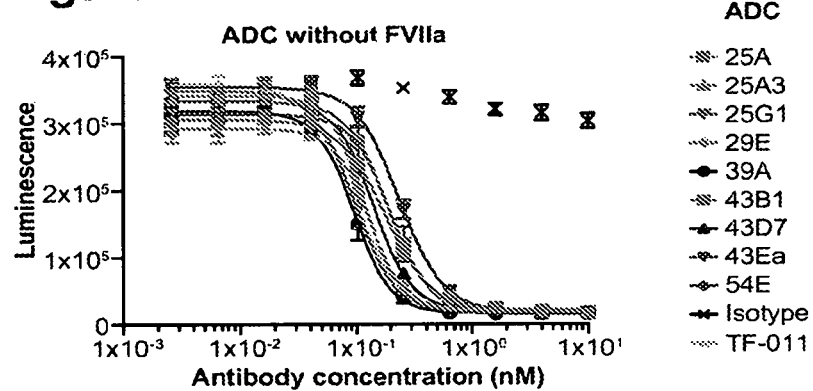
Figure 21B
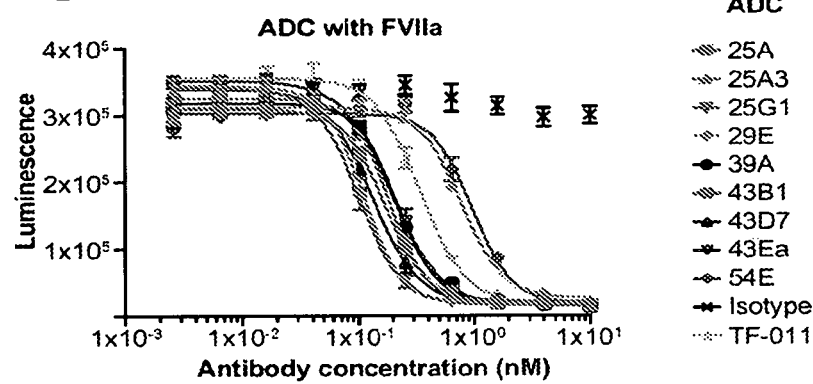
Figure 21C
| ADC | IC50 (nM) | |
| --- | --- | --- |
| | Without FVIIa | With FVIIa |
| 25A | 0.18 | 0.17 |
| 25A3 | 0.12 | 0.11 |
| 25G1 | 0.10 | 0.10 |
| 29E | 0.13 | 0.77 |
| 39A | 0.09 | 0.22 |
| 43B1 | 0.19 | 0.19 |
| 43D7 | 0.14 | 0.13 |
| 43Ea | 0.24 | 0.19 |
| 54E | 0.20 | 0.97 |
| Isotype | na | na |
| TF-011 | 0.09 | 0.34 |

Figure 22A
| Cell line | Copy number | SEM (n) |
|---|---|---|
| A431 | $1.9 \times 10^5$ | $4.7 \times 10^4$ (8) |
| CHO | BLOQ | BLOQ (2) |
| HCT-116 | $2.2 \times 10^4$ | $6.5 \times 10^3$ (6) |
| HPAF-II | $5.7 \times 10^5$ | $4.5 \times 10^4$ (8) |
| MDA-MB-231 | $3.2 \times 10^5$ | $2.7 \times 10^4$ (7) |
| RF/6A | $7.3 \times 10^4$ | $1.7 \times 10^4$ (4) |
Figure 22B
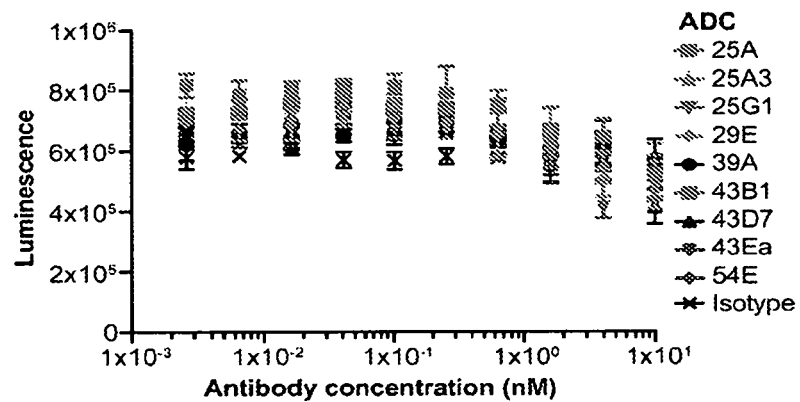
Figure 22C
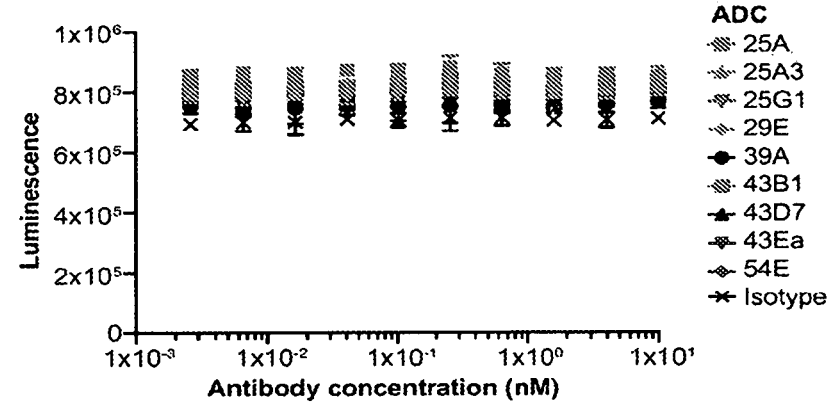

| Treatment | Donor number (#) | Copy # | SEM |
|---|---|---|---|
| no treatment | 6 | $2.4 \times 10^3$ | $4.2 \times 10^2$ |
| 3 h of cytokines | 5 | $8.7 \times 10^3$ | $7.7 \times 10^2$ |
| 6 h of cytokines | 5 | $1.2 \times 10^4$ | $8.5 \times 10^2$ |
| 20 h of cytokines | 2 | $4.6 \times 10^3$ | $2.9 \times 10^2$ |

Figure 29A
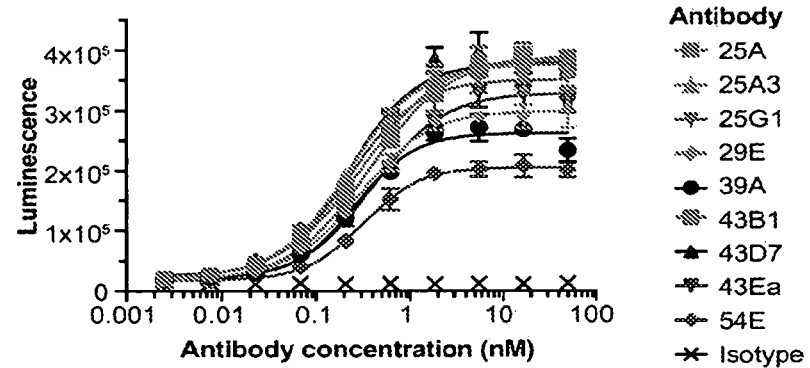
Figure 29B
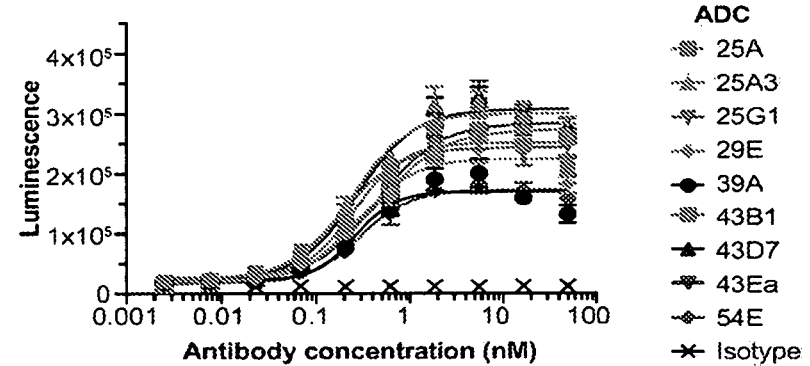
Figure 29C
| Antibody | EC50 (nM) Naked | ADC |
|---|---|---|
| 25A | 0.31 | 0.26 |
| 25A3 | 0.22 | 0.24 |
| 25G1 | 0.22 | 0.18 |
| 29E | 0.29 | 0.28 |
| 39A | 0.26 | 0.26 |
| 43B1 | 0.36 | 0.42 |
| 43D7 | 0.23 | 0.27 |
| 43Ea | 0.40 | 0.43 |
| 54E | 0.31 | 0.30 |
| Isotype | na | na |

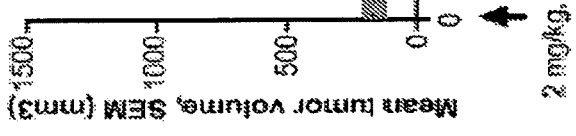
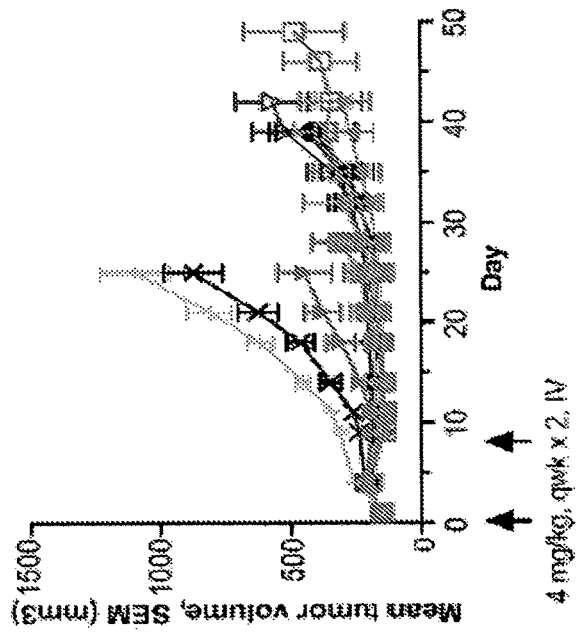
Figure 31A
Figure 31B

Figure 36

```
hTF (SEQ ID NO:810)        SGTTNTVAAYNLTWKSTNFKTILEWEPKPVNQVYTVQISTKSGDWKSKCFYTTDTECDLT  60
rTF (SEQ ID NO:838)        -AGTPPGKAFNLTWISTDFKTILEWQPKPTNYTYTVQISDRSRNWKYKCTGTTDTECDLT  60
h1-107_r (SEQ ID NO:839)   -AGTPPGKAFNLTWISTDFKTILEWQPKPTNYTYTVQISDRSRNWKYKCTGTTDTECDLT  60
h1-77_r (SEQ ID NO:840)    -AGTPPGKAFNLTWISTDFKTILEWQPKPTNYTYTVQISDRSRNWKYKCTGTTDTECDLT  60
h1-38_r (SEQ ID NO:841)    -AGTPPGKAFNLTWISTDFKTILEWQPKPTNYTYTVQISTKSGDWKSKCFYTTDTECDLT  60
h39-77_r (SEQ ID NO:842)   SGTTNTVAAYNLTWKSTNFKTILEWEPKPVNQVYTVQISDRSRNWKYKCTGTTDTECDLT  60
h78-107_r (SEQ ID NO:843)  SGTTNTVAAYNLTWKSTNFKTILEWEPKPVNQVYTVQISTKSGDWKSKCFYTTDTECDLT  60
h78-107_r.v2 (SEQ ID NO:844) SGTTNTVAAYNLTWKSTNFKTILEWEPKPVNQVYTVQISTKSGDWKSKCFYTTDTECDLT  60
h78-93_r (SEQ ID NO:845)   SGTTNTVAAYNLTWKSTNFKTILEWEPKPVNQVYTVQISTKSGDWKSKCFYTTDTECDLT  60
h94-107_r (SEQ ID NO:846)  SGTTNTVAAYNLTWKSTNFKTILEWEPKPVNQVYTVQISTKSGDWKSKCFYTTDTECDLT  60
h108-219_r (SEQ ID NO:847) SGTTNTVAAYNLTWKSTNFKTILEWEPKPVNQVYTVQISTKSGDWKSKCFYTTDTECDLT  60
h108-158_r (SEQ ID NO:848) SGTTNTVAAYNLTWKSTNFKTILEWEPKPVNQVYTVQISTKSGDWKSKCFYTTDTECDLT  60
h108-132_r (SEQ ID NO:849) SGTTNTVAAYNLTWKSTNFKTILEWEPKPVNQVYTVQISTKSGDWKSKCFYTTDTECDLT  60
h133-158_r (SEQ ID NO:850) SGTTNTVAAYNLTWKSTNFKTILEWEPKPVNQVYTVQISTKSGDWKSKCFYTTDTECDLT  60
h133-145_r (SEQ ID NO:851) SGTTNTVAAYNLTWKSTNFKTILEWEPKPVNQVYTVQISTKSGDWKSKCFYTTDTECDLT  60
h133-139_r (SEQ ID NO:852) SGTTNTVAAYNLTWKSTNFKTILEWEPKPVNQVYTVQISTKSGDWKSKCFYTTDTECDLT  60
h140-145_r (SEQ ID NO:853) SGTTNTVAAYNLTWKSTNFKTILEWEPKPVNQVYTVQISTKSGDWKSKCFYTTDTECDLT  60
h146-158_r (SEQ ID NO:854) SGTTNTVAAYNLTWKSTNFKTILEWEPKPVNQVYTVQISTKSGDWKSKCFYTTDTECDLT  60
h146-151_r (SEQ ID NO:855) SGTTNTVAAYNLTWKSTNFKTILEWEPKPVNQVYTVQISTKSGDWKSKCFYTTDTECDLT  60
h152-158_r (SEQ ID NO:856) SGTTNTVAAYNLTWKSTNFKTILEWEPKPVNQVYTVQISTKSGDWKSKCFYTTDTECDLT  60
h159-219_r (SEQ ID NO:857) SGTTNTVAAYNLTWKSTNFKTILEWEPKPVNQVYTVQISTKSGDWKSKCFYTTDTECDLT  60
h159-189_r (SEQ ID NO:859) SGTTNTVAAYNLTWKSTNFKTILEWEPKPVNQVYTVQISTKSGDWKSKCFYTTDTECDLT  60
h159-174_r (SEQ ID NO:859) SGTTNTVAAYNLTWKSTNFKTILEWEPKPVNQVYTVQISTKSGDWKSKCFYTTDTECDLT  60
h159-166_r (SEQ ID NO:860) SGTTNTVAAYNLTWKSTNFKTILEWEPKPVNQVYTVQISTKSGDWKSKCFYTTDTECDLT  60
h167-174_r (SEQ ID NO:861) SGTTNTVAAYNLTWKSTNFKTILEWEPKPVNQVYTVQISTKSGDWKSKCFYTTDTECDLT  60
h175-189_r (SEQ ID NO:862) SGTTNTVAAYNLTWKSTNFKTILEWEPKPVNQVYTVQISTKSGDWKSKCFYTTDTECDLT  60
h190-219_r (SEQ ID NO:863) SGTTNTVAAYNLTWKSTNFKTILEWEPKPVNQVYTVQISTKSGDWKSKCFYTTDTECDLT  60
                            *:*****.*******:***:******* ****:*******:*  .:** **********
```

Figure 36 (continued)

```
hTF     (SEQ ID NO:310)            DEIVKDVKQTYLARVFSYPAGNVEST----GSAGEPLYENSPEFTPYLETNLGQPTTIQ  114
rTF     (SEQ ID NO:838)            DEIVKDVNWTYEARVLSVPWRNSTHGKETLFGTHGEEPPFTNARKFLPYRDTKIGQPVIQ  114
h1-107_r  (SEQ ID NO:839)          DEIVKDVNWTYEARVLSVPWRNSTHGKETLFGTHGEEPPFTNARKFLPYRDTKLGQPTIQ  114
h1-77_r   (SEQ ID NO:840)          DEIVKDVNWTYEARVLSYPAGNVEST----GSAGEPLYENSPEFTPYLETNLGQPTIQ    114
h1-38_r   (SEQ ID NO:841)          DEIVKDVKQTYLARVFSYPAGNVEST----GSAGEPLYENSPEFTPYLETNLGQPTIQ    114
h39-77_r  (SEQ ID NO:842)          DEIVKDVNWTYEARVLSYPWRNSTHG----THGEEPPFTNARKFLPYRDTKLGQPTIQ    114
h78-107_r (SEQ ID NO:843)          DEIVKDVKQTYLARVFSVPWRNSTHGKETLFGTHGEEPPFTNARKFLPYRDTKLGQPTIQ  114
h78-107_r.v2 (SEQ ID NO:844)       DEIVKDVKQTYLARVFSVPWRNSTHGKETLFGTHGEEPPYENSPEFTPYLETNLGQPTIQ  114
h78-93_r  (SEQ ID NO:845)          DEIVKDVKQTYLARVFSYPAGNVEST----GSAGEPLFTNARKFLPYRDTKLGQPTIQ    114
h94-107_r (SEQ ID NO:846)          DEIVKDVKQTYLARVFSYPAGNVEST----GSAGEPLYENSPEFTPYLETNIGQPVIQ    114
h108-219_r (SEQ ID NO:847)         DEIVKDVKQTYLARVFSYPAGNVEST----GSAGEPLYENSPEFTPYLETNIGQPVIQ    114
h108-158_r (SEQ ID NO:848)         DEIVKDVKQTYLARVFSYPAGNVEST----GSAGEPLYENSPEFTPYLETNIGQPVIQ    114
h108-132_r (SEQ ID NO:849)         DEIVKDVKQTYLARVFSYPAGNVEST----GSAGEPLYENSPEFTPYLETNLGQPTIQ    114
h133-158_r (SEQ ID NO:850)         DEIVKDVKQTYLARVFSYPAGNVEST----GSAGEPLYENSPEFTPYLETNLGQPTIQ    114
h133-145_r (SEQ ID NO:851)         DEIVKDVKQTYLARVFSYPAGNVEST----GSAGEPLYENSPEFTPYLETNLGQPTIQ    114
h133-139_r (SEQ ID NO:852)         DEIVKDVKQTYLARVFSYPAGNVEST----GSAGEPLYENSPEFTPYLETNLGQPTIQ    114
h140-145_r (SEQ ID NO:853)         DEIVKDVKQTYLARVFSYPAGNVEST----GSAGEPLYENSPEFTPYLETNLGQPTIQ    114
h146-158_r (SEQ ID NO:854)         DEIVKDVKQTYLARVFSYPAGNVEST----GSAGEPLYENSPEFTPYLETNLGQPTIQ    114
h146-151_r (SEQ ID NO:855)         DEIVKDVKQTYLARVFSYPAGNVEST----GSAGEPLYENSPEFTPYLETNLGQPTIQ    114
h152-158_r (SEQ ID NO:856)         DEIVKDVKQTYLARVFSYPAGNVEST----GSAGEPLYENSPEFTPYLETNLGQPTIQ    114
h159-219_r (SEQ ID NO:857)         DEIVKDVKQTYLARVFSYPAGNVEST----GSAGEPLYENSPEFTPYLETNLGQPTIQ    114
h159-189_r (SEQ ID NO:858)         DEIVKDVKQTYLARVFSYPAGNVEST----GSAGEPLYENSPEFTPYLETNLGQPTIQ    114
h159-174_r (SEQ ID NO:859)         DEIVKDVKQTYLARVFSYPAGNVEST----GSAGEPLYENSPEFTPYLETNLGQPTIQ    114
h159-166_r (SEQ ID NO:860)         DEIVKDVKQTYLARVFSYPAGNVEST----GSAGEPLYENSPEFTPYLETNLGQPTIQ    114
h167-174_r (SEQ ID NO:861)         DEIVKDVKQTYLARVFSYPAGNVEST----GSAGEPLYENSPEFTPYLETNLGQPTIQ    114
h175-189_r (SEQ ID NO:862)         DEIVKDVKQTYLARVFSYPAGNVEST----GSAGEPLYENSPEFTPYLETNLGQPTIQ    114
h190-219_r (SEQ ID NO:863)         DEIVKDVKQTYLARVFSYPAGNVEST----GSAGEPLYENSPEFTPYLETNLGQPTIQ    114
                                   ********:** *****:            *    * *:  ** *:****:****
```

Figure 36 (continued)

```
hTF     (SEQ ID NO:810)           SFEQVGTKVNVTVEDERTLVRRNTFLSLRDVFGKDLIYTLYWKSSSSGKKTAKTNTNE  174
rTF     (SEQ ID NO:838)           KYEQGGTKLKVTVKDSFTLVRKNGTFLTLRQVFGNDLGYILTYRKDSSTGRKTNTTHTNE 174
h1-107_r   (SEQ ID NO:839)        SFEQVGTKVNVTVEDERTLVRRNTFLSLRDVFGKDLIYTLYWKSSSSGKKTAKTNTNE  174
h1-77_r    (SEQ ID NO:840)        SFEQVGTKVNVTVEDERTLVRRNTFLSLRDVFGKDLIYTLYWKSSSSGKKTAKTNTNE  174
h1-38_r    (SEQ ID NO:841)        SFEQVGTKVNVTVEDERTLVRRNTFLSLRDVFGKDLIYTLYWKSSSSGKKTAKTNTNE  174
h39-77_r   (SEQ ID NO:842)        SFEQVGTKVNVTVEDERTLVRRNTFLSLRDVFGKDLIYTLYWKSSSSGKKTAKTNTNE  174
h78-107_r  (SEQ ID NO:843)        SFEQVGTKVNVTVEDERTLVRRNTFLSLRDVFGKDLIYTLYWKSSSSGKKTAKTNTNE  174
h78-107_r.v2 (SEQ ID NO:844)      SFEQVGTKVNVTVEDERTLVRRNTFLSLRDVFGKDLIYTLYWKSSSSGKKTAKTNTNE  174
h78-93_r   (SEQ ID NO:845)        SFEQVGTKVNVTVEDERTLVRRNTFLSLRDVFGKDLIYTLYWKSSSSGKKTAKTNTNE  174
h94-107_r  (SEQ ID NO:846)        SFEQVGTKVNVTVEDERTLVRRNTFLSLRDVFGKDLIYTLYWKSSSSGKKTAKTNTNE  174
h108-219_r (SEQ ID NO:847)        KYEQGGTKLKVTVKDSFTLVRKNGTFLTLRQVFGNDLGYILTYRKSSSSGKKTAKTNTNE 174
h108-158_r (SEQ ID NO:848)        KYEQGGTKLKVTVKDSFTLVRKNGTFLTLRQVFGNDLGYILTYRKSSSSGKKTAKTNTNE 174
h108-132_r (SEQ ID NO:849)        KYEQGGTKLKVTVKDSFTLVRKNGTFLTLRQVFGNDLGYILTYRKSSSSGKKTAKTNTNE 174
h133-158_r (SEQ ID NO:850)        SFEQVGTKVNVTVEDERTLVRKNGTFLTLRQVFGNDLGYILTYRKSSSSGKKTAKTNTNE 174
h133-145_r (SEQ ID NO:851)        SFEQVGTKVNVTVEDERTLVRKNGTFLTLRQVFGNDLGYILTYRKSSSSGKKTAKTNTNE 174
h133-139_r (SEQ ID NO:852)        SFEQVGTKVNVTVEDERTLVRKNGTFLTLRQVFGNDLGYILTYRKSSSSGKKTAKTNTNE 174
h140-145_r (SEQ ID NO:853)        SFEQVGTKVNVTVEDERTLVRRNTFLTLRQVFGNDLGYILTYRKSSSSGKKTAKTNTNE 174
h146-158_r (SEQ ID NO:854)        SFEQVGTKVNVTVEDERTLVRRNTFLSLRDVFGKDLGYILTYRKSSSSGKKTAKTNTNE 174
h146-151_r (SEQ ID NO:855)        SFEQVGTKVNVTVEDERTLVRRNTFLSLRDVFGKDLGYILTYRKSSSSGKKTAKTNTNE 174
h152-158_r (SEQ ID NO:856)        SFEQVGTKVNVTVEDERTLVRRNTFLSLRDVFGKDLGYILTYRKSSSSGKKTAKTNTNE 174
h159-219_r (SEQ ID NO:857)        SFEQVGTKVNVTVEDERTLVRRNTFLSLRDVFGKDLIYTLYWKDSSTGRKTNTTHTNE  174
h159-189_r (SEQ ID NO:858)        SFEQVGTKVNVTVEDERTLVRRNTFLSLRDVFGKDLIYTLYWKDSSTGRKTNTTHTNE  174
h159-174_r (SEQ ID NO:859)        SFEQVGTKVNVTVEDERTLVRRNTFLSLRDVFGKDLIYTLYWKDSSTGRKTNTTHTNE  174
h159-166_r (SEQ ID NO:860)        SFEQVGTKVNVTVEDERTLVRRNTFLSLRDVFGKDLIYTLYWKDSSTGRKTNTTHTNE  174
h167-174_r (SEQ ID NO:861)        SFEQVGTKVNVTVEDERTLVRRNTFLSLRDVFGKDLIYTLYWKSSSSGKKTAKTNTNE  174
h175-189_r (SEQ ID NO:862)        SFEQVGTKVNVTVEDERTLVRRNTFLSLRDVFGKDLIYTLYWKSSSSGKKTAKTNTNE  174
h190-219_r (SEQ ID NO:863)        SFEQVGTKVNVTVEDERTLVRRNTFLSLRDVFGKDLIYTLYWKSSSSGKKTAKTNTNE  174
                                  :** .*** :******* *******.***:****.***  **:***:.*  *:**
```

Figure 36 (continued)

```
hTF     (SEQ ID NO:810)              FLIDVDKGENYCFSVQAVIPSRTVNRKSTDSPVECMGQEKGEFRE      219
rTF     (SEQ ID NO:838)              FLIDVEKGVSYCFFAQAVIPSRTVNRKTNHKSPESITKCTEQWKSVLGE  219
h1-107_r (SEQ ID NO:839)             FLIDVDKGENYCFSVQAVIPSRTVNRKSTDSPVECMGQEKGEFRE      219
h1-77_r  (SEQ ID NO:840)             FLIDVDKGENYCFSVQAVIPSRTVNRKSTDSPVECMGQEKGEFRE      219
h1-38_r  (SEQ ID NO:841)             FLIDVDKGENYCFSVQAVIPSRTVNRKSTDSPVECMGQEKGEFRE      219
h39-77_r (SEQ ID NO:842)             FLIDVDKGENYCFSVQAVIPSRTVNRKSTDSPVECMGQEKGEFRE      219
h78-107_r (SEQ ID NO:843)            FLIDVDKGENYCFSVQAVIPSRTVNRKSTDSPVECMGQEKGEFRE      219
h78-107_r.v2 (SEQ ID NO:844)         FLIDVDKGENYCFSVQAVIPSRTVNRKSTDSPVECMGQEKGEFRE      219
h78-93_r  (SEQ ID NO:845)            FLIDVDKGENYCFSVQAVIPSRTVNRKSTDSPVECMGQEKGEFRE      219
h94-107_r (SEQ ID NO:846)            FLIDVDKGENYCFSVQAVIPSRTVNRKSTDSPVECMGQEKGEFRE      219
h108-219_r (SEQ ID NO:847)           FLIDVEKGVSYCFFAQAVIPSRTVNRKTNHKSPESITKCTEQWKSVLGE  219
h108-158_r (SEQ ID NO:848)           FLIDVDKGENYCFSVQAVIPSRTVNRKSTDSPVECMGQEKGEFRE      219
h108-132_r (SEQ ID NO:849)           FLIDVDKGENYCFSVQAVIPSRTVNRKSTDSPVECMGQEKGEFRE      219
h133-158_r (SEQ ID NO:850)           FLIDVDKGENYCFSVQAVIPSRTVNRKSTDSPVECMGQEKGEFRE      219
h133-145_r (SEQ ID NO:851)           FLIDVDKGENYCFSVQAVIPSRTVNRKSTDSPVECMGQEKGEFRE      219
h133-139_r (SEQ ID NO:852)           FLIDVDKGENYCFSVQAVIPSRTVNRKSTDSPVECMGQEKGEFRE      219
h140-145_r (SEQ ID NO:853)           FLIDVDKGENYCFSVQAVIPSRTVNRKSTDSPVECMGQEKGEFRE      219
h146-158_r (SEQ ID NO:854)           FLIDVDKGENYCFSVQAVIPSRTVNRKSTDSPVECMGQEKGEFRE      219
h146-151_r (SEQ ID NO:855)           FLIDVDKGENYCFSVQAVIPSRTVNRKSTDSPVECMGQEKGEFRE      219
h152-158_r (SEQ ID NO:856)           FLIDVDKGENYCFSVQAVIPSRTVNRKSTDSPVECMGQEKGEFRE      219
h159-219_r (SEQ ID NO:857)           FLIDVEKGVSYCFFAQAVIPSRTVNRKTNHKSPESITKCTEQWKSVLGE  219
h159-189_r (SEQ ID NO:858)           FLIDVDKGENYCFSVQAVIPSRTVNRKSTDSPVECMGQEKGEFRE      219
h159-174_r (SEQ ID NO:859)           FLIDVDKGENYCFSVQAVIPSRTVNRKSTDSPVECMGQEKGEFRE      219
h159-166_r (SEQ ID NO:860)           FLIDVDKGENYCFSVQAVIPSRTVNRKSTDSPVECMGQEKGEFRE      219
h167-174_r (SEQ ID NO:861)           FLIDVDKGENYCFSVQAVIPSRTVNRKSTDSPVECMGQEKGEFRE      219
h175-189_r (SEQ ID NO:862)           FLIDVEKGVSYCFFAQAVIPSRTVNRKTNHKSPESITKCTEQWKSVLGE  219
h190-219_r (SEQ ID NO:863)           FLIDVDKGENYCFSVQAVIPSRTVNRKSTDSPVECMGQEKGEFRE      219
                                     *****:******** *.***********.:.*** *:***:***:     
```

Figure 37

```
rTF     (SEQ ID NO:838)  -AGTPPGKAFNETWISTDFKTILEWQPKPTNYTYTVQISDRSRNWKYKCTGTTDTECDLT 59
hTF     (SEQ ID NO:810)  SGTTNTVAAYNLITWKSTNFKTILEWEPKPVNQVYTVQISTKSGDWKSKCFYTTDTECDLT 59
r141-194_h (SEQ ID NO:864) -AGTPPGKAFNETWISTDFKTILEWQPKPTNYTYTVQISDRSRNWKYKCTGTTDTECDLT 59
                          .*  *:**.****:.*.********  :*    ******** rTF     (SEQ ID NO:838)  DEIVKDVNWTYEARVLSVFWRNSTHGKETLFGTHGEEPPFTNARKFLPYRDTKIGQPVIQ 119
hTF     (SEQ ID NO:810)  DEIVKDVKQTYLARVFSYPAGNVEST-----GSAGEPLYENSPEFTPYLETNLGQPTIQ 119
r141-194_h (SEQ ID NO:864) DEIVKDVNWTYEARVLSVFWRNSTHGKETLFGTHGEEPPFTNARKFLPYRDTKIGQPVIQ 119
                          *****:  ***:*  :.:*          :  *:: * rTF     (SEQ ID NO:838)  KYEQGGTKLKVTVKDSFTIVRKNGTFLITRQVFGNDIGYILTYRKDSSTGRKTNTHTNE 179
hTF     (SEQ ID NO:810)  SFEQVGTKVNVTVEDERTLVRRNNTFLSLRDVFGKDLIYTLYYWKSSSSGKKTAKTNTNE 179
r141-194_h (SEQ ID NO:864) KYEQGGTKLKVTVKDSFTIVRKNGTFLITRQVFGNDIGYILTYRKDSSTGRKTNTHTNE 179
                          .: *::***::  *: *::* ** :*:***:*: * * *:.:*.. *:*: *** rTF     (SEQ ID NO:838)  FLIDVEKGVSYCFFAQAVIFSRKTNHKSPESITKCTEQWKSVLGE 224
hTF     (SEQ ID NO:810)  FLIDVDKGENYCFSVQAVIPSRTVNRKSTDSPVECMGQEKGEFRE 225
r141-194_h (SEQ ID NO:864) FLIDVDKGENYCFSVQAVIFSRKTNHKSPESITKCTEQWKSVLGE 224
                          *****:**  ***  .*** **  *:**. :* *  **: * *
```

Figure 38

```
hTF              (SEQ ID NO:810)    SGTTNTVAAYNLIWKSTNFKTILEWEPKPVNQVYTVQISTKSGDWKSKCFYTTDTECDLT     60
rTF              (SEQ ID NO:838)    -AGTPPGKAFNLIWISTDFKTILEWQPKPTNYTYTVQISDRSRNWKYKCTGTTDTECDLT     60
hTF_K68N         (SEQ ID NO:865)    SGTTNTVAAYNLIWKSTNFKTILEWEPKPVNQVYTVQISTKSGDWKSKCFYTTDTECDLT     60
hTF_K149N        (SEQ ID NO:866)    SGTTNTVAAYNLIWKSTNFKTILEWEPKPVNQVYTVQISTKSGDWKSKCFYTTDTECDLT     60
hTF_N171H_T197K  (SEQ ID NO:867)    SGTTNTVAAYNLIWKSTNFKTILEWEPKPVNQVYTVQISTKSGDWKSKCFYTTDTECDLT     60
                                      * *:**.:*******:::*****.* . ******** hTF              (SEQ ID NO:810)    DEIVKDVKQTYLARVFSYPAGNVEST------GSAGEPLYENSPEFTPYLETNLGQPTIQ    114
rTF              (SEQ ID NO:838)    DEIVKDVNWTYEARVLSVPWRNSTHGKETLFGTHGEEPFFTNARKFLPYRDTKIGQPVIQ    114
hTF_K68N         (SEQ ID NO:865)    DEIVKDVNQTYLARVFSYPAGNVEST------GSAGEPLYENSPEFTPYLETNLGQPTIQ    114
hTF_K149N        (SEQ ID NO:866)    DEIVKDVKQTYLARVFSYPAGNVEST------GSAGEPLYENSPEFTPYLETNLGQPTIQ    114
hTF_N171H_T197K  (SEQ ID NO:867)    DEIVKDVKQTYLARVFSYPAGNVEST------GSAGEPLYENSPEFTPYLETNLGQPTIQ    114
                                    *******: **.***:*.*..*.*       ..* :* :.*:.  **  * .**:**

hTF              (SEQ ID NO:810)    SFEQVGTKVNVTVEDERTLVRRNTFLSLRDVFGKDLIYTLYYWKSSSSGKKTAKTNTNE    174
rTF              (SEQ ID NO:838)    KYEQGGTKLKVTVKDSFTLVRKNGTFLTLRQVFGNDLGYILTYRKDSSTGRKTNTHTNE    174
hTF_K68N         (SEQ ID NO:865)    SFEQVGTKVNVTVEDERTLVRRNTFLSLRDVFGKDLIYTLYYWKSSSSGKKTAKTNTNE    174
hTF_K149N        (SEQ ID NO:866)    SFEQVGTKVNVTVEDERTLVRRNGFLSLRDVFGNDLIYTLYYWKSSSSGKKIAKTNTNE    174
hTF_N171H_T197K  (SEQ ID NO:867)    SFEQVGTKVNVTVEDERTLVRRNTFLSLRDVFGKDLIYTLYYWKSSSSGKKTAKTHTNE    174
                                     : *:.**:*.*:*****.* ::*: * * * :*:: * hTF              (SEQ ID NO:810)    FLIDVDKGENYCFSVQAVIPSRTVNRKSTDSPVECMGQEKGEFRE                219
rTF              (SEQ ID NO:838)    FLIDVEKGVSYCFFAQAVIFSRKTNHKSPESITKCTEQWKSVLGE                219
hTF_K68N         (SEQ ID NO:865)    FLIDVDKGENYCFSVQAVIPSRTVNRKSTDSPVECMGQEKGEFRE                219
hTF_K149N        (SEQ ID NO:866)    FLIDVDKGENYCFSVQAVIPSRTVNRKSTDSPVECMGQEKGEFRE                219
hTF_N171H_T197K  (SEQ ID NO:867)    FLIDVDKGENYCFSVQAVIPSRKVNRKSTDSPVECMGQEKGEFRE                219
                                    *****:** .***. *:***.*:.*:*:.*. *:* *:*.. *
```

ANTI-TISSUE FACTOR ANTIBODIES, ANTIBODY-DRUG CONJUGATES, AND RELATED METHODS

CROSS REFERENCE TO RELATED APPLICATIONS

This application is a continuation of U.S. application Ser. No. 16/959,652, filed Jul. 1, 2020, which is a U.S. National Phase Application of International Application No. PCT/US2019/012427, filed Jan. 4, 2019, which claims the benefit of U.S. Provisional Application Nos. 62/613,545, filed Jan. 4, 2018; 62/613,564, filed Jan. 4, 2018; 62/646,788, filed Mar. 22, 2018; 62/713,797, filed Aug. 2, 2018; and 62/713,804, filed Aug. 2, 2018, each of which is hereby incorporated by reference in its entirety.

SEQUENCE LISTING

The instant application contains a Sequence Listing which has been submitted via EFS-Web and is hereby incorporated by reference in its entirety. Said ASCII copy, created on Aug. 26, 2021, is named ITI-001USC1_Sequence-Listing.txt, and is 383,046 bytes in size.

BACKGROUND

Blood coagulation involves a complex set of processes that result in blood clotting. Tissue factor (TF) plays an important role in these coagulation processes. TF is a cell surface receptor for the serine protease factor VIIa (FVIIa). The TF/FVIIa complex catalyzes conversion of the inactive protease factor X (FX) into the active protease factor Xa (FXa). FXa and its co-factor FVa form the prothrombinase complex, which generates thrombin from prothrombin. Thrombin converts soluble fibrinogen into insoluble strands of fibrin and catalyzes many other coagulation-related processes.

TF is over-expressed on multiple types of solid tumors. In cancer, TF/FVIIa signaling can support angiogenesis, tumor progression, and metastasis. Increased TF expression can also induce inflammation and/or angiogenesis in many other diseases, including wet age-related macular degeneration (AMD) and diabetic retinopathy.

SUMMARY

Provided herein are antibodies that specifically bind human Tissue Factor (TF), anti-TF antibody-drug conjugates, and related methods.

In one aspect, provided herein is an isolated human antibody which binds to the extracellular domain of human Tissue Factor (TF), wherein the antibody binds human TF at a human TF binding site that is distinct from a human TF binding site bound by human FVIIa.

In some embodiments, (1) the isolated antibody does not inhibit human thrombin generation as determined by thrombin generation assay (TGA) compared to a reference antibody comprising a $V_H$ sequence of SEQ ID NO:821 and a $V_L$ sequence of SEQ ID NO: 822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO: 822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody allows human thrombin generation to a greater extent as determined by thrombin generation assay (TGA) compared to a reference antibody comprising a $V_H$ sequence of SEQ ID NO:821 and a $V_L$ sequence of SEQ ID NO: 822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody allows human thrombin generation by a greater amount as determined by thrombin generation assay (TGA) compared to a reference antibody comprising a $V_H$ sequence of SEQ ID NO:821 and a $V_L$ sequence of SEQ ID NO: 822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784.

In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the isolated antibody does not inhibit human thrombin generation as determined by thrombin generation assay (TGA) compared to a reference antibody comprising a $V_H$ sequence of SEQ ID NO:821 and a $V_L$ sequence of SEQ ID NO: 822.

In some embodiments, the isolated antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO: 822.

In some embodiments, the isolated antibody allows human thrombin generation to a greater extent as determined by thrombin generation assay (TGA) compared to a reference antibody comprising a $V_H$ sequence of SEQ ID NO:821 and a $V_L$ sequence of SEQ ID NO: 822.

In some embodiments, the isolated antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO: 822.

In some embodiments, the isolated antibody allows human thrombin generation by a greater amount as determined by thrombin generation assay (TGA) compared to a reference antibody comprising a $V_H$ sequence of SEQ ID NO:821 and a $V_L$ sequence of SEQ ID NO: 822.

In some embodiments, the antibody does not inhibit human thrombin generation as determined by thrombin generation assay (TGA). In some embodiments, the antibody does not reduce the thrombin peak on a thrombin generation curve (Peak IIa) compared to an isotype control. In some embodiments, the antibody does not increase the time from the assay start to the thrombin peak on a thrombin generation curve (ttPeak) compared to an isotype control. In some embodiments, the antibody does not decrease the endogenous thrombin potential (ETP) as determined by the area under a thrombin generation curve compared to an isotype control. In some embodiments, the antibody allows human thrombin generation as determined by thrombin generation assay (TGA). In some embodiments, the antibody maintains the thrombin peak on a thrombin generation curve (Peak IIa) compared to an isotype control. In some embodiments, the antibody maintains the time from the assay start to the thrombin peak on a thrombin generation curve (ttPeak) compared to an isotype control. In some embodiments, the antibody preserves the endogenous thrombin potential (ETP) as determined by the area under a thrombin generation curve compared to an isotype control.

In some embodiments, the antibody binds human TF at a human TF binding site that is distinct from a human TF binding site bound by human FX. In some embodiments, the antibody does not interfere with the ability of TF:FVIIa to convert FX into FXa.

In some embodiments, the antibody does not compete for binding to human TF with human FVIIa.

In some embodiments, the antibody does not inhibit human thrombin generation as determined by thrombin generation assay (TGA), allows human thrombin generation as determined by thrombin generation assay (TGA), binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not decrease the endogenous thrombin potential (ETP) as determined by the area under a thrombin generation curve compared to an isotype control, allows human thrombin generation as determined by thrombin generation assay (TGA), preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not reduce the thrombin peak on a thrombin generation curve (Peak IIa) compared to an isotype control, does not increase the time from the assay start to the thrombin peak on a thrombin generation curve (ttPeak) compared to an isotype control, does not decrease the endogenous thrombin potential (ETP) as determined by the area under a thrombin generation curve compared to an isotype control, allows human thrombin generation as determined by thrombin generation assay (TGA), maintains the thrombin peak on a thrombin generation curve (Peak IIa) compared to an isotype control, maintains the time from the assay start to the thrombin peak on a thrombin generation curve (ttPeak) compared to an isotype control, preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody inhibits FVIIa-dependent TF signaling.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutation at amino acid residue 149 of the sequence shown in SEQ ID NO:810 is K149N.

In some embodiments, the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutation at amino acid residue 68 of the sequence shown in SEQ ID NO:810 is K68N.

In some embodiments, the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutations at amino acid residues 171 and 197 of the sequence shown in SEQ ID NO:810 are N171H and T197K.

In some embodiments, the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810; the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810; the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810; and the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO:810 is K68N.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810; the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810; the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810; the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810; and the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; the mutation at amino acid residue 68 of the sequence shown in SEQ ID NO:810 is K68N; and the mutations at amino acid residues 171 and 197 of the sequence shown in SEQ ID NO:810 are N171H and T197K.

In some embodiments, the antibody binds to cynomolgus TF. In some embodiments, the antibody binds to mouse TF. In some embodiments, the antibody binds to rabbit TF. In some embodiments, the antibody binds to pig TF.

In some embodiments, the antibody reduces lesion size in a swine choroidal neovascularization (CNV) model.

In some embodiments, the antibody: (a) does not inhibit human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) allows human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; and (i) binds to rabbit TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; and (k) binds to rabbit TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; and (o) binds to rabbit TF.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; (i) binds to rabbit TF; (j) binds to pig TF; and (k) reduces lesion size in a swine choroidal neovascularization (CNV) model.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; (k) binds to rabbit TF; (l) binds to pig TF; and (m) reduces lesion size in a swine choroidal neovascularization (CNV) model.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; and (q) reduces lesion size in a swine choroidal neovascularization (CNV) model.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) reduces lesion size in a swine choroidal neovascularization (CNV) model; (r) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (s) the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (t) the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (u) the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (v) the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (w) the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (x) the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (y) the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (z) the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (aa) the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (bb) the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; and (cc) wherein the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) reduces lesion size in a swine choroidal neovascularization (CNV) model; (r) the binding between the isolated antibody and a variant TF extracellular domain comprising a mutation K149N of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (s) the binding between the isolated antibody and a variant TF extracellular domain comprising a mutation K68N of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (t) the binding between the isolated antibody and a variant TF extracellular domain comprising mutations N171H and T197K of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (u) the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (v) the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (w) the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (x) the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (y) the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (z) the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (aa) the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (bb) the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; and (cc) wherein the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody competes for binding to human TF with the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody competes for binding to human TF with the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody competes for binding to human TF with the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody binds to the same human TF epitope bound by the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the three heavy chain CDRs and the three light chain CDRs are determined using Kabat, Chothia, AbM, Contact, or IMGT numbering.

In some embodiments, the antibody comprises all three heavy chain Complementary Determining Regions (CDRs) and all three light chain CDRs from: the antibody designated 25A, the antibody designated 25A5-T, the antibody designated 25A3, the antibody designated 25A5, the antibody designated 25G, the antibody designated 25G1, or the antibody designated 25G9.

In some embodiments, the antibody comprises all three heavy chain Complementary Determining Regions (CDRs) and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G. In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9. In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7. In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO:113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence set forth in SEQ ID NO:801; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25 G9.

In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, or the antibody designated 25 G9.

In some embodiments, the antibody consists of: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an isolated antibody comprising all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody is human, humanized, or chimeric.

In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G. In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9.

In some embodiments, the antibody comprises all three heavy chain CDRs and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7. In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO:113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence set forth in SEQ ID NO:801; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25 G9.

In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists: the antibody designated 25A, the antibody designated 25A3, the antibody designated 25A5, the antibody designated 25A5-T, the antibody designated 25G, the antibody designated 25G1, or the antibody designated 25 G9.

In some embodiments, the antibody consists: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an isolated antibody that competes for binding to human TF with: the antibody designated 1F, the antibody designated 1G, the antibody designated 29D, the antibody designated 29E, the antibody designated 39A, or the antibody designated 54E.

In some embodiments, the antibody is human, humanized, or chimeric.

In some embodiments, the antibody inhibits FVIIa-dependent TF signaling.

In some embodiments, the antibody binds to cynomolgus TF.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; and the binding between the isolated antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the isolated antibody and the extracellular domain of TF of the sequence shown in SEQ ID NO:810; and wherein the binding between the isolated antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody comprises all three heavy chain Complementary Determining Regions (CDRs) and all three light chain CDRs from: the antibody designated 1F, the antibody designated 1G, the antibody designated 29D, the antibody designated 29E, the antibody designated 39A, the antibody designated 43Ea, or the antibody designated 54E. In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from the antibody designated 1F. In some embodiments, the antibody comprises all three heavy chain CDRs and all three light chain CDRs from the antibody designated 1G. In some embodiments, the antibody comprises all three heavy chain CDRs and all three light chain CDRs from the antibody designated 29D. In some embodiments, the antibody comprises all three heavy chain CDRs and all three light chain CDRs from the antibody designated 29E. In some embodiments, the antibody comprises all three heavy chain CDRs and all three light chain CDRs from the antibody designated 39A. In some embodiments, the antibody comprises all three heavy chain CDRs and all three light chain CDRs from the antibody designated 54E.

In some embodiments, the antibody comprises a $V_H$ sequence of SEQ ID NO:37 and a $V_L$ sequence of SEQ ID NO:38. In some embodiments, the antibody comprises a $V_H$ sequence of SEQ ID NO:75 and a $V_L$ sequence of SEQ ID NO:76. In some embodiments, the antibody comprises a $V_H$ sequence of SEQ ID NO:341 and a $V_L$ sequence of SEQ ID NO:342. In some embodiments, the antibody comprises a $V_H$ sequence of SEQ ID NO:379 and a $V_L$ sequence of SEQ ID NO:380. In some embodiments, the antibody comprises a $V_H$ sequence of SEQ ID NO:417 and a $V_L$ sequence of SEQ ID NO:418. In some embodiments, the antibody comprises a $V_H$ sequence of SEQ ID NO:759 and a $V_L$ sequence of SEQ ID NO:760.

In some embodiments, the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778. In some embodiments, the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790. In some embodiments, the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796. In some embodiments, the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In some embodiments, the antibody comprises a $V_H$ sequence of SEQ ID NO:761 and a $V_L$ sequence of SEQ ID NO:762. In some embodiments, the antibody comprises a $V_H$ sequence of SEQ ID NO:765 and a $V_L$ sequence of SEQ ID NO:766. In some embodiments, the antibody comprises a $V_H$ sequence of SEQ ID NO:767 and a $V_L$ sequence of SEQ ID NO:768. In some embodiments, the antibody comprises a $V_H$ sequence of SEQ ID NO:771 and a $V_L$ sequence of SEQ ID NO:772.

In some embodiments, the antibody comprises: the antibody designated 1F, the antibody designated 1G, the antibody designated 29D, the antibody designated 29E, the antibody designated 39A, or the antibody designated 54E.

In some embodiments, the antibody consists of: the antibody designated 1F, the antibody designated 1G, the antibody designated 29D, the antibody designated 29E, the antibody designated 39A, or the antibody designated 54E.

In another aspect, provided herein is an isolated antibody comprising: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778.

In another aspect, provided herein is an isolated antibody comprising: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784.

In another aspect, provided herein is an isolated antibody comprising: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790.

In another aspect, provided herein is an isolated antibody comprising: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796.

In another aspect, provided herein is an isolated antibody comprising: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence set forth in SEQ ID NO:801; and a VL-CDR3 comprising the sequence set forth in SEQ ID NO:802.

In another aspect, provided herein is an isolated antibody comprising: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In another aspect, provided herein is an isolated antibody comprising: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In another aspect, provided herein is an isolated antibody comprising: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody binds to human TF with a $K_D$ of less than or equal to 50 nM, 10 nM, 5 nM, 1 nM, 0.5 nM or 0.1 nM, as measured by Octet QK384 or Biacore assay.

In some embodiments, the antibody is a monoclonal antibody.

In some embodiments, the antibody is multispecific.

In some embodiments, the antibody is a Fab, Fab', F(ab')$_2$, Fv, scFv, (scFv)$_2$, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1.

In some embodiments, the Fc comprises one or more modifications, wherein the one or more modifications result in increased half-life, increased antibody-dependent cellular cytotoxicity (ADCC), increased antibody-dependent cellular phagocytosis (ADCP), increased complement-dependent cytotoxicity (CDC), or decreased effector function, compared with the Fc without the one or more modifications.

In another aspect, provided herein is an isolated antibody that competes for binding to human TF with any antibody above.

In another aspect, provided herein is an isolated antibody that binds the human TF epitope bound by any antibody above.

In another aspect, provided herein is an isolated polynucleotide or set of polynucleotides encoding any antibody above, a $V_H$ thereof, a $V_L$ thereof, a light chain thereof, a heavy chain thereof, or an antigen-binding portion thereof.

In another aspect, provided herein is a vector or set of vectors comprising the polynucleotide or set of polynucleotides above.

In another aspect, provided herein is a host cell comprising the polynucleotide or set of polynucleotides above or the vector or set of vectors above.

In another aspect, provided herein is a method of producing an antibody comprising expressing the antibody with the host cell above and isolating the expressed antibody.

In another aspect, provided herein is a pharmaceutical composition comprising any antibody above and a pharmaceutically acceptable excipient.

In another aspect, provided herein is a method of treating or preventing a disease or condition in a subject in need thereof, comprising administering to the subject an effective amount of any antibody above or the pharmaceutical composition above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In some embodiments, the method further comprises administering one or more additional therapeutic agents to the subject. In some embodiments, the additional therapeutic agent is formulated in the same pharmaceutical composition as the antibody. In some embodiments, the additional therapeutic agent is formulated in a different pharmaceutical composition from the antibody. In some embodiments, the additional therapeutic agent is administered prior to administering the antibody. In some embodiments, the additional therapeutic agent is administered after administering the antibody. In some embodiments, the additional therapeutic agent is administered contemporaneously with the antibody.

In another aspect, provided herein is a method of detecting TF in a subject having or suspected of having a disease or condition, the method comprising: (a) receiving a sample from the subject; and (b) detecting the presence or the level of TF in the sample by contacting the sample with any antibody above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In another aspect, provided herein is a method of detecting TF in a subject having or suspected of having a disease or condition, the method comprising: (a) administering to the subject any antibody above; and (b) detecting the presence or the level of TF in the subject.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In another aspect, provided herein is a kit comprising any antibody above or the pharmaceutical composition above and instructions for use.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody binds to the extracellular domain of human Tissue Factor (TF) at a human TF binding site that is distinct from a human TF binding site bound by human FVIIa.

In some embodiments, (1) the antibody does not inhibit human thrombin generation as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody allows human thrombin generation to a greater extent as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody allows human thrombin generation by a greater amount as determined by thrombin generation assay (TGA) compared to a reference antibody comprising a $V_H$ sequence of SEQ ID NO:821 and a $V_L$ sequence of SEQ ID NO: 822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784.

In some embodiments, the antibody comprises: a VH-CDR1 comprising the sequence set forth in SEQ ID NO:872; a VH-CDR2 HI comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody does not inhibit human thrombin generation as determined by thrombin generation assay (TGA) compared to a reference antibody comprising a $V_H$ sequence of SEQ ID NO:821 and a $V_L$ sequence of SEQ ID NO:822.

In some embodiments, the antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO: 822.

In some embodiments, the antibody allows human thrombin generation to a greater extent as determined by thrombin generation assay (TGA) compared to a reference antibody comprising a $V_H$ sequence of SEQ ID NO:821 and a $V_L$ sequence of SEQ ID NO: 822.

In some embodiments, the antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO: 822.

In some embodiments, the antibody allows human thrombin generation by a greater amount as determined by thrombin generation assay (TGA) compared to a reference antibody comprising a $V_H$ sequence of SEQ ID NO:821 and a $V_L$ sequence of SEQ ID NO: 822.

In some embodiments, the antibody does not inhibit human thrombin generation as determined by thrombin generation assay (TGA). In some embodiments, the antibody does not reduce the thrombin peak on a thrombin generation curve (Peak IIa) compared to an isotype control. In some embodiments, the antibody does not increase the time from the assay start to the thrombin peak on a thrombin generation curve (ttPeak) compared to an isotype control. In some embodiments, the antibody does not decrease the endogenous thrombin potential (ETP) as determined by the area under a thrombin generation curve compared to an isotype control. In some embodiments, the antibody allows human thrombin generation as determined by thrombin generation assay (TGA). In some embodiments, the antibody maintains the thrombin peak on a thrombin generation curve (Peak IIa) compared to an isotype control. In some embodiments, the antibody maintains the time from the assay start to the thrombin peak on a thrombin generation curve (ttPeak) compared to an isotype control. In some embodiments, the antibody preserves the endogenous thrombin potential (ETP) as determined by the area under a thrombin generation curve compared to an isotype control.

In some embodiments, the antibody binds human TF at a human TF binding site that is distinct from a human TF binding site bound by human FX. In some embodiments, the antibody does not interfere with the ability of TF:FVIIa to convert FX into FXa.

In some embodiments, the antibody does not compete for binding to human TF with human FVIIa.

In some embodiments, the antibody does not inhibit human thrombin generation as determined by thrombin generation assay (TGA), allows human thrombin generation as determined by thrombin generation assay (TGA), binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not decrease the endogenous thrombin potential (ETP) as determined by the area under a thrombin generation curve compared to an isotype control, allows human thrombin generation as determined by thrombin generation assay (TGA), preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not reduce the thrombin peak on a thrombin generation curve (Peak IIa) compared to an isotype control, does not increase the time from the assay start to the thrombin peak on a thrombin generation curve (ttPeak) compared to an isotype control, does not decrease the endogenous thrombin potential (ETP) as determined by the area under a thrombin generation curve compared to an isotype control, allows human thrombin generation as determined by thrombin generation assay (TGA), maintains the thrombin peak on a thrombin generation curve (Peak IIa) compared to an isotype control, maintains the time from the assay start to the thrombin peak on a thrombin generation curve (ttPeak) compared to an isotype control, preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody inhibits FVIIa-dependent TF signaling.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N.

In some embodiments, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 68 of the sequence shown in SEQ ID NO:810 is K68N.

In some embodiments, the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO:810 is K68N.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, and wherein the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; the mutation at amino acid residue 68 of the sequence shown in SEQ ID NO:810 is K68N; and the mutations at amino acid residues 171 and 197 of the sequence shown in SEQ ID NO:810 are N171H and T197K.

In some embodiments, the antibody binds to cynomolgus TF. In some embodiments, the antibody binds to mouse TF. In some embodiments, the antibody binds to rabbit TF. In some embodiments, the antibody binds to pig TF.

In some embodiments, the antibody: (a) does not inhibit human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) allows human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; and (i) binds to rabbit TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; and (k) binds to rabbit TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; and (o) binds to rabbit TF.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; (i) binds to rabbit TF; and (j) binds to pig TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; (k) binds to rabbit TF; and (l) binds to pig TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; and (p) binds to pig TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (r) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (s) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (bb) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (r) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (s) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (bb) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody competes for binding to human TF with the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody competes for binding to human TF with the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody competes for binding to human TF with the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody binds to the same human TF epitope bound by the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the three heavy chain CDRs and the three light chain CDRs are determined using Kabat, Chothia, AbM, Contact, or IMGT numbering.

In some embodiments, the antibody comprises all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises all three heavy chain Complementary Determining Regions (CDRs) and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G. In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9. In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7. In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO:113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence set forth in SEQ ID NO:801; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25G9. In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the antibody consists of: the antibody designated 25A, the antibody designated 25A3, the antibody designated 25A5, the antibody designated 25A5-T, the antibody designated 25G, the antibody designated 25G1, or the antibody designated 25G9. In some embodiments, the antibody consists of: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody competes for binding to human TF with: the antibody designated 1F, the antibody designated 1G, the antibody designated 29D, the antibody designated 29E, the antibody designated 39A, or the antibody designated 54E.

In some embodiments, the antibody inhibits FVIIa-dependent TF signaling.

In some embodiments, the antibody binds to cynomolgus TF.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; and the binding between the antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between the antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the antibody and the extracellular domain of TF of the sequence shown in SEQ ID NO:810; and the binding between the antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody comprises all three heavy chain Complementary Determining Regions (CDRs) and all three light chain CDRs from: the antibody designated 1F, the antibody designated 1G, the antibody designated 29D, the antibody designated 29E, the antibody designated 39A, the antibody designated 43Ea, or the antibody designated 54E. In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from the antibody designated 1F. In some embodiments, the antibody comprises all three heavy chain CDRs and all three light chain CDRs from the antibody designated 1G. In some embodiments, the antibody comprises all three heavy chain CDRs and all three light chain CDRs from the antibody designated 29D. In some embodiments, the antibody comprises all three heavy chain CDRs and all three light chain CDRs from the antibody designated 29E. In some embodiments, the antibody comprises all three heavy chain CDRs and all three light chain CDRs from the antibody designated 39A. In some embodiments, the antibody comprises all three heavy chain CDRs and all three light chain CDRs from the antibody designated 54E.

In some embodiments, the antibody comprises a $V_H$ sequence of SEQ ID NO:37 and a $V_L$ sequence of SEQ ID NO:38. In some embodiments, the antibody comprises a $V_H$ sequence of SEQ ID NO:75 and a $V_L$ sequence of SEQ ID NO:76. In some embodiments, the antibody comprises a $V_H$ sequence of SEQ ID NO:341 and a $V_L$ sequence of SEQ ID NO:342. In some embodiments, the antibody comprises a $V_H$ sequence of SEQ ID NO:379 and a $V_L$ sequence of SEQ ID NO:380. In some embodiments, the antibody comprises a $V_H$ sequence of SEQ ID NO:417 and a $V_L$ sequence of SEQ ID NO:418. In some embodiments, the antibody comprises a $V_H$ sequence of SEQ ID NO:759 and a $V_L$ sequence of SEQ ID NO:760.

In some embodiments, the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778. In some embodiments, the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790. In some embodiments, the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796. In some embodiments, the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In some embodiments, the antibody comprises a $V_H$ sequence of SEQ ID NO:761 and a $V_L$ sequence of SEQ ID NO:762. In some embodiments, the antibody comprises a $V_H$ sequence of SEQ ID NO:765 and a $V_L$ sequence of SEQ ID NO:766. In some embodiments, the antibody comprises a $V_H$ sequence of SEQ ID NO:767 and a $V_L$ sequence of SEQ ID NO:768. In some embodiments, the antibody comprises a $V_H$ sequence of SEQ ID NO:771 and a $V_L$ sequence of SEQ ID NO:772.

In some embodiments, the antibody comprises: the antibody designated 1F, the antibody designated 1G, the antibody designated 29D, the antibody designated 29E, the antibody designated 39A, or the antibody designated 54E. In some embodiments, the antibody consists of: the antibody designated 1F, the antibody designated 1G, the antibody designated 29D, the antibody designated 29E, the antibody designated 39A, or the antibody designated 54E.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence set forth in SEQ ID NO:783; and a VL-CDR3 comprising the sequence set forth in SEQ ID NO:784.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence set forth in SEQ ID NO:801; and a VL-CDR3 comprising the sequence set forth in SEQ ID NO:802.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In another aspect, provided herein is an antibody-drug conjugate comprising: antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody is human, humanized, or chimeric.

In some embodiments, the antibody binds to human TF with a $K_D$ of less than or equal to 50 nM, 10 nM, 5 nM, 1 nM, 0.5 nM or 0.1 nM, as measured by Octet QK384 or Biacore assay.

In some embodiments, the antibody is a monoclonal antibody.

In some embodiments, the antibody is multispecific.

In some embodiments, the antibody is a Fab, Fab', F(ab')$_2$, Fv, scFv, (scFv)$_2$, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1. In some embodiments, the Fc comprises one or more modifications, wherein the one or more modifications result in increased half-life, increased antibody-dependent cellular cytotoxicity (ADCC), increased antibody-dependent cellular phagocytosis (ADCP), increased complement-dependent cytotoxicity (CDC), or decreased effector function, compared with the Fc without the one or more modifications.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody competes for binding to human TF with any antibody above.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody binds the human TF epitope bound by any antibody above.

In some embodiments, the cytotoxic agent comprises an anti-angiogenic agent, a pro-apoptotic agent, an anti-mitotic agent, an anti-kinase agent, an alkylating agent, a hormone, a hormone agonist, a hormone antagonist, a chemokine, a drug, a prodrug, a toxin, an enzyme, an antimetabolite, an antibiotic, an alkaloid, or a radioactive isotope. In some embodiments, the cytotoxic agent comprises at least one of: calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, vinca alkaloid, maytansinoid, maytansinoid analog, pyrrolobenzodiazepine, taxoid, duocarmycin, dolastatin, and auristatin.

In some embodiments, the linker comprises a labile linker, an acid labile linker, a photolabile linker, a charged linker, a disulfide-containing linker, a peptidase-sensitive linker, a β-glucuronide-linker, a dimethyl linker, a thio-ether linker, or a hydrophilic linker. In some embodiments, the linker is a cleavable linker. In some embodiments, the linker is a non-cleavable linker.

In another aspect, provided herein is a pharmaceutical composition comprising any antibody-drug conjugate above and a pharmaceutically acceptable excipient.

In another aspect, provided herein is a method of treating or preventing a disease or condition in a subject in need thereof, comprising administering to the subject an effective amount of any antibody-drug conjugate above or the pharmaceutical composition above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the method further comprises administering one or more additional therapeutic agents to the subject. In some embodiments, the additional therapeutic agent is formulated in the same pharmaceutical composition as the antibody-drug conjugate. In some embodiments, the additional therapeutic agent is formulated in a different pharmaceutical composition from the antibody-drug conjugate. In some embodiments, the additional therapeutic agent is administered prior to administering the antibody-drug conjugate. In some embodiments, the additional therapeutic agent is administered after administering the antibody-drug conjugate. In some embodiments, the additional therapeutic agent is administered contemporaneously with the antibody-drug conjugate.

In another aspect, provided herein is a method of detecting TF in a subject having or suspected of having a disease or condition, the method comprising: (a) administering to the subject any antibody-drug conjugate above; and (b) detecting the presence or the level of TF in the subject.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER-), progesterone receptors negative (PR-), and HER2 negative (HER2-) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In another aspect, provided herein is a kit comprising any antibody-drug conjugate above or the pharmaceutical composition above and instructions for use.

BRIEF DESCRIPTION OF THE DRAWINGS

These and other features, aspects, and advantages of the present invention will become better understood with regard to the following description, and accompanying drawings, where:

FIG. 1A shows the median fluorescence intensity (MFI) of antibody bound to HCT-116 cells plotted against concentrations of antibodies from groups 1, 25, and 29 and the reportable cell $EC_{50}$. FIG. 1B shows the median fluorescence intensity of antibody bound to HCT-116 cells plotted against concentrations of antibodies from groups 39, 43, and 54 and the reportable cell $EC_{50}$. The isotype control in FIG. 1B applies to both FIGS. 1A and 1B.

FIG. 2A shows the median fluorescence intensity (MFI) of antibody bound to CHO cells recombinantly expressing mouse TF (CHO-mTF) plotted against concentrations of antibodies from groups 1, 25, and 29 and the reportable cell $EC_{50}$. FIG. 2B shows the median fluorescence intensity of antibody bound to CHO-mTF cells plotted against concentrations of antibodies from groups 39, 43, and 54 and the reportable cell $EC_{50}$. The isotype control in FIG. 2B applies to both FIGS. 2A and 2B.

FIG. 3A shows Peak IIa/Thrombin generation (% Peak IIa) as measured by the Thrombin Generation Assay (TGA) without antibody incubation prior to addition of calcium and thrombin substrate in the presence of titrations of anti-TF antibodies from groups 1, 25, 29, 39, 43, and 54. FIG. 3B shows Peak IIa/Thrombin generation (% Peak IIa) as measured by the Thrombin Generation Assay (TGA) with a 10-min antibody incubation prior to addition of calcium and thrombin substrate in the presence of titrations of anti-TF antibodies from groups 1, 25, 29, 39, 43, and 54.

FIG. 4A shows the percentage of FXa conversion (% FXa) by TF:FVIIa in MDA-MB-231 cells in the presence of titrations of anti-TF antibodies from groups 1, 25, and 29. FIG. 4B shows the percentage of FXa conversion (% FXa) by TF:FVIIa in MDA-MB-231 cells in the presence of titrations of anti-TF antibodies from groups 39, 43, and 54. % FXa conversion at a reported concentration is calculated relative to an antibody-free FXa conversion reaction. The isotype control in FIG. 4B applies to both FIGS. 4A and 4B.

FIG. 5A shows the percentage of FVIIa binding (% FVIIa) in TF-positive MDA-MB-231 cells in the presence of titrations of anti-TF antibodies from groups 1, 25, and 29. FIG. 5B shows the percentage of FVIIa binding (% FVIIa) in MDA-MB-231 cells in the presence of titrations of anti-TF antibodies from groups 39, 43, and 54. % FVIIa binding at a reported concentration is calculated relative to antibody-free FVIIa binding. The isotype control in FIG. 5B applies to both FIGS. 5A and 5B.

FIG. 6A shows the concentration of IL8 (IL8 conc) in MDA-MB-231 cells in the presence of titrations of anti-TF antibodies from groups 1, 25, and 29. FIG. 6B shows the concentration of IL8 (IL8 conc) in MDA-MB-231 cells in the presence of titrations of anti-TF antibodies from groups 39, 43, and 54. The control in FIG. 6B applies to both FIGS. 6A and 6B. FIG. 6C shows the concentration of GM-CSF (GM-CSF conc) in MDA-MB-231 cells in the presence of titrations of anti-TF antibodies from groups 1, 25, and 29. FIG. 6D shows the concentration of GM-CSF (GM-CSF conc) in MDA-MB-231 cells in the presence of titrations of anti-TF antibodies from groups 39, 43, and 54. The control in FIG. 6D applies to both FIGS. 6C and 6D.

FIG. 7A shows the cell viability of TF-positive A431 cell cultures after the addition of an anti-TF antibody from groups 1, 25, and 29 and a secondary antibody against the human Fc conjugated to mono-methyl auristatin F (MMAF). FIG. 7B shows the cell viability of TF-positive A431 cell cultures after the addition of an anti-TF antibody from groups 39, 43, and 54 and a secondary antibody against the human Fc conjugated to mono-methyl auristatin F (MMAF). The isotype control in FIG. 7B applies to both FIGS. 7A and 7B.

FIG. 8A shows Peak IIa/Thrombin generation (% Peak IIa) as measured by the Thrombin Generation Assay (TGA) without antibody incubation prior to addition of calcium and thrombin substrate in the presence of titrations of anti-TF antibodies from groups 25, 39, 43, and anti-TF M1593. FIG. 8B shows Peak IIa/Thrombin generation (% Peak IIa) as measured by the Thrombin Generation Assay (TGA) with a 10-min antibody incubation prior to addition of calcium and thrombin substrate in the presence of titrations of anti-TF antibodies from groups 25, 39, 43, and anti-TF M1593.

FIG. 9A shows cell viability of TF-positive A431 cells after a 3-day incubation with titrations of anti-TF antibodies conjugated to MC-vc-PAB-MMAE (DAR of 3-4). FIG. 9B shows cell viability of TF-positive HPAF-II cells after a 4-day incubation with titrations of anti-TF antibodies conjugated to MC-vc-PAB-MMAE (DAR of 3-4).

FIG. 10A shows the efficacy of anti-TF ADCs in the A431 xenograft model. FIG. 10B shows the efficacy of anti-TF ADCs in the HPAF-II xenograft model. The arrows indicate treatments with ADC or vehicle (PBS) dosed at 5 mg/kg once per week for 3 weeks.

FIG. 12A shows the median fluorescence intensity (MFI) of antibody bound to A431 cells plotted against concentrations of antibodies from groups 1, 25, 29, 39, 43, and 54. Reportable cell $EC_{50}$'s and their 95% confidence intervals are listed. FIG. 12B shows the median fluorescence intensity of antibody bound to MDA-MB-231 cells plotted against concentrations of antibodies from groups 25, 29, 39, and 43. Reportable cell $EC_{50}$'s and their 95% confidence intervals are listed.

FIG. 13A shows the thrombin generation curves in the absence or presence of 100 nM anti-TF antibodies from groups 1, 25, and 29 and previously generated anti-TF antibodies TF-011, 5G9, and 10H10 (samples on plate 1 of Table 44). FIG. 13B shows the thrombin generation curves in the absence or presence of 100 nM anti-TF antibodies from groups 39, 43, and 54 (samples on plate 2 of Table 44). FIG. 13C shows the peak thrombin concentration in the absence or presence of titrations of anti-TF antibodies. The mean of a triplicate data set is shown. The standard deviation of the mean is listed in Table 44.

FIG. 14A shows TF:FVIIa-dependent conversion of FX into FXa on the cell surface of MDA-MB-231 cells in the absence or presence of titrations of anti-TF antibodies TF-011, 5G9 and 10H10. FIG. 14B shows FVII binding in the absence or presence of titrations of anti-TF antibodies TF-011, 5G9 and 10H10 after pre-incubation of MDA-MB-231 cells with the anti-TF antibodies. For antibodies that exhibited no less than 25% competition with FVII, the $IC_{50}$ is reported.

FIG. 15A shows percent binding of 25A3 after pre-incubation with unlabeled competitor antibodies from groups 1, 25, 29, 39, 43, and 54. FIG. 15B shows percent binding of 25A3 after pre-incubation with unlabeled competitor antibodies TF-011, 5G9, and 10H10. The $IC_{50}$ value of antibodies that compete with 25A3 is listed.

FIG. 16A shows percent binding of 43D7 after pre-incubation with unlabeled competitor antibodies from groups 1, 25, 29, 39, 43, and 54. FIG. 16B shows percent binding of 43D7 after pre-incubation with unlabeled competitor antibodies TF-011, 5G9, and 10H10. The $IC_{50}$ value of antibodies that compete with 43D7 is listed.

FIG. 17A shows percent binding of 39A after pre-incubation with unlabeled competitor antibodies from groups 1, 25, 29, 39, 43, and 54. FIG. 17B shows percent binding of 39A after pre-incubation with unlabeled competitor antibodies TF-011, 5G9, and 10H10. The $IC_{50}$ value of antibodies that compete with 39A is listed.

FIG. 18A shows cell viability of TF-positive A431 cell cultures three days after titrations of anti-TF antibodies. FIG. 18B shows cell viability of TF-positive A431 cell cultures three days after titrations of anti-TF antibodies complexed with a Fab fragment against the human Fc conjugated to mono-methyl auristatin F (Fab:MMAF). The $IC_{50}$ of the anti-TF antibody Fab:MMAF complexes is listed. FIG. 18C shows internalization of anti-TF antibodies conjugated to A488. Percent internalization of A488-conjugated anti-TF antibodies at 4 h is listed.

FIGS. 19A, 19B, and 19C show the binding of anti-TF antibodies and ADCs to human TF-positive HCT-116 cells. FIG. 19A shows the binding of anti-TF antibodies HCT-116 cells. FIG. 19B shows the binding of anti-TF ADCs to HCT-116 cells. FIG. 19C lists reportable cell $EC_{50}$'s and their 95% confidence intervals.

FIGS. 20A, 20B, and 20C show cell viability of A431 cells after titrations of anti-TF ADCs. FIG. 20A shows the cell viability after titrations of anti-TF ADCs with a continuous 72 h incubation. FIG. 20B shows the cell viability after titrations of anti-TF ADCs with a 4 h incubation followed by removal of excess ADC and culture for another 68 h. FIG. 20C lists the reportable $IC_{50}$ values of ADCs.

FIGS. 21A, 21B, and 21C show the effect of FVIIa on the in vitro efficacy of anti-TF ADCs. FIG. 21A shows the cell viability after titrations of anti-TF ADCs with a 4 h incubation followed by removal of excess ADC and culture for another 68 h in the absence of FVIIa. FIG. 21B shows the cell viability after titrations of anti-TF ADCs with a 4 h incubation followed by removal of excess ADC and culture for another 68 h in the presence of FVIIa. FIG. 21C lists the reportable $IC_{50}$ values.

FIGS. 22A, 22B, 22C, 22D, and 22E show cell viability of additional cancer cell lines after titrations of anti-TF ADCs. FIG. 22A shows the TF copy number in various cell lines with the anti-TF antibody 5G9. The standard error of the mean and the number of measurements (n) are also presented. FIG. 22B shows the cell viability of HCT-116 cells after 72 h culture in the absence or presence of titrations of anti-TF MMAE ADCs. FIG. 22C shows the cell viability of CHO cells after 72 h culture in the absence or presence of titrations of anti-TF MMAE ADCs. FIG. 22D shows the cell viability of MDA-MB-231 cells after 5-day culture in the absence or presence of titrations of anti-TF MMAE ADCs. FIG. 22E shows the cell viability of HPAF-II cells after 5-day culture in the absence or presence of titrations of anti-TF MMAE ADCs.

FIG. 23A shows staining of the microtubule network of A431 cells after treatment. FIG. 23B shows staining of the microtubule network of HPAF-II cells after treatment. Scale bar, 10 microns.

FIG. 24A shows copy numbers of surface TF on HUVECs treated with or without an inflammatory cytokine cocktail for 3, 6, or 20 h prior to analysis. FIG. 24B shows cell viability of inflammatory cytokine-treated HUVEC cultures after 4 days of culture in the presence of titrations of anti-TF or isotype-control MMAE ADCs.

FIG. 25A shows the percentage of pH3-positive cells (% pH3) with titrations of anti-TF ADCs of HUVECs in the absence of inflammatory cytokines. FIG. 25B shows the percentage of pH3-positive cells (% pH3) with titrations of anti-TF ADCs of HUVECs in the presence of inflammatory cytokines. FIG. 25C shows the percentage of pH3-positive cells (% pH3) with titrations of anti-TF ADCs of HCT-116 cells.

FIG. 26A shows the pH3 versus DNA content dot plot after treatment of 10 nM Isotype-vc-MMAE. FIG. 26B shows the pH3 versus DNA content dot plot after treatment of 10 nM 25A-vc-MMAE.

FIG. 27A shows the percentage of pH3-positive HUVECs (% pH3) in the absence or presence of 24 h of MMAE treatment. FIG. 27B shows the percentage of pH3-positive HCT-116 cells (% pH3) in the absence or presence of 24 h of MMAE treatment.

FIGS. 29A, 29B, and 29C show antibody-dependent cellular cytotoxicity (ADCC) reporter luminescence after a 6 h incubation of the reporter Jurkat cell line with TF-positive A431 cells. FIG. 29A shows the ADCC reporter luminescence in the absence or presence of titrations anti-TF antibodies. FIG. 29B shows the ADCC reporter luminescence in the absence or presence of titrations anti-TF ADCs. FIG. 29C lists the ADCC reporter luminescence $EC_{50}$ values for each anti-TF antibody or ADC.

FIG. 30A shows the mean tumor volume after weekly treatment of an anti-TF ADC at 5 mg/kg for 3 weeks. FIG. 30B shows the mean tumor volume after weekly treatment of an anti-TF ADC at 2 mg/kg for 2 weeks. The mean tumor volumes (Mean) and tumor growth inhibition (TGI) percentages on day 21 are listed. The P-values for the mean tumor volume comparison between each ADC and the vehicle control are also listed. In addition, the number of partial regression (PR), complete regression (CR), and tumor-free survivor (TFS) animals at the end of the study (day 59 for FIG. 30A and day 39 for FIG. 30B) are also listed.

FIGS. 31A and 31B show in vivo efficacy of anti-TF ADCs in MDA-MB-231 xenograft model. FIG. 31A shows the mean tumor volume after weekly treatment of an anti-TF ADC at 4 mg/kg for 2 weeks. FIG. 31B shows the mean tumor volume after weekly treatment of an anti-TF ADC at 2 mg/kg for 2 weeks. The mean tumor volume and tumor growth inhibition on day 25 (FIG. 31A) and day 27 (FIG. 31B) are listed. The P-values for the mean tumor volume comparison between each ADC and the vehicle control are also listed. In addition, the number of partial regression (PR), complete regression (CR), and tumor-free survivor (TFS) animals at the end of the study (day 49 for FIG. 31A and day 41 for FIG. 31B) are also listed.

FIG. 33A shows the mean tumor volume in the PDX model of a head and neck carcinoma after treatment of an anti-TF ADC. FIG. 33B shows the mean tumor volume in the PDX model of an ovarian carcinoma after treatment of an anti-TF ADC. FIG. 33C shows the mean tumor volume in the PDX model of a gastric adenocarcinoma after treatment of an anti-TF ADC. The mean tumor volume and tumor growth inhibition on day 44 (FIG. 33A), day 15 (FIG. 33B), and day 25 (FIG. 33C) are listed. The P-values for the mean tumor volume comparison between each ADC and the isotype control are also listed. In addition, the number of patial responder (PR), complete responder (CR), and tumor free survivor (TFS) animals at the end of the study (day 60 for FIG. 33A and day 46 for FIGS. 33B-C) are also listed.

FIG. 34A shows the percentage change in lesion size from day 7 (baseline) to day 14 as measured by Fluorescein Angiography (FA) after intravitreal administration of anti-TF antibodies 25G9, 43D8, 1G, and 29D respectively. FIG. 34B shows the percentage change in lesion size from day 7 (baseline) to day 28 as measured by Fluorescein Angiography (FA) after intravitreal administration of anti-TF antibodies 25G9, 43D8, 1G, and 29D respectively.

FIG. 36 shows Clustal Omega alignment of chimeric TF constructs. Rat sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly equivalent to scoring=<0.5 and >0 in the Gonnet Percent Accepted Mutation 250 matrix.

FIG. 37 shows Clustal Omega alignment of chimeric TF constructs. Human sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly equivalent to scoring=<0.5 and >0 in the Gonnet Percent Accepted Mutation 250 matrix.

FIG. 38 shows Clustal Omega alignment of chimeric TF constructs. Rat sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly FIG. 39A shows the titration curves of anti-TF antibodies on human TF construct. FIG. 39B shows the titration curves of anti-TF antibodies on rat TF construct. FIG. 39C shows the titration curves of anti-TF antibodies on chimeric human-rat TF construct hTF_K68N. FIG. 39D shows the titration curves of anti-TF antibodies on chimeric human-rat TF construct hTF_K149N. FIG. 39E shows the titration curves of anti-TF antibodies on chimeric human-rat TF construct hTF_N171H_T197K. FIG. 39F shows the titration curves of anti-TF antibodies on chimeric rat-human TF construct r141-194_h.

DETAILED DESCRIPTION

1. Definitions

Figure 1A:
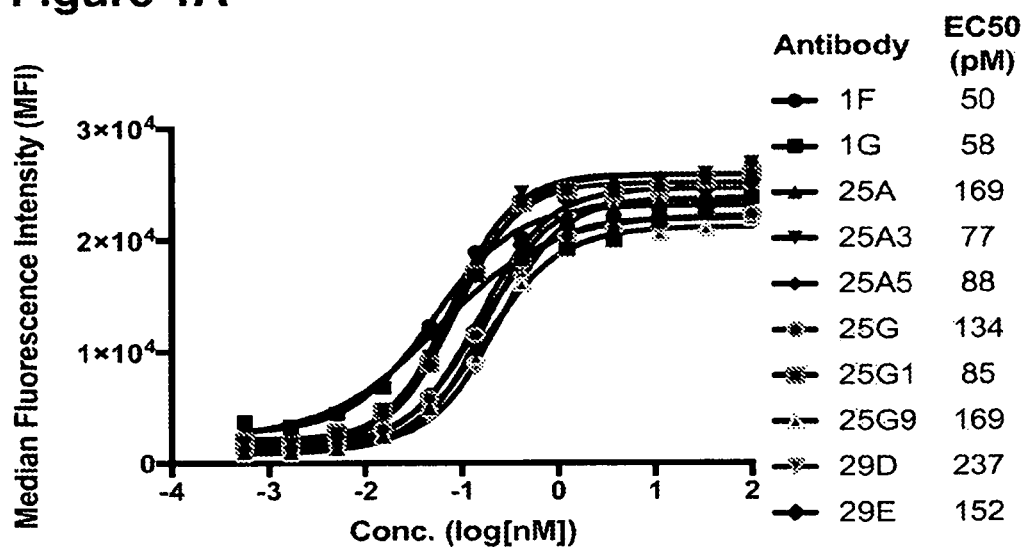
FIGS. 1A and 1B show binding of anti-TF antibodies to human TF-positive cells.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

The terms "Tissue Factor," "TF," "platelet tissue factor," "factor III," "thromboplastin," and "CD142" are used interchangeably herein to refer to TF, or any variants (e.g., splice variants and allelic variants), isoforms, and species homologs of TF that are naturally expressed by cells, or that are expressed by cells transfected with a TF gene. In some aspects, the TF protein is a TF protein naturally expressed by a primate (e.g., a monkey or a human), a rodent (e.g., a mouse or a rat), a dog, a camel, a cat, a cow, a goat, a horse, a pig or a sheep. In some aspects, the TF protein is human TF (hTF; SEQ ID NO:809). In some aspects, the TF protein is cynomolgus TF (cTF; SEQ ID NO:813). In some aspects, the TF protein is mouse TF (mTF; SEQ ID NO:817). In some aspects, the TF protein is pig TF (pTF; SEQ ID NO:824). TF is a cell surface receptor for the serine protease factor VIIa. It is often times constitutively expressed by certain cells surrounding blood vessels and in some disease settings.

The term "antibody-drug conjugate" or "ADC" refers to a conjugate comprising an antibody conjugated to one or more cytotoxic agents, optionally through one or more linkers. The term "anti-TF antibody-drug conjugate" or "anti-TF ADC" refers to a conjugate comprising an anti-TF antibody conjugated to one or more cytotoxic agents, optionally through one or more linkers.

The term "cytotoxic agent," as used herein, refers to a substance that inhibits or prevents a cellular function and/or causes cell death or destruction. The cytotoxic agent can be an anti-angiogenic agent, a pro-apoptotic agent, an anti-mitotic agent, an anti-kinase agent, an alkylating agent, a hormone, a hormone agonist, a hormone antagonist, a chemokine, a drug, a prodrug, a toxin, an enzyme, an antimetabolite, an antibiotic, an alkaloid, or a radioactive isotope. Exemplary cytotoxic agents include calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, vinca alkaloid, maytansinoid, maytansinoid analog, pyrrolobenzodiazepine, taxoid, duocarmycin, dolastatin, auristatin, and derivatives thereof.

A "linker" refers to a molecule that connects one composition to another, e.g., an antibody to an agent. Linkers described herein can conjugate an antibody to a cytotoxic agent. Exemplary linkers include a labile linker, an acid labile linker, a photolabile linker, a charged linker, a disulfide-containing linker, a peptidase-sensitive linker, a □-glucuronide-linker, a dimethyl linker, a thio-ether linker, and a hydrophilic linker. A linker can be cleavable or non-cleavable.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an antibody. Exemplary alternative scaffolds include those derived from fibronectin (e.g., Adnectins™), the (β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD3 (e.g., Tetranectins), Fynomers, and (LDLR-A module) (e.g., Avimers). Additional information on alternative scaffolds is provided in Binz et al., *Nat. Biotechnol.*, 2005 23:1257-1268; Skerra, *Current Opin. in Biotech.*, 2007 18:295-304; and Silacci et al., *J. Biol. Chem.*, 2014, 289:14392-14398; each of which is incorporated by reference in its entirety.

The term "antigen-binding domain" means the portion of an antibody that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an Adnectin. Antigen-binding domains can be found in various contexts including antibodies and chimeric antigen receptors (CARs), for example CARs derived from antibodies or antibody fragments such as scFvs.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

A "Complementary Determining Region (CDR)" refers to one of three hypervariable regions (H1, H2 or H3) within the non-framework region of the immunoglobulin (Ig or antibody) $V_H$ β-sheet framework, or one of three hypervariable regions (L1, L2 or L3) within the non-framework region of the antibody $V_L$ β-sheet framework. CDRs are variable region sequences interspersed within the framework region sequences. CDRs are well recognized in the art and have been defined by, for example, Kabat as the regions of most hypervariability within the antibody variable (V) domains. See Kabat et al., *J Biol Chem*, 1977, 252:6609-6616 and Kabat, *Adv Protein Chem*, 1978, 32:1-75, each of which is incorporated by reference in its entirety. CDRs have also been defined structurally by Chothia as those residues that are not part of the conserved β-sheet framework, and thus are able to adapt different conformations. See Chothia and Lesk, *J Mol Biol*, 1987, 196:901-917, incorporated by reference in its entirety. Both the Kabat and Chothia nomenclatures are well known in the art. AbM, Contact and IMGT also defined CDRs. CDR positions within a canonical antibody variable domain have been determined by comparison of numerous structures. See Morea et al., *Methods*, 2000, 20:267-279 and Al-Lazikani et al., *J Mol Biol*, 1997, 273: 927-48, each of which is incorporated by reference in its entirety. Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra). Such terminology is well known to those skilled in the art.

A number of hypervariable region delineations are in use and are included herein. The Kabat CDRs are based on sequence variability and are the most commonly used. See Kabat et al. (1992) *Sequences of Proteins of Immunological Interest*, DIANE Publishing: 2719, incorporated by reference in its entirety. Chothia refers instead to the location of the structural loops (Chothia and Lesk, supra). The AbM hypervariable regions represent a compromise between the Kabat CDRs and Chothia structural loops, and are used by Oxford Molecular's AbM antibody modeling software. The Contact hypervariable regions are based on an analysis of the available complex crystal structures. The residues from each of these hypervariable regions are noted in Table 1.

More recently, a universal numbering system ImMunoGeneTics (IMGT) Information System™ has been developed and widely adopted. See Lefranc et al., *Dev Comp Immunol*, 2003, 27:55-77, incorporated by reference in its entirety. IMGT is an integrated information system specializing in immunoglobulins (IG), T cell receptors (TR) and major histocompatibility complex (MI-IC) of human and other vertebrates. The IMGT CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. Correspondence between the Kabat, Chothia and IMGT numbering is also well known in the art (Lefranc et al., supra). An Exemplary system, shown herein, combines Kabat and Chothia CDR definitions.

TABLE 1

| | Exemplary (Kabat + Chothia) | Kabat | Chothia | AbM | Contact | IMGT |
|---|---|---|---|---|---|---|
| VH CDR1 | 26-35 | 31-35 | 26-32 | 26-35 | 30-35 | 27-38 |
| VH CDR2 | 50-65 | 50-65 | 52a-55 | 50-58 | 47-58 | 56-65 |
| VH CDR3 | 95-102 | 95-102 | 96-101 | 95-102 | 93-101 | 105-117 |
| VL CDR1 | 24-34 | 24-34 | 26-32 | 24-34 | 30-36 | 27-38 |
| VL CDR2 | 50-56 | 50-56 | 50-52 | 50-56 | 46-55 | 56-65 |
| VL CDR3 | 89-97 | 89-97 | 91-96 | 89-97 | 89-96 | 105-117 |

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen-binding site. The constant domain contains the $C_{H1}$, $C_{H2}$ and $C_{H3}$ domains of the heavy chain and the $C_L$ domain of the light chain.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen-binding or variable region of an intact antibody. Antibody fragments include, for example, Fv fragments, Fab fragments, F(ab')₂ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')₂" fragments contain two Fab' fragments joined, near the hinge region, by disulfide bonds. F(ab')₂ fragments may be generated, for example, by recombinant methods or by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a (GGGG-S)$_n$(SEQ ID NO:823). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies.

A "multispecific antibody" is an antibody that comprises two or more different antigen-binding domains that collectively specifically bind two or more different epitopes. The two or more different epitopes may be epitopes on the same antigen (e.g., a single TF molecule expressed by a cell) or on different antigens (e.g., a TF molecule and a non-TF molecule). In some aspects, a multi-specific antibody binds two different epitopes (i.e., a "bispecific antibody"). In some aspects, a multi-specific antibody binds three different epitopes (i.e., a "trispecific antibody"). In some aspects, a multi-specific antibody binds four different epitopes (i.e., a "quadspecific antibody"). In some aspects, a multi-specific antibody binds five different epitopes (i.e., a "quintspecific antibody"). In some aspects, a multi-specific antibody binds 6, 7, 8, or more different epitopes. Each binding specificity may be present in any suitable valency. Examples of multispecific antibodies are provided elsewhere in this disclosure.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" or "isolated nucleic acid" is an antibody or nucleic acid that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. In some embodiments, an isolated antibody may include an antibody in situ within recombinant cells, since at least one component of the antibody's natural environment is not present. In some aspects, an isolated antibody or isolated nucleic acid is prepared by at least one purification step. In some embodiments, an isolated antibody or isolated nucleic acid is purified to at least 80%, 85%, 90%, 95%, or 99% by weight. In some embodiments, an isolated antibody or isolated nucleic acid is purified to at least 80%, 85%, 90%, 95%, or 99% by volume. In some embodiments, an isolated antibody or isolated nucleic acid is provided as a solution comprising at least 85%, 90%, 95%, 98%, 99% to 100% antibody or nucleic acid by weight. In some embodiments, an isolated antibody or isolated nucleic acid is provided as a solution comprising at least 85%, 90%, 95%, 98%, 99% to 100% antibody or nucleic acid by volume.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some aspects, the affinity of a TF antibody for a non-target molecule is less than about 50% of the affinity for TF. In some aspects, the affinity of a TF antibody for a non-target molecule is less than about 40% of the affinity for TF. In some aspects, the affinity of a TF antibody for a non-target molecule is less than about 30% of the affinity for TF. In some aspects, the affinity of a TF antibody for a non-target molecule is less than about 20% of the affinity for TF. In some aspects, the affinity of a TF antibody for a non-target molecule is less than about 10% of the affinity for TF. In some aspects, the affinity of a TF antibody for a non-target molecule is less than about 1% of the affinity for TF. In some aspects, the affinity of a TF antibody for a non-target molecule is less than about 0.1% of the affinity for TF.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "KA" ($M^{-1}$), as used herein, refers to the association equilibrium constant of a particular antibody-antigen interaction. $K_A = k_a/k_d$.

An "affinity matured" antibody is an antibody with one or more alterations (e.g., in one or more CDRs or FRs) relative to a parent antibody (i.e., an antibody from which the altered antibody is derived or designed) that result in an improvement in the affinity of the antibody for its antigen, compared to the parent antibody which does not possess the alteration(s). In some embodiments, an affinity matured antibody has nanomolar or picomolar affinity for the target antigen. Affinity matured antibodies may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al., *Proc. Nat. Acad. Sci. U.S.A.*, 1994, 91:3809-3813; Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896; each of which is incorporated by reference in its entirety.

"Fc effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more antibodies, the term "competes with" or "cross-competes with" indicates that the two or more antibodies compete for binding to an antigen (e.g., TF). In one exemplary assay, TF is coated on a surface and contacted with a first TF antibody, after which a second TF antibody is added. In another exemplary assay, first a TF antibody is coated on a surface and contacted with TF, and then a second TF antibody is added. If the presence of the first TF antibody reduces binding of the second TF antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for TF and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual*[Internet], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety. As provided in Example 8, antibodies of group 25 and antibodies of group 43 compete with each other for binding to human TF, while antibodies from groups 1, 29, 39, and 54 do not compete for binding to human TF with antibodies of groups 25 and 43.

As used herein, an antibody that binds specifically to a human antigen is considered to bind the same antigen of mouse origin when a $K_D$ value can be measured on a ForteBio Octet with the mouse antigen. An antibody that binds specifically to a human antigen is considered to be "cross-reactive" with the same antigen of mouse origin when the $K_D$ value for the mouse antigen is no greater than 20 times the corresponding $K_D$ value for the respective human antigen. For example, the antibody M1593 described in U.S. Pat. Nos. 8,722,044, 8,951,525, and 8,999,333, each of which is herein incorporated by reference for all purposes, the humanized 5G9 antibody described in Ngo et al., 2007, *Int J Cancer*, 120(6):1261-1267, incorporated by reference in its entirety, and chimeric ALT-836 antibody described in Hong et al, 2012, *J Nucl Med*, 53(11):1748-1754, incorporated by reference in its entirety, do not bind to mouse TF. As provided in Examples 1 and 2, TF antibodies from groups 25 and 43 bind to mouse TF, e.g., the TF antibodies 25G, 25G1, 25G9, and 43D8 are cross-reactive with mouse TF.

As used herein, an antibody that binds specifically to a human antigen is considered to be "cross-reactive" with the same antigen of cynomolgus monkey origin when the $K_D$ value for the cynomolgus monkey antigen is no greater than 15 times the corresponding $K_D$ value for the respective human antigen. As provided in Example 1, all tested antibodies from groups 1, 25, 29, 39, 43, and 54 are cross-reactive with cynomolgus monkey TF.

The term "epitope" means a portion of an antigen that is specifically bound by an antibody. Epitopes frequently include surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to TF variants with different point-mutations, or to chimeric TF variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F Y and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an antibody or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, pigs and sheep. In certain embodiments, the subject is a human. In some embodiments the subject has a disease or condition that can be treated with an antibody provided herein. In some aspects, the disease or condition is a cancer. In some aspects, the disease or condition involves neovascularization or vascular inflammation. In certain aspects, the disease or condition involving neovascularization is age-related macular degeneration (AMD), diabetic retinopathy, or cancer.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

2. TF Antibodies

2.1. TF Binding

Provided herein are isolated antibodies that specifically bind to TF. In some aspects, the TF is hTF (SEQ ID NO:809). In some aspects, the TF is cTF (SEQ ID NO:813). In some aspects, the TF is mTF (SEQ ID NO:817). In some aspects, the TF is rabbit TF (SEQ ID NO:832). In some aspects, the TF is pTF (SEQ ID NO:824). In some embodiments, the antibodies provided herein specifically bind to hTF (SEQ ID NO:809), cTF (SEQ ID NO:813), mTF (SEQ ID NO:817), rabbit TF (SEQ ID NO:832), and pTF (SEQ ID NO:824). In some embodiments, the antibodies provided herein specifically bind to hTF (SEQ ID NO:809), cTF (SEQ ID NO:813), mTF (SEQ ID NO:817), and pTF (SEQ ID NO:824). In some embodiments, the antibodies provided herein specifically bind to hTF (SEQ ID NO:809), cTF (SEQ ID NO:813), and mTF (SEQ ID NO:817). In some embodiments, the antibodies provided herein specifically bind to hTF (SEQ ID NO:809) and cTF (SEQ ID NO:813). In some embodiments, the antibodies provided herein do not bind mTF (SEQ ID NO:817). In some embodiments, the antibodies provided herein do not bind pTF (SEQ ID NO:824). In some embodiments, the antibodies provided herein do not bind rabbit TF (SEQ ID NO:832).

In various embodiments, the antibodies provided herein specifically bind to the extracellular domain of human TF (SEQ ID NO:810).

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N.

In some embodiments, the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 68 of the sequence shown in SEQ ID NO:810 is K68N.

In some embodiments, the binding between an antibody provided herein and a variant TF extracellular domain comprising mutations at amino acid residues 171 and 197 of the sequence shown in SEQ ID NO:810 is less than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810; the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810; the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810; and the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO:810 is K68N.

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810; the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810; the binding between an antibody provided herein and a variant TF extracellular domain comprising mutations at amino acid residues 171 and 197 of the sequence shown in SEQ ID NO:810 is less than 50% of the binding between the antibody provided herein and the extracellular domain of TF of the sequence shown in SEQ ID NO:810; the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810; and the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; the mutation at amino acid residue 68 of the sequence shown in SEQ ID NO:810 is K68N; and the mutations at amino acid residues 171 and 197 of the sequence shown in SEQ ID NO:810 are N171H and T197K.

In some embodiments, the antibodies provided herein are inert in inhibiting human thrombin generation as determined by thrombin generation assay (TGA) compared to a reference antibody M1593, wherein the reference antibody M1593 comprises a $V_H$ sequence of SEQ ID NO:821 and a $V_L$ sequence of SEQ ID NO:822.

In some embodiments, the antibodies provided herein do not inhibit human thrombin generation as determined by thrombin generation assay (TGA). In certain embodiments, the antibodies provided herein allow human thrombin generation as determined by thrombin generation assay (TGA).

In some embodiments, the antibodies provided herein bind human TF at a human TF binding site that is distinct from a human TF binding site bound by human FX. In certain embodiments, the antibodies provided herein do not interfere with the ability of TF:FVIIa to convert FX into FXa.

In some embodiments, the antibodies provided herein bind human TF at a human TF binding site that is distinct from a human TF binding site bound by human FVIIa. In certain embodiments, the antibodies provided herein do not compete for binding to human TF with human FVIIa.

In some embodiments, the antibodies provided herein bind to the extracellular domain of human TF, bind human TF at a human TF binding site that is distinct from a human TF binding site bound by human FVIIa, bind human TF at a human TF binding site that is distinct from a human TF binding site bound by human FX, and allow human thrombin generation as determined by thrombin generation assay (TGA).

In some embodiments, the antibodies provided herein bind to the extracellular domain of human TF, do not inhibit human thrombin generation as determined by thrombin generation assay (TGA), do not interfere with the ability of TF:FVIIa to convert FX into FXa, and do not compete for binding to human TF with human FVIIa.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, and do not compete for binding to human TF with human FVIIa.

In some embodiments, the antibodies provided herein inhibit FVIIa-dependent TF signaling.

In some embodiments, the antibodies provided herein reduce lesion size in a swine choroidal neovascularization (CNV) model.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, do not compete for binding to human TF with human FVIIa, and bind to cynomolgus and mouse TF.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, do not compete for binding to human TF with human FVIIa, bind to cynomolgus, mouse, and pig TF, and reduce lesion size in a swine choroidal neovascularization (CNV) model.

In some embodiments, the antibodies provided herein bind to the extracellular domain of human TF, inhibit FVIIa-dependent TF signaling, and bind to cynomolgus TF.

2.2. Sequences of TF Antibodies 2.2.1. $V_H$ Domains

In some embodiments, an antibody provided herein comprises a $V_H$ sequence selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises a $V_H$ sequence of SEQ ID NO:37. In some embodiments, an antibody provided herein comprises a $V_H$ sequence of SEQ ID NO:75. In some embodiments, an antibody provided herein comprises a $V_H$ sequence of SEQ ID NO:113. In some embodiments, an antibody provided herein comprises a $V_H$ sequence of SEQ ID NO:151. In some embodiments, an antibody provided herein comprises a $V_H$ sequence of SEQ ID NO:189. In some embodiments, an antibody provided herein comprises a $V_H$ sequence of SEQ ID NO:836. In some embodiments, an antibody provided herein comprises a $V_H$ sequence of SEQ ID NO:227. In some embodiments, an antibody provided herein comprises a $V_H$ sequence of SEQ ID NO:265. In some embodiments, an antibody provided herein comprises a $V_H$ sequence of SEQ ID NO:303. In some embodiments, an antibody provided herein comprises a $V_H$ sequence of SEQ ID NO:341. In some embodiments, an antibody provided herein comprises a $V_H$ sequence of SEQ ID NO:379. In some embodiments, an antibody provided herein comprises a $V_H$ sequence of SEQ ID NO:417. In some embodiments, an antibody provided herein comprises a $V_H$ sequence of SEQ ID NO:455. In some embodiments, an antibody provided herein comprises a $V_H$ sequence of SEQ ID NO:493. In some embodiments, an antibody provided herein comprises a $V_H$ sequence of SEQ ID NO:531. In some embodiments, an antibody provided herein comprises a $V_H$ sequence of SEQ ID NO:569. In some embodiments, an antibody provided herein comprises a $V_H$ sequence of SEQ ID NO:607. In some embodiments, an antibody provided herein comprises a $V_H$ sequence of SEQ ID NO:645. In some embodiments, an antibody provided herein comprises a $V_H$ sequence of SEQ ID NO:683. In some embodiments, an antibody provided herein comprises a $V_H$ sequence of SEQ ID NO:721. In some embodiments, an antibody provided herein comprises a $V_H$ sequence of SEQ ID NO:759.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 37, 75, 113, 151, 189, 227, 265, 303, 341, 379, 417, 455, 493, 531, 569, 607, 645, 683, 721, and 759. In some embodiments, an antibody provided herein comprises a $V_H$ sequence provided in SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.2. $V_L$ Domains

In some embodiments, an antibody provided herein comprises a $V_L$ sequence selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_L$ sequence of SEQ ID NO:38. In some embodiments, an antibody provided herein comprises a $V_L$ sequence of SEQ ID NO:76. In some embodiments, an antibody provided herein comprises a $V_L$ sequence of SEQ ID NO:114. In some embodiments, an antibody provided herein comprises a $V_L$ sequence of SEQ ID NO:152. In some embodiments, an antibody provided herein comprises a $V_L$ sequence of SEQ ID NO:190. In some embodiments, an antibody provided herein comprises a $V_L$ sequence of SEQ ID NO:837. In some embodiments, an antibody provided herein comprises a $V_L$ sequence of SEQ ID NO:228. In some embodiments, an antibody provided herein comprises a $V_L$ sequence of SEQ ID NO:266. In some embodiments, an antibody provided herein comprises a $V_L$ sequence of SEQ ID NO:304. In some embodiments, an antibody provided herein comprises a $V_L$ sequence of SEQ ID NO:342. In some embodiments, an antibody provided herein comprises a $V_L$ sequence of SEQ ID NO:380. In some embodiments, an antibody provided herein comprises a $V_L$ sequence of SEQ ID NO:418. In some embodiments, an antibody provided herein comprises a $V_L$ sequence of SEQ ID NO:456. In some embodiments, an antibody provided herein comprises a $V_L$ sequence of SEQ ID NO:494. In some embodiments, an antibody provided herein comprises a $V_L$ sequence of SEQ ID NO:532. In some embodiments, an antibody provided herein comprises a $V_L$ sequence of SEQ ID NO:570. In some embodiments, an antibody provided herein comprises a $V_L$ sequence of SEQ ID NO:608. In some embodiments, an antibody provided herein comprises a $V_L$ sequence of SEQ ID NO:646. In some embodiments, an antibody provided herein comprises a $V_L$ sequence of SEQ ID NO:684. In some embodiments, an antibody provided herein comprises a $V_L$ sequence of SEQ ID NO:722. In some embodiments, an antibody provided herein comprises a $V_L$ sequence of SEQ ID NO:760.

In some embodiments, an antibody provided herein comprises a $V_L$ sequence having at least about 50%, 60%, 70%, 80%, 90%, 95%, or 99% identity to an illustrative $V_L$ sequence provided in SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_L$ sequence provided in SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.3. $V_H$-$V_L$ Combinations

In some embodiments, an antibody provided herein comprises a $V_H$ sequence selected from SEQ ID NOs: 37, 75, 113, 151, 189, 227, 265, 303, 341, 379, 417, 455, 493, 531, 569, 607, 645, 683, 721, and 759 and a $V_L$ sequence selected from SEQ ID NOs: 38, 76, 114, 152, 190, 228, 266, 304, 342, 380, 418, 456, 494, 532, 570, 608, 646, 684, 722, and 760.

In some embodiments, an antibody provided herein comprises a $V_H$ sequence of SEQ ID NO:37 and a $V_L$ sequence of SEQ ID NO:38. In some embodiments, an antibody provided herein comprises a $V_H$ sequence of SEQ ID NO:75 and a $V_L$ sequence of SEQ ID NO:76. In some embodiments, an antibody provided herein comprises a $V_H$ sequence of SEQ ID NO:113 and a $V_L$ sequence of SEQ ID NO:114. In some embodiments, an antibody provided herein comprises a $V_H$ sequence of SEQ ID NO:151 and a $V_L$ sequence of SEQ ID NO:152. In some embodiments, an antibody provided herein comprises a $V_H$ sequence of SEQ ID NO:189 and a $V_L$ sequence of SEQ ID NO:190. In some embodiments, an antibody provided herein comprises a $V_H$ sequence of SEQ ID NO:836 and a $V_L$ sequence of SEQ ID NO:837. In some embodiments, an antibody provided herein comprises a $V_H$ sequence of SEQ ID NO:227 and a $V_L$ sequence of SEQ ID NO:228. In some embodiments, an antibody provided herein comprises a $V_H$ sequence of SEQ ID NO:265 and a $V_L$ sequence of SEQ ID NO:266. In some embodiments, an antibody provided herein comprises a $V_H$ sequence of SEQ ID NO:303 and a $V_L$ sequence of SEQ ID NO:304. In some embodiments, an antibody provided herein comprises a $V_H$ sequence of SEQ ID NO:341 and a $V_L$ sequence of SEQ ID NO:342. In some embodiments, an antibody provided herein comprises a $V_H$ sequence of SEQ ID NO:379 and a $V_L$ sequence of SEQ ID NO:380. In some embodiments, an antibody provided herein comprises a $V_H$ sequence of SEQ ID NO:417 and a $V_L$ sequence of SEQ ID NO:418. In some embodiments, an antibody provided herein comprises a $V_H$ sequence of SEQ ID NO:455 and a $V_L$ sequence of SEQ ID NO:456. In some embodiments, an antibody provided herein comprises a $V_H$ sequence of SEQ ID NO:493 and a $V_L$ sequence of SEQ ID NO:494. In some embodiments, an antibody provided herein comprises a $V_H$ sequence of SEQ ID NO:531 and a $V_L$ sequence of SEQ ID NO:532. In some embodiments, an antibody provided herein comprises a $V_H$ sequence of SEQ ID NO:569 and a $V_L$ sequence of SEQ ID NO:570. In some embodiments, an antibody provided herein comprises a $V_H$ sequence of SEQ ID NO:607 and a $V_L$ sequence of SEQ ID NO:608. In some embodiments, an antibody provided herein comprises a $V_H$ sequence of SEQ ID NO:645 and a $V_L$ sequence of SEQ ID NO:646. In some embodiments, an antibody provided herein comprises a $V_H$ sequence of SEQ ID NO:683 and a $V_L$ sequence of SEQ ID NO:684. In some embodiments, an antibody provided herein comprises a $V_H$ sequence of SEQ ID NO:721 and a $V_L$ sequence of SEQ ID NO:722. In some embodiments, an antibody provided herein comprises a $V_H$ sequence of SEQ ID NO:759 and a $V_L$ sequence of SEQ ID NO:760.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 37, 75, 113, 151, 189, 227, 265, 303, 341, 379, 417, 455, 493, 531, 569, 607, 645, 683, 721, and 759, and a $V_L$ sequence having at least about 50%, 60%, 70%, 80%, 90%, 95%, or 99% identity to an illustrative $V_L$ sequence provided in SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_H$ sequence provided in SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.4. CDRs

In some embodiments, an antibody provided herein comprises one to three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises two to three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 37, 75, 113, 151, 189, 227, 265, 303, 341, 379, 417, 455, 493, 531, 569, 607, 645, 683, 721, and 759. In some embodiments, the CDR-H1 is a CDR-H1 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, or 5 amino acid substitutions. In some embodiments, the CDR-H2 is a CDR-H2 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions. In some embodiments, the CDR-H3 is a CDR-H3 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises two to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NOs: 38, 76, 114, 152, 190, 228, 266, 304, 342, 380, 418, 456, 494, 532, 570, 608, 646, 684, 722, and 760. In some embodiments, the CDR-L1 is a CDR-L1 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, or 5 amino acid substitutions. In some embodiments, the CDR-L2 is a CDR-L2 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, or 8 amino acid substitutions. In some embodiments, the CDR-L3 is a CDR-L3 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and one to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises two to three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and two to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 37, 75, 113, 151, 189, 227, 265, 303, 341, 379, 417, 455, 493, 531, 569, 607, 645, 683, 721, and 759 and at least about 50%, 75%, 80%, 85%, 90%, or 95% identity with a CDR-L1, CDR-L2, or CDR-L3 of SEQ ID NOs: 38, 76, 114, 152, 190, 228, 266, 304, 342, 380, 418, 456, 494, 532, 570, 608, 646, 684, 722, and 760. In some embodiments, the CDR-H1 is a CDR-H1 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, or 5 amino acid substitutions; the CDR-H2 is a CDR-H2 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions; the CDR-H3 is a CDR-H3 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions; the CDR-L1 is a CDR-L1 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, or 6 amino acid substitutions; the CDR-L2 is a CDR-L2 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, or 4 amino acid substitutions; and the CDR-L3 is a CDR-L3 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, as determined by the Exemplary numbering system. In some aspects, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 selected from SEQ ID NOs: 2, 40, 78, 116, 154, 192, 230, 268, 306, 344, 382, 420, 458, 496, 534, 572, 610, 648, 686, and 724, as determined by the Exemplary numbering system. In some aspects, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724. In some embodiments, the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 selected from SEQ ID NOs: 1, 39, 77, 115, 153, 191, 229, 267, 305, 343, 381, 419, 457, 495, 533, 571, 609, 647, 685, and 723, as determined by the Exemplary numbering system. In some aspects, the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723. In some embodiments, the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725 and a CDR-H2 selected from SEQ ID NOs: 2, 40, 78, 116, 154, 192, 230, 268, 306, 344, 382, 420, 458, 496, 534, 572, 610, 648, 686, and 724. In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, a CDR-H2 selected from SEQ ID NOs: 2, 40, 78, 116, 154, 192, 230, 268, 306, 344, 382, 420, 458, 496, 534, 572, 610, 648, 686, and 724, and a CDR-H1 selected from SEQ ID NOs: 1, 39, 77, 115, 153, 191, 229, 267, 305, 343, 381, 419, 457, 495, 533, 571, 609, 647, 685, and 723. In some embodiments, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724, and the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions; the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions; and the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728, as determined by the Exemplary numbering system. In some aspects, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728. In some embodiments, the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 selected from SEQ ID NOs: 5, 43, 81, 119, 157, 195, 233, 271, 309, 347, 385, 423, 461, 499, 537, 575, 613, 651, 689, and 727, as determined by the Exemplary numbering system. In some aspects, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727. In some embodiments, the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 selected from SEQ ID NOs: 4, 42, 80, 118, 156, 194, 232, 270, 308, 346, 384, 422, 460, 498, 536, 574, 612, 650, 688, and 726, as determined by the Exemplary numbering system. In some aspects, the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728 and a CDR-L2 selected from SEQ ID NOs: 5, 43, 81, 119, 157, 195, 233, 271, 309, 347, 385, 423, 461, 499, 537, 575, 613, 651, 689, and 727. In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728, a CDR-L2 selected from SEQ ID NOs: 5, 43, 81, 119, 157, 195, 233, 271, 309, 347, 385, 423, 461, 499, 537, 575, 613, 651, 689, and 727, and a CDR-L1 selected from SEQ ID NOs: 4, 42, 80, 118, 156, 194, 232, 270, 308, 346, 384, 422, 460, 498, 536, 574, 612, 650, 688, and 726. In some embodiments, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727, and the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, or 5 amino acid substitutions; the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, or 4 amino acid substitutions; and the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, a CDR-H2 selected from SEQ ID NOs: 2, 40, 78, 116, 154, 192, 230, 268, 306, 344, 382, 420, 458, 496, 534, 572, 610, 648, 686, and 724, a CDR-H1 selected from SEQ ID NOs: 1, 39, 77, 115, 153, 191, 229, 267, 305, 343, 381, 419, 457, 495, 533, 571, 609, 647, 685, and 723, a CDR-L3 selected from SEQ ID NOs: 6, 44, 82, 120, 158, 196, 234, 272, 310, 348, 386, 424, 462, 500, 538, 576, 614, 652, 690, and 728, a CDR-L2 selected from SEQ ID NOs: 5, 43, 81, 119, 157, 195, 233, 271, 309, 347, 385, 423, 461, 499, 537, 575, 613, 651, 689, and 727, and a CDR-L1 selected from SEQ ID NOs: 4, 42, 80, 118, 156, 194, 232, 270, 308, 346, 384, 422, 460, 498, 536, 574, 612, 650, 688, and 726. In some embodiments, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724, the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727, and the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions; the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions; the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, or 5 amino acid substitutions; the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, or 5 amino acid substitutions; the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, or 4 amino acid substitutions; and the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO:1, a CDR-H2 of SEQ ID NO:2, a CDR-H3 of SEQ ID NO:3, a CDR-L1 of SEQ ID NO:4, a CDR-L2 of SEQ ID NO:5, and a CDR-L1 of SEQ ID NO:6, as determined by the Exemplary numbering system.

In some embodiments, an antibody provided herein comprises a CDR-H1 of SEQ ID NO:39, a CDR-H2 of SEQ ID NO:40, a CDR-H3 of SEQ ID NO:41, a CDR-L1 of SEQ ID NO:42, a CDR-L2 of SEQ ID NO:43, and a CDR-L1 of SEQ ID NO:44, as determined by the Exemplary numbering system.

In some embodiments, an antibody provided herein comprises a CDR-H1 of SEQ ID NO:77, a CDR-H2 of SEQ ID NO:78, a CDR-H3 of SEQ ID NO:79, a CDR-L1 of SEQ ID NO:80, a CDR-L2 of SEQ ID NO:81, and a CDR-L1 of SEQ ID NO:82, as determined by the Exemplary numbering system.

In some embodiments, an antibody provided herein comprises a CDR-H1 of SEQ ID NO:115, a CDR-H2 of SEQ ID NO:116, a CDR-H3 of SEQ ID NO:117, a CDR-L1 of SEQ ID NO:118, a CDR-L2 of SEQ ID NO:119, and a CDR-L1 of SEQ ID NO:120, as determined by the Exemplary numbering system.

In some embodiments, an antibody provided herein comprises a CDR-H1 of SEQ ID NO:153, a CDR-H2 of SEQ ID NO:154, a CDR-H3 of SEQ ID NO:155, a CDR-L1 of SEQ ID NO:156, a CDR-L2 of SEQ ID NO:157, and a CDR-L1 of SEQ ID NO:158, as determined by the Exemplary numbering system.

In some embodiments, an antibody provided herein comprises a CDR-H1 of SEQ ID NO:884, a CDR-H2 of SEQ ID NO:885, a CDR-H3 of SEQ ID NO:886, a CDR-L1 of SEQ ID NO:887, a CDR-L2 of SEQ ID NO:888, and a CDR-L1 of SEQ ID NO:889, as determined by the Exemplary numbering system.

In some embodiments, an antibody provided herein comprises a CDR-H1 of SEQ ID NO:191, a CDR-H2 of SEQ ID NO:192, a CDR-H3 of SEQ ID NO:193, a CDR-L1 of SEQ ID NO:194, a CDR-L2 of SEQ ID NO:195, and a CDR-L1 of SEQ ID NO:196, as determined by the Exemplary numbering system.

In some embodiments, an antibody provided herein comprises a CDR-H1 of SEQ ID NO:229, a CDR-H2 of SEQ ID NO:230, a CDR-H3 of SEQ ID NO:231, a CDR-L1 of SEQ ID NO:232, a CDR-L2 of SEQ ID NO:233, and a CDR-L1 of SEQ ID NO:234, as determined by the Exemplary numbering system.

In some embodiments, an antibody provided herein comprises a CDR-H1 of SEQ ID NO:267, a CDR-H2 of SEQ ID NO:268, a CDR-H3 of SEQ ID NO:269, a CDR-L1 of SEQ ID NO:270, a CDR-L2 of SEQ ID NO:271, and a CDR-L1 of SEQ ID NO:272, as determined by the Exemplary numbering system.

In some embodiments, an antibody provided herein comprises a CDR-H1 of SEQ ID NO:305, a CDR-H2 of SEQ ID NO:306, a CDR-H3 of SEQ ID NO:307, a CDR-L1 of SEQ ID NO:308, a CDR-L2 of SEQ ID NO:309, and a CDR-L1 of SEQ ID NO:310, as determined by the Exemplary numbering system.

In some embodiments, an antibody provided herein comprises a CDR-H1 of SEQ ID NO:343, a CDR-H2 of SEQ ID NO:344, a CDR-H3 of SEQ ID NO:345, a CDR-L1 of SEQ ID NO:346, a CDR-L2 of SEQ ID NO:347, and a CDR-L1 of SEQ ID NO:348, as determined by the Exemplary numbering system.

In some embodiments, an antibody provided herein comprises a CDR-H1 of SEQ ID NO:381, a CDR-H2 of SEQ ID NO:382, a CDR-H3 of SEQ ID NO:383, a CDR-L1 of SEQ ID NO:384, a CDR-L2 of SEQ ID NO:385, and a CDR-L1 of SEQ ID NO:386, as determined by the Exemplary numbering system.

In some embodiments, an antibody provided herein comprises a CDR-H1 of SEQ ID NO:419, a CDR-H2 of SEQ ID NO:420, a CDR-H3 of SEQ ID NO:421, a CDR-L1 of SEQ ID NO:422, a CDR-L2 of SEQ ID NO:423, and a CDR-L1 of SEQ ID NO:424, as determined by the Exemplary numbering system.

In some embodiments, an antibody provided herein comprises a CDR-H1 of SEQ ID NO:457, a CDR-H2 of SEQ ID NO:458, a CDR-H3 of SEQ ID NO:459, a CDR-L1 of SEQ ID NO:460, a CDR-L2 of SEQ ID NO:461, and a CDR-L1 of SEQ ID NO:462, as determined by the Exemplary numbering system.

In some embodiments, an antibody provided herein comprises a CDR-H1 of SEQ ID NO:495, a CDR-H2 of SEQ ID NO:496, a CDR-H3 of SEQ ID NO:497, a CDR-L1 of SEQ ID NO:498, a CDR-L2 of SEQ ID NO:499, and a CDR-L1 of SEQ ID NO:500, as determined by the Exemplary numbering system.

In some embodiments, an antibody provided herein comprises a CDR-H1 of SEQ ID NO:533, a CDR-H2 of SEQ ID NO:534, a CDR-H3 of SEQ ID NO:535, a CDR-L1 of SEQ ID NO:536, a CDR-L2 of SEQ ID NO:537, and a CDR-L1 of SEQ ID NO:538, as determined by the Exemplary numbering system.

In some embodiments, an antibody provided herein comprises a CDR-H1 of SEQ ID NO:571, a CDR-H2 of SEQ ID NO:572, a CDR-H3 of SEQ ID NO:573, a CDR-L1 of SEQ ID NO:574, a CDR-L2 of SEQ ID NO:575, and a CDR-L1 of SEQ ID NO:576, as determined by the Exemplary numbering system.

In some embodiments, an antibody provided herein comprises a CDR-H1 of SEQ ID NO:609, a CDR-H2 of SEQ ID NO:610, a CDR-H3 of SEQ ID NO:611, a CDR-L1 of SEQ ID NO:612, a CDR-L2 of SEQ ID NO:613, and a CDR-L1 of SEQ ID NO:614, as determined by the Exemplary numbering system.

In some embodiments, an antibody provided herein comprises a CDR-H1 of SEQ ID NO:647, a CDR-H2 of SEQ ID NO:648, a CDR-H3 of SEQ ID NO:649, a CDR-L1 of SEQ ID NO:650, a CDR-L2 of SEQ ID NO:651, and a CDR-L1 of SEQ ID NO:652, as determined by the Exemplary numbering system.

In some embodiments, an antibody provided herein comprises a CDR-H1 of SEQ ID NO:685, a CDR-H2 of SEQ ID NO:686, a CDR-H3 of SEQ ID NO:687, a CDR-L1 of SEQ ID NO:688, a CDR-L2 of SEQ ID NO:689, and a CDR-L1 of SEQ ID NO:690, as determined by the Exemplary numbering system.

In some embodiments, an antibody provided herein comprises a CDR-H1 of SEQ ID NO:723, a CDR-H2 of SEQ ID NO:724, a CDR-H3 of SEQ ID NO:725, a CDR-L1 of SEQ ID NO:726, a CDR-L2 of SEQ ID NO:727, and a CDR-L1 of SEQ ID NO:728, as determined by the Exemplary numbering system.

2.2.5. Consensus Sequences

In some embodiments, provided herein is a first family of antibodies, wherein an antibody of such family comprises the following six CDR sequences: (a) a CDR-H1 having the sequence G-F-T-F-S-$X_1$-Y-A-M-$X_2$, wherein $X_1$ is D or S and $X_2$ is A or G (SEQ ID NO:773); (b) a CDR-H2 having the sequence $X_3$-I-S-G-S-G-G-L-T-Y-Y-A-D-S-V-K-G, wherein $X_3$ is A or T (SEQ ID NO:774); (c) a CDR-H3 having the sequence APYGYYMDV (SEQ ID NO:775); (d) a CDR-L1 having the sequence RASQSISSWLA (SEQ ID NO:776); (e) a CDR-L2 having the sequence KASSLES (SEQ ID NO:777); and (f) a CDR-L3 having the sequence QQYKSYIT (SEQ ID NO:778). In some embodiments, an antibody of such family comprises a $V_H$ sequence of SEQ ID NO:761 and a $V_L$ sequence of SEQ ID NO:762. In some embodiments, provided herein is an antibody within such first family.

In some embodiments, provided herein is a second family of antibodies, wherein an antibody of such family comprises the following six CDR sequences: (a) a CDR-H1 having the sequence G-Y-T-F-$X_1$$X_2$Y-G-I-S, wherein $X_1$ is D or R and $X_2$ is S or V (SEQ ID NO:779); (b) a CDR-H2 having the sequence W-$X_3$A-P-Y-$X_4$G-N-T-N-Y-A-Q-K-L-Q-G, wherein $X_3$ is I or V and $X_4$ is S or N (SEQ ID NO:780); (c) a CDR-H3 having the sequence D-A-G-T-Y-S-P-$X_5$G-Y-G-M-D-V, wherein $X_5$ is F or Y (SEQ ID NO:781); (d) a CDR-L1 having the sequence $X_6$A-S-$X_7$S-I-$X_8$$X_9$W-L-A, wherein $X_6$ is R or Q, $X_7$ is Q, E, or H, $X_8$ is S, D, or N, and $X_9$ is S or N (SEQ ID NO:782); (e) a CDR-L2 having the sequence $X_{10}$-A-$X_{11}$-$X_{12}$-L-E-$X_{13}$, wherein $X_{10}$ is K or S, $X_{11}$ is S or Y, $X_{12}$ is S, Y, or N, and $X_{13}$ is S or Y (SEQ ID NO:783); and (f) a CDR-L3 having the sequence Q-$X_{14}$-F-Q-$X_{15}$-L-P-P-F-T, wherein $X_{14}$ is Q, L, or R, and $X_{15}$ is S or K (SEQ ID NO:784). In some embodiments, an antibody of such family comprises a $V_H$ sequence of SEQ ID NO:763 and a $V_L$ sequence of SEQ ID NO:764. In some embodiments, provided herein is an antibody within such second family.

In some embodiments, provided herein is a third family of antibodies, wherein an antibody of such family comprises the following six CDR sequences: (a) a CDR-H1 having the sequence G-F-T-F-$X_1$-S-$X_2$G-M-H, wherein $X_1$ is H or R and $X_2$ is R or Y (SEQ ID NO:785); (b) a CDR-H2 having the sequence VITYDGINKYYADSVEG (SEQ ID NO:786); (c) a CDR-H3 having the sequence DGVYYGVYDY (SEQ ID NO:787); (d) a CDR-L1 having the sequence KSSQSVLFSSNNKNYLA (SEQ ID NO:788); (e) a CDR-L2 having the sequence WASTRES (SEQ ID NO:789); and (f) a CDR-L3 having the sequence QQFHSYPLT (SEQ ID NO:790). In some embodiments, an antibody of such family comprises a $V_H$ sequence of SEQ ID NO:765 and a $V_L$ sequence of SEQ ID NO:766. In some embodiments, provided herein is an antibody within such third family.

In some embodiments, provided herein is a fourth family of antibodies, wherein an antibody of such family comprises the following six CDR sequences: (a) a CDR-H1 having the sequence GGTFSSNAIG (SEQ ID NO:791); (b) a CDR-H2 having the sequence SIIPIIGFANYAQKFQG (SEQ ID NO:792); (c) a CDR-H3 having the sequence DSGYYY-GASSFGMDV (SEQ ID NO:793); (d) a CDR-L1 having the sequence RASQSVSSNLA (SEQ ID NO:794); (e) a CDR-L2 having the sequence GASTRAT (SEQ ID NO:795); and (f) a CDR-L3 having the sequence EQYNNLPLT (SEQ ID NO:796). In some embodiments, an antibody of such family comprises a $V_H$ sequence of SEQ ID NO:767 and a $V_L$ sequence of SEQ ID NO:768. In some embodiments, provided herein is an antibody within such fourth family.

In some embodiments, provided herein is a fifth family of antibodies, wherein an antibody of such family comprises the following six CDR sequences: (a) a CDR-H1 having the sequence G-G-S-$X_1$-S-S-G-$X_2$-Y-W-S, wherein $X_1$ is I or L and $X_2$ is Q or Y (SEQ ID NO:797); (b) a CDR-H2 having the sequence E-I-$X_3$$X_4$-S-G-S-T-R-Y-N-P-S-L-K-S, wherein $X_3$ is Y or G and $X_4$ is Y or A (SEQ ID NO:798); (c) a CDR-H3 having the sequence D-$X_5$-P-Y-Y-Y-$X_6$-G-G-Y-Y-Y-M-D-V, wherein $X_5$ is T or A and $X_6$ is E, G, or D (SEQ ID NO:799); (d) a CDR-L1 having the sequence R-A-S-$X_7$-S-V-$X_8$-S-S-$X_9$-L-A, wherein $X_7$ is Q, E, or D, $X_8$ is S or D, and $X_9$ is Y or F (SEQ ID NO:800); (e) a CDR-L2 having the sequence G-A-$X_{10}$-$X_{11}$-R-$X_{12}$-$X_{13}$, wherein $X_{10}$ is S, D, F, or Y, $X_{11}$ is S or T, $X_{12}$ is A or Q, and $X_{13}$ is T or N (SEQ ID NO:801); and (f) a CDR-L3 having the sequence Q-Q-$X_{14}$-G-V-V-P-Y-T, wherein $X_{14}$ is V, A, or D (SEQ ID NO:802). In some embodiments, an antibody of such family comprises a $V_H$ sequence of SEQ ID NO:769 and a $V_L$ sequence of SEQ ID NO:770. In some embodiments, provided herein is an antibody within such fifth family.

In some embodiments, provided herein is a sixth family of antibodies, wherein an antibody of such family comprises the following six CDR sequences: (a) a CDR-H1 having the sequence GYTFANYYMH (SEQ ID NO:803); (b) a CDR-H2 having the sequence IINPSGGITVYAQKFQG (SEQ ID NO:804); (c) a CDR-H3 having the sequence GGSK-VAALAFDI (SEQ ID NO:805); (d) a CDR-L1 having the sequence QASQDISNSLN (SEQ ID NO:806); (e) a CDR-L2 having the sequence DASNLET (SEQ ID NO:807); and (f) a CDR-L3 having the sequence QQYNFHPLT (SEQ ID NO:808). In some embodiments, an antibody of such family comprises a $V_H$ sequence of SEQ ID NO:771 and a $V_L$ sequence of SEQ ID NO:772. In some embodiments, provided herein is an antibody within such sixth family.

In some embodiments, provided herein is a seventh family of antibodies, wherein an antibody of such family comprises the following six CDR sequences: (a) a CDR-H1 having the sequence G-Y-T-F-D-$X_1$-Y-G-I-S, wherein $X_1$ is V or A (SEQ ID NO:872); (b) a CDR-H2 having the sequence W-I-A-P-Y-$X_2$-G-N-T-N-Y-A-Q-K-L-Q-G, wherein $X_2$ is N or S (SEQ ID NO:873); (c) a CDR-H3 having the sequence D-A-G-T-Y-S-P-F-G-Y-G-M-D-V (SEQ ID NO:874); (d) a CDR-L1 having the sequence $X_3$-A-S-$X_4$-S-I-$X_5$$X_6$-W-L-A, wherein $X_3$ is R or Q, $X_4$ is Q or E, $X_5$ is S or N, and $X_6$ is S or N (SEQ ID NO:875); (e) a CDR-L2 having the sequence K-A-$X_7$$X_8$-L-E-$X_9$, wherein $X_7$ is S or Y, $X_8$ is S or N, and $X_9$ is S or Y (SEQ ID NO:876); and (f) a CDR-L3 having the sequence Q-$X_{10}$-F-Q-$X_{11}$-L-P-P-F-T, wherein $X_{10}$ is Q or L, and $X_{11}$ is S or K (SEQ ID NO:877). In some embodiments, an antibody of such family comprises a $V_H$ sequence of SEQ ID NO:868 and a $V_L$ sequence of SEQ ID NO:869. In some embodiments, provided herein is an antibody within such seventh family.

In some embodiments, provided herein is an eighth family of antibodies, wherein an antibody of such family comprises the following six CDR sequences: (a) a CDR-H1 having the sequence G-Y-T-F-R-S-Y-G-I-S (SEQ ID NO:878); (b) a CDR-H2 having the sequence W-V-A-P-Y-$X_1$-G-N-T-N-Y-A-Q-K-L-Q-G, wherein $X_1$ is S or N (SEQ ID NO: 879); (c) a CDR-H3 having the sequence D-A-G-T-Y-S-P-Y-G-Y-G-M-D-V (SEQ ID NO:880); (d) a CDR-L1 having the sequence $X_2$-A-S-$X_3$-S-I-$X_4$-S-W-L-A, wherein $X_2$ is R or Q, $X_3$ is Q or H, $X_4$ is S or D (SEQ ID NO:881); (e) a CDR-L2 having the sequence $X_5$-A-S-$X_6$-L-E-S, wherein $X_5$ is K or S, $X_6$ is S or Y (SEQ ID NO:882); and (f) a CDR-L3 having the sequence Q-$X_7$-F-Q-S-L-P-P-F-T, wherein $X_7$ is Q, L, or R (SEQ ID NO:883). In some embodiments, an antibody of such family comprises a VH sequence of SEQ ID NO:870 and a VL sequence of SEQ ID NO:871. In some embodiments, provided herein is an antibody within such eighth family.

2.2.6. Functional Properties of Antibody Variants

As described above, and elsewhere in this disclosure, provided herein are antibody variants defined based on percent identity to an illustrative antibody sequence provided herein, or substitution of amino acid residues in comparison to an illustrative antibody sequence provided herein.

In some embodiments, a variant of an antibody provided herein has specificity for hTF. In some embodiments, a variant of an antibody provided herein has specificity for cTF. In some embodiments, a variant of an antibody provided herein has specificity for mTF. In some embodiments, a variant of an antibody provided herein has specificity for hTF and cTF. In some embodiments, a variant of an antibody provided herein has specificity for hTF and mTF. In some embodiments, a variant of an antibody provided herein has specificity for cTF and mTF. In some embodiments, a variant of an antibody provided herein has specificity for hTF, cTF and mTF.

In some embodiments, a variant of an antibody that is derived from an illustrative antibody sequence provided herein retains affinity, as measured by $K_D$, for hTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for cTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both hTF and cTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both hTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both cTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for all three of hTF, cTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody.

In some embodiments, a variant of an antibody provided herein retains the ability to inhibit TF signaling, as measured by one or more assays or biological effects described herein. In some embodiments, a variant of an antibody provided herein retains the normal function of TF in the blood coagulation processes.

In some embodiments, a variant of an antibody provided herein competes for binding to TF with an antibody selected from 1F, 1G, 25A, 25A3, 25A5, 25A5-T, 25G, 25G1, 25G9, 29D, 29E, 39A, 43B, 43B1, 43B7, 43D, 43D7, 43D8, 43E, 43Ea, and 54E, each as provided in Table 13 of this disclosure. In some embodiments, a variant of an antibody provided herein competes for binding to TF with an antibody selected from 25A, 25A3, 25A5, 25A5-T, 25G, 25G1, and 25G9. In some embodiments, a variant of an antibody provided herein competes for binding to TF with an antibody selected from 43B, 43B1, 43B7, 43D, 43D7, 43D8, 43E, and 43Ea. In some embodiments, a variant of an antibody provided herein competes for binding to TF with an antibody selected from 25A, 25A3, 25A5, 25A5-T, 25G, 25G1, 25G9, 43B, 43B1, 43B7, 43D, 43D7, 43D8, 43E, and 43Ea. In some embodiments, a variant of an antibody provided herein competes for binding to TF with an antibody selected from 1F, 1G, 29D, 29E, 39A, or 54E.

In some embodiments, a variant of an antibody provided herein allows human thrombin generation as determined by thrombin generation assay (TGA). In some embodiments, a variant of an antibody provided herein does not inhibit human thrombin generation as determined by thrombin generation assay (TGA).

In some embodiments, a variant of an antibody provided herein binds human TF at a human TF binding site that is distinct from a human TF binding site bound by human FX. In some embodiments, a variant of an antibody provided herein does not interfere with the ability of TF:FVIIa to convert FX into FXa.

In some embodiments, a variant of an antibody provided herein binds human TF at a human TF binding site that is distinct from a human TF binding site bound by human FVIIa. In some embodiments, a variant of an antibody provided herein does not compete for binding to human TF with human FVIIa.

In some embodiments, a variant of an antibody provided herein inhibits FVIIa-dependent TF signaling.

In some embodiments, a variant of an antibody provided herein binds mouse TF (SEQ ID NO:817). In some embodiments, a variant of an antibody provided herein binds mouse TF with an affinity lower (as indicated by higher $K_D$) than the affinity of the antibody for hTF. In some embodiments, a variant of an antibody provided herein does not bind mTF.

In some embodiments, a variant of an antibody provided herein binds pig TF (SEQ ID NO:824). In some embodiments, a variant of an antibody provided herein binds pig TF with an affinity lower (as indicated by higher $K_D$) than the affinity of the antibody for hTF. In some embodiments, a variant of an antibody provided herein does not bind pTF.

In some embodiments, a variant of an antibody provided herein binds the same epitope of TF as such antibody.

2.2.7. Other Functional Properties of Antibodies

In some embodiments, an antibody provided herein has one or more of the characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, an antibody provided herein has two or more of the characteristics listed in the foregoing (a)-(dd). In some embodiments, an antibody provided herein has three or more of the characteristics listed in the foregoing (a)-(dd). In some embodiments, an antibody provided herein has four or more of the characteristics listed in the foregoing (a)-(dd). In some embodiments, an antibody provided herein has five or more of the characteristics listed in the foregoing (a)-(dd). In some embodiments, an antibody provided herein has six or more of the characteristics listed in the foregoing (a)-(dd). In some embodiments, an antibody provided herein has seven or more of the characteristics listed in the foregoing (a)-(dd). In some embodiments, an antibody provided herein has eight or more of the characteristics listed in the foregoing (a)-(dd). In some embodiments, an antibody provided herein has nine or more of the characteristics listed in the foregoing (a)-(dd). In some embodiments, an antibody provided herein has ten or more of the characteristics listed in the foregoing (a)-(dd). In some embodiments, an antibody provided herein has eleven or more of the characteristics listed in the foregoing (a)-(dd). In some embodiments, an antibody provided herein has twelve or more of the characteristics listed in the foregoing (a)-(dd). In some embodiments, an antibody provided herein has thirteen or more of the characteristics listed in the foregoing (a)-(dd). In some embodiments, an antibody provided herein has fourteen or more of the characteristics listed in the foregoing (a)-(dd). In some embodiments, an antibody provided herein has fifteen or more of the characteristics listed in the foregoing (a)-(dd). In some embodiments, an antibody provided herein has sixteen or more of the characteristics listed in the foregoing (a)-(dd). In some embodiments, an antibody provided herein has seventeen or more of the characteristics listed in the foregoing (a)-(dd). In some embodiments, an antibody provided herein has eighteen or more of the characteristics listed in the foregoing (a)-(dd). In some embodiments, an antibody provided herein has nineteen or more of the characteristics listed in the foregoing (a)-(dd). In some embodiments, an antibody provided herein has twenty or more of the characteristics listed in the foregoing (a)-(dd). In some embodiments, an antibody provided herein has twenty-one or more of the characteristics listed in the foregoing (a)-(dd). In some embodiments, an antibody provided herein has twenty-two or more of the characteristics listed in the foregoing (a)-(dd). In some embodiments, an antibody provided herein has twenty-three of the characteristics listed in the foregoing (a)-(dd). In some embodiments, an antibody provided herein has twenty-four of the characteristics listed in the foregoing (a)-(dd). In some embodiments, an antibody provided herein has twenty-five of the characteristics listed in the foregoing (a)-(dd). In some embodiments, an antibody provided herein has twenty-six of the characteristics listed in the foregoing (a)-(dd). In some embodiments, an antibody provided herein has twenty-seven of the characteristics listed in the foregoing (a)-(dd). In some embodiments, an antibody provided herein has twenty-eight of the characteristics listed in the foregoing (a)-(dd). In some embodiments, an antibody provided herein has twenty-nine of the characteristics listed in the foregoing (a)-(dd). In some embodiments, an antibody provided herein has all thirty of the characteristics listed in the foregoing (a)-(dd).

In some embodiments, an antibody provided herein has one or more of the characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, an antibody provided herein has two or more of the characteristics listed in the foregoing (a)-(dd). In some embodiments, an antibody provided herein has three or more of the characteristics listed in the foregoing (a)-(dd). In some embodiments, an antibody provided herein has four or more of the characteristics listed in the foregoing (a)-(dd). In some embodiments, an antibody provided herein has five or more of the characteristics listed in the foregoing (a)-(dd). In some embodiments, an antibody provided herein has six or more of the characteristics listed in the foregoing (a)-(dd). In some embodiments, an antibody provided herein has seven or more of the characteristics listed in the foregoing (a)-(dd). In some embodiments, an antibody provided herein has eight or more of the characteristics listed in the foregoing (a)-(dd). In some embodiments, an antibody provided herein has nine or more of the characteristics listed in the foregoing (a)-(dd). In some embodiments, an antibody provided herein has ten or more of the characteristics listed in the foregoing (a)-(dd). In some embodiments, an antibody provided herein has eleven or more of the characteristics listed in the foregoing (a)-(dd). In some embodiments, an antibody provided herein has twelve or more of the characteristics listed in the foregoing (a)-(dd). In some embodiments, an antibody provided herein has thirteen or more of the characteristics listed in the foregoing (a)-(dd). In some embodiments, an antibody provided herein has fourteen or more of the characteristics listed in the foregoing (a)-(dd). In some embodiments, an antibody provided herein has fifteen or more of the characteristics listed in the foregoing (a)-(dd). In some embodiments, an antibody provided herein has sixteen or more of the characteristics listed in the foregoing (a)-(dd). In some embodiments, an antibody provided herein has seventeen or more of the characteristics listed in the foregoing (a)-(dd). In some embodiments, an antibody provided herein has eighteen or more of the characteristics listed in the foregoing (a)-(dd). In some embodiments, an antibody provided herein has nineteen or more of the characteristics listed in the foregoing (a)-(dd). In some embodiments, an antibody provided herein has twenty or more of the characteristics listed in the foregoing (a)-(dd). In some embodiments, an antibody provided herein has twenty-one or more of the characteristics listed in the foregoing (a)-(dd). In some embodiments, an antibody provided herein has twenty-two or more of the characteristics listed in the foregoing (a)-(dd). In some embodiments, an antibody provided herein has twenty-three of the characteristics listed in the foregoing (a)-(dd). In some embodiments, an antibody provided herein has twenty-four of the characteristics listed in the foregoing (a)-(dd). In some embodiments, an antibody provided herein has twenty-five of the characteristics listed in the foregoing (a)-(dd). In some embodiments, an antibody provided herein has twenty-six of the characteristics listed in the foregoing (a)-(dd). In some embodiments, an antibody provided herein has twenty-seven of the characteristics listed in the foregoing (a)-(dd). In some embodiments, an antibody provided herein has twenty-eight of the characteristics listed in the foregoing (a)-(dd). In some embodiments, an antibody provided herein has twenty-nine of the characteristics listed in the foregoing (a)-(dd). In some embodiments, an antibody provided herein has all thirty of the characteristics listed in the foregoing (a)-(dd).

In some embodiments, an antibody provided herein exhibits a combination of characteristics comprising two or more of characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of characteristics comprising two or more of characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); binds to cynomolgus TF; the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); binds to cynomolgus TF; the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); binds to cynomolgus TF; the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); binds to cynomolgus TF; the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

2.3. Affinity and Other Properties of TF Antibodies 2.3.1. Affinity of TF Antibodies In some embodiments, the affinity of an antibody provided herein for TF as indicated by $K_D$, is less than about $10^{-5}$M, less than about $10^{-6}$ M, less than about $10^{-7}$M, less than about $10^{-8}$ M, less than about $10^{-9}$M, less than about $10^{-10}$ M, less than about $10^{-11}$ M, or less than about $10^{-12}$ M. In some embodiments, the affinity of the antibody is between about $10^{-7}$ M and $10^{-12}$ M. In some embodiments, the affinity of the antibody is between about $10^{-7}$ M and $10^{-11}$M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-12}$ M. In some embodiments, the affinity of the antibody is between about $10^{-8}$ M and $10^{-11}$ M. In some embodiments, the affinity of the antibody is between about $10^{-9}$M and $10^{-11}$ M. In some embodiments, the affinity of the antibody is between about $10^{-10}$ M and $10^{-11}$ M.

In some embodiments, the $K_D$ value of an antibody provided herein for cTF is no more than 15× of the $K_D$ value of the antibody for hTF. In some embodiments, the $K_D$ value of an antibody provided herein for cTF is no more than 10× of the $K_D$ value of the antibody for hTF. In some embodiments, the $K_D$ value of an antibody provided herein for cTF is no more than 8× of the $K_D$ value of the antibody for hTF. In some embodiments, the $K_D$ value of an antibody provided herein for cTF is no more than 5× of the $K_D$ value of the antibody for hTF. In some embodiments, the $K_D$ value of an antibody provided herein for cTF is no more than 3× of the $K_D$ value of the antibody for hTF. In some embodiments, the $K_D$ value of an antibody provided herein for cTF is no more than 2× of the $K_D$ value of the antibody for hTF.

In some embodiments, the $K_D$ value of an antibody provided herein for mTF is no more than 20× of the $K_D$ value of the antibody for hTF. In some embodiments, the $K_D$ value of an antibody provided herein for mTF is no more than 15× of the $K_D$ value of the antibody for hTF. In some embodiments, the $K_D$ value of an antibody provided herein for mTF is no more than 10× of the $K_D$ value of the antibody for hTF. In some embodiments, the $K_D$ value of an antibody provided herein for mTF is no more than 5× of the $K_D$ value of the antibody for hTF. In some embodiments, the $K_D$ value of an antibody provided herein for mTF is no more than 2× of the $K_D$ value of the antibody for hTF.

In some embodiments, the affinity of an antibody provided herein for hTF as indicated by $K_D$ measured by Biacore, as set forth in Table 5 is selected from about 0.31 nM, about 6.20 nM, about 0.36 nM, about 0.08 nM, about 23.0 nM, about 0.94 nM, about 13.3 nM, about 0.47 nM, about 0.09 nM, about 1.75 nM, about 0.07 nM, about 0.14 nM, about 2.09 nM, about 0.06 nM, about 0.15 nM, about 1.46 nM, about 1.60 nM, and about 0.42 nM. In some embodiments, such affinity as indicated by $K_D$ ranges from about 23.0 nM to about 0.06 nM. In some embodiments, such is about 23.0 nM or less.

In some embodiments, the affinity of an antibody provided herein for hTF as indicated by $K_D$ measured by ForteBio, as set forth in Table 5 is selected from about 1.28 nM, about 2.20 nM, about 8.45 nM, about 1.67 nM, about 0.64 nM, about 21.9 nM, about 3.97 nM, about 35.8 nM, about 3.30 nM, about 2.32 nM, about 0.83 nM, about 2.40 nM, about 0.96 nM, about 0.86 nM, about 3.84 nM, about 1.02 nM, about 1.61 nM, about 2.52 nM, about 2.28 nM, and about 1.59 nM. In some embodiments, such affinity as indicated by $K_D$ ranges from about 35.8 nM to about 0.64 nM. In some embodiments, such $K_D$ is about 35.8 nM or less.

In some embodiments, the affinity of an antibody provided herein for cTF as indicated by $K_D$ measured by Biacore, as set forth in Table 5 is selected from about 0.26 nM, about 5.42 nM, about 0.21 nM, about 0.04 nM, about 18.0 nM, about 0.78 nM, about 16.4 nM, about 5.06 nM, about 0.08 nM, about 5.64 nM, about 0.12 nM, about 0.24 nM, about 5.66 nM, about 0.39 nM, about 5.69 nM, about 6.42 nM, and about 1.83 nM. In some embodiments, such affinity as indicated by $K_D$ ranges from about 18.0 nM to about 0.04 nM. In some embodiments, such $K_D$ is about 18.0 nM or less.

In some embodiments, the affinity of an antibody provided herein for cTF as indicated by $K_D$ measured by ForteBio, as set forth in Table 5 is selected from about 1.43 nM, about 2.70 nM, about 7.65 nM, about 1.36 nM, about 0.76 nM, about 17.5 nM, about 4.99 nM, about 42.9 nM, about 12.0 nM, about 15.0 nM, about 0.57 nM, about 3.40 nM, about 1.05 nM, about 0.94 nM, about 4.12 nM, about 1.11 nM, about 1.96 nM, about 4.07 nM, about 2.71 nM, and about 4.16 nM. In some embodiments, such affinity as indicated by $K_D$ ranges from about 42.9 nM to about 0.57 nM. In some embodiments, such $K_D$ is about 42.9 nM or less.

In some embodiments, the affinity of an antibody provided herein for mTF as indicated by $K_D$ measured by Biacore, as set forth in Table 5 is selected from about 5.4 nM, about 2.9 nM, about 21 nM, and about 2.4 nM. In some embodiments, such affinity as indicated by $K_D$ ranges from about 21 nM to about 2.4 nM. In some embodiments, such $K_D$ is about 21 nM or less.

In some embodiments, the affinity of an antibody provided herein for mTF as indicated by $K_D$ measured by ForteBio, as set forth in Table 5 is selected from about 263 nM, about 131 nM, about 188 nM, about 114 nM, about 34.2 nM, about 9.16 nM, about 161 nM, about 72.1 nM, about 360 nM, about 281 nM, about 41.4 nM, about 6.12 nM, about 121 nM, and about 140 nM. In some embodiments, such affinity as indicated by $K_D$ ranges from about 360 nM to about 6.12 nM. In some embodiments, such $K_D$ is about 360 nM or less.

Figure 1B:
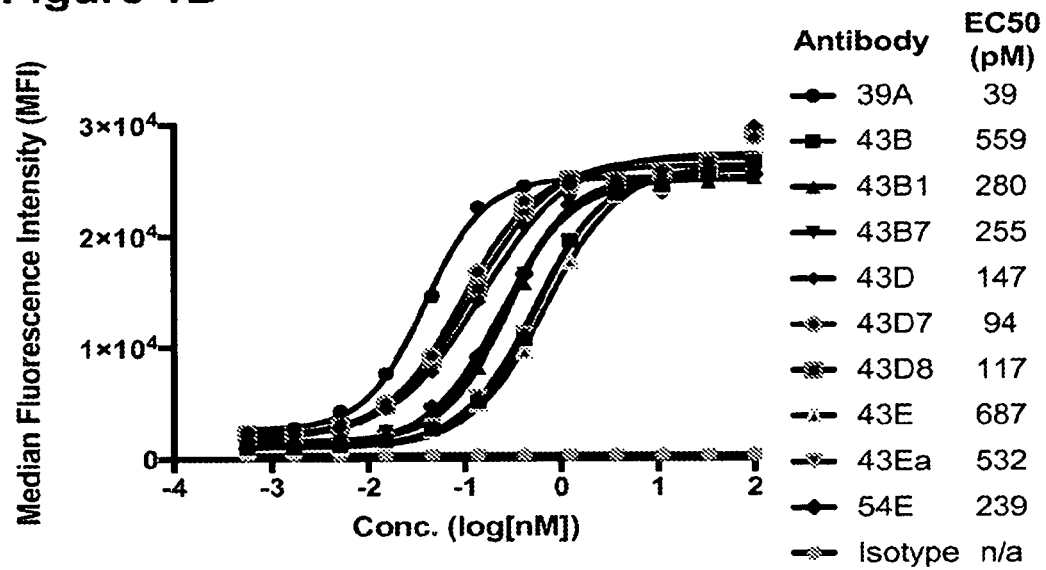

In some embodiments, the affinity of an antibody provided herein for hTF as indicated by $EC_{50}$ measured with human TF-positive HCT-116 cells, as set forth in FIGS. 1A and 1B is selected from about 50 pM, about 58 pM, about 169 pM, about 77 pM, about 88 pM, about 134 pM, about 85 pM, about 237 pM, about 152 pM, about 39 pM, about 559 pM, about 280 pM, about 255 pM, about 147 pM, about 94 pM, about 117 pM, about 687 pM, about 532 pM, and about 239 pM. In some embodiments, such affinity ranges from about 687 pM to about 39 pM. In some embodiments, such $EC_{50}$ is about 687 pM or less.

Figure 2A:
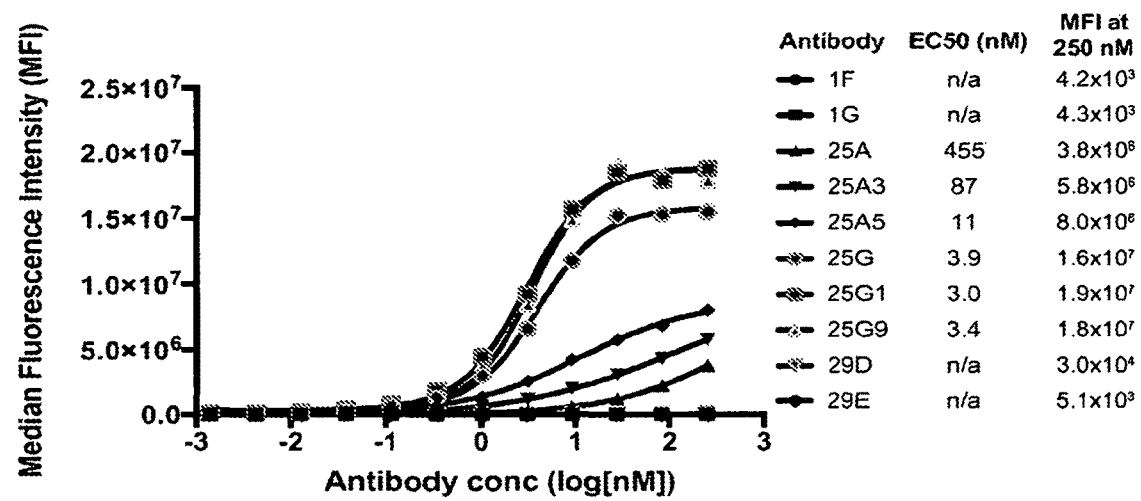
FIGS. 2A and 2B show binding of anti-TF antibodies to mouse TF-positive cells.
Figure 2B:
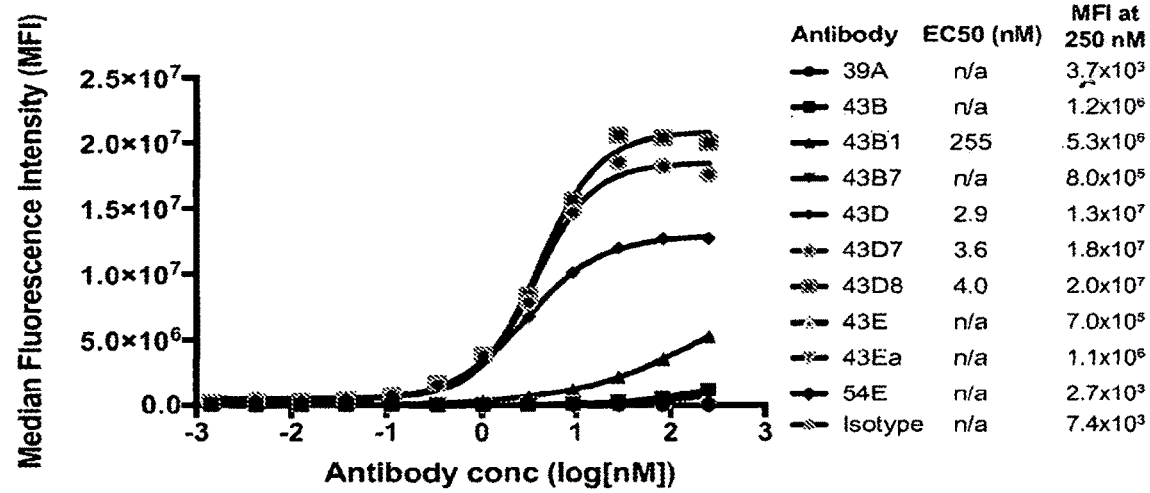

In some embodiments, the affinity of an antibody provided herein for mTF as indicated by $EC_{50}$ measured with mouse TF-positive CHO cells, as set forth in FIGS. 2A and 2B is selected from about 455 nM, about 87 nM, about 11 nM, about 3.9 nM, about 3.0 nM, about 3.4 nM, about 255 nM, about 2.9 nM, about 3.6 nM, and about 4.0 nM. In some embodiments, such affinity ranges from about 455 nM to about 2.9 nM. In some embodiments, such $EC_{50}$ is about 455 pM or less.

In some embodiments, the $K_D$ value of an antibody provided herein for pTF is no more than 20× of the $K_D$ value of the antibody for hTF. In some embodiments, the $K_D$ value of an antibody provided herein for pTF is no more than 15× of the $K_D$ value of the antibody for hTF. In some embodiments, the $K_D$ value of an antibody provided herein for pTF is no more than 10× of the $K_D$ value of the antibody for hTF. In some embodiments, the $K_D$ value of an antibody provided herein for pTF is no more than 5× of the $K_D$ value of the antibody for hTF. In some embodiments, the $K_D$ value of an antibody provided herein for pTF is no more than 2× of the $K_D$ value of the antibody for hTF.

In some embodiments, the affinity of an antibody provided herein for pTF as indicated by $K_D$ measured by Biacore, as set forth in Table 40 is 3.31 nM or 12.9 nM.

2.3.2. Thrombin Generation in the Presence of TF Antibodies

In some embodiments, the TF antibodies provided herein do not inhibit human thrombin generation as determined by thrombin generation assay (TGA). In certain embodiments, the TF antibodies provided herein allow human thrombin generation as determined by thrombin generation assay (TGA).

In some embodiments, the percent peak thrombin generation (% Peak IIa) is at least 40% in the presence of no less than 100 nM TF antibody compared to the control conditions without the antibody, as determined by thrombin generation assay (TGA). In some embodiments, the % Peak IIa is at least 50% in the presence of no less than 100 nM TF antibody compared to the control conditions without the antibody, as determined by thrombin generation assay (TGA). In some embodiments, the % Peak IIa is at least 60% in the presence of no less than 100 nM TF antibody compared to the control conditions without the antibody, as determined by thrombin generation assay (TGA). In some embodiments, the % Peak IIa is at least 70% in the presence of no less than 100 nM TF antibody compared to the control conditions without the antibody, as determined by thrombin generation assay (TGA). In some embodiments, the % Peak IIa is at least 80% in the presence of no less than 100 nM TF antibody compared to the control conditions without the antibody, as determined by thrombin generation assay (TGA). In some embodiments, the % Peak IIa is at least 90% in the presence of no less than 100 nM TF antibody compared to the control conditions without the antibody, as determined by thrombin generation assay (TGA). In some embodiments, the % Peak IIa is at least 95% in the presence of no less than 100 nM TF antibody compared to the control conditions without the antibody, as determined by thrombin generation assay (TGA). In some embodiments, the % Peak IIa is at least 99% in the presence of no less than 100 nM TF antibody compared to the control conditions without the antibody, as determined by thrombin generation assay (TGA).

In some embodiments, the % Peak IIa is at least 40% in the presence of no less than 50 nM TF antibody compared to the control conditions without the antibody, as determined by thrombin generation assay (TGA). In some embodiments, the % Peak IIa is at least 50% in the presence of no less than 50 nM TF antibody compared to the control conditions without the antibody, as determined by thrombin generation assay (TGA). In some embodiments, the % Peak IIa is at least 60% in the presence of no less than 50 nM TF antibody compared to the control conditions without the antibody, as determined by thrombin generation assay (TGA). In some embodiments, the % Peak IIa is at least 70% in the presence of no less than 50 nM TF antibody compared to the control conditions without the antibody, as determined by thrombin generation assay (TGA). In some embodiments, the % Peak IIa is at least 80% in the presence of no less than 50 nM TF antibody compared to the control conditions without the antibody, as determined by thrombin generation assay (TGA). In some embodiments, the % Peak IIa is at least 90% in the presence of no less than 50 nM TF antibody compared to the control conditions without the antibody, as determined by thrombin generation assay (TGA). In some embodiments, the % Peak IIa is at least 95% in the presence of no less than 50 nM TF antibody compared to the control conditions without the antibody, as determined by thrombin generation assay (TGA). In some embodiments, the % Peak IIa is at least 99% in the presence of no less than 50 nM TF antibody compared to the control conditions without the antibody, as determined by thrombin generation assay (TGA).

In some embodiments, the % Peak IIa is at least 60% in the presence of no less than 10 nM TF antibody compared to the control conditions without the antibody, as determined by thrombin generation assay (TGA). In some embodiments, the % Peak IIa is at least 70% in the presence of no less than 10 nM TF antibody compared to the control conditions without the antibody, as determined by thrombin generation assay (TGA). In some embodiments, the % Peak IIa is at least 80% in the presence of no less than 10 nM TF antibody compared to the control conditions without the antibody, as determined by thrombin generation assay (TGA). In some embodiments, the % Peak IIa is at least 90% in the presence of no less than 10 nM TF antibody compared to the control conditions without the antibody, as determined by thrombin generation assay (TGA). In some embodiments, the % Peak IIa is at least 95% in the presence of no less than 10 nM TF antibody compared to the control conditions without the antibody, as determined by thrombin generation assay (TGA). In some embodiments, the % Peak IIa is at least 99% in the presence of no less than 10 nM TF antibody compared to the control conditions without the antibody, as determined by thrombin generation assay (TGA).

In some embodiments, the % Peak IIa in the presence of 100 nM TF antibody, as set forth in Table 6 and Table 37 is selected from about 99%, about 100%, about 103%, about 64%, about 52%, about 87%, about 96%, about 98%, and about 53% compared to the control conditions without the antibody, as determined by thrombin generation assay (TGA) without antibody pre-incubation. In some embodiments, such % Peak IIa ranges from about 52% to about 103%. In some embodiments, such % Peak IIa is about 52% or more.

In some embodiments, the % Peak IIa in the presence of 50 nM TF antibody, as set forth in Table 6 and Table 37 is selected from about 99%, about 100%, about 103%, about 67%, about 58%, about 89%, about 96%, about 98%, about 68%, about 62%, and about 88% compared to the control conditions without the antibody, as determined by thrombin generation assay (TGA) without antibody pre-incubation. In some embodiments, such % Peak IIa ranges from about 58% to about 103%. In some embodiments, such % Peak IIa is about 58% or more.

In some embodiments, the % Peak IIa in the presence of 10 nM TF antibody, as set forth in Table 6 and Table 37 is selected from about 100%, about 99%, about 103%, about 87%, about 83%, about 95%, about 98%, about 86%, and about 96% compared to the control conditions without the antibody, as determined by thrombin generation assay (TGA) without antibody pre-incubation. In some embodiments, such % Peak IIa ranges from about 83% to about 103%. In some embodiments, such % Peak IIa is about 83% or more.

In some embodiments, the % Peak IIa in the presence of 100 nM TF antibody, as set forth in Table 7 and Table 38 is selected from about 108%, about 105%, about 111%, about 58%, about 47%, about 91%, about 103%, about 109%, about 107%, and about 45% compared to the control conditions without the antibody, as determined by thrombin generation assay (TGA) with 10 min antibody pre-incubation. In some embodiments, such % Peak IIa ranges from about 45% to about 111%. In some embodiments, such % Peak IIa is about 45% or more.

In some embodiments, the % Peak IIa in the presence of 50 nM TF antibody, as set forth in Table 7 and Table 38 is selected from about 107%, about 104%, about 114%, about 62%, about 49%, about 87%, about 105%, about 109%, about 55%, and about 92% compared to the control conditions without the antibody, as determined by thrombin generation assay (TGA) with 10 min antibody pre-incubation. In some embodiments, such % Peak IIa ranges from about 49% to about 114%. In some embodiments, such % Peak IIa is about 49% or more.

In some embodiments, the % Peak IIa in the presence of 10 nM TF antibody, as set forth in Table 7 and Table 38 is selected from about 105%, about 114%, about 76%, about 68%, about 94%, about 108%, about 104%, about 74%, and about 93% compared to the control conditions without the antibody, as determined by thrombin generation assay (TGA) with 10 min antibody pre-incubation. In some embodiments, such % Peak IIa ranges from about 68% to about 114%. In some embodiments, such % Peak IIa is about 68% or more.

In some embodiments, the percent endogenous thrombin potential (% ETP) is at least 80% in the presence of no less than 100 nM TF antibody compared to the control conditions without the antibody, as determined by thrombin generation assay (TGA). In some embodiments, the % ETP is at least 90% in the presence of no less than 100 nM TF antibody compared to the control conditions without the antibody, as determined by thrombin generation assay (TGA). In some embodiments, the % ETP is at least 95% in the presence of no less than 100 nM TF antibody compared to the control conditions without the antibody, as determined by thrombin generation assay (TGA). In some embodiments, the % ETP is at least 99% in the presence of no less than 100 nM TF antibody compared to the control conditions without the antibody, as determined by thrombin generation assay (TGA).

In some embodiments, the % ETP is at least 80% in the presence of no less than 50 nM TF antibody compared to the control conditions without the antibody, as determined by thrombin generation assay (TGA). In some embodiments, the % ETP is at least 90% in the presence of no less than 50 nM TF antibody compared to the control conditions without the antibody, as determined by thrombin generation assay (TGA). In some embodiments, the % ETP is at least 95% in the presence of no less than 50 nM TF antibody compared to the control conditions without the antibody, as determined by thrombin generation assay (TGA). In some embodiments, the % ETP is at least 99% in the presence of no less than 50 nM TF antibody compared to the control conditions without the antibody, as determined by thrombin generation assay (TGA).

In some embodiments, the % ETP is at least 80% in the presence of no less than 10 nM TF antibody compared to the control conditions without the antibody, as determined by thrombin generation assay (TGA). In some embodiments, the % ETP is at least 90% in the presence of no less than 10 nM TF antibody compared to the control conditions without the antibody, as determined by thrombin generation assay (TGA). In some embodiments, the % ETP is at least 95% in the presence of no less than 10 nM TF antibody compared to the control conditions without the antibody, as determined by thrombin generation assay (TGA). In some embodiments, the % ETP is at least 99% in the presence of no less than 10 nM TF antibody compared to the control conditions without the antibody, as determined by thrombin generation assay (TGA).

In some embodiments, the % ETP in the presence of 100 nM TF antibody, as set forth in Table 6 and Table 37 is selected from about 108%, about 103%, about 109%, about 100%, about 96%, about 102%, about 105%, and about 92% compared to the control conditions without the antibody, as determined by thrombin generation assay (TGA) without antibody pre-incubation. In some embodiments, such % ETP ranges from about 92% to about 109%. In some embodiments, such % ETP is about 92% or more.

In some embodiments, the % ETP in the presence of 50 nM TF antibody, as set forth in Table 6 and Table 37 is selected from about 108%, about 103%, about 111%, about 101%, about 97%, about 104%, about 106%, about 93%, about 96%, and about 105% compared to the control conditions without the antibody, as determined by thrombin generation assay (TGA) without antibody pre-incubation. In some embodiments, such % ETP ranges from about 93% to about 111%. In some embodiments, such % ETP is about 93% or more.

In some embodiments, the % ETP in the presence of 10 nM TF antibody, as set forth in Table 6 and Table 37 is selected from about 106%, about 109%, about 105%, about 104%, about 107%, about 99%, about 101%, and about 102% compared to the control conditions without the antibody, as determined by thrombin generation assay (TGA) without antibody pre-incubation. In some embodiments, such % ETP ranges from about 99% to about 109%. In some embodiments, such % ETP is about 99% or more.

In some embodiments, the % ETP in the presence of 100 nM TF antibody, as set forth in Table 7 and Table 38 is selected from about 110%, about 104%, about 106%, about 98%, about 95%, about 108%, about 107%, about 96%, about 92%, and about 103% compared to the control conditions without the antibody, as determined by thrombin generation assay (TGA) with 10 min antibody pre-incubation. In some embodiments, such % ETP ranges from about 92% to about 110%. In some embodiments, such % ETP is about 92% or more.

In some embodiments, the % ETP in the presence of 50 nM TF antibody, as set forth in Table 7 and Table 38 is selected from about 110%, about 106%, about 108%, about 103%, about 96%, about 109%, about 102%, about 104%, about 94%, and about 98% compared to the control conditions without the antibody, as determined by thrombin generation assay (TGA) with 10 min antibody pre-incubation. In some embodiments, such % ETP ranges from about 94% to about 110%. In some embodiments, such % ETP is about 94% or more.

In some embodiments, the % ETP in the presence of 10 nM TF antibody, as set forth in Table 7 and Table 38 is selected from about 107%, about 106%, about 110%, about 103%, about 100%, about 105%, about 102%, and about 101% compared to the control conditions without the antibody, as determined by thrombin generation assay (TGA) with 10 min antibody pre-incubation. In some embodiments, such % ETP ranges from about 100% to about 110%. In some embodiments, such % ETP is about 100% or more.

2.3.3. FXa Conversion in the Presence of TF Antibodies

In some embodiments, the antibodies provided herein bind human TF at a human TF binding site that is distinct from a human TF binding site bound by human FX. In certain embodiments, the antibodies provided herein do not interfere with the ability of TF:FVIIa to convert FX into FXa.

In some embodiments, the percentage of FXa conversion (% FXa) is at least 75% in the presence of no less than 100 nM TF antibody compared to the control conditions without the antibody. In some embodiments, the % FXa is at least 80% in the presence of no less than 100 nM TF antibody compared to the control conditions without the antibody. In some embodiments, the % FXa is at least 85% in the presence of no less than 100 nM TF antibody compared to the control conditions without the antibody. In some embodiments, the % FXa is at least 90% in the presence of no less than 100 nM TF antibody compared to the control conditions without the antibody. In some embodiments, the % FXa is at least 95% in the presence of no less than 100 nM TF antibody compared to the control conditions without the antibody.

In some embodiments, the % FXa is at least 75% in the presence of no less than 50 nM TF antibody compared to the control conditions without the antibody. In some embodiments, the % FXa is at least 80% in the presence of no less than 50 nM TF antibody compared to the control conditions without the antibody. In some embodiments, the % FXa is at least 85% in the presence of no less than 50 nM TF antibody compared to the control conditions without the antibody. In some embodiments, the % FXa is at least 90% in the presence of no less than 50 nM TF antibody compared to the control conditions without the antibody. In some embodiments, the % FXa is at least 95% in the presence of no less than 50 nM TF antibody compared to the control conditions without the antibody.

In some embodiments, the % FXa is at least 75% in the presence of no less than 25 nM TF antibody compared to the control conditions without the antibody. In some embodiments, the % FXa is at least 80% in the presence of no less than 25 nM TF antibody compared to the control conditions without the antibody. In some embodiments, the % FXa is at least 85% in the presence of no less than 25 nM TF antibody compared to the control conditions without the antibody. In some embodiments, the % FXa is at least 90% in the presence of no less than 25 nM TF antibody compared to the control conditions without the antibody. In some embodiments, the % FXa is at least 95% in the presence of no less than 25 nM TF antibody compared to the control conditions without the antibody.

In some embodiments, the % FXa is at least 75% in the presence of no less than 12.5 nM TF antibody compared to the control conditions without the antibody. In some embodiments, the % FXa is at least 80% in the presence of no less than 12.5 nM TF antibody compared to the control conditions without the antibody. In some embodiments, the % FXa is at least 85% in the presence of no less than 12.5 nM TF antibody compared to the control conditions without the antibody. In some embodiments, % FXa is at least 90% in the presence of no less than 12.5 nM TF antibody compared to the control conditions without the antibody. In some embodiments, the % FXa is at least 95% in the presence of no less than 12.5 nM TF antibody compared to the control conditions without the antibody.

In some embodiments, the % FXa in the presence of 100 nM TF antibody, as set forth in Table 8 is selected from about 89%, about 96%, about 116%, about 108%, about 117%, about 105%, about 112%, about 106%, about 103%, about 111%, about 98%, and about 101% compared to the control conditions without the antibody. In some embodiments, such % FXa ranges from about 89% to about 117%. In some embodiments, such % FXa is about 89% or more.

In some embodiments, the % FXa in the presence of 50 nM TF antibody, as set forth in Table 8 is selected from about 94%, about 93%, about 78%, about 102%, about 99%, about 104%, about 105%, about 108%, about 107%, about 97%, and about 106% compared to the control conditions without the antibody. In some embodiments, such % FXa ranges from about 78% to about 108%. In some embodiments, such % FXa is about 78% or more.

In some embodiments, the % FXa in the presence of 25 nM TF antibody, as set forth in Table 8 is selected from about 81%, about 89%, about 85%, about 109%, about 96%, about 97%, about 108%, about 104%, about 103%, about 112%, and about 89% compared to the control conditions without the antibody. In some embodiments, such % FXa ranges from about 81% to about 112%. In some embodiments, such % FXa is about 81% or more.

In some embodiments, the % FXa in the presence of 12.5 nM TF antibody, as set forth in Table 8 is selected from about 87%, about 89%, about 82%, about 99%, about 101%, about 98%, about 113%, about 106%, about 115%, about 110%, about 120%, about 85%, and about 108% compared to the control conditions without the antibody. In some embodiments, such % FXa ranges from about 82% to about 120%. In some embodiments, such % FXa is about 82% or more.

2.3.4. FVIIa Binding in the Presence of TF Antibodies

In some embodiments, the antibodies provided herein bind human TF at a human TF binding site that is distinct from a human TF binding site bound by human FVIIa. In certain embodiments, the antibodies provided herein do not compete for binding to human TF with human FVIIa.

In some embodiments, the percentage of FVIIa binding (% FVIIa) is at least 75% in the presence of no less than 250 nM TF antibody compared to the control conditions without the antibody. In some embodiments, the % FVIIa is at least 80% in the presence of no less than 250 nM TF antibody compared to the control conditions without the antibody. In some embodiments, the % FVIIa is at least 85% in the presence of no less than 250 nM TF antibody compared to the control conditions without the antibody. In some embodiments, the % FVIIa is at least 90% in the presence of no less than 250 nM TF antibody compared to the control conditions without the antibody. In some embodiments, the % FVIIa is at least 95% in the presence of no less than 250 nM TF antibody compared to the control conditions without the antibody.

In some embodiments, the % FVIIa is at least 75% in the presence of no less than 83 nM TF antibody compared to the control conditions without the antibody. In some embodiments, the % FVIIa is at least 80% in the presence of no less than 83 nM TF antibody compared to the control conditions without the antibody. In some embodiments, the % FVIIa is at least 85% in the presence of no less than 83 nM TF antibody compared to the control conditions without the antibody. In some embodiments, the % FVIIa is at least 90% in the presence of no less than 83 nM TF antibody compared to the control conditions without the antibody. In some embodiments, the % FVIIa is at least 95% in the presence of no less than 83 nM TF antibody compared to the control conditions without the antibody.

In some embodiments, the % FVIIa is at least 75% in the presence of no less than 28 nM TF antibody compared to the control conditions without the antibody. In some embodiments, the % FVIIa is at least 80% in the presence of no less than 28 nM TF antibody compared to the control conditions without the antibody. In some embodiments, the % FVIIa is at least 85% in the presence of no less than 28 nM TF antibody compared to the control conditions without the antibody. In some embodiments, the % FVIIa is at least 90% in the presence of no less than 28 nM TF antibody compared to the control conditions without the antibody. In some embodiments, the % FVIIa is at least 95% in the presence of no less than 28 nM TF antibody compared to the control conditions without the antibody.

In some embodiments, the % FVIIa is at least 75% in the presence of no less than 9.25 nM TF antibody compared to the control conditions without the antibody. In some embodiments, the % FVIIa is at least 80% in the presence of no less than 9.25 nM TF antibody compared to the control conditions without the antibody. In some embodiments, the % FVIIa is at least 85% in the presence of no less than 9.25 nM TF antibody compared to the control conditions without the antibody. In some embodiments, the % FVIIa is at least 90% in the presence of no less than 9.25 nM TF antibody compared to the control conditions without the antibody. In some embodiments, the % FVIIa is at least 95% in the presence of no less than 9.25 nM TF antibody compared to the control conditions without the antibody.

In some embodiments, the % FVIIa in the presence of 250 nM TF antibody, as set forth in Table 9 is selected from about 98%, about 87%, about 80%, about 92%, about 95%, about 89%, about 91%, about 97%, about 94%, about 101%, and about 96% compared to the control conditions without the antibody. In some embodiments, such % FVIIa ranges from about 80% to about 101%. In some embodiments, such % FVIIa is about 80% or more.

In some embodiments, the % FVIIa in the presence of 83 nM TF antibody, as set forth in Table 9 is selected from about 97%, about 88%, about 77%, about 93%, about 94%, about 91%, about 98%, about 100%, and about 92% compared to the control conditions without the antibody. In some embodiments, such % FVIIa ranges from about 77% to about 100%. In some embodiments, such % FVIIa is about 77% or more.

In some embodiments, the % FVIIa in the presence of 28 nM TF antibody, as set forth in Table 9 is selected from about 101%, about 87%, about 79%, about 96%, about 93%, about 95%, about 98%, about 100%, about 102%, about 99%, about 92%, and about 91% compared to the control conditions without the antibody. In some embodiments, such % FVIIa ranges from about 79% to about 102%. In some embodiments, such % FVIIa is about 79% or more.

In some embodiments, the % FVIIa in the presence of 9.25 nM TF antibody, as set forth in Table 9 is selected from about 100%, about 90%, about 76%, about 97%, about 93%, about 99%, about 98%, about 102%, about 101%, and about 95% compared to the control conditions without the antibody. In some embodiments, such % FVIIa ranges from about 76% to about 102%. In some embodiments, such % FVIIa is about 76% or more.

2.3.5. FVIIa-dependent TF Signaling in the Presence of TF Antibodies

In some embodiments, the antibodies provided herein inhibit FVIIa-dependent TF signaling. In some embodiments, the inhibition of FVIIa-dependent TF signaling is measured by the reduction of IL8. In some embodiments, the inhibition of FVIIa-dependent TF signaling is measured by the reduction of GM-CSF.

In some embodiments, the Interleukin 8 concentration (IL8 conc) is reduced by at least 70% in the presence of no less than 100 nM TF antibody compared to the control conditions without the antibody. In some embodiments, the IL8 conc is reduced by at least 80% in the presence of no less than 100 nM TF antibody compared to the control conditions without the antibody. In some embodiments, the IL8 conc is reduced by at least 90% in the presence of no less than 100 nM TF antibody compared to the control conditions without the antibody.

In some embodiments, the IL8 conc is reduced by at least 70% in the presence of no less than 40 nM TF antibody compared to the control conditions without the antibody. In some embodiments, the IL8 conc is reduced by at least 80% in the presence of no less than 40 nM TF antibody compared to the control conditions without the antibody. In some embodiments, the IL8 conc is reduced by at least 90% in the presence of no less than 40 nM TF antibody compared to the control conditions without the antibody.

In some embodiments, the IL8 conc is reduced by at least 60% in the presence of no less than 16 nM TF antibody compared to the control conditions without the antibody. In some embodiments, the IL8 conc is reduced by at least 70% in the presence of no less than 16 nM TF antibody compared to the control conditions without the antibody. In some embodiments, the IL8 conc is reduced by at least 80% in the presence of no less than 16 nM TF antibody compared to the control conditions without the antibody. In some embodiments, the IL8 conc is reduced by at least 90% in the presence of no less than 16 nM TF antibody compared to the control conditions without the antibody.

In some embodiments, the IL8 conc is reduced by at least 50% in the presence of no less than 6.4 nM TF antibody compared to the control conditions without the antibody. In some embodiments, the IL8 conc is reduced by at least 60% in the presence of no less than 6.4 nM TF antibody compared to the control conditions without the antibody. In some embodiments, the IL8 conc is reduced by at least 70% in the presence of no less than 6.4 nM TF antibody compared to the control conditions without the antibody. In some embodiments, the IL8 conc is reduced by at least 80% in the presence of no less than 6.4 nM TF antibody compared to the control conditions without the antibody. In some embodiments, the IL8 conc is reduced by at least 90% in the presence of no less than 6.4 nM TF antibody compared to the control conditions without the antibody.

In some embodiments, the Granulocyte-Macrophage Colony-Stimulating Factor concentration (GM-CSF conc) is reduced by at least 70% in the presence of no less than 100 nM TF antibody compared to the control conditions without the antibody. In some embodiments, the GM-CSF conc is reduced by at least 80% in the presence of no less than 100 nM TF antibody compared to the control conditions without the antibody. In some embodiments, the GM-CSF conc is reduced by at least 90% in the presence of no less than 100 nM TF antibody compared to the control conditions without the antibody.

In some embodiments, the GM-CSF conc is reduced by at least 70% in the presence of no less than 40 nM TF antibody compared to the control conditions without the antibody. In some embodiments, the GM-CSF conc is reduced by at least 80% in the presence of no less than 40 nM TF antibody compared to the control conditions without the antibody. In some embodiments, the GM-CSF conc is reduced by at least 90% in the presence of no less than 40 nM TF antibody compared to the control conditions without the antibody.

In some embodiments, the GM-CSF conc is reduced by at least 60% in the presence of no less than 16 nM TF antibody compared to the control conditions without the antibody. In some embodiments, the GM-CSF conc is reduced by at least 70% in the presence of no less than 16 nM TF antibody compared to the control conditions without the antibody. In some embodiments, the GM-CSF conc is reduced by at least 80% in the presence of no less than 16 nM TF antibody compared to the control conditions without the antibody. In some embodiments, the GM-CSF conc is reduced by at least 90% in the presence of no less than 16 nM TF antibody compared to the control conditions without the antibody.

In some embodiments, the GM-CSF conc is reduced by at least 50% in the presence of no less than 6.4 nM TF antibody compared to the control conditions without the antibody. In some embodiments, the GM-CSF conc is reduced by at least 60% in the presence of no less than 6.4 nM TF antibody compared to the control conditions without the antibody. In some embodiments, the GM-CSF conc is reduced by at least 70% in the presence of no less than 6.4 nM TF antibody compared to the control conditions without the antibody. In some embodiments, the GM-CSF conc is reduced by at least 80% in the presence of no less than 6.4 nM TF antibody compared to the control conditions without the antibody. In some embodiments, the GM-CSF conc is reduced by at least 90% in the presence of no less than 6.4 nM TF antibody compared to the control conditions without the antibody.

In some embodiments, the percentage of Interleukin 8 (% IL8) in the presence of 100 nM TF antibody, as set forth in Table 10 is selected from about 2%, about 9%, about 8%, about 6%, about 13%, about 1%, about 3%, about 4%, and about 5% compared to the control conditions without the antibody. In some embodiments, such % IL8 ranges from about 1% to about 13%. In some embodiments, such % IL8 is about 13% or less.

In some embodiments, the % IL8 in the presence of 40 nM TF antibody, as set forth in Table 10 is selected from about 2%, about 8%, about 7%, about 10%, about 14%, about 4%, about 5%, and about 6% compared to the control conditions without the antibody. In some embodiments, such % IL8 ranges from about 2% to about 14%. In some embodiments, such % IL8 is about 14% or less.

In some embodiments, the % IL8 in the presence of 16 nM TF antibody, as set forth in Table 10 is selected from about 2%, about 3%, about 10%, about 8%, about 7%, about 16%, about 9%, about 15%, about 5%, and about 6% compared to the control conditions without the antibody. In some embodiments, such % IL8 ranges from about 2% to about 16%. In some embodiments, such % IL8 is about 16% or less.

In some embodiments, the % IL8 in the presence of 6.4 nM TF antibody, as set forth in Table 10 is selected from about 3%, about 4%, about 11%, about 9%, about 14%, about 22%, about 12%, about 6%, about 5%, about 15%, about 21%, and about 8% compared to the control conditions without the antibody. In some embodiments, such % IL8 ranges from about 3% to about 22%. In some embodiments, such % IL8 is about 22% or less.

In some embodiments, the percentage of Granulocyte-Macrophage Colony-Stimulating Factor (% GM-CSF) in the presence of 100 nM TF antibody, as set forth in Table 11 is selected from about 6%, about 7%, about 22%, about 20%, about 12%, about 19%, about 17%, about 25%, about 5%, about 14%, about 11%, and about 10% compared to the control conditions without the antibody. In some embodiments, such % GM-CSF ranges from about 5% to about 25%. In some embodiments, such % GM-CSF is about 25% or less.

In some embodiments, the % GM-CSF in the presence of 40 nM TF antibody, as set forth in Table 11 is selected from about 6%, about 7%, about 19%, about 15%, about 18%, about 16%, about 26%, about 5%, about 13%, about 11%, and about 10% compared to the control conditions without the antibody. In some embodiments, such % GM-CSF ranges from about 5% to about 26%. In some embodiments, such % GM-CSF is about 26% or less.

In some embodiments, the % GM-CSF in the presence of 16 nM TF antibody, as set forth in Table 11 is selected from about 6%, about 7%, about 22%, about 19%, about 14%, about 32%, about 17%, about 26%, about 5%, about 12%, about 13%, about 9%, about 11%, and about 15% compared to the control conditions without the antibody. In some embodiments, such % GM-CSF ranges from about 5% to about 32%. In some embodiments, such % GM-CSF is about 32% or less.

In some embodiments, the % GM-CSF in the presence of 6.4 nM TF antibody, as set forth in Table 11 is selected from about 8%, about 9%, about 24%, about 20%, about 18%, about 39%, about 34%, about 15%, about 21%, about 16%, about 17%, and about 10% compared to the control conditions without the antibody. In some embodiments, such % GM-CSF ranges from about 8% to about 39%. In some embodiments, such % GM-CSF is about 39% or less.

2.3.6. Lesion Size Reduction in Swine Choroidal Neovascularization (CNV) Model

In some embodiments, the antibodies provided herein reduce lesion size in a swine choroidal neovascularization (CNV) model. In some embodiments, the reduction in lesion size is measured by Fluorescein Angiography (FA).

In some embodiments, the lesion size in a swine CNV model is reduced by at least 5% 7 days after administration of the anti-TF antibody. In some embodiments, the lesion size in a swine CNV model is reduced by at least 10% 7 days after administration of the anti-TF antibody. In some embodiments, the lesion size in a swine CNV model is reduced by at least 20% 7 days after administration of the anti-TF antibody. In some embodiments, the lesion size in a swine CNV model is reduced by at least 40% 7 days after administration of the anti-TF antibody. In some embodiments, the lesion size in a swine CNV model is reduced by at least 60% 7 days after administration of the anti-TF antibody.

In some embodiments, the lesion size in a swine CNV model is reduced by at least 10% 21 days after administration of the anti-TF antibody. In some embodiments, the lesion size in a swine CNV model is reduced by at least 20% 21 days after administration of the anti-TF antibody. In some embodiments, the lesion size in a swine CNV model is reduced by at least 40% 21 days after administration of the anti-TF antibody. In some embodiments, the lesion size in a swine CNV model is reduced by at least 60% 21 days after administration of the anti-TF antibody. In some embodiments, the lesion size in a swine CNV model is reduced by at least 80% 21 days after administration of the anti-TF antibody.

2.4. Germlines

The antibodies provided herein may comprise any suitable $V_H$ and $V_L$ germline sequences.

In some embodiments, the $V_H$ region of an antibody provided herein is from the VH3 germline. In some embodiments, the $V_H$ region of an antibody provided herein is from the VH1 germline. In some embodiments, the $V_H$ region of an antibody provided herein is from the VH4 germline.

In some embodiments, the $V_H$ region of an antibody provided herein is from the VH3-23 germline. In some embodiments, the $V_H$ region of an antibody provided herein is from the VH1-18 germline. In some embodiments, the $V_H$ region of an antibody provided herein is from the VH3-30 germline. In some embodiments, the $V_H$ region of an antibody provided herein is from the VH1-69 germline. In some embodiments, the $V_H$ region of an antibody provided herein is from the VH4-31 germline. In some embodiments, the $V_H$ region of an antibody provided herein is from the VH4-34 germline. In some embodiments, the $V_H$ region of an antibody provided herein is from the VH1-46 germline.

In some embodiments, the $V_L$ region of an antibody provided herein is from the VK1 germline. In some embodiments, the $V_L$ region of an antibody provided herein is from the VK4 germline. In some embodiments, the $V_L$ region of an antibody provided herein is from the VK3 germline In some embodiments, the $V_L$ region of an antibody provided herein is from the VK1-05 germline. In some embodiments, the $V_L$ region of an antibody provided herein is from the VK4-01 germline. In some embodiments, the $V_L$ region of an antibody provided herein is from the VK3-15 germline. In some embodiments, the $V_L$ region of an antibody provided herein is from the VK3-20 germline. In some embodiments, the $V_L$ region of an antibody provided herein is from the VK1-33 germline.

2.5. Monospecific and Multispecific TF Antibodies

In some embodiments, the antibodies provided herein are monospecific antibodies.

In some embodiments, the antibodies provided herein are multispecific antibodies.

In some embodiments, a multispecific antibody provided herein binds more than one antigen. In some embodiments, a multispecific antibody binds two antigens. In some embodiments, a multispecific antibody binds three antigens. In some embodiments, a multispecific antibody binds four antigens. In some embodiments, a multispecific antibody binds five antigens.

In some embodiments, a multispecific antibody provided herein binds more than one epitope on a TF antigen. In some embodiments, a multispecific antibody binds two epitopes on a TF antigen. In some embodiments, a multispecific antibody binds three epitopes on a TF antigen.

Many multispecific antibody constructs are known in the art, and the antibodies provided herein may be provided in the form of any suitable multispecific suitable construct.

In some embodiments, the multispecific antibody comprises an immunoglobulin comprising at least two different heavy chain variable regions each paired with a common light chain variable region (i.e., a "common light chain antibody"). The common light chain variable region forms a distinct antigen-binding domain with each of the two different heavy chain variable regions. See Merchant et al., *Nature Biotechnol.*, 1998, 16:677-681, incorporated by reference in its entirety.

In some embodiments, the multispecific antibody comprises an immunoglobulin comprising an antibody or fragment thereof attached to one or more of the N- or C-termini of the heavy or light chains of such immunoglobulin. See Coloma and Morrison, *Nature Biotechnol.*, 1997, 15:159-163, incorporated by reference in its entirety. In some aspects, such antibody comprises a tetravalent bispecific antibody.

In some embodiments, the multispecific antibody comprises a hybrid immunoglobulin comprising at least two different heavy chain variable regions and at least two different light chain variable regions. See Milstein and Cuello, Nature, 1983, 305:537-540; and Staerz and Bevan, *Proc. Natl. Acad. Sci. USA*, 1986, 83:1453-1457; each of which is incorporated by reference in its entirety.

In some embodiments, the multispecific antibody comprises immunoglobulin chains with alterations to reduce the formation of side products that do not have multispecificity. In some aspects, the antibodies comprise one or more "knobs-into-holes" modifications as described in U.S. Pat. No. 5,731,168, incorporated by reference in its entirety.

In some embodiments, the multispecific antibody comprises immunoglobulin chains with one or more electrostatic modifications to promote the assembly of Fc hetero-multimers. See WO 2009/089004, incorporated by reference in its entirety.

In some embodiments, the multispecific antibody comprises a bispecific single chain molecule. See Traunecker et al., *EMBO J*, 1991, 10:3655-3659; and Gruber et al., I Immunol., 1994, 152:5368-5374; each of which is incorporated by reference in its entirety.

In some embodiments, the multispecific antibody comprises a heavy chain variable domain and a light chain variable domain connected by a polypeptide linker, where the length of the linker is selected to promote assembly of multispecific antibodies with the desired multispecificity. For example, monospecific scFvs generally form when a heavy chain variable domain and light chain variable domain are connected by a polypeptide linker of more than 12 amino acid residues. See U.S. Pat. Nos. 4,946,778 and 5,132,405, each of which is incorporated by reference in its entirety. In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting antibodies therefore have multispecificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) are favored. However, the exact type of oligomerization appears to depend on the amino acid residue composition and the order of the variable domain in each polypeptide chain (e.g., $V_H$-linker-$V_L$ vs. $V_L$-linker-$V_H$), in addition to the linker length. A skilled person can select the appropriate linker length based on the desired multispecificity.

In some embodiments, the multispecific antibody comprises a diabody. See Hollinger et al., *Proc. Natl. Acad. Sci. USA*, 1993, 90:6444-6448, incorporated by reference in its entirety. In some embodiments, the multispecific antibody comprises a triabody. See Todorovska et al., *J. Immunol. Methods*, 2001, 248:47-66, incorporated by reference in its entirety. In some embodiments, the multispecific antibody comprises a tetrabody. See id, incorporated by reference in its entirety.

In some embodiments, the multispecific antibody comprises a trispecific F(ab')3 derivative. See Tutt et al. *J. Immunol.*, 1991, 147:60-69, incorporated by reference in its entirety.

In some embodiments, the multispecific antibody comprises a cross-linked antibody. See U.S. Pat. No. 4,676,980; Brennan et al., *Science*, 1985, 229:81-83; Staerz, et al.

*Nature,* 1985, 314:628-631; and EP 0453082; each of which is incorporated by reference in its entirety.

In some embodiments, the multispecific antibody comprises antigen-binding domains assembled by leucine zippers. See Kostelny et al., *J. Immunol.,* 1992, 148:1547-1553, incorporated by reference in its entirety.

In some embodiments, the multispecific antibody comprises complementary protein domains. In some aspects, the complementary protein domains comprise an anchoring domain (AD) and a dimerization and docking domain (DDD). In some embodiments, the AD and DDD bind to each other and thereby enable assembly of multispecific antibody structures via the "dock and lock" (DNL) approach. Antibodies of many specificities may be assembled, including bispecific antibodies, trispecific antibodies, tetraspecific antibodies, quintspecific antibodies, and hexaspecific antibodies. Multispecific antibodies comprising complementary protein domains are described, for example, in U.S. Pat. Nos. 7,521,056; 7,550,143; 7,534,866; and 7,527,787; each of which is incorporated by reference in its entirety.

In some embodiments, the multispecific antibody comprises a dual action Fab (DAF) antibody as described in U.S. Pat. Pub. No. 2008/0069820, incorporated by reference in its entirety.

In some embodiments, the multispecific antibody comprises an antibody formed by reduction of two parental molecules followed by mixing of the two parental molecules and reoxidation to assembly a hybrid structure. See Carlring et al., *PLoS One,* 2011, 6:e22533, incorporated by reference in its entirety.

In some embodiments, the multispecific antibody comprises a DVD-Ig™. A DVD-Ig™ is a dual variable domain immunoglobulin that can bind to two or more antigens. DVD-Igs™ are described in U.S. Pat. No. 7,612,181, incorporated by reference in its entirety.

In some embodiments, the multispecific antibody comprises a DART™. DARTS™ are described in Moore et al., *Blood,* 2011, 117:454-451, incorporated by reference in its entirety.

In some embodiments, the multispecific antibody comprises a DuoBody®. DuoBodies® are described in Labrijn et al., *Proc. Natl. Acad. Sci. USA,* 2013, 110:5145-5150; Gramer et al., *mAbs,* 2013, 5:962-972; and Labrijn et al., *Nature Protocols,* 2014, 9:2450-2463; each of which is incorporated by reference in its entirety.

In some embodiments, the multispecific antibody comprises an antibody fragment attached to another antibody or fragment. The attachment can be covalent or non-covalent. When the attachment is covalent, it may be in the form of a fusion protein or via a chemical linker. Illustrative examples of multispecific antibodies comprising antibody fragments attached to other antibodies include tetravalent bispecific antibodies, where an scFv is fused to the C-terminus of the $C_{H3}$ from an IgG. See Coloma and Morrison, *Nature Biotechnol.,* 1997, 15:159-163. Other examples include antibodies in which a Fab molecule is attached to the constant region of an immunoglobulin. See Miler et al., *J. Immunol.,* 2003, 170:4854-4861, incorporated by reference in its entirety. Any suitable fragment may be used, including any of the fragments described herein or known in the art.

In some embodiments, the multispecific antibody comprises a CovX-Body. CovX-Bodies are described, for example, in Doppalapudi et al., *Proc. Natl. Acad. Sci. USA,* 2010, 107:22611-22616, incorporated by reference in its entirety.

In some embodiments, the multispecific antibody comprises an Fcab antibody, where one or more antigen-binding domains are introduced into an Fc region. Fcab antibodies are described in Wozniak-Knopp et al., *Protein Eng. Des. Sel.,* 2010, 23:289-297, incorporated by reference in its entirety.

In some embodiments, the multispecific antibody comprises a TandAb® antibody. TandAb® antibodies are described in Kipriyanov et al., *J. Mol. Biol.,* 1999, 293:41-56 and Zhukovsky et al., *Blood,* 2013, 122:5116, each of which is incorporated by reference in its entirety.

In some embodiments, the multispecific antibody comprises a tandem Fab. Tandem Fabs are described in WO 2015/103072, incorporated by reference in its entirety.

In some embodiments, the multispecific antibody comprises a Zybody™. Zybodies™ are described in LaFleur et al., *mAbs,* 2013, 5:208-218, incorporated by reference in its entirety.

2.6. Glycosylation Variants

In certain embodiments, an antibody provided herein may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an antibody provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In some embodiments, an antibody provided herein comprises a glycosylation motif that is different from a naturally occurring antibody. Any suitable naturally occurring glycosylation motif can be modified in the antibodies provided herein. The structural and glycosylation properties of immunoglobulins, for example, are known in the art and summarized, for example, in Schroeder and Cavacini, *J. Allergy Clin. Immunol.,* 2010, 125:S41-52, incorporated by reference in its entirety.

In some embodiments, an antibody provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH,* 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create antibodies having altered ADCC. In some embodiments, the oligosaccharide is altered to improve ADCC. In some embodiments, the oligosaccharide is altered to reduce ADCC.

In some aspects, an antibody provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87:614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which is incorporated by reference in its entirety.

Examples of cell lines capable of producing defucosylated antibodies include Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87:614-622; Kanda et al., *Biotechnol. Bioeng.*, 2006, 94:680-688; and WO 2003/085107; each of which is incorporated by reference in its entirety).

In some embodiments, an antibody provided herein is an aglycosylated antibody. An aglycosylated antibody can be produced using any method known in the art or described herein. In some aspects, an aglycosylated antibody is produced by modifying the antibody to remove all glycosylation sites. In some aspects, the glycosylation sites are removed only from the Fc region of the antibody. In some aspects, an aglycosylated antibody is produced by expressing the antibody in an organism that is not capable of glycosylation, such as *E. coli*, or by expressing the antibody in a cell-free reaction mixture.

In some embodiments, an antibody provided herein has a constant region with reduced effector function compared to a native IgG1 antibody. In some embodiments, the affinity of a constant region of an Fc region of an antibody provided herein for Fc receptor is less than the affinity of a native IgG1 constant region for such Fc receptor.

2.7. Fc Region Amino Acid Sequence Variants

In certain embodiments, an antibody provided herein comprises an Fc region with one or more amino acid substitutions, insertions, or deletions in comparison to a naturally occurring Fc region. In some aspects, such substitutions, insertions, or deletions yield antibodies with altered stability, glycosylation, or other characteristics. In some aspects, such substitutions, insertions, or deletions yield aglycosylated antibodies.

In some aspects, the Fc region of an antibody provided herein is modified to yield an antibody with altered affinity for an Fc receptor, or an antibody that is more immunologically inert. In some embodiments, the antibody variants provided herein possess some, but not all, effector functions. Such antibodies may be useful, for example, when the half-life of the antibody is important in vivo, but when certain effector functions (e.g., complement activation and ADCC) are unnecessary or deleterious.

In some embodiments, the Fc region of an antibody provided herein is a human IgG4 Fc region comprising one or more of the hinge stabilizing mutations S228P and L235E. See Aalberse et al., *Immunology*, 2002, 105:9-19, incorporated by reference in its entirety. In some embodiments, the IgG4 Fc region comprises one or more of the following mutations: E233P, F234V, and L235A. See Armour et al., *Mol. Immunol.*, 2003, 40:585-593, incorporated by reference in its entirety. In some embodiments, the IgG4 Fc region comprises a deletion at position G236.

In some embodiments, the Fc region of an antibody provided herein is a human IgG1 Fc region comprising one or more mutations to reduce Fc receptor binding. In some aspects, the one or more mutations are in residues selected from 5228 (e.g., S228A), L234 (e.g., L234A), L235 (e.g., L235A), D265 (e.g., D265A), and N297 (e.g., N297A). In some aspects, the antibody comprises a PVA236 mutation. PVA236 means that the amino acid sequence ELLG, from amino acid position 233 to 236 of IgG1 or EFLG of IgG4, is replaced by PVA. See U.S. Pat. No. 9,150,641, incorporated by reference in its entirety.

In some embodiments, the Fc region of an antibody provided herein is modified as described in Armour et al., *Eur. J. Immunol.*, 1999, 29:2613-2624; WO 1999/058572; and/or U.K. Pat. App. No. 98099518; each of which is incorporated by reference in its entirety.

In some embodiments, the Fc region of an antibody provided herein is a human IgG2 Fc region comprising one or more of mutations A330S and P331S.

In some embodiments, the Fc region of an antibody provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the antibody comprises an alanine at amino acid position 265. In some embodiments, the antibody comprises an alanine at amino acid position 297.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., *Proc. Natl. Acad. Sci. USA,* 2006, 103:4005-4010, incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., *J. Immunol.,* 2000, 164:4178-4184; each of which is incorporated by reference in its entirety.

In some embodiments, an antibody provided herein comprises one or more alterations to increase half-life. Antibodies with increased half-lives and improved binding to the neonatal Fc receptor (FcRn) are described, for example, in Hinton et al., *J. Immunol.,* 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an antibody provided herein comprises one or more Fc region variants as described in U.S. Pat. Nos. 7,371,826, 5,648,260, and 5,624,821; Duncan and Winter, *Nature,* 1988, 322:738-740; and WO 94/29351; each of which is incorporated by reference in its entirety.

2.8. Pyroglutamate

As is known in the art, both glutamate (E) and glutamine (Q) at the N-termini of recombinant proteins can cyclize spontaneously to form pyroglutamate (pE) in vitro and in vivo. See Liu et al., *J. Biol. Chem.,* 2011, 286:11211-11217, incorporated by reference in its entirety.

In some embodiments, provided herein are antibodies comprising a polypeptide sequence having a pE residue at the N-terminal position. In some embodiments, provided herein are antibodies comprising a polypeptide sequence in which the N-terminal residue has been converted from Q to pE. In some embodiments, provided herein are antibodies comprising a polypeptide sequence in which the N-terminal residue has been converted from E to pE.

2.9. Cysteine Engineered Antibody Variants

In certain embodiments, provided herein are cysteine engineered antibodies, also known as "thioMAbs," in which one or more residues of the antibody are substituted with cysteine residues. In particular embodiments, the substituted residues occur at solvent accessible sites of the antibody. By substituting such residues with cysteine, reactive thiol groups are introduced at solvent accessible sites of the antibody and may be used to conjugate the antibody to other moieties, such as drug moieties or linker-drug moieties, for example, to create an immunoconjugate.

In certain embodiments, any one or more of the following residues may be substituted with cysteine: V205 of the light chain; A118 of the heavy chain Fc region; and S400 of the heavy chain Fc region. Cysteine engineered antibodies may be generated as described, for example, in U.S. Pat. No. 7,521,541, which is incorporated by reference in its entirety.

3. Anti-TF Antibody-Drug Conjugates

Provided herein are antibody-drug conjugates (ADCs) comprising an antibody that binds specifically to TF and a cytotoxic agent. In some embodiments, the cytotoxic agent is linked directly to the anti-TF antibody. In some embodiments, the cytotoxic agent is linked indirectly to the anti-TF antibody.

In some embodiments, the ADCs further comprise a linker. In some embodiments, the linker links the anti-TF antibody to the cytotoxic agent.

In some embodiments, the ADCs provided herein have a drug-antibody ratio (DAR) of 1. In some embodiments, the ADCs provided herein have a DAR of 2. In some embodiments, the ADCs provided herein have a DAR of 3. In some embodiments, the ADCs provided herein have a DAR of 4. In some embodiments, the ADCs provided herein have a DAR of 5. In some embodiments, the ADCs provided herein have a DAR of 1-2, 1-3, 1-4, 1-5, 2-3, 2-4, 2-5, 3-4, 3-5, 4-5, 1, 2, 3, 4, or 5. In some embodiments, the ADCs provided herein have a DAR greater than 5. In some embodiments, the DAR is measured by UV/vis spectroscopy, hydrophobic interaction chromatography (HIC), and/or reverse phase liquid chromatography separation with time-of-flight detection and mass characterization (RP-UPLC/Mass spectrometry).

4. Methods for Making TF Antibodies 4.1. TF Antigen Preparation

The TF antigen used for isolation of the antibodies provided herein may be intact TF or a fragment of TF. The TF antigen may be, for example, in the form of an isolated protein or a protein expressed on the surface of a cell.

In some embodiments, the TF antigen is a non-naturally occurring variant of TF, such as a TF protein having an amino acid sequence or post-translational modification that does not occur in nature.

In some embodiments, the TF antigen is truncated by removal of, for example, intracellular or membrane-spanning sequences, or signal sequences. In some embodiments, the TF antigen is fused at its C-terminus to a human IgG1 Fc domain or a polyhistidine tag.

4.2. Methods of Making Monoclonal Antibodies

Monoclonal antibodies may be obtained, for example, using the hybridoma method first described by Kohler et al., *Nature,* 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage-display libraries (see e.g., U.S. Pat. No. 8,258,082, which is incorporated by reference in its entirety) or, alternatively, using yeast-based libraries (see e.g., U.S. Pat. No. 8,691,730, which is incorporated by reference in its entirety).

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

4.3. Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

4.4. Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. USA.*, 1989, 86:10029-10033; and U.S. Pat. Nos. 5,585,089, 5,693,761, 5,693,762, and 6,180,370; each of which is incorporated by reference in its entirety. 4.5. Methods of Making Human Antibodies Human antibodies can be generated by a variety of techniques known in the art, for example by using transgenic animals (e.g., humanized mice). See, e.g., Jakobovits et al., *Proc. Natl. Acad. Sci. USA.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

4.6. Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., *Nat. Med.*, 2003, 9:129-134, incorporated by reference in its entirety. Methods of making scFv antibodies are described, for example, in Plückthun, in *The Pharmacology of Monoclonal Antibodies*, vol. 113, Rosenburg and Moore eds., Springer-Verlag, New York, pp. 269-315 (1994); WO 93/16185; and U.S. Pat. Nos. 5,571,894 and 5,587,458; each of which is incorporated by reference in its entirety.

4.7. Methods of Making Alternative Scaffolds

The alternative scaffolds provided herein may be made by any suitable method, including the illustrative methods described herein or those known in the art. For example, methods of preparing Adnectins™ are described in Emanuel et al., *mAbs*, 2011, 3:38-48, incorporated by reference in its entirety. Methods of preparing iMabs are described in U.S. Pat. Pub. No. 2003/0215914, incorporated by reference in its entirety. Methods of preparing Anticalins® are described in Vogt and Skerra, *Chem. Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, *Curr. Opinion in Biotech.*, 2004, 15:364-373, incorporated by reference in its entirety. Methods of preparing DARPins are provided in Zahnd et al., *J. Mol. Biol.*, 2007, 369:1015-1028, incorporated by reference in its entirety. Methods of preparing Affilins are provided in Ebersbach et al., *J. Mol. Biol.*, 2007, 372:172-185, incorporated by reference in its entirety. Methods of preparing Tetranectins are provided in Graversen et al., *J. Biol. Chem.*, 2000, 275:37390-37396, incorporated by reference in its entirety. Methods of preparing Avimers are provided in Silverman et al., *Nature Biotech.*, 2005, 23:1556-1561, incorporated by reference in its entirety. Methods of preparing Fynomers are provided in Silacci et al., *J. Biol. Chem.*, 2014, 289:14392-14398, incorporated by reference in its entirety.

Further information on alternative scaffolds is provided in Binz et al., *Nat. Biotechnol.*, 2005 23:1257-1268; and Skerra, *Current Opin. in Biotech.*, 2007 18:295-304, each of which is incorporated by reference in its entirety.

4.8. Methods of Making Multispecific Antibodies

The multispecific antibodies provided herein may be made by any suitable method, including the illustrative methods described herein or those known in the art. Methods of making common light chain antibodies are described in Merchant et al., *Nature Biotechnol.*, 1998, 16:677-681, incorporated by reference in its entirety. Methods of making tetravalent bispecific antibodies are described in Coloma and Morrison, *Nature Biotechnol.*, 1997, 15:159-163, incorporated by reference in its entirety. Methods of making hybrid immunoglobulins are described in Milstein and Cuello, *Nature*, 1983, 305:537-540; and Staerz and Bevan, *Proc. Natl. Acad. Sci. USA*, 1986, 83:1453-1457; each of which is incorporated by reference in its entirety. Methods of making immunoglobulins with knobs-into-holes modification are described in U.S. Pat. No. 5,731,168, incorporated by reference in its entirety. Methods of making immunoglobulins with electrostatic modifications are provided in WO 2009/089004, incorporated by reference in its entirety. Methods of making bispecific single chain antibodies are described in Traunecker et al., *EMBO J.*, 1991, 10:3655-3659; and Gruber et al., *J. Immunol.*, 1994, 152:5368-5374; each of which is incorporated by reference in its entirety. Methods of making single-chain antibodies, whose linker length may be varied, are described in U.S. Pat. Nos. 4,946,778 and 5,132,405, each of which is incorporated by reference in its entirety. Methods of making diabodies are described in Hollinger et al., *Proc. Natl. Acad. Sci. USA*, 1993, 90:6444-6448, incorporated by reference in its entirety. Methods of making triabodies and tetrabodies are described in Todorovska et al., *J. Immunol. Methods*, 2001, 248:47-66, incorporated by reference in its entirety. Methods of making trispecific F(ab')3 derivatives are described in Tutt et al. *J. Immunol.*, 1991, 147:60-69, incorporated by reference in its entirety. Methods of making cross-linked antibodies are described in U.S. Pat. No. 4,676,980; Brennan et al., *Science*, 1985, 229:81-83; Staerz, et al. *Nature*, 1985, 314:628-631; and EP 0453082; each of which is incorporated by reference in its entirety. Methods of making antigen-binding domains assembled by leucine zippers are described in Kostelny et al., *J. Immunol.*, 1992, 148:1547-1553, incorporated by reference in its entirety. Methods of making antibodies via the DNL approach are described in U.S. Pat. Nos. 7,521,056; 7,550,143; 7,534,866; and 7,527,787; each of which is incorporated by reference in its entirety. Methods of making hybrids of antibody and non-antibody molecules are described in WO 93/08829, incorporated by reference in its entirety, for examples of such antibodies. Methods of making DAF antibodies are described in U.S. Pat. Pub. No. 2008/0069820, incorporated by reference in its entirety. Methods of making antibodies via reduction and oxidation are described in Carlring et al., *PLoS One*, 2011, 6:e22533, incorporated by reference in its entirety. Methods of making DVD-Igs™ are described in U.S. Pat. No. 7,612,181, incorporated by reference in its entirety. Methods of making DARTs™ are described in Moore et al., *Blood*, 2011, 117:454-451, incorporated by reference in its entirety. Methods of making DuoBodies® are described in Labrijn et al., *Proc. Natl. Acad. Sci. USA*, 2013, 110:5145-5150; Gramer et al., *mAbs*, 2013, 5:962-972; and Labrijn et al., *Nature Protocols*, 2014, 9:2450-2463; each of which is incorporated by reference in its entirety. Methods of making antibodies comprising scFvs fused to the C-terminus of the $C_{H3}$ from an IgG are described in Coloma and Morrison, *Nature Biotechnol.*, 1997, 15:159-163, incorporated by reference in its entirety. Methods of making antibodies in which a Fab molecule is attached to the constant region of an immunoglobulin are described in Miler et al., *J. Immunol.*, 2003, 170:4854-4861, incorporated by reference in its entirety. Methods of making CovX-Bodies are described in Doppalapudi et al., *Proc. Natl. Acad. Sci. USA*, 2010, 107:22611-22616, incorporated by reference in its entirety. Methods of making Fcab antibodies are described in Wozniak-Knopp et al., *Protein Eng. Des. Sel.*, 2010, 23:289-297, incorporated by reference in its entirety. Methods of making TandAb® antibodies are described in Kipriyanov et al., *J. Mol. Biol.*, 1999, 293:41-56 and Zhukovsky et al., *Blood*, 2013, 122:5116, each of which is incorporated by reference in its entirety. Methods of making tandem Fabs are described in WO 2015/103072, incorporated by reference in its entirety. Methods of making Zybodies™ are described in LaFleur et al., *mAbs*, 2013, 5:208-218, incorporated by reference in its entirety.

4.9. Methods of Making Variants

In some embodiments, an antibody provided herein is an affinity matured variant of a parent antibody, which may be generated, for example, using phage display-based affinity maturation techniques. Briefly, one or more CDR residues may be mutated and the variant antibodies, or portions thereof, displayed on phage and screened for affinity. Such alterations may be made in CDR "hotspots," or residues encoded by codons that undergo mutation at high frequency during the somatic maturation process (see Chowdhury, *Methods Mol. Biol.*, 2008, 207:179-196, incorporated by reference in its entirety), and/or residues that contact the antigen.

Any suitable method can be used to introduce variability into a polynucleotide sequence(s) encoding an antibody, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify antibody variants with improved affinity. Affinity maturation by constructing and reselecting from secondary libraries has been described, for example, in Hoogenboom et al., *Methods in Molecular Biology*, 2001, 178:1-37, incorporated by reference in its entirety.

4.10. Vectors, Host Cells, and Recombinant Methods

Also provided are isolated nucleic acids encoding TF antibodies, vectors comprising the nucleic acids, and host cells comprising the vectors and nucleic acids, as well as recombinant techniques for the production of the antibodies.

For recombinant production of an antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the antibodies provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella, Bacilli* (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for TF antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K fragilis, K bulgaricus K wickeramii, K. waltii, K drosophilarum, K thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells, baby hamster kidney (BHK) cells, Chinese hamster ovary (CHO), mouse sertoli cells, African green monkey kidney cells (VERO-76), and the like.

The host cells used to produce the TF antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology*, 1992, 10:163-167, incorporated by reference in its entirety) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs*, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that comprise human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

5. Cytotoxic Agents

In some embodiments, ADCs provided herein comprise a cytotoxic agent. The cytotoxic agents provided herein include various anti-tumor or anti-cancer agents known in the art. In some embodiments, the cytotoxic agents cause destruction of cancer cells. In some embodiments, the cytotoxic agents inhibit the growth or proliferation of cancer cells.

Suitable cytotoxic agents include anti-angiogenic agents, pro-apoptotic agents, anti-mitotic agents, anti-kinase agents, alkylating agents, hormones, hormone agonists, hormone antagonists, chemokines, drugs, prodrugs, toxins, enzymes, antimetabolites, antibiotics, alkaloids, and radioactive isotopes.

In some embodiments, the cytotoxic agent comprises at least one of: calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, vinca alkaloid, maytansinoid, maytansinoid analog, pyrrolobenzodiazepine, taxoid, duocarmycin, dolastatin, auristatin and derivatives thereof. In certain embodiments, the cytotoxic agent is monomethyl auristatin E (MMAE).

In some embodiments, the cytotoxic agent is a diagnostic agent, such as a radioactive isotope, a metal chelator, an enzyme, a fluorescent compound, a bioluminescent compound, or a chemiluminescent compound.

In some embodiments, the cytotoxic agent is a cytotoxic payload improved safety profile, for example XMT-1267 and other cytotoxic payloads described in Trail et al., *Pharmacol Ther,* 2018, 181:126-142.

6. Linkers

In some embodiments, ADCs provided herein comprise a linker. In some embodiments, an unbound linker comprises two reactive termini: an antibody conjugation reactive termini and an cytotoxic agent conjugation reactive termini. The antibody conjugation reactive terminus of the linker can be conjugated to the antibody through a cysteine thiol or lysine amine group on the antibody, typically a thiol-reactive group such as a double bond, a leaving group such as a chloro, bromo or iodo, an R-sulfanyl group or sulfonyl group, or an amine-reactive group such as a carboxyl group. The cytotoxic agent conjugation reactive terminus of the linker can be conjugated to the cytotoxic agent through formation of an amide bond with a basic amine or carboxyl group on the cytotoxin, typically a carboxyl or basic amine group.

In some embodiments, the linker is a non-cleavable linker. In some embodiments, the linker is a cleavable linker. In some embodiments, the cytotoxic agent is released from the ADC in a cell.

Suitable linkers of ADCs include labile linkers, acid labile linkers (e.g., hydrazone linkers), photolabile linkers, charged linkers, disulfide-containing linkers, peptidase-sensitive linkers (e.g., peptide linkers comprising amino acids, for example, valine and/or citrulline such as citrulline-valine or phenylalanine-lysine), β-glucuronide-linkers (See e.g., Graaf et al., *Curr Pharm Des,* 2002, 8:1391-1403), dimethyl linkers (See e.g., Chari et al., *Cancer Research,* 1992, 52:127-131; U.S. Pat. No. 5,208,020), thio-ether linkers, or hydrophilic linkers (See e.g., Kovtun et al., *Cancer Res.,* 2010, 70:2528-2537). In certain embodiments, the cytotoxic agent is conjugated to the antibody using a valine-citrulline (vc) linker.

7. Methods for Making Antibody-Drug Conjugates

The antibody-drug conjugates (ADCs) provided herein can be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfoSIAB, sulfo-SMCC, and sulfo-SMPB, and SVSB (succinimidyl-(4-vinylsulfone)benzoate)). For example, a ricin immunotoxin can be prepared as described in Vitetta et al., *Science,* 1987, 238:1098. Additionally, the ADCs can be prepared using any suitable methods as disclosed in the art, e.g., in *Bioconjugate Techniques,* 2nd Ed., G. T. Hermanson, ed., Elsevier, San Francisco, 2008.

In some embodiments, the ADCs are made with site-specific conjugation techniques, resulting in homogeneous drug loading and avoiding ADC subpopulations with altered antigen-binding or pharmacokinetics. In some embodiments, "thiomabs" comprising cysteine substitutions at positions on the heavy and light chains are engineered to provide reactive thiol groups that do not disrupt immunoglobulin folding and assembly or alter antigen binding (Junutula et al., *J. Immunol. Meth.,* 2008, 332: 41-52; Junutula et al., *Nat. Biotechnol.,* 2008, 26: 925-932). In some embodiments, selenocysteine is co-translationally inserted into an antibody sequence by recoding the stop codon UGA from termination to selenocysteine insertion, allowing site specific covalent conjugation at the nucleophilic selenol group of selenocysteine in the presence of the other natural amino acids (See e.g., Hofer et al., *Proc. Natl. Acad. Sci. USA,* 2008, 105: 12451-12456; Hofer et al., *Biochemistry,* 2009, 48(50): 12047-12057). In certain embodiments, ADCs were synthesized as described in Behrens et al., *Mol Pharm,* 2015, 12:3986-98.

8. Assays

A variety of assays known in the art may be used to identify and characterize anti-TF antibodies and anti-TF ADCs provided herein.

8.1. Binding, Competition, and Epitope Mapping Assays

Specific antigen-binding activity of the antibodies provided herein may be evaluated by any suitable method, including using SPR, BLI, RIA and MSD-SET, as described elsewhere in this disclosure. Additionally, antigen-binding activity may be evaluated by ELISA assays and Western blot assays.

Assays for measuring competition between two antibodies, or an antibody and another molecule (e.g., one or more ligands of TF) are described elsewhere in this disclosure and, for example, in Harlow and Lane, *Antibodies: A Laboratory Manual* ch. 14, 1988, Cold Spring Harbor Laboratory, Cold Spring Harbor, N.Y, incorporated by reference in its entirety.

Assays for mapping the epitopes to which the antibodies provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

8.2. Thrombin Generation, FXa Conversion, and TF Signaling Assays

Thrombin generation in the presence of the antibodies provided herein can be determined by the Thrombin Generation Assay (TGA), as described elsewhere in this disclosure.

Assays for measuring FXa conversion in the presence of the antibodies provided herein are described elsewhere in this disclosure.

Inhibition of TF signaling can be determined by measuring the production of a cytokine regulated by the TF signaling, such as IL8 and GM-CSF. Assays for determining the IL8 and/or GM-CSF level are provided elsewhere in this disclosure and, for example, in Hjortoe et al., *Blood,* 2004, 103:3029-3037.

8.3. Assays for Effector Functions

Effector function following treatment with the antibodies provided herein may be evaluated using a variety of in vitro and in vivo assays known in the art, including those described in Ravetch and Kinet, *Annu. Rev. Immunol.,* 1991, 9:457-492; U.S. Pat. Nos. 5,500,362, 5,821,337; Hellstrom et al., Proc. Nat'l Acad. Sci. USA, 1986, 83:7059-7063; Hellstrom et al., *Proc. Nat'l Acad. Sci. USA,* 1985, 82:1499-1502; Bruggemann et al., *J. Exp. Med.,* 1987, 166:1351-1361; Clynes et al., *Proc. Nat'l Acad. Sci. USA,* 1998, 95:652-656; WO 2006/029879; WO 2005/100402; Gazzano-Santoro et al., *J. Immunol. Methods,* 1996, 202:163-171; Cragg et al., *Blood,* 2003, 101:1045-1052; Cragg et al. *Blood,* 2004, 103:2738-2743; and Petkova et al., *Int'l. Immunol.,* 2006, 18:1759-1769; each of which is incorporated by reference in its entirety.

8.4. Cytotoxicity Assays and In Vivo Studies

Assays for evaluating cytotoxicity of the antibody-drug conjugates (ADCs) provided herein are described elsewhere in this disclosure.

Xenograft studies in immune compromised mice for evaluating the in vivo efficacy of the ADCs provided herein are described elsewhere in this disclosure.

Syngeneic studies in immune competent mice for evaluating the in vivo efficacy of the ADCs are included in this disclosure.

8.5. Immunohistochemistry (IHC) Assays

Immunohistochemistry (IHC) assays for evaluating the TF expression in patient samples are described elsewhere in this disclosure.

8.6. Chimeric Construct Mapping and Epitope Binning Assays

Epitope binding differences between the anti-human TF antibodies provided herein can be determined by the chimeric TF construct mapping experiments and the epitope binning assays, as described elsewhere in this disclosure.

9. Pharmaceutical Compositions

The antibodies or ADCs provided herein can be formulated in any appropriate pharmaceutical composition and administered by any suitable route of administration. Suitable routes of administration include, but are not limited to, the intravitreal, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the Handbook of *Pharmaceutical Excipients*, Rowe et al. (Eds.) 6th Ed. (2009), incorporated by reference in its entirety.

9.1. Parenteral Dosage Forms

In certain embodiments, the antibodies or ADCs provided herein are formulated as parenteral dosage forms. Parenteral dosage forms can be administered to subjects by various routes including, but not limited to, subcutaneous, intravenous (including infusions and bolus injections), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

10. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies or ADCs.

The amount of the antibody/ADC or composition which will be effective in the prevention or treatment of a disorder or one or more symptoms thereof can vary with the nature and severity of the disease or condition, and the route by which the antibody/ADC is administered. The frequency and dosage can also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies or ADCs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

As discussed in more detail elsewhere in this disclosure, an antibody or ADC provided herein may optionally be administered with one or more additional agents useful to prevent or treat a disease or disorder. The effective amount of such additional agents may depend on the amount of ADC present in the formulation, the type of disorder or treatment, and the other factors known in the art or described herein.

11. Therapeutic Applications

For therapeutic applications, the antibodies or ADCs of the invention are administered to a mammal, generally a human, in a pharmaceutically acceptable dosage form such as those known in the art and those discussed above. For example, the antibodies or ADCs of the invention may be administered to a human intravenously as a bolus or by continuous infusion over a period of time, by intravitreal, intramuscular, intraperitoneal, intra-cerebrospinal, subcutaneous, intra-articular, intrasynovial, intrathecal, or intratumoral routes. The antibodies or ADCs also are suitably administered by peritumoral, intralesional, or perilesional routes, to exert local as well as systemic therapeutic effects. The intraperitoneal route may be particularly useful, for example, in the treatment of ovarian tumors.

The antibodies or ADCs provided herein may be useful for the treatment of any disease or condition involving TF. In some embodiments, the disease or condition is a disease or condition that can benefit from treatment with an anti-TF antibody or ADC.

In some embodiments, the antibodies or ADCs provided herein are provided for use as a medicament. In some embodiments, the antibodies or ADCs provided herein are provided for use in the manufacture or preparation of a medicament. In some embodiments, the medicament is for the treatment of a disease or condition that can benefit from an anti-TF antibody or ADC.

In some embodiments, provided herein is a method of treating a disease or condition in a subject in need thereof by administering an effective amount of an anti-TF antibody or ADC provided herein to the subject.

In some embodiments, the disease or condition that can benefit from treatment with an anti-TF antibody or ADC is cancer. In some embodiments, the anti-TF antibodies or ADCs provided herein are provided for use as a medicament for the treatment of cancer. In some embodiments, the anti-TF antibodies or ADCs provided herein are provided for use in the manufacture or preparation of a medicament for the treatment of cancer. In some embodiments, provided herein is a method of treating cancer in a subject in need thereof by administering an effective amount of an anti-TF antibody or ADC provided herein to the subject.

TF is involved in thrombosis, metastasis, tumor growth, and/or tumor angiogenesis of various types of cancers, such as ovarian cancer (See Sakurai et al., *Int J Gynecol Cancer*, 2017, 27:37-43; Koizume et al., *Biomark Cancer*, 2015, 7:1-13; each of which is incorporated by reference in its entirety), cervical cancer (See Cocco et al., *BMC Cancer*, 2011, 11:263, incorporated by reference in its entirety), head and neck cancer (See Christensen et al., *BMC Cancer*, 2017, 17:572, incorporated by reference in its entirety), prostate cancer (See Yao et al., *Cancer Invest.*, 2009, 27:430-434; Abdulkadir et al., *Hum Pathol.*, 2009, 31:443-447; each of which is incorporated by reference in its entirety), pancreatic cancer (See Zhang et al., *Oncotarget*, 2017, 8:59086-59102, incorporated by reference in its entirety), triple negative breast cancer (See Zhang et al., *Oncotarget*, 2017, 8:59086-59102, incorporated by reference in its entirety), glioblastoma (See Guan et al., *Clin Biochem.*, 2002, 35:321-325; Carneiro-Lobo et al., *J Thromb Haemost*, 2009, 7:1855-1864; each of which is incorporated by reference in its entirety), lung cancer (See Yeh et al., *PLoS One*, 2013, 8:e75287; Regina et al., *Clin Chem.*, 2009, 55:1834-42; each of which is incorporated by reference in its entirety), gastric cancer (See Lo et al., *Br J Cancer.*, 2012, 107:1125-1130, incorporated by reference in its entirety), esophageal cancer (See Chen et al., *Acta Histochem.*, 2010, 3:233-239, incorporated by reference in its entirety), bladder cancer (See Patry et al., *Int J Cancer.*, 2008, 122:1592-1597, incorporated by reference in its entirety), melanoma (See Bromberg et al., *Proc Natl Acad Sci USA.*, 1995, 92:8205-8209, incorporated by reference in its entirety), and kidney cancer (See Silva et al., *Int Braz J Urol.*, 2014, 40:499-506, incorporated by reference in its entirety).

Any suitable cancer may be treated with the antibodies or ADCs provided herein. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer. Additional information on the types of cancers that can be treated with anti-TF antibodies or ADCs is provided in van den Berg et al., *Blood*, 2012, 119:924-932, which is incorporated by reference in its entirety.

In some embodiments, provided herein is a method of delaying the onset of a cancer in a subject in need thereof by administering an effective amount of an antibody or ADC provided herein to the subject.

In some embodiments, provided herein is a method of preventing the onset of a cancer in a subject in need thereof by administering an effective amount of an antibody or ADC provided herein to the subject.

In some embodiments, provided herein is a method of reducing the size of a tumor in a subject in need thereof by administering an effective amount of an antibody or ADC provided herein to the subject.

In some embodiments, provided herein is a method of reducing the number of metastases in a subject in need thereof by administering an effective amount of an antibody or ADC provided herein to the subject.

In some embodiments, provided herein is a method for extending the period of overall survival, median survival time, or progression-free survival in a subject in need thereof by administering an effective amount of an antibody or ADC provided herein to the subject.

In some embodiments, provided herein is a method for treating a subject who has become resistant to a standard of care therapeutic by administering an effective amount of an antibody or ADC provided herein to the subject.

In some embodiments, the disease or condition that can benefit from treatment with an anti-TF antibody is a disease or condition involving neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the disease or condition that can benefit from treatment with an anti-TF antibody is a disease or condition involving vascular inflammation.

In some embodiments, the anti-TF antibodies provided herein are provided for use as a medicament for the treatment of a disease or condition involving neovascularization. In some embodiments, the anti-TF antibodies provided herein are provided for use in the manufacture or preparation of a medicament for the treatment of a disease or condition involving neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the anti-TF antibodies provided herein are provided for use as a medicament for the treatment of a disease or condition involving vascular inflammation. In some embodiments, the anti-TF antibodies provided herein are provided for use in the manufacture or preparation of a medicament for the treatment of a disease or condition involving vascular inflammation.

In some embodiments, provided herein is a method of treating a disease or condition involving neovascularization in a subject in need thereof by administering an effective amount of an anti-TF antibody provided herein to the subject. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, provided herein is a method of treating a disease or condition involving vascular inflammation in a subject in need thereof by administering an effective amount of an anti-TF antibody provided herein to the subject.

In some embodiments, provided herein is a method of delaying the onset of a disease or condition involving neovascularization in a subject in need thereof by administering an effective amount of an antibody provided herein to the subject.

In some embodiments, provided herein is a method of preventing the onset of a disease or condition involving neovascularization in a subject in need thereof by administering an effective amount of an antibody provided herein to the subject.

In some embodiments, provided herein is a method of delaying the onset of age-related macular degeneration (AMD) in a subject in need thereof by administering an effective amount of an antibody provided herein to the subject.

In some embodiments, provided herein is a method of preventing the onset of age-related macular degeneration (AMD) in a subject in need thereof by administering an effective amount of an antibody provided herein to the subject.

In some embodiments, provided herein is a method of delaying the onset of diabetic retinopathy in a subject in need thereof by administering an effective amount of an antibody provided herein to the subject.

In some embodiments, provided herein is a method of preventing the onset of diabetic retinopathy in a subject in need thereof by administering an effective amount of an antibody provided herein to the subject.

In some embodiments, provided herein is a method of delaying the onset of a disease or condition involving vascular inflammation in a subject in need thereof by administering an effective amount of an antibody provided herein to the subject.

In some embodiments, provided herein is a method of preventing the onset of a disease or condition involving vascular inflammation in a subject in need thereof by administering an effective amount of an antibody provided herein to the subject.

12. Combination Therapies

In some embodiments, an antibody or ADC provided herein is administered with at least one additional therapeutic agent. Any suitable additional therapeutic agent may be administered with an antibody or ADC provided herein. In some aspects, the additional therapeutic agent is selected from radiation, a cytotoxic agent, a chemotherapeutic agent, a cytostatic agent, an anti-hormonal agent, an immunostimulatory agent, an anti-angiogenic agent, and combinations thereof.

The additional therapeutic agent may be administered by any suitable means. In some embodiments, an antibody or ADC provided herein and the additional therapeutic agent are included in the same pharmaceutical composition. In some embodiments, an antibody or ADC provided herein and the additional therapeutic agent are included in different pharmaceutical compositions.

In embodiments where an antibody or ADC provided herein and the additional therapeutic agent are included in different pharmaceutical compositions, administration of the antibody or ADC can occur prior to, simultaneously, and/or following, administration of the additional therapeutic agent.

13. Diagnostic Methods

Also provided are methods for detecting the presence of TF on cells from a subject. Such methods may be used, for example, to predict and evaluate responsiveness to treatment with an antibody or ADC provided herein.

In some embodiments, the method can be used to detect TF in a subject having or suspected of having a disease or condition. In some embodiments, the methods comprise (a) receiving a sample from the subject; and (b) detecting the presence or the level of TF in the sample by contacting the sample with the antibody provided herein. In some embodiments, the methods comprise (a) administering to the subject the antibody provided herein; and (b) detecting the presence or the level of TF in the subject. In some embodiments, the disease or condition is a cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer. In some embodiments, the disease or condition involves neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the disease or condition involves vascular inflammation.

In some embodiments, the methods comprise (a) administering to the subject the ADC provided herein; and (b) detecting the presence or the level of TF in the subject. In some embodiments, the disease or condition is a cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the antibody provided herein is conjugated with a fluorescent label. In some embodiments, the antibody provided herein is conjugated with a radioactive label. In some embodiments, the antibody provided herein is conjugated with an enzyme label.

In some embodiments, the ADC provided herein comprises a fluorescent label. In some embodiments, the ADC provided herein comprises a radioactive label. In some embodiments, the ADC provided herein comprises an enzyme label.

In some embodiments, the relative amount of TF expressed by such cells is determined. The fraction of cells expressing TF and the relative amount of TF expressed by such cells can be determined by any suitable method. In some embodiments, flow cytometry is used to make such measurements. In some embodiments, fluorescence assisted cell sorting (FACS) is used to make such measurement.

14. Kits

Also provided are kits comprising the antibodies or ADCs provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an antibody or ADC provided herein. The label or package insert indicates that the composition is used for treating the selected condition.

In some embodiments, the kit comprises (a) a first container with a first composition contained therein, wherein the first composition comprises an antibody or ADC provided herein; and (b) a second container with a second composition contained therein, wherein the second composition comprises a further therapeutic agent. The kit in this embodiment of the invention may further comprise a package insert indicating that the compositions can be used to treat a particular condition.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

The following are examples of methods and compositions of the invention. It is understood that various other embodiments may be practiced, given the general description provided herein.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Generation of TF Antibodies

Human, cynomolgus monkey, and mouse TF extracellular domain (ECD) fragments were expressed as C-terminal His or Fcγ fragment fusions. Expi293 cells (ThermoFisher Scientific, Waltham, Mass., USA) were transiently transfected as recommended by the manufacturer with pcDNA3.1V5-HisA (ThermoFisher Scientific) encoding human, cynomolgus, or mouse TF ECD-His6 (TF-His; SEQ ID NOs:811, 815, and 819, respectively) or pFUSE-hIgG1-Fc (Invivogen, San Diego, Calif., USA) encoding human, cynomolgus or mouse TF ECD-Fc (TF-Fc; SEQ ID NOs:812, 816, and 820, respectively). For the His-tagged proteins, cell culture supernatants cleared from cells by centrifugation were preconditioned with 330 mM sodium chloride and 13.3 mM imidazole. Using recommended procedures, the TF-His6 and TF-Fc proteins were purified by affinity chromatography with a HisTrap HP and MabSelect SuRe column (GE Healthcare Bio-Sciences, Marlborough, Mass., USA), respectively. FVII-Fc expressed in Expi293 was purified by affinity chromatography with a MabSelect SuRe column, followed by size exclusion chromatography. The TF-His6 and TF-Fc proteins were biotinylated with a 15× molar excess of Sulfo-NHS-SS-biotin as recommended (ThermoFisher Scientific). The non-labeled and biotinylated proteins were further purified by size exclusion chromatography using a Superdex 200 Increase 10/300 column (GE Healthcare Bio-Sciences).

Human antibodies against human TF were generated by Adimab™ yeast-based antibody presentation using the biotinylated recombinant TF proteins as screening antigens, as described below. All antibodies against human TF were evaluated for cross-reactivity with cynomolgus monkey and mouse TF. The binding activity of the antibodies to human, cynomolgus monkey, and mouse TF is shown in Table 5.

I. Library Interrogation and Selection Methodology for Isolation of Anti-TF Antibodies Naive Library Selections Eight naïve human synthetic yeast libraries each of ~$10^9$ diversity were designed, generated, and propagated as described previously (see, e.g., WO2009036379; WO2010105256, WO2012009568; Xu et al., *Protein Eng Des Sel.*, 2013, 26(10):663-70). Eight parallel selections were performed, using the eight naïve libraries for monomeric human TF selections.

For the first two rounds of selection, a magnetic bead sorting technique utilizing the Miltenyi MACS system was performed, essentially as described (Siegel et al., *J Immunol Methods*, 2004, 286(1-2):141-53). Briefly, yeast cells (~$10^{10}$ cells/library) were incubated with 10 nM of biotinylated human TF Fc-fusion antigen for 15 min at room temperature in FACS wash buffer PBS with 0.1% BSA. After washing once with 50 mL ice-cold wash buffer, the cell pellet was resuspended in 40 mL wash buffer, and 500 µl Streptavidin MicroBeads (Miltenyi Biotec, Bergisch Gladbach, Germany; Cat #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany; Cat. #130-042-401). After the 5 mL was loaded, the column was washed 3 times with 3 mL FACS wash buffer. The column was then removed from the magnetic field, and the yeast were eluted with 5 mL of growth media and then grown overnight.

Subsequent to the two rounds of MACS, the following four rounds of sorting were performed using flow cytometry (FACS). For the first round of FACS, approximately $5\times10^{-7}$ yeast were pelleted, washed three times with wash buffer, and incubated with 10 nM of each the biotinylated Fc-fusion proteins of mouse and/or cynomolgus TF antigen for 10-15 min at room temperature. Yeast were then washed twice and stained with LC-FITC diluted 1:100 (Southern Biotech, Birmingham, Ala.; Cat #2062-02) and either SA-633 (Life Technologies, Grand Island, N.Y.; Cat #S21375) diluted 1:500, or EA-PE (Sigma-Aldrich, St Louis; Cat #E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences), and sort gates were determined to select for TF binding. The mouse- and cyno-selected populations from the first round of FACS were grown out and expanded through sub-culturing in selective media. The second, third, and fourth rounds of FACS involved positive sorts to enrich for TF binders and/or negative sorts to decrease the number of non-specific binders using soluble membrane proteins from CHO cells (see, e.g., WO2014179363 and Xu et al., *PEDS*, 2013, 26(10): 663-70). After the final round of sorting, yeast were plated and sequenced.

Affinity Maturation of Clones Identified in Naïve selections

Heavy chains from the naïve outputs (described above) were used to prepare light chain diversification libraries, which were then used for additional selection rounds. In particular, heavy chain variable regions were extracted from the fourth naïve selection round outputs and transformed into a light chain library with a diversity of $1\times10^6$.

The first of selection round utilized Miltenyi MACS beads and 10 nM biotinylated human TF Fc-fusion as antigen. Subsequent to the MACS bead selections, three rounds of FACS sorting were performed as described above using cynomolgus and mouse Fc-fusion TF at 10 nM or either biotinylated Fc-fusion TF antigens or biotinylated monomeric HIS-forms of human, mouse or cynomolgus TF. Individual colonies from each FACS selection round were sequenced.

Optimization of Leads Identified from Naïve or Light Chain Diversification Selections Optimization of lead clones was carried out utilizing three maturation strategies: diversification of CDR-H1 and CDR-H2; diversification of CDR-H3 following CDR-H1 and CDR-H2 diversity pool optimization; and diversification of CDR-L3 within selected CDR-L1 and CDR-L2 diversity pools.

CDR-H1 and CDR-H2 selection: The CDR-H3s from clones selected from either naïve or light chain diversification procedure were recombined into a premade library with CDR-H1 and CDR-H2 variants of a diversity of $1\times10^8$ and selections were performed using biotinylated Fc-fusion cynomolgus TF antigen, biotinylated cynomolgus HIS-TF antigen, and/or biotinylated human HIS-TF. Affinity pressures were applied by using decreasing concentrations of biotinylated HIS-TF antigens (down to 1 nM) under equilibrium conditions at room temperature.

CDR-H3/CDR-H1/CDR-H2 selections: Oligos were ordered from IDT which comprised the CDR-H3 as well as a homologous flanking region on either side of the CDR-H3. Amino acid positions in the CDR-H3 were variegated via NNK diversity at two positions per oligo across the entire CDR-H3. The CDR-H3 oligos were double-stranded using primers which annealed to the flanking region of the CDR-H3. The remaining FR1 to FR3 of the heavy chain variable region was amplified from pools of antibodies with improved affinity that were isolated from the CDR-H1 and CDR-H2 diversities selected above. The library was then created by transforming the double stranded CDR-H3 oligo, the FR1 to FR3 pooled fragments, and the heavy chain expression vector into yeast already containing the light chain of the parent. Selections were performed as during previous cycles using FACS sorting. FACS rounds assessed non-specific binding, species cross-reactivity, and affinity pressure, and sorting was performed to obtain populations with the desired characteristics. Affinity pressures for these selections were performed as described above in the CDR-H1 and CDR-H2 selection.

CDR-L3/CDR-L1/CDR-L2 selections: Oligos were ordered from IDT which comprised the CDR-L3 as well as a homologous flanking region on either side of the CDR-L3. Amino acid positions in the CDR-L3 were variegated via NNK diversity at one position per oligo across the entire CDR-L3. The CDR-L3 oligos were double-stranded using primers which annealed to the flanking region of the CDR-L3. The remaining FR1 to FR3 of the light chain variable region was amplified from pools of antibodies with improved affinity that were isolated from the CDR-L1 and CDR-L2 diversities selected above. The library was then created by transforming the double stranded CDR-L3 oligo, the FR1 to FR3 pooled fragments, and the light chain expression vector into yeast already containing the heavy chain of the parent. Selections were performed as during previous cycles using FACS sorting. FACS rounds assessed non-specific binding, species cross-reactivity, and affinity pressure, and sorting was performed to obtain populations with the desired characteristics. Affinity pressures included titrations as well as incorporation of the parental Fab in antigen pre-complexation.

II. IgG and Fab Production and Purification

In order to produce sufficient amounts of selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (LifeTechnologies, Cat #1943200250).

Example 2: Binding Affinity Assay

Kinetic measurements for the anti-TF antibodies were conducted on an Octet QK384 (Pall ForteBio, Fremont, Calif., USA) or a Biacore (GE Healthcare Bio-Sciences).

ForteBio affinity measurements were performed generally as previously described (Estep et al., MAbs. 2013 Mar.-Apr.; 5(2):270-8). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen (human, cynomolgus, or mouse TF) for 3 min, afterwards they were transferred to assay buffer for 3 min for off-rate measurement. Alternatively, binding measurements were obtained by loading biotinylated TF monomer on SA sensors followed by exposure to 100 nM antibody Fab in solution. Kinetic data was analyzed and fitted using a 1:1 Langmuir binding model and the $K_D$ was calculated by dividing the $k_{off}$ by the $k_{on}$. The $K_D$ values of the TF antibodies measured by the Octet-based experiments are shown in Table 5.

For the Biacore-based measurements, the antibody was covalently coupled to a CM5 or C1 chip using an amine-coupling kit (GE Healthcare Bio-Sciences). Association between the anti-TF antibodies and a five-point three-fold titration of TF-His starting at 25 to 500 nM was measured for 300 sec. Subsequently, dissociation between the anti-TF antibody and TF-His was measured for up to 1800 sec. Kinetic data was analyzed and fitted globally using a 1:1 binding model. The $K_D$ values of the TF antibodies measured by the Biacore-based experiments are shown in Table 5.

As shown in Table 5, the affinity of the antibodies for hTF, as indicated by $K_D$, is between $10^{-7}$ M and $10^{-11}$ M. All anti-hTF antibodies are cross-reactive with cTF. In addition, all anti-hTF antibodies from groups 25 and 43 exhibit binding activity to mTF. The anti-hTF antibodies 25G, 25G1, 25G9, and 43D8 are cross-reactive with mTF. There are no other known human or humanized anti-hTF monoclonal antibodies that exhibit binding activity and cross-reactivity to mouse TF, indicating that the antibodies from groups 25 and 43 bind to a novel TF epitope.

tific) encoding full-length mouse TF with a C-terminal FLAG tag. A mouse TF-positive CHO clone was isolated by limiting dilution in tissue culture-treated 96-well plates.

Cell-based antibody binding was assessed as previously described in Liao-Chan et al., *PLoS One*, 2015, 10:e0124708, which is incorporated by reference in its entirety. $1.2 \times 10^5$ cells collected with Cellstripper (Mediatech, Manassas, Va., USA) were incubated with a twelve-point 1:3 dilution titration of anti-human TF IgG1 or Fab antibody starting at 250 nM or 100 nM for 2 hr on ice. After 2 washes, cells labeled with IgG1 or Fab were incubated for 30 min on ice with 150 nM of Goat Phycoerythrin (PE) F(ab')$_2$ fragment goat anti-human IgG, Fcγ fragment specific (Jackson ImmunoResearch, West Grove, Pa., USA) or FITC-labeled F(ab')$_2$ fragment goat anti-human kappa (SouthernBiotech, Birmingham, Ala., USA), respectively. After 2 washes, dead cells were labeled with TO-PRO-3 Iodide (ThermoFisher Scientific) and samples were analyzed on a CytoFLEX flow cytometer (Beckman Coulter, Brea, Calif., USA) or Novocyte flow cytometer (ACEA Biosciences, San Diego, Calif., USA). The median fluorescence intensities (MFIs) at each dilution were plotted and cell $EC_{50}$'s were derived using a 4-parameter binding model in Prism (GraphPad, La Jolla, Calif., USA). The results of binding of anti-TF antibodies to human TF-positive HCT-116 cells are shown in FIGS. 1A and 1B. The results of binding of anti-TF antibodies to CHO cells expressing mouse TF are shown in FIGS. 2A and 2B.

All anti-hTF antibodies in FIGS. 1A and 1B exhibit high affinity to human TF-positive HCT-116 cells with an $EC_{50}$

TABLE 5

Antibody Kinetics

| Ab | Human $K_D$ (nM) [Biacore] | Cynomolgus $K_D$ (nM) [Biacore] | Mouse $K_D$ (nM) [Biacore] | Human $K_D$ (nM) [ForteBio] | Cynomolgus $K_D$ (nM) [ForteBio] | Mouse $K_D$ (nM) [ForteBio] |
|---|---|---|---|---|---|---|
| 1F | 0.31 | 0.26 | nd* | 1.28 | 1.43 | no binding* |
| 1G | nd* | nd* | nd* | 2.20 | 2.70 | nd* |
| 25A | 6.20 | 5.42 | nd* | 8.45 | 7.65 | 263 |
| 25A3 | 0.36 | 0.21 | nd* | 1.67 | 1.36 | 131 |
| 25A5 | 0.08 | 0.04 | nd* | 0.64 | 0.76 | 188 |
| 25G | 23.0 | 18.0 | nd* | 21.9 | 17.5 | 114 |
| 25G1 | 0.94 | 0.78 | 5.4 | 3.97 | 4.99 | 34.2 |
| 25G9 | 13.3 | 16.4 | 2.9 | 35.8 | 42.9 | 9.16 |
| 29D | nd* | nd* | nd* | 3.30 | 12.0 | nd |
| 29E | 0.47 | 5.06 | nd* | 2.32 | 15.0 | no binding* |
| 39A | 0.09 | 0.08 | nd* | 0.83 | 0.57 | no binding* |
| 43B | 1.75 | 5.64 | nd* | 2.40 | 3.40 | 161 |
| 43B1 | 0.07 | 0.12 | nd* | 0.96 | 1.05 | 72.1 |
| 43B7 | 0.14 | 0.24 | nd* | 0.86 | 0.94 | 360 |
| 43D | 2.09 | 5.66 | nd* | 3.84 | 4.12 | 281 |
| 43D7 | 0.06 | 0.12 | 21 | 1.02 | 1.11 | 41.4 |
| 43D8 | 0.15 | 0.39 | 2.4 | 1.61 | 1.96 | 6.12 |
| 43E | 1.46 | 5.69 | nd* | 2.52 | 4.07 | 121 |
| 43Ea | 1.60 | 6.42 | nd* | 2.28 | 2.71 | 140 |
| 54E | 0.42 | 1.83 | nd* | 1.59 | 4.16 | no binding* | no binding*: no to weak binding, with no reportable $K_D$
nd*: not determined

Example 3: Cell-Based Binding Assay

HCT116 cells with endogenous expression of human TF were obtained from the American Tissue Culture Collection (ATCC, Manassas, Va., USA) and were maintained as recommended. Flp-In-CHO cells expressing mouse TF were generated by transfection of Flp-In-CHO cells as recommended with a pcDNA5/FRT vector (ThermoFisher Scienranging from about 687 pM to about 39 pM. Antibodies from groups 25 and 43 exhibit binding to CHO cells expressing mouse TF with an $EC_{50}$ ranging from about 455 nM to about 2.9 nM, as shown in FIGS. 2A and 2B. The binding activity to mouse TF is a unique property of the anti-hTF antibodies from groups 25 and 43. This is advantageous for pre-clinical studies of these antibodies with mouse models.

Example 4: Thrombin Generation Assay (TGA)

The TGA assay was performed using the calibrated-automated-thrombogram (CAT) instrument manufactured and distributed by STAGO. The test method design was equivalent to a standard CAT assay measurement, except that the plasma source was NPP in citrate/CTI. The anti-TF antibodies were titrated at 0, 10, 50 and 100 nM and mixed with normal pooled plasma (NPP) collected in 11 mM citrate supplemented with 100 microgram/mL of corn trypsin inhibitor (citrate/CTI). Relipidated TF was added to a 96-well assay plate, followed by addition of the antibody/NPP mixture. After a 10-min incubation or directly after combining the relipidated TF with antibody/NPP, thrombin generation was initiated by the addition of calcium and the thrombin substrate. The STAGO software was used to report the following parameters: Peak IIa (highest thrombin concentration generated [nM]); Lag Time (time to IIa generation [min]); ETP (endogenous thrombin potential, area under the curve [nM×min]); and ttPeak (time to Peak IIa [min]). Percent peak thrombin generation (% Peak IIa) and percent endogenous thrombin potential (% ETP) in the presence of each antibody relative to a no antibody plasma control on the same plate were also reported.

Figure 3A:
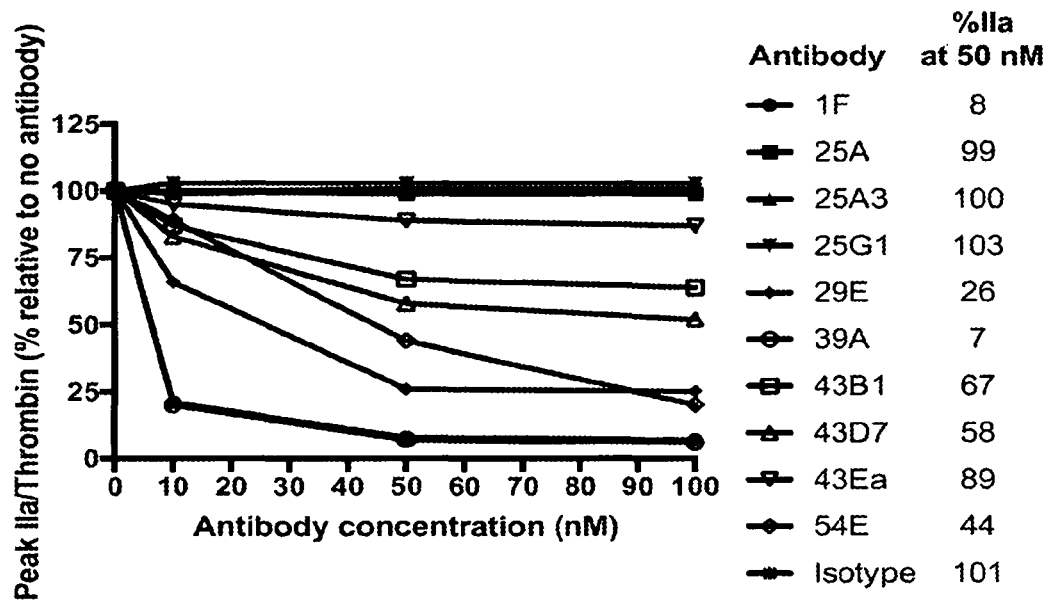
FIGS. 3A and 3B show thrombin generation in the presence of anti-TF antibody.
Figure 3B:
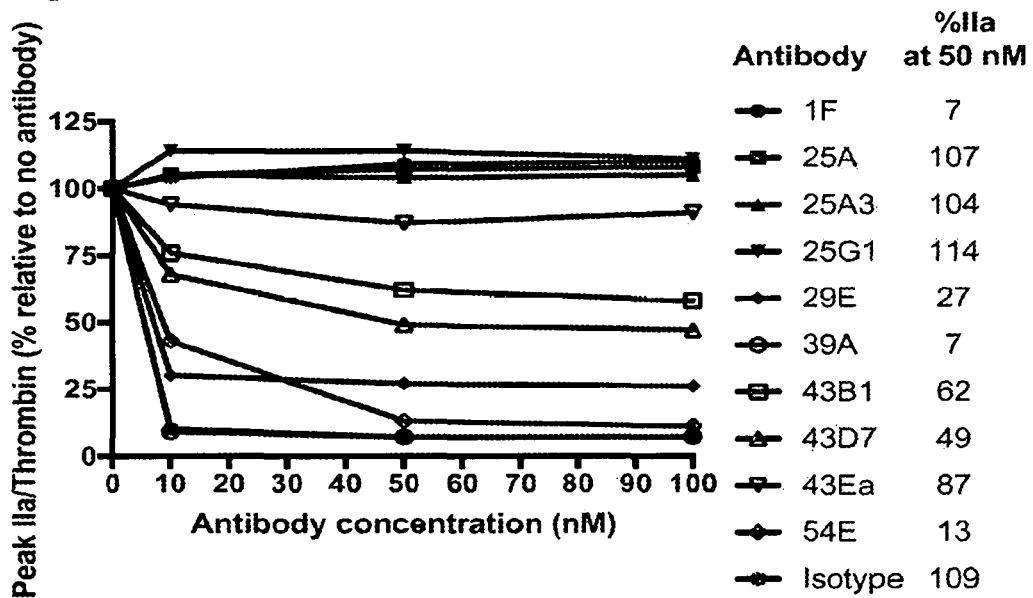

The Peak IIa, Lag Time, ETP, ttPeak, % Peak IIa, and % ETP in the presence of each antibody selected from 1F, 25A, 25A3, 25G1, 29E, 39A, 43B1, 43D7, 43Ea, and 54E without antibody incubation prior to addition of calcium and thrombin substrate are shown in Table 6. The Peak IIa, Lag Time, ETP, ttPeak, % Peak IIa, and % ETP in the presence of each antibody selected from 1F, 25A, 25A3, 25G1, 29E, 39A, 43B1, 43D7, 43Ea, and 54E with 10 min antibody incubation prior to addition of calcium and thrombin substrate are shown in Table 7. The % Peak IIa in the presence of titrations of anti-TF antibodies without antibody incubation prior to addition of calcium and thrombin substrate is plotted in FIG. 3A. The % Peak IIa in the presence of titrations of anti-TF antibodies with 10 min antibody incubation prior to addition of calcium and thrombin substrate is plotted in FIG. 3B.

The % Peak IIa is greater than 90% in the presence of antibodies from group 25, including 25A, 25A3, and 25G1. The % ETP is greater than 100% in the presence of antibodies from group 25, including 25A, 25A3, and 25G1. The % Peak IIa is greater than 40% in the presence of antibodies from group 43, including 43B1, 43D7, and 43Ea. The % ETP is greater than 90% in the presence of antibodies from group 43, including 43B1, 43D7, and 43Ea.

This data indicates that antibodies from groups 25 and 43 allow normal thrombin generation, and therefore are not inhibitors of thrombin generation.

TABLE 6

Thrombin Generation Assay without Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 1 | 1F | 100 | 29 | 25.9 | * | 37.9 | 7 | * |
|   |    | 50  | 32 | 27.2 | * | 36.8 | 8 | * |
|   |    | 10  | 83 | 12.1 | 1395 | 19.8 | 21 | 58 |
| 1 | 25A | 100 | 398 | 4.4 | 2610 | 7.1 | 99 | 108 |
|   |     | 50  | 399 | 4.2 | 2621 | 7.1 | 99 | 108 |
|   |     | 10  | 403 | 4.1 | 2555 | 6.8 | 100 | 106 |
| 1 | 25A3 | 100 | 405 | 3.9 | 2493 | 6.5 | 100 | 103 |
|   |      | 50  | 404 | 3.9 | 2495 | 6.6 | 100 | 103 |
|   |      | 10  | 401 | 4.2 | 2550 | 7.3 | 99 | 106 |
| 1 | 25G1 | 100 | 416 | 4.5 | 2626 | 7.1 | 103 | 109 |
|   |      | 50  | 416 | 4.5 | 2680 | 7.1 | 103 | 111 |
|   |      | 10  | 417 | 4.5 | 2635 | 7.0 | 103 | 109 |
| 1 | 29E | 100 | 99 | 17.3 | * | 26.4 | 25 | * |
|   |     | 50  | 107 | 14.4 | 1747 | 22.7 | 26 | 72 |
|   |     | 10  | 266 | 5.7 | 2189 | 10.0 | 66 | 91 |
| 1 | 39A | 100 | 26 | 28.9 | * | 40.1 | 6 | * |
|   |     | 50  | 30 | 30.5 | * | 40.0 | 7 | * |
|   |     | 10  | 82 | 12.1 | 1330 | 19.6 | 20 | 55 |
| 1 | Plasma ctrl. | NA | 403 | 4.1 | 2417 | 6.8 | 100 | 100 |
| 2 | 43B1 | 100 | 221 | 5.2 | 2167 | 10.6 | 64 | 100 |
|   |      | 50  | 232 | 5.2 | 2195 | 10.3 | 67 | 101 |
|   |      | 10  | 299 | 4.9 | 2288 | 8.9 | 87 | 105 |
| 2 | 43D7 | 100 | 179 | 5.4 | 2094 | 11.8 | 52 | 96 |
|   |      | 50  | 202 | 5.3 | 2116 | 11.1 | 58 | 97 |
|   |      | 10  | 287 | 5.0 | 2263 | 9.0 | 83 | 104 |
| 2 | 43Ea | 100 | 300 | 4.6 | 2219 | 8.1 | 87 | 102 |
|   |      | 50  | 307 | 4.6 | 2234 | 8.1 | 89 | 103 |
|   |      | 10  | 328 | 5.0 | 2329 | 8.3 | 95 | 107 |
| 2 | 54E | 100 | 68 | 14.8 | 1175 | 23.9 | 20 | 54 |
|   |     | 50  | 154 | 8.9 | 2019 | 15.9 | 44 | 93 |
|   |     | 10  | 307 | 5.7 | 2307 | 9.6 | 89 | 106 |
| 2 | Isotype | 100 | 348 | 5.0 | 2415 | 8.3 | 101 | 111 |
|   |         | 50  | 347 | 5.0 | 2360 | 8.0 | 101 | 109 |
|   |         | 10  | 346 | 4.3 | 2260 | 7.6 | 100 | 104 |
| 2 | Plasma ctrl. | NA | 345 | 4.7 | 2171 | 7.8 | 100 | 100 |

* Groups with "No Tail Found" Errors when the software cannot calculate the ETP.

TABLE 7

Thrombin Generation Assay with 10 min Antibody Pre-Incubation

| Plate | Antibody | Ab conc. (nM) | Peak IIa (nM) | Lag Time (mm) | ETP (nM·min) | ttPeak (mm) | % Peak IIa | % ETP |
|---|---|---|---|---|---|---|---|---|
| 1 | 1F | 100 | 17 | 30.3 | * | 42.0 | 7 | * |
|   |    | 50  | 20 | 27.6 | * | 38.9 | 7 | * |
|   |    | 10  | 27 | 18.8 | 540 | 28.6 | 10 | 31 |
| 1 | 25A | 100 | 285 | 3.3 | 1898 | 6.7 | 108 | 110 |
|   |     | 50  | 284 | 3.3 | 1887 | 6.6 | 107 | 110 |
|   |     | 10  | 277 | 3.3 | 1842 | 6.7 | 105 | 107 |
| 1 | 25A3 | 100 | 277 | 3.1 | 1785 | 6.3 | 105 | 104 |
|   |      | 50  | 275 | 3.2 | 1824 | 6.4 | 104 | 106 |
|   |      | 10  | 278 | 3.2 | 1827 | 6.6 | 105 | 106 |
| 1 | 25G1 | 100 | 293 | 3.3 | 1827 | 6.4 | 111 | 106 |
|   |      | 50  | 301 | 3.3 | 1853 | 6.3 | 114 | 108 |
|   |      | 10  | 302 | 3.3 | 1891 | 6.3 | 114 | 110 |
| 1 | 29E | 100 | 68 | 15.1 | 1098 | 25.3 | 26 | 64 |
|   |     | 50  | 70 | 14.2 | 1168 | 24.3 | 27 | 68 |
|   |     | 10  | 78 | 10.4 | 1254 | 20.2 | 30 | 73 |
| 1 | 39A | 100 | 17 | 28.0 | * | 40.2 | 7 | * |
|   |     | 50  | 17 | 28.4 | 346 | 38.9 | 7 | 20 |
|   |     | 10  | 25 | 20.8 | 482 | 30.7 | 9 | 28 |
| 1 | Plasma ctrl. | NA | 264 | 3.3 | 1720 | 6.8 | 100 | 100 |
| 2 | 43B1 | 100 | 152 | 3.2 | 1712 | 9.3 | 58 | 98 |
|   |      | 50  | 163 | 3.2 | 1797 | 9.0 | 62 | 103 |
|   |      | 10  | 200 | 3.2 | 1788 | 8.1 | 76 | 103 |
| 2 | 43D7 | 100 | 124 | 3.6 | 1656 | 10.3 | 47 | 95 |
|   |      | 50  | 128 | 3.6 | 1677 | 10.3 | 49 | 96 |
|   |      | 10  | 178 | 3.6 | 1745 | 8.8 | 68 | 100 |
| 2 | 43Ea | 100 | 239 | 2.9 | 1820 | 6.9 | 91 | 104 |
|   |      | 50  | 227 | 2.9 | 1791 | 7.1 | 87 | 103 |
|   |      | 10  | 247 | 3.2 | 1825 | 7.0 | 94 | 105 |
| 2 | 54E | 100 | 29 | 22.1 | 580 | 32.3 | 11 | 33 |
|   |     | 50  | 35 | 18.3 | 680 | 28.4 | 13 | 39 |
|   |     | 10  | 112 | 6.1 | 1530 | 13.4 | 43 | 88 |
| 2 | Isotype | 100 | 288 | 3.2 | 1888 | 6.6 | 110 | 108 |
|   |         | 50  | 285 | 3.2 | 1879 | 6.6 | 109 | 108 |
|   |         | 10  | 273 | 3.2 | 1804 | 6.6 | 104 | 104 |
| 2 | Plasma ctrl. | NA | 262 | 3.2 | 1742 | 6.9 | 100 | 100 |

* Groups with "No Tail Found" Errors when the software cannot calculate the ETP.

Example 5: FXa Conversion Assay

Figure 4A:
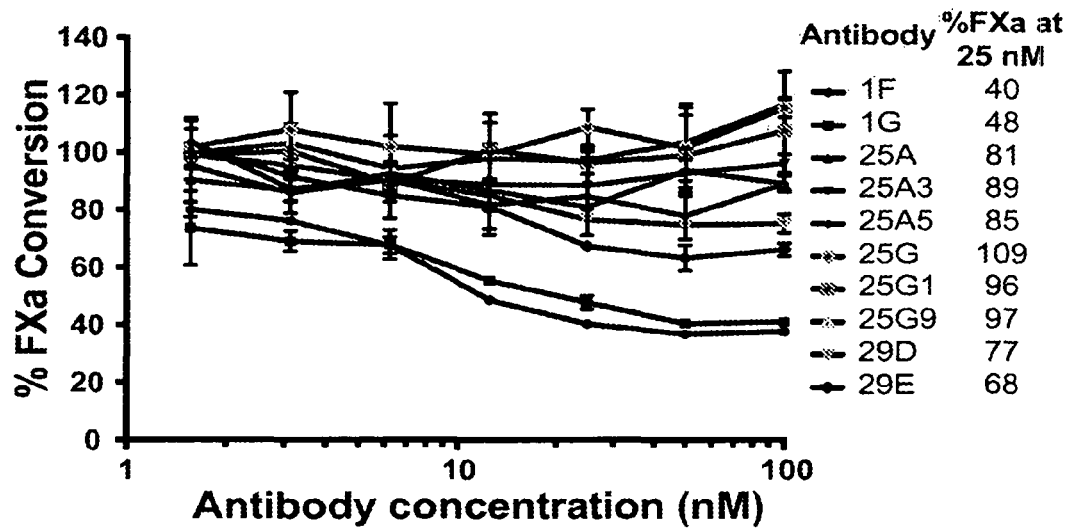
FIGS. 4A and 4B show FXa conversion in the presence of anti-TF antibody.
Figure 4B:
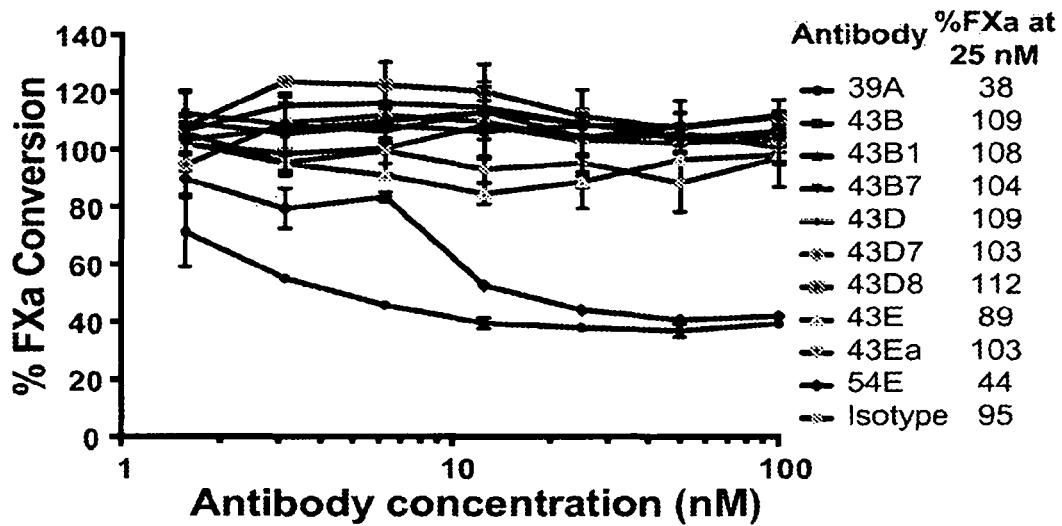

To evaluate the ability of TF:FVIIa to convert FX into FXa in the presence of human antibodies against TF, $5\times10^4$ MDA-MB-231 cells (ATCC, Manassas, Va., USA) were plated into tissue culture-treated black 96-well plates (Greiner Bio-One, Monroe, N.C., USA). After removal of the cell culture media and addition of a final concentration of 200 nM of FX in a HEPES buffer with 1.5 mM $CaCl_2$, cells were incubated with a titration of the antibodies for 15 min at 37° C. Upon reconstitution of the binary TF:FVIIa complex with a final concentration of 20 nM of FVIIa, cells were incubated for 5 min at 37° C. After quenching the reaction with ethylenediaminetetraacetic acid (EDTA), generated FXa was measured with 50 μM of SN-7 6-amino-1-naphthalenesulfonamide-based fluorogenic substrate (Haematologic Technologies, Essex Junction, Vt., USA) on an Envision plate reader equipped with an Umbelliferone 355 excitation filter, an Umbelliferone 460 emission filter, and a LANCE/DELFIA top mirror (Perkin Elmer, Waltham, Mass., USA). FXa conversion percentages (% FXa) in the presence of an anti-TF antibody titration relative to a no-antibody control are summarized in Table 8 and plotted in FIGS. 4A and 4B.

The FXa conversion percentage ranges from about 78% to about 120% in presence of different concentrations of antibodies from groups 25 and 43, including 25A, 25A3, 25G, 25G1, 25G5, 25G9, 43B, 43B1, 43B7, 43D, 43D7, 43D8, 43E, and 43Ea.

This data indicates that anti-TF antibodies from groups 25 and 43 do not inhibit TF:FVIIa mediated FXa conversion from FX. This data also indicates that anti-TF antibodies from groups 25 and 43 have a human TF binding site that is distinct from the human TF binding site bound by FX.

TABLE 8

% FXa conversion

| Antibody | % FXa | | | |
|---|---|---|---|---|
|  | 12.5 nM | 25 nM | 50 nM | 100 nM |
| 1F | 49 | 40 | 37 | 38 |
| 1G | 55 | 48 | 41 | 41 |
| 25A | 87 | 81 | 94 | 89 |
| 25A3 | 89 | 89 | 93 | 96 |
| 25A5 | 82 | 85 | 78 | 89 |
| 25G | 99 | 109 | 102 | 116 |
| 25G1 | 101 | 96 | 99 | 108 |
| 25G9 | 98 | 97 | 104 | 117 |
| 29D | 85 | 77 | 75 | 75 |
| 29E | 81 | 68 | 63 | 66 |
| 39A | 39 | 38 | 37 | 39 |
| 43B | 113 | 109 | 105 | 105 |
| 43B1 | 106 | 108 | 108 | 112 |
| 43B7 | 113 | 104 | 108 | 108 |
| 43D | 115 | 109 | 104 | 106 |
| 43D7 | 110 | 103 | 102 | 103 |
| 43D8 | 120 | 112 | 107 | 111 |
| 43E | 85 | 89 | 97 | 98 |

TABLE 8-continued

% FXa conversion

| Antibody | % FXa | | | |
|---|---|---|---|---|
| | 12.5 nM | 25 nM | 50 nM | 100 nM |
| 43Ea | 108 | 103 | 106 | 101 |
| 54E | 53 | 44 | 41 | 42 |
| 5G9 | 37 | 33 | 30 | 30 |
| Isotype ctrl | 93 | 95 | 89 | 97 |

Example 6: FVIIa Competition Assay

FVII-Fc conjugates were generated using Alexa Fluor 488 5-sulfo-dichlorophenol esters (ThermoFisher Scientific). Excess Alexa Fluor dye was removed from the conjugate preparations by gel filtration (ThermoFisher Scientific).

Figure 5A:
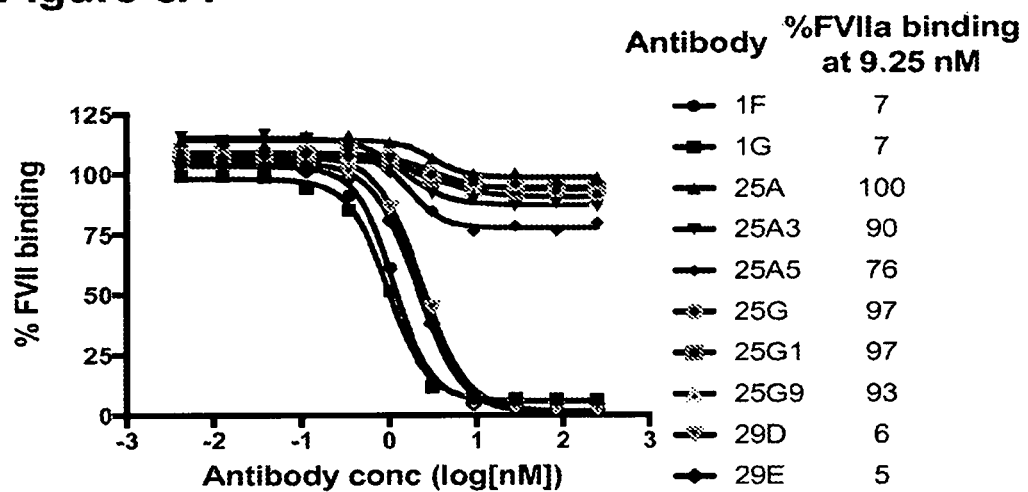
FIGS. 5A and 5B show FVIIa binding in the presence of anti-TF antibody.
Figure 5B:
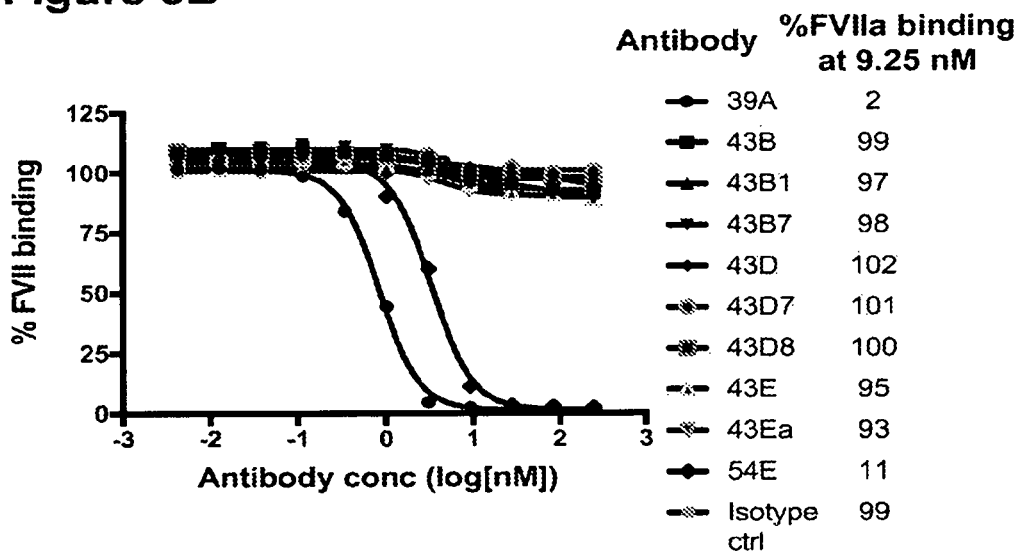

To evaluate competition between FVIIa and the human antibodies against TF, TF-positive MDA-MB-231 cells (ATCC, Manassas, Va., USA) were first incubated for 1 hr on ice with a titration of the human antibodies against TF. Subsequently, a final concentration of 20 nM of FVII-Fc conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. FVII-Fc binding was summarized with % FVII-Fc binding= [$MFI_{antibody\ labeled\ cells}$−$MFI_{unstained}$ cells]/[$MFI_{IgG1\ control\ labeled\ cells}$−$MFI_{unstained}$ cells]. Percentage of FVIIa binding (% FVIIa) in the presence of an anti-TF antibody titration relative to a no-antibody control is summarized in Table 9 and plotted in FIGS. 5A and 5B.

The FVIIa binding percentage ranges from about 76% to about 102% in the presence of antibodies of different concentrations from groups 25 and 43, including 25A, 25A3, 25G, 25G1, 25G5, 25G9, 43B, 43B1, 43B7, 43D, 43D7, 43D8, 43E, and 43Ea.

This data indicates that anti-TF antibodies from groups 25 and 43 do not compete for binding to human TF with FVIIa. This data also indicates that anti-TF antibodies from groups 25 and 43 have a human TF binding site that is distinct from the human TF binding cite hound by FVIIa.

Example 7: TF Signaling Assay

Figure 6A:
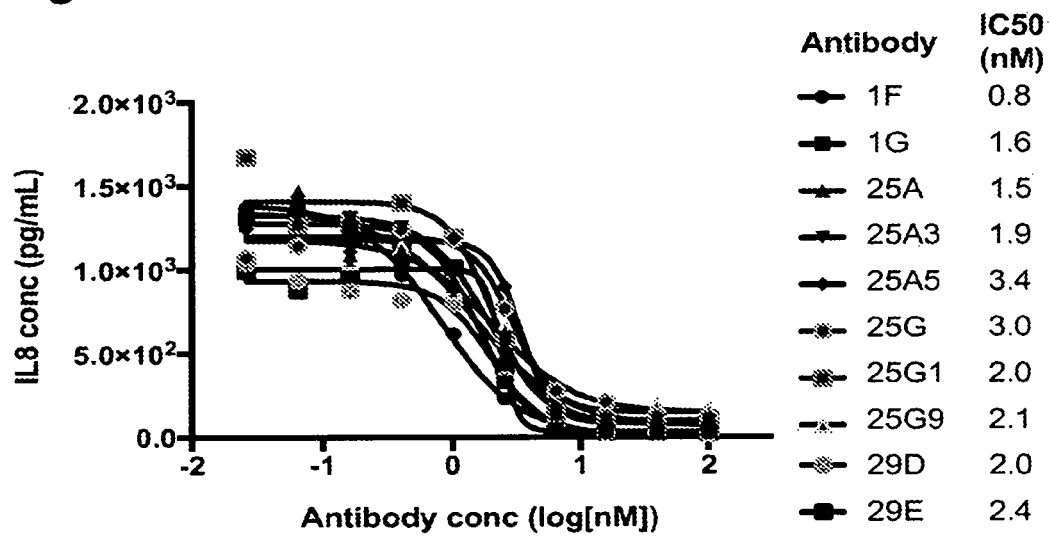
FIGS. 6A, 6B, 6C, and 6D show FVIIa-dependent TF signaling in the presence of anti-TF antibody.
Figure 6B:
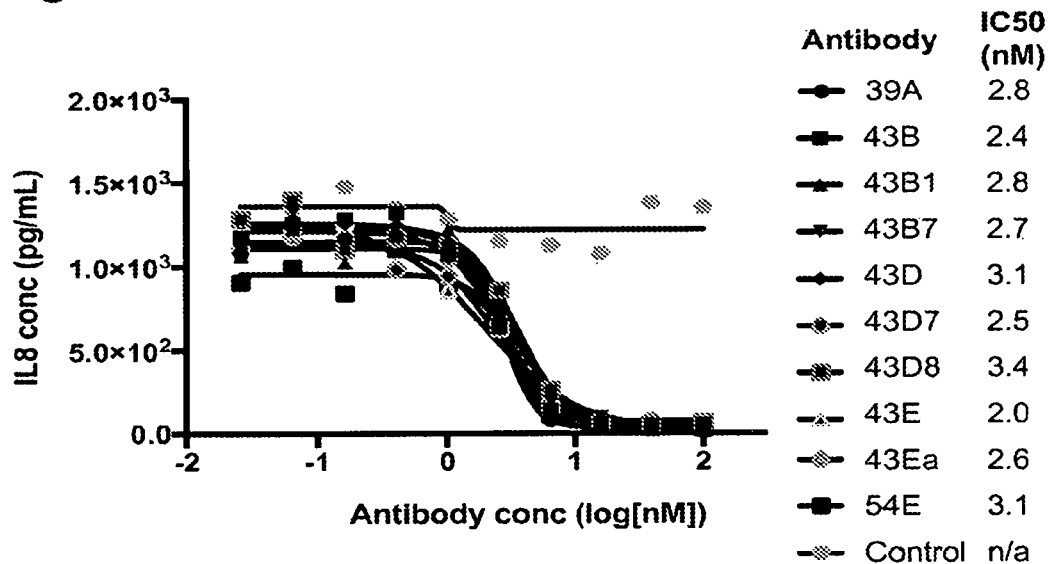
Figure 6C:
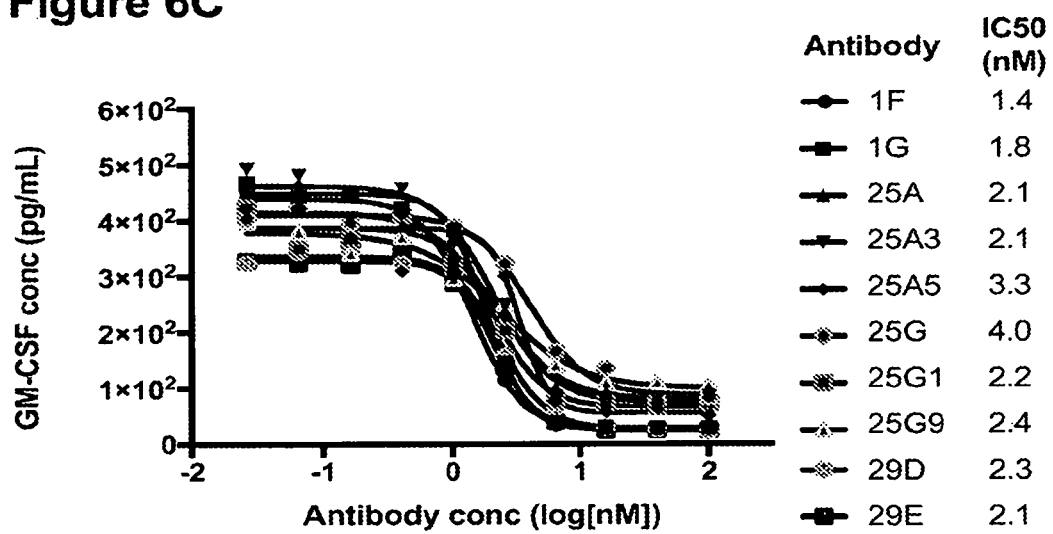
Figure 6D:
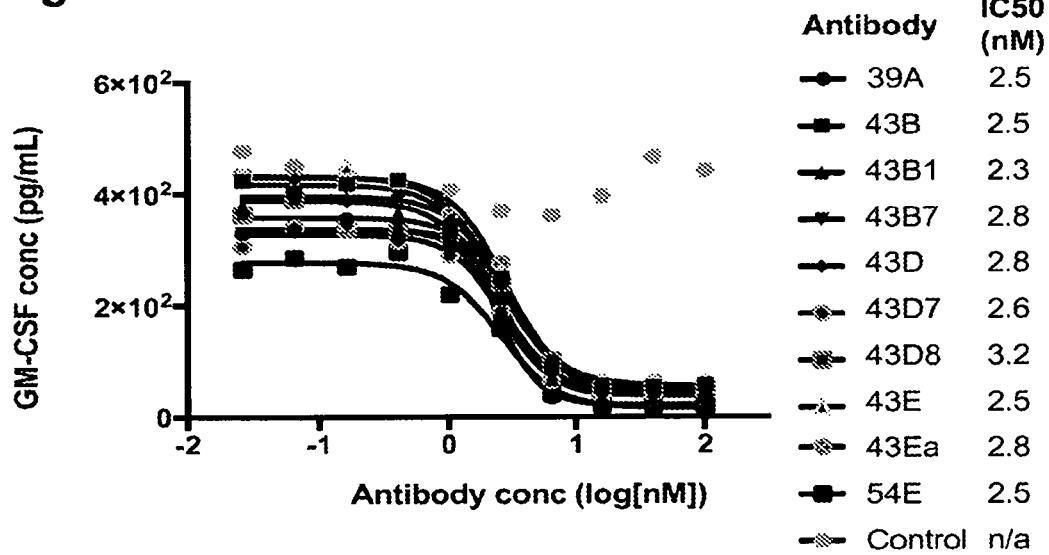

IL-8 and GM-CSF protein levels were measured as described previously in Hjortoe et al., *Blood,* 2004, 103: 3029-3037. TF-positive MDA-MB-231 cells (ATCC, Manassas, Va., USA) that underwent a 2 hr serum starvation with Leibovitz's L-15 medium were incubated with an 8-point 1:2.5 titration starting at 100 nM of anti-TF antibody. After 30 min at 37° C., FVIIa (NovoSeven RT, Novo Nordisk, Bagsvaerd, Denmark) was added to the cells at a final concentration of 20 nM. 5 hr later cell culture supernatants were harvested and analyzed by ELISA for IL8 or GM-CSF as recommended (R&D Biosystems, Minneapolis, Minn., USA). A standard curve using recombinant IL8 or GM-CSF (R&D Biosystems, Minneapolis, Minn., USA) was used in Prism to calculate cytokine concentration in the cell culture supernatants. Percent IL8 and GM-CSF (% IL8 and % GM-CSF) at reported antibody concentration were calculated relative to a no antibody control. The concentration of IL8 with the anti-TF antibody titration is plotted in FIGS. 6A and 6B and the % IL8 at different antibodies concentrations are shown in Table 10. The concentration of GM-CSF with the anti-TF antibody titration is plotted in FIGS. 6C and 6D and the % IL8 at different antibodies concentrations are shown in Table 11.

IL8 concentrations were reduced by more than 75% in the presence of the anti-TF antibodies at concentrations greater than or equal to 6.4 nM. GM-CSF concentrations were reduced by more than 60% in the presence of the anti-TF antibodies at concentrations greater than or equal to 6.4 nM.

This data indicates that all tested anti-TF antibodies inhibit FVIIa-dependent TF signaling.

TABLE 9

Competition of Anti-TF Antibody with FVIIa

| Antibody | % FVIIa | | | |
|---|---|---|---|---|
| | 9.25 nM | 28 nM | 83 nM | 250 nM |
| 1F | 7 | 7 | 7 | 6 |
| 1G | 7 | 7 | 7 | 6 |
| 25A | 100 | 101 | 97 | 98 |
| 25A3 | 90 | 87 | 88 | 87 |
| 25A5 | 76 | 79 | 77 | 80 |
| 25G | 97 | 96 | 93 | 92 |
| 25G1 | 97 | 93 | 94 | 95 |
| 25G9 | 93 | 93 | 91 | 89 |
| 29D | 6 | 4 | 3 | 3 |
| 29E | 5 | 3 | 2 | 2 |
| 39A | 2 | 2 | 2 | 2 |
| 43B | 99 | 95 | 93 | 91 |
| 43B1 | 97 | 95 | 93 | 91 |
| 43B7 | 98 | 98 | 97 | 97 |
| 43D | 102 | 100 | 98 | 94 |
| 43D7 | 101 | 102 | 100 | 101 |
| 43D8 | 100 | 99 | 98 | 96 |

TABLE 9-continued

Competition of Anti-TF Antibody with FVIIa

| Antibody | % FVIIa | | | |
|---|---|---|---|---|
| | 9.25 nM | 28 nM | 83 nM | 250 nM |
| 43E | 95 | 92 | 91 | 89 |
| 43Ea | 93 | 91 | 92 | 89 |
| 54E | 11 | 3 | 3 | 2 |
| Isotype | 99 | 98 | 97 | 99 |

TABLE 10

Inhibition of IL8

| Antibody | % IL8 | | | | |
|---|---|---|---|---|---|
| | 100 nM | 40 nM | 16 nM | 6.4 nM | 2.56 nM |
| 1F | 2 | 2 | 2 | 3 | 18 |
| 1G | 2 | 2 | 3 | 4 | 26 |
| 25A | 9 | 8 | 10 | 11 | 43 |
| 25A3 | 8 | 8 | 8 | 9 | 47 |
| 25A5 | 6 | 7 | 7 | 14 | 70 |
| 25G | 9 | 10 | 16 | 22 | 60 |
| 25G1 | 9 | 8 | 9 | 12 | 46 |
| 25G9 | 13 | 14 | 15 | 22 | 51 |
| 29D | 1 | 2 | 2 | 6 | 27 |
| 29E | 2 | 2 | 2 | 5 | 33 |
| 39A | 3 | 2 | 2 | 6 | 52 |
| 43B | 4 | 4 | 5 | 11 | 50 |
| 43B1 | 5 | 5 | 6 | 12 | 56 |
| 43B7 | 4 | 4 | 8 | 15 | 55 |
| 43D | 5 | 5 | 7 | 21 | 58 |
| 43D7 | 5 | 4 | 5 | 11 | 48 |
| 43D8 | 5 | 5 | 5 | 21 | 67 |

TABLE 10-continued

Inhibition of IL8

| Antibody | % IL8 | | | | |
|---|---|---|---|---|---|
| | 100 nM | 40 nM | 16 nM | 6.4 nM | 2.56 nM |
| 43E | 5 | 5 | 6 | 15 | 49 |
| 43Ea | 6 | 6 | 6 | 14 | 52 |
| 54E | 2 | 2 | 3 | 8 | 48 |
| Control | 106 | 108 | 84 | 88 | 90 |

TABLE 11

Inhibition of GM-CSF

| Antibody | % GM-CSF | | | | |
|---|---|---|---|---|---|
| | 100 nM | 40 nM | 16 nM | 6.4 nM | 2.56 nM |
| 1F | 6 | 6 | 6 | 8 | 27 |
| 1G | 7 | 7 | 7 | 9 | 34 |
| 25A | 22 | 19 | 22 | 24 | 57 |
| 25A3 | 20 | 19 | 19 | 20 | 59 |
| 25A5 | 12 | 15 | 14 | 18 | 72 |
| 25G | 19 | 18 | 32 | 39 | 77 |
| 25G1 | 17 | 16 | 17 | 18 | 48 |
| 25G9 | 25 | 26 | 26 | 34 | 60 |
| 29D | 5 | 6 | 7 | 15 | 38 |
| 29E | 6 | 6 | 5 | 9 | 33 |
| 39A | 7 | 5 | 5 | 8 | 42 |
| 43B | 14 | 13 | 12 | 21 | 59 |
| 43B1 | 11 | 11 | 13 | 16 | 50 |
| 43B7 | 11 | 11 | 13 | 17 | 50 |
| 43D | 12 | 11 | 13 | 24 | 56 |
| 43D7 | 10 | 10 | 9 | 15 | 45 |
| 43D8 | 12 | 11 | 11 | 24 | 57 |
| 43E | 14 | 15 | 15 | 21 | 61 |
| 43Ea | 14 | 15 | 14 | 21 | 65 |
| 54E | 5 | 5 | 5 | 10 | 38 |
| Control | 105 | 111 | 94 | 86 | 88 |

Example 8: Antibody Competition Assay

Alexa Fluor antibodies were generated using Alexa Fluor 488 5-sulfo-dichlorophenol esters (ThermoFisher Scientific). Excess Alexa Fluor dye was removed from the antibody dye conjugate preparations by gel filtration (ThermoFisher Scientific).

To evaluate competition between a first human antibody against TF and 25A, TF-positive A431 cells (ATCC, Manassas, Va., USA) were first incubated for 1 hr on ice with a titration of the first human antibody against TF. Subsequently, a final concentration of 20 nM of 25A conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 25A binding was summarized with % 25A binding=[$MFI_{antibody\ labeled\ cells}$-$MFI_{unstained}$ cells]/[$MFI_{IgG1\ control\ labeled\ cells}$-$MFI_{unstained}$ cells].

To evaluate competition between a first human antibody against TF and 43Ea, TF-positive A431 cells (ATCC, Manassas, Va., USA) were first incubated for 1 hr on ice with a titration of the first human antibody against TF. Subsequently, a final concentration of 20 nM of 43Ea conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 43Ea binding was summarized with % 43Ea binding=[$MFI_{antibody\ labeled\ cells}$-$MFI_{unstained}$ cells]/[$MFI_{IgG1\ control\ labeled\ cells}$-$MFI_{unstained}$ cells].

% 25A binding and % 43Ea binding are shown in Table 12. Antibodies from group 25 and group 43 reduced the % 25A binding and % 43Ea binding to less than 10%.

This data indicates that antibodies of group 25 and antibodies of group 43 compete with each other for binding to human TF, and may bind the same or an overlapping epitope of human TF.

TABLE 12

Competition of Anti-TF Antibody with Antibody Clone 25A or 43Ea

| Antibody (100 nM) | % 25A binding | % 43Ea binding |
|---|---|---|
| 1F | 95 | 77 |
| 1G | 75 | 58 |
| 25A | 3 | 1 |
| 25G | 7 | 3 |
| 29D | 70 | 64 |
| 29E | 96 | 85 |
| 39A | 99 | 96 |
| 43B | 0 | 0 |
| 43D | 0 | 0 |
| 43E | 0 | 0 |
| 54E | 99 | 96 |
| Isotype | 100 | 100 |

Example 9: Cell Viability Assay

To evaluate internalization of the anti-TF antibodies, a cytotoxicity assay was conducted. Briefly, cells were plated in 384-well plates (Greiner Bio-One, Monroe, N.C., USA) at $4 \times 10^3$ cells per well in 40 µl of media. Antibodies and secondary anti-human Fc antibodies conjugated to the tubulin inhibitor mono-methyl auristatin F (MMAF) (Moradec, San Diego, Calif., USA) were serially diluted starting at 5 and 30 nM, respectively. Plates were incubated for 3 days, followed by lysis in CellTiter-Glo (CTG) assay reagent (Promega, Madison, Wis., USA). CTG luminescence was measured on an Envision plate reader and the mean and standard deviation of 4 replicates graphed in Prism. For each anti-TF antibody, the $IC_{50}$ and its associated 95% confidence interval were calculated in Prism using a 4-parameter binding model.

Figure 7A:
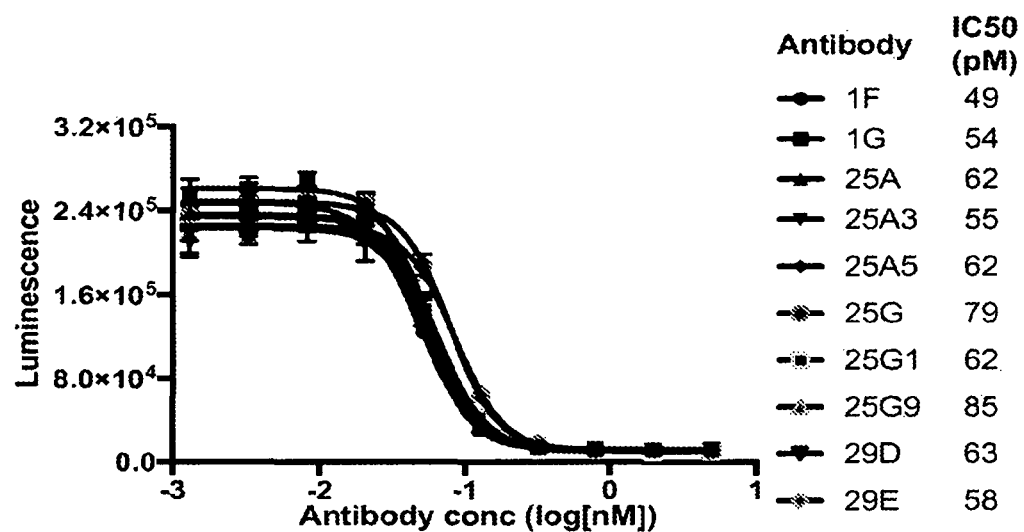
FIGS. 7A and 7B show internalization of anti-TF antibody by TF-positive cells.
Figure 7B:
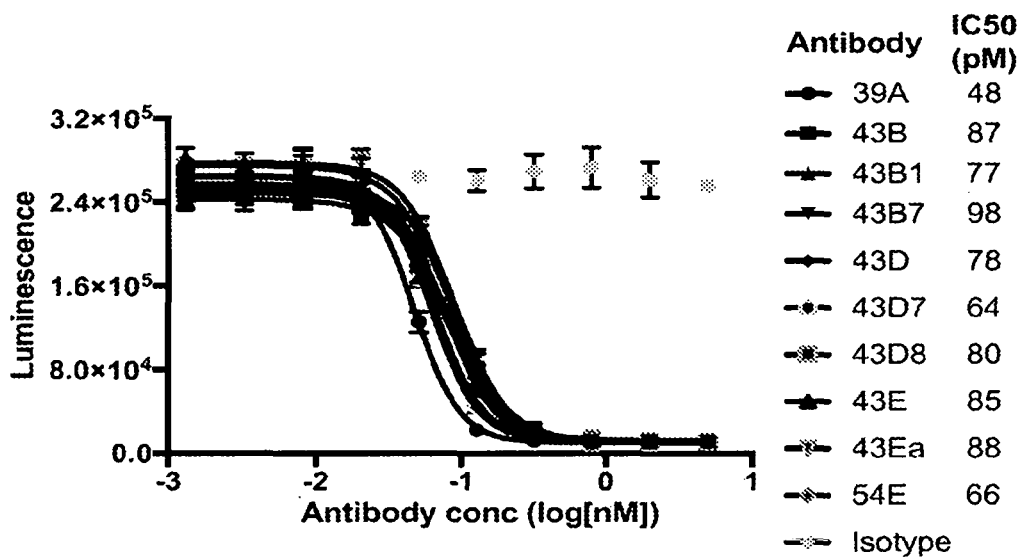

FIGS. 7A and 7B show the cell viability as indicated by the level of luminescence and the calculated $IC_{50}$.

This data indicates that all anti-TF antibodies tested from groups 1, 25, 29, 39, 43, and 54 were effective in reducing the viability of TF-positive A431 cells.

Example 10: Thrombin Generation Assay (TGA)

The TGA assay was performed using the calibrated-automated-thrombogram (CAT) instrument manufactured and distributed by STAGO. The test method design was equivalent to a standard CAT assay measurement, except that the plasma source was normal pooled plasma (NPP) in citrate supplemented with corn trypsin inhibitor (citrate/CTI). The anti-TF antibodies were titrated at 0, 10, 50 and 100 nM and mixed with normal pooled plasma (NPP) collected in 11 mM citrate supplemented with 100 microgram/mL of corn trypsin inhibitor (citrate/CTI). Relipidated TF was added to a 96-well assay plate, followed by addition of the antibody/NPP mixture. After a 10-min incubation or directly after combining the relipidated TF with antibody/

NPP, thrombin generation was initiated by the addition of calcium and the thrombin substrate. The STAGO software was used to report the following parameters: Peak IIa (highest thrombin concentration generated [nM]); Lag Time (time to IIa generation [min]); ETP (endogenous thrombin potential, area under the curve [nM×min]); and ttPeak (time to Peak IIa [min]). Percent peak thrombin generation (% Peak IIa) and percent endogenous thrombin potential (% ETP) in the presence of each antibody relative to a no antibody plasma control on the same plate were also reported.

Figure 8A:
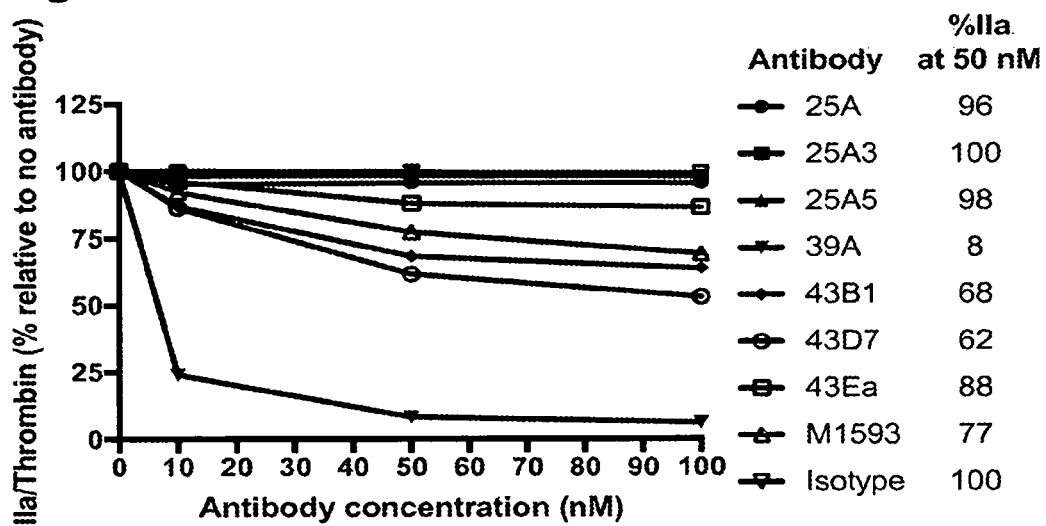
FIGS. 8A and 8B show thrombin generation in the presence of anti-TF antibody.
Figure 8B:
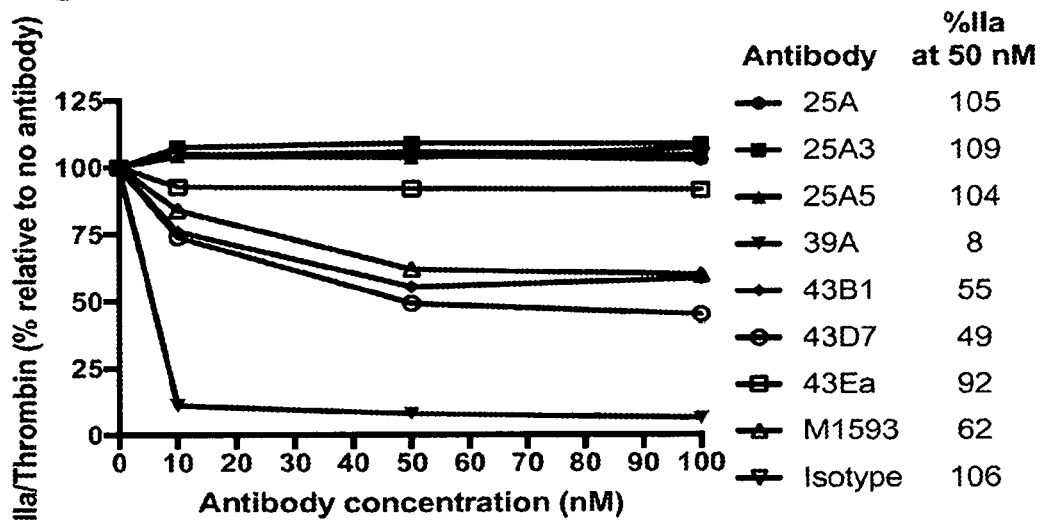

The Peak IIa, Lag Time, ETP, ttPeak, % Peak IIa, and % ETP in the presence of each antibody selected from 25A, 25A3, 25A5, 39A, 43B1, 43D7, 43Ea, and M1593 without antibody incubation prior to addition of calcium and thrombin substrate are shown in Table 37. The Peak IIa, Lag Time, ETP, ttPeak, % Peak IIa, and % ETP in the presence of each antibody selected from 25A, 25A3, 25A5, 39A, 43B1, 43D7, 43Ea, and M1593 with 10 min antibody incubation prior to addition of calcium and thrombin substrate are shown in Table 38. The % Peak IIa in the presence of titrations of anti-TF antibodies without antibody incubation prior to addition of calcium and thrombin substrate is plotted in FIG. 8A. The % Peak IIa in the presence of titrations of anti-TF antibodies with 10 min antibody incubation prior to addition of calcium and thrombin substrate is plotted in FIG. 8B. The M1593 antibody has a $V_H$ sequence of SEQ ID NO:821 and $V_L$ sequence of SEQ ID NO:822.

The % Peak IIa is 95% or greater in the presence of antibodies from group 25, including 25A, 25A3, and 25A5 without antibody pre-incubation. The % Peak IIa is 100% or greater in the presence of antibodies from group 25, including 25A, 25A3, and 25A5 with 10 min antibody pre-incubation. The % ETP is 99% or greater in the presence of the tested antibodies from group 25.

The % Peak IIa is greater than 50% but equal to or less than 96% in the presence of antibodies from group 43, including 43B1, 43D7, and 43Ea and anti-TF antibody M1593 without antibody pre-incubation. The % Peak IIa is greater than 40% but equal to or less than 93% in the presence of antibodies from group 43, including 43B1, 43D7, and 43Ea and anti-TF antibody M1593 with 10 min antibody pre-incubation. The % ETP is 92% or greater in the presence of the tested antibodies from group 43 and M1593 antibody.

This data indicates that antibodies from groups 25 and 43 allow normal thrombin generation, and therefore are not inhibitors of thrombin generation. The percent peak thrombin generation (% Peak IIa) is greater in the presence of antibodies of group 25 compared to antibodies of group 43 and M1593 antibody.

TABLE 37

Thrombin Generation Assay without Antibody Pre-Incubation

| Plate | Antibody | Ab conc. (nM) | Peak IIa (nM) | Lag Time (mm) | ETP (nM · min) | ttPeak (mm) | % Peak IIa | % ETP |
| --- | --- | --- | --- | --- | --- | --- | --- | --- |
| 3 | 25A | 100 | 334 | 5.0 | 2390 | 8.7 | 96 | 105 |
|   |     | 50  | 335 | 5.0 | 2380 | 8.7 | 96 | 104 |
|   |     | 10  | 333 | 5.0 | 2387 | 8.6 | 95 | 104 |
| 3 | 25A3 | 100 | 343 | 5.0 | 2405 | 8.4 | 98 | 105 |
|   |     | 50  | 349 | 5.0 | 2433 | 8.4 | 100 | 106 |
|   |     | 10  | 350 | 5.0 | 2426 | 8.0 | 100 | 106 |
| 3 | 25A5 | 100 | 342 | 5.1 | 2393 | 8.5 | 98 | 105 |
|   |     | 50  | 344 | 4.8 | 2317 | 8.1 | 98 | 101 |
|   |     | 10  | 343 | 4.7 | 2270 | 8.0 | 98 | 99 |
| 3 | 39A | 100 | 22 | 38.1 | * | 48.3 | 6 | * |
|   |     | 50  | 29 | 33.1 | * | 43.2 | 8 | * |
|   |     | 10  | 84 | 12.4 | 1332 | 20.7 | 24 | 58 |
| 3 | 43B1 | 100 | 223 | 4.8 | 2111 | 10.0 | 64 | 92 |
|   |     | 50  | 239 | 4.9 | 2134 | 9.9 | 68 | 93 |
|   |     | 10  | 303 | 5.1 | 2318 | 9.1 | 87 | 101 |
| 3 | 43D7 | 100 | 186 | 5.6 | 2105 | 12.2 | 53 | 92 |
|   |     | 50  | 216 | 5.5 | 2183 | 11.3 | 62 | 96 |
|   |     | 10  | 301 | 5.4 | 2338 | 9.3 | 86 | 102 |
| 3 | 43Ea | 100 | 302 | 5.1 | 2347 | 9.1 | 87 | 103 |
|   |     | 50  | 308 | 5.1 | 2392 | 8.8 | 88 | 105 |
|   |     | 10  | 336 | 4.5 | 2305 | 7.8 | 96 | 101 |
| 3 | M1593 | 100 | 242 | 5.1 | 2235 | 10.4 | 69 | 98 |
|   |     | 50  | 270 | 5.1 | 2282 | 9.8 | 77 | 100 |
|   |     | 10  | 322 | 5.1 | 2368 | 8.8 | 92 | 104 |
| 3 | Isotype | 100 | 347 | 5.0 | 2319 | 8.1 | 99 | 101 |
|   |     | 50  | 348 | 5.0 | 2324 | 8.1 | 100 | 102 |
|   |     | 10  | 348 | 5.0 | 2326 | 8.3 | 100 | 102 |
| 3 | Plasma ctrl. | NA | 349 | 4.7 | 2285 | 7.7 | 100 | 100 |

* Groups with "No Tail Found" Errors when the software cannot calculate the ETP.

TABLE 38

Thrombin Generation Assay with 10 min Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 3 | 25A | 100 | 274 | 3.3 | 1879 | 7.0 | 103 | 106 |
|  |  | 50 | 279 | 3.3 | 1876 | 7.0 | 105 | 106 |
|  |  | 10 | 280 | 3.6 | 1872 | 7.0 | 105 | 106 |
| 3 | 25A3 | 100 | 290 | 3.4 | 1906 | 6.8 | 109 | 108 |
|  |  | 50 | 291 | 3.6 | 1925 | 6.8 | 109 | 109 |
|  |  | 10 | 287 | 3.3 | 1886 | 6.8 | 108 | 107 |
| 3 | 25A5 | 100 | 286 | 3.7 | 1883 | 7.0 | 107 | 107 |
|  |  | 50 | 277 | 3.7 | 1803 | 7.0 | 104 | 102 |
|  |  | 10 | 278 | 3.7 | 1808 | 7.0 | 104 | 102 |
| 3 | 39A | 100 | 17 | 32.1 | * | 43.2 | 6 | * |
|  |  | 50 | 21 | 29.0 | * | 39.7 | 8 | * |
|  |  | 10 | 30 | 20.9 | * | 30.8 | 11 | * |
| 3 | 43B1 | 100 | 156 | 3.6 | 1701 | 9.3 | 58 | 96 |
|  |  | 50 | 148 | 3.3 | 1667 | 9.6 | 55 | 94 |
|  |  | 10 | 203 | 3.7 | 1776 | 8.2 | 76 | 101 |
| 3 | 43D7 | 100 | 120 | 3.7 | 1633 | 10.8 | 45 | 92 |
|  |  | 50 | 131 | 3.7 | 1724 | 10.4 | 49 | 98 |
|  |  | 10 | 197 | 3.7 | 1784 | 8.8 | 74 | 101 |
| 3 | 43Ea | 100 | 244 | 3.3 | 1817 | 7.3 | 91 | 103 |
|  |  | 50 | 246 | 3.3 | 1833 | 7.3 | 92 | 104 |
|  |  | 10 | 247 | 3.3 | 1779 | 7.1 | 93 | 101 |
| 3 | M1593 | 100 | 160 | 3.7 | 1737 | 9.4 | 60 | 98 |
|  |  | 50 | 165 | 3.7 | 1739 | 9.3 | 62 | 99 |
|  |  | 10 | 224 | 3.7 | 1807 | 8.0 | 84 | 102 |
| 3 | Isotype | 100 | 279 | 3.7 | 1829 | 7.2 | 105 | 104 |
|  |  | 50 | 283 | 3.7 | 1839 | 7.0 | 106 | 104 |
|  |  | 10 | 279 | 3.7 | 1814 | 7.1 | 105 | 103 |
| 3 | Plasma ctrl. | NA | 267 | 3.7 | 1766 | 7.2 | 100 | 100 |

* Groups with "No Tail Found" Errors when the software cannot calculate the ETP.

Example 11: Synthesis of Antibody-Drug Conjugates (ADCs)

Antibody-Drug Conjugates (ADCs) were synthesized as described in Behrens et al., *Mol Pharm*, 2015, 12:3986-98. 5 mg/mL of antibody in phosphate-buffered saline (PBS), pH 7.4 was reduced with 2.5 molar equivalents of Tris(2-carboxyehtyl)phosphine. After 2 hr at 37° C., the partially reduced antibody was cooled to room temperature and conjugated for 1 hr to 3 to 5 molar equivalents of MC-vc-PAB-MMAE (maleimidocaproyl-valine-citrulline-p-aminobenzoyloxycarbonyl-monomethyl auristatin E). The reaction was buffer exchanged into PBS to remove small molecular weight reagents. The drug-antibody ratio (DAR) of the resulting ADCs was 3-4. The DAR was determined with the following formula: Absorbance (248 nm)/Absorbance (280 nm)=(n×$Ex_{PAB[248\ nm]}$+$Ex_{antibody[248\ nm]}$)/(n× $Ex_{PAB[280\ nm]}$+$Ex_{antibody[280\ nm]}$) with n as a variable for the DAR and Ex as the extinction coefficients of PAB and the antibody. Hydrophobic interaction chromatography and size exclusion chromatography were used to corroborate the absorbance-based DAR estimation and to ensure the ADC preparation was at least 95% monomeric, respectively.

Example 12: Cytotoxicity Assays of Antibody-Drug Conjugates (ADCs)

To evaluate cytotoxicity of ADCs, TF-positive A431 and HPAF-II cells were plated in 384-well plates (Greiner Bio-One, Monroe, N.C., USA) at 4×$10^3$ cells per well in 40 μL of media. Anti-TF antibodies conjugated to MC-vc-PAB-MMAE were serially diluted starting at 5 nM. Plates were incubated for 3 to 4 days, followed by lysis in CellTiter-Glo (CTG) assay reagent (Promega, Madison, Wis., USA). CTG luminescence was measured on an Envision plate reader and the mean and standard deviation of 4 replicates were graphed in Prism. For each ADC, the $IC_{50}$ and its associated 95% confidence interval were calculated in Prism using a 4-parameter binding model.

Figure 9A:
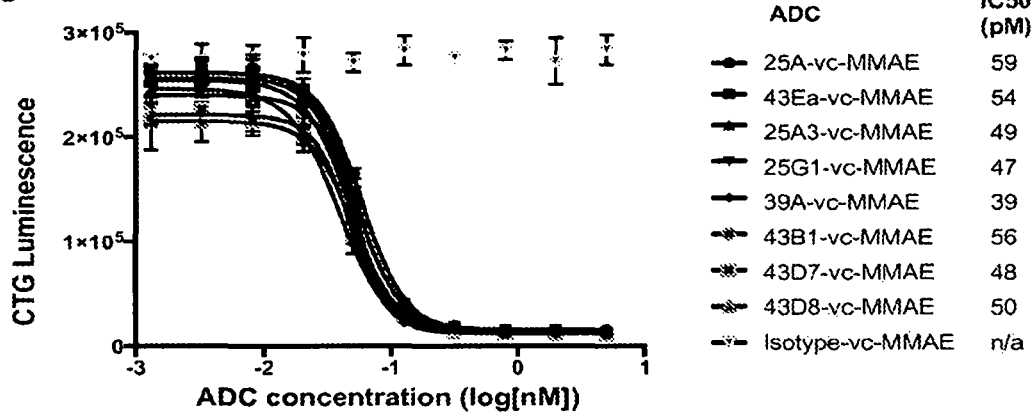
FIGS. 9A and 9B show anti-TF ADC-induced cell death in TF-positive cells.
Figure 9B:
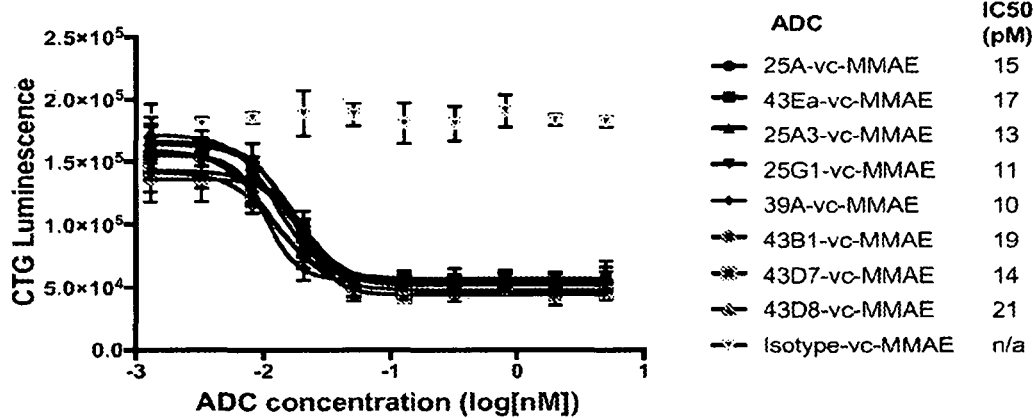

FIGS. 9A and 9B show the cell viability as indicated by CTG luminescence and the calculated $IC_{50}$ in TF-positive A431 and HPAF-II cells, respectively. ADCs comprising anti-TF antibodies from groups 25, 43, and 39 conjugated to MC-vc-PAB-MMAE resulted in cytotoxicity in TF-positive A431 and HPAF-II cells.

This data indicates that anti-TF antibody-drug conjugates reduced the viability of TF-positive cells in vitro.

Example 13: Xenograft Cell Line Studies

Xenograft studies in immune compromised mice were performed to evaluate the efficacy of the ADCs in vivo. The TF-positive A431 epidermoid carcinoma and the HPAF-II pancreatic carcinoma xenografts were implanted subcutaneously in the flank of athymic nude mice (Charles River Laboratories, Wilmington, Mass.). Animals were randomized when tumors reached an average size of 150-200 mm$^3$ and treated with 5 mg/kg of the indicated ADC or vehicle (PBS) intraperitoneally (i.p.) once weekly for 3 weeks. Body weight and tumor size assessments were performed bi-weekly. Animals were removed from study and euthanized once tumor size reached 1200 mm$^3$ or skin ulceration was evident.

Figure 10A:
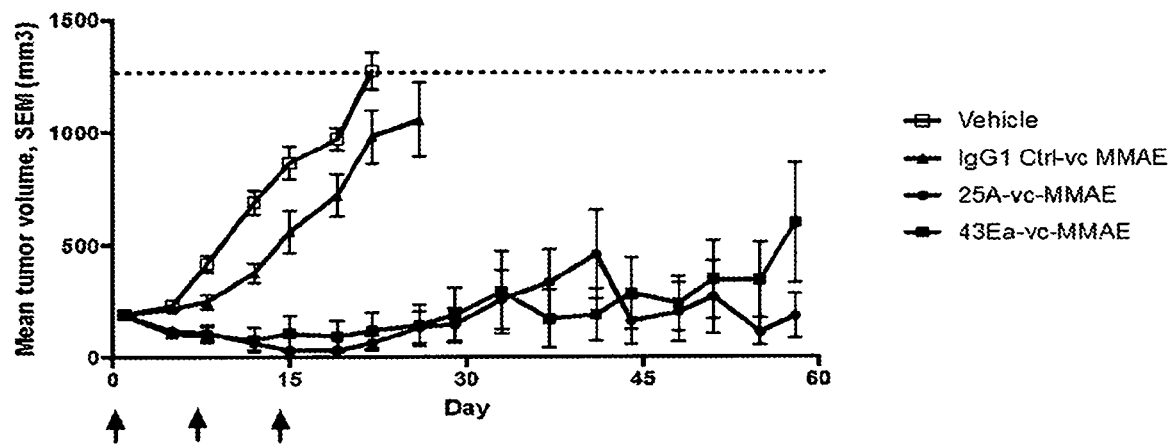
FIGS. 10A and 10B show the effect of anti-TF ADCs on tumor size in xenograft models.
Figure 10B:
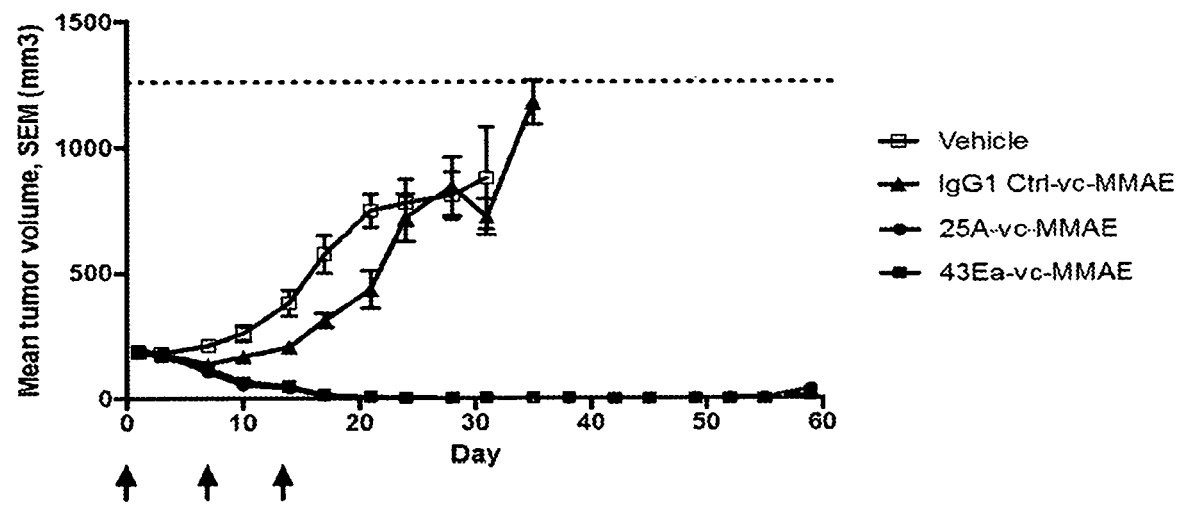

FIGS. 10A and 10B show the tumor size of vehicle-treated, IgG1 ADC-treated, and anti-TF ADC-treated groups in the TF-positive A431 epidermoid carcinoma and the HPAF-II pancreatic carcinoma xenograft models, respectively. ADCs comprising anti-TF antibodies 25A and 43Ea conjugated to MC-vc-PAB-MMAE decreased the tumor size in both xenograft models compared to the vehicle-treated or IgG1 ADC-treated groups.

This data indicates that anti-TF antibody-drug conjugates 25A-vc-MMAE and 43Ea-vc-MMAE were effective in reducing the tumor size in vivo.

Example 14: Studies of Patient-Derived Xenograft (PDX) Model

A TF-positive head and neck cancer patient-derived xenograft model was generated in athymic nude mice (Envigo, Indianapolis, Ind.) to further evaluate the efficacy of the ADCs in vivo. Tumors were passaged in stock animals and harvested for re-implantation. Study animals were implanted unilaterally on the left flank with tumor fragments and were randomized to treatment group when tumors reached an average size of 150-200 mm³. Animals were treated with 5 mg/kg of the indicated ADC intraperitoneally (i.p.) once weekly for 2 weeks. Body weight and tumor size assessments were performed bi-weekly. Animals were removed from study and euthanized once tumor size reached 1200 mm³ or skin ulceration was evident.

Figure 11:
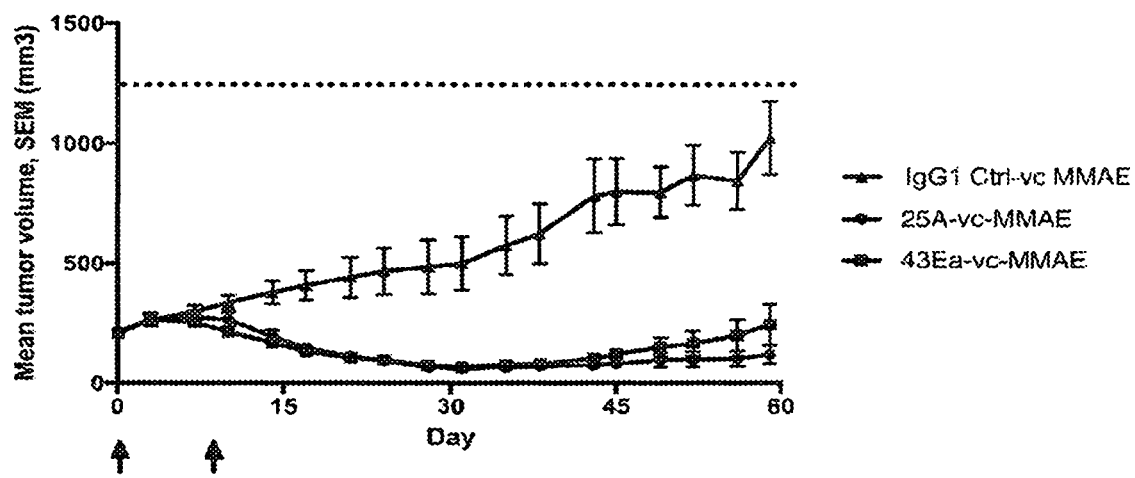
FIG. 11 shows the effect of anti-TF ADCs on tumor size in a head and neck cancer patient-derived xenograft model. The arrows indicate treatments with anti-TF ADC or IgG1 control ADC dosed at 5 mg/kg once per week for 2 weeks.

FIG. 11 shows the tumor size of IgG1 ADC-treated and anti-TF ADC-treated groups in the head and neck cancer patient-derived xenograft model. ADCs comprising anti-TF antibodies 25A and 43Ea conjugated to MC-vc-PAB-MMAE decreased the tumor size in the cancer patient-derived xenograft model compared to the IgG1 ADC-treated group.

This data indicates that anti-TF antibody-drug conjugates 25A-vc-MMAE and 43Ea-vc-MMAE were effective in reducing the tumor size in a cancer patient-derived xenograft model in vivo.

Example 15: Binding Affinity Assay For Pig TF

The ability of certain antibodies was tested for binding to pig TF. For pig TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of pig TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 40.

As shown in Table 40, anti-hTF antibodies from groups 25 and 43, 25G9 and 43D8, exhibit binding activity and cross-reactivity to pig TF.

TABLE 40

| Antibody kinetics for pig TF | |
|---|---|
| Ab | Pig $K_D$ (nM) [standard deviation] |
| 1G | no binding* |
| 29D | no binding* |
| 25G9 | 3.31 [0.08] |
| 43D8 | 12.9 [0.03] | no binding*: no binding to weak binding, with no reportable $K_D$

Example 16: Cell-Based Binding Assay

Human TF-positive cancer cell lines A431 and MDA-MB-231 and *Macaca mulatta* TF-positive cell line RF/6A were obtained from the American Tissue Culture Collection (ATCC, Manassas, Va., USA) and were maintained as recommended.

Figure 12A:
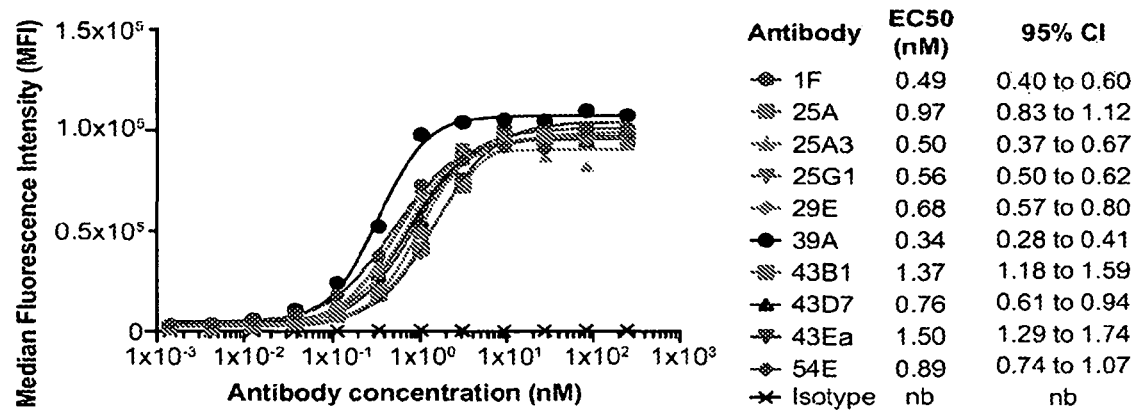
FIGS. 12A and 12B show binding of anti-TF antibodies to human TF-positive cancer cells.
Figure 12B:
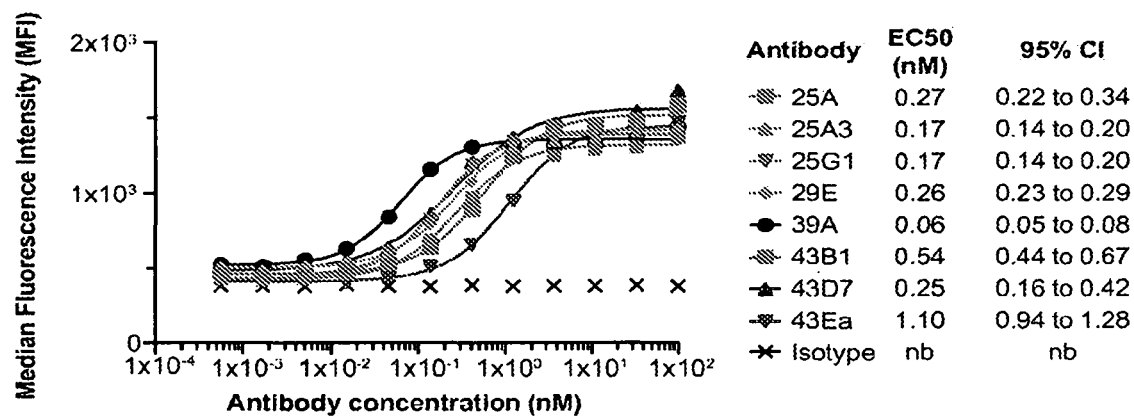

Cell-based antibody binding was assessed as previously described in Liao-Chan et al., *PLoS One*, 2015, 10:e0124708, which is incorporated by reference in its entirety. $1.2 \times 10^5$ cells collected with Cellstripper (Mediatech, Manassas, Va., USA) were incubated with a twelve-point 1:3 dilution titration of anti-human TF IgG1 antibody starting at 250 nM or 100 nM for 2 hr on ice. After 2 washes, cells labeled with IgG1 antibody were incubated for 30 min on ice with 150 nM of Goat Phycoerythrin (PE) F(ab')₂ fragment goat anti-human IgG, Fcγ fragment specific (Jackson ImmunoResearch, West Grove, Pa., USA) or FITC-labeled F(ab')₂ fragment goat anti-human kappa (SouthernBiotech, Birmingham, Ala., USA), respectively. After 2 washes, dead cells were labeled with TO-PRO-3 Iodide (ThermoFisher Scientific) and samples were analyzed on a CytoFLEX flow cytometer (Beckman Coulter, Brea, Calif., USA) or Novocyte flow cytometer (ACEA Biosciences, San Diego, Calif., USA). The median fluorescence intensities (MFIs) at each dilution were plotted and cell $EC_{50}$'s were derived using a 4-parameter binding model in Prism (GraphPad, La Jolla, Calif., USA). Antibodies that does not substantially affect FX conversion (i.e. 25A, 25A3, 25G1, 43B1, 43D7 and 43Ea) and antibodies that inhibited FX conversion by more than 50% (i.e. 1F, 29E, 39A and 54E) were included in the assay. The results of binding of anti-TF antibodies to human TF-positive A431 cells are shown in FIG. 12A. The results of binding of anti-TF antibodies to human TF-positive MDA-MB-231 cells are shown in FIG. 12B.

All tested anti-hTF antibodies in FIG. 12A exhibit high affinity to human TF-positive A431 cells with an $EC_{50}$ ranging from about 1.50 nM to about 0.34 nM. An IgG1 isotype control did not bind A431 cells (no binding, nb). All tested anti-hTF antibodies in FIG. 12B exhibit high affinity to human TF-positive MDA-MB-231 cells with an $EC_{50}$ ranging from about 1.50 nM to about 0.06 nM. An IgG1 isotype control did not bind MDA-MB-231 cells (no binding, nb).

As described in Example 2 and shown in Table 5, the binding affinity of anti-hTF antibodies was evaluated on TF from cynomolgus monkey (*Macaca fascicularis*). The protein sequences of *Macaca fascicularis* TF and *Macaca mulatta* TF are identical. The binding of the TF-specific antibodies to cynomolgus monkey was confirmed using the *Macaca mulatta* RF/6A cell line as shown in Table 42. All tested anti-hTF antibodies exhibit high affinity to TF-positive *Macaca mulatta* RF/6A cells with an $EC_{50}$ ranging from about 1.28 nM to about 0.17 nM. The ability of the anti-TF antibodies to bind to cynomolgus monkey is advantageous for toxicology studies of these antibodies with nonhuman primate models.

TABLE 42

| Binding of anti-TF antibodies to *Macaca mulatta* RF/6A cells | | |
|---|---|---|
| Ab | RF/6A EC50 (nM) | RF/6A 95% CI |
| 1F | 0.17 | 0.14 to 0.21 |
| 25A | 0.43 | 0.37 to 0.50 |
| 25A3 | 0.27 | 0.24 to 0.30 |
| 25G1 | 0.27 | 0.23 to 0.32 |
| 29E | 0.53 | 0.46 to 0.61 |

TABLE 42-continued

Binding of anti-TF antibodies to
*Macaca mulatta* RF/6A cells

| Ab | RF/6A EC50 (nM) | RF/6A 95% CI |
|---|---|---|
| 39A | 0.27 | 0.23 to 0.32 |
| 43B1 | 0.47 | 0.40 to 0.55 |
| 43D7 | 0.41 | 0.35 to 0.49 |
| 43Ea | 0.92 | 0.83 to 1.01 |
| 54E | 1.28 | 1.16 to 1.41 |

Example 17: Binding Assay to *E. Coli*-Derived TF

*E. coli*-derived TF was expressed as a fusion between the OmpA signal sequence and TF ECD-His6, and purified by affinity and anion exchange chromatography. The binding of anti-TF antibodies 1F, 25A, 25A3, 25G1, 29E, 39A, 43B1, 43D7, 43Ea, and 54E to Expi293- or *E. coli*-derived TF was determined by protein ELISA studies. Plates coated with Expi293- or *E. coli*-derived TF-His were incubated with increasing concentrations of antibodies. After incubation with an HRP-conjugated secondary antibody (Jackson Immunoresearch), luminescence data were obtained and used to calculate an $EC_{50}$ with 95% confidence intervals using Prism. The $EC_{50}$'s and 95% confidence intervals of the antibodies are listed in Table 43.

TABLE 43

Binding of anti-TF antibodies to Expi293- or *E. coli*-derived TF

| Ab | Expi293-derived TF protein EC50 (nM) | Expi293-derived TF protein 95% CI | *E. coli*-derived TF protein EC50 (nM) | *E. coli*-derived TF protein 95% CI |
|---|---|---|---|---|
| 1F | 0.41 | 0.37 to 0.46 | 0.32 | 0.30 to 0.34 |
| 25A | 0.54 | 0.49 to 0.60 | 0.35 | 0.30 to 0.41 |
| 25A3 | 0.47 | 0.39 to 0.56 | 0.36 | 0.31 to 0.42 |
| 25G1 | 0.42 | 0.36 to 0.47 | 0.31 | 0.29 to 0.33 |
| 29E | 0.98 | 0.78 to 1.24 | 0.68 | 0.39 to 1.26 |
| 39A | 0.45 | 0.39 to 0.53 | 0.34 | 0.28 to 0.40 |
| 43B1 | 0.57 | 0.53 to 0.61 | 0.39 | 0.34 to 0.44 |
| 43D7 | 0.71 | 0.62 to 0.80 | 0.43 | 0.35 to 0.53 |
| 43Ea | 0.74 | 0.68 to 0.81 | 0.46 | 0.40 to 0.53 |
| 54E | 0.96 | 0.73 to 1.29 | 0.38 | 0.22 to 0.62 |

All tested anti-hTF antibodies exhibit high affinity to *E. coli*-derived TF with an $EC_{50}$ ranging from about 0.68 nM to about 0.31 nM, which is comparable to the binding affinity of the antibodies to Expi293-derived TF (about 0.98 nM to 0.41 nM). These results indicate that although the anti-TF antibodies were selected against glycosylated TF from a human cell line, the antibodies can bind to *E. coli*-derived TF with similar affinity when measured by protein ELISA.

Example 18: Thrombin Generation Assay (TGA)

TGA assay was performed using the calibrated-automated-thrombogram (CAT) instrument manufactured and distributed by STAGO (Diagnostica Stago SAS, Asnieres sur Seine, France). See Samama et al., *Thromb Res*, 2012, 129:e77-82, which is incorporated by reference in its entirety. The test method design was equivalent to a standard CAT assay measurement, except that the plasma source was normal pooled plasma (NPP) collected in 11 mM citrate supplemented with 100 µg/mL of corn trypsin inhibitor (citrate/CTI). The anti-TF antibodies were titrated at 0, 10, 50 and 100 nM and mixed with NPP in citrate/CTI. Relipidated TF was added to a 96-well assay plate, followed by addition of the antibody/NPP mixture. After a 10-min incubation or directly after combining the relipidated TF with antibody/NPP, thrombin generation was initiated by the addition of calcium and the thrombin substrate. The STAGO software was used to report the following parameters: Peak IIa (highest thrombin concentration generated on the thrombin generation curve [nM]); Lag Time (time from assay start to the moment 10 nM of thrombin is formed [min]); ETP (endogenous thrombin potential, area under the curve [nM× min]); and ttPeak (time from assay start to Peak IIa [min]). Percent peak thrombin generation (% Peak IIa), percent endogenous thrombin potential (% ETP), and percent ttPeak (% ttPeak) in the presence of each antibody relative to a no-antibody plasma control on the same plate were also reported. As used herein, the term "thrombin generation assay" (TGA) refers to the TGA used in this example.

The Peak IIa, Lag Time, ETP, ttPeak, % Peak IIa, % ETP, and % ttPeak in the presence of each antibody selected from 1F, 25A, 25A3, 25G1, 29E, 39A, 43B1, 43D7, 43Ea, 54E, TF-011, 5G9, and 10H10 without antibody incubation prior to addition of calcium and thrombin substrate are shown in Table 44. The Peak IIa, Lag Time, ETP, ttPeak, % Peak IIa, % ETP, and % ttPeak in the presence of each antibody selected from 1F, 25A, 25A3, 25G1, 29E, 39A, 43B1, 43D7, 43Ea, 54E, TF-011, 5G9, and 10H10 with 10 min antibody incubation prior to addition of calcium and thrombin substrate are shown in Table 45. The thrombin generation curve in the presence of 100 nM anti-TF antibody without antibody pre-incubation is plotted in FIGS. 13A and 13B. The Peak thrombin concentration in the presence of titrations of anti-TF antibodies without antibody pre-incubation is plotted in FIG. 13C.

Figure 13A:
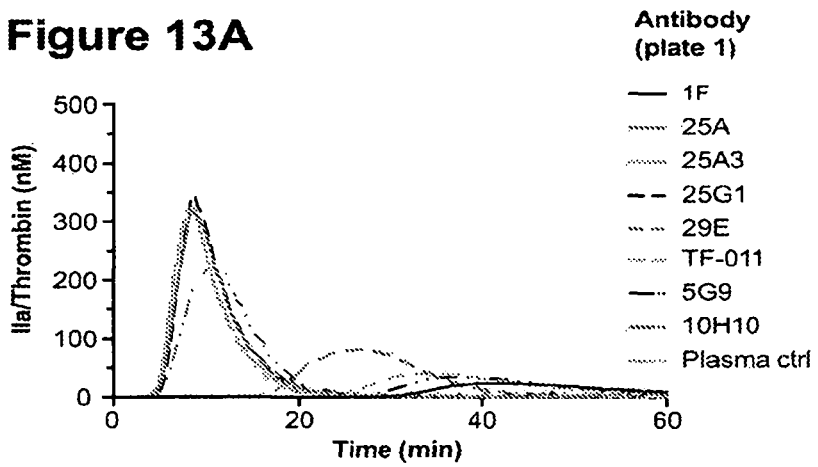
FIGS. 13A, 13B and 13C show thrombin generation in the presence of anti-TF antibody.
Figure 13B:
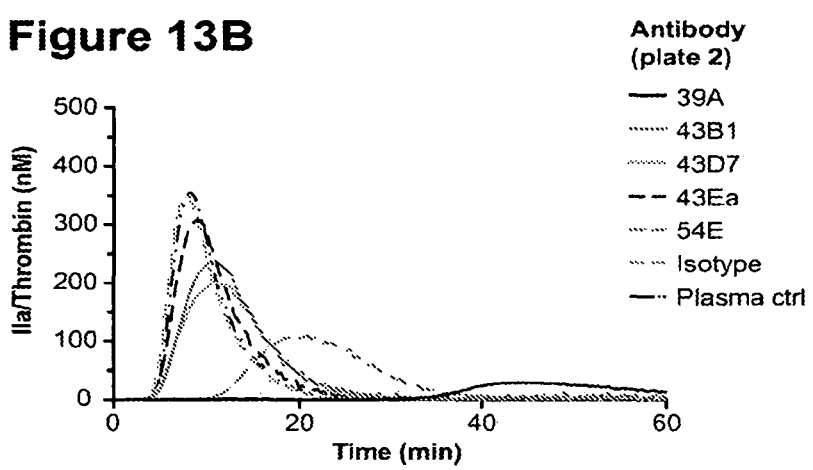
Figure 13C:
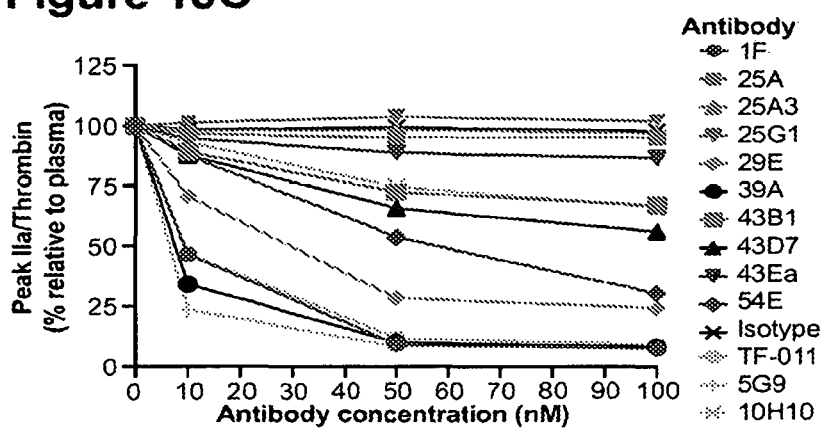

As shown in FIGS. 13A, 13B, and 13C and Table 44, under the conditions without antibody pre-incubation, at the 100 nM antibody concentration, 1F, 29E, 39A, 54E diminished the peak IIa concentration by 92, 76, 91 and 70%, respectively. Similarly, 100 nM of 5G9 and TF-011 inhibited peak IIa concentration by 92% and 91%, respectively. Severely reduced thrombin generation in the presence of the two highest concentrations of 1F, 39A, 5G9 and TF-011 hampered endogenous thrombin generation (ETP) calculations and increased time to Peak IIa/thrombin generation (ttPeak) by at least 284% and 353% at 50 nM and 100 nM respectively. In contrast, antibodies from group 25 did not impact the peak IIa concentration or ttPeak by more than 9%. Group 43 antibodies and 10H10 exhibited mild interference with the peak IIa concentration: 100 nM of 43B1, 43D7, 43Ea and 10H10 reduced the peak IIa concentration by 33, 44, 13 and 34%, respectively. In addition, 100 nM of 43B1, 43D7 and 10H10 showed at least a 29% increase in ttPeak. However, the observed decline in peak IIa concentration and delayed ttPeak for group 43 antibodies and 10H10 did not result in more than a 10% decline in the ETP.

Similar results are shown in Table 45 under the conditions with 10 min antibody pre-incubation. At the 100 nM antibody concentration, 1F, 29E, 39A, 54E diminished the peak IIa concentration by 93, 72, 93 and 87%, respectively. Similarly, 100 nM of 5G9 and TF-011 inhibited peak IIa concentration by 92% and 91%, respectively. Severely reduced thrombin generation in the presence of the two highest concentrations of 1F, 39A, 54E and TF-011 and all tested concentrations of 5G9 hampered endogenous thrombin generation (ETP) calculations and increased time to Peak IIa/thrombin generation (ttPeak) by at least 303% and 371% at 50 nM and 100 nM respectively. In contrast, antibodies from group 25 did not decrease the peak IIa concentration or increase ttPeak. Group 43 antibodies and 10H10 exhibited mild interference with the peak IIa concentration: 100 nM of 43B1, 43D7, 43Ea and 10H10 reduced the peak IIa concentration by 41, 56, 13 and 48%, respectively. In addition, 100 nM of 43B1, 43D7 and 10H10 showed at least a 33% increase in ttPeak. However, the observed decline in peak IIa concentration and delayed ttPeak for group 43 antibodies and 10H10 did not result in more than an 11% decline in the ETP.

Overall, these results indicate that group 25 antibodies are completely inert in the penultimate step of the coagulation cascade when all three TGA parameters (ETP, Peak IIa concentration and ttPeak) are taken into consideration.

TABLE 44

Thrombin Generation Assay without Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | 1F | 100 | 25 (1) | 31 (1) | * | 41 (0.7) | 8 | * | 419 |
|   |    | 50  | 31 (0) | 25.6 (0.3) | * | 35.3 (0.3) | 9 | * | 347 |
|   |    | 10  | 155 (1) | 8.2 (0.2) | 1738 (25) | 14.9 (0.2) | 47 | 86 | 89 |
| 1 | 25A | 100 | 317 (6) | 5.2 (0.2) | 2134 (28) | 8.6 (0.2) | 95 | 105 | 9 |
|   |    | 50  | 317 (2) | 5.2 (0.2) | 2122 (30) | 8.6 (0.2) | 95 | 105 | 9 |
|   |    | 10  | 322 (2) | 5 (0) | 2108 (29) | 8.2 (0.2) | 97 | 104 | 4 |
| 1 | 25A3 | 100 | 323 (1) | 4.6 (0.2) | 2031 (19) | 7.9 (0.2) | 97 | 100 | 0 |
|   |    | 50  | 328 (2) | 4.7 (0) | 2080 (23) | 8 (0) | 98 | 103 | 1 |
|   |    | 10  | 326 (4) | 5.3 (0) | 2152 (14) | 8.4 (0.2) | 98 | 106 | 6 |
| 1 | 25G1 | 100 | 340 (3) | 5.3 (0) | 2160 (27) | 8.3 (0) | 102 | 107 | 5 |
|   |    | 50  | 346 (6) | 5.1 (0.2) | 2221 (40) | 8.2 (0.2) | 104 | 110 | 4 |
|   |    | 10  | 337 (1) | 4.7 (0) | 2061 (34) | 7.8 (0.2) | 101 | 102 | -1 |
| 1 | 29E | 100 | 81 (0) | 17.1 (0.2) | 1257 (18) | 26.2 (0.2) | 24 | 62 | 232 |
|   |    | 50  | 95 (1) | 14.1 (0.2) | 1365 (26) | 22.6 (0.4) | 29 | 67 | 186 |
|   |    | 10  | 235 (3) | 7 (0) | 1926 (9) | 11.7 (0) | 71 | 95 | 48 |
| 1 | Isotype | 100 | 326 (3) | 5.3 (0) | 2132 (13) | 8.6 (0.2) | 98 | 105 | 9 |
|   |    | 50  | 331 (3) | 5.3 (0) | 2177 (19) | 8.3 (0) | 99 | 108 | 5 |
|   |    | 10  | 328 (4) | 5.3 (0) | 2129 (26) | 8.4 (0.2) | 98 | 105 | 6 |
| 1 | TF-011 | 100 | 30 (1) | 26 (0.3) | * | 35.8 (0.2) | 9 | * | 353 |
|   |    | 50  | 39 (3) | 21.3 (0.5) | * | 30.3 (1.1) | 12 | * | 284 |
|   |    | 10  | 156 (7) | 8 (0) | 1714 (41) | 14.7 (0.5) | 47 | 85 | 86 |
| 1 | 5G9 | 100 | 27 (1) | 29.9 (0.4) | * | 39.6 (0.4) | 8 | * | 401 |
|   |    | 50  | 28 (0) | 25.1 (0.4) | * | 34.6 (0.2) | 8 | * | 338 |
|   |    | 10  | 79 (1) | 10.4 (0.2) | 1176 (16) | 18.6 (0.2) | 24 | 58 | 135 |
| 1 | 10H10 | 100 | 221 (4) | 5.2 (0.2) | 1945 (37) | 10.2 (0.2) | 66 | 96 | 29 |
|   |    | 50  | 248 (3) | 5.2 (0.2) | 1978 (32) | 9.8 (0.3) | 74 | 98 | 24 |
|   |    | 10  | 310 (2) | 5.2 (0.2) | 2036 (33) | 8.6 (0.2) | 93 | 101 | 9 |
| 1 | Plasma ctrl. | NA | 333 (0) | 4.7 (0) | 2023 (30) | 7.9 (0.2) | 100 | 100 | 0 |
| 2 | 39A | 100 | 29 (0) | 34.7 (0) | * | 44.6 (0.2) | 9 | * | 465 |
|   |    | 50  | 36 (1) | 29.8 (0.7) | * | 39.3 (0.7) | 11 | * | 397 |
|   |    | 10  | 122 (3) | 10.8 (0.3) | 1694 (57) | 18.6 (0.2) | 37 | 84 | 135 |
| 2 | 43B1 | 100 | 238 (4) | 5.3 (0) | 2300 (32) | 10.8 (0.2) | 67 | 99 | 37 |
|   |    | 50  | 258 (5) | 5.2 (0.2) | 2301 (29) | 10.2 (0.2) | 72 | 99 | 29 |
|   |    | 10  | 317 (1) | 5 (0) | 2341 (34) | 8.6 (0.2) | 89 | 101 | 9 |
| 2 | 43D7 | 100 | 199 (6) | 5.1 (0.2) | 2124 (27) | 11.2 (0.2) | 56 | 91 | 42 |
|   |    | 50  | 234 (1) | 5 (0) | 2190 (15) | 10.3 (0) | 66 | 94 | 30 |
|   |    | 10  | 312 (3) | 5 (0) | 2343 (49) | 8.9 (0.2) | 88 | 101 | 13 |
| 2 | 43Ea | 100 | 308 (2) | 5 (0) | 2349 (9) | 9 (0) | 87 | 101 | 14 |
|   |    | 50  | 316 (3) | 5 (0) | 2430 (69) | 8.7 (0) | 89 | 105 | 10 |
|   |    | 10  | 337 (4) | 5 (0) | 2416 (82) | 8.3 (0) | 95 | 104 | 5 |
| 2 | 54E | 100 | 108 (3) | 12.2 (0.2) | 1589 (13) | 20.2 (0.2) | 30 | 68 | 156 |
|   |    | 50  | 191 (2) | 8 (0) | 2109 (51) | 14.3 (0) | 54 | 91 | 81 |
|   |    | 10  | 311 (5) | 5 (0) | 2275 (41) | 8.8 (0) | 87 | 98 | 11 |
| 2 | Isotype | 100 | 351 (2) | 4.7 (0) | 2304 (14) | 7.9 (0) | 99 | 99 | 0 |
|   |    | 50  | 353 (1) | 5 (0) | 2391 (29) | 8.2 (0) | 99 | 103 | 4 |
|   |    | 10  | 348 (1) | 5 (0) | 2367 (9) | 8.3 (0) | 98 | 102 | 5 |
| 2 | Plasma ctrl. | NA | 356 (1) | 4.9 (0.2) | 2323 (76) | 8.11 (0.3) | 100 | 100 | 3 |

* Groups with "No Tail Found" Errors when the software cannot calculate the ETP.

TABLE 45

Thrombin Generation Assay with 10 min Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | 1F | 100 | 20 (1) | 29.5 (0.2) | * | 40.8 (0.6) | 7 | * | 483 |
|   |    | 50 | 23 (0) | 26.5 (0.7) | * | 37.3 (0.4) | 8 | * | 433 |
|   |    | 10 | 44 (2) | 13.8 (0.5) | 742 (23) | 22.4 (0.4) | 16 | 41 | 220 |
| 1 | 25A | 100 | 291 (3) | 3.3 (0.1) | 1964 (36) | 6.7 (0.1) | 106 | 108 | −4 |
|   |    | 50 | 290 (0) | 3.3 (0.1) | 1972 (22) | 6.8 (0) | 106 | 108 | −3 |
|   |    | 10 | 284 (1) | 3.3 (0.1) | 1899 (21) | 6.8 (0) | 104 | 104 | −3 |
| 1 | 25A3 | 100 | 290 (3) | 3.1 (0) | 1893 (28) | 6.4 (0) | 106 | 104 | −9 |
|   |    | 50 | 284 (4) | 3.1 (0) | 1875 (16) | 6.4 (0) | 104 | 103 | −9 |
|   |    | 10 | 288 (3) | 3.1 (0) | 1901 (26) | 6.4 (0) | 105 | 105 | −9 |
| 1 | 25G1 | 100 | 311 (3) | 3.1 (0) | 1954 (20) | 6.3 (0.1) | 114 | 107 | −10 |
|   |    | 50 | 311 (1) | 3.1 (0) | 1951 (22) | 6.1 (0) | 114 | 107 | −13 |
|   |    | 10 | 302 (3) | 3.1 (0) | 1877 (33) | 6.1 (0) | 110 | 103 | −13 |
| 1 | 29E | 100 | 76 (1) | 14.7 (0.1) | 1201 (24) | 24.3 (0.3) | 28 | 66 | 247 |
|   |    | 50 | 83 (1) | 14.1 (0) | 1300 (17) | 23.6 (0.1) | 30 | 72 | 237 |
|   |    | 10 | 98 (1) | 9.4 (0) | 1408 (11) | 18.1 (0) | 36 | 77 | 159 |
| 1 | Isotype | 100 | 288 (2) | 3.4 (0) | 1922 (28) | 6.8 (0) | 105 | 106 | −3 |
|   |    | 50 | 292 (2) | 3.4 (0) | 1921 (25) | 6.8 (0) | 107 | 106 | −3 |
|   |    | 10 | 290 (3) | 3.4 (0) | 1926 (38) | 6.8 (0) | 106 | 106 | −3 |
| 1 | TF-011 | 100 | 26 (0) | 23.8 (1.1) | * | 34.2 (0.9) | 9 | * | 389 |
|   |    | 50 | 27 (1) | 22.4 (0.1) | * | 33 (0.1) | 10 | * | 371 |
|   |    | 10 | 46 (3) | 13.5 (0.5) | 792 (55) | 22.5 (0.2) | 17 | 44 | 221 |
| 1 | 5G9 | 100 | 22 (0) | 26.7 (0.3) | * | 37.5 (0.5) | 8 | * | 436 |
|   |    | 50 | 23 (3) | 23.6 (2.2) | * | 34 (2.4) | 8 | * | 386 |
|   |    | 10 | 30 (1) | 19.3 (0.4) | * | 29 (0.8) | 11 | * | 314 |
| 1 | 10H10 | 100 | 169 (3) | 3.4 (0) | 1795 (36) | 9.3 (0.1) | 62 | 99 | 33 |
|   |    | 50 | 175 (4) | 3.4 (0) | 1754 (20) | 9.2 (0.1) | 64 | 96 | 31 |
|   |    | 10 | 235 (8) | 3.4 (0) | 1807 (42) | 7.8 (0) | 86 | 99 | 11 |
| 1 | Plasma ctrl. | NA | 274 (1) | 3.4 (0) | 1818 (24) | 7 (0.1) | 100 | 100 | 0 |
| 2 | 39A | 100 | 19 (1) | 33.6 (0.7) | * | 44.6 (0.9) | 7 | * | 537 |
|   |    | 50 | 22 (0) | 30.7 (0.1) | * | 41.4 (0.1) | 8 | * | 491 |
|   |    | 10 | 36 (1) | 19.6 (0.7) | * | 29.3 (0.8) | 13 | 0 | 319 |
| 2 | 43B1 | 100 | 167 (0) | 4 (0) | 1806 (15) | 9.8 (0.1) | 59 | 98 | 40 |
|   |    | 50 | 174 (1) | 3.8 (0.1) | 1831 (22) | 9.6 (0) | 62 | 99 | 37 |
|   |    | 10 | 222 (5) | 3.7 (0.1) | 1841 (37) | 8.3 (0) | 79 | 100 | 19 |
| 2 | 43D7 | 100 | 123 (2) | 4 (0) | 1673 (27) | 11.5 (0.1) | 44 | 91 | 64 |
|   |    | 50 | 122 (1) | 3.7 (0.1) | 1639 (29) | 11.3 (0) | 43 | 89 | 61 |
|   |    | 10 | 194 (5) | 4 (0) | 1796 (35) | 8.8 (0.1) | 69 | 97 | 26 |
| 2 | 43Ea | 100 | 244 (2) | 3.5 (0.1) | 1857 (42) | 7.5 (0.1) | 87 | 101 | 7 |
|   |    | 50 | 245 (0) | 3.6 (0) | 1851 (29) | 7.6 (0) | 87 | 100 | 9 |
|   |    | 10 | 262 (1) | 3.6 (0) | 1877 (15) | 7.3 (0) | 93 | 102 | 4 |
| 2 | 54E | 100 | 37 (1) | 22.3 (0.2) | * | 33 (0.5) | 13 | * | 371 |
|   |    | 50 | 44 (1) | 18.3 (0.4) | * | 28.2 (1) | 16 | * | 303 |
|   |    | 10 | 121 (4) | 6.5 (0.1) | 1523 (20) | 13.7 (0.3) | 43 | 83 | 96 |
| 2 | Isotype | 100 | 275 (2) | 3.6 (0) | 1862 (23) | 7.3 (0) | 98 | 101 | 4 |
|   |    | 50 | 284 (0) | 3.6 (0) | 1899 (15) | 7.2 (0.1) | 101 | 103 | 3 |
|   |    | 10 | 281 (3) | 3.6 (0) | 1877 (13) | 7.3 (0) | 100 | 102 | 4 |
| 2 | Plasma ctrl. | NA | 282 (2) | 3.8 (0.1) | 1845 (22) | 7.3 (0) | 100 | 100 | 4 |

* Groups with "No Tail Found" Errors when the software cannot calculate the ETP.

Example 19: FXa Conversion Assay and FVIIa Competition Assay with Previously Described Anti-TF Antibodies The previously described TF-specific antibodies TF-011, 5G9 and 10H10 (Breij et al., *Cancer Res*, 2014, 74:1214-1226; Versteeg et al., *Blood*, 2008, 111:190-199; each of which is incorporated by reference in its entirety) were tested in FXa conversion assay and FVIIa competition assay.

To evaluate the ability of TF:FVIIa to convert FX into FXa in the presence of human antibodies against TF, a cell-based FX conversion assay was conducted as described in Larsen et al., *J Biol Chem*, 2010, 285:19959-19966, which is incorporated by reference in its entirety. Briefly, $5 \times 10^4$ MDA-MB-231 cells (ATCC, Manassas, Va., USA) were plated into tissue culture-treated black 96-well plates (Greiner Bio-One, Monroe, N.C., USA) and cultured overnight. After removal of the cell culture media and addition of a final concentration of 200 nM of FX in a HEPES buffer with 1.5 mM $CaCl_2$, cells were incubated with a titration of the antibodies for 15 min at 37° C. Upon reconstitution of the binary TF:FVIIa complex with a final concentration of 20 nM of FVIIa, cells were incubated for 5 min at 37° C. After quenching the reaction with ethylenediaminetetraacetic acid (EDTA) in a black 94-well plate, generated FXa was measured with 50 µM of SN-7 6-amino-1-naphthalenesulfonamide-based fluorogenic substrate (Haematologic Technologies, Essex Junction, Vt., USA) on an Envision plate reader equipped with an Umbelliferone 355 excitation filter, an Umbelliferone 460 emission filter, and a LANCE/DELFIA top mirror (Perkin Elmer, Waltham, Mass., USA). FXa conversion percentages (% FXa) in the presence of an anti-TF antibody titration relative to a no antibody control are plotted in FIG. 14A.

To evaluate competition between FVIIa and the human antibodies against TF, TF-positive MDA-MB-231 cells (ATCC, Manassas, Va., USA) were first incubated for 1 hr on ice with a titration of the human antibodies against TF or an isotype control. Subsequently, FVII-Fc conjugated to Alexa488 was added to the antibody-cell mixture at a final concentration of 20 nM. After another 1 hr incubation on ice, cells were washed, stained with a viability dye, and analyzed by flow cytometry. The Alexa488 fluorescence data from viable cells was summarized using median fluorescence intensity (MFI). FVII-Fc binding was summarized with % FVII-Fc binding=[$MFI_{antibody\ labeled\ cells}$−$MFI_{unstained}$ cells]/ [$MFI_{IgG1\ control\ labeled\ cells}$−$MFI_{unstained}$ cells]. Percentage of FVIIa binding (% FVIIa) in the presence of an anti-TF antibody titration relative to an isotype control is plotted in FIG. 14B.

Figure 14A:
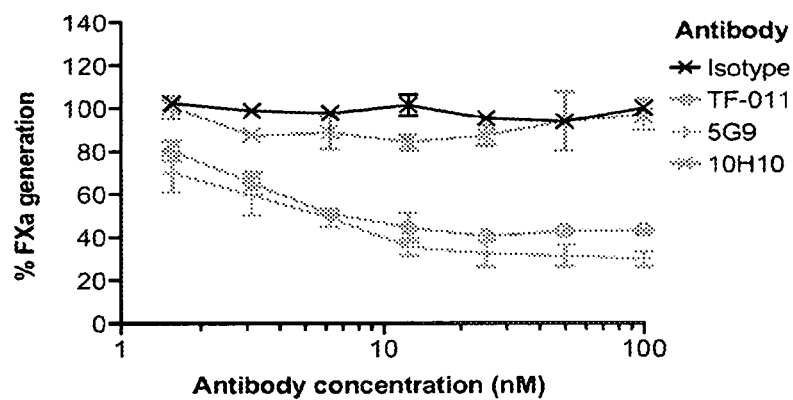
FIGS. 14A and 14B show TF:FVIIa-dependent FXa Conversion and FVII binding in the presence of anti-TF antibodies TF-011, 5G9, and 10H10.

As presented in FIG. 14A, TF-011 and 5G9 inhibited FX conversion by 57-59% and 67-70% at concentrations of 25, 50, and 100 nM. 10H10 did not significantly inhibit FX conversion at these three concentraions.

Figure 14B:
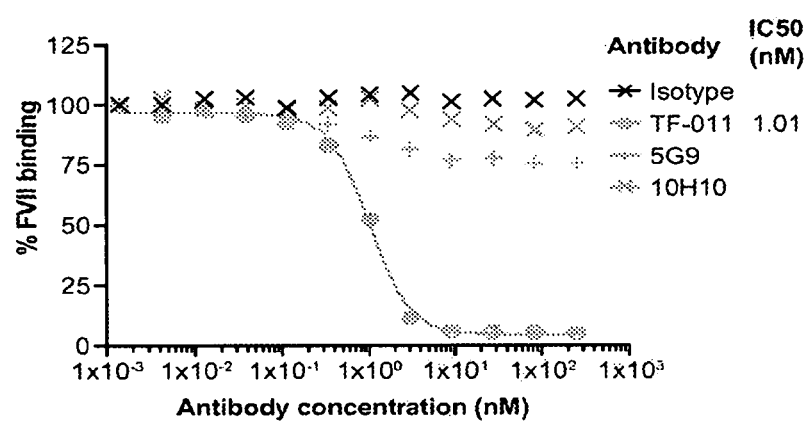
Figure 15A:
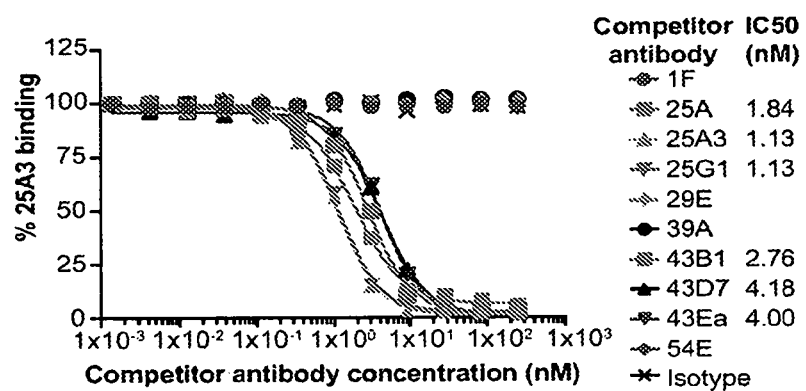
FIGS. 15A and 15B show percent binding (% Binding) of A488-conjugated 25A3 anti-TF antibody to MDA-MB-231 cells after pre-incubation of the cells with titrations of unlabeled competitor antibodies.
Figure 15B:
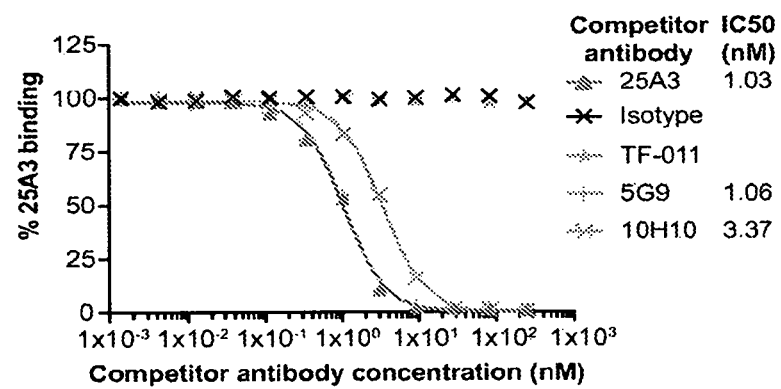
Figure 16A:
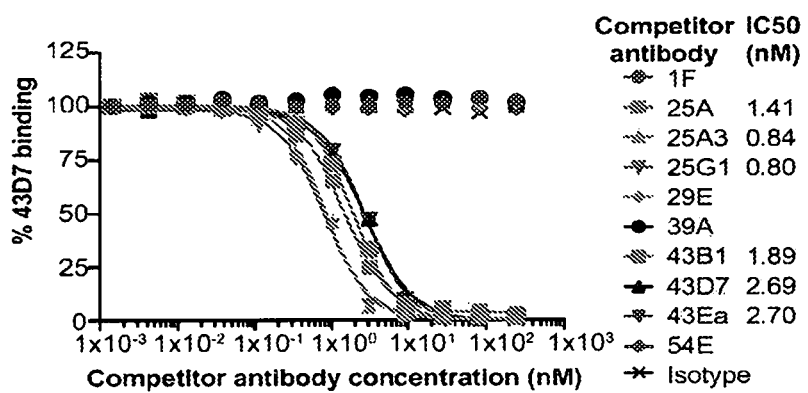
FIGS. 16A and 16B show percent binding (% Binding) of A488-conjugated 43D7 anti-TF antibody to MDA-MB-231 cells after pre-incubation of the cells with titrations of unlabeled competitor antibodies.
Figure 16B:
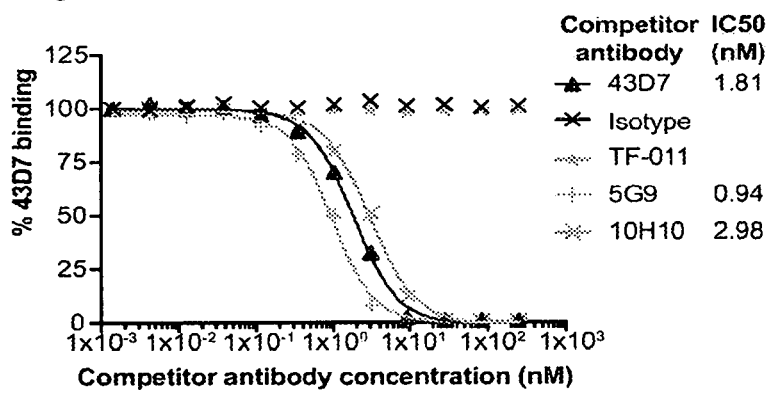
Figure 17A:
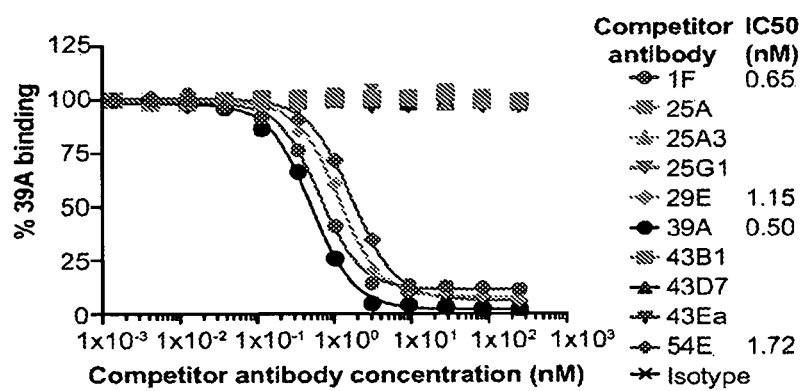
FIGS. 17A and 17B show percent binding (% Binding) of A488-conjugated 39A anti-TF antibody to MDA-MB-231 cells after pre-incubation of the cells with titrations of unlabeled competitor antibodies.
Figure 17B:
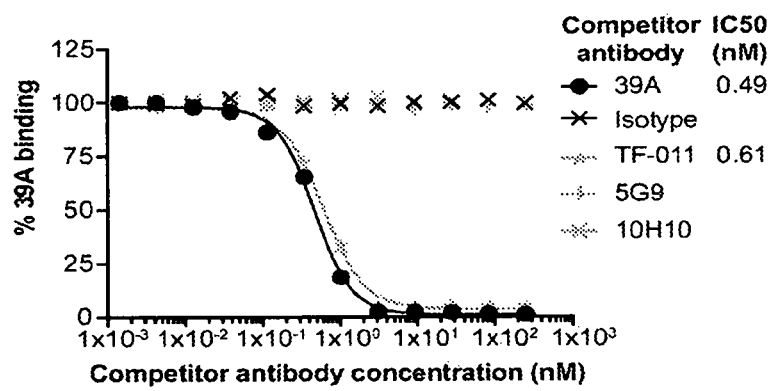

As presented in FIG. 14B, TF-011 effectively competed with FVII, whereas 5G9 and 10H10 showed less than 25% and 10% competition at the highest concentration of antibody, respectively.

These results indicate that 5G9 predominantly competes with substrate FX binding, resulting in the observed inhibition of FX conversion and thrombin generation. TF-011 inhibits thrombin generation by competing with FVIIa for binding to TF. However, 10H10 inhibits TF-FVIIa mediated signaling without substantially affecting binding of FVIIa to TF. These findings are consistent with previous observations described in Huang et al., *J Mol Biol*, 1998, 275:873-894; Ruf et al., *Biochem J*, 1991, 278:729-733; and Teplyakov et al., *Cell Signal*, 2017, 36:139-144; each of which is incorporated by reference in its entirety.

Example 20: Antibody Competition Assay

Alexa Fluor antibodies were generated using Alexa Fluor 488 5-sulfo-dichlorophenol esters (ThermoFisher Scientific) following manufacturer's protocol. Excess Alexa Fluor dye was removed from the antibody dye conjugate preparations by gel filtration (ThermoFisher Scientific).

To evaluate competition between a first human antibody against TF and 25A3, TF-positive MDA-MB-231 cells (ATCC, Manassas, Va., USA) were first incubated for 1 hr on ice with a titration of the first human antibody against TF. Subsequently, a final concentration of 20 nM of 25A3 conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 25A3 binding was summarized with % 25A3 binding= [$MFI_{antibody\ labeled\ cells}$−$MFI_{unstained}$ cells]/ [$MFI_{IgG1\ control\ labeled\ cells}$−$MFI_{unstained}$ cells].

To evaluate competition between a first human antibody against TF and 43D7, TF-positive MDA-MB-231 cells (ATCC, Manassas, Va., USA) were first incubated for 1 hr on ice with a titration of the first human antibody against TF. Subsequently, a final concentration of 20 nM of 43D7 conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 43D7 binding was summarized with % 43D7 binding= [$MFI_{antibody\ labeled\ cells}$−$MFI_{unstained}$ cells]/ [$MFI_{IgG1\ control\ labeled\ cells}$−$MFI_{unstained}$ cells].

To evaluate competition between a first human antibody against TF and 39A, TF-positive MDA-MB-231 cells (ATCC, Manassas, Va., USA) were first incubated for 1 hr on ice with a titration of the first human antibody against TF. Subsequently, a final concentration of 20 nM of 39A conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 39A binding was summarized with % 39A binding= [$MFI_{antibody\ labeled\ cells}$−$MFI_{unstained}$ cells]/ [$MFI_{IgG1\ control\ labeled\ cells}$−$MFI_{unstained}$ cells].

% 25A3 binding, % 43D7 binding, and % 39A binding are shown in FIGS. 15A and 15B, FIGS. 16A and 16B, and FIGS. 17A and 17B, respectively. Antibodies from groups 25 and 43, 5G9, and 10H10 reduced % 25A3 binding and % 43D7 binding and did not reduce % 39A binding. Antibodies from groups 1, 29, 39, and 54, and TF-011 reduced % 39A binding and did not reduce % 25A3 binding and % 43D7 binding.

While the antibody competition assay results indicate that groups 25 and 43 antibodies, 5G9, and 10H10 may bind to the same or an overlapping epitope of human TF or may affect the TF binding of each other through an allosteric mechanism, the chimeric TF construct mapping experiments as described elsewhere in this disclosure demonstrate that group 25 antibodies, group 43 antibodies, 5G9 and 10H10 bind distinct epitopes. In addition, while the antibody competition assay results indicate that antibodies of groups 1, 29, 39, and 54, and TF-011 may bind to the same or an overlapping epitope of human TF or may affect the TF binding of each other through an allosteric mechanism, the chimeric TF construct mapping experiments as described elsewhere in this disclosure demonstrate that the antibodies of groups 29, 39 and 54 bind epitopes distinct from TF-011's epitope.

Example 21: Anti-TF Antibody Internalization

Figure 18A:
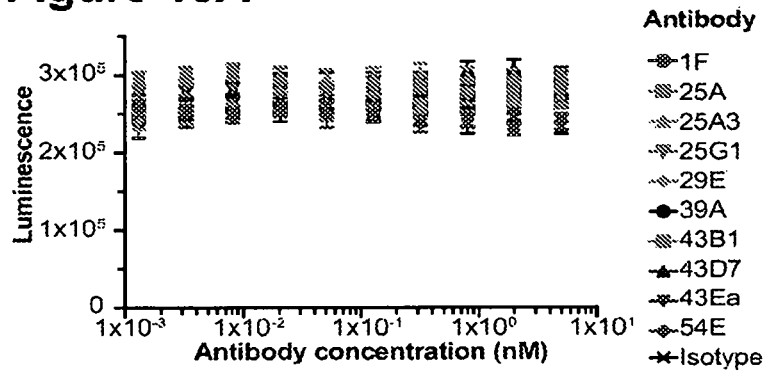
FIGS. 18A, 18B, and 18C show the internalization of anti-TF antibodies as measured by cell viability assay and internalization assay.
Figure 18B:
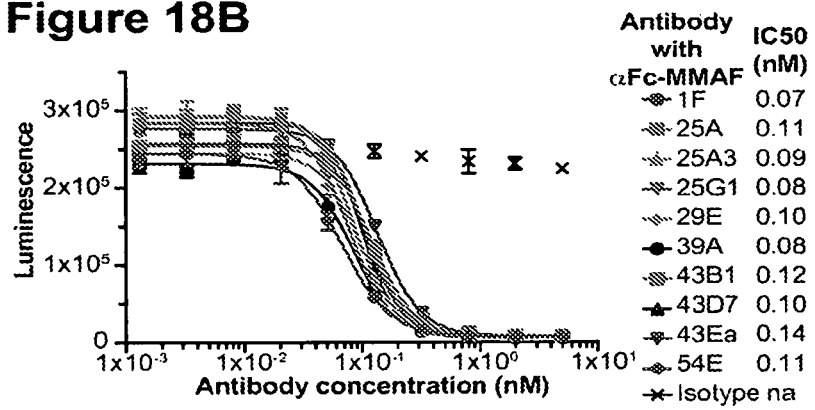

To evaluate internalization of the anti-TF antibodies, a cytotoxicity assay was conducted as described in Liao-Chan et al., *PLoS One*, 2015, 10:e0124708, which is incorporated by reference in its entirety. Briefly, cells were plated in 384-well plates (Greiner Bio-One, Monroe, N.C., USA) at $4 \times 10^3$ cells per well in 40 µl of media. Antibodies and an anti-human Fc Fab conjugated to the tubulin inhibitor monomethyl auristatin F (MMAF) (Moradec, San Diego, Calif., USA) were serially diluted starting at 5 and 30 nM, respectively. The anti-human Fc Fab conjugated to MMAF consisted of a polyclonal antibody specific to the Fc region of human IgGs with a DAR of 1.2 to 1.5. Plates were incubated for 3 days, followed by lysis in CellTiter-Glo (CTG) assay reagent (Promega, Madison, Wis., USA). CTG luminescence was measured on an Envision plate reader and the mean and standard deviation of 4 replicates graphed in Prism (GraphPad, La Jolla, Calif., USA). For each anti-TF antibody, the $IC_{50}$ and its associated 95% confidence interval were calculated in Prism using a 4-parameter binding model. The cell viability results after incubation with anti-TF antibodies and anti-TF antibody Fab:MMAF complexes are shown in FIGS. 18A and 18B. The 95% confidence intervals for the $IC_{50}$ values are shown in Table 46.

Figure 18C:
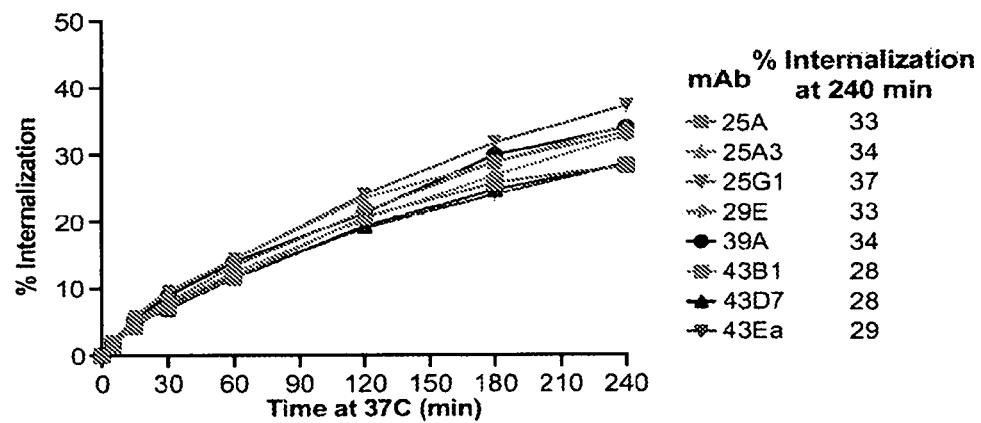

Internalization of the anti-TF antibodies was also evaluated by a quantitative assay based on internalized fluorescence and quenched surface-fluorescence. Cell surface fluorescence quenching was assessed as described in Liao-Chan et al., *PLoS One*, 2015, 10:e0124708. Briefly, $1.2 \times 10^5$ MDA-MB-231 cells were pre-incubated with 100 nM of A488-conjugated antibodies in media for 2 hr on ice. After 2 washes, cells were resuspended in cold media and pulsed for up to 4 hr at 37° C. Cells were rapidly chilled and incubated with or without 300 nM of anti-A488 antibody (clone 19A) for 30 min on ice. After 2 washes, dead cells were labeled with DAPI and samples were analyzed on a Novocyte flow cytometer (ACEA Biosciences). The median fluorescence intensities (MFIs) at each anti-A488 mAb concentration were normalized against the isotype control to obtain a normalized MFI percentage. Internalized fluorescence was calculated from quenched and non-quenched sample data by correcting for incomplete surface quenching: $1-(N_1-Q_1)/(N_1-(N_1Q_0/N_0))$ with $N_1$=unquenched MFI at each time point ($t_1$); $Q_1$=Quenched MFI at $t_1$; $Q_0$=Quenched MFI for the sample kept on ice ($t_0$); $N_0$=Unquenched MFI at $t_0$. Percent internalization of anti-TF antibodies conjugated to A488 is shown in FIG. 18C.

Because Fab:MMAF binds the Fc region of the TF-specific antibodies, cellular uptake of these complexes can trigger cell death. While the TF-specific antibodies alone had no impact on cell viability in three-day cultures of TF-positive A431 cells (FIG. 18A), the TF-specific antibodies in complex with Fab:MMAF showed dose-dependent cell killing with $IC_{50}$ values ranging between 0.07 and 0.14 nM (FIG. 18B).

Cellular uptake was corroborated with fluorescently labeled TF-specific antibodies. In a quantitative assay based on internalized fluorescence and quenched surface-fluorescence, the TF-specific antibodies showed between 28 and 37% internalization after a 4 h incubation (FIG. 18C).

These results indicate that the tested anti-TF antibodies can medicate internalization and toxin delivery into TF-positive cells.

TABLE 46

ADC Data With Ranking (Continuous Incubation)

| | Cell line: ADC format: Treatment: Figure: | A431 Secondary ADC Continuous Figure 18B | | | A431 Primary ADC Continuous Figure 20A | | | MDA-MB-231 Primary ADC Continuous Figure 22D | | | HPAF-II Primary ADC Continuous Figure 22E | | | Continuous Primary |
|---|---|---|---|---|---|---|---|---|---|---|---|---|---|---|
| | Binding data: | $IC_{50}$ (nM) | 95% CI | rank | $IC_{50}$ (nM) | 95% CI | rank | $IC_{50}$ (nM) | 95% CI | rank | $IC_{50}$ (nM) | 95% CI | rank | ADC RANK |
| Antibody: | 1F | 0.07 | 0.06 to 0.07 | Not tested | | Not tested | | | Not tested | | | Not tested | | Not included |
| | 25A | 0.11 | 0.10 to 0.11 | 6 | 0.09 | 0.08 to 0.09 | 7 | 0.14 | 0.12 to 0.16 | 7 | 0.06 | 0.05 to 0.07 | 8 | 7 |
| | 25A3 | 0.09 | 0.08 to 0.09 | 3 | 0.07 | 0.07 to 0.08 | 5 | 0.11 | 0.10 to 0.12 | 4 | 0.05 | 0.04 to 0.05 | 5 | 4 |
| | 25G1 | 0.08 | 0.07 to 0.08 | 1 | 0.06 | 0.06 to 0.06 | 3 | 0.09 | 0.08 to 0.10 | 3 | 0.04 | 0.04 to 0.05 | 3 | 3 |
| | 29E | 0.10 | 0.09 to 0.10 | 4 | 0.06 | 0.05 to 0.06 | 2 | 0.07 | 0.07 to 0.08 | 2 | 0.04 | 0.04 to 0.05 | 2 | 2 |
| | 39A | 0.08 | 0.08 to 0.09 | 2 | 0.05 | 0.05 to 0.05 | 1 | 0.05 | 0.05 to 0.05 | 1 | 0.04 | 0.03 to 0.05 | 1 | 1 |
| | 43B1 | 0.12 | 0.11 to 0.13 | 7 | 0.08 | 0.08 to 0.08 | 6 | 0.14 | 0.13 to 0.15 | 5 | 0.05 | 0.04 to 0.06 | 4 | 5 |
| | 43D7 | 0.10 | 0.10 to 0.10 | 5 | 0.06 | 0.06 to 0.07 | 4 | 0.14 | 0.12 to 0.16 | 6 | 0.05 | 0.05 to 0.06 | 6 | 6 |
| | 43Ea | 0.13 | 0.13 to 0.14 | 8 | 0.09 | 0.09 to 0.10 | 8 | 0.15 | 0.13 to 0.17 | 8 | 0.06 | 0.05 to 0.06 | 7 | 8 |
| | 54E | 0.11 | 0.11 to 0.12 | Not tested | 0.07 | 0.07 to 0.07 | Not tested | | Not tested | | | Not tested | | Not included |
| | Isotype | Not applicable | | | Not applicable | | | Not applicable | | | Not applicable | | | Not included |
| | TF-011 | Not tested | | | 0.05 | 0.05 to 0.05 | | Not tested | | | Not tested | | | Not included |

TABLE 47

ADC Data With Ranking (4 h Incubation)

| | Cell line: ADC format: Treatment: Figure: | A431 Primary ADC 4 hr, followed by washout Figure 20B | | | A431 Primary ADC 4 hr, followed by washout Figure 21A | | | 4 hr Primary |
|---|---|---|---|---|---|---|---|---|
| | Measurement: | $IC_{50}$ (nM) | 95% CI | rank | $IC_{50}$ (nM) | 95% CI | rank | ADC RANK |
| Antibody: | 1F | Not tested | | | Not tested | | | Not included |
| | 25A | 0.35 | 0.32 to 0.39 | 6 | 0.18 | 0.17 to 0.19 | 6 | 6 |
| | 25A3 | 0.19 | 0.17 to 0.21 | 3 | 0.12 | 0.11 to 0.12 | 3 | 3 |
| | 25G1 | 0.19 | 0.17 to 0.20 | 2 | 0.10 | 0.09 to 0.10 | 2 | 2 |
| | 29E | 0.20 | 0.18 to 0.21 | 4 | 0.13 | 0.12 to 0.14 | 4 | 4 |
| | 39A | 0.12 | 0.11 to 0.13 | 1 | 0.09 | 0.09 to 0.10 | 1 | 1 |
| | 43B1 | 0.36 | 0.32 to 0.41 | 7 | 0.19 | 0.17 to 0.20 | 7 | 7 |

TABLE 47-continued

ADC Data With Ranking (4 h Incubation)

| Cell line: | A431 | | | A431 | | | |
|---|---|---|---|---|---|---|---|
| ADC format: | Primary ADC | | | Primary ADC | | | |
| Treatment: | 4 hr, followed by washout | | | 4 hr, followed by washout | | | 4 hr Primary |
| Figure: | Figure 20B | | | Figure 21A | | | |
| Measurement: | IC$_{50}$ (nM) | 95% CI | rank | IC$_{50}$ (nM) | 95% CI | rank | ADC RANK |
| 43D7 | 0.28 | 0.25 to 0.30 | 5 | 0.14 | 0.13 to 0.15 | 5 | 5 |
| 43Ea | 0.43 | 0.39 to 0.48 | 8 | 0.24 | 0.22 to 0.25 | 8 | 8 |
| 54E | 0.26 | 0.24 to 0.29 | | 0.20 | 0.18 to 0.22 | | Not included |
| Isotype | Not applicable | | | Not applicable | | | Not included |
| TF-011 | 0.17 | 0.16 to 0.18 | | 0.09 | 0.09 to 0.10 | | Not included |

Example 22: Cell-Based Binding Assay of Antibody-Drug Conjugates (ADCs)

To evaluate the cell binding properties of ADCs, binding of anti-TF antibodies and anti-TF ADCs to endogenous human TF expressing HCT116 cells was was assessed as previously described in Liao-Chan et al., *PLoS One*, 2015, 10:e0124708, which is incorporated by reference in its entirety. Briefly, 1.2×10$^5$ cells collected with Cellstripper (Mediatech, Manassas, Va., USA) were incubated with a twelve-point 1:3 dilution titration of anti-human TF antibody or ADC starting at 100 nM for 2 hr on ice. After 2 washes, cells labeled with antibody or ADC were incubated for 30 min on ice with 150 nM of Goat Phycoerythrin (PE) F(ab')$_2$ fragment goat anti-human IgG, Fcγ fragment specific (Jackson ImmunoResearch, West Grove, Pa., USA) or FITC-labeled F(ab')$_2$ fragment goat anti-human kappa (SouthernBiotech, Birmingham, Ala., USA), respectively. After 2 washes, dead cells were labeled with TO-PRO-3 Iodide (ThermoFisher Scientific) and samples were analyzed on a CytoFLEX flow cytometer (Beckman Coulter, Brea, Calif., USA) or Novocyte flow cytometer (ACEA Biosciences, San Diego, Calif., USA). The median fluorescence intensities (MFIs) at each dilution were plotted and cell EC$_{50}$'s were derived using a 4-parameter binding model in Prism (GraphPad, La Jolla, Calif., USA). FIGS. 19A and 19B exhibit the binding curves of anti-TF antibodies and anti-TF ADCs, respectively. FIG. 19C lists the reportable cell EC$_{50}$'s and their 95% confidence intervals of the anti-TF antibodies and ADCs.

As shown in FIGS. 19A, 19B, and 19C, the cell binding properties of TF-specific ADCs are comparable to the cell binding properties of TF-specific antibodies, which indicates that the conjugation process of ADC did not alter the cell-binding properties of the TF-specific antibody moiety of the ADC.

Example 23: Cytotoxicity Assays of Antibody-Drug Conjugates (ADCs)

To evaluate ADC cytotoxicity, A431 cells were plated in 384-well plates (Greiner Bio-One). Anti-TF antibodies conjugated to MC-vc-PAB-MMAE were serially diluted as shown. The TF-specific ADCs were added to A431 cells, with either a 72 h incubation or a 4 h incubation followed by removal of excess ADC and culture for another 68 h. A431 cells were lysed in CTG assay reagent after treatment. CTG luminescence was measured and the mean and standard deviation of 4 replicates graphed in Prism. For each ADC, the IC$_{50}$ and its associated 95% confidence interval were calculated in Prism using a 4-parameter binding model.

FIG. 20A shows the cell viability after titrations of anti-TF ADCs with a continuous 72 h incubation. FIG. 20B shows the cell viability after titrations of anti-TF ADCs with a 4 h incubation followed by removal of excess ADC and culture for another 68 h. FIG. 20C shows the reportable IC$_{50}$ values of ADCs under both the continuous treatment and the pulse treatment. The 95% confidence intervals for the IC$_{50}$'s of the continuous treatment and the pulse treatment are listed in Table 46 and Table 47 respectively.

Both treatments resulted in efficacious cell killing, with a 2.4 to 4.7-fold increase in IC$_{50}$ when excess ADC was removed from the culture after the 4 h incubation compared to the 72 h incubation. Removal of excess 25A3 and 39A ADC had the smallest impact on IC$_{50}$, with a 2.7 and 2.4-fold increase from 0.07 and 0.05 nM, respectively.

These results indicate that similar to the TF-specific antibodies, the TF-specific ADCs undergo substantial cellular internalization.

Example 24: Cytotoxicity Assays in the Presence of FVIIa

To understand whether FVIIa interfered with the activity of the TF-specific ADC, we treated A431 cells for 4 h with the TF-specific ADCs (anti-TF antibodies conjugated to MC-vc-PAB-MMAE) in the absence or presence of FVIIa and measured cell viability 68 h later. A431 cells were pre-incubated for 30 min without or with 50 nM of FVIIa prior to the addition of an anti-TF ADC titration. Cell viability was determined by CTG assay. The mean and standard deviation of 4 replicates were graphed in Prism. For each ADC, the IC$_{50}$ were calculated in Prism using a 4-parameter binding model.

The cell viability after titrations of anti-TF ADCs in the absence or presence of FVIIa is shown in FIGS. 21A and 21B respectively. The reportable IC$_{50}$ values of ADCs in the absence or presence of FVIIa are listed in FIG. 21C.

While the ADCs that competed with FVIIa (29E, 39A, 54E and TF-011) were negatively affected by the presence of FVIIa by at least 2.3-fold, the ADCs that did not compete with FVIIa (group 25 and 43 antibodies) were equally efficacious in the absence or presence of FVIIa.

These results indicate that FVIIa does not interfere with the activity of anti-TF ADCs from groups 25 and 43.

Example 25: Cytotoxicity Assays on Additional Cancer Cell Lines

To evaluate TF copy number on the cell surface of different cell lines, 1.2×10$^5$ cells were harvested and incubated with 133 nM of anti-human TF antibody 5G9 on a mouse IgG2a backbone for 2 hr on ice. After 2 washes, QIFIKIT beads (Agilent) and cells labeled with anti-TF antibody were incubated for 30 min on ice with 150 nM of Goat Phycoerythrin (PE) F(ab')$_2$ fragment goat anti-mouse IgG, Fc-gamma fragment specific (Jackson ImmunoResearch). After 2 washes, dead cells were labeled with TO-PRO-3 Iodide (ThermoFisher Scientific) and samples were analyzed on a CytoFLEX flow cytometer (Beckman Coulter). After gating for single live cells, the MFI's were determined using FlowJo (Flowjo, Ashland, Oreg., USA). A standard curve using QIFIKIT beads was generated in Prism using a 5-parameter binding model to determine copy number. The lower limit of quantitation was $1.9 \times 10^3$ antibody binding sites (also referred to as copy number) and the upper limit of quantitation was $8.0 \times 10^5$ antibody binding sites.

The TF copy number on A431, CHO, HCT-116, HPAF-II, MDA-MB-231, and RF/6A is listed in FIG. 22A. The level of surface TF ranged from $1.9 \times 10^5$ to $5.7 \times 10^5$ copies in A431, MDA-MB-231 and HPAF-II cells. HCT-116 cells expressed $2.2 \times 10^4$ copies of surface TF and TF expression in CHO cells was below limit of quantitation (BLOQ). As 5G9 cross-reacts with *Macaca fascicularis* TF and the TF protein sequence between *M. fascicularis* and *mulatta* is identical, the level of surface TF in the *M. mulatta* cell line RF/6A was also quantified ($1.7 \times 10^4$ copies).

Cell viability of HCT-116, CHO, MDA-MB-231, and HPAF-II cells in the presence of titrations of anti-TF MMAE ADCs was shown in FIGS. 22B, 22C, 22D, and 22E respectively.

Figure 22D:
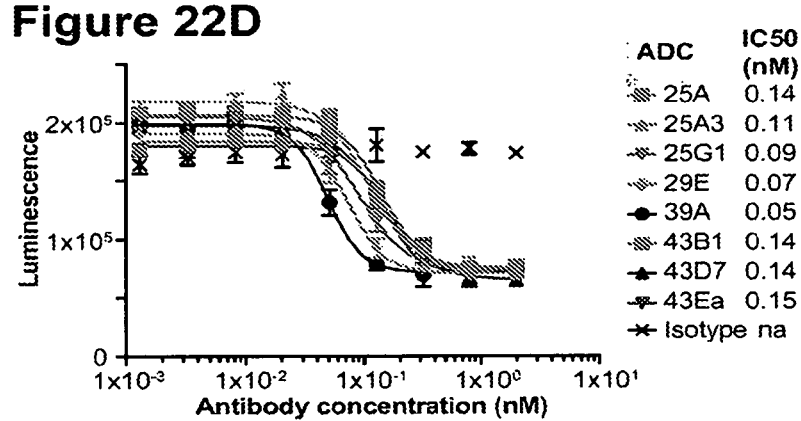
Figure 22E:
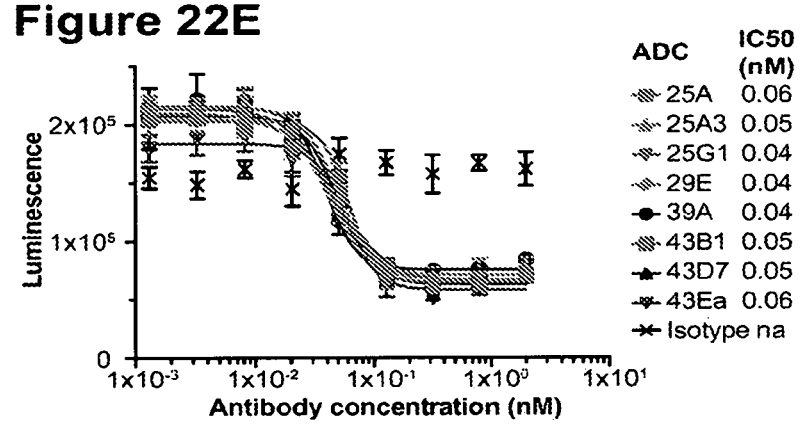

The TF-specific ADCs effectively reduced the viability of MDA-MB-231 and HPAF-II cancer cell lines (FIGS. 22D and 22E). Compared to the activity on MDA-MB-231 and HPAF-II cells, the ADCs were less efficacious on HCT-116 cells, with some activity at the highest concentration and no reportable IC$_{50}$ value (FIG. 22B). The TF-specific ADCs did not affect the viability of the CHO cultures (FIG. 22C).

These results indicate that the cytotoxicity of anti-TF ADCs is specific for TF positive cells.

When ranking the cell-killing efficacy of the ADCs on A431, HPAF-II and MDA-MB-231 cells, the top four ADCs in descending order were 39A, 29E, 25G1 and 25A3 (Table 46). When A431 cells were incubated for 4 h with the TF-specific ADCs followed by a washout, the top four ADCs in descending order were 39A, 25G1, 25A3 and 29E (Table 47). Thus, the top 2 ranking ADCs with no impact on coagulation were 25G1 and 25A3.

Example 26: Intracellular Microtubule Network in the Presence of Antibody-Drug Conjugates (ADCs)

Figure 23A:
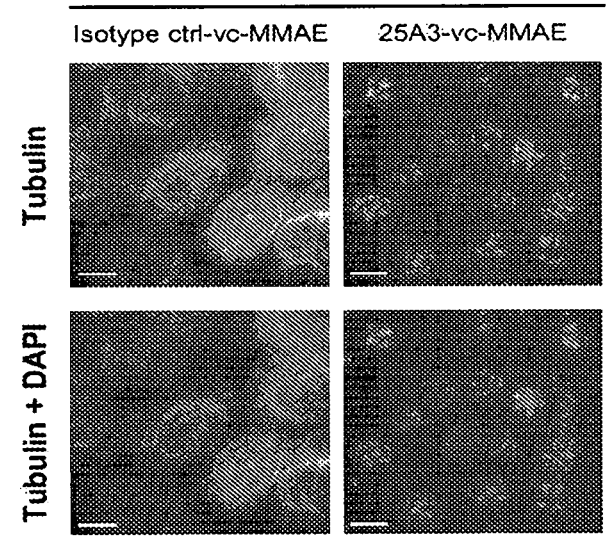
FIGS. 23A and 23B show staining of the microtubule network after treatment with anti-TF 25A3 MMAE ADC (25A3-vc-MMAE) or isotype control MMAE ADC (isotype ctrl-vc-MMAE).
Figure 23B:
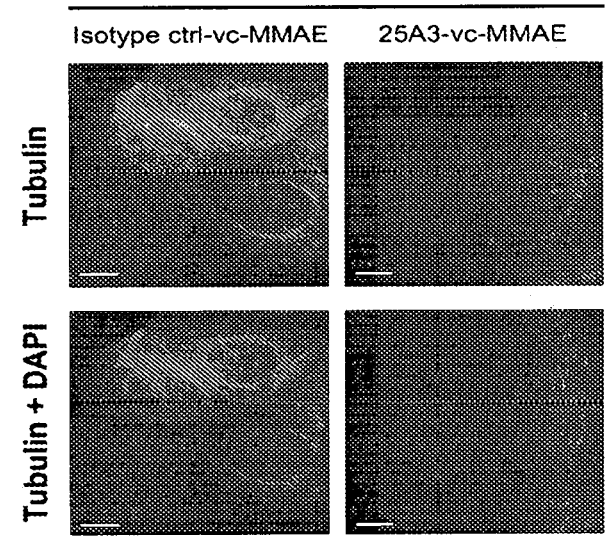

Immunofluorescence of the intracellular microtubule network of cells was conducted to illustrate the mechanism of action of the ADC. See Theunissen et al., *Methods Enzymol*, 2006, 409:251-284. Briefly, A431 or HPAF-II cells were seeded onto 8-well poly-D-lysine treated slides (Corning Inc, Corning, N.Y., USA). One day later, the culture medium was replaced with medium containing ADC at 5 nM. After twenty hours of ADC exposure, the cells were fixed for 15 min at room temperature with 4% paraformaldehyde (ThermoFisher Scientific). After three washes with PBS, the cells were permeabilized for 1 h with PBS containing 0.3% Triton X-100 and 5% normal goat serum. Next, the microtubule networks were stained for 3 h with anti-tubulin (11H10) rabbit mAb (Alexa Fluor 488 conjugate) (Cell Signaling Technology, Danvers, Mass., USA) in PBS containing 1% BSA and 0.3% Triton X-100. After three washes, ProLong Gold Antifade reagent with DAPI (ThermoFisher Scientific) was added to the cells and the slide was mounted for microscopy by using a 0.17 mm coverslip. Image acquisition was conducted on a DMi8 fluorescence microscope (Leica Microsystems, Buffalo Grove, Ill., USA) equipped with a sCMOS camera. The Leica LAS X software was used to acquire a system-optimized Z-stack of 6 to 7 microns. A sharp two-dimensional image from this Z-stack was created automatically with the extended depth of field (EDF) image feature. Representative images of tubulin staining of A431 or HPAF-II cells are shown in FIGS. 23A and 23B respectively.

While the isotype control ADC did not affect the microtubule network, the 25A3 ADC disrupted the microtubule network effectively in both A431 and HPAF-II cells.

These results indicate the MMAE-based anti-TF ADCs induce cytotoxicity in TF-positive cancer cells through disruption of the intracellular microtubule network.

Example 27: Cytotoxicity Assays and G$_2$/M Arrest in HUVECs

To evaluate TF copy number on the cell surface of human umbilical vein endothelial cells (HUVECs), $1.2 \times 10^5$ HUVECs were harvested and incubated with 133 nM of anti-human TF antibody 5G9 on a mouse IgG2a backbone for 2 hr on ice. After 2 washes, QIFIKIT beads (Agilent) and cells labeled with anti-TF antibody were incubated for 30 min on ice with 150 nM of Goat Phycoerythrin (PE) F(ab')$_2$ fragment goat anti-mouse IgG, Fc-gamma fragment specific (Jackson ImmunoResearch). After 2 washes, dead cells were labeled with TO-PRO-3 Iodide (ThermoFisher Scientific) and samples were analyzed on a CytoFLEX flow cytometer (Beckman Coulter). After gating for single live cells, the MFI's were determined using FlowJo (Flowjo, Ashland, Oreg., USA). A standard curve using QIFIKIT beads was generated in Prism using a 5-parameter binding model to determine copy number. The lower limit of quantitation was $1.9 \times 10^3$ antibody binding sites (also referred to as copy number) and the upper limit of quantitation was $8.0 \times 10^5$ antibody binding sites.

Figures 24A, 24B:
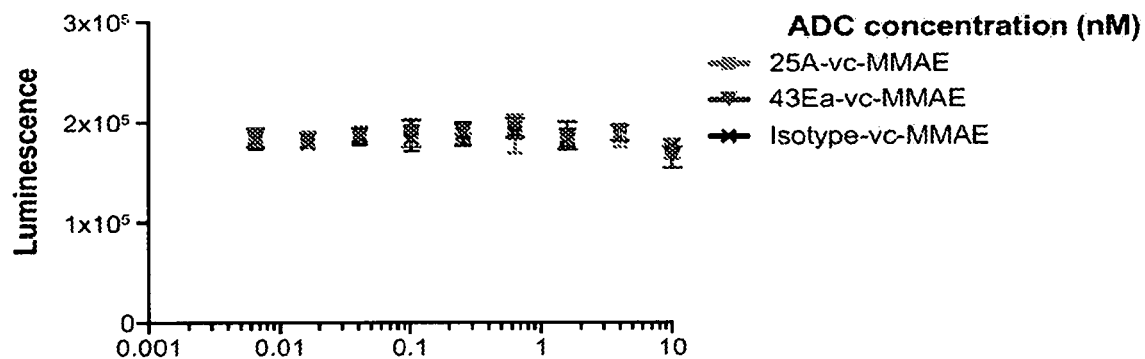
FIGS. 24A and 24B show the TF expression after cytokine treatment and the effect of anti-TF ADCs on the viability of cytokine-treated human umbilical vein endothelial cells (HUVECs).

In response to injury, inflammatory and angiogenic factors transiently increase expression of surface TF in the vasculature. See Holy et al., *Adv Pharmacol*, 2010, 59:259-592, which is incorporated by reference in its entirety. The transient upregulation of TF in cell culture was mimicked by treating HUVECs with a combination of inflammatory cytokines (5 ng/mL IL1-beta, 25 ng/mL TNF-alpha and 50 ng/mL VEGF). As shown in FIG. 24A, surface TF levels increased from $2.4 \times 10^3$ copies in the absence of inflammatory cytokines to $1.2 \times 10^4$ copies after 6 h of cytokine treatment. The surface TF was ~3-fold lower after 20 h of cytokine treatment relative to 6 h of treatment, which indicates that the cytokine-induced TF upregulation was transient.

For the ADC cytotoxicity assay, HUVEC cultures were seeded on half-area 96-well plates. The next day, the combination of inflammatory cytokines and a titration of ADCs was added to the cultures. Four days later viability of the cultures was assessed by lysis in CellTiter-Glo (CTG) assay reagent. As shown in FIG. 24B, the cell viability of inflammatory cytokine-treated HUVEC cultures was unaffected by the anti-TF ADCs, 25A-vc-MMAE and 43Ea-vc-MMAE. The results indicates that the inflammatory cytokine-treated endothelial cells are resistant to anti-TF ADCs.

To further understand the resistance of endothelial cells to anti-TF ADCs, cell cycle progression was evaluated 24 h after addition of the cytokines and TF-specific ADCs. Arrest at the G$_2$/M phase of the cell cycle was analyzed as previously described in Theunissen et al, *Methods Enzymol*, 2006, 409:251-284. Briefly, low-passage HUVECs (Lifeline Cell Technologies, Frederick, Md., USA), propagated in VascuLife VEGF-Mv Endothelial media (Lifeline Cell Technologies), and HCT-116 cells were seeded on 12-well plates. The next day, media was removed and replaced with fresh media (no cytokines) or media containing 5 ng/mL IL1-beta, 25 ng/mL TNF-alpha and 50 ng/mL VEGF (with cytokines). A titration of MMAE-linked ADCs or free MMAE was added to the cells. After 24 h of treatment, cells were fixed in ice-cold 70% ethanol. Subsequently, the cells were washed with flow cytometry buffer (PBS, 1% FBS, 0.1% Triton) and stained for 1 h with a 1:100 dilution of phospho-Histone H3 (Ser10) (D2C8 PE Conjugate, Cell Signaling Technology). After 2 washes, the cells were treated for 20 min with 100 µg/mL PureLink RNAse A (ThermoFisher Scientific), followed by the addition of the viability dye TO-PRO-3 Iodide (ThermoFisher Scientific). 40,000 events were collected on a Novocyte flow cytometer. In the Flowjo data analysis software cell doublets and aneuploid cells were excluded. The pH3 signal was plotted against DNA content to determine the percentage of pH3-positive cells.

Figure 25A:
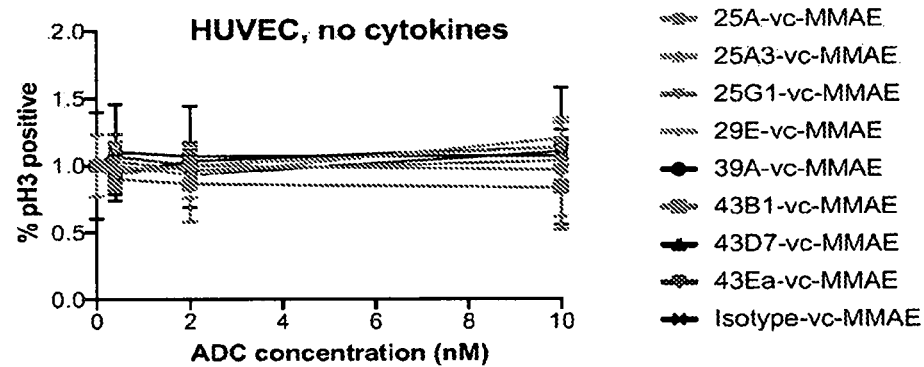
FIGS. 25A, 25B, and 25C show the quantitation of the $G_2/M$ arrest in HUVECs or HCT-116 cells treated for 24 h with titrations of anti-TF ADCs.
Figure 25B:
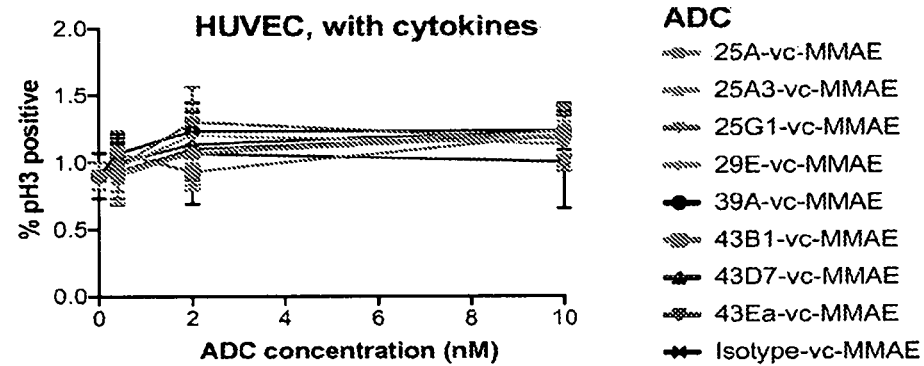
Figure 25C:
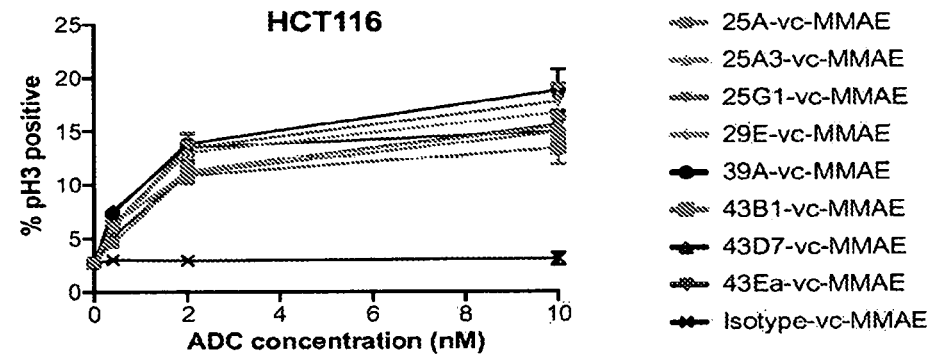

The percentage of pH3-positive cells (% pH3) with titrations of anti-TF ADCs on HUVECs in the absence or presence of inflammatory cytokines is shown in FIGS. 25A and 25B respectively. The percentage of pH3-positive cells (% pH3) with titrations of anti-TF ADCs on HCT-116 cells is shown in FIG. 25C.

Figure 26A:
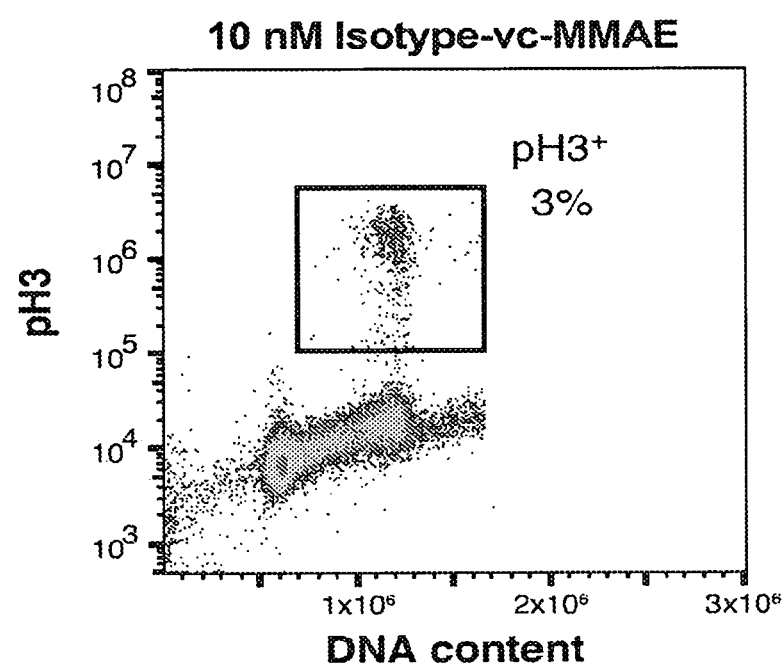
FIGS. 26A and 26B show the percentage of pH3-positive HCT-116 cells analyzed by flow cytometry with or without anti-TF ADC treatment.
Figure 26B:
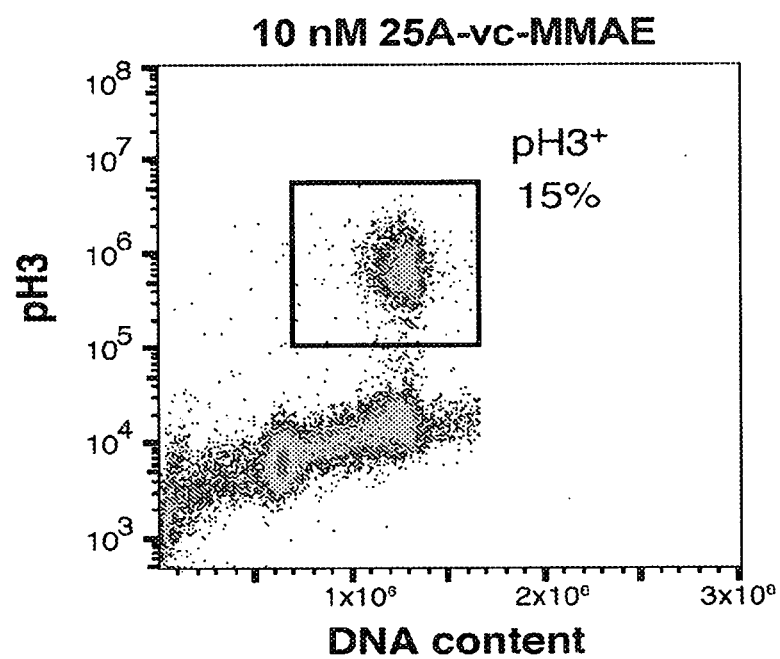

While the TF-specific ADCs induced an arrest at the G$_2$/M phase of the cell cycle in HCT-116 cells, the ADCs did not impact cell cycle progression in HUVECs with or without inflammatory cytokine treatment. As shown in FIGS. 26A and 26B, the percentage of pH3-positive HCT-116 cells increased 5 times after treatment of 25A-vc-MMAE as compared to treatment of Isotype-vc-MMAE.

Figure 27A:
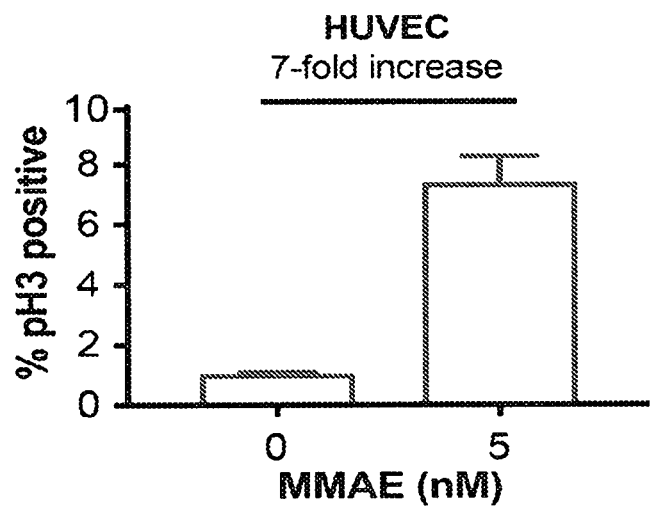
FIGS. 27A and 27B show the sensitivity of HUVECs and HCT-116 cells to MMAE.
Figure 27B:
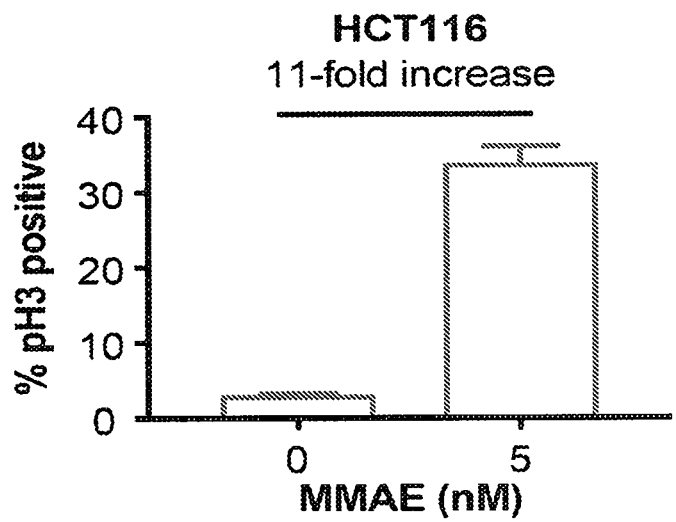

FIGS. 27A and 27B show that unconjugated MMAE increase the phosphorylation of histone H3 to a similar extent in both HCT-116 cells and HUVECs, indicating that the resistance in endothelial cells is specific for the MMAE-based ADC.

Taken together, these results indicate that the anti-TF ADCs do not affect the viability of HUVECs in the absence or presence of inflammatory cytokines.

Example 28: Erk Phosphorylation Assay

For assessment of Erk phosphorylation, A431 cells were plated in 6-well plates (Corning) in media overnight. The following day, cells were washed once and serum starved in serum-free media. After starvation, cells were preincubated with 100 nM of anti-TF antibodies for 30 min at 37° C. FVIIa was spiked into the wells at 50 nM and incubated for 20 min at 37° C. for p-ERK induction. After induction, cells were lysed with RIPA Lysis and Extraction Buffer with Halt™ Protease and Phosphatase Inhibitor Cocktail (ThermoFisher Scientific). Western blot was performed with 20 µg of cell lysate using Phospho-p44/42 MAPK (Erk1/2) (Thr202/Tyr204) and p44/42 MAPK (Erk1/2) (137F5) (Cell Signaling Technology) as primary antibodies and Peroxidase AffiniPure Donkey Anti-Rabbit IgG (H+L) (Jackson ImmunoResearch) as a secondary antibody. Non-saturating band intensities for pErk and Erk were measured on an Amersham AI600 (GE Healthcare). Each pErk intensity was normalized against its respective Erk intensity and the no-antibody no-FVIIa sample intensity.

Figure 28:
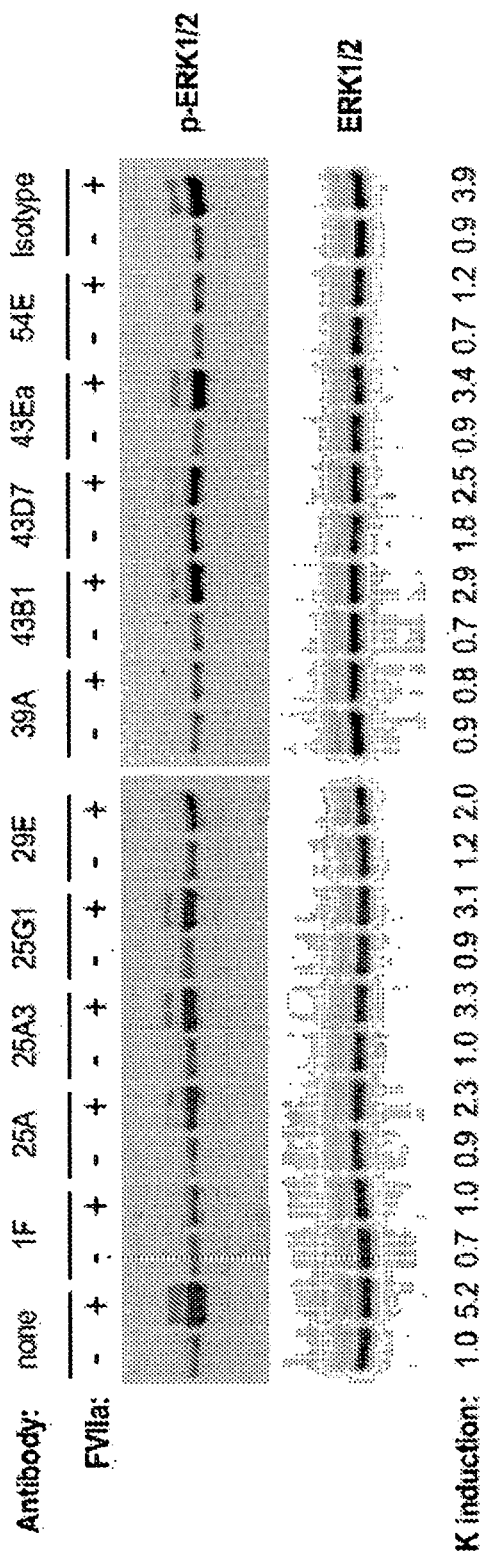
FIG. 28 shows the analysis of Erk phosphorylation by Western blotting with an anti-phospho-Erk1/2 antibody and an anti-Erk1/2 antibody. The values of pErk induction are listed.

The Western blot results of pErk and Erk are shown in FIG. 28. Treatment with FVIIa induced Erk phosphorylation by 5.2 fold in cell cultures without pretreatment of anti-TF antibodies. The inducation of Erk phosphorylation was ablated by pretreatment with 1F, 39A and 54E (fold induction between 0.8 and 1.2) and attenuated by 29E and the members of groups 25 and 43 (fold induction between 2.0 and 3.4).

This data indicates that anti-TF antibodies inhibit FVIIa-dependent TF signaling when assessing Erk phosphorylation.

Example 29: Antibody-Dependent Cellular Cytotoxicity (ADCC) Assay

To evaluate ADCC activity, an ADCC Reporter Bioassay Core Kit (Promega) was used following the manufacturer's protocol. Briefly, A431 cells were plated on a microtiter plate (Corning). The following day, the cells were incubated with a ten-point 1:3 dilution titration of anti-TF antibodies or the ADCs starting at 50 nM. An ADCC effector-to-target cell ratio of 8:1 was added to each well and incubated for 6 h at 37° C. Bio-Glo™ Luciferase Assay Reagent was added to each well to measure luminescence on an Envision plate reader (PerkinElmer, Waltham, Mass., USA). The mean and standard deviation of 4 replicates were graphed in Prism. For each antibody and ADC, the EC$_{50}$ and its associated 95% confidence interval were calculated in Prism using a 4-parameter binding model.

ADCC reporter luminescence after incubation with the reporter Jurkat cell line in the represece titrations of anti-TF antibodies or anti-TF ADCs is shown in FIGS. 29A and 29B respectively. The ADCC reporter luminescence EC$_{50}$ values for each anti-TF antibody or ADC are listed in FIG. 29C.

All the tested TF-specific antibodies and ADCs exerted induction of luciferase-dependent luminescence with EC$_{50}$ values ranging between 0.18 and 0.43 nM.

These data indicate that both the TF-specific antibodies and ADCs can induce antibody-dependent cellular cytotoxicity (ADCC) via the IgG1 Fc domain of the antibody.

Example 30: Studies in Cell Line-Derived Xenograft (CDX) Models

To evaluate the efficacy of the ADCs in vivo, xenograft studies in immune compromised mice were performed as described in Kim et al., *Blood Cancer J*, 2015, 5:e316, which is incorporated by reference in its entirety. Briefly, the A431 epidermoid carcinoma and the HPAF-II pancreatic carcinoma cell lines were implanted subcutaneously in the flank of athymic nude mice (Charles River Laboratories, Wilmington, Mass.). Animals were randomized and treated as indicated in the figures. Body weight and tumor size assessments were performed bi-weekly. Animals were removed from study and euthanized once tumor size reached 1200 mm$^3$ or skin ulceration was evident. In addition, the MTV curve for the treatment group in question was no longer shown once an animal was removed from study due to size. The animals' care was in accordance with institutional guidelines. Mean tumor volume (MTV) with the standard error of the mean (SEM) was plotted over time. Treatment efficacy was determined by calculating tumor growth inhibition (% TGI=100%×[1−(final MTV−initial MTV of a treated group)/(final MTV−initial MTV of the control group)]) before any of the animals in the vehicle arm were euthanized due to a tumor size≥1200 mm$^3$. Statistical comparisons between the MTVs were conducted using one-way ANOVA followed by Tukey's multiple comparisons test comparing all groups. The P-values for each ADC compared to the vehicle control arm are reported. At the end of the study, efficacy was also determined in each treatment arm by counting the number of animals with a partial regression (PR) or a complete regression (CR) of the tumor. In a PR response, the tumor volume was 50% or less of its day 1 volume for 3 consecutive measurements during the course of study, and equal to or greater than 14 mm$^3$ for 1 or more of these measurements. In a CR response, the tumor volume was less than 14 mm$^3$ for 3 consecutive measurements. When an animal exhibited a CR response at the end of the study, it was classified as a tumor-free survivor (TFS) instead of a CR. Throughout the ADC studies no significant body weight changes due to ADC treatment were observed.

Figure 30B:
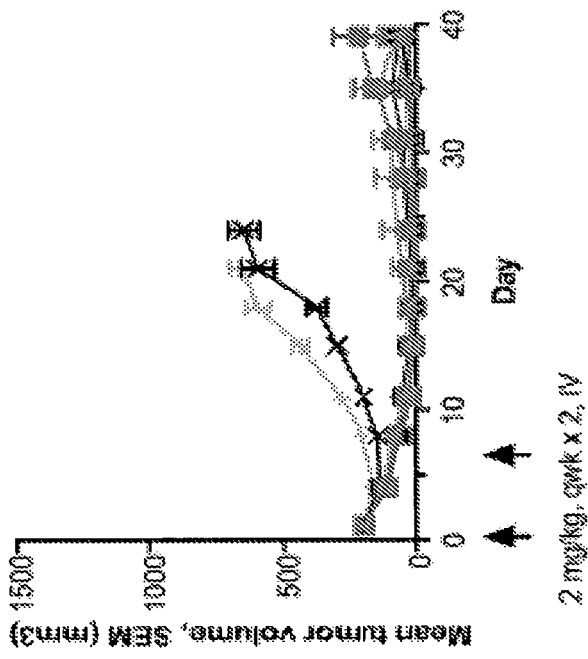
FIGS. 30A and 30B show in vivo efficacy of anti-TF ADCs in HPAF-II xenograft model.
Figure 30A:
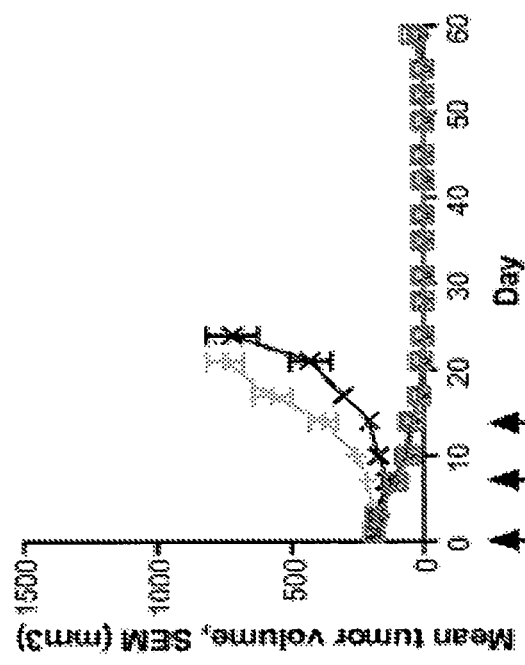

As shown in FIG. 30A, HPAF-II tumor-bearing mice were treated with 5 mg/kg of ADC on day 1, 8 and 15 after randomization. The effect of TF-011 ADC was compared with two representative clones from the two groups that did not impact coagulation (i.e. 25A and 43Ea). Twenty-one days after randomization the efficacy of the 25A, 43Ea and TF-011 ADCs was equivalent, with tumor growth inhibition ranging between 131 and 136%.

In the second HPAF-II study as shown in FIG. 30B, the highest affinity antibody that affected coagulation (i.e. 39A) and six antibodies with varying affinities from groups 25 and 43 (i.e. 25A, 25A3, 25G1, 43Ea, 43B1 and 43D7) were equally efficacious when dosed twice at 2 mg/kg. Tumor growth inhibition for the TF-specific ADCs ranged between 129 and 139% on day 21, and 6 to 9 out of 10 animals per treatment arm were classified as tumor-free survivors at the end of the study.

In the MDA-MB-231 xenograft model, the ADCs were administered on day 1 and 8 post-randomization at 4 or 2 mg/kg. As shown in FIG. 31A, all the TF-specific ADCs were active at 4 mg/kg, with tumor growth inhibition ranging between 69 and 100%, and a significant difference in mean tumor volume for each TF-specific ADC compared to the vehicle control arm. While a notable difference was observed in mean tumor volume between 25G1 and the other TF-specific ADCs, it was not statistically significant ($P>0.05$).

At 2 mg/kg of ADC as shown in FIG. 31B, all the TF-specific antibodies showed suboptimal activity with varying degrees of significance in mean tumor volume compared to the vehicle control arm. 25A3, 39A and 43B1 showed the greatest degree of significance in mean tumor volume compared to the vehicle control arm ($P<1\times10^{-4}$). The difference in mean tumor volume between 39A and the other antibodies was only significant for the comparison between 39A and 43Ea ($P<0.05$).

Figure 32:
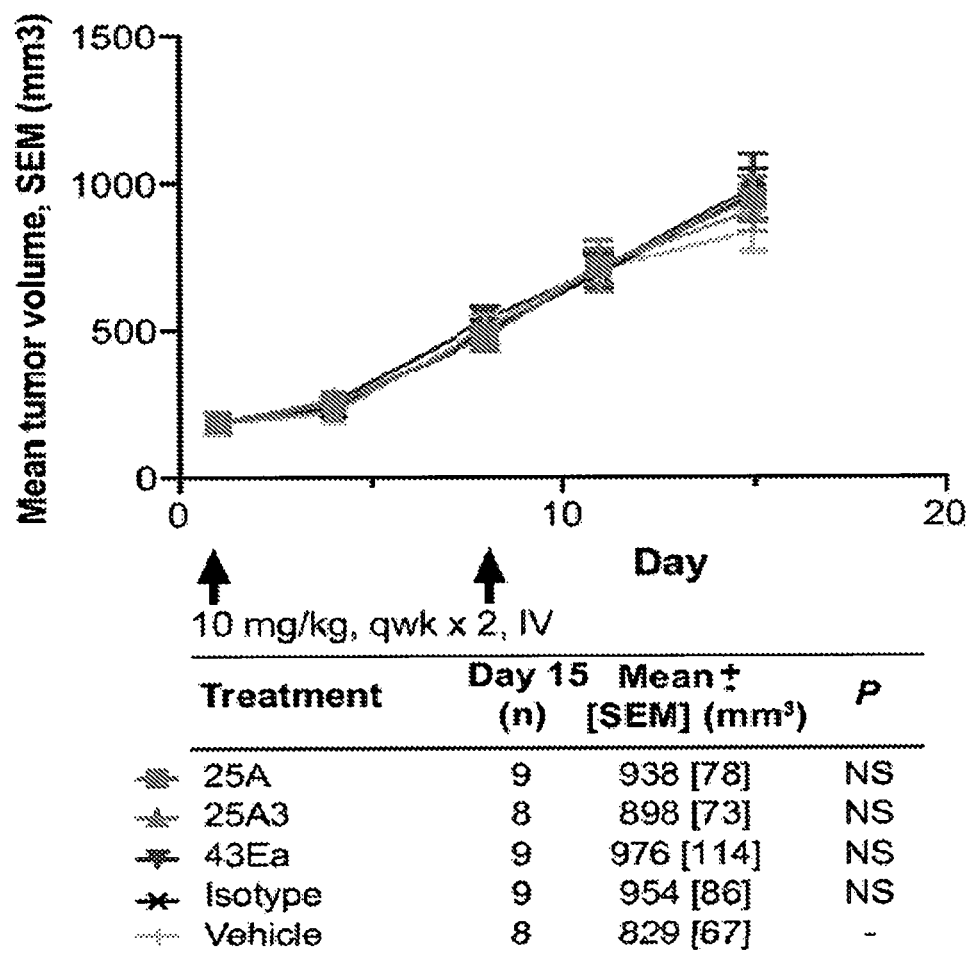
FIG. 32 shows the mean tumor volume after weekly treatment of unconjugated anti-TF antibodies at 10 mg/kg for 2 weeks in the HPAF-II xenograft model. The mean tumor volume on day 15 is listed.

In contrast, the unconjugated antibodies of 25A, 25A3 and 43Ea lacked substantial anticancer activity when dosed twice at 10 mg/kg in the HPAF-II xenograft model (FIG. 32).

There results indicate that the TF-specific ADCs are efficacious in the HPAF-II and MDA-MB-231 xenograft model under various dosing regimens. The activity of the ADCs are caused by the toxin delivery of the anti-TF antibodies.

Example 31: Studies in Patient-Derived Xenograft (PDX) Models

TF-positive PDX models were performed in athymic nude mice (Envigo, Indianapolis, Ind.) to evaluate the efficacy of the ADCs in vivo. The animals' care was in accordance with institutional guidelines. Study animals were implanted unilaterally on the left flank with tumor fragments.

For immunohistochemistry (IHC) analysis, tissues underwent pretreatment using Rip Tide (Mosaic Laboratories, Lake Forest, Calif.) for 40 min at 95-97° C. in a water bath, cooled for 10 min on the bench, rinsed 3 times with distilled water, and rinsed for 5 min with Splash-T Buffer (Mosaic Laboratories). Tissue sections were blocked in EnVision Peroxidase-Blocking Reagent (EnVision+ Mouse HRP Detection Kit, Agilent, Carpinteria, Calif.) for 5 min, followed by 2 rinses in Splash-T Buffer for 5 min each. Next, the tissue sections were stained with an anti-TF antibody (mouse clone HTF-1) or a mouse negative control reagent for 30 min, followed by 2 rinses in Splash-T Buffer for 5 min each. The second staining step of the tissue sections was carried out for 30 min with EnVision+ Mouse HRP (EnVision+ Mouse HRP Detection Kit), followed by 2 rinses in Splash-T Buffer for 5 min each. To visualize the anti-TF staining, tissue sections were developed with DAB chromogen (EnVision+ Mouse HRP Detection Kit) for 5 min, followed by 10 dips and a 5 min rinse in distilled water. Tissue sections were counterstained with Hematoxylin for 5 min followed by 3 rinses in distilled water.

Animals were randomized and treated as indicated in the figures. Animals were removed from study and euthanized once tumor size reached 1200 mm$^3$ or skin ulceration was evident. In addition, the MTV curve for the treatment group in question was no longer shown once an animal was removed from study due to size. TGI and statistical analyses were conducted in the same manner as for the CDX studies. The CR and PR response definitions were as follows for the PDX studies: a PR responder had a MTV≤30% of MTV at day 1 for 2 consecutive measurements; a CR responder had an undetectable MTV for 2 consecutive measurements. When an animal exhibited a CR response at the end of the study, it was classified as a TFS instead of a CR.

Figure 33A:
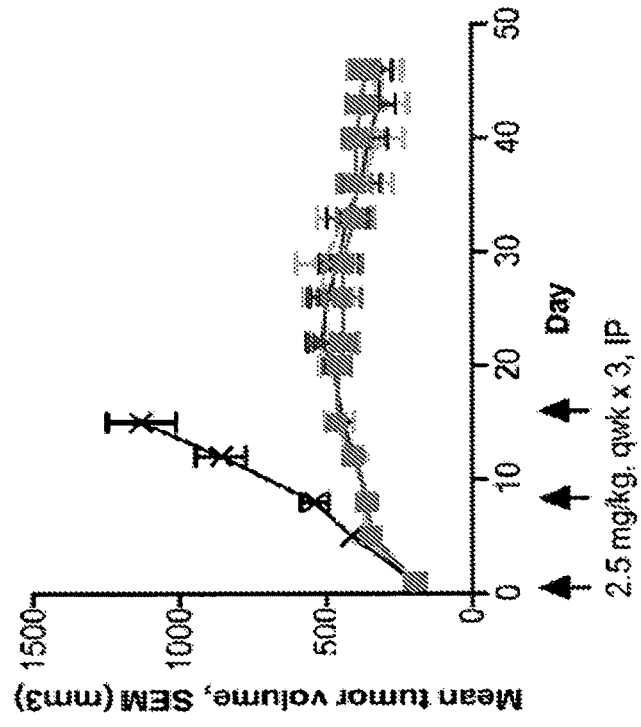
FIGS. 33A, 33B, and 33C show in vivo efficacy of anti-TF ADCs in patient-derived xenograft (PDX) models.
Figure 33B:
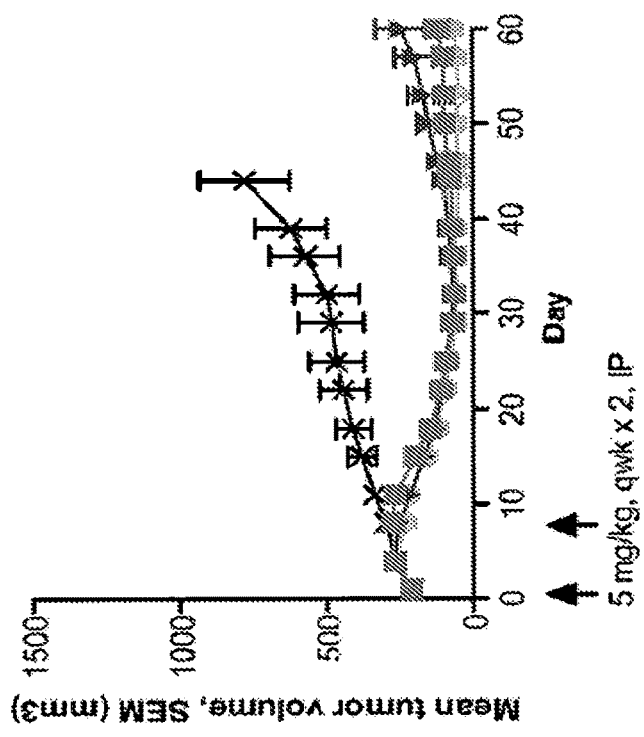
Figure 33C:
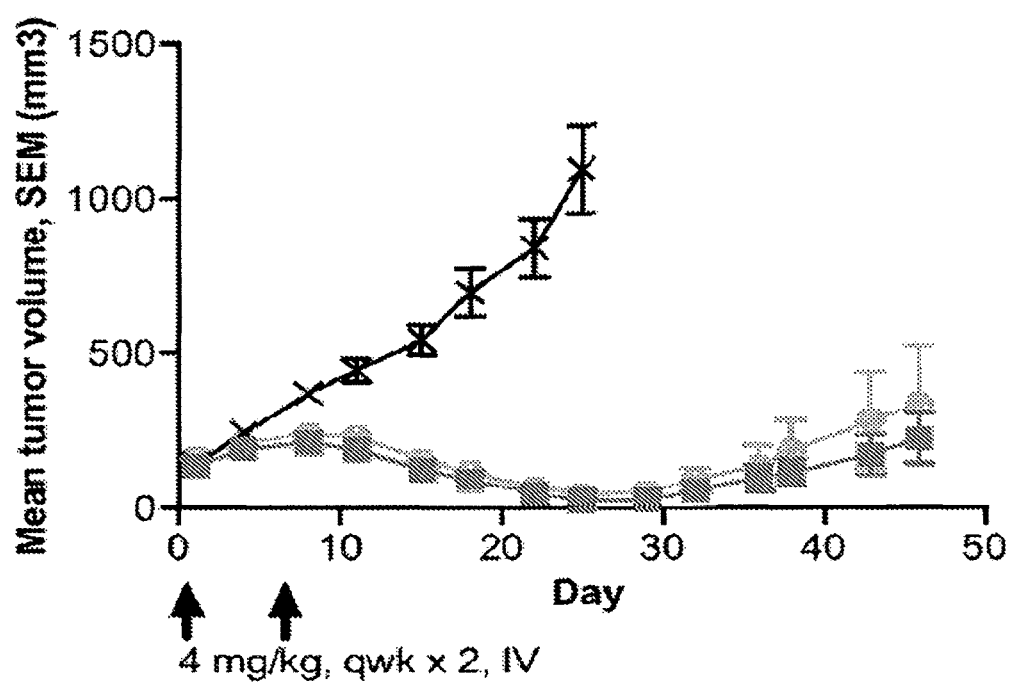

While the squamous cell carcinoma of the head and neck (SCCHN) and ovarian adenocarcinoma PDX had H-scores of 250 and 220, respectively, the gastric adenocarcinoma PDX had an H-score of 155 (data not shown). Upon randomization of tumor-bearing mice, treatment occurred on a weekly basis either twice or three times with the dose ranging between 2.5 and 5 mg/kg. As shown in FIGS. 33A, 33B, and 33C in all the PDX models a significant reduction in mean tumor volume was observed for each TF-specific ADC compared to the isotype control arm ($P<1\times10^{-4}$), with no significant difference between the various TF-specific ADCs ($P>0.05$). In the head and neck and ovarian PDX model, the number of complete responders and tumor-free survivors did not exceed 2 out of 10 animals at the end of the study in any of the treatment groups (FIGS. 33A and 33B). However, in the gastric PDX the 25A treatment arm had 2 partial responders, 2 complete responders and 3 tumor-free survivors, and the TF-011 arm contained 1 complete responder and 5 tumor-free survivors at the end of the study (FIG. 33C).

These data indicate that the anti-TF ADCs from groups 25 and 43 (i.e. 25A and 43Ea) were equally efficacious as tisotumab vedotin (TF-011) ADC.

Example 32: Efficacy Study in Swine CNV Model

An efficacy study in a swine choroidal neovascularization (CNV) model was performed to determine the effect 4 different anti-TF antibodies in reducing lesion size.

Figure 34A:
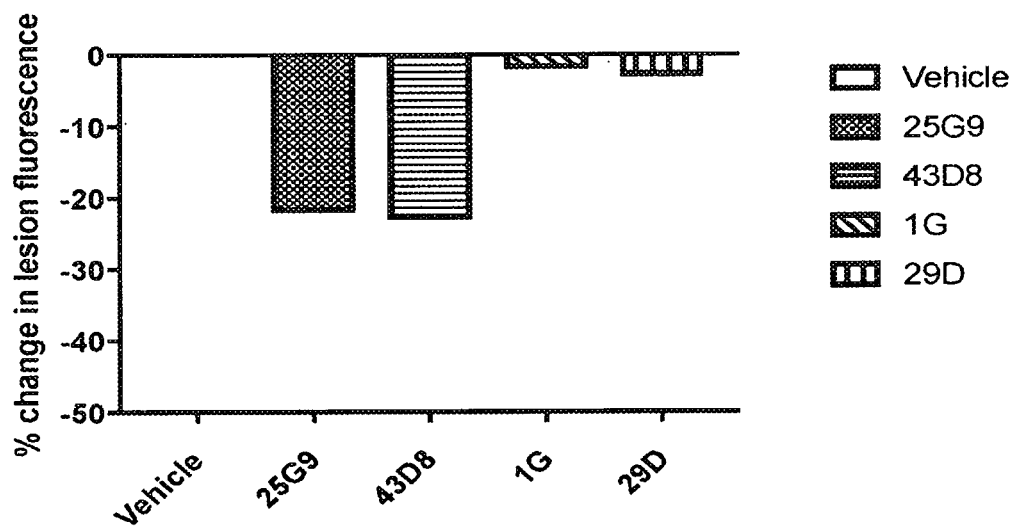
FIGS. 34A and 34B show the change in lesion size after administration of anti-TF antibody in a swine choroidal neovascularization (CNV) model.
Figure 34B:
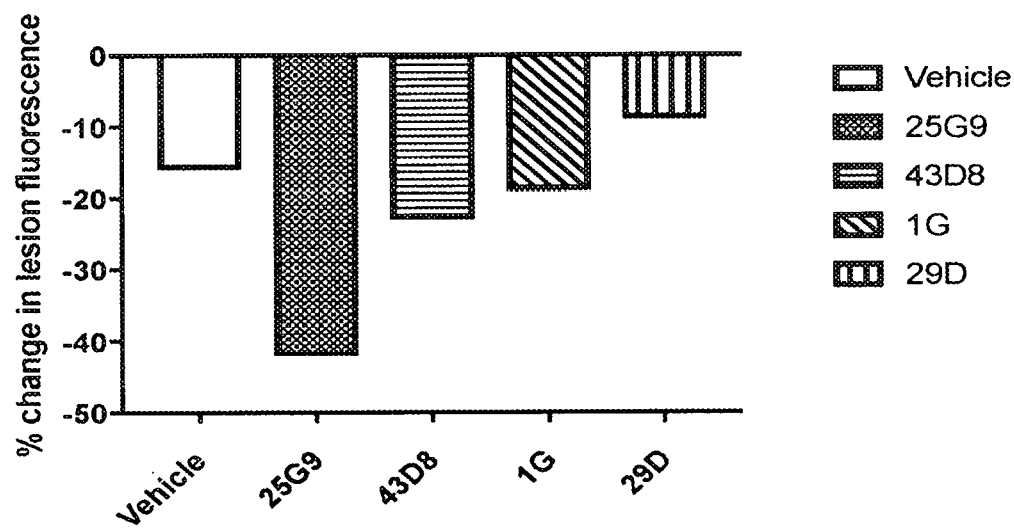

10-12 week old animals (Swine/Hampshire Cross) underwent bilateral laser using an 810 nm Diode laser delivered through an indirect ophthalmoscope to create approximately 6 single laser spots between retinal veins in each eye of each animal. For efficacy assessments, 2 mg of each anti-TF antibody, 25G9, 43D8, 1G, and 29D respectively, were administered intravitreally on day 7 post-laser treatment. A vehicle control group was also included in the study. Fluorescein Angiography (FA) to determine total lesion fluorescence was performed on day 7 (baseline), day 14 and day 28. FA was evaluated using a Corrected Total Lesion Fluorescence (CTLF) measurement for each individual lesion. The perimeter of the lesion was traced, and an integrated density value was obtained. CTLF was then calculated by subtracting the mean fluorescence background adjacent to the lesion from the integrated density measurement. Percent change in lesion size from day 7 to day 14 and from day 7 to day 28 are shown in FIG. 34A and FIG. 34B, respectively.

From day 7 to day 14, anti-hTF antibodies from groups 25 and 43, 25G9 and 43D8, reduced lesion size by greater than 20%. From day 7 to day 28, anti-hTF antibody 25G9 reduced lesion size by greater than 40%. Anti-hTF antibodies 1G and 29D did not reduce lesion size significantly as compared to the vehicle control group.

This data indicates that antibodies from groups 25 and 43, 25G9 and 43D8, were effective in reducing lesion size in a swine CNV model.

Example 33: Efficacy of 25G9 in Swine CNV Model

An efficacy study in a swine choroidal neovascularization (CNV) model was performed to compare different doses of anti-TF antibody 25G9 for their ability to reduce lesion size.

Figure 35:
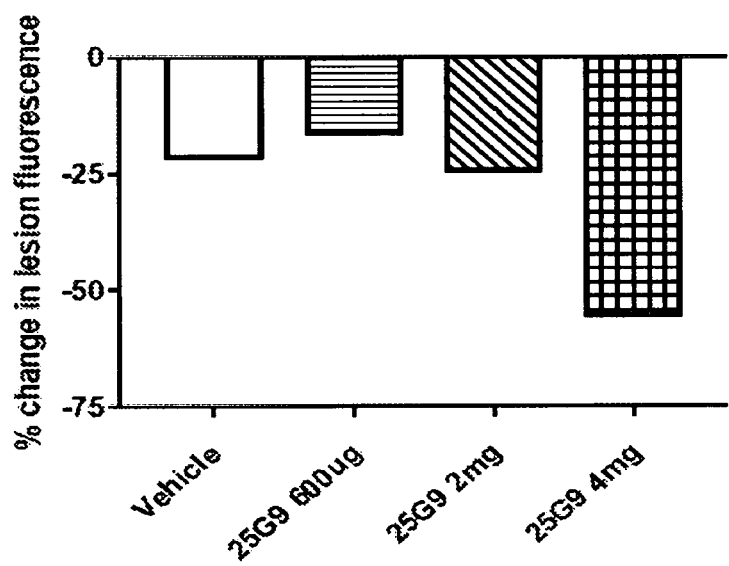
FIG. 35 shows the change in lesion size in a swine choroidal neovascularization (CNV) model from day 7 (baseline) to day 28 as measured by Fluorescein Angiography (FA) after intravitreal administration of anti-TF antibodies 25G9 at 600 ug, 2 mg and 4 mg respectively.

10-12 week old animals (Swine/Hampshire Cross) underwent bilateral laser using an 810 nm Diode laser delivered through an indirect ophthalmoscope to create approximately 6 single laser spots between retinal veins in each eye. For efficacy assessments 600 ug, 2 mg and 4 mg of anti-TF antibody 25G9 were administered intravitreally on Day 7 post-laser treatment. Fluorescein Angiography (FA) to determine total lesion fluorescence was performed on day 7 (baseline) and day 28. FA was evaluated using a Corrected Total Lesion Fluorescence (CTLF) measurement for each individual lesion. The perimeter of the lesion was traced, and an integrated density value was obtained. CTLF was then calculated by subtracting the mean fluorescence background adjacent to the lesion from the integrated density measurement. Percent changes in lesion size from day 7 to day 28 are shown in FIG. 35.

From day 7 to day 28, anti-hTF antibody 25G9 reduced lesion size in a dose-dependent matter. 25G9 reduced lesion size by greater than 50% at 4 mg. This data indicates that antibody 25G9 was effective in reducing lesion size in the swine CNV model in a dose-dependent matter.

Example 34: Binding Affinity Assay For Pig TF and Rabbit TF

The ability of certain antibodies was tested for binding to pig TF. For pig TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of pig TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 48.

The ability of certain antibodies was tested for binding to rabbit TF. For rabbit TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of rabbit TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 48.

As shown in Table 48, anti-hTF antibodies from groups 25 and 43 exhibit binding activity and cross-reactivity to pig TF and rabbit TF. In contrast, antibodies from groups 1 and 29 show no binding activity to pig TF or rabbit TF.

TABLE 48

Antibody kinetics for pig and rabbit TF

| Antibody | Pig $K_D$, nM | Rabbit $K_D$, nM |
| --- | --- | --- |
| 1G | no binding | no binding |
| 25A | 18.7 | 50.5 |
| 25A3 | 5.5 | 12.4 |
| 25A5 | 5.2 | 5.4 |
| 25A5-T | 4.5 | 5.4 |
| 25G | 26.0 | 75.5 |
| 25G1 | 2.6 | 3.6 |
| 25G9 | 3.3 | 4.2 |
| 29D | no binding | no binding |
| 43D7 | 8.8 | 6.8 |
| 43D8 | 19.2 | 7.7 | no binding*: no binding to weak binding, with no reportable $K_D$

Example 35: Immunohistochemistry (IHC) Assay

Tissues underwent pretreatment using Rip Tide (Mosaic Laboratories, Lake Forest, Calif.) for 40 min at 95-97° C. in a water bath, cooled for 10 min on the bench, rinsed 3 times with distilled water, and rinsed for 5 min with Splash-T Buffer (Mosaic Laboratories). Tissue sections were blocked in EnVision Peroxidase-Blocking Reagent (EnVision+ Mouse HRP Detection Kit, Agilent, Carpinteria, Calif.) for 5 min, followed by 2 rinses in Splash-T Buffer for 5 min each. The tissue sections were then stained with an anti-TF antibody (mouse clone HTF-1) or a mouse negative control reagent for 30 min, followed by 2 rinses in Splash-T Buffer for 5 min each. The second staining step of the tissue sections was carried out for 30 min with EnVision+ Mouse HRP (EnVision+ Mouse HRP Detection Kit), followed by 2 rinses in Splash-T Buffer for 5 min each. To visualize the anti-TF staining, tissue sections were developed with DAB chromogen (EnVision+ Mouse HRP Detection Kit) for 5 min, followed by 10 dips and a 5 min rinse in distilled water. Tissue sections were counterstained with Hematoxylin for 5 min followed by 3 rinses in distilled water.

Staining intensity was scored on a semi-quantitative integer scale from 0 (negative) to 3 (or "3+") by a certified anatomic pathologist. The percentage of cells staining positively at each intensity level was recorded. Scoring was based on localization of TF to the cell membrane. The H score combines components of staining intensity with the percentage of positive cells. It has a value between 0 and 300 and is defined as: 1×(percentage of cells staining at 1+ intensity)+2×(percentage of cells staining at 2+ intensity)+ 3×(percentage of cells staining at 3+ intensity)=H score.

Tissue sections from patients with kidney cancer, head & neck cancer, ovarian cancer, gastric cancer, prostate cancer, gastroesophageal junction cancer, cervical cancer, and glioblastoma were stained. The number of patients with scores within each H score range and the total number of patient for each cancer are shown in Table 50. These results indicate that TF is expressed in kidney cancer, head & neck cancer, ovarian cancer, gastric cancer, prostate cancer, gastroesophageal junction cancer, cervical cancer, and glioblastoma.

TABLE 50

Results of IHC assay

| Indication | H score 0 | H score 1-100 | H score 101-200 | H score 201-300 |
|---|---|---|---|---|
| Kidney | 19/28 | 6/28 | 1/28 | 2/28 |
| Head & Neck | 4/74 | 31/74 | 19/74 | 20/74 |
| Ovarian | 13/26 | 11/26 | 0/26 | 2/26 |
| Gastric | 1/20 | 9/20 | 4/20 | 6/20 |
| Prostate | 1/24 | 8/24 | 7/24 | 8/24 |
| Pancreatic | 14/37 | 18/37 | 5/37 | 0/37 |
| Gastroesophageal junction | 28/59 | 23/59 | 6/59 | 2/59 |
| Cervical | 31/60 | 21/60 | 7/60 | 1/60 |
| Glioblastoma | 2/41 | 7/41 | 23/41 | 9/41 |

Example 36: Epitope Binning of Anti-TF Antibodies

To establish epitope binding differences between the anti-human TF antibodies, chimeric TF construct mapping experiments were conducted. This mapping technique enables discrimination of antibody epitopes.

Because all the anti-human TF antibodies evaluated do not bind rat TF, the rat TF sequence was used for the construction of chimeric human-rat TF constructs. Chimeric human-rat construct design was guided by the N- and C-terminal domain of TF extracellular domain (amino acids 1-107 and 108-219 of the extracellular domain, respectively), with an alignment shown in FIG. 36. Based on the chimera mapping results using the constructs from FIG. 36, rat amino acid segment 141-194 was replaced by the human sequence (amino acid 136-189 of hTF extracelluar domain), with an alignment shown in FIG. 37. Design of three human TF constructs with either 1 or 2 human-rat substitutions (hTF_K68N, hTF_K149N and hTF_N171H_T197K) was based on reported contact residues K68, K149 and N171 and T197 for the 10H10 antibody (Teplyakov et al., Cell Signal., 2017, 36:139-144), with an alignment shown in FIG. 38.

To establish binding of the anti-human TF antibodies to the various TF constructs, HEK293 cells were transfected with a DNA plasmid that co-expresses the TF construct and a green fluorescent protein marker. For a subset of the antibodies, an antibody titration (a 12-point 1:3 dilution series starting at 250 nM) was evaluated on select TF constructs (FIGS. 39A-F). These antibody titrations demonstrated that the antibody concentration of 15 µg/ml (100 nM) used in Tables 51 and 52 was appropriate to establish "Percentage antibody binding to TF construct relative to hTF". Two days after transfection, cells were collected from the tissue culture plate, stained with 15 µg/ml of the indicated anti-TF antibody, washed, stained with anti-human IgG-Fc Alexa Fluor 647 polyclonal antibody, washed, and stained with the viability dye 4',6-Diamidino-2-Phenylindole, Dihydrochloride. Upon acquisition of 80,000 live events on a flow cytometer, live cells marked with the fluorescent marker were analyzed for the degree of staining by the anti-TF antibody. The median fluorescence intensity values relative to an isotype control for each TF expression construct were divided by the median fluorescence intensity value relative to an isotype control for the hTF expression construct, and the resulting percentage listed as "Percentage antibody binding to TF construct relative to hTF" in Tables 51 and 52. As used herein, the term "live cell staining assay" refers to the antibody binding assay used in this example.

The assumption that all chimeric TF constructs were expressed on the cell surface at levels between 50% and 150% of the hTF control construct was met for all TF constructs for at least one anti-human TF antibody in the antibody collection, with the exception of the h1-107_r construct (human amino acid segment 1-107 replaced by rat sequence). Lack of binding of the anti-human TF antibodies to cell surface-expressed rat TF was expected. When "Percentage antibody binding to TF construct relative to hTF" in Tables 51 and 52 was less than 50%, the antibody was considered a non-binder (0) in Tables 53 and 54. When "Percentage antibody binding to TF construct relative to hTF" in Tables 51 and 52 was between 50% and 150%, the antibody was considered a binder (1) in Tables 53 and 54.

Each antibody was assigned to an epitope bin in Table 55 based on the combination of unbound constructs from Table 53. The antibodies from Lineage 25 (25A, 25A3, 25A5-T, 25G1 and 25G9) bind a unique epitope, referred to as Epitope Bin 6 in Table 55. The antibodies from Lineage 43 (43B1, 43D7, 43D8 and 43Ea) also bind a unique epitope, referred to as Epitope Bin 7 in Table 55. The antibody from Lineage 29 (29E) binds a unique epitope, referred to as Epitope Bin 2 in Table 55. The antibodies from Lineage 39 and 54 (39A and 54E) bind a unique epitope, referred to as Epitope Bin 3 in Table 55.

Figure 39A:
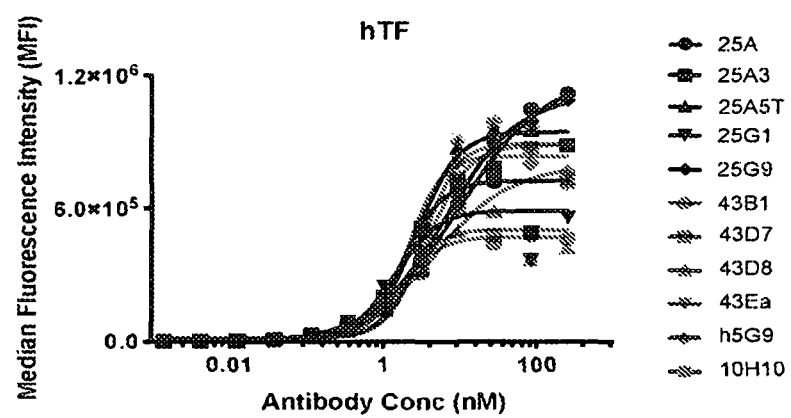
FIGS. 39A-F show the titration curves of anti-TF antibodies from lineages 25 and 43, h5G9, and 10H10 on select TF constructs.
Figure 39B:
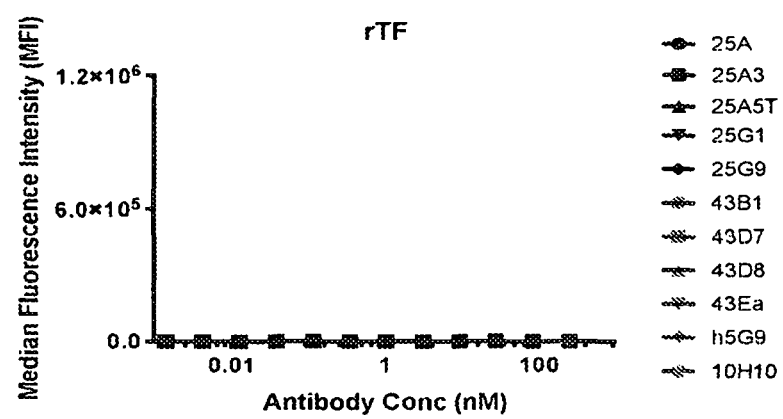
Figure 39C:
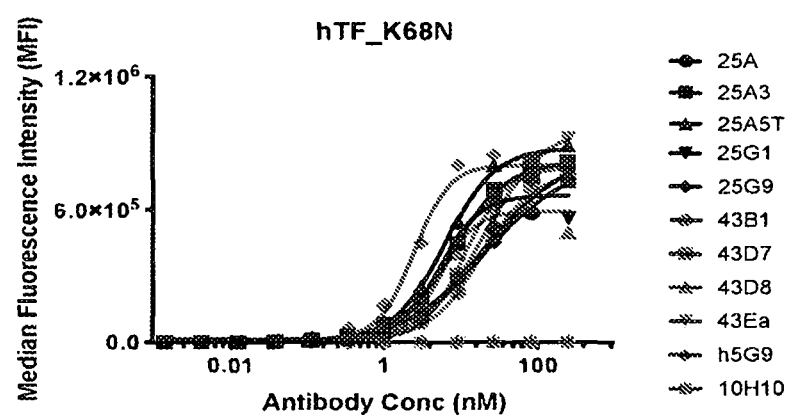
Figure 39D:
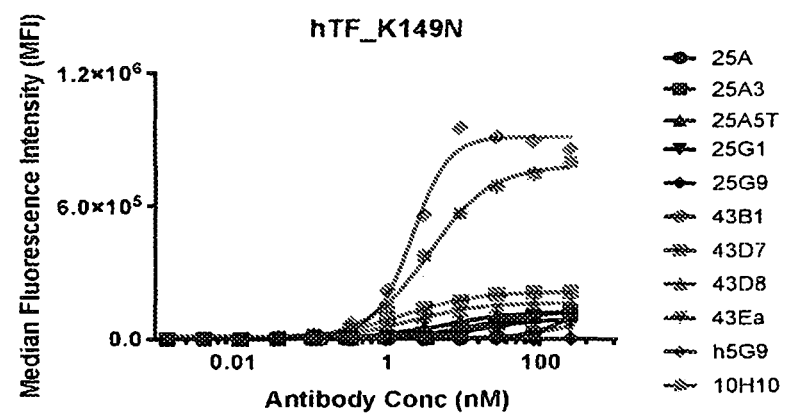
Figure 39E:
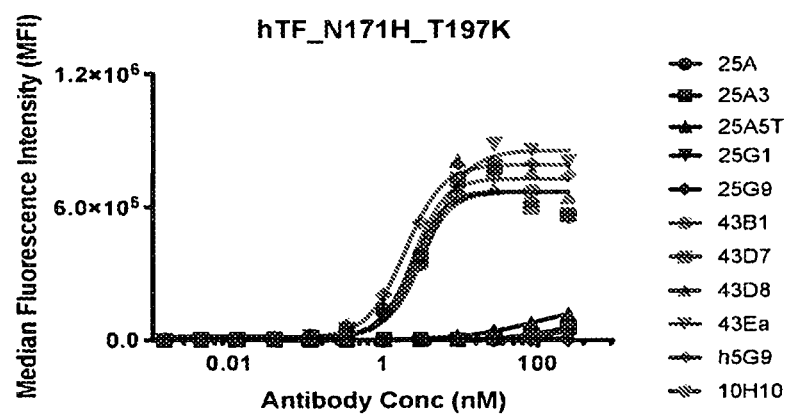
Figure 39F:
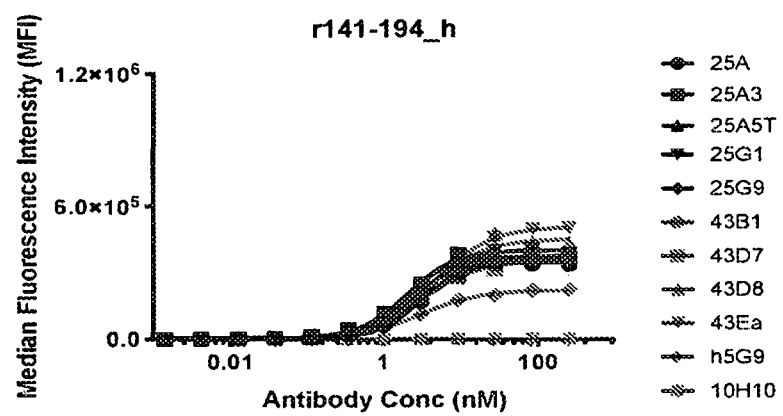

Lineage 25 and 43 antibodies are the only antibodies in the antibody panel that bind r141-194_h, the chimeric construct in which rat amino acids 141-194 were replaced by human sequence (FIG. 39F; Table 54). Furthermore, while M1593 cannot bind hTF_K68N, all the other antibodies in the antibody panel bind hTF_K68N (FIG. 39C; Table 54). Only Lineage 25 and 43 antibodies cannot bind hTF_K149N (FIG. 39D; Table 54). Only Lineage 25 antibodies cannot bind hTF_N171H_T197K (FIG. 39E; Table 54).

In summary, these results indicate that lineage 25 antibodies bind a unique epitope on human TF compared to all other antibodies tested. Lineage 43 antibodies bind a unique epitope on human TF compared to all other antibodies tested. Lineage 25 and lineage 43 antibodies bind a different epitope on human TF from M1593.

TABLE 51

Percent antibody binding to TF construct relative to hTF

| | Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|---|
| | hTF | 100 | 100 | 100 | 100 | 100 | 100 | 100 | 100 | 100 | 100 | 100 | 100 | 100 | 100 | 100 | 100 |
| | rTF | 0 | 0 | 0 | 0 | 0 | 0 | 0 | 0 | 0 | 0 | 0 | 0 | 0 | 0 | 0 | 0 |
| Human | h1-107r (52) | 0 | 0 | 0 | 0 | 0 | 41 | 0 | 32 | 36 | 36 | 37 | 28 | 33 | 35 | 31 | 37 |
| amino | h1-77_r (25) | 0 | 0 | 0 | 0 | 0 | 94 | 0 | 86 | 95 | 84 | 88 | 64 | 64 | 75 | 69 | 69 |
| acid | h1-38r (14) | 91 | 87 | 100 | 102 | 104 | 100 | 104 | 101 | 104 | 93 | 101 | 88 | 97 | 106 | 104 | 103 |
| segment | h39-77r (11) | 0 | 0 | 0 | 0 | 0 | 88 | 2 | 82 | 88 | 80 | 87 | 71 | 59 | 75 | 71 | 69 |
| replaced | h78-107r (21) | 0 | 8 | 81 | 68 | 32 | 114 | 74 | 108 | 116 | 103 | 113 | 108 | 113 | 114 | 117 | 114 |
| by rat | h78-107_r.v2 (27) | 0 | 0 | 76 | 62 | 23 | 101 | 59 | 95 | 96 | 91 | 94 | 93 | 97 | 100 | 101 | 101 |
| segment (in parentheses: | h78-93r (18) | 102 | 0 | 77 | 91 | 110 | 102 | 104 | 106 | 105 | 92 | 101 | 98 | 101 | 104 | 102 | 103 |
| number of | h94-107r (9) | 1 | 82 | 85 | 89 | 27 | 91 | 46 | 82 | 86 | 78 | 83 | 77 | 84 | 92 | 89 | 91 |
| amino acid | h108-219r (46) | 119 | 118 | 118 | 122 | 128 | 0 | 0 | 0 | 0 | 0 | 0 | 0 | 0 | 0 | 0 | 0 |
| changes | h108-158r (19) | 98 | 101 | 107 | 108 | 108 | 63 | 4 | 1 | 0 | 0 | 11 | 22 | 0 | 1 | 0 | 0 |
| relative to | h108-132r (10) | 105 | 108 | 109 | 107 | 124 | 125 | 124 | 112 | 112 | 106 | 111 | 118 | 122 | 126 | 122 | 124 |
| human TF) | h133-158r (9) | 113 | 122 | 119 | 130 | 134 | 91 | 0 | 0 | 0 | 0 | 2 | 3 | 0 | 4 | 1 | 0 |
| | h133-145r (4) | 84 | 95 | 96 | 104 | 104 | 108 | 100 | 77 | 80 | 80 | 87 | 100 | 99 | 104 | 103 | 106 |
| | h133-139r (2) | 82 | 90 | 95 | 103 | 102 | 104 | 103 | 88 | 89 | 88 | 91 | 86 | 94 | 101 | 97 | 101 |
| | h140-145r (2) | 89 | 100 | 101 | 110 | 109 | 113 | 97 | 80 | 87 | 86 | 89 | 105 | 101 | 104 | 104 | 109 |
| | h146-158r (5) | 115 | 122 | 125 | 134 | 134 | 91 | 133 | 2 | 17 | 18 | 17 | 0 | 3 | 20 | 10 | 0 |
| | h146-151r (1) | 122 | 133 | 139 | 142 | 143 | 141 | 118 | 3 | 14 | 17 | 7 | 0 | 11 | 39 | 23 | 2 |
| | h152-158r (4) | 110 | 121 | 128 | 127 | 136 | 82 | 132 | 110 | 116 | 112 | 116 | 111 | 119 | 134 | 129 | 134 |
| | h159-219r (27) | 132 | 134 | 141 | 142 | 155 | 0 | 137 | 0 | 0 | 0 | 0 | 0 | 132 | 130 | 130 | 76 |
| | h159-189r (11) | 94 | 101 | 104 | 110 | 112 | 0 | 105 | 0 | 0 | 0 | 0 | 0 | 100 | 106 | 104 | 94 |
| | h159-174r (6) | 96 | 98 | 101 | 118 | 120 | 0 | 98 | 0 | 0 | 0 | 0 | 0 | 103 | 115 | 112 | 101 |
| | h159-166r (3) | 89 | 93 | 96 | 100 | 98 | 104 | 100 | 93 | 95 | 87 | 91 | 88 | 99 | 106 | 105 | 110 |
| | h167-174r (3) | 96 | 112 | 96 | 122 | 128 | 0 | 118 | 0 | 0 | 0 | 0 | 0 | 109 | 121 | 112 | 104 |
| | h175-189r (5) | 97 | 113 | 112 | 118 | 123 | 119 | 114 | 86 | 95 | 99 | 100 | 86 | 109 | 118 | 114 | 122 |
| | h190-219r (16) | 111 | 138 | 149 | 141 | 145 | 12 | 143 | 125 | 124 | 119 | 127 | 144 | 133 | 140 | 136 | 147 |

TABLE 52

Percent antibody binding to TF construct relative to hTF

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| hTF | 100 | 100 | 100 | 100 | 100 | 100 | 100 | 100 | 100 | 100 | 100 | 100 | 100 | 100 | 100 | 100 |
| rTF | 0 | 0 | 0 | 0 | 0 | 0 | 0 | 0 | 0 | 0 | 0 | 0 | 0 | 0 | 0 | 0 |
| r141-194_h* | 0 | 0 | 0 | 0 | 0 | 32 | 0 | 65 | 89 | 88 | 83 | 108 | 90 | 102 | 95 | 81 |
| hTF_K68N | 105 | 115 | 119 | 118 | 111 | 132 | 0 | 93 | 124 | 126 | 115 | 103 | 107 | 116 | 119 | 118 |
| hTF_K149N | 115 | 117 | 131 | 127 | 132 | 145 | 111 | 2 | 12 | 13 | 7 | 0 | 10 | 29 | 20 | 1 |
| hTF_N171H_T197K | 83 | 98 | 94 | 89 | 109 | 102 | 113 | 1 | 4 | 7 | 1 | 0 | 98 | 101 | 103 | 118 |

*rat amino acid segment replaced by human segment, resulting in 20 amino acid changes

TABLE 53

Antibody binding to TF construct

| | Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|---|
| | hTF | 1 | 1 | 1 | 1 | 1 | 1 | 1 | 1 | 1 | 1 | 1 | 1 | 1 | 1 | 1 | 1 |
| | rTF | 0 | 0 | 0 | 0 | 0 | 0 | 0 | 0 | 0 | 0 | 0 | 0 | 0 | 0 | 0 | 0 |
| Human amino | h1-107_r (52) | 0 | 0 | 0 | 0 | 0 | 0 | 0 | 0 | 0 | 0 | 0 | 0 | 0 | 0 | 0 | 0 |
| acid segment | h1-77_r (25) | 0 | 0 | 0 | 0 | 0 | 1 | 0 | 1 | 1 | 1 | 1 | 1 | 1 | 1 | 1 | 1 |
| replaced by | h1-38_r (14) | 1 | 1 | 1 | 1 | 1 | 1 | 1 | 1 | 1 | 1 | 1 | 1 | 1 | 1 | 1 | 1 |
| rat segment | h39-77_r (11) | 0 | 0 | 0 | 0 | 0 | 1 | 0 | 1 | 1 | 1 | 1 | 1 | 1 | 1 | 1 | 1 |
| (in parentheses: | h78-107_r (21) | 0 | 0 | 1 | 1 | 0 | 1 | 1 | 1 | 1 | 1 | 1 | 1 | 1 | 1 | 1 | 1 |
| number of | h78-107_r.v2 (27) | 0 | 0 | 1 | 1 | 0 | 1 | 1 | 1 | 1 | 1 | 1 | 1 | 1 | 1 | 1 | 1 |
| amino acid | h78-93_r (18) | 1 | 0 | 1 | 1 | 1 | 1 | 1 | 1 | 1 | 1 | 1 | 1 | 1 | 1 | 1 | 1 |
| changes relative | h94-107_r (9) | 0 | 1 | 1 | 1 | 0 | 1 | 0 | 1 | 1 | 1 | 1 | 1 | 1 | 1 | 1 | 1 |
| to human TF) | h108-219_r (46) | 1 | 1 | 1 | 1 | 1 | 0 | 0 | 0 | 0 | 0 | 0 | 0 | 0 | 0 | 0 | 0 |

TABLE 53-continued

Antibody binding to TF construct

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| h108-158_r (19) | 1 | 1 | 1 | 1 | 1 | 1 | 0 | 0 | 0 | 0 | 0 | 0 | 0 | 0 | 0 | 0 |
| h108-132_r (10) | 1 | 1 | 1 | 1 | 1 | 1 | 1 | 1 | 1 | 1 | 1 | 1 | 1 | 1 | 1 | 1 |
| h133-158_r (9) | 1 | 1 | 1 | 1 | 1 | 1 | 0 | 0 | 0 | 0 | 0 | 0 | 0 | 0 | 0 | 0 |
| h133-145_r (4) | 1 | 1 | 1 | 1 | 1 | 1 | 1 | 1 | 1 | 1 | 1 | 1 | 1 | 1 | 1 | 1 |
| h133-139_r (2) | 1 | 1 | 1 | 1 | 1 | 1 | 1 | 1 | 1 | 1 | 1 | 1 | 1 | 1 | 1 | 1 |
| h140-145_r (2) | 1 | 1 | 1 | 1 | 1 | 1 | 1 | 1 | 1 | 1 | 1 | 1 | 1 | 1 | 1 | 1 |
| h146-158_r (5) | 1 | 1 | 1 | 1 | 1 | 1 | 1 | 0 | 0 | 0 | 0 | 0 | 0 | 0 | 0 | 0 |
| h146-151_r (1) | 1 | 1 | 1 | 1 | 1 | 1 | 1 | 0 | 0 | 0 | 0 | 0 | 0 | 0 | 0 | 0 |
| h152-158_r (4) | 1 | 1 | 1 | 1 | 1 | 1 | 1 | 1 | 1 | 1 | 1 | 1 | 1 | 1 | 1 | 1 |
| h159-219_r (27) | 1 | 1 | 1 | 1 | 1 | 0 | 1 | 0 | 0 | 0 | 0 | 0 | 1 | 1 | 1 | 1 |
| h159-189_r (11) | 1 | 1 | 1 | 1 | 1 | 0 | 1 | 0 | 0 | 0 | 0 | 0 | 1 | 1 | 1 | 1 |
| h159-174_r (6) | 1 | 1 | 1 | 1 | 1 | 0 | 1 | 0 | 0 | 0 | 0 | 0 | 1 | 1 | 1 | 1 |
| h159-166_r (3) | 1 | 1 | 1 | 1 | 1 | 1 | 1 | 1 | 1 | 1 | 1 | 1 | 1 | 1 | 1 | 1 |
| h167-174_r (3) | 1 | 1 | 1 | 1 | 1 | 0 | 1 | 0 | 0 | 0 | 0 | 0 | 1 | 1 | 1 | 1 |
| h175-189_r (5) | 1 | 1 | 1 | 1 | 1 | 1 | 1 | 1 | 1 | 1 | 1 | 1 | 1 | 1 | 1 | 1 |
| h190-219_r (16) | 1 | 1 | 1 | 1 | 1 | 0 | 1 | 1 | 1 | 1 | 1 | 1 | 1 | 1 | 1 | 1 |

TABLE 54

Antibody binding to TF construct

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| hTF | 1 | 1 | 1 | 1 | 1 | 1 | 1 | 1 | 1 | 1 | 1 | 1 | 1 | 1 | 1 | 1 |
| rTF | 0 | 0 | 0 | 0 | 0 | 0 | 0 | 0 | 0 | 0 | 0 | 0 | 0 | 0 | 0 | 0 |
| r141-194_h* | 0 | 0 | 0 | 0 | 0 | 0 | 0 | 1 | 1 | 1 | 1 | 1 | 1 | 1 | 1 | 1 |
| hTF_K68N | 1 | 1 | 1 | 1 | 1 | 1 | 0 | 1 | 1 | 1 | 1 | 1 | 1 | 1 | 1 | 1 |
| hTF_K149N | 1 | 1 | 1 | 1 | 1 | 1 | 1 | 0 | 0 | 0 | 0 | 0 | 0 | 0 | 0 | 0 |
| hTF_N171H_T197K | 1 | 1 | 1 | 1 | 1 | 1 | 1 | 0 | 0 | 0 | 0 | 0 | 1 | 1 | 1 | 1 |

*rat amino acid segment replaced by human segment, resulting in 20 amino acid changes

TABLE 55

Epitope Bin assignment based on unbound chimeric constructs

| Antibody | Constructs not bound by antibody | Epitope Bin |
|---|---|---|
| 1F | rTF, h1-107_r, h1-77_r, h39-77_r, h78-107_r, h78-107_r.v2. h94-107_r | 1 |
| 29E | rTF, h1-107_r, h1-77_r, h39-77_r, h78-107_r, H78-107_r.v2, H78-93_r | 2 |
| 39A | rTF, h1-107_r, h1-77_r, h39-77_r | 3 |
| 54E | rTF, h1-107_r, h1-77_r, h39-77_r | 3 |
| TF-011 | rTF, h1-107_r, h1-77_r, h39-77_r, h78-107_r, h78-107_r.v2, h94-107_r | 1 |
| 5G9 | rTF, h1-107_r, h108-219_r, h159-219_r, h159-189_r, h159-174_r, h 167-174_r, h190-219_r | 4 |
| M1593 | rTF, h1-107_r, h1-77_r, h39-77_r, h94-107_r, h108-219_r, h 108-158_r, h133-158_r | 5 |
| 25A | rTF, h1-107_r, h108-219_r, h108-158_r, h133-158_r, h146-158_r, h146-151_r, h159-219_r, h159-189_r, h159-174_r, h167-174_r | 6 |
| 25A3 | rTF, h1-107_r, h108-219_r, h108-158_r, h133-158_r, h146-158_r, h146-151_r, h159-219 r, h159-189_r, h159-174_r, h167-174_r | 6 |
| 25A5-T | rTF, h1-107_r, h108-219_r, h108-158_r, h133-158_r, h146-158_r, h146-151_r, h159-219_r, h 159-189_r, h159-174_r, h167-174_r | 6 |
| 25G1 | rTF, h1-107_r, h108-219_r, h108-158_r, h133-158_r, h146-158_r, h146-151_r, h159-219_r, h159-189_r, h159-174_r, h167-174_r | 6 |
| 25G9 | rTF, h1-107_r, h108-219_r, h108-158_r, h133-158_r, h146-158_r, h146-151_r, h159-219_r, h159-189_r, h159-174 r, h167-174_r | 6 |
| 43B1 | rTF, h1-107_r, h108-219_r, h108-158_r, h133-158_r, h146-158_r, h146-151_r | 7 |
| 43D7 | rTF, h1-107_r, h108-219_r, h108-158_r, h133-158_r, h146-158_r, h146-151_r | 7 |
| 43D8 | rTF, h1-107_r, h108-219_r, h108-158_r, h133-158_r, h146-158_r, h146-151_r | 7 |
| 43Ea | rTF, h1-107_r, h108-219_r, h108-158_r, h133-158_r, h146-158_r, h146-151_r | 7 |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Sequences

TABLE 13

| | Variable region sequences | |
|---|---|---|
| Clone | VH Domains (SEQ ID NO) | VL Domains (SEQ ID NO) |
| 1F | EVQLLESGGGLVQPGGSLRLSCAASG FTFSDYAMGWVRQAPGKGLEWVSTIS GSGGLTYYADSVKGRFTISRDNSKNT LYLQMNSLRAEDTAVYYCAKAPYGYY MDVWGKGTTVTVSS (SEQ ID NO: 37) | DIQMTQSPSTLSASVGDRVTITCRASQ SISSWLAWYQQKPGKAPKLLIYKASSL ESGVPSRFSGSGSGTEFTLTISSLQPD DFATYYCQQYKSYITFGGGTKVEIK (SEQ ID NO: 38) |
| 1G | EVQLLESGGGLVQPGGSLRLSCAASG FTFSSYAMAWVRQAPGKGLEWVSAIS GSGGLTYYADSVKGRFTISRDNSKNT LYLQMNSLRAEDTAVYYCAKAPYGYY MDVWGKGTTVTVSS (SEQ ID NO: 75) | DIQMTQSPSTLSASVGDRVTITCRASQ SISSWLAWYQQKPGKAPKLLIYKASSL ESGVPSRFSGSGSGTEFTLTISSLQPD DFATYYCQQYKSYITFGGGTKVEIK (SEQ ID NO: 76) |
| 25A | QVQLVQSGAEVKKPGASVKVSCKASG YTFDVYGISWVRQAPGQGLEWMGWIA PYNGNTNYAQKLQGRVTMTTDTSTST AYMELRSLRSDDTAVYYCARDAGTYS PFGYGMDVWGQGTTVTVSS (SEQ ID NO: 113) | DIQMTQSPSTLSASVGDRVTITCRASQ SISSWLAWYQQKPGKAPKLLIYKASSL ESGVPSRFSGSGSGTEFTLTISSLQPD DFATYYCQQFQSLPPFTFGGGTKVEIK (SEQ ID NO: 114) |
| 25A3 | QVQLVQSGAEVKKPGASVKVSCKASG YTFDVYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 151) | DIQMTQSPSTLSASVGDRVTITCQASQ SINNWLAWYQQKPGKAPKLLIYKAYNL ESGVPSRFSGSGSGTEFTLTISSLQPD DFATYYCQLFQSLPPFTFGGGTKVEIK (SEQ ID NO: 152) |
| 25A5 | QVQLVQSGAEVKKPGASVKVSCKASG YTFDVYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 189) | DIQMTQSPSTLSASVGDRVTITCRASE SISNWLAWYQQKPGKAPKLLIYKAYSL EYGVPSRFSGSGSGTEFTLTISSLQPD DFATYYCQQFQKLPPFTFGGGTKVEIK (SEQ ID NO: 190) |
| 25A5-T | QVQLVQSGAEVKKPGASVKVSCKASG YTFDAYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 836) | DIQMTQSPSTLSASVGDRVTITCRASE SISNWLAWYQQKPGKAPKLLIYKAYSL EYGVPSRFSGSGSGTEFTLTISSLQPD DFATYYCQQFQKLPPFTFGGGTKVEIK (SEQ ID NO: 837) |
| 25G | QVQLVQSGAEVKKPGASVKVSCKASG YTFRSYGISWVRQAPGQGLEWMGWVA PYNGNTNYAQKLQGRVTMTTDTSTST AYMELRSLRSDDTAVYYCARDAGTYS PYGYGMDVWGQGTTVTVSS (SEQ ID NO: 227) | DIQMTQSPSTLSASVGDRVTITCRASQ SISSWLAWYQQKPGKAPKLLIYKASSL ESGVPSRFSGSGSGTEFTLTISSLQPD DFATYYCQQFQSLPPFTFGGGTKVEIK (SEQ ID NO: 228) |
| 25G1 | QVQLVQSGAEVKKPGASVKVSCKASG YTFRSYGISWVRQAPGQGLEWMGWVA PYSGNTNYAQKLQGRVTMTTDTSTST AYMELRSLRSDDTAVYYCARDAGTYS PYGYGMDVWGQGTTVTVSS (SEQ ID NO: 265) | DIQMTQSPSTLSASVGDRVTITCRASH SIDSWLAWYQQKPGKAPKLLIYKASYL ESGVPSRFSGSGSGTEFTLTISSLQPD DFATYYCQLFQSLPPFTFGGGTKVEIK (SEQ ID NO: 266) |
| 25G9 | QVQLVQSGAEVKKPGASVKVSCKASG YTFRSYGISWVRQAPGQGLEWMGWVA PYSGNTNYAQKLQGRVTMTTDTSTST AYMELRSLRSDDTAVYYCARDAGTYS PYGYGMDVWGQGTTVTVSS (SEQ ID NO: 303) | DIQMTQSPSTLSASVGDRVTITCQASQ SIDSWLAWYQQKPGKAPKLLIYSASYL ESGVPSRFSGSGSGTEFTLTISSLQPD DFATYYCQRFQSLPPFTFGGGTKVEIK (SEQ ID NO: 304) |

TABLE 13-continued

Variable region sequences

| Clone | VH Domains (SEQ ID NO) | VL Domains (SEQ ID NO) |
|---|---|---|
| 29D | QVQLVESGGGVVQPGRSLRLSCAASG FTFHSRGMHWVRQAPGKGLEWVAVIT YDGINKYYADSVEGRFTISRDNSKNT LYLQMNSLRAEDTAVYYCARDGVYYG VYDYWGQGTLVTVSS (SEQ ID NO: 341) | DIVMTQSPDSLAVSLGERATINCKSSQ SVLFSSNNKNYLAWYQQKPGQPPKLLI YWASTRESGVPDRFSGSGSGTDFTLTI SSLQAEDVAVYYCQQFHSYPLTFGGGT KVEIK (SEQ ID NO: 342) |
| 29E | QVQLVESGGGVVQPGRSLRLSCAASG FTFRSYGMHWVRQAPGKGLEWVAVIT YDGINKYYADSVEGRFTISRDNSKNT LYLQMNSLRAEDTAVYYCARDGVYYG VYDYWGQGTLVTVSS (SEQ ID NO: 379) | DIVMTQSPDSLAVSLGERATINCKSSQ SVLFSSNNKNYLAWYQQKPGQPPKLLI YWASTRESGVPDRFSGSGSGTDFTLTI SSLQAEDVAVYYCQQFHSYPLTFGGGT KVEIK (SEQ ID NO: 380) |
| 39A | QVQLVQSGAEVKKPGSSVKVSCKASG GTFSSNAIGWVRQAPGQGLEWMGSII PIIGFANYAQKFQGRVTITADESTST AYMELSSLRSEDTAVYYCARDSGYYY GASSFGMDVWGQGTTVTVSS (SEQ ID NO: 417) | EIVMTQSPATLSVSPGERATLSCRASQ SVSSNLAWYQQKPGQAPRLLIYGASTR ATGIPARFSGSGSGTEFTLTISSLQSE DFAVYYCEQYNNLPLTFGGGTKVEIK (SEQ ID NO: 418) |
| 43B | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS (SEQ ID NO: 455) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 456) |
| 43B1 | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS (SEQ ID NO: 493) | EIVLTQSPGTLSLSPGERATLSCRASE SVDSSYLAWYQQKPGQAPRLLIYGAST RQTGIPDRFSGSGSGTDFTLTISRLEP EDFAVYYCQQAGVVPYTFGGGTKVEIK (SEQ ID NO: 494) |
| 43B7 | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS (SEQ ID NO: 531) | EIVLTQSPGTLSLSPGERATLSCRASE SVDSSYLAWYQQKPGQAPRLLIYGADS RATGIPDRFSGSGSGTDFTLTISRLEP EDFAVYYCQQDGVVPYTFGGGTKVEIK (SEQ ID NO: 532) |
| 43D | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS (SEQ ID NO: 569) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 570) |
| 43D7 | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS (SEQ ID NO: 607) | EIVLTQSPGTLSLSPGERATLSCRASD SVDSSYLAWYQQKPGQAPRLLIYGAFS RANGIPDRFSGSGSGTDFTLTISRLEP EDFAVYYCQQAGVVPYTFGGGTKVEIK (SEQ ID NO: 608) |
| 43D8 | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS (SEQ ID NO: 645) | EIVLTQSPGTLSLSPGERATLSCRASQ SVSSSFLAWYQQKPGQAPRLLIYGAYS RATGIPDRFSGSGSGTDFTLTISRLEP EDFAVYYCQQAGVVPYTFGGGTKVEIK (SEQ ID NO: 646) |
| 43E | QVQLQESGPGLVKPSQTLSLTCTVSG GSISSGQYWSWIRQHPGKGLEWIGEI YYSGSTRYNPSLKSRVTISVDTSKDQ FSLKLSSVTAADTAVYYCARDTPYYY DGGYYYYMDVWGKGTTVTVSS (SEQ ID NO: 683) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 684) |
| 43Ea | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDTPYYY DGGYYYYMDVWGKGTTVTVSS (SEQ ID NO: 721) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 722) |

TABLE 13-continued

Variable region sequences

| Clone | VH Domains (SEQ ID NO) | VL Domains (SEQ ID NO) |
|---|---|---|
| 54E | QVQLVQSGAEVKKPGASVKVSCKASG YTFANYYMHWVRQAPGQGLEWMGIIN PSGGITVYAQKFQGRVTMTRDTSTST VYMELSSLRSEDTAVYYCARGGSKVA ALAFDIWGQGTMVTVSS (SEQ ID NO: 759) | DIQMTQSPSSLSASVGDRVTITCQASQ DISNSLNWYQQKPGKAPKLLIYDASNL ETGVPSRFSGSRSGTDFTFTISSLQPE DIATYYCQQYNFHPLTFGGGTKVEIK (SEQ ID NO: 760) |

TABLE 14

Variable region sequence consensus

| Group | VH Domain Consensus (SEQ ID NO) | VL Domain Consensus (SEQ ID NO) |
|---|---|---|
| 1 | EVQLLESGGGLVQPGGSLR LSCAASGFTFSx[D/S]YA Mx[A/G]WVRQAPGKGLEW VSx[A/T]ISGSGGLTYYA DSVKGRFTISRDNSKNTLY LQMNSLRAEDTAVYYCAKA PYGYYMDVWGKGTTVTVSS (SEQ ID NO: 761) | DIQMTQSPSTLSASVGDRV TITCRASQSISSWLAWYQQ KPGKAPKLLIYKASSLESG VPSRFSGSGSGTEFTLTIS SLQPDDFATYYCQQYKSYI TFGGGTKVEIK (SEQ ID NO: 762) |
| 25 | QVQLVQSGAEVKKPGASVK VSCKASGYTFx[D/R]x[ S/V/A]YGISWVRQAPGQG LEWMGWx[I/V]APYx[S/ N]GNTNYAQKLQGRVTMTT DTSTSTAYMELRSLRSDDT AVYYCARDAGTYSPx[F/ Y]GYGMDVWGQGTTVTVSS (SEQ ID NO: 763) | DIQMTQSPSTLSASVGDRV TITCx[R/Q]ASx[Q/E/ H]SIx[S/D/N]x[S/N]W LAWYQQKPGKAPKLLIYx[ K/S]Ax[S/Y]x[S/Y/N] LEx[S/Y]GVPSRFSGSGS GTEFTLTISSLQPDDFATY YCQx[Q/L/R]FQx[S/K] LPPFTFGGGTKVEIK |
| 29 | QVQLVESGGGVVQPGRSLR LSCAASGFTFx[H/R]Sx[ R/Y]GMHWVRQAPGKGLEW VAVITYDGINKYYADSVEG RFTISRDNSKNTLYLQMNS LRAEDTAVYYCARDGVYYG VYDYWGQGTLVTVSS (SEQ ID NO: 765) | DIVMTQSPDSLAVSLGERA TINCKSSQSVLFSSNNKNY LAWYQQKPGQPPKLLIYWA STRESGVPDRFSGSGSGTD FTLTISSLQAEDVAVYYCQ QFHSYPLTFGGGTKVEIK (SEQ ID NO: 766) |
| 39 | QVQLVQSGAEVKKPGSSVK VSCKASGGTFSSNAIGWVR QAPGQGLEWMGSIIPIIGF ANYAQKFQGRVTITADEST STAYMELSSLRSEDTAVYY CARDSGYYYGASSFGMDVW GQGTTVTVSS (SEQ ID NO: 767) | EIVMTQSPATLSVSPGERA TLSCRASQSVSSNLAWYQQ KPGQAPRLLIYGASTRATG IPARFSGSGSGTEFTLTIS SLQSEDFAVYYCEQYNNLP LTFGGGTKVEIK (SEQ ID NO: 768) |
| 43 | QVQLQx[E/Q]x[S/W]Gx [P/A]GLx[V/L]KPSx[ Q/E]TLSLTCx[T/A]Vx[ S/Y]GGSx[I/L]SSGx[ Q/Y]YWSWIRQx[H/P]PG KGLEWIGEIx[Y/G]x[Y/ A]SGSTRYNPSLKSRVTIS VDTSKx[N/D]QFSLKLSS VTAADTAVYYCARDx[T/ A]PYYYx[E/G/D]GGYYY YMDVWGKGTTVTVSS (SEQ ID NO: 769) | EIVLTQSPGTLSLSPGERA TLSCRASx[Q/E/D]SVx[ S/D]SSx[Y/F]LAWYQQK PGQAPRLLIYGAx[S/D/ F/Y]x[S/T]Rx[A/Q]x[ T/N]GIPDRFSGSGSGTDF TLTISRLEPEDFAVYYCQQ x[V/A/D]GVVPYTFGGGT KVEIK (SEQ ID NO: 770) |
| 54 | QVQLVQSGAEVKKPGASVK VSCKASGYTFANYYMHWVR QAPGQGLEWMGHNPSGGIT VYAQKFQGRVTMTRDTSTS TVYMELSSLRSEDTAVYYC ARGGSKVAALAFDIWGQGT MVTVSS (SEQ ID NO: 771) | DIQMTQSPSSLSASVGDRV TITCQASQDISNSLNWYQQ KPGKAPKLLIYDASNLETG VPSRFSGSRSGTDFTFTIS SLQPEDIATYYCQQYNFHP LTFGGGTKVEIK (SEQ ID NO: 772) |

TABLE 15

Antibody 1F-CDR Sequences

| | | Exemplary* | Kabat | Chothia | AbM | Contact | IMGT |
|---|---|---|---|---|---|---|---|
| VH CDR Seq. | VH CDR1 | GFTFSDYAMG (SEQ ID NO: 1) | DYAMG (SEQ ID NO: 7) | GFTFSDY (SEQ ID NO: 13) | GFTFSDYAMG (SEQ ID NO: 19) | SDYAMG (SEQ ID NO: 25) | GFTFSDYA (SEQ ID NO: 31) |
| | VH CDR2 | TISGSGGLTY YADSVKG (SEQ ID NO: 2) | TISGSGGLTYY ADSVKG (SEQ ID NO: 8) | GSGG (SEQ ID NO: 14) | TISGSGGLTY (SEQ ID NO: 20) | WVSTISG SGGLTY (SEQ ID NO: 26) | ISGSGGLT (SEQ ID NO: 32) |
| | VH CDR3 | APYGYYMDV (SEQ ID NO: 3) | APYGYYMDV (SEQ ID NO: 9) | PYGYYMD (SEQ ID NO: 15) | APYGYYMDV (SEQ ID NO: 21) | AKAPYGY YMD (SEQ ID NO: 27) | AKAPYGY YMDV (SEQ ID NO: 33) |
| VL CDR Seq. | VL CDR1 | RASQSISSWLA (SEQ ID NO: 4) | RASQSISSWLA (SEQ ID NO: 10) | SQSISSW A (SEQ ID NO: 16) | RASQSISSWL (SEQ ID NO: 22) | SSWLAWY (SEQ ID NO: 28) | QSISSW (SEQ ID NO: 34) |

TABLE 15-continued

Antibody 1F-CDR Sequences

|  | Exemplary* | Kabat | Chothia | AbM | Contact | IMGT |
|---|---|---|---|---|---|---|
| VL CDR2 | KASSLES (SEQ ID NO: 5) | KASSLES (SEQ ID NO: 11) | KAS (SEQ ID NO: 17) | KASSLES (SEQ ID NO: 23) | LLIYKAS SLE (SEQ ID NO: 29) | KAS (SEQ ID NO: 35) |
| VL CDR3 | QQYKSYIT (SEQ ID NO: 6) | QQYKSYIT) (SEQ ID NO: 12) | YKSYI (SEQ ID NO: 18) | QQYKSYIT (SEQ ID NO: 24) | QQYKSYI (SEQ ID NO: 30) | QQYKSYIT (SEQ ID NO: 36) |

VH Sequence*:
EVQLLESGGGLVQPGGSLRLSCAASGFTFSDYAMGWVRQAPGKGLEWVSTISGSGGLTYYADSVKGR
FTISRDNSKNTLYLQMNSLRAEDTAVYYCAKAPYGYYMDVWGKGTTVTVSS (SEQ ID NO: 37)

VL Sequence*:
DIQMTQSPSTLSASVGDRVTITCRASQSISSWLAWYQQKPGKAPKWYKASSLESGVPSRFSGSGSGT
EFTLTISSLQPDDFATYYCQQYKSYITFGGGTKVEIK (SEQ ID NO: 38)

*Exemplary CDR sequences encompass amino acids as determined by Kabat plus Chothia

TABLE 16

Antibody 1G-CDR Sequences

|  |  | Exemplary* | Kabat | Chothia | AbM | Contact | IMGT |
|---|---|---|---|---|---|---|---|
| VH CDR Seq. | VH CDR1 | GFTFSSYAMA (SEQ ID NO: 39) | SYAMA (SEQ ID NO: 45) | GFTFSSY (SEQ ID NO: 51) | GFTFSSYAMA (SEQ ID NO: 57) | SSYAMA (SEQ ID NO: 63) | GFTFSSYA (SEQ ID NO: 69) |
|  | VH CDR2 | AISGSGGLTY YADSVKG (SEQ ID NO: 40) | AISGSGGLTY YADSVKG (SEQ ID NO: 46) | GSGG (SEQ ID NO: 52) | AISGSGGLTY (SEQ ID NO: 58) | WVSAISGSGGL TY (SEQ ID NO: 64) | ISGSGGLT (SEQ ID NO: 70) |
|  | VH CDR3 | APYGYYMDV (SEQ ID NO: 41) | APYGYYMDV (SEQ ID NO: 47) | PYGYYMD (SEQ ID NO: 53) | APYGYYMDV (SEQ ID NO: 59) | AKAPYGYYMD (SEQ ID NO: 65) | AKAPYGYY MDV (SEQ ID NO: 71) |
| VL CDR Seq. | VL CDR1 | RASQSISSWL A (SEQ ID NO: 42) | RASQSISSWL A (SEQ ID NO: 48) | SQSISSW (SEQ ID NO: 54) | RASQSISSWL A (SEQ ID NO: 60) | SSWLAWY (SEQ ID NO: 66) | QSISSW (SEQ ID NO: 72) |
|  | VL CDR2 | KASSLES (SEQ ID NO: 43) | KASSLES (SEQ ID NO: 49) | KAS (SEQ ID NO: 55) | KASSLES (SEQ ID NO: 61) | LLIYKASSLE (SEQ ID NO: 67) | KAS (SEQ ID NO: 73) |
|  | VL CDR3 | QQYKSYIT (SEQ ID NO: 44) | QQYKSYIT (SEQ ID NO: 50) | YKSYI (SEQ ID NO: 56) | QQYKSYIT (SEQ ID NO: 62) | QQYKSYI (SEQ ID NO: 68) | QQYKSYIT (SEQ ID NO: 74) |

VH Sequence*:
EVQLLESGGGLVQPGGSLRLSCAASGFTFSSYAMAWVRQAPGKGLEWVSAISGSGGLTYYADSVKGRF
TISRDNSKNTLYLQMNSLRAEDTAVYYCAKAPYGYYMDVWGKGTTVTVSS (SEQ ID NO: 75)

VL Sequence*:
DIQMTQSPSTLSASVGDRVTITCRASQSISSWLAWYQQKPGKAPKLLIYKASSLESGVPSRFSGSGSG
TEFTLTISSLQPDDFATYYCQQYKSYITFGGGTKVEIK (SEQ ID NO: 76)

*Exemplary CDR sequences encompass amino acids as determined by Kabat plus Chothia

TABLE 17

Antibody 25A-CDR Sequences

|  |  | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 77) | VYGIS (SEQ ID NO: 83) | GYTFDVY (SEQ ID NO: 89) | GYTFDVYGIS (SEQ ID NO: 95) | DVYGIS (SEQ ID NO: 101) | GYTFDVYG (SEQ ID NO: 107) |

TABLE 17-continued

Antibody 25A-CDR Sequences

|  |  | Exemplary* | Kabat | Chothia | AbM | Contact | IMGT |
|---|---|---|---|---|---|---|---|
|  | VH CDR2 | WIAPYNGNTNYAQKLQG (SEQ ID NO: 78) | WIAPYNGNTNYAQKLQG (SEQ ID NO: 84) | PYNG (SEQ ID NO: 90) | WIAPYNGNTN (SEQ ID NO: 96) | WMGWIAPYNGNTN (SEQ ID NO: 102) | IAPYNGNT (SEQ ID NO: 108) |
|  | VH CDR3 | DAGTYSPFGYGMDV (SEQ ID NO: 79) | DAGTYSPFGYGMDV (SEQ ID NO: 85) | AGTYSPFGYGMD (SEQ ID NO: 91) | DAGTYSPFGYGMDV (SEQ ID NO: 97) | ARDAGTYSPFGYGMD (SEQ ID NO: 103) | ARDAGTYSPFGTGMDV (SEQ ID NO: 109) |
| VL CDR Seq. | VL CDR1 | RASQSISSWLA (SEQ ID NO: 80) | RASQSISSWLA (SEQ ID NO: 86) | SQSISSW (SEQ ID NO: 92) | RASQSISSWLA (SEQ ID NO: 98) | SSWLAWY (SEQ ID NO: 104) | QSISSW (SEQ ID NO: 110) |
|  | VL CDR2 | KASSLES (SEQ ID NO: 81) | KASSLES (SEQ ID NO: 87) | KAS (SEQ ID NO: 93) | KASSLES (SEQ ID NO: 99) | LLIYKASSLE (SEQ ID NO: 105) | KAS (SEQ ID NO: 111) |
|  | VL CDR3 | QQFQSLPPFT (SEQ ID NO: 82) | QQFQSLPPFT (SEQ ID NO: 88) | FQSLPPF (SEQ ID NO: 94) | QQFQSLPPFT (SEQ ID NO: 100) | QQFQSLPPF (SEQ ID NO: 106) | QQFQSLPPFT (SEQ ID NO: 112) |

VH Sequence*:
QVQLVQSGAEVKKPGASVKVSCKASGYTFDVYGISWVRQAPGQGLEWMGWIAPYNGNTNYAQKLQGRVTMT
TDTSTSTAYMELRSLRSDDTAVYYCARDAGTYSPFGYGMDVWGQGTTVTVSS (SEQ ID NO: 113)

VL Sequence*:
DIQMTQSPSTLSASVGDRVTITCRASQSISSWLAWYQQKPGKAPKWYKASSLESGVPSRFSGSGSGTEFTL
TISSLQPDDFATYYCQQFQSLPPFTFGGGTKVEIK (SEQ ID NO: 114)

*Exemplary CDR sequences encompass amino acids as determined by Kabat plus Chothia

TABLE 18

Antibody 25A3-CDR Sequences

|  |  | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 115) | VYGIS (SEQ ID NO: 121) | GYTFDVY (SEQ ID NO: 127) | GYTFDVYGIS (SEQ ID NO: 133) | DVYGIS (SEQ ID NO: 139) | GYTFDVYG (SEQ ID NO: 145) |
|  | VH CDR2 | WIAPYSGNTNYAQKLQG (SEQ ID NO: 116) | WIAPYSGNTNYAQKLQG (SEQ ID NO: 122) | PYSG (SEQ ID NO: 128) | WIAPYSGNTN (SEQ ID NO: 134) | WMGWIAPYSGNTN (SEQ ID NO: 140) | IAPYSGNT (SEQ ID NO: 146) |
|  | VH CDR3 | DAGTYSPFGYGMDV (SEQ ID NO: 117) | DAGTYSPFGYGMDV (SEQ ID NO: 123) | AGTYSPFGYGMD (SEQ ID NO: 129) | DAGTYSPFGYGMDV (SEQ ID NO: 135) | ARDAGTYSPFGYGMD (SEQ ID NO: 141) | ARDACTYSPFGTGMDV (SEQ ID NO: 147) |
| VL CDR Seq. | VL CDR1 | QASQSINNNWLA (SEQ ID NO: 118) | QASQSINNWLA (SEQ ID NO: 124) | SQSINNW (SEQ ID NO: 130) | QASQSINNWLA (SEQ ID NO: 136) | NNWLAWY (SEQ ID NO: 142) | QSINNW (SEQ ID NO: 148) |
|  | VL CDR2 | KAYNLES (SEQ ID NO: 119) | KAYNLES (SEQ ID NO: 125) | KAY (SEQ ID NO: 131) | KAYNLES (SEQ ID NO: 137) | LLIYKAYNLE (SEQ ID NO: 143) | KAY (SEQ ID NO: 149) |
|  | VL CDR3 | QLFQSLPPFT (SEQ ID NO: 120) | QLFQSLPPFT (SEQ ID NO: 126) | FQSLPPF (SEQ ID NO: 132) | QLFQSLPPFT (SEQ ID NO: 138) | QLFQSLPPF (SEQ ID NO: 144) | QLFQSLPPFT (SEQ ID NO: 150) |

VH Sequence*:
QVQLVQSGAEVKKPGASVKVSCKASGYTFDVYGISWVRQAPGQGLEWMGWIAPYSGNTNYAQKLQGRVTM
TTDTSTSTAYMELRSLRSDDTAVYYCARDAGTYSPFGYGMDVWGQGTTVTVSS (SEQ ID NO: 151)

VL Sequence*:
DIQMTQSPSTLSASVGDRVTITCQASQSINNWLAWYQQKPGKAPKLLIYKAYNLESGVPSRFSGSGSGTE
FTLTISSLQPDDFATYYCQLFQSLPPFTFGGGTKVEIK (SEQ ID NO: 152)

*Exemplary CDR sequences encompass amino acids as determined by Kabat plus Chothia TABLE 19a Antibody 25A5-CDR Sequences

| | | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 153) | VYGIS (SEQ ID NO: 159) | GYTFDVY (SEQ ID NO: 165) | GYTFDVYGIS (SEQ ID NO: 171) | DVYGIS (SEQ ID NO: 177) | GYTFDVYG (SEQ ID NO: 183) |
| | VH CDR2 | WIAPYSGNTNYAQKLQG (SEQ ID NO: 154) | WIAPYSGNTNYAQKLQG (SEQ ID NO: 160) | PYSG (SEQ ID NO: 166) | WIAPYSGNTN (SEQ ID NO: 172) | WMGWIAPYSGNTN (SEQ ID NO: 178) | IAPYSGNT (SEQ ID NO: 184) |
| | VH CDR3 | DAGTYSPFGYGMDV (SEQ ID NO: 155) | DAGTYSPFGYGMDV (SEQ ID NO: 161) | AGTYSPFGYGMD (SEQ ID NO: 167) | DAGTYSPFGYGMDV (SEQ ID NO: 173) | ARDAGTYSPFGYGMD (SEQ ID NO: 179) | ARDACTYSPFGTGMDV (SEQ ID NO: 185) |
| VL CDR Seq. | VL CDR1 | RASESISNWLA (SEQ ID NO: 156) | RASESISNWLA (SEQ ID NO: 162) | SESISNW (SEQ ID NO: 168) | RASESISNWLA (SEQ ID NO: 174) | SNWLAWY (SEQ ID NO: 180) | ESISNW (SEQ ID NO: 186) |
| | VL CDR2 | KAYSLEY (SEQ ID NO: 157) | KAYSLEY (SEQ ID NO: 163) | KAY (SEQ ID NO: 169) | KAYSLEY (SEQ ID NO: 175) | LLIYKAYSLE (SEQ ID NO: 181) | KAY (SEQ ID NO: 187) |
| | VL CDR3 | QQFQKLPPFT (SEQ ID NO: 158) | QQFQKLPPFT (SEQ ID NO: 164) | FQKLPPF (SEQ ID NO: 170) | QQFQKLPPFT (SEQ ID NO: 176) | QQFQKLPPF (SEQ ID NO: 182) | QQFQKLPPFT (SEQ ID NO: 188) |

VH Sequence*:
QVQLVQSGAEVKKPGASVKVSCKASGYTFDVYGISWVRQAPGQGLEWMGWIAPYSGNTNYAQKLQGRVTMTTDTSTSTAYMELRSLRSDDTAVYYCARDAGTYSPFGYGMDVWGQGTTVTVSS (SEQ ID NO: 189)

VL Sequence*:
DIQMTQSPSTLSASVGDRVTITCRASESISNWLAWYQQKPGKAPKWYKAYSLEYGVPSRFSGSGSGTEFTLTISSLQPDDFATYYCQQFQKLPPFTFGGGTKVEIK (SEQ ID NO: 190)

*Exemplary CDR sequences encompass amino acids as determined by Kabat plus Chothia TABLE 19b Antibody 25A5-T-CDR Sequences

| | | Exemplary* | Kabat | Chothia | AbM | Contact | IMGT |
|---|---|---|---|---|---|---|---|
| VH CDR Seq. | VH CDR1 | GYTFDAYGIS (SEQ ID NO: 884) | AYGIS (SEQ ID NO: 890) | GYTFDAY (SEQ ID NO: 896) | GYTFDAYGIS (SEQ ID NO: 902) | DAYGIS (SEQ ID NO: 908) | GYTFDAYG (SEQ ID NO: 914) |
| | VH CDR2 | WIAPYSGNTNYAQKLQG (SEQ ID NO: 885) | WIAPYSGNTNYAQKLQG (SEQ ID NO: 891) | PYSG (SEQ ID NO: 897) | WIAPYSGNTN (SEQ ID NO: 903) | WMGWIAPYSGNTN (SEQ ID NO: 909) | IAPYSGNT (SEQ ID NO: 915) |
| | VH CDR3 | DAGTYSPFGYGMDV (SEQ ID NO: 886) | DAGTYSPFGYGMDV (SEQ ID NO: 892) | AGTYSPFGYGMD (SEQ ID NO: 898) | DAGTYSPFGYGMDV (SEQ ID NO: 904) | ARDAGTYSPFGYGMD (SEQ ID NO: 910) | ARDACTYSPFGTGMDV (SEQ ID NO: 916) |
| VL CDR Seq. | VL CDR1 | RASESISNWLA (SEQ ID NO: 887) | RASESISNWLA (SEQ ID NO: 893) | SESISNW (SEQ ID NO: 899) | RASESISNWLA (SEQ ID NO: 905) | SNWLAWT (SEQ ID NO: 911) | ESISNW (SEQ ID NO: 917) |
| | VL CDR2 | KAYSLEY (SEQ ID NO: 888) | KAYSLEY (SEQ ID NO: 894) | KAY (SEQ ID NO: 900) | KAYSLEY (SEQ ID NO: 906) | LLIYKAYSLE (SEQ ID NO: 912) | KAY (SEQ ID NO: 918) |
| | VL CDR3 | QQFQKLPPFT (SEQ ID NO: 889) | QQFQKLPPFT (SEQ ID NO: 895) | FQKLPPF (SEQ ID NO: 901) | QQFQKLPPFT (SEQ ID NO: 907) | QQFQKLPPF (SEQ ID NO: 913) | QQFQKLPPFT (SEQ ID NO: 919) |

VH Sequence*:
QVQLVQSGAEVKKPGASVKVSCKASGYTFDAYGISWVRQAPGQGLEWMGWIAPYSGNTNYAQKLQGRVTMTTDTSTSTAYMELRSLRSDDTAVYYCARDAGTYSPFGYGMDVWGQGTTVTVSS (SEQ ID NO: 836)

TABLE 19b-continued

Antibody 25A5-T-CDR Sequences

| | Exemplary* | Kabat | Chothia | AbM | Contact | IMGT |
|---|---|---|---|---|---|---|

VL Sequence*:
DIQMTQSPSTLSASVGDRVTITCRASESISNWLAWYQQKPGKAPKWYKAYSLEYGVPSRFSGSGSGTEFT
LTISSLQPDDFATYYCQQFQKLPPFTFGGGTKVEIK (SEQ ID NO: 837)

*Exemplary CDR sequences encompass amino acids as determined by Kabat plus Chothia

TABLE 20

Antibody 25G-CDR Sequences

| | | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 191) | SYGIS (SEQ ID NO: 197) | GYTFRSY (SEQ ID NO: 203) | GYTFRSYGIS (SEQ ID NO: 209) | RSYGIS (SEQ ID NO: 215) | GYTFRSYG (SEQ ID NO: 221) |
| | VH CDR2 | WVAPYNGNTNYAQKLQG (SEQ ID NO: 192) | WVAPYNGNTNYAQKLQG (SEQ ID NO: 198) | PYNG (SEQ ID NO: 204) | WVAPYNGNTN (SEQ ID NO: 210) | WMGWVAPYNGNTN (SEQ ID NO: 216) | VAPYNGNT (SEQ ID NO: 222) |
| | VH CDR3 | DAGTYSPYGYGMDV (SEQ ID NO: 193) | DAGTYSPYGYGMDV (SEQ ID NO: 199) | AGTYSPYGYGMD (SEQ ID NO: 205) | DAGTYSPYGYGMDV (SEQ ID NO: 211) | ARDAGTYSPYGYGMD (SEQ ID NO: 217) | ARDAGTYSPYGYGMDV (SEQ ID NO: 223) |
| VL CDR Seq. | VL CDR1 | RASQSISSWLA (SEQ ID NO: 194) | RASQSISSWLA (SEQ ID NO: 200) | SQSISSW (SEQ ID NO: 206) | RASQSISSWLA (SEQ ID NO: 212) | SSWLAWY (SEQ ID NO: 218) | QSISSW (SEQ ID NO: 224) |
| | VL CDR2 | KASSLES (SEQ ID NO: 195) | KASSLES (SEQ ID NO: 201) | KAS (SEQ ID NO: 207) | KASSLES (SEQ ID NO: 213) | LLIYKASSLE (SEQ ID NO: 219) | KAS (SEQ ID NO: 225) |
| | VL CDR3 | QQFQSLPPFT (SEQ ID NO: 196) | QQFQSLPPFT (SEQ ID NO: 202) | FQSLPPF (SEQ ID NO: 208) | QQFQSLPPFT (SEQ ID NO: 214) | QQFQSLPPF (SEQ ID NO: 220) | QQFQSLPPFT (SEQ ID NO: 226) |

VH Sequence*:
QVQLVQSGAEVKKPGASVKVSCKASGYTFRSYGISWVRQAPGQGLEWMGWVAPYNGNTNYAQKLQGRVTM
TTDTSTSTAYMELRSLRSDDTAVYYCARDAGTYSPYGYGMDVWGQGTTVTVSS (SEQ ID NO: 227)

VL Sequence*:
DIQMTQSPSTLSASVGDRVTITCRASQSISSWLAWYQQKPGKAPKWYKASSLESGVPSRFSGSGSGTEFT
LTISSLQPDDFATYYCQQFQSLPPFTFGGGTKVEIK (SEQ ID NO: 228)

*Exemplary CDR sequences encompass amino acids as determined by Kabat plus Chothia

TABLE 21

Antibody 25G1-CDR Sequences

| | | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 229) | SYGIS (SEQ ID NO: 235) | GYTFRSY (SEQ ID NO 241) | GYTFRSYGIS (SEQ ID NO: 247) | RSYGIS (SEQ ID NO: 253) | GYTFRSYG (SEQ ID NO: 259) |
| | VH CDR2 | WVAPYSGNTNYAQKLQG (SEQ ID NO: 230) | WVAPYSGNTNYAQKLQG (SEQ ID NO: 236) | PYSG (SEQ ID NO: 242) | WVAPYSGNTN (SEQ ID NO: 248) | WMGWVAPYSGNTN (SEQ ID NO: 254) | VAPYSGNT (SEQ ID NO: 260) |

TABLE 21-continued

Antibody 25G1-CDR Sequences

|   |   | Exemplary* | Kabat | Chothia | AbM | Contact | IMGT |
|---|---|---|---|---|---|---|---|
|   | VH CDR3 | DAGTYSPYGYG MDV (SEQ ID NO: 231) | DAGTYSPYGYG MDV (SEQ ID NO: 237) | AGTYSPYGY GMD (SEQ ID NO: 243) | DAGTYSPYGYG MDV (SEQ ID NO: 240) | ARDAGTYS PYGYGMD (SEQ ID NO: 255) | ARDAGTYS PYGYGMDV (SEQ ID NO: 261) |
| VL CDR Seq. | VL CDR1 | RASHSIDSWLA (SEQ ID NO: 232) | RASHSIDSWLA (SEQ ID NO: 238) | SHSIDSW (SEQ ID NO: 244) | RASHSIDSWLA (SEQ ID NO: 250) | DSWLAWY (SEQ ID NO: 256) | HSIDSW (SEQ ID NO: 262) |
|   | VL CDR2 | KASYLES (SEQ ID NO: 233) | KASYLES (SEQ ID NO: 239) | KAS (SEQ ID NO: 245) | KASYLES (SEQ ID NO: 251) | LLIYKASY LE (SEQ ID NO: 257) | KAS (SEQ ID NO: 263) |
|   | VL CDR3 | QLFQSLPPFT (SEQ ID NO: 234) | QLFQSLPPFT (SEQ ID NO: 240) | FQSLPPF (SEQ ID NO: 246) | QLFQSLPPFT (SEQ ID NO: 252) | QLFQSLPP F (SEQ ID NO: 258) | QLFQSLPP FT (SEQ ID NO: 264) |

VH Sequence*:
QVQLVQSGAEVKKPGASVKVSCKASGYTFRSYGISWVRQAPGQGLEWMGWVAPYSGNTNYAQKLQGRVTM
TTDTSTSTAYMELRSLRSDDTAVYYCARDAGTYSPYGYGMDVWGQGTTVTVSS (SEQ ID NO: 265)

VL Sequence*:
DIQMTQSPSTLSASVGDRVTITCRASHSIDSWLAWYQQKPGKAPKWYKASYLESGVPSRFSGSGSGTEFT
LTISSLQPDDFATYYCQLFQSLPPFTFGGGTKVEIK (SEQ ID NO: 266)

*Exemplary CDR sequences encompass amino acids as determined by Kabat plus Chothia

TABLE 22

Antibody 25G9-CDR Sequences

|   |   | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 267) | SYGIS (SEQ ID NO: 273) | GYTFRSY (SEQ ID NO: 279) | GYTFRSYGIS (SEQ ID NO: 285) | RSYGIS (SEQ ID NO: 291) | GYTFRSYG (SEQ ID NO: 297) |
|   | VH CDR2 | WVAPYSGNTNY AQKLQG (SEQ ID NO: 268) | WVAPYSGNTNY AQKLQG (SEQ ID NO: 274) | PYSG (SEQ ID NO: 280) | WVAPYSGNTN (SEQ ID NO: 286) | WMGWVAPYSGN TN (SEQ ID NO: 292) | VAPYSGNT (SEQ ID NO: 298) |
|   | VH CDR3 | DAGTYSPYGYG MDV (SEQ ID NO: 269) | DAGTYSPYGYG MDV (SEQ ID NO: 275) | AGTYSPYG YGMD (SEQ ID NO: 281) | DAGTYSPYGYG MDV (SEQ ID NO: 287) | ARDAGTYSPYG YGMD (SEQ ID NO: 293) | ARDAGTYS PYGYGMDV (SEQ ID NO: 299) |
| VL CDR Seq. | VL CDR1 | QASQSIDSWLA (SEQ ID NO: 270) | QASQSIDSWLA (SEQ ID NO: 276) | SQSIDSW (SEQ ID NO: 282) | QASQSIDSWLA (SEQ ID NO: 288) | DSWLAWY (SEQ ID NO: 294) | QSIDSW (SEQ ID NO: 300) |
|   | VL CDR2 | SASYLES (SEQ ID NO: 271) | SASYLES (SEQ ID NO: 277) | SAS (SEQ ID NO: 283) | SASYLES (SEQ ID NO: 289) | LLIYSASYLE (SEQ ID NO: 295) | SAS (SEQ ID NO: 301) |
|   | VL CDR3 | QRFQSLPPFT (SEQ ID NO: 272) | QRFQSLPPFT (SEQ ID NO: 278) | FQSLPPF (SEQ ID NO: 284) | QRFQSLPPFT (SEQ ID NO: 290) | QRFQSLPPF (SEQ ID NO: 296) | QRFQSLPP FT (SEQ ID NO: 302) |

VH Sequence*:
QVQLVQSGAEVKKPGASVKVSCKASGYTFRSYGISWVRQAPGQGLEWMGWVAPYSGNTNYAQKLQGRVTM
TTDTSTSTAYMELRSLRSDDTAVYYCARDAGTYSPYGYGMDVWGQGTTVTVSS (SEQ ID NO: 303)

VL Sequence*:
DIQMTQSPSTLSASVGDRVTITCQASQSIDSWLAWYQQKPGKAPKWYSASYLESGVPSRFSGSGSGTEFT
LTISSLQPDDFATYYCQRFQSLPPFTFGGGTKVEIK (SEQ ID NO: 304)

*Exemplary CDR sequences encompass amino acids as determined by Kabat plus Chothia

TABLE 23

Antibody 29D-CDR Sequences

|  |  | Exemplary* | Kabat | Chothia | AbM | Contact | IMGT |
|---|---|---|---|---|---|---|---|
| VH CDR Seq. | VH CDR1 | GFTFHSRGMH (SEQ ID NO: 305) | SRGMH (SEQ ID NO: 311) | GFTFHSR (SEQ ID NO: 317) | GFTFHSRGMH (SEQ ID NO: 323) | HSRGMH (SEQ ID NO: 329) | GFTFHSRG (SEQ ID NO: 335) |
|  | VH CDR2 | VITYDGINKYYADSVEG (SEQ ID NO: 306) | VITYDGINKYYADSVEG (SEQ ID NO: 312) | YDGI (SEQ ID NO: 318) | VITYDGINKY (SEQ ID NO: 324) | WVAVITYDGINKY (SEQ ID NO: 330) | ITYDGINK (SEQ ID NO: 336) |
|  | VH CDR3 | DGVYYGVYDY (SEQ ID NO: 307) | DGVYYGVYDY (SEQ ID NO: 313) | GVYYGVYD (SEQ ID NO: 319) | DGVYYGVYDY (SEQ ID NO: 325) | ARDGVYYGVYDY (SEQ ID NO: 331) | ARDGVYYGVYDY (SEQ ID NO: 337) |
| VL CDR Seq. | VL CDR1 | KSSQSVLFSSNNKNYLA (SEQ ID NO: 308) | KSSQSVLFSSNNKNYLA (SEQ ID NO: 314) | SQSVLFSSNNKNY (SEQ ID NO: 320) | KSSQSVLFSSNNKNYLA (SEQ ID NO: 326) | LFSSNNKNYLAWY (SEQ ID NO: 332) | QSVLFSSNNKNY (SEQ ID NO: 338) |
|  | VL CDR2 | WASTRES (SEQ ID NO: 309) | WASTRES (SEQ ID NO: 315) | WAS (SEQ ID NO: 321) | WASTRES (SEQ ID NO: 327) | LLIYWASTRES (SEQ ID NO: 333) | WAS (SEQ ID NO: 339) |
|  | VL CDR3 | QQFHSYPLT (SEQ ID NO: 310) | QQFHSYPLT (SEQ ID NO: 316) | FHSYPL (SEQ ID NO: 322) | QQFHSYPLT (SEQ ID NO: 328) | QQFHSYPL (SEQ ID NO: 334) | QQFHSYPLT (SEQ ID NO: 340) |

VH Sequence*:
QVQLVESGGGVVQPGRSLRLSCAASGFTFHSRGMHWVRQAPGKGLEWVAVITYDGINKYYADSVEGRFTIS
RDNSKNTLYLQMNSLRAEDTAVYYCARDGVYYGVYDYWGQGTLVTVSS (SEQ ID NO: 341)

VL Sequence*:
DIVMTQSPDSLAVSLGERATINCKSSQSVLFSSNNKNYLAWYQQKPGQPPKWYWASTRESGVPDRFSGSGS
GTDFTLTISSLQAEDVAVYYCQQFHSYPLTFGGGTKVEIK (SEQ ID NO: 342)

*Exemplary CDR sequences encompass amino acids as determined by Kabat plus Chothia

TABLE 24

Antibody 29E-CDR Sequences

|  |  | Exemplary* | Kabat | Chothia | AbM | Contact | IMGT |
|---|---|---|---|---|---|---|---|
| VH CDR Seq. | VH CDR1 | GFTFRSYGMH (SEQ ID NO: 343) | SYGMH (SEQ ID NO: 349) | GFTFRSY (SEQ ID NO: 355) | GFTFRSYGMH (SEQ ID NO: 361) | RSYGMH (SEQ ID NO: 367) | GFTFRSYG (SEQ ID NO: 373) |
|  | VH CDR2 | VITYDGINKYYADSVEG (SEQ ID NO: 344) | VITYDGINKYYADSVEG (SEQ ID NO: 350) | YDGI (SEQ ID NO: 356) | VITYDGINKY (SEQ ID NO: 362) | WVAVITYDGINKY (SEQ ID NO: 368) | ITYDGINK (SEQ ID NO: 374) |
|  | VH CDR3 | DGVYYGVYDY (SEQ ID NO: 345) | DGVYYGVYDY (SEQ ID NO: 351) | GVYYGVYD (SEQ ID NO: 357) | DGVYYGVYDY (SEQ ID NO: 363) | ARDGVYYGVYDY (SEQ ID NO: 369) | ARDGVYYGVYDY (SEQ ID NO: 375) |
| VL CDR Seq. | VL CDR1 | KSSQSVLFSSNNKNYLA (SEQ ID NO: 346) | KSSQSVLFSSNNKNYLA (SEQ ID NO: 352) | SQSVLFSSNNKNY (SEQ ID NO: 358) | KSSQSVLFSSNNKNYLA (SEQ ID NO: 364) | LFSSNNKNYLAWY (SEQ ID NO: 370) | QSVLFSSNNKNY (SEQ ID NO: 376) |
|  | VL CDR2 | WASTRES (SEQ ID NO: 347) | WASTRES (SEQ ID NO: 353) | WAS (SEQ ID NO: 359) | WASTRES (SEQ ID NO: 365) | LLIYWASTRES (SEQ ID NO: 371) | WAS (SEQ ID NO: 377) |
|  | VL CDR3 | QQFHSYPLT (SEQ ID NO: 348) | QQFHSYPLT (SEQ ID NO: 354) | FHSYPL (SEQ ID NO: 360) | QQFHSYPLT (SEQ ID NO: 366) | QQFHSYPL (SEQ ID NO: 372) | QQFHSYPLT (SEQ ID NO: 378) |

TABLE 24-continued

Antibody 29E-CDR Sequences

| Exemplary* | Kabat | Chothia | AbM | Contact | IMGT |
|---|---|---|---|---|---|

VH Sequence*:
QVQLVESGGGVVQPGRSLRLSCAASGFTFRSYGMHWVRQAPGKGLEWVAVITYDGINKYYADSVEGRF
TISRDNSKNTLYLQMNSLRAEDTAVYYCARDGVYYGVYDYWGQGTLVTVSS (SEQ ID NO: 379)

VL Sequence*:
DIVMTQSPDSLAVSLGERATINCKSSQSVLFSSNNICNYLAWYQQKPGQPPKWYWASTRESGVPDRFS
GSGSGTDFTLTISSLQAEDVAVYYCQQFHSYPLTFGGGTKVEIK (SEQ ID NO: 380)

*Exemplary CDR sequences encompass amino acids as determined by Kabat plus Chothia

TABLE 25

Antibody 39A-CDR Sequences

| | | Exemplary* | Kabat | Chothia | AbM | Contact | IMGT |
|---|---|---|---|---|---|---|---|
| VH CDR Seq. | VH CDR1 | GGTFSSNAIG (SEQ ID NO: 381) | SNAIG (SEQ ID NO: 387) | GGTFSSN (SEQ ID NO: 393) | GGTFSSNAIG (SEQ ID NO: 399) | SSNAIG (SEQ ID NO: 405) | GGTFSSNA (SEQ ID NO: 411) |
| | VH CDR2 | SIIPIIGFANY AQKFQG (SEQ ID NO: 382) | SIIPIIGFANY AQKFQG (SEQ ID NO: 388) | PIIG (SEQ ID NO: 394) | SIIPIIGFAN (SEQ ID NO: 400) | WMGSIIPIIGF AN (SEQ ID NO: 406) | IIPIIGFA (SEQ ID NO: 412) |
| | VH CDR3 | DSGYYYGASSF GMDV (SEQ ID NO: 383) | DSGYYYGASSF GMDV (SEQ ID NO: 389) | SGYYYGAS SFGMD (SEQ ID NO: 395) | DSGYYYGASSF GMDV (SEQ ID NO: 401) | ARDSGYYYGAS SFGMD (SEQ ID NO: 407) | ARDSGYYY GASSFGMD V (SEQ ID NO: 413) |
| VL CDR Seq. | VL CDR1 | RASQSVSSNLA (SEQ ID NO: 384) | RASQSVSSNLA (SEQ ID NO: 390) | SQSVSSN (SEQ ID NO: 396) | RASQSVSSNLA (SEQ ID NO: 402) | SSNLAWY (SEQ ID NO: 408) | QSVSSN (SEQ ID NO: 414) |
| | VL CDR2 | GASTRAT (SEQ ID NO: 385) | GASTRAT (SEQ ID NO: 391) | GAS (SEQ ID NO: 397) | GASTRAT (SEQ ID NO: 403) | LLIYGASTRA (SEQ ID NO: 409) | GAS (SEQ ID NO: 415) |
| | VL CDR3 | EQYNNLPLT (SEQ ID NO: 386) | EQYNNLPLT (SEQ ID NO: 392) | YNNLPL (SEQ ID NO: 398) | EQYNNLPLT (SEQ ID NO: 404) | EQYNNLPL (SEQ ID NO: 410) | EQYNNLPL T (SEQ ID NO: 416) |

VH Sequence*:
QVQLVQSGAEVKKPGSSVKVSCKASGGTFSSNAIGWVRQAPGQGLEWMGSIIPIIGFANYAQKFQGRVTIT
ADESTSTAYMELSSLRSEDTAVYYCARDSGYYYGASSFGMDVWGQGTTVTVSS (SEQ ID NO: 417)

VL Sequence*:
EIVMTQSPATLSVSPGERATLSCRASQSVSSNLAWYQQKPGQAPRLLIYGASTRATGIPARFSGSGSGTEF
TLTISSLQSEDFAVYYCEQYNNLPLTFGGGTKVEIK (SEQ ID NO: 418)

*Exemplary CDR sequences encompass amino acids as determined by Kabat plus Chothia

TABLE 26

Antibody 43B-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 419) | SGQYWS (SEQ ID NO: 425) | GGSISSGQ (SEQ ID NO: 431) | GGSISSGQYWS (SEQ ID NO: 437) | SSGQYWS (SEQ ID NO: 443) | GGSISSGQY (SEQ ID NO: 449) |
| | VH CDR2 | EIYYSGSTRYN PSLKS (SEQ ID NO: 420) | EIYYSGSTRYN PSLKS (SEQ ID NO: 426) | YSG (SEQ ID NO: 432) | EIYYSGSTR (SEQ ID NO: 438) | WIGEIYYSGST R (SEQ ID NO: 444) | IYYSGST (SEQ ID NO: 450) |
| | VH CDR3 | DAPYYYGGGYY YMDV (SEQ | DAPYYYGGGYY YMDV (SEQ | APYYYGGG YYYYMD | DAPYYYGGGYY YMDV (SEQ | ARDAPYYYGGG YYYYMD (SEQ | ARDAPYYYG GGYYYMDV |

TABLE 26-continued

Antibody 43B-CDR Sequences

|  |  | Exemplary* | Kabat | Chothia | AbM | Contact | IMGT |
|---|---|---|---|---|---|---|---|
|  |  | ID NO: 421) | ID NO: 427) | (SEQ ID NO: 433) | ID NO: 439) | ID NO: 445) | (SEQ ID NO: 451) |
| VL CDR Seq. | VL CDR1 | RASQSVSSSYLA (SEQ ID NO: 422) | RASQSVSSSYLA (SEQ ID NO: 428) | SQSVSSSY (SEQ ID NO: 434) | RASQSVSSSYLA (SEQ ID NO: 440) | SSSYLAWY (SEQ ID NO: 446) | QSVSSSY (SEQ ID NO: 452) |
|  | VL CDR2 | GASSRAT (SEQ ID NO: 423) | GASSRAT (SEQ ID NO: 429) | GAS (SEQ ID NO: 435) | GASSRAT (SEQ ID NO: 441) | LLIYGASSRA (SEQ ID NO: 447) | GAS (SEQ ID NO: 453) |
|  | VL CDR3 | QQVGVVPYT (SEQ ID NO: 424) | QQVGVVPYT (SEQ ID NO: 430) | VGVVPY (SEQ ID NO: 436) | QQVGVVPYT (SEQ ID NO: 442) | QQVGVVPY (SEQ ID NO: 448) | QQVGVVPYT (SEQ ID NO: 454) |

VH Sequence*:
QVQLQESGPGLVKPSQTLSLTCTVSGGSISSGQYWSWIRQHPGKGLEWIGEIYYSGSTRYNPSLKSRVTIS
VDTSKNQFSLKLSSVTAADTAVYYCARDAPYYYGGGYYYYMDVWGKGTTVTVSS (SEQ ID NO: 455)

VL Sequence*:
EIVLTQSPGTLSLSPGERATLSCRASQSVSSSYLAWYQQKPGQAPRLLIYGASSRATGIPDRFSGSGSGTD
FTLTISRLEPEDFAVYYCQQVGVVPYTFGGGTKVEIK (SEQ ID NO: 456)

*Exemplary CDR sequences encompass amino acids as determined by Kabat & Chothia

TABLE 27

Antibody 43B1-CDR Sequences

|  |  | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 457) | SGQYWS (SEQ ID NO: 463) | GGSISSGQ (SEQ ID NO: 469) | GGSISSGQYWS (SEQ ID NO: 475) | SSGQYWS (SEQ ID NO: 481) | GGSISSGQY (SEQ ID NO: 487) |
|  | VH CDR2 | EIYYSGSTRYNPSLKS (SEQ ID NO: 458) | EIYYSGSTRYNPSLKS (SEQ ID NO: 464) | YSG (SEQ ID NO: 470) | EIYYSGSTR (SEQ ID NO: 476) | WIGEIYYSGSTR (SEQ ID NO: 482) | IYYSGST (SEQ ID NO: 488) |
|  | VH CDR3 | DAPYYYGGGYYYYMDV (SEQ ID NO: 459) | DAPYYYGGGYYYYMDV (SEQ ID NO: 465) | APYYYGGGYYYYMD (SEQ ID NO: 471) | DAPYYYGGGYYYYMDV (SEQ ID NO: 477) | ARDAPYYYGGGYYYYMDV (SEQ ID NO: 483) | ARDAPYYYGGGYYYYMDV (SEQ ID NO: 489) |
| VL CDR Seq. | VL CDR1 | RASESVDSSYLA (SEQ ID NO: 460) | RASESVDSSYLA (SEQ ID NO: 466) | SESVDSSY (SEQ ID NO: 472) | RASESVDSSYLA (SEQ ID NO: 478) | DSSYLAWY (SEQ ID NO: 484) | ESVDSSY (SEQ ID NO: 490) |
|  | VL CDR2 | GASTRQT (SEQ ID NO: 461) | GASTRQT (SEQ ID NO: 467) | GAS (SEQ ID NO: 473) | GASTRQT (SEQ ID NO: 479) | LLIYGASTRQ (SEQ ID NO: 485) | GAS (SEQ ID NO: 491) |
|  | VL CDR3 | QQAGVVPYT (SEQ ID NO: 462) | QQAGVVPYT (SEQ ID NO: 468) | AGVVPY (SEQ ID NO: 474) | QQAGVVPYT (SEQ ID NO: 480) | QQAGVVPYT (SEQ ID NO: 486) | QQAGVVPYT (SEQ ID NO: 492) |

VH Sequence*:
QVQLQESGPGLVKPSQTLSLTCTVSGGSISSGQYWSWIRQHPGKGLEWIGEIYYSGSTRYNPSLKSRVTIS
VDTSKNQFSLKLSSVTAADTAVYYCARDAPYYYGGGYYYYMDVWGKGTTVTVSS (SEQ ID NO: 493)

VL Sequence*:
EIVLTQSPGTLSLSPGERATLSCRASESVDSSYLAWYQQKPGQAPRLLIYGASTRQTGIPDRFSGSGSGTD
FTLTISRLEPEDFAVYYCQQAGVVPYTFGGGTKVEIK (SEQ ID NO: 494)

*Exemplary CDR sequences encompass amino acids as determined by Kabat & Chothia

TABLE 28

Antibody 43B7-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 495) | SGQYWS (SEQ ID NO: 501) | GGSISSGQ (SEQ ID NO: 507) | GGSISSGQYWS (SEQ ID NO: 513) | SSGQYWS (SEQ ID NO: 519) | GGSISSGQY (SEQ ID NO: 525) |
| | VH CDR2 | EIYYSGSTRYNPSLKS (SEQ ID NO: 496) | EIYYSGSTRYNPSLKS (SEQ ID NO: 502) | YSG (SEQ ID NO: 508) | EIYYSGSTR (SEQ ID NO: 514) | WIGEIYYSGSTR (SEQ ID NO: 520) | IYYSGST (SEQ ID NO: 526) |
| | VH CDR3 | DAPYYYGGYYYYMDV (SEQ ID NO: 497) | DAPYYYGGYYYYMDV (SEQ ID NO: 503) | APYYYGGGYYYYMD (SEQ ID NO: 509) | DAPYYYGGYYYYMDV (SEQ ID NO: 515) | ARDAPYYYGGGYYYYMD (SEQ ID NO: 521) | ARDAPYYYGGGYYYYMDV (SEQ ID NO: 527) |
| VL CDR Seq. | VL CDR1 | RASESVDSSYLA (SEQ ID NO: 498) | RASESVDSSYLA (SEQ ID NO: 504) | SESVDSSY (SEQ ID NO: 510) | RASESVDSSYLA (SEQ ID NO: 516) | DSSYLAWY (SEQ ID NO: 522) | ESVDSSY (SEQ ID NO: 528) |
| | VL CDR2 | GADSRAT (SEQ ID NO: 499) | GADSRAT (SEQ ID NO: 505) | GAD (SEQ ID NO: 511) | GADSRAT (SEQ ID NO: 517) | LLIYGADSRA (SEQ ID NO: 523) | GAD (SEQ ID NO: 529) |
| | VL CDR3 | QQDGVVPYT (SEQ ID NO: 500) | QQDGVVPYT (SEQ ID NO: 506) | DGVVPY (SEQ ID NO: 512) | QQDGVVPYT (SEQ ID NO: 518) | QQDGVVPYT (SEQ ID NO: 524) | QQDGVVPYT (SEQ ID NO: 530) |

VH Sequence*:
QVQLQESGPGLVKPSQTLSLTCTVSGGSISSGQYW SWIRQHPGKGLEWIGEIYYSGSTRYNPSLKSRVTI SVDTSKNQFSLKLSSVTAADTAVYYCARDAPYYYG GGYYYYMDVWGKGTTVTVSS
(SEQ ID NO: 531)

VL Sequence*:
EIVLTQSPGTLSLSPGERATLSCRASESVDSSYL AWYQQKPGQAPRLLIYGADSRATGIPDRFSGSGS GTDFTLTISRLEPEDFAVYYCQQDGVVP YTFGGGTKVEIK (SEQ ID NO: 532)

*Exemplary CDR sequences encompass amino acids as determined by Kabat & Chothia

TABLE 29

Antibody 43D-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 533) | GYYWS (SEQ ID NO: 539) | GGSLSGY (SEQ ID NO: 545) | GGSLSGYYWS (SEQ ID NO: 551) | SGYYWS (SEQ ID NO: 557) | GGSLSGYY (SEQ ID NO: 563) |
| | VH CDR2 | EIGASGSTRYNPSLKS (SEQ ID NO: 534) | EIGASGSTRYNPSLKS (SEQ ID NO: 540) | ASG (SEQ ID NO: 546) | EIGASGSTR (SEQ ID NO: 552) | WIGEIGASGSTR (SEQ ID NO: 558) | IGASGST (SEQ ID NO: 564) |
| | VH CDR3 | DTPYYYEGGYYYYMDV (SEQ ID NO: 535) | DTPYYYEGGYYYYMDV (SEQ ID NO: 541) | TPYYYEGGYYYYMD (SEQ ID NO: 547) | DTPYYYEGGYYYYMDV (SEQ ID NO: 553) | ARDTPYYYEGGYYYYMD (SEQ ID NO: 559) | ARDTPYYYEGGYYYYMDV (SEQ ID NO: 565) |
| VL CDR Seq. | VL CDR1 | RASQSVSSSYLA (SEQ ID NO: 536) | RASQSVSSSYLA (SEQ ID NO: 542) | SQSVSSSY (SEQ ID NO: 548) | RASQSVSSSYLA (SEQ ID NO: 554) | SSSYLAWY (SEQ ID NO: 560) | QSVSSSY (SEQ ID NO: 566) |
| | VL CDR2 | GASSRAT (SEQ ID NO: 537) | GASSRAT (SEQ ID NO: 543) | GAS (SEQ ID NO: 549) | GASSRAT (SEQ ID NO: 555) | LLIYGASSRA (SEQ ID NO: 561) | GAS (SEQ ID NO: 567) |
| | VL CDR3 | QQVGVVPYT (SEQ ID NO: 538) | QQVGVVPYT (SEQ ID NO: 544) | VGVVPY (SEQ ID NO: 550) | QQVGVVPYT (SEQ ID NO: 556) | QQVGVVPYT (SEQ ID NO: 562) | QQVGVVPYT (SEQ ID NO: 568) |

VH Sequence*:
QVQLQQWGAGLLKPSETLSLTCAVYGGSLSGYYWSWIRQ PPGKGLEWIGEIGASGSTRYNPSLKSRVTISVDTSKNQF SLKLSSVTAADTAVYYCARDTPYYYEGGYYYYMDVWGKG TTVTVSS (SEQ ID NO: 569)

VL Sequence*:
EIVLTQSPGTLSLSPGERATLSCRASQSVSSSYLAWYQQ KPGQAPRLLIYGASSRATGIPDRFSGSGSGTDFTLTISR LEPEDFAVYYCQQVGVVPYTFGGGTKVEIK
(SEQ ID NO: 570)

*Exemplary CDR sequences encompass amino acids as determined by Kabat & Chothia

TABLE 30

Antibody 43D7-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 571) | GYYWS (SEQ ID NO: 577) | GGSLSGY (SEQ ID NO: 583) | GGSLSGYYWS (SEQ ID NO: 589) | SGYYWS (SEQ ID NO: 595) | GGSLSGYY (SEQ ID NO: 601) |
| | VH CDR2 | EIGASGSTRYNPSLKS (SEQ ID NO: 572) | EIGASGSTRYNPSLKS (SEQ ID NO: 578) | ASGSTR (SEQ ID NO: 584) | EIGASGSTR (SEQ ID NO: 590) | WIGEIGASGSTR (SEQ ID NO: 596) | IGASGSTR (SEQ ID NO: 602) |
| | VH CDR3 | DTPYYYEGGYYYYMDV (SEQ ID NO: 573) | DTPYYYEGGYYYYMDV (SEQ ID NO: 579) | TPYYEGGYYYYMD (SEQ ID NO: 585) | DTPYYYEGGYYYYMDV (SEQ ID NO: 591) | ARDTPYYYEGGYYYYMD (SEQ ID NO: 597) | ARDTPYYYEGGYYYYMDV (SEQ ID NO: 603) |
| VL CDR Seq. | VL CDR1 | RASDSVDSSYLA (SEQ ID NO: 574) | RASDSVDSSYLA (SEQ ID NO: 580) | SDSVDSSY (SEQ ID NO: 586) | RASDSVDSSYLA (SEQ ID NO: 592) | DSSYLAWY (SEQ ID NO: 598) | DSVDSSY (SEQ ID NO: 604) |
| | VL CDR2 | GAFSRAN (SEQ ID NO: 575) | GAFSRAN (SEQ ID NO: 581) | GAF (SEQ ID NO: 587) | GAFSRAN (SEQ ID NO: 593) | LLIYGAFSRA (SEQ ID NO: 599) | GAF (SEQ ID NO: 605) |
| | VL CDR3 | QQAGVVPYT (SEQ ID NO: 576) | QQAGVVPYT (SEQ ID NO: 582) | AGVVPY (SEQ ID NO: 588) | QQAGVVPYT (SEQ ID NO: 594) | QQAGVVPYT (SEQ ID NO: 600) | QQAGVVPYT (SEQ ID NO: 606) |

VH Sequence*:
QVQLQQWGAGLLKPSETLSLTCAVYGGSLSGYYWSWIRQPPGKGLEWIGEIGASGSTRYNPSLKSRVTISVDTSKNQFSLKLSSVTAADTAVYYCARDTPYYYEGGYYYYMDVWGKGTTVTVSS
(SEQ ID NO: 607)

VL Sequence*:
EIVLTQSPGTLSLSPGERATLSCRASDSVDSSYLAWYQQKPGQAPRLLIYGAFSRANGIPDRFSGSGSGTDFTLTISRLEPEDFAVYYCQQAGVVPYTFGGGTKVEIK
(SEQ ID NO: 608)

*Exemplary CDR sequences encompass amino acids as determined by Kabat & Chothia

TABLE 31

Antibody 43D8-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 609) | GYYWS (SEQ ID NO: 615) | GGSLSGY (SEQ ID NO: 621) | GGSLSGYYWS (SEQ ID NO: 627) | SGYYWS (SEQ ID NO: 633) | GGSLSGYY (SEQ ID NO: 639) |
| | VH CDR2 | EIGASGSTRYNPSLKS (SEQ ID NO: 610) | EIGASGSTRYNPSLKS (SEQ ID NO: 616) | ASGSTR (SEQ ID NO: 622) | EIGASGSTR (SEQ ID NO: 628) | WIGEIGASGSTR (SEQ ID NO: 634) | IGASGSTR (SEQ ID NO: 640) |
| | VH CDR3 | DTPYYYEGGYYYYMDV (SEQ ID NO: 611) | DTPYYYEGGYYYYMDV (SEQ ID NO: 617) | TPYYEGGYYYYMD (SEQ ID NO: 623) | DTPYYYEGGYYYYMDV (SEQ ID NO: 629) | ARDTPYYYEGGYYYYMD (SEQ ID NO: 635) | ARDTPYYYEGGYYYYMDV (SEQ ID NO: 641) |
| VL CDR Seq. | VL CDR1 | RASQSVSSSFLA (SEQ ID NO: 612) | RASQSVSSSFLA (SEQ ID NO: 618) | SQSVSSSF (SEQ ID NO: 624) | RASQSVSSSFLA (SEQ ID NO: 630) | SSSFLAWY (SEQ ID NO: 636) | QSVSSSF (SEQ ID NO: 642) |
| | VL CDR2 | GAYSRAT (SEQ ID NO: 613) | GAYSRAT (SEQ ID NO: 619) | GAY (SEQ ID NO: 625) | GAYSRAT (SEQ ID NO: 631) | LLIYGAYSRA (SEQ ID NO: 637) | GAY (SEQ ID NO: 643) |
| | VL CDR3 | QQAGVVPYT (SEQ ID NO: 614) | QQAGVVPYT (SEQ ID NO: 620) | AGVVPY (SEQ ID NO: 626) | QQAGVVPYT (SEQ ID NO: 632) | QQAGVVPYT (SEQ ID NO: 638) | QQAGVVPYT (SEQ ID NO: 644) |

VH Sequence*:
QVQLQQWGAGLLKPSETLSLTCAVYGGSLSGYYWSWIRQPPGKGLEWIGEIGASGSTRYNPSLKSRVTISVDTSKNQFSLKLSSVTAADTAVYYCARDTPYYYEGGYYYYMDVWGKGTTVTVSS (SEQ ID NO: 645)

VL Sequence*:
EIVLTQSPGTLSLSPGERATLSCRASQSVSSSFLAWYQQKPGQAPRLLIYGAYSRATGIPDRFSGSGSGTDFTLTISRLEPEDFAVYYCQQAGVVPYTFGGGTKVEIK (SEQ ID NO: 646)

*Exemplary CDR sequences encompass amino acids as determined by Kabat & Chothia

TABLE 32

Antibody 43E-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 647) | SGQYWS (SEQ ID NO: 653) | GGSISSGQ (SEQ ID NO: 659) | GGSISSGQYWS (SEQ ID NO: 666) | SSGQYWS (SEQ ID NO: 671) | GGSISSGQY (SEQ ID NO: 677) |
| | VH CDR2 | EIYYSGSTRYNPSLKS (SEQ ID NO: 648) | EIYYSGSTRYNPSLKS (SEQ ID NO: 654) | YSG (SEQ ID NO: 660) | EIYYSGSTR (SEQ ID NO: 666) | WIGEIYYSGSTR (SEQ ID NO: 672) | IYYSGST (SEQ ID NO: 678) |
| | VH CDR3 | DTPYYYDGGYYYYMDV (SEQ ID NO: 649) | DTPYYYDGGYYYYMDV (SEQ ID NO: 655) | TPYYYDGGYYYYMD (SEQ ID NO: 661) | DTPYYYDGGYYYYMDV (SEQ ID NO: 667) | ARDTPYYYDGGYYYYMD (SEQ ID NO: 673) | ARDTPYYYDGGYYYYMDV (SEQ ID NO: 679) |
| VL CDR Seq. | VL CDR1 | RASQSVSSSYLA (SEQ ID NO: 650) | RASQSVSSSYLA (SEQ ID NO: 656) | SQSVSSSY (SEQ ID NO: 662) | RASQSVSSSYLA (SEQ ID NO: 668) | SSSYLAWY (SEQ ID NO: 674) | QSVSSSY (SEQ ID NO: 680) |
| | VL CDR2 | GASSRAT (SEQ ID NO: 651) | GASSRAT (SEQ ID NO: 657) | GAS (SEQ ID NO: 663) | GASSRAT (SEQ ID NO: 669) | LLIYGASSRA (SEQ ID NO: 675) | GAS (SEQ ID NO: 681) |
| | VL CDR3 | QQVGVVPYT (SEQ ID NO: 652) | QQVGVVPYT (SEQ ID NO: 658) | VGVVPY (SEQ ID NO: 664) | QQVGVVPYT (SEQ ID NQ: 670) | QQVGVVPYT (SEQ ID NO: 676) | QQVGVVPYT (SEQ ID NO: 682) |

VH Sequence*:
QVQLQESGPGLVKPSQTLSLTCTVSGGSISSGQYWSWIRQHPGKGLEWIGEIYYSGSTRYNPSLKSRVTISVDTSKDQFSLKLSSVTAADTAVYYCARDTPYYYDGGYYYMDVWGKGTTVTVSS (SEQ ID NO: 683)

VL Sequence*:
EIVLTQSPGTLSLSPGERATLSCRASQSVSSSYLAWYQQKPGQAPRLLIYGASSRATGIPDRFSGSGSGTDFTLTISRLEPEDFAVYYCQQVGVVPYTFGGGTKVEIK (SEQ ID NO: 684)

*Exemplary CDR sequences encompass amino acids as determined by Kabat & Chothia

TABLE 33

Antibody 43Ea-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 685) | SGQYWS (SEQ ID NO: 691) | GGSISSGQ (SEQ ID NO: 697) | GGSISSGQYWS (SEQ ID NO: 703) | SSGQYWS (SEQ ID NO: 709) | GGSISSGQY (SEQ ID NO: 715) |
| | VH CDR2 | EIYYSGSTRYNPSLK (SEQ ID NO: 686) | EIYYSGSTRYNPSLK (SEQ ID NO: 692) | YSG (SEQ ID NO: 698) | EIYYSGSTR (SEQ ID NO: 704) | WIGEIYYSGSTR (SEQ ID NO: 710) | IYYSGST (SEQ ID NO: 716) |
| | VH CDR3 | DTPYYYDGGYYYYMDV (SEQ ID NO: 687) | DTPYYYDGGYYYYMDV (SEQ ID NO: 693) | TPYYYDGGYYYYMD (SEQ ID NO: 699) | DTPYYYDGGYYYYMDV (SEQ ID NO: 705) | ARDTPYYYDGGYYYYMD (SEQ ID NO: 711) | ARDTPYYYDGGYYYYMDV (SEQ ID NO: 717) |
| VL CDR Seq. | VL CDR1 | RASQSVSSSYLA (SEQ ID NO: 688) | RASQSVSSSYLA (SEQ ID NO: 694) | SQSVSSSY (SEQ ID NO: 700) | RASQSVSSSYLA (SEQ ID NO: 706) | SSSYLAWY (SEQ ID NO: 712) | QSVSSSY (SEQ ID NO: 718) |
| | VL CDR2 | GASSRAT (SEQ ID NO: 689) | GASSRAT (SEQ ID NO: 695) | GAS (SEQ ID NO: 701) | GASSRAT (SEQ ID NO: 707) | LLIYGASSRA (SEQ ID NO: 713) | GAS (SEQ ID NO: 719) |
| | VL CDR3 | QQVGVVPYT (SEQ ID NO: 690) | QQVGVVPYT (SEQ ID NO: 696) | VGVVPY (SEQ ID NO: 702) | QQVGVVPYT (SEQ ID NO: 708) | QQVGVVPYT (SEQ ID NO: 714) | QQVGVVPYT (SEQ ID NO: 720) |

VH Sequence*:
QVQLQESGPGLVKPSQTLSLTCTVSGGSISSGQYWSWIRQHPGKGLEWIGEIYYSGSTRYNPSLKSRVTISVDTSNQFSLKLSSVTAADTAVYYCARDTPYYYDGGYYYYMDVWGKGTTVTVSS (SEQ ID NO: 721)

VL Sequence*:
EIVLTQSPGTLSLSPGERATLSCRASQSVSSSYLAWYQQKPGQAPRLLIYGASSRATGIPDRFSGSGSGTDFTLTISRLEPEDFAVYYCQQVGVVPYTFGGGTKVEIK (SEQ ID NO: 722)

*Exemplary CDR sequences encompass amino acids as determined by Kabat & Chothia

TABLE 34

Antibody 54E-CDR Sequences

| | | Exemplary* | Kabat | Chothia | AbM | Contact | IMGT |
|---|---|---|---|---|---|---|---|
| VH CDR Seq. | VH CDR1 | GYTF ANYY MH (SEQ ID NO: 723) | NYYM H (SEQ ID NO: 729) | GYTF ANY (SEQ ID NO: 735) | GYTF ANYY MH (SEQ ID NO: 741) | ANYY MH (SEQ ID NO: 747) | GYTF ANYY (SEQ ID NO: 753) |
| | VH CDR2 | IINP SGGI TVYA Q KFQG (SEQ ID NO: 724) | IINP SGGI TVYA Q KFQG (SEQ ID NO: 730) | PSGG I (SEQ ID NO: 736) | IINP SGGI TV (SEQ ID NO: 742) | WMGI INPS GGIT V (SEQ ID NO: 748) | INPS GGIT (SEQ ID NO: 754) |
| | VH CDR3 | GGSK VAAL AFDI (SEQ ID NO: 725) | GGSK VAAL AFDI (SEQ ID NO: 731) | GSKV AALA FD (SEQ ID NO: 737) | GGSK VAAL AFDI (SEQ ID NO: 743) | ARGG SKVA ALA FD (SEQ ID NO: 749) | ARGG SKVA ALA FDI (SEQ ID NO: 755) |
| VL CDR Seq. | VL CDR1 | QASQ DISN SLN (SEQ ID NO: 726) | QASQ DISN SLN (SEQ ID NO: 732) | SQDI SNS (SEQ ID NO: 738) | QASQ DISN SLN (SEQ ID NO: 744) | SNSL NWY (SEQ ID NO: 750) | QDIS NS (SEQ ID NO: 756) |
| | VL CDR2 | DASN LET (SEQ ID NO: 727) | DASN LET (SEQ ID NO: 733) | DAS (SEQ ID NO: 739) | DASN LET (SEQ ID NO: 745) | LLIY DASN LE (SEQ ID NO: 751) | DAS (SEQ ID NO: 757) |
| | VL CDR3 | QQYN FHPL T (SEQ ID NO: 728) | QQYN FHPL T (SEQ ID NO: 734) | YNFH PL (SEQ ID NO: 740) | QQYN FHPL T (SEQ ID NO: 746) | QQYN FHPL T (SEQ ID NO: 752) | QQYN FHPL T (SEQ ID NO: 758) |

VH Sequence*:
QVQLVQSGAEVKKPGASVKVSCKASGYTFANYYMHW
VRQAPGQGLEWMGIIINPSGGITVYAQKFQGRVTMTR
TDSTSTVYMELSSLRSEDTAVYYCAR**GGSKVAALAF
DI**WGQGTMVTVSS (SEQ ID NO: 759)

VL Sequence*:
DIQMTQSPSSLSASVGDRVTITCQASQDISNSLNW
YQQKPGKAPKLLIYDASNLETGVPSRFSGSRSGTD
FTFTISSLQPEDIATYYCQQYNFHPLTFGGGTKVE
IK (SEQ ID NO: 760)

*Exemplary CDR sequences encompass amino acids as determined by Kabat plus Chothia

TABLE 35

Consensus CDRs

| | Antibody Group | 1 | 25 | 29 | 39 | 43 | 54 |
|---|---|---|---|---|---|---|---|
| VH CDR Seq.* | VH CDR1 | GFTFS x[D/S] YAMx [A/G] (SEQ ID NO: 773) | GYTF x[D/R] YGIS (SEQ ID NO: 779) | GFTF x[H/R] Sx[R/ Y]GMH (SEQ ID NO: 785) | GGTF SSNA IG (SEQ ID NO: 791) | GGSx [I/L] SSGx [Q/Y] YWS (SEQ ID NO: 797) | GYTF ANYY MH (SEQ ID NO: 803) |
| | VH CDR2 | x[A/T] ISGS GGLT YYAD SVKG (SEQ ID NO: 774) | Wx[I/V] APYx [S/N] GNTNY AQKL QG (SEQ ID NO: 780) | VITY DGIN KYYA DSVE G (SEQ ID NO: 786) | SIIP IIGF ANYA QK FQG (SEQ ID NO: 792) | Eix [Y/G] x[Y/A] SGST RYNP SLKS (SEQ ID NO: 798) | IINP SGGI TVYA QKFQ G (SEQ ID NO: 804) |
| | VH CDR3 | APYG YYMD V (SEQ ID NO: 775) | DAGT YSPx [F/Y] GYG MDV (SEQ ID NO: 781) | DGVY YGVY DY (SEQ ID NO: 787) | DSGY YYGA SSFG MDV (SEQ ID NO: 793) | Dx[T/A] PYYYx [E/G/D] GGYYY YMDV (SEQ ID NO: 799) | GGSK VAAL AFDI (SEQ ID NO: 805) |
| VL CDR Seq.* | VL CDR1 | RASQ SISS WLA (SEQ ID NO: 776) | X[R/Q] Asx [Q/E/H] SIx[S/ D/N] x[S/N] WLA (SEQ ID NO: 782) | KSSQ SVLF SSNN KNY LA (SEQ ID NO: 788) | RASQ SVSS NLA (SEQ ID NO: 794) | RASx [Q/E/D] SVx [S/D] SSx [Y/F] LA (SEQ ID NO: 795) | QASQ DISN SLN (SEQ ID NO: 806) |
| | VL CDR2 | KASS LES (SEQ ID NO: 777) | X[K/S] Ax [S/Y] X[S/ Y/N] Lex [S/Y] (SEQ ID NO: 783) | WAST RES (SEQ ID NO: 789) | GAST RAT (SEQ ID NO: 795) | Gax [S/D/ F/Y] Rx[A/Q] x[T/N] (SEQ ID NO: 801) | DASN LET (SEQ ID NO: 807) |
| | VL CDR3 | QQYK SYIT (SEQ ID NO: 778) | Qx[Q/ L/R] FQx [S/K] LPPF T (SEQ ID NO: 784) | QQFH SYPL T (SEQ ID NO: 790) | EQYN NLPL T (SEQ ID NO: 796) | QQx [V/A/ D]GV VPYT (SEQ ID NO: 802) | QQYN FHPL T (SEQ ID NO: 808) |

*Exemplary CDR sequences encompass amino acids as determined by Kabat plus Chothia

TABLE 36

Human, Cynomolgus Monkey, and Mouse TF Sequences

| Species | Human (Homo sapiens) | Cynomolgus Monkey (Macaca fascicularis) | Mouse (Mus musculus) |
|---|---|---|---|
| Full-length sequence [signal sequence underlined] | METPAWPRVP RPETAVARTL LLGWVFAQVA GASGTTNTVA AYNLTWKSTN FKTILEWEPK PVNQVYTVQI STKSGDWKSK CFYTTDTECD LTDEIVKDVK QTYLARVFSY PAGNVESTGS AGEPLYENSP EFTPYLETNL GQPTIQSFEQ VGTKVNVTVE DERTLVRRNN TFLSLRDVFG KDLIYTLYYW KSSSSGKKTA KTNTNEFLID VDKGENYCFS VQAVIPSRTV NRKSTDSPVE CMGQEKGEFR EIFYIIGAVV FVVIILVIIL AISLHKCRKA GVGQSWKENS PLNVS (SEQ ID NO: 809) | METPAWPRVP RPETAVARTL LLGWVFAQVA GASGTTNTVA AYNLTWKSTN FKTILEWEPK PINQVYTVQI STKSGDWKSK CFYTADTECD LTDEIVKDVK QTYLARVFSY PAGHVESTGS TEEPPYENSP EFTPYLETNL GQPTIQSFEQ VGTKVNVTVQ DEWTLVRRND TFLSLRDVFG KDLIYTLYYW KSSSSGKKTA KTNTNEFLID VDKGENYCFS VQAVIPSRRT ANRKSTDSPV ECMGHEKGES REIFYIIGAV VFVVIILVII LAISLHKCK KARVGRS WKENSPLNVA (SEQ ID NO: 813) | MAILVRPRLL AALAPTFLGC LLLQVTAGAG IPEKAFNLTW ISTDFKTILE WQPKPTNYTY TVQISDRSRN WKNKCFSTTD TECDLTDEIV KDVTWAYEAK VLSVPRRNSV HGDGDQLVIH GEEPPFTNAP KFLPYRDTNL GQPVIQQFEQ DGRKLNVVVK DSLTLVRKNG TFLTLRQVFG KDLGYIITYR KGSSTGKKTN ITNTNEFSID VEEGVSYCFF VQAMIFSRKT NQNSPGSSTV CTEQWKSFLG ETLIIVGAVV VFVVIILVII LLATIFIILL SISLCKRRKN RAGQKGKNTP SRLA (SEQ ID NO: 817) |
| Extracellular domain (ECD) | SGTTNTVAAY NLTWKSTNFK TILEWEPKPV NQVYTVQIST KSGDWKSKCF YTTDTECDLT DEIVKDVKQT YLARVFSYPA GNVESTGSAG EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR KSTDSPVECM GQEKGEFRET (SEQ ID NO: 810) | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN RKSTDSPVEC MGHEKGESRE (SEQ ID NO: 814) | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR KTNQNSPGSS TVCTEQWKSF LGE (SEQ ID NO: 818) |
| Sequence of TF ECD-His (TF-His) protein | SGTTNTVAAY NLTWKSTNFK TILEWEPKPV NQVYTVQIST KSGDWKSKCF YTTDTECDLT DEIVKDVKQT YLARVFSYPA GNVESTGSAG EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR KSTDSPVECM GQEKGEFRET GHHHHHH (SEQ ID NO: 811) | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN RKSTDSPVEC MGHEKGESRE TGHHHHHH (SEQ ID NO: 815) | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR KTNQNSPGSS TVCTEQWKSF LGETGHHHHH H (SEQ ID NO: 819) |
| Sequence of TF ECD-Fc (TF-Fc) fusion protein | SGTTNTVAAY NLTWKSTNFK TILEWEPKPV NQVYTVQIST KSGDWKSCF YTTDTECDLT DEIVKDVKQT YLARVFSYPA GNVESTGSAG EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR KSTDSPVECM GQEKGEFRET GENLYFQGDK THTCPPCPAP ELLGGPSVFL FPPKPKDTLM ISRTPEVTCV VVDVSHEDPE VKFNWYVDGV EVHNAKTPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGK (SEQ ID NO: 812) | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN RKSTDSPVEC MGHEKGESRE TGENLYFQGD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 816) | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR KTNQNSPGSS TVCTEQWKSF LGETGENLYF QGDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO: 820) |

TABLE 39

Sequences of Anti-TF Antibodies

| Antibody | VH domain | VL domain |
|---|---|---|
| 10H10 (M1593) | EVQLVQSGAEVKKPGESLRISCKGSGYTFAPYWIEWVRQMPGKGLEWMGDILPGTGFTTYSPSFQGHVTISADKSISTAYLQWSSLKASDTAMYYCARSGYYGNSGPAYWGQGTLVTVSS (SEQ ID NO: 821) | DIVMTQTPLSLPVTPGEPASISCKSSQSLLSSGNQKNYLTWYLQKPGQSPQLLIYWASTRESGVPDRFSGSGSGTDFTLKISRVEAEDVGVYYCQNDYTYPLTFGQGTKLEIK (SEQ ID NO: 822) |
| TF-011 | EVQLLESGGGLVQPGGSLRLSCAASGFTFSNYAMSWVRQAPGKGLEWVSSISGSGDYTYYTDSVKGRFTISRDNSKNTLYLQMNSLRAEDTAVYYCARSPWGYYLDSWGQGTLVTVSSID (SEQ NO: 828) | DIQMTQSPPSLSASAGDRVTITCRASQGISSRLAWYQQKPEKAPKSLIYAASSLQSGVPSRFSGSGSGTDFTLTISSLQPEDFATYYCQQYNSYPYTFGQGTKLEIK (SEQ ID NO: 829) |
| 5G9 | QVQLVESGGGVVQPGRSLRLSCKASGFNIKDYYMHWVRQAPGKGLEWIGLIDPENGNTIY | DIQMTQSPSSLSASVGDRVTITCKASQDIRKYLNWYQQKPGKAPKLLIYYATSLADGVPS |
| (humanized TF8-5G9, CNTO 860) | DPKFQGRFTISADNSKNTLFLQMDSLRPEDTAVYYCARDNSYYFDYWGQGTPVTVSS (SEQ ID NO: 830) | RFSGSGSGTDYTFTISSLQPEDIATYYCLQHGESPYTFGQGTKLEIT (SEQ ID NO: 831) |

TABLE 41

Pig TF sequences

| Species | Pig (Sus scrofa) |
|---|---|
| Full-length sequence [signal sequence underlined] | <u>MATPTGPPVSCPKAAVARALLLGWV LVQVAGA</u>TGTTDVIVAYNLTWKSTN FKTILEWEPKPINYVYTVQISPRLG DWKNKCFHTTDTECDVTDEIMRNVK ETYVARVLSYPADTVLTAQEPPFTN SPPPFTPYLDTNLGQPVIQSFEQVGT KLNVTVEAARTLVRVNGTFLRLRDV FGKDLNYTLYYWRASSTGKKKATTN TNEFLIDVDKGENYCFSVQAVIPSR RVNQKSPESRIECTSQEKAVSRELF LIVGAVVFAVIVFVLVLSVSLYKCR KERAGPSGKENAPLNVA (SEQ ID NO: 824) |
| Extracellular domain (ECD) | TGTTDVIVAYNLTWKSTNFKTILEW EPKPINYVYTVQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY TLYYWRASSTGKKKATTNTNEFLID VDKGENYCFSVQAVIPSRRVNQKSP ESRIECTSQEKAVSRE (SEQ ID NO: 825) |
| Sequence of TF ECD-His (TF-His) protein | TGTTDVIVAYNLTWKSTNFKTILEW EPKPINYVYTVQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY TLYYWRASSTGKKKATTNTNEFLID VDKGENYCFSVQAVIPSRRVNQKSP ESRIECTSQEKAVSRETGHHHHHH (SEQ ID NO: 826) |

TABLE 41-continued

Pig TF sequences

| Species | Pig (Sus scrofa) |
|---|---|
| Sequence of TF ECD-Fc (TF-Fc) fusion protein | TGTTDVIVAYNLTWKSTNFKTILEW EPKPINYVYTVQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY TLYYWRASSTGKKKATTNTNEFLID VDKGENYCFSVQAVIPSRRVNQKSP ESRIECTSQEKAVSRETGENLYFQG DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GK (SEQ ID NO: 827) |

TABLE 49

Rabbit TF sequences

| Species | Rabbit (Oryctolagus cuniculus) |
|---|---|
| Full-length sequence [signal sequence underlined] | <u>MAPPTRLQVPRPGTAVPYTV LLGWLLAQVARA</u>ADTTGRAY NLTWKSTNFKTILEWEPKSI DHVYTVQISTRLENWKSKCF LTAETECDLTDEVVKDVGQT YMARVLSYPARNGNTTGFPE EPPFRNSPEFTPYLDTNLGQ PTIQSFEQVGTKLNVTVQDA RTLVRRNGTFLSLRAVFGKD LNYTLYYWRASSTGKKTATT NTNEFLIDVDKGENYCFSVQ AVIPSRKRKQRSPESLTECT SREQGRAREMFFIIGAVVVV ALLIIVLSVTVYKCRKARAG PSGKESSPLNIA (SEQ ID NO: 832) |
| Extracellular domain (ECD) | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREM (SEQ ID NO: 833) |
| Sequence of TF ECD-His (TF-His) protein | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREMTG HHHHHH (SEQ ID NO: 834) |

TABLE 49-continued

Rabbit TF sequences

| Species | Rabbit (Oryctolagus cuniculus) |
|---|---|
| Sequence of TF ECD-Fc (TF-Fc) fusion protein | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREMEN LYFQGDKTHTCPPCPAPELL GGPSVFLFPPKPKDTLMISR TPEVTCVVVDVSHEDPEVKF NWYVDGVEVHNAKTKPREEQ YNSTYRVVSVLTVLHQDWLN GKEYKCKVSNKALPAPIEKT ISKAKGQPREPQVYTLPPSR EEMTKNQVSLTCLVKGFYPS DIAVEWESNGQPENNYKTTP PVLDSDGSFFLYSKLTVDKS RWQQGNVFSCSVMHEALHNH YTQKSLSLSPGK (SEQ ID NO: 835) |

TABLE 56

Rat TF ECD and chimeric construct ECD sequences

| Rat/Chimeric construct | Extracellular domain (ECD) sequence |
|---|---|
| rTF (rat TF) | AGTPPGKAFNLTWISTDFKTILEWQ PKPTNYTYTVQISDRSRNWKYKCTG TTDTECDLTDEIVKDVNWTYEARVL SVPWRNSTHGKETLFGTHGEEPPFT NARKFLPYRDTKIGQPVIQKYEQGG TKLKVTVKDSFTLVRKNGTFLTLRQ VFGNDLGYILTYRKDSSTGRKTNTT HTNEFLIDVEKGVSYCFFAQAVIFS RKTNHKSPESITKCTEQWKSVLGE (SEQ ID NO: 838) |
| h1-107_r | AGTPPGKAFNLTWISTDFKTILEWQ PKPTNYTYTVQISDRSRNWKYKCTG TTDTECDLTDEIVKDVNWTYEARVL SVPWRNSTHGKETLFGTHGEEPPFT NARKFLPYRDTKLGQPTIQSFEQVG TKVNVTVEDERTLVRRNNTFLSLRD VFGKDLIYTLYYWKSSSSGKKTAKT NTNEFLIDVDKGENYCFSVQAVIPS RTVNRKSTDSPVECMGQEKGEFRE (SEQ ID NO: 839) |
| h1-77_r | AGTPPGKAFNLTWISTDFKTILEWQ PKPTNYTYTVQISDRSRNWKYKCTG TTDTECDLTDEIVKDVNWTYEARVL SYPAGNVESTGSAGEPLYENSPEFT PYLETNLGQPTIQSFEQVGTKVNVT VEDERTLVRRNNTFLSLRDVFGKDL IYTLYYWKSSSSGKKTAKTNTNEFL IDVDKGENYCFSVQAVIPSRTVNRK STDSPVECMGQEKGEFRE (SEQ ID NO: 840) |
| h1-38_r | AGTPPGKAFNLTWISTDFKTILEWQ PKPTNYTYTVQISTKSGDWKSKCFY TTDTECDLTDEIVKDVKQTYLARVF SYPAGNVESTGSAGEPLYENSPEFT PYLETNLGQPTIQSFEQVGTKVNVT VEDERTLVRRNNTFLSLRDVFGKDL IYTLYYWKSSSSGKKTAKTNTNEFL IDVDKGENYCFSVQAVIPSRTVNRK STDSPVECMGQEKGEFRE (SEQ ID NO: 841) |
| h39-77_r | SGTTNTVAAYNLTWKSTNFKTILEW EPKPVNQVYTVQISDRSRNWKYKCT GTTDTECDLTDEIVKDVNWTYEARV LSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 842) |
| h78-107_r | SGTTNTVAAYNLTWKSTNFKTILEW EPKPVNQVYTVQISTKSGDWKSKCF YTTDTECDLTDEIVKDVKQTYLARV FSVPWRNSTHGTHGEEPPFTNARKF LPYRDTKLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 843) |
| h78-107_r.v2 | SGTTNTVAAYNLTWKSTNFKTILEW EPKPVNQVYTVQISTKSGDWKSKCF YTTDTECDLTDEIVKDVKQTYLARV FSVPWRNSTHGKETLFGTHGEEPPF TNARKFLPYRDTKLGQPTIQSFEQV GTKVNVTVEDERTLVRRNNTFLSLR DVFGKDLIYTLYYWKSSSSGKKTAK TNTNEFLIDVDKGENYCFSVQAVIP SRTVNRKSTDSPVECMGQEKGEFRE (SEQ ID NO: 844) |
| h78-93_r | SGTTNTVAAYNLTWKSTNFKTILEW EPKPVNQVYTVQISTKSGDWKSKCF YTTDTECDLTDEIVKDVKQTYLARV FSVPWRNSTHGKETLFGTHGEEPPY ENSPEFTPYLETNLGQPTIQSFEQV GTKVNVTVEDERTLVRRNNTFLSLR DVFGKDLIYTLYYWKSSSSGKKTAK TNTNEFLIDVDKGENYCFSVQAVIP SRTVNRKSTDSPVECMGQEKGEFRE (SEQ ID NO: 845) |
| h94-107_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLFTNARKF LPYRDTKLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 846) |
| h108-219_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNIGQPVIQKYEQGGTKLKV TVKDSFTLVRKNGTFLTLRQVFGND LGYILTYRKDSSTGRKTNTTHTNEF LIDVEKGVSYCFFAQAVIFSRKTNH KSPESITKCTEQWKSVLGE (SEQ ID NO: 847) |

TABLE 56-continued

Rat TF ECD and chimeric construct ECD sequences

| Rat/Chimeric construct | Extracellular domain (ECD) sequence |
|---|---|
| h108-158_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNIGQPVIQKYEQGGTKLKV TVKDSFTLVRKNGTFLTLRQVFGND LGYILTYRKSSSSGKKTAKTNTNEF LIDVDKGENYCFSVQAVIPSRTVNR KSTDSPVECMGQEKGEFRE (SEQ ID NO: 848) |
| h108-132_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNIGQPVIQKYEQGGTKLKV TVKDSFTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 849) |
| h133-158_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRKNGTFLTLRQVFGND LGYILTYRKSSSSGKKTAKTNTNEF LIDVDKGENYCFSVQAVIPSRTVNR KSTDSPVECMGQEKGEFRE (SEQ ID NO: 850) |
| h133-145_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRKNGTFLTLRQVFGKD LIYTLYYWKSSSSGKKTAKTNTNEF LIDVDKGENYCFSVQAVIPSRTVNR KSTDSPVECMGQEKGEFRE (SEQ ID NO: 851) |
| h133-139_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRKNGTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 852) |
| h140-145_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLTLRQVFGKD LIYTLYYWKSSSSGKKTAKTNTNEF LIDVDKGENYCFSVQAVIPSRTVNR KSTDSPVECMGQEKGEFRE (SEQ ID NO: 853) |
| h146-158_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGND LGYILTYRKSSSSGKKTAKTNTNEF LIDVDKGENYCFSVQAVIPSRTVNR KSTDSPVECMGQEKGEFRE (SEQ ID NO: 854) |
| h146-151_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGND LIYTLYYWKSSSSGKKTAKTNTNEF LIDVDKGENYCFSVQAVIPSRTVNR KSTDSPVECMGQEKGEFRE (SEQ ID NO: 855) |
| h152-158_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LGYILTYRKSSSSGKKTAKTNTNEF LIDVDKGENYCFSVQAVIPSRTVNR KSTDSPVECMGQEKGEFRE (SEQ ID NO: 856) |
| h159-219_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKDSSTGRKTNTTHTNEF LIDVEKGVSYCFFAQAVIFSRKTNH KSPESITKCTEQWKSVLGE (SEQ ID NO: 857) |
| h159-189_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKDSSTGRKTNTTHTNEF LIDVEKGVSYCFFAQAVIPSRTVNR KSTDSPVECMGQEKGEFRE (SEQ ID NO: 858) |
| h159-174_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKDSSTGRKTNTTHTNEF LIDVDKGENYCFSVQAVIPSRTVNR KSTDSPVECMGQEKGEFRE (SEQ ID NO: 859) |
| h159-166_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKDSSTGRKTAKTNTNEF LIDVDKGENYCFSVQAVIPSRTVNR KSTDSPVECMGQEKGEFRE (SEQ ID NO: 860) |
| h167-174_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF |

TABLE 56-continued

Rat TF ECD and chimeric construct ECD sequences

| Rat/Chimeric construct | Extracellular domain (ECD) sequence |
|---|---|
| | TPYLETNLGQPTIQSFEQVGTKVNV TVEDERTLVRRNNTFLSLRDVFGKD LIYTLYYWKSSSSGKKTNTTHTNEF LIDVDKGENYCFSVQAVIPSRTVNR KSTDSPVECMGOEKGEFRE (SEQ ID NO: 861) |
| h175-189_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTNTNEF LIDVEKGVSYCFFAQAVIPSRTVNR KSTDSPVECMGOEKGEFRE (SEQ ID NO: 862) |
| h190-219_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTNTNEF LIDVDKGENYCFSVQAVIFSRKTNH KSPESITKCTEQWKSVLGE (SEQ ID NO: 863) |
| hTF_K68N | SGTTNTVAAYNLTWKSTNFKTILEW EPKPVNQVYTVQISTKSGDWKSKCF YTTDTECDLTDEIVKDVNQTYLARV FSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGOEKGEFRE (SEQ ID NO: 865) |
| hTF_K149N | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGND LIYTLYYWKSSSSGKKTAKTNTNEF LIDVDKGENYCFSVQAVIPSRTVNR KSTDSPVECMGOEKGEFRE (SEQ ID NO: 866) |
| hTF_N171H_T197K | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTHTNEF LIDVDKGENYCFSVQAVIPSRKVNR KSTDSPVECMGOEKGEFRE (SEQ ID NO: 867) |
| 1441-194_11 | AGTPPGKAFNLTWISTDFKTILEWQ PKPTNYTYTVQISDRSRNWKYKCTG TTDTECDLTDEIVKDVNWTYEARVL SVPWRNSTHOKETLFGTHGEEPPFT NARKFLPYRDTKIGQPVIQKYEQGG TKLKVTVKDSFTLVRRNNTFLSRD VFGKDLIYTLYYWKSSSSGKKTAKT NTNEFLIDVDKGENYCFSVQAVIFS RKTNHKSPESITKCTEQWKSVLGE (SEQ ID NO: 864) |

TABLE 57

Variable region sequence consensus

| Group | VH Domain Consensus (SEQ ID NO) | VL Domain Consensus (SEQ ID NO) |
|---|---|---|
| Lineage 25A | QVQLVQSGAEVKKP GASVKVSCKASGYT FDx[V/A]YGISWV RQAPGQGLEWMGWI APYx[N/S]GNTNY AQKLQGRVTMTTDT STSTAYMELRSLRS DDTAVYYCARDAGT YSPFGYGMDVWGQG TTVTVSS (SEQ ID NO: 868) | DIQMTSPSTLSAS VGDRVTITCx[R/Q] ASx[Q/E]Six [S/N]x[S/N\|WLA WYQQKPGKAPKLLI YKAx[S/Y]x[S/N] LEx\|S/Y]GVPSRFS GSGSGTEFTLTISS LQPDDFATYYCQx [Q/L]FQx[S/K] LPPFTFGGGTKV EIK (SEQ ID NO: 869) |
| Lineage 25G | QVQLVQSGAEVKKP GASVKVSCKASGYT FRSYGISWVRQAPG QGLEWMGWVAPYx [N/S]GNTNYAQKL QGRVTMTT DTSTSTAYMELRSL RSDDTAVYYCARDA GTYSPYGYGMDVWG QGTTVTVSS (SEQ ID NO: 870) | DIQMTSPSTLSAS VGDRVTITCx[R/Q] ASx[Q/H) SIx[S/D] SWLAWYQQKPGKA PKLLIYx\|K/S]Asx [S/Y]LESGVPSRFSG SGSGTEFTLTISSLQP DDFATYYCQx[Q/L/R] FQSLPPFTFGGGT KVEIK (SEQ ID NO: 871) |

TABLE 58

Consensus CDRs

| Antibody Group | | | Lineage 25A | Lineage 25G |
|---|---|---|---|---|
| VH CDR Seq.* | | VH CDR1 | GYTFDx[V/A]YGIS (SEQ ID NO: 872) | GYTFR SYGIS (SEQ ID NO: 878) |
| | | VH CDR2 | WIAPYx[N/S] GNTNYA QKLQG (SEQ ID NO: 873) | WVAPYx [N/S]GN TNYAQK LQG (SEQ ID NO: 879) |
| | | VH CDR3 | DAGTYSPF GYGMDV (SEQ ID NO: 874) | DAGTYSP YGYGMDV (SEQ ID NO: 880) |
| VL CDR Seq.* | | VL CDR1 | x[R/Q]Asx [Q/E]Six [S/N]x[S/N]WLA (SEQ ID NO: 875) | x[R/Q]AS x[Q/H]S Ix[S/D] SWLA (SEQ ID NO: 881) |
| | | VL CDR2 | KAx[S/Y] x[S/N]LE x[S/Y] (SEQ ID NO: 876) | x[K/S]AS x[S/Y]LES (SEQ ID NO: 882) |
| | | VL CDR3 | Qx[Q/L]F Qx[S/K]L PPFT (SEQ ID NO: 877) | Qx[Q/L/R] FQSLPPFT (SEQ ID NO: 883) |

The invention claimed is:

1. An isolated antibody which binds to human Tissue Factor (TF), wherein the isolated antibody comprises three heavy chain complementarity determining regions (CDRs) (VH-CDR1, VH-CDR2, and VH-CDR3) and three light chain complementarity determining regions (CDRs) (VL-CDR1, VL-CDR2, and VL-CDR3), wherein the VH-CDR1, VH-CDR2, and VH-CDR3 are from a heavy chain variable domain (VH) comprising the amino acid sequence set forth in SEQ ID NO:836, and wherein the VL-CDR1, VL-CDR2, and VL-CDR3 are from a light chain variable domain (VL) comprising the amino acid sequence set forth in SEQ ID NO:837.

2. An isolated antibody which binds to human TF and comprises three heavy chain complementarity determining regions (CDRs) (VH-CDR1, VH-CDR2, and VH-CDR3) and three light chain CDRs (VL-CDR1, VL-CDR2, and VL-CDR3), wherein: the VH-CDR1 comprises the amino acid sequence set forth in SEQ ID NO: 890, the VH-CDR2 comprises the amino acid sequence set forth in SEQ ID NO: 891, and the VH-CDR3 comprises the amino acid sequence set forth in SEQ ID NO: 892, the VL-CDR1 comprises the amino acid sequence set forth in SEQ ID NO: 893, the VL-CDR2 comprises the amino acid sequence set forth in SEQ ID NO: 894, and the VL-CDR3 comprises the amino acid sequence set forth in SEQ ID NO:895, and wherein the VH-CDR1, VH-CDR2, VH-CDR3, VL-CDR1, VL-CDR2, and VL-CDR3 are defined according to the Kabat numbering system.

3. The isolated antibody of claim 1, wherein
    (i) the isolated antibody binds to the extracellular domain of human Tissue Factor (TF), wherein the antibody binds human TF at a human TF binding site that is distinct from a human TF binding site bound by human FVIIa the isolated antibody binds to the extracellular domain; and (ii) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810;

the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810;

the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810;

the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810;

the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810;

the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810; or the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the antibody relative to an isotype control in a live cell staining assay.

4. The isolated antibody of claim 1, wherein the antibody:
(i) binds to cynomolgus TF;
(ii) binds to rabbit TF; and
(iii) binds to pig TF.

5. The isolated antibody of claim 1, wherein the antibody:
(a) does not inhibit human thrombin generation as determined by thrombin generation assay (TGA);
(b) allows human thrombin generation as determined by thrombin generation assay (TGA);
(c) binds human TF at a human TF binding site that is distinct from a human TF binding site bound by human FX;
(d) does not interfere with the ability of TF:FVIIa to convert FX into FXa;
(e) does not compete for binding to human TF with FVIIa; and
(f) inhibits FVIIa-dependent TF signaling.

6. The isolated antibody of claim 1, wherein the antibody:
(a) does not reduce the thrombin peak on a thrombin generation curve (Peak IIa) compared to an isotype control;
(b) does not increase the time from the assay start to the thrombin peak on a thrombin generation curve (ttPeak) compared to an isotype control;
(c) does not decrease the endogenous thrombin potential (ETP) as determined by the area under a thrombin generation curve compared to an isotype control;
(d) maintains the thrombin peak on a thrombin generation curve (Peak IIa) compared to an isotype control;
(e) maintains the time from the assay start to the thrombin peak on a thrombin generation curve (ttPeak) compared to an isotype control; and
(f) preserves the endogenous thrombin potential (ETP) as determined by the area under a thrombin generation curve compared to an isotype control.

7. The isolated antibody of claim 1, wherein the antibody reduces lesion size in a swine choroidal neovascularization (CNV) model.

8. The isolated antibody of claim 1, wherein the antibody binds to human TF with a $K_D$ of less than or equal to 50 nM, as measured by Octet QK384 or Biacore assay.

9. The isolated antibody of claim 1, wherein the antibody is human, humanized, or chimeric.

10. The isolated antibody of claim 1, wherein the antibody is a monoclonal antibody.

11. The isolated antibody of claim 1, wherein the antibody is multispecific.

12. The isolated antibody of claim 1, wherein the antibody is a Fab, Fab', F(ab')2, Fv, scFv, (scFv)2, single chain antibody molecule, dual variable domain antibody, linear antibody, or V domain antibody.

13. The isolated antibody of claim 1, wherein the antibody comprises an Fc region.

14. The isolated antibody of claim 1, wherein:
(i) the antibody comprises a heavy chain constant region of a class selected from IgG, IgA, IgD, IgE, and IgM, or
(ii) the antibody comprises a heavy chain constant region of the class IgG and a subclass selected from IgG1, IgG2, IgG3, and IgG4.

15. The isolated antibody of claim 2, wherein:
(i) the antibody comprises a heavy chain constant region of a class selected from IgG, IgA, IgD, IgE, and IgM, or
(ii) the antibody comprises a heavy chain constant region of the class IgG and a subclass selected from IgG1, IgG2, IgG3, and IgG4.

16. The isolated antibody of claim 1, wherein the antibody comprises a heavy chain constant region of human IgG1.

17. The isolated antibody of claim 2, wherein the antibody comprises a heavy chain constant region of human IgG1.

18. A pharmaceutical composition comprising (i) the isolated antibody of claim 1 and (ii) a pharmaceutically acceptable excipient.

19. A kit comprising the isolated antibody of claim 1 and instructions for use.

20. The isolated antibody of claim 1, wherein the sequence of the VH comprises the amino acid sequence set forth in SEQ ID NO:836, and the sequence of the VL comprises the amino acid sequence set forth in SEQ ID NO:837.

21. The isolated antibody of claim 1, wherein the sequence of the VH consists of the amino acid sequence set forth in SEQ ID NO:836, and the sequence of the VL consists of the amino acid sequence set forth in SEQ ID NO:837.

22. The isolated antibody of claim 20, wherein the antibody comprises a heavy chain constant region of human IgG1.

23. The isolated antibody of claim 21, wherein the antibody comprises a heavy chain constant region of human IgG1.

24. A pharmaceutical composition comprising (i) the isolated antibody of claim 20 and (ii) a pharmaceutically acceptable excipient.

25. A pharmaceutical composition comprising (i) the isolated antibody of claim 21 and (ii) a pharmaceutically acceptable excipient.

26. A pharmaceutical composition comprising (i) the isolated antibody of claim 22 and (ii) a pharmaceutically acceptable excipient.

27. A pharmaceutical composition comprising (i) the isolated antibody of claim 23 and (ii) a pharmaceutically acceptable excipient.

28. The isolated antibody of claim 2, wherein the sequence of the VH comprises the amino acid sequence set forth in SEQ ID NO:836, and the sequence of the VL comprises the amino acid sequence set forth in SEQ ID NO:837.

29. The isolated antibody of claim 2, wherein the sequence of the VH consists of the amino acid sequence set forth in SEQ ID NO:836 and the sequence of the VL consists of the amino acid sequence set forth in SEQ ID NO:837.

30. The isolated antibody of claim 28, wherein the antibody comprises a heavy chain constant region of human IgG1.

31. The isolated antibody of claim 29, wherein the antibody comprises a heavy chain constant region of human IgG1.

32. A pharmaceutical composition comprising (i) the isolated antibody of claim 28 and (ii) a pharmaceutically acceptable excipient.

33. A pharmaceutical composition comprising (i) the isolated antibody of claim 29 and (ii) a pharmaceutically acceptable excipient.

34. A pharmaceutical composition comprising (i) the isolated antibody of claim 30 and (ii) a pharmaceutically acceptable excipient.

35. A pharmaceutical composition comprising (i) the isolated antibody of claim 31 and (ii) a pharmaceutically acceptable excipient.

36. The isolated antibody of claim 1, wherein the antibody binds to human TF with a $K_D$ of less than or equal to 10 nM, as measured by Octet QK384 or Biacore assay.

37. The isolated antibody of claim 1, wherein the antibody binds to human TF with a $K_D$ of less than or equal to 5 nM, as measured by Octet QK384 or Biacore assay.

38. The isolated antibody of claim 1, wherein the antibody binds to human TF with a $K_D$ of less than or equal to 1 nM, as measured by Octet QK384 or Biacore assay.

39. The isolated antibody of claim 1, wherein the antibody binds to human TF with a $K_D$ of less than or equal to 0.5 nM, as measured by Octet QK384 or Biacore assay.

40. The isolated antibody of claim 1, wherein the antibody binds to human TF with a $K_D$ of less than or equal to 0.1 nM, as measured by Octet QK384 or Biacore assay.

* * * * *

SEQUENCE LISTING

<160> NUMBER OF SEQ ID NOS: 922

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser Asp Tyr Ala Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ile Ser Gly Ser Gly Gly Leu Thr Tyr Tyr Ala Asp Ser Val Lys
1               5                   10                  15
Gly

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Pro Tyr Gly Tyr Tyr Met Asp Val
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Ser Ile Ser Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala Ser Ser Leu Glu Ser
1               5

<210> SEQ ID NO 6
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Gln Gln Tyr Lys Ser Tyr Ile Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Tyr Ala Met Gly
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Ile Ser Gly Ser Gly Gly Leu Thr Tyr Tyr Ala Asp Ser Val Lys
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Pro Tyr Gly Tyr Tyr Met Asp Val
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Ser Ile Ser Ser Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ala Ser Ser Leu Glu Ser
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr Lys Ser Tyr Ile Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Phe Thr Phe Ser Asp Tyr
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ser Gly Gly
1

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Tyr Gly Tyr Tyr Met Asp
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Ser Ile Ser Ser Trp
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 17

Lys Ala Ser
1

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Lys Ser Tyr Ile
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Phe Thr Phe Ser Asp Tyr Ala Met Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Ile Ser Gly Ser Gly Gly Leu Thr Tyr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Pro Tyr Gly Tyr Tyr Met Asp Val
1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Gln Ser Ile Ser Ser Trp Leu Ala
1               5                   10

<210> SEQ ID NO 23

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ala Ser Ser Leu Glu Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr Lys Ser Tyr Ile Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Asp Tyr Ala Met Gly
1               5

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Val Ser Thr Ile Ser Gly Ser Gly Gly Leu Thr Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Lys Ala Pro Tyr Gly Tyr Tyr Met Asp
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Ser Ser Trp Leu Ala Trp Tyr
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Leu Ile Tyr Lys Ala Ser Ser Leu Glu
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Tyr Lys Ser Tyr Ile
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Ser Asp Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ser Gly Ser Gly Gly Leu Thr
1               5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Lys Ala Pro Tyr Gly Tyr Tyr Met Asp Val
1               5                   10

<210> SEQ ID NO 34
<211> LENGTH: 6
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 34

Gln Ser Ile Ser Ser Trp
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 35

Lys Ala Ser
1

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 36

Gln Gln Tyr Lys Ser Tyr Ile Thr
1               5

<210> SEQ ID NO 37
<211> LENGTH: 118
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Val
        35                  40                  45

Ser Thr Ile Ser Gly Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Tyr Gly Tyr Tyr Met Asp Val Trp Gly Lys Gly Thr
            100                 105                 110

Thr Val Thr Val Ser Ser
        115

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ile Thr
                85                  90                  95

Phe Gly Gly Gly Thr Lys Val Glu Ile Lys
            100                 105

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Thr Phe Ser Ser Tyr Ala Met Ala
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Ile Ser Gly Ser Gly Gly Leu Thr Tyr Tyr Ala Asp Ser Val Lys
1               5                   10                  15

Gly

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Pro Tyr Gly Tyr Tyr Met Asp Val
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ala Ser Gln Ser Ile Ser Ser Trp Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Ala Ser Ser Leu Glu Ser
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Tyr Lys Ser Tyr Ile Thr
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Tyr Ala Met Ala
1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ile Ser Gly Ser Gly Gly Leu Thr Tyr Tyr Ala Asp Ser Val Lys
1               5                   10                  15

Gly

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Pro Tyr Gly Tyr Tyr Met Asp Val
1               5

<210> SEQ ID NO 48
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Ser Ile Ser Ser Trp Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ala Ser Ser Leu Glu Ser
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Tyr Lys Ser Tyr Ile Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Thr Phe Ser Ser Tyr
1               5

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ser Gly Gly
1

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Tyr Gly Tyr Tyr Met Asp
1               5
```

```
<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gln Ser Ile Ser Ser Trp
1               5

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Ala Ser
1

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Tyr Lys Ser Tyr Ile
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Phe Thr Phe Ser Ser Tyr Ala Met Ala
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Ile Ser Gly Ser Gly Gly Leu Thr Tyr
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 59

Ala Pro Tyr Gly Tyr Tyr Met Asp Val
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Ser Ile Ser Ser Trp Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Ala Ser Ser Leu Glu Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Tyr Lys Ser Tyr Ile Thr
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ser Tyr Ala Met Ala
1               5

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Trp Val Ser Ala Ile Ser Gly Ser Gly Gly Leu Thr Tyr
1               5                   10

<210> SEQ ID NO 65
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Lys Ala Pro Tyr Gly Tyr Tyr Met Asp
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Ser Trp Leu Ala Trp Tyr
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Leu Ile Tyr Lys Ala Ser Ser Leu Glu
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Tyr Lys Ser Tyr Ile
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Phe Thr Phe Ser Ser Tyr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70
```

```
Ile Ser Gly Ser Gly Gly Leu Thr
1               5

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Lys Ala Pro Tyr Gly Tyr Tyr Met Asp Val
1               5                   10

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ser Ile Ser Ser Trp
1               5

<210> SEQ ID NO 73
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Ala Ser
1

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Lys Ser Tyr Ile Thr
1               5

<210> SEQ ID NO 75
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ala Trp Val Arg Gln Ala Pro Gly Lys Gly Leu Glu Trp Val
        35                  40                  45
```

Ser Ala Ile Ser Gly Ser Gly Gly Leu Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Tyr Gly Tyr Tyr Met Asp Val Trp Gly Lys Gly Thr
            100                 105                 110

Thr Val Thr Val Ser Ser
            115

<210> SEQ ID NO 76
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ile Thr
                85                  90                  95

Phe Gly Gly Gly Thr Lys Val Glu Ile Lys
            100                 105

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Tyr Thr Phe Asp Val Tyr Gly Ile Ser
1               5                   10

<210> SEQ ID NO 78
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Ile Ala Pro Tyr Asn Gly Asn Thr Asn Tyr Ala Gln Lys Leu Gln
1               5                   10                  15

Gly

<210> SEQ ID NO 79

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ala Gly Thr Tyr Ser Pro Phe Gly Tyr Gly Met Asp Val
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ala Ser Gln Ser Ile Ser Ser Trp Leu Ala
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Ala Ser Ser Leu Glu Ser
1               5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Phe Gln Ser Leu Pro Pro Phe Thr
1               5                   10

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Tyr Gly Ile Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84
```

```
Trp Ile Ala Pro Tyr Asn Gly Asn Thr Asn Tyr Ala Gln Lys Leu Gln
1               5                   10                  15
Gly

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ala Gly Thr Tyr Ser Pro Phe Gly Tyr Gly Met Asp Val
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Ser Gln Ser Ile Ser Ser Trp Leu Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Ala Ser Ser Leu Glu Ser
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Phe Gln Ser Leu Pro Pro Phe Thr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Tyr Thr Phe Asp Val Tyr
1               5

<210> SEQ ID NO 90
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 90

Pro Tyr Asn Gly
1

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Gly Thr Tyr Ser Pro Phe Gly Tyr Gly Met Asp
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Gln Ser Ile Ser Ser Trp
1               5

<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Ala Ser
1

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Phe Gln Ser Leu Pro Pro Phe
1               5

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Tyr Thr Phe Asp Val Tyr Gly Ile Ser
1               5                   10
```

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Trp Ile Ala Pro Tyr Asn Gly Asn Thr Asn
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Ala Gly Thr Tyr Ser Pro Phe Gly Tyr Gly Met Asp Val
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Ser Ile Ser Ser Trp Leu Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Ala Ser Ser Leu Glu Ser
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Phe Gln Ser Leu Pro Pro Phe Thr
1               5                   10

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Asp Val Tyr Gly Ile Ser
1               5

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Met Gly Trp Ile Ala Pro Tyr Asn Gly Asn Thr Asn
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Asp Ala Gly Thr Tyr Ser Pro Phe Gly Tyr Gly Met Asp
1               5                   10                  15

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Trp Leu Ala Trp Tyr
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Leu Ile Tyr Lys Ala Ser Ser Leu Glu
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gln Phe Gln Ser Leu Pro Pro Phe
1               5

<210> SEQ ID NO 107
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Tyr Thr Phe Asp Val Tyr Gly
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Ala Pro Tyr Asn Gly Asn Thr
1               5

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Arg Asp Ala Gly Thr Tyr Ser Pro Phe Gly Thr Gly Met Asp Val
1               5                   10                  15

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Ser Ile Ser Ser Trp
1               5

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Lys Ala Ser
1

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Gln Phe Gln Ser Leu Pro Pro Phe Thr
```

<210> SEQ ID NO 113
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Asp Val Tyr
            20                  25                  30

Gly Ile Ser Trp Val Arg Gln Ala Pro Gly Gln Gly Leu Glu Trp Met
        35                  40                  45

Gly Trp Ile Ala Pro Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Phe Gly Tyr Gly Met Asp Val
            100                 105                 110

Trp Gly Gln Gly Thr Thr Val Thr Val Ser Ser
        115                 120
```

<210> SEQ ID NO 114
<211> LENGTH: 108
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Ser Leu Pro Pro
                85                  90                  95

Phe Thr Phe Gly Gly Gly Thr Lys Val Glu Ile Lys
            100                 105
```

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

```
Gly Tyr Thr Phe Asp Val Tyr Gly Ile Ser
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Trp Ile Ala Pro Tyr Ser Gly Asn Thr Asn Tyr Ala Gln Lys Leu Gln
1               5                   10                  15

Gly

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Ala Gly Thr Tyr Ser Pro Phe Gly Tyr Gly Met Asp Val
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Ala Ser Gln Ser Ile Asn Asn Trp Leu Ala
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Lys Ala Tyr Asn Leu Glu Ser
1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Leu Phe Gln Ser Leu Pro Pro Phe Thr
1               5                   10

<210> SEQ ID NO 121
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Val Tyr Gly Ile Ser
1               5

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Ile Ala Pro Tyr Ser Gly Asn Thr Asn Tyr Ala Gln Lys Leu Gln
1               5                   10                  15

Gly

<210> SEQ ID NO 123
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Asp Ala Gly Thr Tyr Ser Pro Phe Gly Tyr Gly Met Asp Val
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Ala Ser Gln Ser Ile Asn Asn Trp Leu Ala
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Lys Ala Tyr Asn Leu Glu Ser
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126
```

Gln Leu Phe Gln Ser Leu Pro Pro Phe Thr
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Tyr Thr Phe Asp Val Tyr
1               5

<210> SEQ ID NO 128
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Pro Tyr Ser Gly
1

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Gly Thr Tyr Ser Pro Phe Gly Tyr Gly Met Asp
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Gln Ser Ile Asn Asn Trp
1               5

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Ala Tyr
1

<210> SEQ ID NO 132
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 132

Phe Gln Ser Leu Pro Pro Phe
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Tyr Thr Phe Asp Val Tyr Gly Ile Ser
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Trp Ile Ala Pro Tyr Ser Gly Asn Thr Asn
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ala Gly Thr Tyr Ser Pro Phe Gly Tyr Gly Met Asp Val
1               5                   10

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Ala Ser Gln Ser Ile Asn Asn Trp Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Ala Tyr Asn Leu Glu Ser
1               5
```

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gln Leu Phe Gln Ser Leu Pro Pro Phe Thr
1               5                   10

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Val Tyr Gly Ile Ser
1               5

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Met Gly Trp Ile Ala Pro Tyr Ser Gly Asn Thr Asn
1               5                   10

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Arg Asp Ala Gly Thr Tyr Ser Pro Phe Gly Tyr Gly Met Asp
1               5                   10                  15

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asn Asn Trp Leu Ala Trp Tyr
1               5

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Leu Ile Tyr Lys Ala Tyr Asn Leu Glu
1               5                   10

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gln Leu Phe Gln Ser Leu Pro Pro Phe
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Tyr Thr Phe Asp Val Tyr Gly
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Ala Pro Tyr Ser Gly Asn Thr
1               5

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Arg Asp Ala Gly Thr Tyr Ser Pro Phe Gly Thr Gly Met Asp Val
1               5                   10                  15

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Ser Ile Asn Asn Trp
1               5

<210> SEQ ID NO 149
<211> LENGTH: 3
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 149

Lys Ala Tyr
1

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Leu Phe Gln Ser Leu Pro Pro Phe Thr
1               5                   10

<210> SEQ ID NO 151
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Val Tyr
                20                  25                  30

Gly Ile Ser Trp Val Arg Gln Ala Pro Gly Gln Gly Leu Glu Trp Met
            35                  40                  45

Gly Trp Ile Ala Pro Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Phe Gly Tyr Gly Met Asp Val
                100                 105                 110

Trp Gly Gln Gly Thr Thr Val Thr Val Ser Ser
            115                 120

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asn Asn Trp
                20                  25                  30

Leu Ala Trp Tyr Gln Gln Lys Pro Gly Lys Ala Pro Lys Leu Leu Ile
            35                  40                  45

```
Tyr Lys Ala Tyr Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Leu Phe Gln Ser Leu Pro Pro
                 85                  90                  95

Phe Thr Phe Gly Gly Gly Thr Lys Val Glu Ile Lys
                100                 105
```

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

```
Gly Tyr Thr Phe Asp Val Tyr Gly Ile Ser
 1               5                  10
```

<210> SEQ ID NO 154
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Trp Ile Ala Pro Tyr Ser Gly Asn Thr Asn Tyr Ala Gln Lys Leu Gln
 1               5                  10                  15

Gly
```

<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

```
Asp Ala Gly Thr Tyr Ser Pro Phe Gly Tyr Gly Met Asp Val
 1               5                  10
```

<210> SEQ ID NO 156
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Arg Ala Ser Glu Ser Ile Ser Asn Trp Leu Ala
 1               5                  10
```

<210> SEQ ID NO 157
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 157

Lys Ala Tyr Ser Leu Glu Tyr
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Gln Phe Gln Lys Leu Pro Pro Phe Thr
1               5                   10

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Val Tyr Gly Ile Ser
1               5

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Ile Ala Pro Tyr Ser Gly Asn Thr Asn Tyr Ala Gln Lys Leu Gln
1               5                   10                  15

Gly

<210> SEQ ID NO 161
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Asp Ala Gly Thr Tyr Ser Pro Phe Gly Tyr Gly Met Asp Val
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Ala Ser Glu Ser Ile Ser Asn Trp Leu Ala
1               5                   10

<210> SEQ ID NO 163
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Lys Ala Tyr Ser Leu Glu Tyr
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Phe Gln Lys Leu Pro Pro Phe Thr
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Tyr Thr Phe Asp Val Tyr
1               5

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Pro Tyr Ser Gly
1

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Gly Thr Tyr Ser Pro Phe Gly Tyr Gly Met Asp
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168
```

-continued

Ser Glu Ser Ile Ser Asn Trp
1               5

<210> SEQ ID NO 169
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Ala Tyr
1

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Phe Gln Lys Leu Pro Pro Phe
1               5

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Tyr Thr Phe Asp Val Tyr Gly Ile Ser
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Ile Ala Pro Tyr Ser Gly Asn Thr Asn
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asp Ala Gly Thr Tyr Ser Pro Phe Gly Tyr Gly Met Asp Val
1               5                   10

<210> SEQ ID NO 174
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 174

Arg Ala Ser Glu Ser Ile Ser Asn Trp Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Ala Tyr Ser Leu Glu Tyr
1               5

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gln Gln Phe Gln Lys Leu Pro Pro Phe Thr
1               5                   10

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Val Tyr Gly Ile Ser
1               5

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Trp Met Gly Trp Ile Ala Pro Tyr Ser Gly Asn Thr Asn
1               5                   10

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Arg Asp Ala Gly Thr Tyr Ser Pro Phe Gly Tyr Gly Met Asp
1               5                   10                  15

```
<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Asn Trp Leu Ala Trp Tyr
1               5

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Leu Leu Ile Tyr Lys Ala Tyr Ser Leu Glu
1               5                   10

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Gln Phe Gln Lys Leu Pro Pro Phe
1               5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Tyr Thr Phe Asp Val Tyr Gly
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ile Ala Pro Tyr Ser Gly Asn Thr
1               5

<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185
```

```
Ala Arg Asp Ala Gly Thr Tyr Ser Pro Phe Gly Thr Gly Met Asp Val
 1               5                  10                 15
```

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

```
Glu Ser Ile Ser Asn Trp
 1               5
```

<210> SEQ ID NO 187
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Lys Ala Tyr
 1
```

<210> SEQ ID NO 188
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

```
Gln Gln Phe Gln Lys Leu Pro Pro Phe Thr
 1               5                  10
```

<210> SEQ ID NO 189
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asp Val Tyr
            20                  25                  30

Gly Ile Ser Trp Val Arg Gln Ala Pro Gly Gln Gly Leu Glu Trp Met
        35                  40                  45

Gly Trp Ile Ala Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Phe Gly Tyr Gly Met Asp Val
            100                 105                 110

Trp Gly Gln Gly Thr Thr Val Thr Val Ser Ser
        115                 120
```

<210> SEQ ID NO 190
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Tyr Ser Leu Glu Tyr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Lys Leu Pro Pro
                85                  90                  95

Phe Thr Phe Gly Gly Gly Thr Lys Val Glu Ile Lys
            100                 105

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Tyr Thr Phe Arg Ser Tyr Gly Ile Ser
1               5                   10

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Trp Val Ala Pro Tyr Asn Gly Asn Thr Asn Tyr Ala Gln Lys Leu Gln
1               5                   10                  15

Gly

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Ala Gly Thr Tyr Ser Pro Tyr Gly Tyr Gly Met Asp Val
1               5                   10

```
<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ala Ser Gln Ser Ile Ser Ser Trp Leu Ala
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Lys Ala Ser Ser Leu Glu Ser
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln Phe Gln Ser Leu Pro Pro Phe Thr
1               5                   10

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Tyr Gly Ile Ser
1               5

<210> SEQ ID NO 198
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Trp Val Ala Pro Tyr Asn Gly Asn Thr Asn Tyr Ala Gln Lys Leu Gln
1               5                   10                  15

Gly

<210> SEQ ID NO 199
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 199

Asp Ala Gly Thr Tyr Ser Pro Tyr Gly Tyr Gly Met Asp Val
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ser Gln Ser Ile Ser Ser Trp Leu Ala
1               5                   10

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Lys Ala Ser Ser Leu Glu Ser
1               5

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gln Gln Phe Gln Ser Leu Pro Pro Phe Thr
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Tyr Thr Phe Arg Ser Tyr
1               5

<210> SEQ ID NO 204
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Pro Tyr Asn Gly
1

<210> SEQ ID NO 205
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Gly Thr Tyr Ser Pro Tyr Gly Tyr Gly Met Asp
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Gln Ser Ile Ser Ser Trp
1               5

<210> SEQ ID NO 207
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Lys Ala Ser
1

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Phe Gln Ser Leu Pro Pro Phe
1               5

<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Tyr Thr Phe Arg Ser Tyr Gly Ile Ser
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Trp Val Ala Pro Tyr Asn Gly Asn Thr Asn
```

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Asp Ala Gly Thr Tyr Ser Pro Tyr Gly Tyr Gly Met Asp Val
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ala Ser Gln Ser Ile Ser Ser Trp Leu Ala
1               5                   10

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Lys Ala Ser Ser Leu Glu Ser
1               5

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Gln Phe Gln Ser Leu Pro Pro Phe Thr
1               5                   10

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Ser Tyr Gly Ile Ser
1               5

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Trp Met Gly Trp Val Ala Pro Tyr Asn Gly Asn Thr Asn
1               5                   10

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Arg Asp Ala Gly Thr Tyr Ser Pro Tyr Gly Tyr Gly Met Asp
1               5                   10                  15

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Ser Trp Leu Ala Trp Tyr
1               5

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Leu Leu Ile Tyr Lys Ala Ser Ser Leu Glu
1               5                   10

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Gln Phe Gln Ser Leu Pro Pro Phe
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Tyr Thr Phe Arg Ser Tyr Gly
1               5

<210> SEQ ID NO 222

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Ala Pro Tyr Asn Gly Asn Thr
1               5

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Arg Asp Ala Gly Thr Tyr Ser Pro Tyr Gly Tyr Gly Met Asp Val
1               5                   10                  15

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Gln Ser Ile Ser Ser Trp
1               5

<210> SEQ ID NO 225
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Lys Ala Ser
1

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gln Gln Phe Gln Ser Leu Pro Pro Phe Thr
1               5                   10

<210> SEQ ID NO 227
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Gly Ile Ser Trp Val Arg Gln Ala Pro Gly Gln Gly Leu Glu Trp Met
        35                  40                  45

Gly Trp Val Ala Pro Tyr Asn Gly Asn Thr Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Tyr Gly Tyr Gly Met Asp Val
            100                 105                 110

Trp Gly Gln Gly Thr Thr Val Thr Val Ser Ser
        115                 120

<210> SEQ ID NO 228
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Ser Leu Pro Pro
                85                  90                  95

Phe Thr Phe Gly Gly Gly Thr Lys Val Glu Ile Lys
            100                 105

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Tyr Thr Phe Arg Ser Tyr Gly Ile Ser
1               5                   10

<210> SEQ ID NO 230
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Val Ala Pro Tyr Ser Gly Asn Thr Asn Tyr Ala Gln Lys Leu Gln
1               5                   10                  15

Gly

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asp Ala Gly Thr Tyr Ser Pro Tyr Gly Tyr Gly Met Asp Val
1               5                   10

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Ala Ser His Ser Ile Asp Ser Trp Leu Ala
1               5                   10

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Lys Ala Ser Tyr Leu Glu Ser
1               5

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Gln Leu Phe Gln Ser Leu Pro Pro Phe Thr
1               5                   10

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Tyr Gly Ile Ser
1               5

<210> SEQ ID NO 236

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Val Ala Pro Tyr Ser Gly Asn Thr Asn Tyr Ala Gln Lys Leu Gln
1               5                   10                  15
Gly

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Asp Ala Gly Thr Tyr Ser Pro Tyr Gly Tyr Gly Met Asp Val
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Arg Ala Ser His Ser Ile Asp Ser Trp Leu Ala
1               5                   10

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Lys Ala Ser Tyr Leu Glu Ser
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Leu Phe Gln Ser Leu Pro Pro Phe Thr
1               5                   10

<210> SEQ ID NO 241
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 241

Gly Tyr Thr Phe Arg Ser Tyr
1               5

<210> SEQ ID NO 242
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Pro Tyr Ser Gly
1

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Gly Thr Tyr Ser Pro Tyr Gly Tyr Gly Met Asp
1               5                   10

<210> SEQ ID NO 244
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ser His Ser Ile Asp Ser Trp
1               5

<210> SEQ ID NO 245
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Ala Ser
1

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Phe Gln Ser Leu Pro Pro Phe
1               5

<210> SEQ ID NO 247
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 247

Gly Tyr Thr Phe Arg Ser Tyr Gly Ile Ser
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Val Ala Pro Tyr Ser Gly Asn Thr Asn
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Asp Ala Gly Thr Tyr Ser Pro Tyr Gly Tyr Gly Met Asp Val
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Arg Ala Ser His Ser Ile Asp Ser Trp Leu Ala
1               5                   10

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Lys Ala Ser Tyr Leu Glu Ser
1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Leu Phe Gln Ser Leu Pro Pro Phe Thr
1               5                   10
```

```
<210> SEQ ID NO 253
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Arg Ser Tyr Gly Ile Ser
1               5

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Met Gly Trp Val Ala Pro Tyr Ser Gly Asn Thr Asn
1               5                   10

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Arg Asp Ala Gly Thr Tyr Ser Pro Tyr Gly Tyr Gly Met Asp
1               5                   10                  15

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asp Ser Trp Leu Ala Trp Tyr
1               5

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Leu Leu Ile Tyr Lys Ala Ser Tyr Leu Glu
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 258

Gln Leu Phe Gln Ser Leu Pro Pro Phe
1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Tyr Thr Phe Arg Ser Tyr Gly
1               5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Ala Pro Tyr Ser Gly Asn Thr
1               5

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ala Arg Asp Ala Gly Thr Tyr Ser Pro Tyr Gly Tyr Gly Met Asp Val
1               5                   10                  15

<210> SEQ ID NO 262
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

His Ser Ile Asp Ser Trp
1               5

<210> SEQ ID NO 263
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Ala Ser
1

<210> SEQ ID NO 264
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Leu Phe Gln Ser Leu Pro Pro Phe Thr
1               5                   10

<210> SEQ ID NO 265
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Gly Ile Ser Trp Val Arg Gln Ala Pro Gly Gln Gly Leu Glu Trp Met
        35                  40                  45

Gly Trp Val Ala Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Tyr Gly Tyr Gly Met Asp Val
            100                 105                 110

Trp Gly Gln Gly Thr Thr Val Thr Val Ser Ser
        115                 120

<210> SEQ ID NO 266
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Gln Met Thr Gln Ser Pro Ser Thr Leu Ser Ala Ser Val Gly
1               5                   10                  15

Asp Arg Val Thr Ile Thr Cys Arg Ala Ser His Ser Ile Asp Ser Trp
            20                  25                  30

Leu Ala Trp Tyr Gln Gln Lys Pro Gly Lys Ala Pro Lys Leu Leu Ile
        35                  40                  45

Tyr Lys Ala Ser Tyr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Leu Phe Gln Ser Leu Pro Pro
                85                  90                  95

Phe Thr Phe Gly Gly Gly Thr Lys Val Glu Ile Lys
            100                 105
```

```
<210> SEQ ID NO 267
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Tyr Thr Phe Arg Ser Tyr Gly Ile Ser
1               5                   10

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Trp Val Ala Pro Tyr Ser Gly Asn Thr Asn Tyr Ala Gln Lys Leu Gln
1               5                   10                  15

Gly

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Asp Ala Gly Thr Tyr Ser Pro Tyr Gly Tyr Gly Met Asp Val
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Gln Ala Ser Gln Ser Ile Asp Ser Trp Leu Ala
1               5                   10

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ser Ala Ser Tyr Leu Glu Ser
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 272

Gln Arg Phe Gln Ser Leu Pro Pro Phe Thr
1               5                   10

<210> SEQ ID NO 273
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ser Tyr Gly Ile Ser
1               5

<210> SEQ ID NO 274
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Trp Val Ala Pro Tyr Ser Gly Asn Thr Asn Tyr Ala Gln Lys Leu Gln
1               5                   10                  15

Gly

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asp Ala Gly Thr Tyr Ser Pro Tyr Gly Tyr Gly Met Asp Val
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gln Ala Ser Gln Ser Ile Asp Ser Trp Leu Ala
1               5                   10

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ser Ala Ser Tyr Leu Glu Ser
1               5
```

```
<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Gln Arg Phe Gln Ser Leu Pro Pro Phe Thr
1               5                   10

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Tyr Thr Phe Arg Ser Tyr
1               5

<210> SEQ ID NO 280
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Pro Tyr Ser Gly
1

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ala Gly Thr Tyr Ser Pro Tyr Gly Tyr Gly Met Asp
1               5                   10

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ser Gln Ser Ile Asp Ser Trp
1               5

<210> SEQ ID NO 283
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283
```

Ser Ala Ser
1

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Phe Gln Ser Leu Pro Pro Phe
1               5

<210> SEQ ID NO 285
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Tyr Thr Phe Arg Ser Tyr Gly Ile Ser
1               5                   10

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Trp Val Ala Pro Tyr Ser Gly Asn Thr Asn
1               5                   10

<210> SEQ ID NO 287
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Ala Gly Thr Tyr Ser Pro Tyr Gly Tyr Gly Met Asp Val
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gln Ala Ser Gln Ser Ile Asp Ser Trp Leu Ala
1               5                   10

<210> SEQ ID NO 289
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 289

Ser Ala Ser Tyr Leu Glu Ser
1               5

<210> SEQ ID NO 290
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gln Arg Phe Gln Ser Leu Pro Pro Phe Thr
1               5                   10

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Arg Ser Tyr Gly Ile Ser
1               5

<210> SEQ ID NO 292
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Trp Met Gly Trp Val Ala Pro Tyr Ser Gly Asn Thr Asn
1               5                   10

<210> SEQ ID NO 293
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ala Arg Asp Ala Gly Thr Tyr Ser Pro Tyr Gly Tyr Gly Met Asp
1               5                   10                  15

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Asp Ser Trp Leu Ala Trp Tyr
1               5
```

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Leu Leu Ile Tyr Ser Ala Ser Tyr Leu Glu
1               5                   10

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gln Arg Phe Gln Ser Leu Pro Pro Phe
1               5

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Tyr Thr Phe Arg Ser Tyr Gly
1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Val Ala Pro Tyr Ser Gly Asn Thr
1               5

<210> SEQ ID NO 299
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ala Arg Asp Ala Gly Thr Tyr Ser Pro Tyr Gly Tyr Gly Met Asp Val
1               5                   10                  15

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gln Ser Ile Asp Ser Trp
1               5

<210> SEQ ID NO 301
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Ser Ala Ser
1

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gln Arg Phe Gln Ser Leu Pro Pro Phe Thr
1               5                   10

<210> SEQ ID NO 303
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
                20                  25                  30

Gly Ile Ser Trp Val Arg Gln Ala Pro Gly Gln Gly Leu Glu Trp Met
            35                  40                  45

Gly Trp Val Ala Pro Tyr Ser Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Ala Gly Thr Tyr Ser Pro Tyr Gly Tyr Gly Met Asp Val
                100                 105                 110

Trp Gly Gln Gly Thr Thr Val Thr Val Ser Ser
            115                 120

<210> SEQ ID NO 304
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ala Trp Tyr Gln Gln Lys Pro Gly Lys Ala Pro Lys Leu Leu Ile
        35                  40                  45

Tyr Ser Ala Ser Tyr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Arg Phe Gln Ser Leu Pro Pro
                85                  90                  95

Phe Thr Phe Gly Gly Gly Thr Lys Val Glu Ile Lys
            100                 105
```

<210> SEQ ID NO 305
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

```
Gly Phe Thr Phe His Ser Arg Gly Met His
1               5                   10
```

<210> SEQ ID NO 306
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

```
Val Ile Thr Tyr Asp Gly Ile Asn Lys Tyr Tyr Ala Asp Ser Val Glu
1               5                   10                  15

Gly
```

<210> SEQ ID NO 307
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

```
Asp Gly Val Tyr Tyr Gly Val Tyr Asp Tyr
1               5                   10
```

<210> SEQ ID NO 308
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

```
Lys Ser Ser Gln Ser Val Leu Phe Ser Ser Asn Asn Lys Asn Tyr Leu
1               5                   10                  15
```

Ala

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Trp Ala Ser Thr Arg Glu Ser
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gln Gln Phe His Ser Tyr Pro Leu Thr
1               5

<210> SEQ ID NO 311
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ser Arg Gly Met His
1               5

<210> SEQ ID NO 312
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Val Ile Thr Tyr Asp Gly Ile Asn Lys Tyr Tyr Ala Asp Ser Val Glu
1               5                   10                  15

Gly

<210> SEQ ID NO 313
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Asp Gly Val Tyr Tyr Gly Val Tyr Asp Tyr
1               5                   10

<210> SEQ ID NO 314
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Lys Ser Ser Gln Ser Val Leu Phe Ser Ser Asn Asn Lys Asn Tyr Leu
1               5                   10                  15

Ala

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Trp Ala Ser Thr Arg Glu Ser
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Gln Phe His Ser Tyr Pro Leu Thr
1               5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gly Phe Thr Phe His Ser Arg
1               5

<210> SEQ ID NO 318
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Tyr Asp Gly Ile
1

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gly Val Tyr Tyr Gly Val Tyr Asp

```
<210> SEQ ID NO 320
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ser Gln Ser Val Leu Phe Ser Ser Asn Asn Lys Asn Tyr
1               5                   10

<210> SEQ ID NO 321
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Trp Ala Ser
1

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Phe His Ser Tyr Pro Leu
1               5

<210> SEQ ID NO 323
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gly Phe Thr Phe His Ser Arg Gly Met His
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Val Ile Thr Tyr Asp Gly Ile Asn Lys Tyr
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                                         peptide

<400> SEQUENCE: 325

Asp Gly Val Tyr Tyr Gly Val Tyr Asp Tyr
1               5                   10

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Lys Ser Ser Gln Ser Val Leu Phe Ser Ser Asn Asn Lys Asn Tyr Leu
1               5                   10                  15

Ala

<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Trp Ala Ser Thr Arg Glu Ser
1               5

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Gln Phe His Ser Tyr Pro Leu Thr
1               5

<210> SEQ ID NO 329
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

His Ser Arg Gly Met His
1               5

<210> SEQ ID NO 330
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Trp Val Ala Val Ile Thr Tyr Asp Gly Ile Asn Lys Tyr
1               5                   10
```

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Arg Asp Gly Val Tyr Tyr Gly Val Tyr Asp
1               5                   10

<210> SEQ ID NO 332
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Leu Phe Ser Ser Asn Asn Lys Asn Tyr Leu Ala Trp Tyr
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Leu Leu Ile Tyr Trp Ala Ser Thr Arg Glu
1               5                   10

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gln Gln Phe His Ser Tyr Pro Leu
1               5

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gly Phe Thr Phe His Ser Arg Gly
1               5

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 336

Ile Thr Tyr Asp Gly Ile Asn Lys
1               5

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Arg Asp Gly Val Tyr Tyr Gly Val Tyr Asp Tyr
1               5                   10

<210> SEQ ID NO 338
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gln Ser Val Leu Phe Ser Ser Asn Asn Lys Asn Tyr
1               5                   10

<210> SEQ ID NO 339
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Trp Ala Ser
1

<210> SEQ ID NO 340
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gln Gln Phe His Ser Tyr Pro Leu Thr
1               5

<210> SEQ ID NO 341
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe His Ser Arg
            20                  25                  30

Gly Met His Trp Val Arg Gln Ala Pro Gly Lys Gly Leu Glu Trp Val
```

```
                35                  40                  45
Ala Val Ile Thr Tyr Asp Gly Ile Asn Lys Tyr Tyr Ala Asp Ser Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Val Tyr Tyr Val Tyr Asp Tyr Trp Gly Gln Gly
                100                 105                 110

Thr Leu Val Thr Val Ser Ser
        115

<210> SEQ ID NO 342
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe His Ser Tyr Pro Leu Thr Phe Gly Gly Gly Thr Lys Val Glu Ile
                100                 105                 110

Lys

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Phe Thr Phe Arg Ser Tyr Gly Met His
 1               5                  10

<210> SEQ ID NO 344
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Val Ile Thr Tyr Asp Gly Ile Asn Lys Tyr Tyr Ala Asp Ser Val Glu
 1               5                  10                  15
```

Gly

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Asp Gly Val Tyr Tyr Gly Val Tyr Asp Tyr
1               5                   10

<210> SEQ ID NO 346
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Lys Ser Ser Gln Ser Val Leu Phe Ser Ser Asn Asn Lys Asn Tyr Leu
1               5                   10                  15

Ala

<210> SEQ ID NO 347
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Trp Ala Ser Thr Arg Glu Ser
1               5

<210> SEQ ID NO 348
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gln Gln Phe His Ser Tyr Pro Leu Thr
1               5

<210> SEQ ID NO 349
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ser Tyr Gly Met His
1               5

<210> SEQ ID NO 350
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 350

Val Ile Thr Tyr Asp Gly Ile Asn Lys Tyr Tyr Ala Asp Ser Val Glu
1               5                   10                  15

Gly

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Gly Val Tyr Tyr Gly Val Tyr Asp Tyr
1               5                   10

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Lys Ser Ser Gln Ser Val Leu Phe Ser Ser Asn Asn Lys Asn Tyr Leu
1               5                   10                  15

Ala

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Trp Ala Ser Thr Arg Glu Ser
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Gln Phe His Ser Tyr Pro Leu Thr
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355
```

```
Gly Phe Thr Phe Arg Ser Tyr
1               5

<210> SEQ ID NO 356
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Tyr Asp Gly Ile
1

<210> SEQ ID NO 357
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Gly Val Tyr Tyr Gly Val Tyr Asp
1               5

<210> SEQ ID NO 358
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ser Gln Ser Val Leu Phe Ser Ser Asn Asn Lys Asn Tyr
1               5                   10

<210> SEQ ID NO 359
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Trp Ala Ser
1

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Phe His Ser Tyr Pro Leu
1               5

<210> SEQ ID NO 361
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 361

Gly Phe Thr Phe Arg Ser Tyr Gly Met His
1               5                   10

<210> SEQ ID NO 362
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Val Ile Thr Tyr Asp Gly Ile Asn Lys Tyr
1               5                   10

<210> SEQ ID NO 363
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Asp Gly Val Tyr Tyr Gly Val Tyr Asp Tyr
1               5                   10

<210> SEQ ID NO 364
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Lys Ser Ser Gln Ser Val Leu Phe Ser Ser Asn Asn Lys Asn Tyr Leu
1               5                   10                  15

Ala

<210> SEQ ID NO 365
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Trp Ala Ser Thr Arg Glu Ser
1               5

<210> SEQ ID NO 366
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Gln Gln Phe His Ser Tyr Pro Leu Thr
```

```
1               5

<210> SEQ ID NO 367
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Arg Ser Tyr Gly Met His
1               5

<210> SEQ ID NO 368
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Trp Val Ala Val Ile Thr Tyr Asp Gly Ile Asn Lys Tyr
1               5                   10

<210> SEQ ID NO 369
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Arg Asp Gly Val Tyr Tyr Gly Val Tyr Asp
1               5                   10

<210> SEQ ID NO 370
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Leu Phe Ser Ser Asn Asn Lys Asn Tyr Leu Ala Trp Tyr
1               5                   10

<210> SEQ ID NO 371
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Leu Leu Ile Tyr Trp Ala Ser Thr Arg Glu
1               5                   10

<210> SEQ ID NO 372
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 372

Gln Gln Phe His Ser Tyr Pro Leu
1               5

<210> SEQ ID NO 373
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Phe Thr Phe Arg Ser Tyr Gly
1               5

<210> SEQ ID NO 374
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Ile Thr Tyr Asp Gly Ile Asn Lys
1               5

<210> SEQ ID NO 375
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Arg Asp Gly Val Tyr Tyr Gly Val Tyr Asp Tyr
1               5                   10

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gln Ser Val Leu Phe Ser Ser Asn Asn Lys Asn Tyr
1               5                   10

<210> SEQ ID NO 377
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Trp Ala Ser
1

<210> SEQ ID NO 378

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Gln Gln Phe His Ser Tyr Pro Leu Thr
1               5

<210> SEQ ID NO 379
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Thr Tyr Asp Gly Ile Asn Lys Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Tyr Tyr Gly Val Tyr Asp Tyr Trp Gly Gln Gly
            100                 105                 110

Thr Leu Val Thr Val Ser Ser
        115

<210> SEQ ID NO 380
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe His Ser Tyr Pro Leu Thr Phe Gly Gly Gly Thr Lys Val Glu Ile
            100                 105                 110
```

-continued

Lys

<210> SEQ ID NO 381
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gly Gly Thr Phe Ser Ser Asn Ala Ile Gly
1               5                   10

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ser Ile Ile Pro Ile Ile Gly Phe Ala Asn Tyr Ala Gln Lys Phe Gln
1               5                   10                  15

Gly

<210> SEQ ID NO 383
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Asp Ser Gly Tyr Tyr Tyr Gly Ala Ser Ser Phe Gly Met Asp Val
1               5                   10                  15

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Arg Ala Ser Gln Ser Val Ser Ser Asn Leu Ala
1               5                   10

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gly Ala Ser Thr Arg Ala Thr
1               5

<210> SEQ ID NO 386
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 386

Glu Gln Tyr Asn Asn Leu Pro Leu Thr
1               5

<210> SEQ ID NO 387
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Ser Asn Ala Ile Gly
1               5

<210> SEQ ID NO 388
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ser Ile Ile Pro Ile Ile Gly Phe Ala Asn Tyr Ala Gln Lys Phe Gln
1               5                   10                  15

Gly

<210> SEQ ID NO 389
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Asp Ser Gly Tyr Tyr Tyr Gly Ala Ser Ser Phe Gly Met Asp Val
1               5                   10                  15

<210> SEQ ID NO 390
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Ala Ser Gln Ser Val Ser Ser Asn Leu Ala
1               5                   10

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gly Ala Ser Thr Arg Ala Thr
```

```
1               5

<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Glu Gln Tyr Asn Asn Leu Pro Leu Thr
1               5

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Gly Thr Phe Ser Ser Asn
1               5

<210> SEQ ID NO 394
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Pro Ile Ile Gly
1

<210> SEQ ID NO 395
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Ser Gly Tyr Tyr Tyr Gly Ala Ser Ser Phe Gly Met Asp
1               5                   10

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ser Gln Ser Val Ser Ser Asn
1               5

<210> SEQ ID NO 397
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 397

Gly Ala Ser
1

<210> SEQ ID NO 398
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Tyr Asn Asn Leu Pro Leu
1               5

<210> SEQ ID NO 399
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Gly Thr Phe Ser Ser Asn Ala Ile Gly
1               5                   10

<210> SEQ ID NO 400
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ser Ile Ile Pro Ile Ile Gly Phe Ala Asn
1               5                   10

<210> SEQ ID NO 401
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Asp Ser Gly Tyr Tyr Tyr Gly Ala Ser Ser Phe Gly Met Asp Val
1               5                   10                  15

<210> SEQ ID NO 402
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Arg Ala Ser Gln Ser Val Ser Ser Asn Leu Ala
1               5                   10

<210> SEQ ID NO 403

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Gly Ala Ser Thr Arg Ala Thr
1               5

<210> SEQ ID NO 404
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Glu Gln Tyr Asn Asn Leu Pro Leu Thr
1               5

<210> SEQ ID NO 405
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Ser Ser Asn Ala Ile Gly
1               5

<210> SEQ ID NO 406
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Trp Met Gly Ser Ile Ile Pro Ile Ile Gly Phe Ala Asn
1               5                   10

<210> SEQ ID NO 407
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ala Arg Asp Ser Gly Tyr Tyr Tyr Gly Ala Ser Ser Phe Gly Met Asp
1               5                   10                  15

<210> SEQ ID NO 408
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408
```

```
Ser Ser Asn Leu Ala Trp Tyr
1               5

<210> SEQ ID NO 409
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Leu Leu Ile Tyr Gly Ala Ser Thr Arg Ala
1               5                   10

<210> SEQ ID NO 410
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Glu Gln Tyr Asn Asn Leu Pro Leu
1               5

<210> SEQ ID NO 411
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gly Thr Phe Ser Ser Asn Ala
1               5

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Ile Ile Pro Ile Ile Gly Phe Ala
1               5

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ala Arg Asp Ser Gly Tyr Tyr Tyr Gly Ala Ser Ser Phe Gly Met Asp
1               5                   10                  15

Val

<210> SEQ ID NO 414
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 414

Gln Ser Val Ser Ser Asn
1               5

<210> SEQ ID NO 415
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Gly Ala Ser
1

<210> SEQ ID NO 416
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Glu Gln Tyr Asn Asn Leu Pro Leu Thr
1               5

<210> SEQ ID NO 417
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
                20                  25                  30

Ala Ile Gly Trp Val Arg Gln Ala Pro Gly Gln Gly Leu Glu Trp Met
            35                  40                  45

Gly Ser Ile Ile Pro Ile Ile Gly Phe Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Tyr Tyr Gly Ala Ser Ser Phe Gly Met Asp
            100                 105                 110

Val Trp Gly Gln Gly Thr Thr Val Thr Val Ser Ser
        115                 120

<210> SEQ ID NO 418
<211> LENGTH: 107
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 418

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Glu Gln Tyr Asn Asn Leu Pro Leu
                85                  90                  95

Thr Phe Gly Gly Gly Thr Lys Val Glu Ile Lys
            100                 105

<210> SEQ ID NO 419
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 419

Gly Gly Ser Ile Ser Ser Gly Gln Tyr Trp Ser
1               5                   10

<210> SEQ ID NO 420
<211> LENGTH: 16
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 420

Glu Ile Tyr Tyr Ser Gly Ser Thr Arg Tyr Asn Pro Ser Leu Lys Ser
1               5                   10                  15

<210> SEQ ID NO 421
<211> LENGTH: 16
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 421

Asp Ala Pro Tyr Tyr Tyr Gly Gly Gly Tyr Tyr Tyr Tyr Met Asp Val
1               5                   10                  15

<210> SEQ ID NO 422
<211> LENGTH: 12
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 422

Arg Ala Ser Gln Ser Val Ser Ser Ser Tyr Leu Ala
1               5                   10

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Ala Ser Ser Arg Ala Thr
1               5

<210> SEQ ID NO 424
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gln Gln Val Gly Val Val Pro Tyr Thr
1               5

<210> SEQ ID NO 425
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ser Gly Gln Tyr Trp Ser
1               5

<210> SEQ ID NO 426
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Glu Ile Tyr Tyr Ser Gly Ser Thr Arg Tyr Asn Pro Ser Leu Lys Ser
1               5                   10                  15

<210> SEQ ID NO 427
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Asp Ala Pro Tyr Tyr Tyr Gly Gly Gly Tyr Tyr Tyr Tyr Met Asp Val
1               5                   10                  15

<210> SEQ ID NO 428
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 428

Arg Ala Ser Gln Ser Val Ser Ser Tyr Leu Ala
1               5                   10

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gly Ala Ser Ser Arg Ala Thr
1               5

<210> SEQ ID NO 430
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gln Gln Val Gly Val Val Pro Tyr Thr
1               5

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Gly Gly Ser Ile Ser Ser Gly Gln
1               5

<210> SEQ ID NO 432
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Tyr Ser Gly
1

<210> SEQ ID NO 433
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ala Pro Tyr Tyr Tyr Gly Gly Gly Tyr Tyr Tyr Met Asp
1               5                   10

```
<210> SEQ ID NO 434
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ser Gln Ser Val Ser Ser Ser Tyr
1               5

<210> SEQ ID NO 435
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gly Ala Ser
1

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Val Gly Val Val Pro Tyr
1               5

<210> SEQ ID NO 437
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gly Gly Ser Ile Ser Ser Gly Gln Tyr Trp Ser
1               5                   10

<210> SEQ ID NO 438
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Glu Ile Tyr Tyr Ser Gly Ser Thr Arg
1               5

<210> SEQ ID NO 439
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439
```

```
Asp Ala Pro Tyr Tyr Tyr Gly Gly Tyr Tyr Tyr Met Asp Val
1               5                   10                  15

<210> SEQ ID NO 440
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Arg Ala Ser Gln Ser Val Ser Ser Ser Tyr Leu Ala
1               5                   10

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Ala Ser Ser Arg Ala Thr
1               5

<210> SEQ ID NO 442
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gln Gln Val Gly Val Val Pro Tyr Thr
1               5

<210> SEQ ID NO 443
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Ser Ser Gly Gln Tyr Trp Ser
1               5

<210> SEQ ID NO 444
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Trp Ile Gly Glu Ile Tyr Tyr Ser Gly Ser Thr Arg
1               5                   10

<210> SEQ ID NO 445
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 445

Ala Arg Asp Ala Pro Tyr Tyr Tyr Gly Gly Gly Tyr Tyr Tyr Tyr Met
1               5                   10                  15

Asp

<210> SEQ ID NO 446
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Ser Ser Ser Tyr Leu Ala Trp Tyr
1               5

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Leu Leu Ile Tyr Gly Ala Ser Ser Arg Ala
1               5                   10

<210> SEQ ID NO 448
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gln Gln Val Gly Val Val Pro Tyr
1               5

<210> SEQ ID NO 449
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Gly Gly Ser Ile Ser Ser Gly Gln Tyr
1               5

<210> SEQ ID NO 450
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Ile Tyr Tyr Ser Gly Ser Thr
```

```
<210> SEQ ID NO 451
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Ala Arg Asp Ala Pro Tyr Tyr Tyr Gly Gly Tyr Tyr Tyr Tyr Met
1               5                   10                  15

Asp Val

<210> SEQ ID NO 452
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Gln Ser Val Ser Ser Ser Tyr
1               5

<210> SEQ ID NO 453
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Ala Ser
1

<210> SEQ ID NO 454
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gln Gln Val Gly Val Val Pro Tyr Thr
1               5

<210> SEQ ID NO 455
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gln Tyr Trp Ser Trp Ile Arg Gln His Pro Gly Lys Gly Leu Glu Trp
        35                  40                  45
```

Ile Gly Glu Ile Tyr Tyr Ser Gly Ser Thr Arg Tyr Asn Pro Ser Leu
            50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Ala Pro Tyr Tyr Tyr Gly Gly Gly Tyr Tyr Tyr Tyr Met
            100                 105                 110

Asp Val Trp Gly Lys Gly Thr Thr Val Thr Val Ser Ser
            115                 120                 125

<210> SEQ ID NO 456
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Gly Val Val Pro
                 85                  90                  95

Tyr Thr Phe Gly Gly Gly Thr Lys Val Glu Ile Lys
            100                 105

<210> SEQ ID NO 457
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Gly Gly Ser Ile Ser Ser Gly Gln Tyr Trp Ser
 1               5                  10

<210> SEQ ID NO 458
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Glu Ile Tyr Tyr Ser Gly Ser Thr Arg Tyr Asn Pro Ser Leu Lys Ser
 1               5                  10                  15

<210> SEQ ID NO 459
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Asp Ala Pro Tyr Tyr Gly Gly Gly Tyr Tyr Tyr Tyr Met Asp Val
1               5                   10                  15

<210> SEQ ID NO 460
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Arg Ala Ser Glu Ser Val Asp Ser Ser Tyr Leu Ala
1               5                   10

<210> SEQ ID NO 461
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Gly Ala Ser Thr Arg Gln Thr
1               5

<210> SEQ ID NO 462
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Gln Gln Ala Gly Val Val Pro Tyr Thr
1               5

<210> SEQ ID NO 463
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Ser Gly Gln Tyr Trp Ser
1               5

<210> SEQ ID NO 464
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Glu Ile Tyr Tyr Ser Gly Ser Thr Arg Tyr Asn Pro Ser Leu Lys Ser
```

-continued

```
1               5                  10                  15
```

<210> SEQ ID NO 465
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

```
Asp Ala Pro Tyr Tyr Gly Gly Gly Tyr Tyr Tyr Met Asp Val
1               5                  10                  15
```

<210> SEQ ID NO 466
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

```
Arg Ala Ser Glu Ser Val Asp Ser Ser Tyr Leu Ala
1               5                  10
```

<210> SEQ ID NO 467
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

```
Gly Ala Ser Thr Arg Gln Thr
1               5
```

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

```
Gln Gln Ala Gly Val Val Pro Tyr Thr
1               5
```

<210> SEQ ID NO 469
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

```
Gly Gly Ser Ile Ser Ser Gly Gln
1               5
```

<210> SEQ ID NO 470
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 470

Tyr Ser Gly
1

<210> SEQ ID NO 471
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Ala Pro Tyr Tyr Tyr Gly Gly Gly Tyr Tyr Tyr Tyr Met Asp
1               5                   10

<210> SEQ ID NO 472
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Ser Glu Ser Val Asp Ser Ser Tyr
1               5

<210> SEQ ID NO 473
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Gly Ala Ser
1

<210> SEQ ID NO 474
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ala Gly Val Val Pro Tyr
1               5

<210> SEQ ID NO 475
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gly Gly Ser Ile Ser Ser Gly Gln Tyr Trp Ser
1               5                   10

<210> SEQ ID NO 476

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Glu Ile Tyr Tyr Ser Gly Ser Thr Arg
1               5

<210> SEQ ID NO 477
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Asp Ala Pro Tyr Tyr Gly Gly Gly Tyr Tyr Tyr Tyr Met Asp Val
1               5                   10                  15

<210> SEQ ID NO 478
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Ala Ser Glu Ser Val Asp Ser Ser Tyr Leu Ala
1               5                   10

<210> SEQ ID NO 479
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Gly Ala Ser Thr Arg Gln Thr
1               5

<210> SEQ ID NO 480
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Gln Gln Ala Gly Val Val Pro Tyr Thr
1               5

<210> SEQ ID NO 481
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481
```

Ser Ser Gly Gln Tyr Trp Ser
1               5

<210> SEQ ID NO 482
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Trp Ile Gly Glu Ile Tyr Tyr Ser Gly Ser Thr Arg
1               5                   10

<210> SEQ ID NO 483
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Arg Asp Ala Pro Tyr Tyr Tyr Gly Gly Tyr Tyr Tyr Tyr Met
1               5                   10                  15

Asp

<210> SEQ ID NO 484
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Asp Ser Ser Tyr Leu Ala Trp Tyr
1               5

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Leu Leu Ile Tyr Gly Ala Ser Thr Arg Gln
1               5                   10

<210> SEQ ID NO 486
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gln Gln Ala Gly Val Val Pro Tyr
1               5

<210> SEQ ID NO 487
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 487

Gly Gly Ser Ile Ser Ser Gly Gln Tyr
1               5

<210> SEQ ID NO 488
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Ile Tyr Tyr Ser Gly Ser Thr
1               5

<210> SEQ ID NO 489
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Ala Arg Asp Ala Pro Tyr Tyr Tyr Gly Gly Gly Tyr Tyr Tyr Tyr Met
1               5                   10                  15

Asp Val

<210> SEQ ID NO 490
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Glu Ser Val Asp Ser Ser Tyr
1               5

<210> SEQ ID NO 491
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gly Ala Ser
1

<210> SEQ ID NO 492
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492
```

Gln Gln Ala Gly Val Val Pro Tyr Thr
1               5

<210> SEQ ID NO 493
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gln Tyr Trp Ser Trp Ile Arg Gln His Pro Gly Lys Gly Leu Glu Trp
        35                  40                  45

Ile Gly Glu Ile Tyr Tyr Ser Gly Ser Thr Arg Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Pro Tyr Tyr Tyr Gly Gly Tyr Tyr Tyr Tyr Tyr Met
            100                 105                 110

Asp Val Trp Gly Lys Gly Thr Thr Val Thr Val Ser Ser
        115                 120                 125

<210> SEQ ID NO 494
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Gln Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Val Val Pro
                85                  90                  95

Tyr Thr Phe Gly Gly Gly Thr Lys Val Glu Ile Lys
            100                 105

<210> SEQ ID NO 495
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 495

Gly Gly Ser Ile Ser Ser Gly Gln Tyr Trp Ser
1               5                   10

<210> SEQ ID NO 496
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Glu Ile Tyr Tyr Ser Gly Ser Thr Arg Tyr Asn Pro Ser Leu Lys Ser
1               5                   10                  15

<210> SEQ ID NO 497
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Asp Ala Pro Tyr Tyr Tyr Gly Gly Tyr Tyr Tyr Met Asp Val
1               5                   10

<210> SEQ ID NO 498
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Arg Ala Ser Glu Ser Val Asp Ser Ser Tyr Leu Ala
1               5                   10

<210> SEQ ID NO 499
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Gly Ala Asp Ser Arg Ala Thr
1               5

<210> SEQ ID NO 500
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Gln Gln Asp Gly Val Val Pro Tyr Thr
1               5

<210> SEQ ID NO 501
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 501

Ser Gly Gln Tyr Trp Ser
1               5

<210> SEQ ID NO 502
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Glu Ile Tyr Tyr Ser Gly Ser Thr Arg Tyr Asn Pro Ser Leu Lys Ser
1               5                   10                  15

<210> SEQ ID NO 503
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Asp Ala Pro Tyr Tyr Tyr Gly Gly Gly Tyr Tyr Tyr Tyr Met Asp Val
1               5                   10                  15

<210> SEQ ID NO 504
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Arg Ala Ser Glu Ser Val Asp Ser Ser Tyr Leu Ala
1               5                   10

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Gly Ala Asp Ser Arg Ala Thr
1               5

<210> SEQ ID NO 506
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Gln Gln Asp Gly Val Val Pro Tyr Thr
1               5
```

```
<210> SEQ ID NO 507
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Gly Gly Ser Ile Ser Ser Gly Gln
1               5

<210> SEQ ID NO 508
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Tyr Ser Gly
1

<210> SEQ ID NO 509
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Ala Pro Tyr Tyr Tyr Gly Gly Gly Tyr Tyr Tyr Tyr Met Asp
1               5                   10

<210> SEQ ID NO 510
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Ser Glu Ser Val Asp Ser Ser Tyr
1               5

<210> SEQ ID NO 511
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Gly Ala Asp
1

<210> SEQ ID NO 512
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 512

Asp Gly Val Val Pro Tyr
1               5

<210> SEQ ID NO 513
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Gly Gly Ser Ile Ser Ser Gly Gln Tyr Trp Ser
1               5                   10

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Glu Ile Tyr Tyr Ser Gly Ser Thr Arg
1               5

<210> SEQ ID NO 515
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Asp Ala Pro Tyr Tyr Tyr Gly Gly Gly Tyr Tyr Tyr Tyr Met Asp Val
1               5                   10                  15

<210> SEQ ID NO 516
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Arg Ala Ser Glu Ser Val Asp Ser Ser Tyr Leu Ala
1               5                   10

<210> SEQ ID NO 517
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Ala Asp Ser Arg Ala Thr
1               5

<210> SEQ ID NO 518
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Gln Gln Asp Gly Val Val Pro Tyr Thr
1               5

<210> SEQ ID NO 519
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Ser Ser Gly Gln Tyr Trp Ser
1               5

<210> SEQ ID NO 520
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Trp Ile Gly Glu Ile Tyr Tyr Ser Gly Ser Thr Arg
1               5                   10

<210> SEQ ID NO 521
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Ala Arg Asp Ala Pro Tyr Tyr Gly Gly Gly Tyr Tyr Tyr Tyr Met
1               5                   10                  15

Asp

<210> SEQ ID NO 522
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Asp Ser Ser Tyr Leu Ala Trp Tyr
1               5

<210> SEQ ID NO 523
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523
```

```
Leu Leu Ile Tyr Gly Ala Asp Ser Arg Ala
1               5                   10

<210> SEQ ID NO 524
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Gln Gln Asp Gly Val Val Pro Tyr
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gly Gly Ser Ile Ser Ser Gly Gln Tyr
1               5

<210> SEQ ID NO 526
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ile Tyr Tyr Ser Gly Ser Thr
1               5

<210> SEQ ID NO 527
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Ala Arg Asp Ala Pro Tyr Tyr Tyr Gly Gly Tyr Tyr Tyr Tyr Met
1               5                   10                  15

Asp Val

<210> SEQ ID NO 528
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Glu Ser Val Asp Ser Ser Tyr
1               5

<210> SEQ ID NO 529
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Gly Ala Asp
1

<210> SEQ ID NO 530
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gln Gln Asp Gly Val Val Pro Tyr Thr
1               5

<210> SEQ ID NO 531
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gln Tyr Trp Ser Trp Ile Arg Gln His Pro Gly Lys Gly Leu Glu Trp
        35                  40                  45

Ile Gly Glu Ile Tyr Tyr Ser Gly Ser Thr Arg Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Ala Pro Tyr Tyr Gly Gly Tyr Tyr Tyr Tyr Met
            100                 105                 110

Asp Val Trp Gly Lys Gly Thr Thr Val Thr Val Ser Ser
        115                 120                 125

<210> SEQ ID NO 532
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ser Val Asp Ser Ser
            20                  25                  30

Tyr Leu Ala Trp Tyr Gln Gln Lys Pro Gly Gln Ala Pro Arg Leu Leu
        35                  40                  45
```

Ile Tyr Gly Ala Asp Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Val Val Pro
                85                  90                  95

Tyr Thr Phe Gly Gly Gly Thr Lys Val Glu Ile Lys
            100                 105

<210> SEQ ID NO 533
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gly Gly Ser Leu Ser Gly Tyr Tyr Trp Ser
1               5                   10

<210> SEQ ID NO 534
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Glu Ile Gly Ala Ser Gly Ser Thr Arg Tyr Asn Pro Ser Leu Lys Ser
1               5                   10                  15

<210> SEQ ID NO 535
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Asp Thr Pro Tyr Tyr Tyr Glu Gly Gly Tyr Tyr Tyr Tyr Met Asp Val
1               5                   10                  15

<210> SEQ ID NO 536
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Arg Ala Ser Gln Ser Val Ser Ser Ser Tyr Leu Ala
1               5                   10

<210> SEQ ID NO 537
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

```
Gly Ala Ser Ser Arg Ala Thr
1               5

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Gln Gln Val Gly Val Val Pro Tyr Thr
1               5

<210> SEQ ID NO 539
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Gly Tyr Tyr Trp Ser
1               5

<210> SEQ ID NO 540
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Glu Ile Gly Ala Ser Gly Ser Thr Arg Tyr Asn Pro Ser Leu Lys Ser
1               5                   10                  15

<210> SEQ ID NO 541
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Asp Thr Pro Tyr Tyr Tyr Glu Gly Gly Tyr Tyr Tyr Tyr Met Asp Val
1               5                   10                  15

<210> SEQ ID NO 542
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Arg Ala Ser Gln Ser Val Ser Ser Ser Tyr Leu Ala
1               5                   10

<210> SEQ ID NO 543
<211> LENGTH: 7
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 543

Gly Ala Ser Ser Arg Ala Thr
1               5

<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Gln Gln Val Gly Val Val Pro Tyr Thr
1               5

<210> SEQ ID NO 545
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gly Gly Ser Leu Ser Gly Tyr
1               5

<210> SEQ ID NO 546
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Ala Ser Gly
1

<210> SEQ ID NO 547
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Thr Pro Tyr Tyr Tyr Glu Gly Gly Tyr Tyr Tyr Tyr Met Asp
1               5                   10

<210> SEQ ID NO 548
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Ser Gln Ser Val Ser Ser Ser Tyr
1               5

<210> SEQ ID NO 549
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Gly Ala Ser
1

<210> SEQ ID NO 550
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Val Gly Val Val Pro Tyr
1               5

<210> SEQ ID NO 551
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Gly Gly Ser Leu Ser Gly Tyr Tyr Trp Ser
1               5                   10

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Glu Ile Gly Ala Ser Gly Ser Thr Arg
1               5

<210> SEQ ID NO 553
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Asp Thr Pro Tyr Tyr Tyr Glu Gly Gly Tyr Tyr Tyr Met Asp Val
1               5                   10                  15

<210> SEQ ID NO 554
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 554

Arg Ala Ser Gln Ser Val Ser Ser Ser Tyr Leu Ala
1               5                   10

<210> SEQ ID NO 555
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Gly Ala Ser Ser Arg Ala Thr
1               5

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gln Gln Val Gly Val Val Pro Tyr Thr
1               5

<210> SEQ ID NO 557
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Ser Gly Tyr Tyr Trp Ser
1               5

<210> SEQ ID NO 558
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

Trp Ile Gly Glu Ile Gly Ala Ser Gly Ser Thr Arg
1               5                   10

<210> SEQ ID NO 559
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Ala Arg Asp Thr Pro Tyr Tyr Tyr Glu Gly Gly Tyr Tyr Tyr Tyr Met
1               5                   10                  15
Asp

<210> SEQ ID NO 560
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Ser Ser Ser Tyr Leu Ala Trp Tyr
1               5

<210> SEQ ID NO 561
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Leu Leu Ile Tyr Gly Ala Ser Ser Arg Ala
1               5                   10

<210> SEQ ID NO 562
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Gln Gln Val Gly Val Val Pro Tyr
1               5

<210> SEQ ID NO 563
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gly Gly Ser Leu Ser Gly Tyr Tyr
1               5

<210> SEQ ID NO 564
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Ile Gly Ala Ser Gly Ser Thr
1               5

<210> SEQ ID NO 565
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565
```

```
Ala Arg Asp Thr Pro Tyr Tyr Tyr Glu Gly Gly Tyr Tyr Tyr Met
1               5                   10                  15

Asp Val
```

<210> SEQ ID NO 566
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

```
Gln Ser Val Ser Ser Ser Tyr
1               5
```

<210> SEQ ID NO 567
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

```
Gly Ala Ser
1
```

<210> SEQ ID NO 568
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

```
Gln Gln Val Gly Val Val Pro Tyr Thr
1               5
```

<210> SEQ ID NO 569
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 569

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
                20                  25                  30

Tyr Trp Ser Trp Ile Arg Gln Pro Pro Gly Lys Gly Leu Glu Trp Ile
            35                  40                  45

Gly Glu Ile Gly Ala Ser Gly Ser Thr Arg Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Thr Pro Tyr Tyr Tyr Glu Gly Gly Tyr Tyr Tyr Met Asp
                100                 105                 110
```

```
Val Trp Gly Lys Gly Thr Thr Val Thr Val Ser Ser
            115                 120
```

<210> SEQ ID NO 570
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 570

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Gly Val Val Pro
                85                  90                  95

Tyr Thr Phe Gly Gly Gly Thr Lys Val Glu Ile Lys
            100                 105
```

<210> SEQ ID NO 571
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

```
Gly Gly Ser Leu Ser Gly Tyr Tyr Trp Ser
1               5                   10
```

<210> SEQ ID NO 572
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

```
Glu Ile Gly Ala Ser Gly Ser Thr Arg Tyr Asn Pro Ser Leu Lys Ser
1               5                   10                  15
```

<210> SEQ ID NO 573
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

```
Asp Thr Pro Tyr Tyr Tyr Glu Gly Gly Tyr Tyr Tyr Tyr Met Asp Val
1               5                   10                  15
```

<210> SEQ ID NO 574

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Arg Ala Ser Asp Ser Val Asp Ser Ser Tyr Leu Ala
1               5                   10

<210> SEQ ID NO 575
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Gly Ala Phe Ser Arg Ala Asn
1               5

<210> SEQ ID NO 576
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Gln Gln Ala Gly Val Val Pro Tyr Thr
1               5

<210> SEQ ID NO 577
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Gly Tyr Tyr Trp Ser
1               5

<210> SEQ ID NO 578
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Glu Ile Gly Ala Ser Gly Ser Thr Arg Tyr Asn Pro Ser Leu Lys Ser
1               5                   10                  15

<210> SEQ ID NO 579
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579
```

```
Asp Thr Pro Tyr Tyr Glu Gly Gly Tyr Tyr Tyr Met Asp Val
1               5                   10                  15

<210> SEQ ID NO 580
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

Arg Ala Ser Asp Ser Val Asp Ser Ser Tyr Leu Ala
1               5                   10

<210> SEQ ID NO 581
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Gly Ala Phe Ser Arg Ala Asn
1               5

<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gln Gln Ala Gly Val Val Pro Tyr Thr
1               5

<210> SEQ ID NO 583
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gly Gly Ser Leu Ser Gly Tyr
1               5

<210> SEQ ID NO 584
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Ala Ser Gly
1

<210> SEQ ID NO 585
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 585

Thr Pro Tyr Tyr Tyr Glu Gly Gly Tyr Tyr Tyr Tyr Met Asp
1               5                   10

<210> SEQ ID NO 586
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Ser Asp Ser Val Asp Ser Ser Tyr
1               5

<210> SEQ ID NO 587
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Gly Ala Phe
1

<210> SEQ ID NO 588
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Ala Gly Val Val Pro Tyr
1               5

<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589

Gly Gly Ser Leu Ser Gly Tyr Tyr Trp Ser
1               5                   10

<210> SEQ ID NO 590
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Glu Ile Gly Ala Ser Gly Ser Thr Arg
1               5
```

```
<210> SEQ ID NO 591
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Asp Thr Pro Tyr Tyr Glu Gly Gly Tyr Tyr Tyr Met Asp Val
1               5                   10                  15

<210> SEQ ID NO 592
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Arg Ala Ser Asp Ser Val Asp Ser Ser Tyr Leu Ala
1               5                   10

<210> SEQ ID NO 593
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gly Ala Phe Ser Arg Ala Asn
1               5

<210> SEQ ID NO 594
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gln Gln Ala Gly Val Val Pro Tyr Thr
1               5

<210> SEQ ID NO 595
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Ser Gly Tyr Tyr Trp Ser
1               5

<210> SEQ ID NO 596
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596
```

```
Trp Ile Gly Glu Ile Gly Ala Ser Gly Ser Thr Arg
1               5                   10
```

<210> SEQ ID NO 597
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

```
Ala Arg Asp Thr Pro Tyr Tyr Tyr Glu Gly Gly Tyr Tyr Tyr Tyr Met
1               5                   10                  15
Asp
```

<210> SEQ ID NO 598
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

```
Asp Ser Ser Tyr Leu Ala Trp Tyr
1               5
```

<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

```
Leu Leu Ile Tyr Gly Ala Phe Ser Arg Ala
1               5                   10
```

<210> SEQ ID NO 600
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

```
Gln Gln Ala Gly Val Val Pro Tyr
1               5
```

<210> SEQ ID NO 601
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

```
Gly Gly Ser Leu Ser Gly Tyr Tyr
1               5
```

<210> SEQ ID NO 602
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Ile Gly Ala Ser Gly Ser Thr
1               5

<210> SEQ ID NO 603
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Ala Arg Asp Thr Pro Tyr Tyr Tyr Glu Gly Gly Tyr Tyr Tyr Tyr Met
1               5                   10                  15

Asp Val

<210> SEQ ID NO 604
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Asp Ser Val Asp Ser Ser Tyr
1               5

<210> SEQ ID NO 605
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Gly Ala Phe
1

<210> SEQ ID NO 606
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Gln Gln Ala Gly Val Val Pro Tyr Thr
1               5

<210> SEQ ID NO 607
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607
```

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
            35                  40                  45

Gly Glu Ile Gly Ala Ser Gly Ser Thr Arg Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Thr Pro Tyr Tyr Tyr Glu Gly Gly Tyr Tyr Tyr Tyr Met Asp
            100                 105                 110

Val Trp Gly Lys Gly Thr Thr Val Thr Val Ser Ser
            115                 120
```

<210> SEQ ID NO 608
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Asp Ser Val Asp Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Val Val Pro
                85                  90                  95

Tyr Thr Phe Gly Gly Gly Thr Lys Val Glu Ile Lys
            100                 105
```

<210> SEQ ID NO 609
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

```
Gly Gly Ser Leu Ser Gly Tyr Tyr Trp Ser
1               5                   10
```

<210> SEQ ID NO 610
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Glu Ile Gly Ala Ser Gly Ser Thr Arg Tyr Asn Pro Ser Leu Lys Ser
1               5                   10                  15

<210> SEQ ID NO 611
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 611

Asp Thr Pro Tyr Tyr Glu Gly Gly Tyr Tyr Tyr Met Asp Val
1               5                   10                  15

<210> SEQ ID NO 612
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Arg Ala Ser Gln Ser Val Ser Ser Ser Phe Leu Ala
1               5                   10

<210> SEQ ID NO 613
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Gly Ala Tyr Ser Arg Ala Thr
1               5

<210> SEQ ID NO 614
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gln Gln Ala Gly Val Val Pro Tyr Thr
1               5

<210> SEQ ID NO 615
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Gly Tyr Tyr Trp Ser
1               5

<210> SEQ ID NO 616
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Glu Ile Gly Ala Ser Gly Ser Thr Arg Tyr Asn Pro Ser Leu Lys Ser
1               5                   10                  15

<210> SEQ ID NO 617
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 617

Asp Thr Pro Tyr Tyr Tyr Glu Gly Gly Tyr Tyr Tyr Met Asp Val
1               5                   10                  15

<210> SEQ ID NO 618
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Arg Ala Ser Gln Ser Val Ser Ser Ser Phe Leu Ala
1               5                   10

<210> SEQ ID NO 619
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gly Ala Tyr Ser Arg Ala Thr
1               5

<210> SEQ ID NO 620
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 620

Gln Gln Ala Gly Val Val Pro Tyr Thr
1               5

<210> SEQ ID NO 621
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Gly Gly Ser Leu Ser Gly Tyr
```

```
1               5
```

<210> SEQ ID NO 622
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 622

```
Ala Ser Gly
1
```

<210> SEQ ID NO 623
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

```
Thr Pro Tyr Tyr Tyr Glu Gly Gly Tyr Tyr Tyr Met Asp
1               5                   10
```

<210> SEQ ID NO 624
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

```
Ser Gln Ser Val Ser Ser Ser Phe
1               5
```

<210> SEQ ID NO 625
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 625

```
Gly Ala Tyr
1
```

<210> SEQ ID NO 626
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

```
Ala Gly Val Val Pro Tyr
1               5
```

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 627

Gly Gly Ser Leu Ser Gly Tyr Tyr Trp Ser
1               5                   10

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Glu Ile Gly Ala Ser Gly Ser Thr Arg
1               5

<210> SEQ ID NO 629
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 629

Asp Thr Pro Tyr Tyr Tyr Glu Gly Gly Tyr Tyr Tyr Tyr Met Asp Val
1               5                   10                  15

<210> SEQ ID NO 630
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Arg Ala Ser Gln Ser Val Ser Ser Ser Phe Leu Ala
1               5                   10

<210> SEQ ID NO 631
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Gly Ala Tyr Ser Arg Ala Thr
1               5

<210> SEQ ID NO 632
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Gln Gln Ala Gly Val Val Pro Tyr Thr
1               5

<210> SEQ ID NO 633

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 633

Ser Gly Tyr Tyr Trp Ser
1               5

<210> SEQ ID NO 634
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Trp Ile Gly Glu Ile Gly Ala Ser Gly Ser Thr Arg
1               5                   10

<210> SEQ ID NO 635
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Ala Arg Asp Thr Pro Tyr Tyr Tyr Glu Gly Gly Tyr Tyr Tyr Tyr Met
1               5                   10                  15

Asp

<210> SEQ ID NO 636
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Ser Ser Ser Phe Leu Ala Trp Tyr
1               5

<210> SEQ ID NO 637
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 637

Leu Leu Ile Tyr Gly Ala Tyr Ser Arg Ala
1               5                   10

<210> SEQ ID NO 638
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 638

Gln Gln Ala Gly Val Val Pro Tyr
1               5

<210> SEQ ID NO 639
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 639

Gly Gly Ser Leu Ser Gly Tyr Tyr
1               5

<210> SEQ ID NO 640
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 640

Ile Gly Ala Ser Gly Ser Thr
1               5

<210> SEQ ID NO 641
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Ala Arg Asp Thr Pro Tyr Tyr Tyr Glu Gly Gly Tyr Tyr Tyr Tyr Met
1               5                   10                  15

Asp Val

<210> SEQ ID NO 642
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Gln Ser Val Ser Ser Ser Phe
1               5

<210> SEQ ID NO 643
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

Gly Ala Tyr
1

<210> SEQ ID NO 644
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 644

Gln Gln Ala Gly Val Val Pro Tyr Thr
1               5

<210> SEQ ID NO 645
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 645

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Glu Ile Gly Ala Ser Gly Ser Thr Arg Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Thr Pro Tyr Tyr Tyr Glu Gly Gly Tyr Tyr Tyr Tyr Met Asp
            100                 105                 110

Val Trp Gly Lys Gly Thr Thr Val Thr Val Ser Ser
        115                 120

<210> SEQ ID NO 646
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 646

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Tyr Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Gly Val Val Pro
                85                  90                  95

Tyr Thr Phe Gly Gly Gly Thr Lys Val Glu Ile Lys
            100                 105
```

<210> SEQ ID NO 647
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Gly Gly Ser Ile Ser Ser Gly Gln Tyr Trp Ser
1               5                   10

<210> SEQ ID NO 648
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 648

Glu Ile Tyr Tyr Ser Gly Ser Thr Arg Tyr Asn Pro Ser Leu Lys Ser
1               5                   10                  15

<210> SEQ ID NO 649
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Asp Thr Pro Tyr Tyr Tyr Asp Gly Gly Tyr Tyr Tyr Tyr Met Asp Val
1               5                   10                  15

<210> SEQ ID NO 650
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Arg Ala Ser Gln Ser Val Ser Ser Ser Tyr Leu Ala
1               5                   10

<210> SEQ ID NO 651
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Gly Ala Ser Ser Arg Ala Thr
1               5

<210> SEQ ID NO 652
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 652

Gln Gln Val Gly Val Val Pro Tyr Thr
1               5

<210> SEQ ID NO 653
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Ser Gly Gln Tyr Trp Ser
1               5

<210> SEQ ID NO 654
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Glu Ile Tyr Tyr Ser Gly Ser Thr Arg Tyr Asn Pro Ser Leu Lys Ser
1               5                   10                  15

<210> SEQ ID NO 655
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Asp Thr Pro Tyr Tyr Tyr Asp Gly Gly Tyr Tyr Tyr Tyr Met Asp Val
1               5                   10                  15

<210> SEQ ID NO 656
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 656

Arg Ala Ser Gln Ser Val Ser Ser Ser Tyr Leu Ala
1               5                   10

<210> SEQ ID NO 657
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Gly Ala Ser Ser Arg Ala Thr
1               5

<210> SEQ ID NO 658
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 658

Gln Gln Val Gly Val Val Pro Tyr Thr
1               5

<210> SEQ ID NO 659
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Gly Gly Ser Ile Ser Ser Gly Gln
1               5

<210> SEQ ID NO 660
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 660

Tyr Ser Gly
1

<210> SEQ ID NO 661
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Thr Pro Tyr Tyr Tyr Asp Gly Gly Tyr Tyr Tyr Tyr Met Asp
1               5                   10

<210> SEQ ID NO 662
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Ser Gln Ser Val Ser Ser Ser Tyr
1               5

<210> SEQ ID NO 663
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Gly Ala Ser
1
```

<210> SEQ ID NO 664
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 664

Val Gly Val Val Pro Tyr
1               5

<210> SEQ ID NO 665
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

Gly Gly Ser Ile Ser Ser Gly Gln Tyr Trp Ser
1               5                   10

<210> SEQ ID NO 666
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

Glu Ile Tyr Tyr Ser Gly Ser Thr Arg
1               5

<210> SEQ ID NO 667
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

Asp Thr Pro Tyr Tyr Tyr Asp Gly Gly Tyr Tyr Tyr Tyr Met Asp Val
1               5                   10                  15

<210> SEQ ID NO 668
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 668

Arg Ala Ser Gln Ser Val Ser Ser Ser Tyr Leu Ala
1               5                   10

<210> SEQ ID NO 669
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 669

Gly Ala Ser Ser Arg Ala Thr
1               5

<210> SEQ ID NO 670
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

Gln Gln Val Gly Val Val Pro Tyr Thr
1               5

<210> SEQ ID NO 671
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

Ser Ser Gly Gln Tyr Trp Ser
1               5

<210> SEQ ID NO 672
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 672

Trp Ile Gly Glu Ile Tyr Tyr Ser Gly Ser Thr Arg
1               5                   10

<210> SEQ ID NO 673
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ala Arg Asp Thr Pro Tyr Tyr Tyr Asp Gly Gly Tyr Tyr Tyr Tyr Met
1               5                   10                  15

Asp

<210> SEQ ID NO 674
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Ser Ser Ser Tyr Leu Ala Trp Tyr
1               5
```

```
<210> SEQ ID NO 675
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 675

Leu Leu Ile Tyr Gly Ala Ser Ser Arg Ala
1               5                   10

<210> SEQ ID NO 676
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Gln Gln Val Gly Val Val Pro Tyr
1               5

<210> SEQ ID NO 677
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 677

Gly Gly Ser Ile Ser Ser Gly Gln Tyr
1               5

<210> SEQ ID NO 678
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Ile Tyr Tyr Ser Gly Ser Thr
1               5

<210> SEQ ID NO 679
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Ala Arg Asp Thr Pro Tyr Tyr Tyr Asp Gly Gly Tyr Tyr Tyr Met
1               5                   10                  15

Asp Val

<210> SEQ ID NO 680
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 680

Gln Ser Val Ser Ser Ser Tyr
1               5

<210> SEQ ID NO 681
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 681

Gly Ala Ser
1

<210> SEQ ID NO 682
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 682

Gln Gln Val Gly Val Val Pro Tyr Thr
1               5

<210> SEQ ID NO 683
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gln Tyr Trp Ser Trp Ile Arg Gln His Pro Gly Lys Gly Leu Glu Trp
        35                  40                  45

Ile Gly Glu Ile Tyr Tyr Ser Gly Ser Thr Arg Tyr Asn Pro Ser Leu
    50                  55                  60

Lys Ser Arg Val Thr Ile Ser Val Asp Thr Ser Lys Asp Gln Phe Ser
65                  70                  75                  80

Leu Lys Leu Ser Ser Val Thr Ala Ala Asp Thr Ala Val Tyr Tyr Cys
                85                  90                  95

Ala Arg Asp Thr Pro Tyr Tyr Tyr Asp Gly Tyr Tyr Tyr Tyr Met
            100                 105                 110

Asp Val Trp Gly Lys Gly Thr Thr Val Thr Val Ser Ser
        115                 120                 125

<210> SEQ ID NO 684
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 684

```
Glu Ile Val Leu Thr Gln Ser Pro Gly Thr Leu Ser Leu Ser Pro Gly
1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Val Gly Val Val Pro
                85                  90                  95

Tyr Thr Phe Gly Gly Gly Thr Lys Val Glu Ile Lys
            100                 105
```

<210> SEQ ID NO 685
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

```
Gly Gly Ser Ile Ser Ser Gly Gln Tyr Trp Ser
1               5                  10
```

<210> SEQ ID NO 686
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

```
Glu Ile Tyr Tyr Ser Gly Ser Thr Arg Tyr Asn Pro Ser Leu Lys Ser
1               5                  10                  15
```

<210> SEQ ID NO 687
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

```
Asp Thr Pro Tyr Tyr Tyr Asp Gly Gly Tyr Tyr Tyr Tyr Met Asp Val
1               5                  10                  15
```

<210> SEQ ID NO 688
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

```
Arg Ala Ser Gln Ser Val Ser Ser Ser Tyr Leu Ala
1               5                  10
```

```
<210> SEQ ID NO 689
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Gly Ala Ser Ser Arg Ala Thr
1               5

<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

Gln Gln Val Gly Val Val Pro Tyr Thr
1               5

<210> SEQ ID NO 691
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 691

Ser Gly Gln Tyr Trp Ser
1               5

<210> SEQ ID NO 692
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Glu Ile Tyr Tyr Ser Gly Ser Thr Arg Tyr Asn Pro Ser Leu Lys Ser
1               5                   10                  15

<210> SEQ ID NO 693
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Asp Thr Pro Tyr Tyr Tyr Asp Gly Gly Tyr Tyr Tyr Tyr Met Asp Val
1               5                   10                  15

<210> SEQ ID NO 694
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694
```

Arg Ala Ser Gln Ser Val Ser Ser Tyr Leu Ala
1               5                   10

<210> SEQ ID NO 695
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Gly Ala Ser Ser Arg Ala Thr
1               5

<210> SEQ ID NO 696
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Gln Gln Val Gly Val Val Pro Tyr Thr
1               5

<210> SEQ ID NO 697
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Gly Gly Ser Ile Ser Ser Gly Gln
1               5

<210> SEQ ID NO 698
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 698

Tyr Ser Gly
1

<210> SEQ ID NO 699
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Thr Pro Tyr Tyr Tyr Asp Gly Gly Tyr Tyr Tyr Met Asp
1               5                   10

<210> SEQ ID NO 700
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 700

Ser Gln Ser Val Ser Ser Ser Tyr
1               5

<210> SEQ ID NO 701
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Gly Ala Ser
1

<210> SEQ ID NO 702
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 702

Val Gly Val Val Pro Tyr
1               5

<210> SEQ ID NO 703
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Gly Gly Ser Ile Ser Ser Gly Gln Tyr Trp Ser
1               5                   10

<210> SEQ ID NO 704
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 704

Glu Ile Tyr Tyr Ser Gly Ser Thr Arg
1               5

<210> SEQ ID NO 705
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 705

Asp Thr Pro Tyr Tyr Tyr Asp Gly Gly Tyr Tyr Tyr Tyr Met Asp Val
1               5                   10                  15
```

<210> SEQ ID NO 706
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 706

Arg Ala Ser Gln Ser Val Ser Ser Ser Tyr Leu Ala
1               5                   10

<210> SEQ ID NO 707
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 707

Gly Ala Ser Ser Arg Ala Thr
1               5

<210> SEQ ID NO 708
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 708

Gln Gln Val Gly Val Val Pro Tyr Thr
1               5

<210> SEQ ID NO 709
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 709

Ser Ser Gly Gln Tyr Trp Ser
1               5

<210> SEQ ID NO 710
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Trp Ile Gly Glu Ile Tyr Tyr Ser Gly Ser Thr Arg
1               5                   10

<210> SEQ ID NO 711
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 711

Ala Arg Asp Thr Pro Tyr Tyr Tyr Asp Gly Gly Tyr Tyr Tyr Met
1               5                   10                  15

Asp

<210> SEQ ID NO 712
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Ser Ser Ser Tyr Leu Ala Trp Tyr
1               5

<210> SEQ ID NO 713
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 713

Leu Leu Ile Tyr Gly Ala Ser Ser Arg Ala
1               5                   10

<210> SEQ ID NO 714
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Gln Gln Val Gly Val Val Pro Tyr
1               5

<210> SEQ ID NO 715
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Gly Gly Ser Ile Ser Ser Gly Gln Tyr
1               5

<210> SEQ ID NO 716
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Ile Tyr Tyr Ser Gly Ser Thr
1               5

<210> SEQ ID NO 717
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 717

Ala Arg Asp Thr Pro Tyr Tyr Tyr Asp Gly Tyr Tyr Tyr Tyr Met
1               5                   10                  15

Asp Val

<210> SEQ ID NO 718
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Gln Ser Val Ser Ser Ser Tyr
1               5

<210> SEQ ID NO 719
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Gly Ala Ser
1

<210> SEQ ID NO 720
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Gln Gln Val Gly Val Val Pro Tyr Thr
1               5

<210> SEQ ID NO 721
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gln Tyr Trp Ser Trp Ile Arg Gln His Pro Gly Lys Gly Leu Glu Trp
            35                  40                  45

Ile Gly Glu Ile Tyr Tyr Ser Gly Ser Thr Arg Tyr Asn Pro Ser Leu
    50                  55                  60
```

```
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Asp Thr Pro Tyr Tyr Tyr Asp Gly Gly Tyr Tyr Tyr Met
            100                 105                 110

Asp Val Trp Gly Lys Gly Thr Thr Val Thr Val Ser Ser
            115                 120                 125

<210> SEQ ID NO 722
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 722

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Val Gly Val Val Pro
                 85                  90                  95

Tyr Thr Phe Gly Gly Gly Thr Lys Val Glu Ile Lys
            100                 105

<210> SEQ ID NO 723
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Gly Tyr Thr Phe Ala Asn Tyr Tyr Met His
 1               5                  10

<210> SEQ ID NO 724
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Ile Ile Asn Pro Ser Gly Gly Ile Thr Val Tyr Ala Gln Lys Phe Gln
 1               5                  10                  15

Gly

<210> SEQ ID NO 725
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 725

Gly Gly Ser Lys Val Ala Ala Leu Ala Phe Asp Ile
1               5                   10

<210> SEQ ID NO 726
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Gln Ala Ser Gln Asp Ile Ser Asn Ser Leu Asn
1               5                   10

<210> SEQ ID NO 727
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Asp Ala Ser Asn Leu Glu Thr
1               5

<210> SEQ ID NO 728
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Gln Gln Tyr Asn Phe His Pro Leu Thr
1               5

<210> SEQ ID NO 729
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 729

Asn Tyr Tyr Met His
1               5

<210> SEQ ID NO 730
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Ile Ile Asn Pro Ser Gly Gly Ile Thr Val Tyr Ala Gln Lys Phe Gln
1               5                   10                  15
```

Gly

<210> SEQ ID NO 731
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Gly Gly Ser Lys Val Ala Ala Leu Ala Phe Asp Ile
1               5                   10

<210> SEQ ID NO 732
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Gln Ala Ser Gln Asp Ile Ser Asn Ser Leu Asn
1               5                   10

<210> SEQ ID NO 733
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 733

Asp Ala Ser Asn Leu Glu Thr
1               5

<210> SEQ ID NO 734
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gln Gln Tyr Asn Phe His Pro Leu Thr
1               5

<210> SEQ ID NO 735
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Gly Tyr Thr Phe Ala Asn Tyr
1               5

<210> SEQ ID NO 736
<211> LENGTH: 4
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 736

Pro Ser Gly Gly
1

<210> SEQ ID NO 737
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 737

Gly Ser Lys Val Ala Ala Leu Ala Phe Asp
1               5                   10

<210> SEQ ID NO 738
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Ser Gln Asp Ile Ser Asn Ser
1               5

<210> SEQ ID NO 739
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Asp Ala Ser
1

<210> SEQ ID NO 740
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Tyr Asn Phe His Pro Leu
1               5

<210> SEQ ID NO 741
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 741

Gly Tyr Thr Phe Ala Asn Tyr Tyr Met His
1               5                   10

<210> SEQ ID NO 742
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Ile Ile Asn Pro Ser Gly Gly Ile Thr Val
1               5                   10

<210> SEQ ID NO 743
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Gly Gly Ser Lys Val Ala Ala Leu Ala Phe Asp Ile
1               5                   10

<210> SEQ ID NO 744
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Gln Ala Ser Gln Asp Ile Ser Asn Ser Leu Asn
1               5                   10

<210> SEQ ID NO 745
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 745

Asp Ala Ser Asn Leu Glu Thr
1               5

<210> SEQ ID NO 746
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Gln Gln Tyr Asn Phe His Pro Leu Thr
1               5

<210> SEQ ID NO 747
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747
```

Ala Asn Tyr Tyr Met His
1               5

<210> SEQ ID NO 748
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Trp Met Gly Ile Ile Asn Pro Ser Gly Gly Ile Thr Val
1               5                   10

<210> SEQ ID NO 749
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 749

Ala Arg Gly Gly Ser Lys Val Ala Ala Leu Ala Phe Asp
1               5                   10

<210> SEQ ID NO 750
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Ser Asn Ser Leu Asn Trp Tyr
1               5

<210> SEQ ID NO 751
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Leu Leu Ile Tyr Asp Ala Ser Asn Leu Glu
1               5                   10

<210> SEQ ID NO 752
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Gln Gln Tyr Asn Phe His Pro Leu
1               5

<210> SEQ ID NO 753
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 753

Gly Tyr Thr Phe Ala Asn Tyr Tyr
1               5

<210> SEQ ID NO 754
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Ile Asn Pro Ser Gly Gly Ile Thr
1               5

<210> SEQ ID NO 755
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Ala Arg Gly Gly Ser Lys Val Ala Ala Leu Ala Phe Asp Ile
1               5                   10

<210> SEQ ID NO 756
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 756

Gln Asp Ile Ser Asn Ser
1               5

<210> SEQ ID NO 757
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Asp Ala Ser
1

<210> SEQ ID NO 758
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Gln Gln Tyr Asn Phe His Pro Leu Thr
1               5

```
<210> SEQ ID NO 759
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 759

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ile Thr Val Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Lys Val Ala Ala Leu Ala Phe Asp Ile Trp Gly
                100                 105                 110

Gln Gly Thr Met Val Thr Val Ser Ser
            115                 120

<210> SEQ ID NO 760
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 760

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ser
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Arg Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Phe His Pro Leu
                85                  90                  95

Thr Phe Gly Gly Gly Thr Lys Val Glu Ile Lys
            100                 105

<210> SEQ ID NO 761
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Asp or Ser
<220> FEATURE:
```

```
<221> NAME/KEY: MOD_RES
<222> LOCATION: (35)..(35)
<223> OTHER INFORMATION: Ala or Gly
<220> FEATURE:
<221> NAME/KEY: MOD_RES
<222> LOCATION: (50)..(50)
<223> OTHER INFORMATION: Ala or Thr

<400> SEQUENCE: 761

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Tyr
            20                  25                  30

Ala Met Xaa Trp Val Arg Gln Ala Pro Gly Lys Gly Leu Glu Trp Val
        35                  40                  45

Ser Xaa Ile Ser Gly Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Tyr Gly Tyr Tyr Met Asp Val Trp Gly Lys Gly Thr
            100                 105                 110

Thr Val Thr Val Ser Ser
            115

<210> SEQ ID NO 762
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 762

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Ile Thr
                85                  90                  95

Phe Gly Gly Gly Thr Lys Val Glu Ile Lys
            100                 105

<210> SEQ ID NO 763
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Asp or Arg
<220> FEATURE:
```

```
<221> NAME/KEY: MOD_RES
<222> LOCATION: (31)..(31)
<223> OTHER INFORMATION: Ser, Val, or Ala
<220> FEATURE:
<221> NAME/KEY: MOD_RES
<222> LOCATION: (51)..(51)
<223> OTHER INFORMATION: Ile or Val
<220> FEATURE:
<221> NAME/KEY: MOD_RES
<222> LOCATION: (55)..(55)
<223> OTHER INFORMATION: Ser or Asn
<220> FEATURE:
<221> NAME/KEY: MOD_RES
<222> LOCATION: (106)..(106)
<223> OTHER INFORMATION: Phe or Tyr

<400> SEQUENCE: 763

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Xaa Xaa Tyr
            20                  25                  30

Gly Ile Ser Trp Val Arg Gln Ala Pro Gly Gln Gly Leu Glu Trp Met
        35                  40                  45

Gly Trp Xaa Ala Pro Tyr Xaa Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Xaa Gly Tyr Gly Met Asp Val
            100                 105                 110

Trp Gly Gln Gly Thr Thr Val Thr Val Ser Ser
        115                 120

<210> SEQ ID NO 764
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Arg or Gln
<220> FEATURE:
<221> NAME/KEY: MOD_RES
<222> LOCATION: (27)..(27)
<223> OTHER INFORMATION: Gln, Glu, or His
<220> FEATURE:
<221> NAME/KEY: MOD_RES
<222> LOCATION: (30)..(30)
<223> OTHER INFORMATION: Ser, Asp, or Asn
<220> FEATURE:
<221> NAME/KEY: MOD_RES
<222> LOCATION: (31)..(31)
<223> OTHER INFORMATION: Ser or Asn
<220> FEATURE:
<221> NAME/KEY: MOD_RES
<222> LOCATION: (50)..(50)
<223> OTHER INFORMATION: Lys or Ser
<220> FEATURE:
<221> NAME/KEY: MOD_RES
<222> LOCATION: (52)..(52)
<223> OTHER INFORMATION: Ser or Tyr
<220> FEATURE:
<221> NAME/KEY: MOD_RES
<222> LOCATION: (53)..(53)
<223> OTHER INFORMATION: Ser, Tyr, or Asn
<220> FEATURE:
```

```
<221> NAME/KEY: MOD_RES
<222> LOCATION: (56)..(56)
<223> OTHER INFORMATION: Ser or Tyr
<220> FEATURE:
<221> NAME/KEY: MOD_RES
<222> LOCATION: (90)..(90)
<223> OTHER INFORMATION: Gln, Leu, or Arg
<220> FEATURE:
<221> NAME/KEY: MOD_RES
<222> LOCATION: (93)..(93)
<223> OTHER INFORMATION: Ser or Lys

<400> SEQUENCE: 764

Asp Ile Gln Met Thr Gln Ser Pro Ser Thr Leu Ser Ala Ser Val Gly
1               5                   10                  15

Asp Arg Val Thr Ile Thr Cys Xaa Ala Ser Xaa Ser Ile Xaa Xaa Trp
            20                  25                  30

Leu Ala Trp Tyr Gln Gln Lys Pro Gly Lys Ala Pro Lys Leu Leu Ile
        35                  40                  45

Tyr Xaa Ala Xaa Xaa Leu Glu Xaa Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Xaa Phe Gln Xaa Leu Pro Pro
                85                  90                  95

Phe Thr Phe Gly Gly Gly Thr Lys Val Glu Ile Lys
            100                 105

<210> SEQ ID NO 765
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: His or Arg
<220> FEATURE:
<221> NAME/KEY: MOD_RES
<222> LOCATION: (32)..(32)
<223> OTHER INFORMATION: Arg or Tyr

<400> SEQUENCE: 765

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Xaa Ser Xaa
            20                  25                  30

Gly Met His Trp Val Arg Gln Ala Pro Gly Lys Gly Leu Glu Trp Val
        35                  40                  45

Ala Val Ile Thr Tyr Asp Gly Ile Asn Lys Tyr Tyr Ala Asp Ser Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Tyr Gly Val Tyr Asp Tyr Trp Gly Gln Gly
            100                 105                 110

Thr Leu Val Thr Val Ser Ser
        115
```

```
<210> SEQ ID NO 766
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 766

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Phe Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe His Ser Tyr Pro Leu Thr Phe Gly Gly Gly Thr Lys Val Glu Ile
            100                 105                 110

Lys

<210> SEQ ID NO 767
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 767

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Ala Ile Gly Trp Val Arg Gln Ala Pro Gly Gln Gly Leu Glu Trp Met
        35                  40                  45

Gly Ser Ile Ile Pro Ile Ile Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Tyr Tyr Tyr Gly Ala Ser Ser Phe Gly Met Asp
            100                 105                 110

Val Trp Gly Gln Gly Thr Thr Val Thr Val Ser Ser
        115                 120

<210> SEQ ID NO 768
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 768
```

-continued

```
Glu Ile Val Met Thr Gln Ser Pro Ala Thr Leu Ser Val Ser Pro Gly
1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Leu Pro Leu
                85                  90                  95

Thr Phe Gly Gly Gly Thr Lys Val Glu Ile Lys
            100                 105
```

<210> SEQ ID NO 769
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (7)..(7)
<223> OTHER INFORMATION: Ser or Trp
<220> FEATURE:
<221> NAME/KEY: MOD_RES
<222> LOCATION: (9)..(9)
<223> OTHER INFORMATION: Pro or Ala
<220> FEATURE:
<221> NAME/KEY: MOD_RES
<222> LOCATION: (12)..(12)
<223> OTHER INFORMATION: Val or Leu
<220> FEATURE:
<221> NAME/KEY: MOD_RES
<222> LOCATION: (16)..(16)
<223> OTHER INFORMATION: Gln or Glu
<220> FEATURE:
<221> NAME/KEY: MOD_RES
<222> LOCATION: (23)..(23)
<223> OTHER INFORMATION: Thr or Ala
<220> FEATURE:
<221> NAME/KEY: MOD_RES
<222> LOCATION: (25)..(25)
<223> OTHER INFORMATION: Ser or Tyr
<220> FEATURE:
<221> NAME/KEY: MOD_RES
<222> LOCATION: (29)..(29)
<223> OTHER INFORMATION: Ile or Leu
<220> FEATURE:
<221> NAME/KEY: MOD_RES
<222> LOCATION: (33)..(33)
<223> OTHER INFORMATION: Gln or Tyr
<220> FEATURE:
<221> NAME/KEY: MOD_RES
<222> LOCATION: (41)..(41)
<223> OTHER INFORMATION: His or Pro
<220> FEATURE:
<221> NAME/KEY: MOD_RES
<222> LOCATION: (53)..(53)
<223> OTHER INFORMATION: Tyr or Gly
<220> FEATURE:
<221> NAME/KEY: MOD_RES
<222> LOCATION: (54)..(54)
<223> OTHER INFORMATION: Tyr or Ala
<220> FEATURE:
<221> NAME/KEY: MOD_RES

```
<222> LOCATION: (77)..(77)
<223> OTHER INFORMATION: Asn or Asp
<220> FEATURE:
<221> NAME/KEY: MOD_RES
<222> LOCATION: (100)..(100)
<223> OTHER INFORMATION: Thr or Ala
<220> FEATURE:
<221> NAME/KEY: MOD_RES
<222> LOCATION: (105)..(105)
<223> OTHER INFORMATION: Glu, Gly, or Asp

<400> SEQUENCE: 769

Gln Val Gln Leu Gln Xaa Xaa Gly Xaa Gly Leu Xaa Lys Pro Ser Xaa
1               5                   10                  15

Thr Leu Ser Leu Thr Cys Xaa Val Xaa Gly Gly Ser Xaa Ser Ser Gly
            20                  25                  30

Xaa Tyr Trp Ser Trp Ile Arg Gln Xaa Pro Gly Lys Gly Leu Glu Trp
        35                  40                  45

Ile Gly Glu Ile Xaa Xaa Ser Gly Ser Thr Arg Tyr Asn Pro Ser Leu
    50                  55                  60

Lys Ser Arg Val Thr Ile Ser Val Asp Thr Ser Lys Xaa Gln Phe Ser
65                  70                  75                  80

Leu Lys Leu Ser Ser Val Thr Ala Ala Asp Thr Ala Val Tyr Tyr Cys
                85                  90                  95

Ala Arg Asp Xaa Pro Tyr Tyr Tyr Xaa Gly Gly Tyr Tyr Tyr Tyr Met
            100                 105                 110

Asp Val Trp Gly Lys Gly Thr Thr Val Thr Val Ser Ser
        115                 120                 125

<210> SEQ ID NO 770
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Gln, Glu, or Asp
<220> FEATURE:
<221> NAME/KEY: MOD_RES
<222> LOCATION: (30)..(30)
<223> OTHER INFORMATION: Ser or Asp
<220> FEATURE:
<221> NAME/KEY: MOD_RES
<222> LOCATION: (33)..(33)
<223> OTHER INFORMATION: Tyr or Phe
<220> FEATURE:
<221> NAME/KEY: MOD_RES
<222> LOCATION: (53)..(53)
<223> OTHER INFORMATION: Ser, Asp, Phe, or Tyr
<220> FEATURE:
<221> NAME/KEY: MOD_RES
<222> LOCATION: (54)..(54)
<223> OTHER INFORMATION: Ser or Thr
<220> FEATURE:
<221> NAME/KEY: MOD_RES
<222> LOCATION: (56)..(56)
<223> OTHER INFORMATION: Ala or Gln
<220> FEATURE:
<221> NAME/KEY: MOD_RES
<222> LOCATION: (57)..(57)
<223> OTHER INFORMATION: Thr or Asn
<220> FEATURE:
<221> NAME/KEY: MOD_RES
<222> LOCATION: (92)..(92)
<223> OTHER INFORMATION: Val, Ala, or Asp

<400> SEQUENCE: 770
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Xaa Ser Val Xaa Ser Ser
            20                  25                  30

Xaa Leu Ala Trp Tyr Gln Gln Lys Pro Gly Gln Ala Pro Arg Leu Leu
        35                  40                  45

Ile Tyr Gly Ala Xaa Xaa Arg Xaa Xaa Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Xaa Gly Val Val Pro
                85                  90                  95

Tyr Thr Phe Gly Gly Gly Thr Lys Val Glu Ile Lys
            100                 105
```

<210> SEQ ID NO 771
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 771

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ile Thr Val Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Lys Val Ala Ala Leu Ala Phe Asp Ile Trp Gly
            100                 105                 110

Gln Gly Thr Met Val Thr Val Ser Ser
        115                 120
```

<210> SEQ ID NO 772
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 772

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Ser
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Arg Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asn Phe His Pro Leu
                 85                  90                  95

Thr Phe Gly Gly Gly Thr Lys Val Glu Ile Lys
            100                 105

<210> SEQ ID NO 773
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp or Ser
<220> FEATURE:
<221> NAME/KEY: MOD_RES
<222> LOCATION: (10)..(10)
<223> OTHER INFORMATION: Ala or Gly

<400> SEQUENCE: 773

Gly Phe Thr Phe Ser Xaa Tyr Ala Met Xaa
1               5                   10

<210> SEQ ID NO 774
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala or Thr

<400> SEQUENCE: 774

Xaa Ile Ser Gly Ser Gly Gly Leu Thr Tyr Tyr Ala Asp Ser Val Lys
1               5                   10                  15

Gly

<210> SEQ ID NO 775
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 775

Ala Pro Tyr Gly Tyr Tyr Met Asp Val
1               5

<210> SEQ ID NO 776
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Arg Ala Ser Gln Ser Ile Ser Ser Trp Leu Ala
1               5                   10
```

<210> SEQ ID NO 777
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Lys Ala Ser Ser Leu Glu Ser
1               5

<210> SEQ ID NO 778
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 778

Gln Gln Tyr Lys Ser Tyr Ile Thr
1               5

<210> SEQ ID NO 779
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Arg
<220> FEATURE:
<221> NAME/KEY: MOD_RES
<222> LOCATION: (6)..(6)
<223> OTHER INFORMATION: Ser or Val

<400> SEQUENCE: 779

Gly Tyr Thr Phe Xaa Xaa Tyr Gly Ile Ser
1               5                   10

<210> SEQ ID NO 780
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (6)..(6)
<223> OTHER INFORMATION: Ser or Asn

<400> SEQUENCE: 780

Trp Xaa Ala Pro Tyr Xaa Gly Asn Thr Asn Tyr Ala Gln Lys Leu Gln
1               5                   10                  15

Gly

<210> SEQ ID NO 781
<211> LENGTH: 14
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phe or Tyr

<400> SEQUENCE: 781

Asp Ala Gly Thr Tyr Ser Pro Xaa Gly Tyr Gly Met Asp Val
1               5                   10

<210> SEQ ID NO 782
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Gln
<220> FEATURE:
<221> NAME/KEY: MOD_RES
<222> LOCATION: (4)..(4)
<223> OTHER INFORMATION: Gln, Glu, or His
<220> FEATURE:
<221> NAME/KEY: MOD_RES
<222> LOCATION: (7)..(7)
<223> OTHER INFORMATION: Ser, Asp, or Asn
<220> FEATURE:
<221> NAME/KEY: MOD_RES
<222> LOCATION: (8)..(8)
<223> OTHER INFORMATION: Ser or Asn

<400> SEQUENCE: 782

Xaa Ala Ser Xaa Ser Ile Xaa Xaa Trp Leu Ala
1               5                   10

<210> SEQ ID NO 783
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Ser
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Ser, Tyr, or Asn
<220> FEATURE:
<221> NAME/KEY: MOD_RES
<222> LOCATION: (7)..(7)
<223> OTHER INFORMATION: Ser or Tyr

<400> SEQUENCE: 783

Xaa Ala Xaa Xaa Leu Glu Xaa
1               5

<210> SEQ ID NO 784
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Leu, or Arg
<220> FEATURE:
<221> NAME/KEY: MOD_RES
<222> LOCATION: (5)..(5)
<223> OTHER INFORMATION: Ser or Lys

<400> SEQUENCE: 784

Gln Xaa Phe Gln Xaa Leu Pro Pro Phe Thr
1               5                   10

<210> SEQ ID NO 785
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: His or Arg
<220> FEATURE:
<221> NAME/KEY: MOD_RES
<222> LOCATION: (7)..(7)
<223> OTHER INFORMATION: Arg or Tyr

<400> SEQUENCE: 785

Gly Phe Thr Phe Xaa Ser Xaa Gly Met His
1               5                   10

<210> SEQ ID NO 786
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Val Ile Thr Tyr Asp Gly Ile Asn Lys Tyr Tyr Ala Asp Ser Val Glu
1               5                   10                  15
Gly

<210> SEQ ID NO 787
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Asp Gly Val Tyr Tyr Gly Val Tyr Asp Tyr
1               5                   10

<210> SEQ ID NO 788
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 788
```

Lys Ser Ser Gln Ser Val Leu Phe Ser Asn Asn Lys Asn Tyr Leu
1               5                   10                  15

Ala

<210> SEQ ID NO 789
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Trp Ala Ser Thr Arg Glu Ser
1               5

<210> SEQ ID NO 790
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 790

Gln Gln Phe His Ser Tyr Pro Leu Thr
1               5

<210> SEQ ID NO 791
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Gly Gly Thr Phe Ser Ser Asn Ala Ile Gly
1               5                   10

<210> SEQ ID NO 792
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 792

Ser Ile Ile Pro Ile Ile Gly Phe Ala Asn Tyr Ala Gln Lys Phe Gln
1               5                   10                  15

Gly

<210> SEQ ID NO 793
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Asp Ser Gly Tyr Tyr Tyr Gly Ala Ser Ser Phe Gly Met Asp Val
1               5                   10                  15

```
<210> SEQ ID NO 794
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 794

Arg Ala Ser Gln Ser Val Ser Ser Asn Leu Ala
1               5                   10

<210> SEQ ID NO 795
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Gly Ala Ser Thr Arg Ala Thr
1               5

<210> SEQ ID NO 796
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 796

Glu Gln Tyr Asn Asn Leu Pro Leu Thr
1               5

<210> SEQ ID NO 797
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Leu
<220> FEATURE:
<221> NAME/KEY: MOD_RES
<222> LOCATION: (8)..(8)
<223> OTHER INFORMATION: Gln or Tyr

<400> SEQUENCE: 797

Gly Gly Ser Xaa Ser Ser Gly Xaa Tyr Trp Ser
1               5                   10

<210> SEQ ID NO 798
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or Gly
<220> FEATURE:
<221> NAME/KEY: MOD_RES
<222> LOCATION: (4)..(4)
<223> OTHER INFORMATION: Tyr or Ala
```

-continued

```
<400> SEQUENCE: 798

Glu Ile Xaa Xaa Ser Gly Ser Thr Arg Tyr Asn Pro Ser Leu Lys Ser
1               5                   10                  15

<210> SEQ ID NO 799
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Ala
<220> FEATURE:
<221> NAME/KEY: MOD_RES
<222> LOCATION: (7)..(7)
<223> OTHER INFORMATION: Glu, Gly, or Asp

<400> SEQUENCE: 799

Asp Xaa Pro Tyr Tyr Tyr Xaa Gly Gly Tyr Tyr Tyr Tyr Met Asp Val
1               5                   10                  15

<210> SEQ ID NO 800
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Gln, Glu, or Asp
<220> FEATURE:
<221> NAME/KEY: MOD_RES
<222> LOCATION: (7)..(7)
<223> OTHER INFORMATION: Ser or Asp
<220> FEATURE:
<221> NAME/KEY: MOD_RES
<222> LOCATION: (10)..(10)
<223> OTHER INFORMATION: Tyr or Phe

<400> SEQUENCE: 800

Arg Ala Ser Xaa Ser Val Xaa Ser Ser Xaa Leu Ala
1               5                   10

<210> SEQ ID NO 801
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Asp, Phe, or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (6)..(6)
<223> OTHER INFORMATION: Ala or Gln
<220> FEATURE:
<221> NAME/KEY: MOD_RES
<222> LOCATION: (7)..(7)
<223> OTHER INFORMATION: Thr or Asn
```

```
<400> SEQUENCE: 801

Gly Ala Xaa Xaa Arg Xaa Xaa
1               5

<210> SEQ ID NO 802
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Val, Ala, or Asp

<400> SEQUENCE: 802

Gln Gln Xaa Gly Val Val Pro Tyr Thr
1               5

<210> SEQ ID NO 803
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 803

Gly Tyr Thr Phe Ala Asn Tyr Tyr Met His
1               5                   10

<210> SEQ ID NO 804
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Ile Ile Asn Pro Ser Gly Gly Ile Thr Val Tyr Ala Gln Lys Phe Gln
1               5                   10                  15

Gly

<210> SEQ ID NO 805
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Gly Gly Ser Lys Val Ala Ala Leu Ala Phe Asp Ile
1               5                   10

<210> SEQ ID NO 806
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 806

Gln Ala Ser Gln Asp Ile Ser Asn Ser Leu Asn
```

-continued

```
<210> SEQ ID NO 807
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Asp Ala Ser Asn Leu Glu Thr
1               5

<210> SEQ ID NO 808
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Gln Gln Tyr Asn Phe His Pro Leu Thr
1               5

<210> SEQ ID NO 809
<211> LENGTH: 295
<212> TYPE: PRT
<213> ORGANISM: Homo sapiens

<400> SEQUENCE: 809

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220
```

```
Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
            245                 250                 255

Gly Ala Val Val Phe Val Val Ile Ile Leu Val Ile Ile Leu Ala Ile
        260                 265                 270

Ser Leu His Lys Cys Arg Lys Ala Gly Val Gly Gln Ser Trp Lys Glu
    275                 280                 285

Asn Ser Pro Leu Asn Val Ser
    290                 295

<210> SEQ ID NO 810
<211> LENGTH: 219
<212> TYPE: PRT
<213> ORGANISM: Homo sapiens

<400> SEQUENCE: 810

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 811
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 811

Ser Gly Thr Thr Asn Thr Val Ala Ala Tyr Asn Leu Thr Trp Lys Ser
1               5                   10                  15
```

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Thr Gly His His His
210                 215                 220

His His His
225

<210> SEQ ID NO 812
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 812

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg

```
                    130                 135                 140
Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                    165                 170                 175

Ile Asp Val Asp Lys Gly Glu Asn Tyr Cys Phe Ser Val Gln Ala Val
                    180                 185                 190

Ile Pro Ser Arg Thr Val Asn Arg Lys Ser Thr Asp Ser Pro Val Glu
                    195                 200                 205

Cys Met Gly Gln Glu Lys Gly Glu Phe Arg Glu Thr Gly Glu Asn Leu
                    210                 215                 220

Tyr Phe Gln Gly Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                    245                 250                 255

Asp Thr Leu Met Ile Ser Arg Thr Pro Glu Val Thr Cys Val Val Val
                    260                 265                 270

Asp Val Ser His Glu Asp Pro Glu Val Lys Phe Asn Trp Tyr Val Asp
                    275                 280                 285

Gly Val Glu Val His Asn Ala Lys Thr Lys Pro Arg Glu Glu Gln Tyr
                    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                    325                 330                 335

Pro Ala Pro Ile Glu Lys Thr Ile Ser Lys Ala Lys Gly Gln Pro Arg
                    340                 345                 350

Glu Pro Gln Val Tyr Thr Leu Pro Pro Ser Arg Glu Glu Met Thr Lys
                    355                 360                 365

Asn Gln Val Ser Leu Thr Cys Leu Val Lys Gly Phe Tyr Pro Ser Asp
                    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                    405                 410                 415

Lys Leu Thr Val Asp Lys Ser Arg Trp Gln Gln Gly Asn Val Phe Ser
                    420                 425                 430

Cys Ser Val Met His Glu Ala Leu His Asn His Tyr Thr Gln Lys Ser
                    435                 440                 445

Leu Ser Leu Ser Pro Gly Lys
450                 455

<210> SEQ ID NO 813
<211> LENGTH: 296
<212> TYPE: PRT
<213> ORGANISM: Macaca fascicularis

<400> SEQUENCE: 813

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                    20                  25                  30

Ser Gly Thr Thr Asn Thr Val Ala Ala Tyr Asn Leu Thr Trp Lys Ser
                    35                  40                  45
```

```
Thr Asn Phe Lys Thr Ile Leu Glu Trp Glu Pro Lys Pro Ile Asn Gln
    50                  55                  60

Val Tyr Thr Val Gln Ile Ser Thr Lys Ser Gly Asp Trp Lys Ser Lys
 65                  70                  75                  80

Cys Phe Tyr Thr Ala Asp Thr Glu Cys Asp Leu Thr Asp Glu Ile Val
                 85                  90                  95

Lys Asp Val Lys Gln Thr Tyr Leu Ala Arg Val Phe Ser Tyr Pro Ala
                100                 105                 110

Gly His Val Glu Ser Thr Gly Ser Thr Glu Pro Pro Tyr Glu Asn
                115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Gln
145                 150                 155                 160

Asp Glu Trp Thr Leu Val Arg Arg Asn Asp Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
    195                 200                 205

Ile Asp Val Asp Lys Gly Glu Asn Tyr Cys Phe Ser Val Gln Ala Val
    210                 215                 220

Ile Pro Ser Arg Arg Thr Ala Asn Arg Lys Ser Thr Asp Ser Pro Val
225                 230                 235                 240

Glu Cys Met Gly His Glu Lys Gly Glu Ser Arg Glu Ile Phe Tyr Ile
                245                 250                 255

Ile Gly Ala Val Val Phe Val Val Ile Ile Leu Val Ile Ile Leu Ala
                260                 265                 270

Ile Ser Leu His Lys Cys Lys Lys Ala Arg Val Gly Arg Ser Trp Lys
    275                 280                 285

Glu Asn Ser Pro Leu Asn Val Ala
    290                 295

<210> SEQ ID NO 814
<211> LENGTH: 220
<212> TYPE: PRT
<213> ORGANISM: Macaca fascicularis

<400> SEQUENCE: 814

Ser Gly Thr Thr Asn Thr Val Ala Ala Tyr Asn Leu Thr Trp Lys Ser
1                5                  10                  15

Thr Asn Phe Lys Thr Ile Leu Glu Trp Glu Pro Lys Pro Ile Asn Gln
                20                  25                  30

Val Tyr Thr Val Gln Ile Ser Thr Lys Ser Gly Asp Trp Lys Ser Lys
            35                  40                  45

Cys Phe Tyr Thr Ala Asp Thr Glu Cys Asp Leu Thr Asp Glu Ile Val
                50                  55                  60

Lys Asp Val Lys Gln Thr Tyr Leu Ala Arg Val Phe Ser Tyr Pro Ala
65                  70                  75                  80

Gly His Val Glu Ser Thr Gly Ser Thr Glu Pro Pro Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Gln
            115                 120                 125
```

```
Asp Glu Trp Thr Leu Val Arg Arg Asn Asp Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Arg Thr Ala Asn Arg Lys Ser Thr Asp Ser Pro Val
        195                 200                 205

Glu Cys Met Gly His Glu Lys Gly Glu Ser Arg Glu
    210                 215                 220

<210> SEQ ID NO 815
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 815

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Ile Asn Gln
            20                  25                  30

Val Tyr Thr Val Gln Ile Ser Thr Lys Ser Gly Asp Trp Lys Ser Lys
        35                  40                  45

Cys Phe Tyr Thr Ala Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly His Val Glu Ser Thr Gly Ser Thr Glu Pro Pro Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Gln
        115                 120                 125

Asp Glu Trp Thr Leu Val Arg Arg Asn Asp Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Arg Thr Ala Asn Arg Lys Ser Thr Asp Ser Pro Val
        195                 200                 205

Glu Cys Met Gly His Glu Lys Gly Glu Ser Arg Glu Thr Gly His His
    210                 215                 220

His His His His
225

<210> SEQ ID NO 816
<211> LENGTH: 456
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 816

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Ile Asn Gln
            20                  25                  30

Val Tyr Thr Val Gln Ile Ser Thr Lys Ser Gly Asp Trp Lys Ser Lys
        35                  40                  45

Cys Phe Tyr Thr Ala Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly His Val Glu Ser Thr Gly Ser Thr Glu Glu Pro Pro Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Gln
        115                 120                 125

Asp Glu Trp Thr Leu Val Arg Arg Asn Asp Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Arg Thr Ala Asn Arg Lys Ser Thr Asp Ser Pro Val
        195                 200                 205

Glu Cys Met Gly His Glu Lys Gly Glu Ser Arg Glu Thr Gly Glu Asn
210                 215                 220

Leu Tyr Phe Gln Gly Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380
```

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 817
<211> LENGTH: 294
<212> TYPE: PRT
<213> ORGANISM: Mus musculus

<400> SEQUENCE: 817

Met Ala Ile Leu Val Arg Pro Arg Leu Leu Ala Leu Ala Pro Thr
1               5                   10                  15

Phe Leu Gly Cys Leu Leu Gln Val Thr Ala Gly Ala Gly Ile Pro
            20                  25                  30

Glu Lys Ala Phe Asn Leu Thr Trp Ile Ser Thr Asp Phe Lys Thr Ile
        35                  40                  45

Leu Glu Trp Gln Pro Lys Pro Thr Asn Tyr Thr Tyr Thr Val Gln Ile
    50                  55                  60

Ser Asp Arg Ser Arg Asn Trp Lys Asn Lys Cys Phe Ser Thr Thr Asp
65                  70                  75                  80

Thr Glu Cys Asp Leu Thr Asp Glu Ile Val Lys Asp Val Thr Trp Ala
                85                  90                  95

Tyr Glu Ala Lys Val Leu Ser Val Pro Arg Arg Asn Ser Val His Gly
            100                 105                 110

Asp Gly Asp Gln Leu Val Ile His Gly Glu Glu Pro Pro Phe Thr Asn
        115                 120                 125

Ala Pro Lys Phe Leu Pro Tyr Arg Asp Thr Asn Leu Gly Gln Pro Val
    130                 135                 140

Ile Gln Gln Phe Glu Gln Asp Gly Arg Lys Leu Asn Val Val Val Lys
145                 150                 155                 160

Asp Ser Leu Thr Leu Val Arg Lys Asn Gly Thr Phe Leu Thr Leu Arg
                165                 170                 175

Gln Val Phe Gly Lys Asp Leu Gly Tyr Ile Ile Thr Tyr Arg Lys Gly
            180                 185                 190

Ser Ser Thr Gly Lys Lys Thr Asn Ile Thr Asn Thr Asn Glu Phe Ser
        195                 200                 205

Ile Asp Val Glu Glu Gly Val Ser Tyr Cys Phe Phe Val Gln Ala Met
    210                 215                 220

Ile Phe Ser Arg Lys Thr Asn Gln Asn Ser Pro Gly Ser Ser Thr Val
225                 230                 235                 240

Cys Thr Glu Gln Trp Lys Ser Phe Leu Gly Glu Thr Leu Ile Ile Val
                245                 250                 255

Gly Ala Val Val Leu Leu Ala Thr Ile Phe Ile Ile Leu Leu Ser Ile
            260                 265                 270

Ser Leu Cys Lys Arg Arg Lys Asn Arg Ala Gly Gln Lys Gly Lys Asn
        275                 280                 285

Thr Pro Ser Arg Leu Ala
    290
```

<210> SEQ ID NO 818
<211> LENGTH: 223
<212> TYPE: PRT
<213> ORGANISM: Mus musculus

<400> SEQUENCE: 818

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
                100                 105                 110

Gly Gln Pro Val Ile Gln Gln Phe Glu Gln Asp Gly Arg Lys Leu Asn
            115                 120                 125

Val Val Val Lys Asp Ser Leu Thr Leu Val Arg Lys Asn Gly Thr Phe
    130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
                180                 185                 190

Val Gln Ala Met Ile Phe Ser Arg Lys Thr Asn Gln Asn Ser Pro Gly
            195                 200                 205

Ser Ser Thr Val Cys Thr Glu Gln Trp Lys Ser Phe Leu Gly Glu
    210                 215                 220

<210> SEQ ID NO 819
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 819

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
    50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Phe Glu Gln Asp Gly Arg Lys Leu Asn
        115                 120                 125

Val Val Val Lys Asp Ser Leu Thr Leu Val Arg Lys Asn Gly Thr Phe
130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu Thr
    210                 215                 220

Gly His His His His His His
225                 230

<210> SEQ ID NO 820
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 820

Ala Gly Ile Pro Glu Lys Ala Phe Asn Leu Thr Trp Ile Ser Thr Asp
1               5                   10                  15

Phe Lys Thr Ile Leu Glu Trp Gln Pro Lys Pro Thr Asn Tyr Thr Tyr
                20                  25                  30

Thr Val Gln Ile Ser Asp Arg Ser Arg Asn Trp Lys Asn Lys Cys Phe
            35                  40                  45

Ser Thr Thr Asp Thr Glu Cys Asp Leu Thr Asp Glu Ile Val Lys Asp
50                  55                  60

Val Thr Trp Ala Tyr Glu Ala Lys Val Leu Ser Val Pro Arg Arg Asn
65                  70                  75                  80

Ser Val His Gly Asp Gly Asp Gln Leu Val Ile His Gly Glu Glu Pro
                85                  90                  95

Pro Phe Thr Asn Ala Pro Lys Phe Leu Pro Tyr Arg Asp Thr Asn Leu
            100                 105                 110

Gly Gln Pro Val Ile Gln Phe Glu Gln Asp Gly Arg Lys Leu Asn
        115                 120                 125

Val Val Val Lys Asp Ser Leu Thr Leu Val Arg Lys Asn Gly Thr Phe
130                 135                 140

Leu Thr Leu Arg Gln Val Phe Gly Lys Asp Leu Gly Tyr Ile Ile Thr
145                 150                 155                 160

Tyr Arg Lys Gly Ser Ser Thr Gly Lys Lys Thr Asn Ile Thr Asn Thr
                165                 170                 175

Asn Glu Phe Ser Ile Asp Val Glu Glu Gly Val Ser Tyr Cys Phe Phe
            180                 185                 190

Val Gln Ala Met Ile Phe Ser Arg Lys Thr Asn Gln Asn Ser Pro Gly
        195                 200                 205

Ser Ser Thr Val Cys Thr Glu Gln Trp Lys Ser Phe Leu Gly Glu Thr

```
                210                 215                 220
Gly Glu Asn Leu Tyr Phe Gln Gly Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
        290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Glu
            355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro Gly Lys
        450                 455

<210> SEQ ID NO 821
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 821

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Ala Pro Tyr
                20                  25                  30

Trp Ile Glu Trp Val Arg Gln Met Pro Gly Lys Gly Leu Glu Trp Met
            35                  40                  45

Gly Asp Ile Leu Pro Gly Thr Gly Phe Thr Thr Tyr Ser Pro Ser Phe
        50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Tyr Tyr Gly Asn Ser Gly Phe Ala Tyr Trp Gly Gln
                100                 105                 110
```

```
Gly Thr Leu Val Thr Val Ser Ser
        115                 120

<210> SEQ ID NO 822
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 822

Asp Ile Val Met Thr Gln Thr Pro Leu Ser Leu Pro Val Thr Pro Gly
1               5                   10                  15

Glu Pro Ala Ser Ile Ser Cys Lys Ser Ser Gln Ser Leu Leu Ser Ser
            20                  25                  30

Gly Asn Gln Lys Asn Tyr Leu Thr Trp Tyr Leu Gln Lys Pro Gly Gln
        35                  40                  45

Ser Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Asn
                85                  90                  95

Asp Tyr Thr Tyr Pro Leu Thr Phe Gly Gln Gly Thr Lys Leu Glu Ile
            100                 105                 110

Lys

<210> SEQ ID NO 823
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 823

Gly Gly Gly Gly Ser
1               5

<210> SEQ ID NO 824
<211> LENGTH: 292
<212> TYPE: PRT
<213> ORGANISM: Sus scrofa

<400> SEQUENCE: 824

Met Ala Thr Pro Thr Gly Pro Pro Val Ser Cys Pro Lys Ala Ala Val
1               5                   10                  15

Ala Arg Ala Leu Leu Leu Gly Trp Val Leu Val Gln Val Ala Gly Ala
            20                  25                  30

Thr Gly Thr Thr Asp Val Ile Val Ala Tyr Asn Leu Thr Trp Lys Ser
        35                  40                  45

Thr Asn Phe Lys Thr Ile Leu Glu Trp Glu Pro Lys Pro Ile Asn Tyr
    50                  55                  60

Val Tyr Thr Val Gln Ile Ser Pro Arg Leu Gly Asp Trp Lys Asn Lys
65                  70                  75                  80

Cys Phe His Thr Thr Asp Thr Glu Cys Asp Val Thr Asp Glu Ile Met
                85                  90                  95

Arg Asn Val Lys Glu Thr Tyr Val Ala Arg Val Leu Ser Tyr Pro Ala
            100                 105                 110
```

```
Asp Thr Val Leu Thr Ala Gln Glu Pro Pro Phe Thr Asn Ser Pro Pro
            115                 120                 125

Phe Thr Pro Tyr Leu Asp Thr Asn Leu Gly Gln Pro Val Ile Gln Ser
        130                 135                 140

Phe Glu Gln Val Gly Thr Lys Leu Asn Val Thr Val Glu Ala Ala Arg
145                 150                 155                 160

Thr Leu Val Arg Val Asn Gly Thr Phe Leu Arg Leu Arg Asp Val Phe
                165                 170                 175

Gly Lys Asp Leu Asn Tyr Thr Leu Tyr Tyr Trp Arg Ala Ser Ser Thr
            180                 185                 190

Gly Lys Lys Lys Ala Thr Thr Asn Thr Asn Glu Phe Leu Ile Asp Val
        195                 200                 205

Asp Lys Gly Glu Asn Tyr Cys Phe Ser Val Gln Ala Val Ile Pro Ser
210                 215                 220

Arg Arg Val Asn Gln Lys Ser Pro Glu Ser Arg Ile Glu Cys Thr Ser
225                 230                 235                 240

Gln Glu Lys Ala Val Ser Arg Glu Leu Phe Leu Ile Val Gly Ala Val
                245                 250                 255

Val Phe Ala Val Ile Val Phe Val Leu Val Leu Ser Val Ser Leu Tyr
            260                 265                 270

Lys Cys Arg Lys Glu Arg Ala Gly Pro Ser Gly Lys Glu Asn Ala Pro
        275                 280                 285

Leu Asn Val Ala
    290

<210> SEQ ID NO 825
<211> LENGTH: 216
<212> TYPE: PRT
<213> ORGANISM: Sus scrofa

<400> SEQUENCE: 825

Thr Gly Thr Thr Asp Val Ile Val Ala Tyr Asn Leu Thr Trp Lys Ser
1               5                   10                  15

Thr Asn Phe Lys Thr Ile Leu Glu Trp Glu Pro Lys Pro Ile Asn Tyr
            20                  25                  30

Val Tyr Thr Val Gln Ile Ser Pro Arg Leu Gly Asp Trp Lys Asn Lys
        35                  40                  45

Cys Phe His Thr Thr Asp Thr Glu Cys Asp Val Thr Asp Glu Ile Met
    50                  55                  60

Arg Asn Val Lys Glu Thr Tyr Val Ala Arg Val Leu Ser Tyr Pro Ala
65                  70                  75                  80

Asp Thr Val Leu Thr Ala Gln Glu Pro Pro Phe Thr Asn Ser Pro Pro
                85                  90                  95

Phe Thr Pro Tyr Leu Asp Thr Asn Leu Gly Gln Pro Val Ile Gln Ser
            100                 105                 110

Phe Glu Gln Val Gly Thr Lys Leu Asn Val Thr Val Glu Ala Ala Arg
        115                 120                 125

Thr Leu Val Arg Val Asn Gly Thr Phe Leu Arg Leu Arg Asp Val Phe
    130                 135                 140

Gly Lys Asp Leu Asn Tyr Thr Leu Tyr Tyr Trp Arg Ala Ser Ser Thr
145                 150                 155                 160

Gly Lys Lys Lys Ala Thr Thr Asn Thr Asn Glu Phe Leu Ile Asp Val
                165                 170                 175

Asp Lys Gly Glu Asn Tyr Cys Phe Ser Val Gln Ala Val Ile Pro Ser
```

```
                    180                 185                 190
Arg Arg Val Asn Gln Lys Ser Pro Glu Ser Arg Ile Glu Cys Thr Ser
            195                 200                 205

Gln Glu Lys Ala Val Ser Arg Glu
        210                 215
```

<210> SEQ ID NO 826
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 826

```
Thr Gly Thr Thr Asp Val Ile Val Ala Tyr Asn Leu Thr Trp Lys Ser
1               5                   10                  15

Thr Asn Phe Lys Thr Ile Leu Glu Trp Glu Pro Lys Pro Ile Asn Tyr
            20                  25                  30

Val Tyr Thr Val Gln Ile Ser Pro Arg Leu Gly Asp Trp Lys Asn Lys
        35                  40                  45

Cys Phe His Thr Thr Asp Thr Glu Cys Asp Val Thr Asp Glu Ile Met
50                  55                  60

Arg Asn Val Lys Glu Thr Tyr Val Ala Arg Val Leu Ser Tyr Pro Ala
65                  70                  75                  80

Asp Thr Val Leu Thr Ala Gln Glu Pro Pro Phe Thr Asn Ser Pro Pro
                85                  90                  95

Phe Thr Pro Tyr Leu Asp Thr Asn Leu Gly Gln Pro Val Ile Gln Ser
            100                 105                 110

Phe Glu Gln Val Gly Thr Lys Leu Asn Val Thr Val Glu Ala Ala Arg
        115                 120                 125

Thr Leu Val Arg Val Asn Gly Thr Phe Leu Arg Leu Arg Asp Val Phe
130                 135                 140

Gly Lys Asp Leu Asn Tyr Thr Leu Tyr Tyr Trp Arg Ala Ser Ser Thr
145                 150                 155                 160

Gly Lys Lys Lys Ala Thr Thr Asn Thr Asn Glu Phe Leu Ile Asp Val
                165                 170                 175

Asp Lys Gly Glu Asn Tyr Cys Phe Ser Val Gln Ala Val Ile Pro Ser
            180                 185                 190

Arg Arg Val Asn Gln Lys Ser Pro Glu Ser Arg Ile Glu Cys Thr Ser
        195                 200                 205

Gln Glu Lys Ala Val Ser Arg Glu Thr Gly His His His His His
    210                 215                 220
```

<210> SEQ ID NO 827
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 827

```
Thr Gly Thr Thr Asp Val Ile Val Ala Tyr Asn Leu Thr Trp Lys Ser
1               5                   10                  15

Thr Asn Phe Lys Thr Ile Leu Glu Trp Glu Pro Lys Pro Ile Asn Tyr
            20                  25                  30

Val Tyr Thr Val Gln Ile Ser Pro Arg Leu Gly Asp Trp Lys Asn Lys
```

```
             35                  40                  45
Cys Phe His Thr Thr Asp Thr Glu Cys Asp Val Thr Asp Glu Ile Met
 50                  55                  60

Arg Asn Val Lys Glu Thr Tyr Val Ala Arg Val Leu Ser Tyr Pro Ala
 65                  70                  75                  80

Asp Thr Val Leu Thr Ala Gln Glu Pro Pro Phe Thr Asn Ser Pro Pro
                 85                  90                  95

Phe Thr Pro Tyr Leu Asp Thr Asn Leu Gly Gln Pro Val Ile Gln Ser
                100                 105                 110

Phe Glu Gln Val Gly Thr Lys Leu Asn Val Thr Val Glu Ala Ala Arg
                115                 120                 125

Thr Leu Val Arg Val Asn Gly Thr Phe Leu Arg Leu Arg Asp Val Phe
130                 135                 140

Gly Lys Asp Leu Asn Tyr Thr Leu Tyr Tyr Trp Arg Ala Ser Ser Thr
145                 150                 155                 160

Gly Lys Lys Lys Ala Thr Thr Asn Thr Asn Glu Phe Leu Ile Asp Val
                165                 170                 175

Asp Lys Gly Glu Asn Tyr Cys Phe Ser Val Gln Ala Val Ile Pro Ser
                180                 185                 190

Arg Arg Val Asn Gln Lys Ser Pro Glu Ser Arg Ile Glu Cys Thr Ser
                195                 200                 205

Gln Glu Lys Ala Val Ser Arg Glu Thr Gly Glu Asn Leu Tyr Phe Gln
210                 215                 220

Gly Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
                450
```

```
<210> SEQ ID NO 828
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 828
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Tyr Thr Tyr Tyr Thr Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Trp Gly Tyr Tyr Leu Asp Ser Trp Gly Gln Gly Thr
            100                 105                 110

Leu Val Thr Val Ser Ser
        115

```
<210> SEQ ID NO 829
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 829
```

Asp Ile Gln Met Thr Gln Ser Pro Pro Ser Leu Ser Ala Ser Ala Gly
1               5                   10                  15

Asp Arg Val Thr Ile Thr Cys Arg Ala Ser Gln Gly Ile Ser Ser Arg
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

```
<210> SEQ ID NO 830
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 830
```

-continued

Gln Val Gln Leu Val Glu Ser Gly Gly Gly Val Val Gln Pro Gly Arg
1               5                   10                  15

Ser Leu Arg Leu Ser Cys Lys Ala Ser Gly Phe Asn Ile Lys Asp Tyr
            20                  25                  30

Tyr Met His Trp Val Arg Gln Ala Pro Gly Lys Gly Leu Glu Trp Ile
        35                  40                  45

Gly Leu Ile Asp Pro Glu Asn Gly Asn Thr Ile Tyr Asp Pro Lys Phe
    50                  55                  60

Gln Gly Arg Phe Thr Ile Ser Ala Asp Asn Ser Lys Asn Thr Leu Phe
65                  70                  75                  80

Leu Gln Met Asp Ser Leu Arg Pro Glu Asp Thr Ala Val Tyr Tyr Cys
                85                  90                  95

Ala Arg Asp Asn Ser Tyr Tyr Phe Asp Tyr Trp Gly Gln Gly Thr Pro
            100                 105                 110

Val Thr Val Ser Ser
            115

<210> SEQ ID NO 831
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 831

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Arg Lys Tyr
            20                  25                  30

Leu Asn Trp Tyr Gln Gln Lys Pro Gly Lys Ala Pro Lys Leu Leu Ile
        35                  40                  45

Tyr Tyr Ala Thr Ser Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln His Gly Glu Ser Pro Tyr
                85                  90                  95

Thr Phe Gly Gln Gly Thr Lys Leu Glu Ile Thr
            100                 105

<210> SEQ ID NO 832
<211> LENGTH: 292
<212> TYPE: PRT
<213> ORGANISM: Oryctolagus cuniculus

<400> SEQUENCE: 832

Met Ala Pro Pro Thr Arg Leu Gln Val Pro Arg Pro Gly Thr Ala Val
1               5                   10                  15

Pro Tyr Thr Val Leu Leu Gly Trp Leu Ala Gln Val Ala Arg Ala
            20                  25                  30

Ala Asp Thr Thr Gly Arg Ala Tyr Asn Leu Thr Trp Lys Ser Thr Asn
            35                  40                  45

Phe Lys Thr Ile Leu Glu Trp Glu Pro Lys Ser Ile Asp His Val Tyr
    50                  55                  60

Thr Val Gln Ile Ser Thr Arg Leu Glu Asn Trp Lys Ser Lys Cys Phe
65                  70                  75                  80

```
Leu Thr Ala Glu Thr Glu Cys Asp Leu Thr Asp Glu Val Val Lys Asp
                85                  90                  95

Val Gly Gln Thr Tyr Met Ala Arg Val Leu Ser Tyr Pro Ala Arg Asn
            100                 105                 110

Gly Asn Thr Thr Gly Phe Pro Glu Glu Pro Pro Phe Arg Asn Ser Pro
        115                 120                 125

Glu Phe Thr Pro Tyr Leu Asp Thr Asn Leu Gly Gln Pro Thr Ile Gln
    130                 135                 140

Ser Phe Glu Gln Val Gly Thr Lys Leu Asn Val Thr Val Gln Asp Ala
145                 150                 155                 160

Arg Thr Leu Val Arg Arg Asn Gly Thr Phe Leu Ser Leu Arg Ala Val
                165                 170                 175

Phe Gly Lys Asp Leu Asn Tyr Thr Leu Tyr Tyr Trp Arg Ala Ser Ser
            180                 185                 190

Thr Gly Lys Lys Thr Ala Thr Thr Asn Thr Asn Glu Phe Leu Ile Asp
        195                 200                 205

Val Asp Lys Gly Glu Asn Tyr Cys Phe Ser Val Gln Ala Val Ile Pro
    210                 215                 220

Ser Arg Lys Arg Lys Gln Arg Ser Pro Glu Ser Leu Thr Glu Cys Thr
225                 230                 235                 240

Ser Arg Glu Gln Gly Arg Ala Arg Glu Met Phe Phe Ile Ile Gly Ala
                245                 250                 255

Val Val Val Val Ala Leu Leu Ile Ile Val Leu Ser Val Thr Val Tyr
            260                 265                 270

Lys Cys Arg Lys Ala Arg Ala Gly Pro Ser Gly Lys Glu Ser Ser Pro
        275                 280                 285

Leu Asn Ile Ala
    290

<210> SEQ ID NO 833
<211> LENGTH: 218
<212> TYPE: PRT
<213> ORGANISM: Oryctolagus cuniculus

<400> SEQUENCE: 833

Ala Asp Thr Thr Gly Arg Ala Tyr Asn Leu Thr Trp Lys Ser Thr Asn
1               5                   10                  15

Phe Lys Thr Ile Leu Glu Trp Glu Pro Lys Ser Ile Asp His Val Tyr
            20                  25                  30

Thr Val Gln Ile Ser Thr Arg Leu Glu Asn Trp Lys Ser Lys Cys Phe
        35                  40                  45

Leu Thr Ala Glu Thr Glu Cys Asp Leu Thr Asp Glu Val Val Lys Asp
    50                  55                  60

Val Gly Gln Thr Tyr Met Ala Arg Val Leu Ser Tyr Pro Ala Arg Asn
65                  70                  75                  80

Gly Asn Thr Thr Gly Phe Pro Glu Glu Pro Pro Phe Arg Asn Ser Pro
                85                  90                  95

Glu Phe Thr Pro Tyr Leu Asp Thr Asn Leu Gly Gln Pro Thr Ile Gln
            100                 105                 110

Ser Phe Glu Gln Val Gly Thr Lys Leu Asn Val Thr Val Gln Asp Ala
        115                 120                 125

Arg Thr Leu Val Arg Arg Asn Gly Thr Phe Leu Ser Leu Arg Ala Val
    130                 135                 140

Phe Gly Lys Asp Leu Asn Tyr Thr Leu Tyr Tyr Trp Arg Ala Ser Ser
145                 150                 155                 160
```

```
Thr Gly Lys Lys Thr Ala Thr Thr Asn Thr Asn Glu Phe Leu Ile Asp
            165                 170                 175

Val Asp Lys Gly Glu Asn Tyr Cys Phe Ser Val Gln Ala Val Ile Pro
        180                 185                 190

Ser Arg Lys Arg Lys Gln Arg Ser Pro Glu Ser Leu Thr Glu Cys Thr
        195                 200                 205

Ser Arg Glu Gln Gly Arg Ala Arg Glu Met
    210                 215

<210> SEQ ID NO 834
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 834

Ala Asp Thr Thr Gly Arg Ala Tyr Asn Leu Thr Trp Lys Ser Thr Asn
1               5                   10                  15

Phe Lys Thr Ile Leu Glu Trp Glu Pro Lys Ser Ile Asp His Val Tyr
            20                  25                  30

Thr Val Gln Ile Ser Thr Arg Leu Glu Asn Trp Lys Ser Lys Cys Phe
        35                  40                  45

Leu Thr Ala Glu Thr Glu Cys Asp Leu Thr Asp Glu Val Val Lys Asp
    50                  55                  60

Val Gly Gln Thr Tyr Met Ala Arg Val Leu Ser Tyr Pro Ala Arg Asn
65                  70                  75                  80

Gly Asn Thr Thr Gly Phe Pro Glu Glu Pro Pro Phe Arg Asn Ser Pro
                85                  90                  95

Glu Phe Thr Pro Tyr Leu Asp Thr Asn Leu Gly Gln Pro Thr Ile Gln
            100                 105                 110

Ser Phe Glu Gln Val Gly Thr Lys Leu Asn Val Thr Val Gln Asp Ala
        115                 120                 125

Arg Thr Leu Val Arg Arg Asn Gly Thr Phe Leu Ser Leu Arg Ala Val
    130                 135                 140

Phe Gly Lys Asp Leu Asn Tyr Thr Leu Tyr Tyr Trp Arg Ala Ser Ser
145                 150                 155                 160

Thr Gly Lys Lys Thr Ala Thr Thr Asn Thr Asn Glu Phe Leu Ile Asp
            165                 170                 175

Val Asp Lys Gly Glu Asn Tyr Cys Phe Ser Val Gln Ala Val Ile Pro
        180                 185                 190

Ser Arg Lys Arg Lys Gln Arg Ser Pro Glu Ser Leu Thr Glu Cys Thr
        195                 200                 205

Ser Arg Glu Gln Gly Arg Ala Arg Glu Met Thr Gly His His His His
    210                 215                 220

His His
225

<210> SEQ ID NO 835
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 835
```

```
Ala Asp Thr Thr Gly Arg Ala Tyr Asn Leu Thr Trp Lys Ser Thr Asn
1               5                   10                  15

Phe Lys Thr Ile Leu Glu Trp Glu Pro Lys Ser Ile Asp His Val Tyr
            20                  25                  30

Thr Val Gln Ile Ser Thr Arg Leu Glu Asn Trp Lys Ser Lys Cys Phe
            35                  40                  45

Leu Thr Ala Glu Thr Glu Cys Asp Leu Thr Asp Glu Val Val Lys Asp
        50                  55                  60

Val Gly Gln Thr Tyr Met Ala Arg Val Leu Ser Tyr Pro Ala Arg Asn
65                  70                  75                  80

Gly Asn Thr Thr Gly Phe Pro Glu Glu Pro Pro Phe Arg Asn Ser Pro
                85                  90                  95

Glu Phe Thr Pro Tyr Leu Asp Thr Asn Leu Gly Gln Pro Thr Ile Gln
            100                 105                 110

Ser Phe Glu Gln Val Gly Thr Lys Leu Asn Val Thr Val Gln Asp Ala
        115                 120                 125

Arg Thr Leu Val Arg Arg Asn Gly Thr Phe Leu Ser Leu Arg Ala Val
        130                 135                 140

Phe Gly Lys Asp Leu Asn Tyr Thr Leu Tyr Tyr Trp Arg Ala Ser Ser
145                 150                 155                 160

Thr Gly Lys Lys Thr Ala Thr Thr Asn Thr Asn Glu Phe Leu Ile Asp
            165                 170                 175

Val Asp Lys Gly Glu Asn Tyr Cys Phe Ser Val Gln Ala Val Ile Pro
            180                 185                 190

Ser Arg Lys Arg Lys Gln Arg Ser Pro Glu Ser Leu Thr Glu Cys Thr
        195                 200                 205

Ser Arg Glu Gln Gly Arg Ala Arg Glu Met Glu Asn Leu Tyr Phe Gln
        210                 215                 220

Gly Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 836
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 836

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Ala Tyr
            20                  25                  30

Gly Ile Ser Trp Val Arg Gln Ala Pro Gly Gln Gly Leu Glu Trp Met
        35                  40                  45

Gly Trp Ile Ala Pro Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Phe Gly Tyr Gly Met Asp Val
            100                 105                 110

Trp Gly Gln Gly Thr Thr Val Thr Val Ser Ser
        115                 120

<210> SEQ ID NO 837
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 837

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Tyr Ser Leu Glu Tyr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Gln Lys Leu Pro Pro
                85                  90                  95

Phe Thr Phe Gly Gly Gly Thr Lys Val Glu Ile Lys
            100                 105

<210> SEQ ID NO 838
<211> LENGTH: 224
```

-continued

```
<212> TYPE: PRT
<213> ORGANISM: Rattus sp.

<400> SEQUENCE: 838

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Asp Arg Ser Arg Asn Trp Lys Tyr Lys Cys
        35                  40                  45

Thr Gly Thr Thr Asp Thr Glu Cys Asp Leu Thr Asp Glu Ile Val Lys
    50                  55                  60

Asp Val Asn Trp Thr Tyr Glu Ala Arg Val Leu Ser Val Pro Trp Arg
65              70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
            100                 105                 110

Ile Gly Gln Pro Val Ile Gln Lys Tyr Glu Gln Gly Thr Lys Leu
        115                 120                 125

Lys Val Thr Val Lys Asp Ser Phe Thr Leu Val Arg Lys Asn Gly Thr
    130                 135                 140

Phe Leu Thr Leu Arg Gln Val Phe Gly Asn Asp Leu Gly Tyr Ile Leu
145                 150                 155                 160

Thr Tyr Arg Lys Asp Ser Ser Thr Gly Arg Lys Thr Asn Thr Thr His
                165                 170                 175

Thr Asn Glu Phe Leu Ile Asp Val Glu Lys Gly Val Ser Tyr Cys Phe
            180                 185                 190

Phe Ala Gln Ala Val Ile Phe Ser Arg Lys Thr Asn His Lys Ser Pro
        195                 200                 205

Glu Ser Ile Thr Lys Cys Thr Glu Gln Trp Lys Ser Val Leu Gly Glu
    210                 215                 220

<210> SEQ ID NO 839
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 839

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Asp Arg Ser Arg Asn Trp Lys Tyr Lys Cys
        35                  40                  45

Thr Gly Thr Thr Asp Thr Glu Cys Asp Leu Thr Asp Glu Ile Val Lys
    50                  55                  60

Asp Val Asn Trp Thr Tyr Glu Ala Arg Val Leu Ser Val Pro Trp Arg
65              70                  75                  80

Asn Ser Thr His Gly Lys Glu Thr Leu Phe Gly Thr His Gly Glu Glu
                85                  90                  95

Pro Pro Phe Thr Asn Ala Arg Lys Phe Leu Pro Tyr Arg Asp Thr Lys
            100                 105                 110
```

Leu Gly Gln Pro Thr Ile Gln Ser Phe Glu Gln Val Gly Thr Lys Val
            115                 120                 125

Asn Val Thr Val Glu Asp Glu Arg Thr Leu Val Arg Arg Asn Asn Thr
130                 135                 140

Phe Leu Ser Leu Arg Asp Val Phe Gly Lys Asp Leu Ile Tyr Thr Leu
145                 150                 155                 160

Tyr Tyr Trp Lys Ser Ser Ser Gly Lys Lys Thr Ala Lys Thr Asn
                165                 170                 175

Thr Asn Glu Phe Leu Ile Asp Val Asp Lys Gly Glu Asn Tyr Cys Phe
            180                 185                 190

Ser Val Gln Ala Val Ile Pro Ser Arg Thr Val Asn Arg Lys Ser Thr
            195                 200                 205

Asp Ser Pro Val Glu Cys Met Gly Gln Glu Lys Gly Glu Phe Arg Glu
            210                 215                 220

<210> SEQ ID NO 840
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 840

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Asp Arg Ser Arg Asn Trp Lys Tyr Lys Cys
        35                  40                  45

Thr Gly Thr Thr Asp Thr Glu Cys Asp Leu Thr Asp Glu Ile Val Lys
    50                  55                  60

Asp Val Asn Trp Thr Tyr Glu Ala Arg Val Leu Ser Tyr Pro Ala Gly
65                  70                  75                  80

Asn Val Glu Ser Thr Gly Ser Ala Gly Glu Pro Leu Tyr Glu Asn Ser
                85                  90                  95

Pro Glu Phe Thr Pro Tyr Leu Glu Thr Asn Leu Gly Gln Pro Thr Ile
            100                 105                 110

Gln Ser Phe Glu Gln Val Gly Thr Lys Val Asn Val Thr Val Glu Asp
        115                 120                 125

Glu Arg Thr Leu Val Arg Arg Asn Asn Thr Phe Leu Ser Leu Arg Asp
    130                 135                 140

Val Phe Gly Lys Asp Leu Ile Tyr Thr Leu Tyr Tyr Trp Lys Ser Ser
145                 150                 155                 160

Ser Ser Gly Lys Lys Thr Ala Lys Thr Asn Thr Asn Glu Phe Leu Ile
                165                 170                 175

Asp Val Asp Lys Gly Glu Asn Tyr Cys Phe Ser Val Gln Ala Val Ile
            180                 185                 190

Pro Ser Arg Thr Val Asn Arg Lys Ser Thr Asp Ser Pro Val Glu Cys
        195                 200                 205

Met Gly Gln Glu Lys Gly Glu Phe Arg Glu
    210                 215

<210> SEQ ID NO 841
<211> LENGTH: 218
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 841

Ala Gly Thr Pro Pro Gly Lys Ala Phe Asn Leu Thr Trp Ile Ser Thr
1               5                   10                  15

Asp Phe Lys Thr Ile Leu Glu Trp Gln Pro Lys Pro Thr Asn Tyr Thr
            20                  25                  30

Tyr Thr Val Gln Ile Ser Thr Lys Ser Gly Asp Trp Lys Ser Lys Cys
        35                  40                  45

Phe Tyr Thr Thr Asp Thr Glu Cys Asp Leu Thr Asp Glu Ile Val Lys
50                  55                  60

Asp Val Lys Gln Thr Tyr Leu Ala Arg Val Phe Ser Tyr Pro Ala Gly
65                  70                  75                  80

Asn Val Glu Ser Thr Gly Ser Ala Gly Glu Pro Leu Tyr Glu Asn Ser
            85                  90                  95

Pro Glu Phe Thr Pro Tyr Leu Glu Thr Asn Leu Gly Gln Pro Thr Ile
            100                 105                 110

Gln Ser Phe Glu Gln Val Gly Thr Lys Val Asn Val Thr Val Glu Asp
        115                 120                 125

Glu Arg Thr Leu Val Arg Arg Asn Asn Thr Phe Leu Ser Leu Arg Asp
130                 135                 140

Val Phe Gly Lys Asp Leu Ile Tyr Thr Leu Tyr Tyr Trp Lys Ser Ser
145                 150                 155                 160

Ser Ser Gly Lys Lys Thr Ala Lys Thr Asn Thr Asn Glu Phe Leu Ile
            165                 170                 175

Asp Val Asp Lys Gly Glu Asn Tyr Cys Phe Ser Val Gln Ala Val Ile
            180                 185                 190

Pro Ser Arg Thr Val Asn Arg Lys Ser Thr Asp Ser Pro Val Glu Cys
        195                 200                 205

Met Gly Gln Glu Lys Gly Glu Phe Arg Glu
        210                 215

<210> SEQ ID NO 842
<211> LENGTH: 219
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 842

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Asp Arg Ser Arg Asn Trp Lys Tyr Lys
        35                  40                  45

Cys Thr Gly Thr Thr Asp Thr Glu Cys Asp Leu Thr Asp Glu Ile Val
    50                  55                  60

Lys Asp Val Asn Trp Thr Tyr Glu Ala Arg Val Leu Ser Tyr Pro Ala
65                  70                  75                  80

Gly Asn Val Glu Ser Thr Gly Ser Ala Gly Glu Pro Leu Tyr Glu Asn
            85                  90                  95

Ser Pro Glu Phe Thr Pro Tyr Leu Glu Thr Asn Leu Gly Gln Pro Thr
            100                 105                 110

-continued

```
Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
            210                 215

<210> SEQ ID NO 843
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 843

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Val Pro Trp
65                  70                  75                  80

Arg Asn Ser Thr His Gly Thr His Gly Glu Glu Pro Pro Phe Thr Asn
                85                  90                  95

Ala Arg Lys Phe Leu Pro Tyr Arg Asp Thr Lys Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
            210                 215

<210> SEQ ID NO 844
<211> LENGTH: 225
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 844

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Val Pro Trp
65                  70                  75                  80

Arg Asn Ser Thr His Gly Lys Glu Thr Leu Phe Gly Thr His Gly Glu
                85                  90                  95

Glu Pro Pro Phe Thr Asn Ala Arg Lys Phe Leu Pro Tyr Arg Asp Thr
            100                 105                 110

Lys Leu Gly Gln Pro Thr Ile Gln Ser Phe Glu Gln Val Gly Thr Lys
        115                 120                 125

Val Asn Val Thr Val Glu Asp Glu Arg Thr Leu Val Arg Arg Asn Asn
    130                 135                 140

Thr Phe Leu Ser Leu Arg Asp Val Phe Gly Lys Asp Leu Ile Tyr Thr
145                 150                 155                 160

Leu Tyr Tyr Trp Lys Ser Ser Ser Ser Gly Lys Lys Thr Ala Lys Thr
                165                 170                 175

Asn Thr Asn Glu Phe Leu Ile Asp Val Asp Lys Gly Glu Asn Tyr Cys
            180                 185                 190

Phe Ser Val Gln Ala Val Ile Pro Ser Arg Thr Val Asn Arg Lys Ser
        195                 200                 205

Thr Asp Ser Pro Val Glu Cys Met Gly Gln Glu Lys Gly Glu Phe Arg
    210                 215                 220

Glu
225

<210> SEQ ID NO 845
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 845

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Val Pro Trp
65                  70                  75                  80

Arg Asn Ser Thr His Gly Lys Glu Thr Leu Phe Gly Thr His Gly Glu

-continued

```
                    85                  90                  95
Glu Pro Pro Tyr Glu Asn Ser Pro Glu Phe Thr Pro Tyr Leu Glu Thr
                100                 105                 110

Asn Leu Gly Gln Pro Thr Ile Gln Ser Phe Glu Gln Val Gly Thr Lys
            115                 120                 125

Val Asn Val Thr Val Glu Asp Glu Arg Thr Leu Val Arg Arg Asn Asn
        130                 135                 140

Thr Phe Leu Ser Leu Arg Asp Val Phe Gly Lys Asp Leu Ile Tyr Thr
145                 150                 155                 160

Leu Tyr Tyr Trp Lys Ser Ser Ser Gly Lys Lys Thr Ala Lys Thr
                165                 170                 175

Asn Thr Asn Glu Phe Leu Ile Asp Val Asp Lys Gly Glu Asn Tyr Cys
                180                 185                 190

Phe Ser Val Gln Ala Val Ile Pro Ser Arg Thr Val Asn Arg Lys Ser
            195                 200                 205

Thr Asp Ser Pro Val Glu Cys Met Gly Gln Glu Lys Gly Glu Phe Arg
        210                 215                 220

Glu
225

<210> SEQ ID NO 846
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 846

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Phe Thr Asn
                85                  90                  95

Ala Arg Lys Phe Leu Pro Tyr Arg Asp Thr Lys Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
        130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205
```

Cys Met Gly Gln Glu Lys Gly Glu Phe Arg Glu
            210                 215

<210> SEQ ID NO 847
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 847

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Ile Gly Gln Pro Val
            100                 105                 110

Ile Gln Lys Tyr Glu Gln Gly Gly Thr Lys Leu Lys Val Thr Val Lys
        115                 120                 125

Asp Ser Phe Thr Leu Val Arg Lys Asn Gly Thr Phe Leu Thr Leu Arg
130                 135                 140

Gln Val Phe Gly Asn Asp Leu Gly Tyr Ile Leu Thr Tyr Arg Lys Asp
145                 150                 155                 160

Ser Ser Thr Gly Arg Lys Thr Asn Thr Thr His Thr Asn Glu Phe Leu
                165                 170                 175

Ile Asp Val Glu Lys Gly Val Ser Tyr Cys Phe Phe Ala Gln Ala Val
            180                 185                 190

Ile Phe Ser Arg Lys Thr Asn His Lys Ser Pro Glu Ser Ile Thr Lys
        195                 200                 205

Cys Thr Glu Gln Trp Lys Ser Val Leu Gly Glu
    210                 215

<210> SEQ ID NO 848
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 848

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

-continued

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Ile Gly Gln Pro Val
            100                 105                 110

Ile Gln Lys Tyr Glu Gln Gly Gly Thr Lys Leu Lys Val Thr Val Lys
        115                 120                 125

Asp Ser Phe Thr Leu Val Arg Lys Asn Gly Thr Phe Leu Thr Leu Arg
130                 135                 140

Gln Val Phe Gly Asn Asp Leu Gly Tyr Ile Leu Thr Tyr Arg Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 849
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 849

Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
     50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Ile Gly Gln Pro Val
            100                 105                 110

Ile Gln Lys Tyr Glu Gln Gly Gly Thr Lys Leu Lys Val Thr Val Lys
        115                 120                 125

Asp Ser Phe Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

```
Cys Met Gly Gln Glu Lys Gly Glu Phe Arg Glu
    210                 215

<210> SEQ ID NO 850
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 850

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Lys Asn Gly Thr Phe Leu Thr Leu Arg
    130                 135                 140

Gln Val Phe Gly Asn Asp Leu Gly Tyr Ile Leu Thr Tyr Arg Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 851
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 851

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60
```

```
Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Lys Asn Gly Thr Phe Leu Thr Leu Arg
    130                 135                 140

Gln Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 852
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 852

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Lys Asn Gly Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
```

Cys Met Gly Gln Glu Lys Gly Glu Phe Arg Glu
    210                 215

<210> SEQ ID NO 853
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 853

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Thr Leu Arg
    130                 135                 140

Gln Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 854
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 854

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val

```
                  50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
130                 135                 140

Asp Val Phe Gly Asn Asp Leu Gly Tyr Ile Leu Thr Tyr Arg Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
                195                 200                 205

Cys Met Gly Gln Glu Lys Gly Glu Phe Arg Glu
                210                 215

<210> SEQ ID NO 855
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 855

Ser Gly Thr Thr Asn Thr Val Ala Ala Tyr Asn Leu Thr Trp Lys Ser
  1               5                  10                  15

Thr Asn Phe Lys Thr Ile Leu Glu Trp Glu Pro Lys Pro Val Asn Gln
                 20                  25                  30

Val Tyr Thr Val Gln Ile Ser Thr Lys Ser Gly Asp Trp Lys Ser Lys
             35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
130                 135                 140

Asp Val Phe Gly Asn Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190
```

Ile Pro Ser Arg Thr Val Asn Arg Lys Ser Thr Asp Ser Pro Val Glu
            195                 200                 205

Cys Met Gly Gln Glu Lys Gly Glu Phe Arg Glu
        210                 215

<210> SEQ ID NO 856
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 856

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Gly Tyr Ile Leu Thr Tyr Arg Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 857
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 857

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

```
Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Asp
145                 150                 155                 160

Ser Ser Thr Gly Arg Lys Thr Asn Thr Thr His Thr Asn Glu Phe Leu
                    165                 170                 175

Ile Asp Val Glu Lys Gly Val Ser Tyr Cys Phe Phe Ala Gln Ala Val
                180                 185                 190

Ile Phe Ser Arg Lys Thr Asn His Lys Ser Pro Glu Ser Ile Thr Lys
                195                 200                 205

Cys Thr Glu Gln Trp Lys Ser Val Leu Gly Glu
210                 215

<210> SEQ ID NO 858
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 858

Ser Gly Thr Thr Asn Thr Val Ala Ala Tyr Asn Leu Thr Trp Lys Ser
 1               5                  10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
                35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
                115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Asp
145                 150                 155                 160

Ser Ser Thr Gly Arg Lys Thr Asn Thr Thr His Thr Asn Glu Phe Leu
                    165                 170                 175

Ile Asp Val Glu Lys Gly Val Ser Tyr Cys Phe Phe Ala Gln Ala Val
                180                 185                 190
```

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215

<210> SEQ ID NO 859
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 859

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Asp
145                 150                 155                 160

Ser Ser Thr Gly Arg Lys Thr Asn Thr Thr His Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
        210                 215

<210> SEQ ID NO 860
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 860

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

```
Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Asp
145                 150                 155                 160

Ser Ser Thr Gly Arg Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 861
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 861

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Asn Thr His Thr Asn Glu Phe Leu
                165                 170                 175

Ile Asp Val Asp Lys Gly Glu Asn Tyr Cys Phe Ser Val Gln Ala Val
```

```
                180             185                 190
Ile Pro Ser Arg Thr Val Asn Arg Lys Ser Thr Asp Ser Pro Val Glu
            195                 200                 205
Cys Met Gly Gln Glu Lys Gly Glu Phe Arg Glu
        210                 215

<210> SEQ ID NO 862
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 862

Ser Gly Thr Thr Asn Thr Val Ala Ala Tyr Asn Leu Thr Trp Lys Ser
1               5                   10                  15
Thr Asn Phe Lys Thr Ile Leu Glu Trp Glu Pro Lys Pro Val Asn Gln
            20                  25                  30
Val Tyr Thr Val Gln Ile Ser Thr Lys Ser Gly Asp Trp Lys Ser Lys
        35                  40                  45
Cys Phe Tyr Thr Thr Asp Thr Glu Cys Asp Leu Thr Asp Glu Ile Val
50                  55                  60
Lys Asp Val Lys Gln Thr Tyr Leu Ala Arg Val Phe Ser Tyr Pro Ala
65                  70                  75                  80
Gly Asn Val Glu Ser Thr Gly Ser Ala Gly Glu Pro Leu Tyr Glu Asn
                85                  90                  95
Ser Pro Glu Phe Thr Pro Tyr Leu Glu Thr Asn Leu Gly Gln Pro Thr
            100                 105                 110
Ile Gln Ser Phe Glu Gln Val Gly Thr Lys Val Asn Val Thr Val Glu
        115                 120                 125
Asp Glu Arg Thr Leu Val Arg Arg Asn Asn Thr Phe Leu Ser Leu Arg
130                 135                 140
Asp Val Phe Gly Lys Asp Leu Ile Tyr Thr Leu Tyr Tyr Trp Lys Ser
145                 150                 155                 160
Ser Ser Ser Gly Lys Lys Thr Ala Lys Thr Asn Thr Asn Glu Phe Leu
                165                 170                 175
Ile Asp Val Glu Lys Gly Val Ser Tyr Cys Phe Phe Ala Gln Ala Val
            180                 185                 190
Ile Pro Ser Arg Thr Val Asn Arg Lys Ser Thr Asp Ser Pro Val Glu
        195                 200                 205
Cys Met Gly Gln Glu Lys Gly Glu Phe Arg Glu
    210                 215

<210> SEQ ID NO 863
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 863

Ser Gly Thr Thr Asn Thr Val Ala Ala Tyr Asn Leu Thr Trp Lys Ser
1               5                   10                  15
Thr Asn Phe Lys Thr Ile Leu Glu Trp Glu Pro Lys Pro Val Asn Gln
            20                  25                  30
Val Tyr Thr Val Gln Ile Ser Thr Lys Ser Gly Asp Trp Lys Ser Lys
```

```
                35                  40                  45
Cys Phe Tyr Thr Thr Asp Thr Glu Cys Asp Leu Thr Asp Glu Ile Val
 50                  55                  60
Lys Asp Val Lys Gln Thr Tyr Leu Ala Arg Val Phe Ser Tyr Pro Ala
 65                  70                  75                  80
Gly Asn Val Glu Ser Thr Gly Ser Ala Gly Pro Leu Tyr Glu Asn
                 85                  90                  95
Ser Pro Glu Phe Thr Pro Tyr Leu Glu Thr Asn Leu Gly Gln Pro Thr
                100                 105                 110
Ile Gln Ser Phe Glu Gln Val Gly Thr Lys Val Asn Val Thr Val Glu
                115                 120                 125
Asp Glu Arg Thr Leu Val Arg Arg Asn Asn Thr Phe Leu Ser Leu Arg
                130                 135                 140
Asp Val Phe Gly Lys Asp Leu Ile Tyr Thr Leu Tyr Tyr Trp Lys Ser
145                 150                 155                 160
Ser Ser Ser Gly Lys Lys Thr Ala Lys Thr Asn Thr Asn Glu Phe Leu
                165                 170                 175
Ile Asp Val Asp Lys Gly Glu Asn Tyr Cys Phe Ser Val Gln Ala Val
                180                 185                 190
Ile Phe Ser Arg Lys Thr Asn His Lys Ser Pro Glu Ser Ile Thr Lys
                195                 200                 205
Cys Thr Glu Gln Trp Lys Ser Val Leu Gly Glu
                210                 215

<210> SEQ ID NO 864
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 864

Ala Gly Thr Pro Pro Gly Lys Ala Phe Asn Leu Thr Trp Ile Ser Thr
 1                5                  10                  15
Asp Phe Lys Thr Ile Leu Glu Trp Gln Pro Lys Pro Thr Asn Tyr Thr
                 20                  25                  30
Tyr Thr Val Gln Ile Ser Asp Arg Ser Arg Asn Trp Lys Tyr Lys Cys
                 35                  40                  45
Thr Gly Thr Thr Asp Thr Glu Cys Asp Leu Thr Asp Glu Ile Val Lys
 50                  55                  60
Asp Val Asn Trp Thr Tyr Glu Ala Arg Val Leu Ser Val Pro Trp Arg
 65                  70                  75                  80
Asn Ser Thr His Gly Lys Glu Thr Leu Phe Gly Thr His Gly Glu Glu
                 85                  90                  95
Pro Pro Phe Thr Asn Ala Arg Lys Phe Leu Pro Tyr Arg Asp Thr Lys
                100                 105                 110
Ile Gly Gln Pro Val Ile Gln Lys Tyr Glu Gln Gly Thr Lys Leu
                115                 120                 125
Lys Val Thr Val Lys Asp Ser Phe Thr Leu Val Arg Arg Asn Asn Thr
130                 135                 140
Phe Leu Ser Leu Arg Asp Val Phe Gly Lys Asp Leu Ile Tyr Thr Leu
145                 150                 155                 160
Tyr Tyr Trp Lys Ser Ser Ser Gly Lys Lys Thr Ala Lys Thr Asn
                165                 170                 175
```

Thr Asn Glu Phe Leu Ile Asp Val Asp Lys Gly Glu Asn Tyr Cys Phe
            180                 185                 190

Ser Val Gln Ala Val Ile Phe Ser Arg Lys Thr Asn His Lys Ser Pro
        195                 200                 205

Glu Ser Ile Thr Lys Cys Thr Glu Gln Trp Lys Ser Val Leu Gly Glu
    210                 215                 220

<210> SEQ ID NO 865
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 865

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
50                  55                  60

Lys Asp Val Asn Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 866
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 866

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

```
Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Asn Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
210                 215
```

<210> SEQ ID NO 867
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 867

```
Ser Gly Thr Thr Asn Thr Val Ala Ala Tyr Asn Leu Thr Trp Lys Ser
 1                5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
 65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr His Thr Asn Glu Phe Leu
                165                 170                 175
```

Ile Asp Val Asp Lys Gly Glu Asn Tyr Cys Phe Ser Val Gln Ala Val
            180                 185                 190

Ile Pro Ser Arg Lys Val Asn Arg Lys Ser Thr Asp Ser Pro Val Glu
        195                 200                 205

Cys Met Gly Gln Glu Lys Gly Glu Phe Arg Glu
    210                 215

<210> SEQ ID NO 868
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(31)
<223> OTHER INFORMATION: Val or Ala
<220> FEATURE:
<221> NAME/KEY: MOD_RES
<222> LOCATION: (55)..(55)
<223> OTHER INFORMATION: Asn or Ser

<400> SEQUENCE: 868

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asp Xaa Tyr
            20                  25                  30

Gly Ile Ser Trp Val Arg Gln Ala Pro Gly Gln Gly Leu Glu Trp Met
        35                  40                  45

Gly Trp Ile Ala Pro Tyr Xaa Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Phe Gly Tyr Gly Met Asp Val
            100                 105                 110

Trp Gly Gln Gly Thr Thr Val Thr Val Ser Ser
        115                 120

<210> SEQ ID NO 869
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Arg or Gln
<220> FEATURE:
<221> NAME/KEY: MOD_RES
<222> LOCATION: (27)..(27)
<223> OTHER INFORMATION: Gln or Glu
<220> FEATURE:
<221> NAME/KEY: MOD_RES
<222> LOCATION: (30)..(30)
<223> OTHER INFORMATION: Ser or Asn
<220> FEATURE:
<221> NAME/KEY: MOD_RES
<222> LOCATION: (31)..(31)
<223> OTHER INFORMATION: Ser or Asn
<220> FEATURE:
<221> NAME/KEY: MOD_RES

```
<222> LOCATION: (52)..(52)
<223> OTHER INFORMATION: Ser or Tyr
<220> FEATURE:
<221> NAME/KEY: MOD_RES
<222> LOCATION: (53)..(53)
<223> OTHER INFORMATION: Ser or Asn
<220> FEATURE:
<221> NAME/KEY: MOD_RES
<222> LOCATION: (56)..(56)
<223> OTHER INFORMATION: Ser or Tyr
<220> FEATURE:
<221> NAME/KEY: MOD_RES
<222> LOCATION: (90)..(90)
<223> OTHER INFORMATION: Gln or Leu
<220> FEATURE:
<221> NAME/KEY: MOD_RES
<222> LOCATION: (93)..(93)
<223> OTHER INFORMATION: Ser or Lys

<400> SEQUENCE: 869

Asp Ile Gln Met Thr Gln Ser Pro Ser Thr Leu Ser Ala Ser Val Gly
1               5                   10                  15

Asp Arg Val Thr Ile Thr Cys Xaa Ala Ser Xaa Ser Ile Xaa Xaa Trp
            20                  25                  30

Leu Ala Trp Tyr Gln Gln Lys Pro Gly Lys Ala Pro Lys Leu Leu Ile
        35                  40                  45

Tyr Lys Ala Xaa Xaa Leu Glu Xaa Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Xaa Phe Gln Xaa Leu Pro Pro
                85                  90                  95

Phe Thr Phe Gly Gly Gly Thr Lys Val Glu Ile Lys
            100                 105

<210> SEQ ID NO 870
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (55)..(55)
<223> OTHER INFORMATION: Asn or Ser

<400> SEQUENCE: 870

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
            20                  25                  30

Gly Ile Ser Trp Val Arg Gln Ala Pro Gly Gln Gly Leu Glu Trp Met
        35                  40                  45

Gly Trp Val Ala Pro Tyr Xaa Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ala Gly Thr Tyr Ser Pro Tyr Gly Tyr Gly Met Asp Val
            100                 105                 110

Trp Gly Gln Gly Thr Thr Val Thr Val Ser Ser
            115                 120
```

```
                115                 120

<210> SEQ ID NO 871
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Arg or Gln
<220> FEATURE:
<221> NAME/KEY: MOD_RES
<222> LOCATION: (27)..(27)
<223> OTHER INFORMATION: Gln or His
<220> FEATURE:
<221> NAME/KEY: MOD_RES
<222> LOCATION: (30)..(30)
<223> OTHER INFORMATION: Ser or Asp
<220> FEATURE:
<221> NAME/KEY: MOD_RES
<222> LOCATION: (50)..(50)
<223> OTHER INFORMATION: Lys or Ser
<220> FEATURE:
<221> NAME/KEY: MOD_RES
<222> LOCATION: (53)..(53)
<223> OTHER INFORMATION: Ser or Tyr
<220> FEATURE:
<221> NAME/KEY: MOD_RES
<222> LOCATION: (90)..(90)
<223> OTHER INFORMATION: Gln, Leu, or Arg

<400> SEQUENCE: 871

Asp Ile Gln Met Thr Gln Ser Pro Ser Thr Leu Ser Ala Ser Val Gly
1               5                   10                  15

Asp Arg Val Thr Ile Thr Cys Xaa Ala Ser Xaa Ser Ile Xaa Ser Trp
            20                  25                  30

Leu Ala Trp Tyr Gln Gln Lys Pro Gly Lys Ala Pro Lys Leu Leu Ile
        35                  40                  45

Tyr Xaa Ala Ser Xaa Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Xaa Phe Gln Ser Leu Pro Pro
                85                  90                  95

Phe Thr Phe Gly Gly Gly Thr Lys Val Glu Ile Lys
            100                 105

<210> SEQ ID NO 872
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Val or Ala

<400> SEQUENCE: 872

Gly Tyr Thr Phe Asp Xaa Tyr Gly Ile Ser
1               5                   10

<210> SEQ ID NO 873
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn or Ser

<400> SEQUENCE: 873

Trp Ile Ala Pro Tyr Xaa Gly Asn Thr Asn Tyr Ala Gln Lys Leu Gln
1               5                   10                  15

Gly

<210> SEQ ID NO 874
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Asp Ala Gly Thr Tyr Ser Pro Phe Gly Tyr Gly Met Asp Val
1               5                   10

<210> SEQ ID NO 875
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Gln
<220> FEATURE:
<221> NAME/KEY: MOD_RES
<222> LOCATION: (4)..(4)
<223> OTHER INFORMATION: Gln or Glu
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Ser or Asn

<400> SEQUENCE: 875

Xaa Ala Ser Xaa Ser Ile Xaa Xaa Trp Leu Ala
1               5                   10

<210> SEQ ID NO 876
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Ser or Asn
<220> FEATURE:
<221> NAME/KEY: MOD_RES
```

```
<222> LOCATION: (7)..(7)
<223> OTHER INFORMATION: Ser or Tyr

<400> SEQUENCE: 876

Lys Ala Xaa Xaa Leu Glu Xaa
1               5

<210> SEQ ID NO 877
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln or Leu
<220> FEATURE:
<221> NAME/KEY: MOD_RES
<222> LOCATION: (5)..(5)
<223> OTHER INFORMATION: Ser or Lys

<400> SEQUENCE: 877

Gln Xaa Phe Gln Xaa Leu Pro Pro Phe Thr
1               5                   10

<210> SEQ ID NO 878
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

Gly Tyr Thr Phe Arg Ser Tyr Gly Ile Ser
1               5                   10

<210> SEQ ID NO 879
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asn or Ser

<400> SEQUENCE: 879

Trp Val Ala Pro Tyr Xaa Gly Asn Thr Asn Tyr Ala Gln Lys Leu Gln
1               5                   10                  15

Gly

<210> SEQ ID NO 880
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 880

Asp Ala Gly Thr Tyr Ser Pro Tyr Gly Tyr Gly Met Asp Val
1               5                   10
```

-continued

```
<210> SEQ ID NO 881
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Arg or Gln
<220> FEATURE:
<221> NAME/KEY: MOD_RES
<222> LOCATION: (4)..(4)
<223> OTHER INFORMATION: Gln or His
<220> FEATURE:
<221> NAME/KEY: MOD_RES
<222> LOCATION: (7)..(7)
<223> OTHER INFORMATION: Ser or Asp

<400> SEQUENCE: 881

Xaa Ala Ser Xaa Ser Ile Xaa Ser Trp Leu Ala
1               5                   10

<210> SEQ ID NO 882
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Ser
<220> FEATURE:
<221> NAME/KEY: MOD_RES
<222> LOCATION: (4)..(4)
<223> OTHER INFORMATION: Ser or Tyr

<400> SEQUENCE: 882

Xaa Ala Ser Xaa Leu Glu Ser
1               5

<210> SEQ ID NO 883
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gln, Leu, or Arg

<400> SEQUENCE: 883

Gln Xaa Phe Gln Ser Leu Pro Pro Phe Thr
1               5                   10

<210> SEQ ID NO 884
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 884

Gly Tyr Thr Phe Asp Ala Tyr Gly Ile Ser
1               5                   10
```

<210> SEQ ID NO 885
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 885

Trp Ile Ala Pro Tyr Ser Gly Asn Thr Asn Tyr Ala Gln Lys Leu Gln
1               5                   10                  15

Gly

<210> SEQ ID NO 886
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Asp Ala Gly Thr Tyr Ser Pro Phe Gly Tyr Gly Met Asp Val
1               5                   10

<210> SEQ ID NO 887
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Arg Ala Ser Glu Ser Ile Ser Asn Trp Leu Ala
1               5                   10

<210> SEQ ID NO 888
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 888

Lys Ala Tyr Ser Leu Glu Tyr
1               5

<210> SEQ ID NO 889
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Gln Gln Phe Gln Lys Leu Pro Pro Phe Thr
1               5                   10

<210> SEQ ID NO 890
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 890

Ala Tyr Gly Ile Ser
1               5

<210> SEQ ID NO 891
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Trp Ile Ala Pro Tyr Ser Gly Asn Thr Asn Tyr Ala Gln Lys Leu Gln
1               5                   10                  15

Gly

<210> SEQ ID NO 892
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 892

Asp Ala Gly Thr Tyr Ser Pro Phe Gly Tyr Gly Met Asp Val
1               5                   10

<210> SEQ ID NO 893
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

Arg Ala Ser Glu Ser Ile Ser Asn Trp Leu Ala
1               5                   10

<210> SEQ ID NO 894
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 894

Lys Ala Tyr Ser Leu Glu Tyr
1               5

<210> SEQ ID NO 895
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

Gln Gln Phe Gln Lys Leu Pro Pro Phe Thr
1               5                   10

<210> SEQ ID NO 896
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 896

Gly Tyr Thr Phe Asp Ala Tyr
1               5

<210> SEQ ID NO 897
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 897

Pro Tyr Ser Gly
1

<210> SEQ ID NO 898
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 898

Ala Gly Thr Tyr Ser Pro Phe Gly Tyr Gly Met Asp
1               5                   10

<210> SEQ ID NO 899
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 899

Ser Glu Ser Ile Ser Asn Trp
1               5

<210> SEQ ID NO 900
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 900

Lys Ala Tyr
1

<210> SEQ ID NO 901
<211> LENGTH: 7
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 901

Phe Gln Lys Leu Pro Pro Phe
1               5

<210> SEQ ID NO 902
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 902

Gly Tyr Thr Phe Asp Ala Tyr Gly Ile Ser
1               5                   10

<210> SEQ ID NO 903
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 903

Trp Ile Ala Pro Tyr Ser Gly Asn Thr Asn
1               5                   10

<210> SEQ ID NO 904
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 904

Asp Ala Gly Thr Tyr Ser Pro Phe Gly Tyr Gly Met Asp Val
1               5                   10

<210> SEQ ID NO 905
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 905

Arg Ala Ser Glu Ser Ile Ser Asn Trp Leu Ala
1               5                   10

<210> SEQ ID NO 906
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 906

Lys Ala Tyr Ser Leu Glu Tyr
1               5

<210> SEQ ID NO 907
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 907

Gln Gln Phe Gln Lys Leu Pro Pro Phe Thr
1               5                   10

<210> SEQ ID NO 908
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 908

Asp Ala Tyr Gly Ile Ser
1               5

<210> SEQ ID NO 909
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 909

Trp Met Gly Trp Ile Ala Pro Tyr Ser Gly Asn Thr Asn
1               5                   10

<210> SEQ ID NO 910
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 910

Ala Arg Asp Ala Gly Thr Tyr Ser Pro Phe Gly Tyr Gly Met Asp
1               5                   10                  15

<210> SEQ ID NO 911
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Ser Asn Trp Leu Ala Trp Tyr
1               5

<210> SEQ ID NO 912
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Leu Leu Ile Tyr Lys Ala Tyr Ser Leu Glu
1               5                   10

<210> SEQ ID NO 913
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Gln Gln Phe Gln Lys Leu Pro Pro Phe
1               5

<210> SEQ ID NO 914
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 914

Gly Tyr Thr Phe Asp Ala Tyr Gly
1               5

<210> SEQ ID NO 915
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Ile Ala Pro Tyr Ser Gly Asn Thr
1               5

<210> SEQ ID NO 916
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Ala Arg Asp Ala Gly Thr Tyr Ser Pro Phe Gly Thr Gly Met Asp Val
1               5                   10                  15

<210> SEQ ID NO 917
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 917

Glu Ser Ile Ser Asn Trp
1               5

<210> SEQ ID NO 918
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 918

Lys Ala Tyr
1

<210> SEQ ID NO 919
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Gln Gln Phe Gln Lys Leu Pro Pro Phe Thr
1               5                   10

<210> SEQ ID NO 920
<211> LENGTH: 4
<212> TYPE: PRT
<213> ORGANISM: Homo sapiens

<400> SEQUENCE: 920

Glu Leu Leu Gly
1

<210> SEQ ID NO 921
<211> LENGTH: 4
<212> TYPE: PRT
<213> ORGANISM: Homo sapiens

<400> SEQUENCE: 921

Glu Phe Leu Gly
1

<210> SEQ ID NO 922
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 922

His His His His His His
1               5
```